US008435980B2

(12) United States Patent
Florjancic et al.

(10) Patent No.: US 8,435,980 B2
(45) Date of Patent: May 7, 2013

(54) PYRROLOPYRIDINE INHIBITORS OF KINASES

(75) Inventors: Alan S. Florjancic, Kenosha, WI (US); Yunsong Tong, Libertyville, IL (US); Thomas D. Penning, Elmhurst, IL (US); Jane Gong, Deerfield, IL (US); Magdalena Przytulinska, Chicago, IL (US); Douglas Steinman, Morton Grove, IL (US); James Holms, Gurnee, IL (US); Chunqiu Lai, Libertyville, IL (US); Gui-Dong Zhu, Gurnee, IL (US); Keith Woods, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 236 days.

(21) Appl. No.: 12/836,753

(22) Filed: Jul. 15, 2010

(65) Prior Publication Data
US 2011/0015173 A1    Jan. 20, 2011

Related U.S. Application Data

(60) Provisional application No. 61/225,742, filed on Jul. 15, 2009.

(51) Int. Cl.
*C07D 471/04*    (2006.01)
*A61K 31/437*    (2006.01)

(52) U.S. Cl.
USPC ............... 514/217.07; 514/228.2; 514/234.5; 514/253.04; 514/255.05; 514/256; 514/300; 540/597; 544/61; 544/127; 544/333; 544/362; 544/405; 546/113

(58) Field of Classification Search .......... 540/597; 544/61, 127, 333, 362, 405; 546/113; 514/217.07, 514/228.2, 234.5, 253.04, 255.05, 256, 300
See application file for complete search history.

(56) References Cited

U.S. PATENT DOCUMENTS

| 2007/0043063 A1 | 2/2007 | Salituro et al. |
| 2007/0293491 A1 | 12/2007 | Shafer et al. |

FOREIGN PATENT DOCUMENTS

| CA | 2648809 A1 | 11/2007 |
| EP | 2070928 A1 | 6/2009 |
| WO | WO9822457 A1 | 5/1998 |
| WO | WO2004078756 A2 | 9/2004 |
| WO | WO2005063747 A1 | 7/2005 |
| WO | WO2005095400 A1 | 10/2005 |
| WO | WO2006058074 A1 | 6/2006 |
| WO | WO2007107221 A1 | 9/2007 |
| WO | WO2007124288 A1 | 11/2007 |
| WO | WO2008046982 A2 | 4/2008 |

OTHER PUBLICATIONS

Kitamura et al., Molecular Mechanisms of Activation of Human Cdc7 Kinase, The Journal of Biological Chemistry, vol. 286, No. 26, pp. 23031-23043, Jul. 1, 2011.*

Simone, Oncology: Introduction, Cecil Textbook of Medicine, 20th Edition, vol. 1, pp. 1004-101 O, 1996.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Cho, W.H. et al., "CDC7 kinase phosphorylates serine residues adjacent to acidic amino acids in the minichromosome maintenance 2 protein," Proceedings of the National Academy of Sciences, 2006, vol. 103 (31), pp. 11521-11526.
Feng, D. et al., "Inhibiting the expression of DNA replication-initiation protein induces apoptosis in human cancer cells," Cancer Res., 2003, pp. 7356-7364, vol. 63.
Guo, B., et al., "High levels of Cdc7 and Dbf4 proteins can arrest cell-cycle progression," European Journal of Cell Biology, 2005, vol. 84, pp. 927-938.
International Search Report and Written Opinion for Application No. PCT/US2010/042067 mailed on Oct. 14, 2010, 6 pages.
Kim, J.M. et al., "Functions of mammalian Cdc7 kinase in initiation/monitoring of DNA replication and development," Mutat. Res., 2003, pp. 29-40, vol. 532.
Kim, J.M. et al., "Genetic dissection of mammalian Cdc7 kinase: cell cycle and developmental roles," Cell Cycle, 2004, pp. 300-304, vol. 3 (3).
Kim, J.M. et al., "Inactivation of Cdc7 kinase in mouse ES cells results in s-phase arrest and p53-dependent cell death," The EMBO Journal, 2002, vol. 21 (9), pp. 2168-2179.
Lau, E. et al., "Is there a pre-RC checkpoint that cancer cells lack?" Cell Cycle, 2006, pp. 1602-1606, vol. 5 (15).
Lau, E. et al., "The functional role of Cdc6 in S-G2/M in mammalian cells," EMBO Rep., 2006, pp. 425-430, vol. 7 (4).
Lau, E. et al., "The role of pre-replicative complex (pre-RC) components in oncogenesis," FASEB J., 2007, pp. 3786-3794, vol. 21 (14).

(Continued)

*Primary Examiner* — Deepak Rao
(74) *Attorney, Agent, or Firm* — Susan L. Steele

(57) ABSTRACT

The present invention relates to compounds of formula (I) or pharmaceutical acceptable salts,

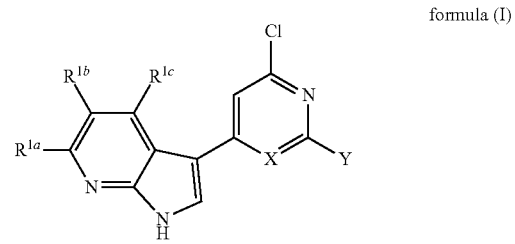

formula (I)

wherein $R^{1a}$, $R^{1b}$, $R^{1c}$, X, and Y are defined in the description. The present invention relates also to compositions containing said compounds which are useful for inhibiting kinases such as Cdc7 and methods of treating diseases such as cancer.

15 Claims, No Drawings

OTHER PUBLICATIONS

Montagnoli, A. et al., "Cdc7 inhibition reveals a p53-dependent replication checkpoint that is defective in cancer cells," Cancer Res., 2004, pp. 7110-7116, vol. 64.

Montagnoli, A. et al., "Identification of Mcm2 phosphorylation sites by S-phase-regulating kinases," The Journal of Biological Chemistry, 2006, vol. 281 (15), pp. 10281-10290.

Stillman, B., "Origin recognition and the chromosome cycle," FEBS Lett., 2005, pp. 877-884, vol. 579.

Tsuji, T. et al., "Essential Role of Phosphorylation of MCM2 by Cdc7/Dbf4 in the Initiation of DNA Replication in Mammalian Cells," Molecular Biology of the Cell, 2006, vol. 17, pp. 4459-4472.

* cited by examiner

PYRROLOPYRIDINE INHIBITORS OF KINASES

CROSS-REFERENCE TO RELATED APPLICATIONS

This application claims priority to U.S. Provisional Application Ser. No. 61/225,742, filed Jul. 15, 2009, which is incorporated by reference in its entirety.

SEQUENCE LISTING

The instant application contains a Sequence Listing which has been submitted in ASCII format via EFS-Web and is hereby incorporated by reference in its entirety. Said ASCII copy, created on Nov. 9, 2012, is named 10097USO.txt and is 615 bytes in size.

BACKGROUND OF THE INVENTION

Eukaryotic cells divide by a directed, step-wise process referred to as the cell cycle. Cells must first replicate their DNA in S phase before separating their sister chromatids in mitosis (karyokinesis) and splitting off into two daughter cells (cytokinesis). In mammalian cells, DNA replication must be initiated at multiple sites (replication origins) throughout the genome to ensure that all the genetic material is duplicated prior to mitosis. To maintain genome integrity, DNA must be replicated only once per cell cycle, and so this process is highly regulated and governed by checkpoints. Before replication is initiated, origins must be licensed through the formation of pre-replication complexes (pre-RCs) in early G1. Formation of pre-RCs involves the step-wise binding of the origin recognition complex (ORC) to origins followed by the binding of the loading factors Cdc6 and Cdt1. These proteins then recruit the putative DNA replicative helicase complex, MCM2-7. Once this pre-RC is formed, replication initiation requires the activation of S-phase-promoting serine/threonine kinases, Cyclin/Cdks and Cdc7/Dbf4. These kinases consist of an enzymatic sub-unit (CDKs and Cdc7) and a regulatory sub-unit (Cyclins for CDKs; Dbf4 or Drf1 for Cdc7). They phosphorylate multiple MCMs in pre-RCs in a sequential manner, thereby activating the helicase and recruiting other DNA replication factors (Cdc45, GINS complex, etc.) for DNA synthesis (for reviews, see Kim et al., 2003; Kim et al., 2004; Lau et al., 2006; Lau et al., 2007; Stillman, 2005). MCM2 Serine-40 and Serine-53 are well-characterized phosphorylation sites for Cdc7/Dbf4 (Cho et al., 2006; Montagnoli et al., 2006; Tsuji et al., 2006).

Inhibiting regulators of replication initiation, such as Cdc6, Cdc7/Dbf4 or Cdc7/Drf1, has lethal consequences in cancerous cells, whereas normal cells are able to arrest and resume normal divisions once initiation activity is restored (Feng et al., 2003; Montagnoli et al., 2004; see Lau and Jiang, 2006, for review). Small molecule inhibitors of the protein kinase Cdc7 are thus attractive candidates for therapeutic intervention in cancer, inflammation and other cell proliferative disorders.

SUMMARY OF THE INVENTION

The present invention has numerous embodiments. One embodiment of this invention, therefore, pertains to compounds that have formula (I)

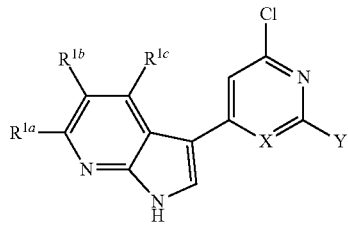

formula (I)

wherein $R^{1a}$, $R^{1b}$, $R^{1c}$, X, and Y are as defined below and subsets therein.

Also provided are pharmaceutically acceptable compositions comprising a therapeutically effective amount of a compound of formula (I) a pharmaceutically acceptable salt in combination with a pharmaceutically suitable carrier.

One embodiment is directed a method of treating cancer in a mammal comprising administering thereto a therapeutically acceptable amount of a compound or pharmaceutically acceptable salt of formula (I). In yet another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

ABBREVIATIONS AND DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl(vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl(cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl(tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of a polycyclic aromatic rings, only one ring the polycyclic system in required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$—$C_y$—", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-5-alkyl(alkyl-sulfanyl-alkyl).

The term "thiol" or "sulfhydryl" (alone or in combination with another term(s)) means a sulfhydryl substituent, and may be depicted as —SH. The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl(azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl(pseudoindolyl), isoindazolyl(benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

In one aspect, the present invention provides compounds of formula (I):

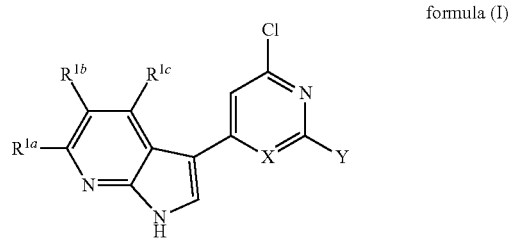

formula (I)

wherein $R^{1a}$ and $R^{1c}$ are independently hydrogen, nitro, halogen, cyano, hydroxy, $C_{1-6}$-alkyl, $C_{1-6}$-haloalkyl, $C_{1-6}$-alkoxy, $C_{1-6}$-haloalkoxy, —$NH_2$, —$NH(C_{1-6}$-alkyl), or —$N(C_{1-6}$-alkyl)$_2$;

$R^{1b}$ is hydrogen, nitro, halogen, cyano, $C_{1-6}$-alkyl, $C_{1-6}$-haloalkyl, —$OR^a$, —$NR^bR^c$; —$C(O)OR^a$, —$C(O)NR^bR^c$, —$NR^bC(O)R^c$, —$NHC(O)NHR^b$, —$NHSO_2R^a$, —$SO_2NR^bR^c$, phenyl, or heteroaryl, wherein the phenyl and heteroaryl are optionally substituted with $R^d$;

X is N or $CR^2$;

$R^2$ is hydrogen or $C_{1-6}$-alkyl;

Y is $NR^3R^4$, $NR^5C(O)R^6$, $NR^5SO_2R^6$, or phenyl, wherein the phenyl is optionally substituted with one or more $C_{1-6}$-alkyl, $C_{1-6}$-haloalkyl, halogen, cyano, hydroxy, $C_{1-6}$-alkoxy, $C_{1-6}$-haloalkoxy, —$NH_2$, —$NH(C_{1-6}$-alkyl), or —$N(C_{1-6}$-alkyl)$_2$;

$R^3$ is hydrogen, $C_{1-8}$-alkyl, $C_{2-8}$-alkenyl, $C_{1-8}$-alkyl-O—$C_{1-8}$-alkyl-, $C_{3-8}$-cycloalkyl, $C_{3-8}$-cycloalkyl-($C_{1-8}$-alkyl)-, heterocycloalkyl, heterocycloalkyl-($C_{1-8}$-alkyl)-, aryl, aryl-($C_{1-8}$-alkyl)-, heteroaryl, or heteroaryl-($C_{1-8}$-alkyl)-, wherein (a) the $R^3$ $C_{1-8}$-alkyl and $C_{2-8}$-alkenyl substituents, alone or as part of another moiety, are optionally substituted with one or more substituents selected from the group consisting of halogen, cyano, nitro, —$OR^e$, —$C(O)R^e$, —$C(O)OR^e$, —$OC(O)$ $R^e$, —$NR^fR^g$, —$NR^fC(O)R^e$, —$NHC(O)NHR^f$, —$C(O)NR^f$ $R^g$, —$NHSO_2R^e$, —$SO_2NR^fNR^g$, and benzyl; and (b) the $R^3$ $C_{3-8}$-cycloalkyl, heterocycloalkyl, aryl, and heteroaryl, alone or as part of another moiety, are optionally substituted with one or more $R^7$;

$R^4$ is hydrogen, $C_{1-6}$-alkyl, —$C(O)C_{1-6}$-alkyl, —$C(O)$ $C_{3-8}$-cycloalkyl, —$S(O)_2C_{1-6}$-alkyl, or —$S(O)_2C_{3-8}$-cycloalkyl, wherein the $R^4$ $C_{1-6}$-alkyl is optionally substituted with one or more substituents selected from the group consisting of halogen, hydroxy, $C_{1-6}$-alkoxy, —$NH_2$, —$NH$ ($C_{1-6}$-alkyl), and —$N(C_{1-6}$-alkyl)$_2$;

or $R^3$ and $R^4$ can be joined together to form a 4-7 membered heterocycloalkyl ring; wherein the heterocycloalkyl ring is optionally substituted with one or more $R^7$;

$R^5$ is hydrogen or $C_{1-8}$-alkyl;

$R^6$ is $C_{1-8}$-alkyl, $C_{2-8}$-alkenyl, $C_{3-8}$-cycloalkyl, $C_{3-8}$-cycloalkyl-($C_{1-8}$-alkyl)-; heterocycloalkyl, heterocycloalkyl-($C_{1-8}$-alkyl)-, aryl, aryl-($C_{1-8}$-alkyl), heteroaryl, or heteroaryl-($C_{1-8}$-alkyl), wherein (a) the $R^6$ $C_{1-8}$-alkyl and $C_{2-8}$-alkenyl substituents, alone or as part of another moiety, are optionally substituted with one or more substituents selected from the group consisting of halogen, hydroxy, $C_{1-6}$-alkoxy, $C_{1-6}$-haloalkoxy, $-NH_2$, $-NH(C_{1-6}$-alkyl), and $-N(C_{1-6}$-alkyl)$_2$, and (b) the $R^6$ $C_{3-8}$-cycloalkyl, heterocycloalkyl, aryl, and heteroaryl, alone or as part of another moiety, are optionally substituted with one or more substituents selected from the group consisting of $C_{1-6}$-alkyl, $C_{1-6}$-haloalkyl, halogen, cyano, hydroxy, $C_{1-6}$-alkoxy, $C_{1-6}$-haloalkoxy, $-NH_2$, $-NH(C_{1-6}$-alkyl), and $-N(C_{1-6}$-alkyl)$_2$;

$R^7$ is $C_{1-6}$-alkyl, $C_{1-6}$-haloalkyl, $C_{2-6}$-alkenyl, $C_{3-8}$-cycloalkyl, $C_{3-8}$-cycloalkyl-($C_{1-4}$-alkyl)-, heterocycloalkyl, heterocycloalkyl-($C_{1-4}$-alkyl)-, aryl, aryl-($C_{1-4}$-alkyl)-, heteroaryl, heteroaryl-($C_{1-4}$-alkyl), halogen, oxo, cyano, nitro, $-OR^8$, $-C(O)R^8$, $-C(O)OR^8$, $-OC(O)R^8$, $-SR^8$, $-S(O)R^8$, $-SO_2R^8$, $-NR^9R^{10}$, $-NHC(O)R^{11}$, $-NHC(O)NHR^{11}$, $-NHC(O)OR^{11}$, $-NHSO_2R^{11}$, $-C(O)NHR^{11}$, or $-SO_2NHNR^{11}$, wherein the $R^7$ cycloalkyl, heterocycloalkyl, aryl, and heteroaryl, alone or as part of another moiety, are optionally substituted with one or more $R^{12}$;

$R^8$ is hydrogen, $C_{1-6}$-alkyl, $C_{1-6}$-haloalkyl, $C_{2-6}$-alkenyl, $C_{3-8}$-cycloalkyl, aryl, heteroaryl, or heterocycloalkyl;

$R^9$ is hydrogen, $C_{1-6}$-alkyl, $C_{1-6}$-haloalkyl, $C_{2-6}$-alkenyl, $C_{3-8}$-cycloalkyl, $C_{3-8}$-cycloalkyl-($C_{1-4}$-alkyl)-, heterocycloalkyl, heterocycloalkyl-($C_{1-4}$-alkyl)-, aryl, aryl-($C_{1-4}$-alkyl)-, heteroaryl, heteroaryl-($C_{1-4}$-alkyl)-, wherein the $R^9$ cycloalkyl, heterocycloalkyl, aryl, and heteroaryl, alone or as part of another moiety, are optionally substituted with one or more substituents selected from the group consisting of $C_{1-6}$-alkyl, $C_{3-8}$-cycloalkyl, heterocycloalkyl, heterocycloalkyl-($C_{1-4}$-alkyl)-, $-C(O)R^h$, $-C(O)OR^h$, $-NR^iR^j$, and $-NHC(O)R^j$;

$R^{10}$ is hydrogen or $C_{1-6}$-alkyl;

$R^{11}$ is $C_{1-6}$-alkyl, $C_{1-6}$-haloalkyl, $C_{2-6}$-alkenyl, $C_{3-8}$-cycloalkyl, $C_{3-8}$-cycloalkyl-($C_{1-4}$-alkyl)-, heterocycloalkyl, heterocycloalkyl-($C_{1-4}$-alkyl)-, aryl, aryl-($C_{1-4}$-alkyl), heteroaryl, heteroaryl-($C_{1-4}$-alkyl), $-(C_{1-4}$-alkyl)-$NR^kR^l$, $-(C_{1-4}$-alkyl)-$NHC(O)R^m$, $-(C_{1-4}$-alkyl)-$NHSO_2R^m$, $-(C_{1-4}$-alkyl)-$NHC(O)NHR^k$, $-(C_{1-4}$-alkyl)-$OR^m$, or $-(C_{1-4}$-alkyl)-$C(O)OR^m$, wherein the $R^{11}$ $C_{3-8}$-cycloalkyl, heterocycloalkyl, aryl, and heteroaryl, alone or as part of another moiety, are optionally substituted with one or more substituents selected from the group consisting of $C_{1-6}$-alkyl, $C_{1-6}$-haloalkyl, $C_{1-6}$-hydroxyalkyl, halogen, cyano, hydroxy, oxo, $C_{1-6}$-alkoxy, $C_{1-6}$-haloalkoxy, $-NH_2$, $-NH(C_{1-6}$-alkyl), $-NH(C_{3-8}$-cycloalkyl), $N(C_{1-6}$-alkyl)$_2$, $-N(C_{1-6}$-alkyl)($C_{1-6}$-hydroxyalkyl), $-C(O)OC_{1-6}$-alkyl, $-S(O)_2$$C_{1-6}$-alkyl, heteroaryl, phenyl, benzyl, cycloalkyl, and heterocycloalkyl, wherein the heteroaryl, phenyl, benzyl, cycloalkyl, and heterocycloalkyl are optionally substituted with one or more $C_{1-6}$-alkyl or halogen;

$R^{12}$ is selected from the group consisting of $C_{1-6}$-alkyl, $C_{3-8}$-cycloalkyl, $-C(O)R''$, $-C(O)OR''$, $-NR^oR^p$, $-NHC(O)R''$, $-SO_2R''$, oxo, phenyl, benzyl, and heterocycloalkyl, wherein the phenyl, benzyl, and heterocycloalkyl are optionally substituted with one or more halogen or $C_{1-6}$ alkyl;

$R^a$, at each occurrence, is selected from the group consisting of hydrogen, $C_{1-6}$-alkyl, $C_{1-6}$-haloalkyl, $C_{2-6}$-alkenyl, $C_{2-6}$-alkynyl, aryl, heterocycloalkyl, heteroaryl, and $C_{3-8}$-cycloalkyl, wherein the $C_{1-6}$-alkyl, $C_{2-6}$-alkenyl, aryl, heterocycloalkyl, heteroaryl, and $C_{3-8}$-cycloalkyl are optionally substituted with one or more substituents independently selected from the group consisting of $C_{1-6}$-alkyl, aryl, heterocycloalkyl, heteroaryl, $C_{3-8}$-cycloalkyl, halogen, cyano, oxo, hydroxy, $C_{1-6}$-alkoxy, $-NH_2$, $-NH(C_{1-6}$-alkyl), and $-N(C_{1-6}$-alkyl)$_2$, wherein the heteroaryl is optionally substituted with $C_{1-6}$-alkyl;

$R^b$ and $R^c$, at each occurrence, are independently selected from the group consisting of hydrogen, $C_{1-6}$-alkyl, $C_{2-6}$-alkenyl, $C_{2-6}$-alkynyl, aryl, heterocycloalkyl, heteroaryl, and $C_{3-8}$-cycloalkyl, wherein the $C_{1-6}$-alkyl, $C_{2-6}$-alkenyl, $C_{2-6}$-alkynyl, aryl, heterocyclyl, $C_{3-8}$-cycloalkyl are optionally substituted with one or more substituents independently selected from the group consisting of $C_{1-6}$-alkyl, aryl, heterocyclyl, $C_{3-8}$-cycloalkyl, halogen, cyano, oxo, hydroxy, $C_{1-6}$-alkoxy, $-NH_2$, $-NH(C_{1-6}$-alkyl), and $-N(C_{1-6}$-alkyl)$_2$;

$R^d$ at each occurrence, is selected from the group consisting of $C_{1-6}$-alkyl, $-NH_2$, $-NH(C_{1-6}$-alkyl), $-N(C_{1-6}$-alkyl)$_2$; $SO_2NH_2$, heterocycloalkyl-($C_{1-4}$)—, and $-C_{1-4}$-hydroxyalkyl, wherein the heterocycloalkyl is optionally substituted with $C_{1-6}$-alkyl;

$R^e$, at each occurrence, is selected from the group consisting of hydrogen, $C_{1-6}$-alkyl, $C_{2-6}$-alkenyl, aryl, heteroaryl, heterocycloalkyl, and $C_{3-8}$-cycloalkyl, wherein the $C_{1-6}$-alkyl, $C_{2-6}$-alkenyl, aryl, heteroaryl, heterocycloalkyl, and $C_{3-8}$-cycloalkyl are optionally substituted with one or more substituents independently selected from the group consisting of $C_{1-6}$-alkyl, aryl, heterocyclyl, $C_{3-8}$-cycloalkyl, halogen, cyano, oxo, hydroxy, $C_{1-6}$-alkoxy, $-NH_2$, $-NH(C_{1-6}$-alkyl), and $-N(C_{1-6}$-alkyl)$_2$;

$R^f$ and $R^g$, at each occurrence, are independently selected from the group consisting of hydrogen, $C_{1-6}$-alkyl, $C_{2-6}$-alkenyl, aryl, heteroaryl, heterocycloalkyl, and $C_{3-8}$-cycloalkyl, wherein the $C_{1-6}$-alkyl, $C_{2-6}$-alkenyl, aryl, heteroaryl, heterocycloalkyl, $C_{3-8}$-cycloalkyl are optionally substituted with one or more substituents independently selected from the group consisting of $C_{1-6}$-alkyl, aryl, heterocyclyl, $C_{3-8}$-cycloalkyl, halogen, cyano, oxo, hydroxy, $C_{1-6}$-alkoxy, $-NH_2$, $-NH(C_{1-6}$-alkyl), and $-N(C_{1-6}$-alkyl)$_2$;

$R^h$, at each occurrence, is independently selected from the group consisting of $C_{1-6}$-alkyl, phenyl, benzyl, heterocycloalkyl, and $C_{3-8}$-cycloalkyl;

$R^i$ and $R^j$, at each occurrence, are independently selected from the group consisting of hydrogen, $C_{1-6}$-alkyl, phenyl, benzyl, and $C_{3-8}$-cycloalkyl;

$R^k$, at each occurrence, is selected from the group consisting of hydrogen, $C_{1-6}$-alkyl, $C_{2-6}$-alkenyl, aryl, heterocycloalkyl, heteroaryl, and $C_{3-8}$-cycloalkyl, wherein the aryl and heteroaryl are optionally substituted with one or more substituents independently selected from the group consisting of $C_{1-6}$-alkyl and $-C(O)C_{1-6}$-alkyl;

$R^l$, at each occurrence, is selected from the group consisting of hydrogen and $C_{1-6}$-alkyl;

$R^m$, at each occurrence, is selected from the group consisting of hydrogen, $C_{1-6}$-alkyl, $C_{2-6}$-alkenyl, aryl, heterocycloalkyl, heteroaryl, and $C_{3-8}$-cycloalkyl, wherein the aryl and heteroaryl are optionally substituted with one or more substituents independently selected from the group consisting of $C_{1-6}$-alkyl and $-C(O)C_{1-6}$-alkyl;

$R^n$, at each occurrence, is selected from the group consisting of hydrogen, $C_{1-6}$-alkyl, $C_{2-6}$-alkenyl, aryl, heterocycloalkyl, heteroaryl, and $C_{3-8}$-cycloalkyl, wherein the aryl and heteroaryl are optionally substituted with one or more substituents independently selected from the group consisting of $C_{1-6}$-alkyl and $-C(O)C_{1-6}$-alkyl;

$R^o$, at each occurrence, is selected from the group consisting of hydrogen, $C_{1-6}$-alkyl, aryl, heteroaryl, heterocycloalkyl, and $C_{3-8}$-cycloalkyl, wherein the aryl and heteroaryl are optionally substituted with one or more substituents independently selected from the group consisting of $C_{1-6}$-alkyl and —C(O)$C_{1-6}$-alkyl;

$R^p$, at each occurrence, is selected from the group consisting of hydrogen and $C_{1-6}$-alkyl;

or a pharmaceutically acceptable salt thereof.

In one embodiment of formula (I), $R^{1a}$, $R^{1b}$, and $R^{1c}$ are each hydrogen. In another embodiment, $R^{1a}$ and $R^{1c}$ are each hydrogen and $R^{1b}$ is nitro, halogen, cyano, $C_{1-6}$-alkyl, $C_{1-6}$-haloalkyl, —$OR^a$, —$NR^bR^c$; —C(O)$OR^a$, —C(O)$NR^bR^c$, —$NR^bC(O)R^c$, —NHC(O)$NHR^b$, —$NHSO_2R^a$, —$SO_2NR^bR^c$, phenyl, or heteroaryl, wherein the phenyl and heteroaryl are optionally substituted with $R^d$. In another embodiment, $R^{1a}$ and $R^{1c}$ are each hydrogen and $R^{1b}$ is halogen, cyano, $C_{1-6}$-alkyl, $C_{1-6}$-haloalkyl, —$OR^a$, phenyl, or heteroaryl.

In one embodiment of formula (I), X is N.

In another embodiment of formula (I), X is $CR^2$ wherein $R^2$ is hydrogen or methyl. In yet another embodiment, $R^2$ is hydrogen.

In one embodiment of formula (I), Y is a phenyl group. In one embodiment of formula (I), Y is an unsubstituted phenyl group. In another embodiment of formula (I), Y is a substituted phenyl substituted with one, two, or three substituents independently selected from the group consisting of fluoro, chloro, methyl, ethyl, methoxy, ethoxy, —$CF_3$, —$CF_2CF_3$, —$OCF_3$, —$OCF_2CF_3$, and cyano.

In one preferred embodiment of formula (I), Y is $NR^3R^4$.

In one embodiment of formula (I), $R^3$ is optionally substituted $C_{1-8}$-alkyl or optionally substituted $C_{2-8}$-alkenyl. In one embodiment, the $R^3$ $C_{1-8}$-alkyl or $C_{2-8}$-alkenyl is unsubstituted. In another embodiment, the $R^3$ $C_{1-8}$-alkyl or $C_{2-8}$-alkenyl is substituted with one or two substituents as defined above. Preferably, the one or two substituents are independently selected from the groups consisting of —$OR^e$, —$NR^fR^g$, —$NR^fC(O)R^e$, —$NHSO_2R^e$, —$SO_2NR^fNR^g$, and benzyl, wherein $R^e$, $R^f$, and $R^g$ are independently selected from the group consisting of H, $C_{1-6}$-alkyl, $C_{3-8}$-cycloalkyl, heteroaryl, and phenyl. More preferably, the $R^3$ $C_{1-8}$-alkyl or $C_{2-8}$-alkenyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

Where $R^3$ is $C_{1-8}$-alkyl, then preferably $R^3$ is methyl, ethyl, propyl, isopropyl, n-butyl, sec-butyl, t-butyl, 3-methylbutan-1-yl, pentyl, neopentyl, or 4,4-dimethylpentan-1-yl.

Where $R^3$ is substituted $C_{1-8}$-alkyl, then preferably $R^3$ is —$CH_2$—, —$CH_2CH_2$—, —$CH_2CH_2CH_2$—, —CH($CH_3$)$CH_2$—, —$CH_2CH_2CH_2CH_2$—, or —$CH_2C(CH_3)_2CH_2$—.

Where $R^3$ is $C_{2-8}$-alkenyl, then preferably $R^3$ is vinyl, prop-2-enyl, or but-3-enyl.

In another embodiment of formula (I), $R^3$ is aryl or heteroaryl. In one embodiment of formula (I), $R^3$ is phenyl, indanyl, tetrahydronaphthyl, or naphthyl, optionally substituted with one or more $R^7$. In one embodiment, $R^3$ is substituted with one, two, or three $R^7$, and $R^7$ is $C_{1-6}$-alkyl, $C_{1-6}$-haloalkyl, —$OR^8$, —$SR^8$, heteroaryl, or heterocycloalkyl, wherein the heteroaryl and heterocycloalkyl are optionally substituted with $C_{1-6}$-alkyl.

In another embodiment of formula (I), $R^3$ is a 5-7-membered heteroaryl, including, for example, furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, and more preferably pyridinyl. In yet another embodiment, $R^3$ is a bicyclic heteroaryl including, for example, quinolinyl, indolyl, benzimidazolyl, or 2,3-dihydrobenzo[b][1,4]dioxinyl.

In one embodiment of formula (I), $R^3$ is an optionally substituted $C_{3-8}$-cycloalkyl. In one embodiment, the $R^3$ $C_{3-8}$-cycloalkyl is substituted with one or two $R^7$. Preferably, the one or two substituents are independently selected from the groups consisting of heterocycloalkyl, $C_{3-8}$-cycloalkyl-($C_{1-4}$-alkyl)-, $OR^8$, —$NR^9R^{10}$, —NHC(O)$R^{11}$, —NHC(O)$NHR^{11}$, and —$NHSO_2R^{11}$. Where $R^3$ is optionally substituted $C_{3-8}$-cycloalkyl, then preferably $R^3$ is cyclobutyl, cyclopentyl, or cyclohexyl. More preferably, $R^3$ is cyclohexyl.

In one embodiment of formula (I), $R^3$ is an optionally substituted heterocycloalkyl. In one embodiment of formula (I), the $R^3$ heterocycloalkyl is substituted with one or two $R^7$, wherein $R^7$ is —$S(O)_2R^8$, —C(O)$R^8$, $C_{3-8}$-cycloalkyl, $C_{1-6}$-alkyl, heterocycloalkyl, or aryl-($C_{1-4}$-alkyl)-.

Where $R^3$ is optionally substituted heterocycloalkyl, then preferably $R^3$ is an optionally substituted 5-7 membered heterocycloalkyl. In another embodiment, the $R^3$ heterocycloalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, and 2,6-dioxopiperidinyl. Preferably, $R^3$ is pyrrolidinyl, tetrahydrofuryl, piperidinyl, or tetrahydropyranyl.

In another embodiment of formula (I), $R^3$ is $C_{3-8}$-cycloalkyl-($C_{1-8}$-alkyl), heterocycloalkyl-($C_{1-8}$-alkyl), aryl-($C_{1-8}$-alkyl)-, or heteroaryl-($C_{1-8}$-alkyl), wherein the $R^3$ $C_{3-8}$-cycloalkyl, heterocycloalkyl, aryl, and heteroaryl are optionally substituted with one or more $R^7$.

In one embodiment, where $R^3$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl), the $R^3$—($C_{1-8}$-alkyl)- is unsubstituted.

In one embodiment, where $R^3$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl), the $R^3$ cycloalkyl, heterocycloalkyl, aryl, or heteroaryl is unsubstituted.

Preferably, where $R^3$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl), the —($C_{1-8}$-alkyl)- is —($C_1$-alkyl)-, —($C_2$-alkyl)-, or —($C_3$-alkyl)-, and more preferably —($C_1$-alkyl)-.

In one embodiment, where $R^3$ is $C_{3-8}$-cycloalkyl-($C_{1-8}$-alkyl)-, the $C_{3-8}$-cycloalkyl is optionally substituted cyclobutyl, cyclopentyl, or cyclohexyl. In another embodiment, the $R^3C_{3-8}$-cycloalkyl is substituted with one or two $R^7$. Preferably, the one or two substituents are independently selected from the groups consisting of heterocycloalkyl, $C_{3-8}$-cycloalkyl-($C_{1-4}$-alkyl)-, $OR^8$, —$NR^9R^{10}$, —NHC(O)$R^{11}$, —NHC(O)$NHR^{11}$, and —$NHSO_2R^{11}$.

In one embodiment, where $R^3$ is heterocycloalkyl-($C_{1-8}$-alkyl), the heterocycloalkyl is an optionally substituted 5-7 membered heterocycloalkyl. In another embodiment, the $R^3$ heterocycloalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, and preferably pyrrolidinyl, tetrahydrofuryl, piperidinyl, or tetrahydropyranyl. In another embodiment, the optionally substituted $R^3$ heterocycloalkyl is substituted with one or two $R^7$, where in $R^7$ is —$S(O)_2R^8$, —C(O)$R^8$, $C_{3-8}$-cycloalkyl, $C_{1-6}$-alkyl, heterocycloalkyl, or aryl-($C_{1-4}$-alkyl)-.

In one embodiment, where $R^3$ is aryl-($C_{1-8}$-alkyl)-, the aryl is an optionally substituted phenyl, indanyl, tetrahydronaphthyl, or naphthyl. In another embodiment, the $R^3$ aryl is optionally substituted with one, two or three $R^7$, wherein $R^7$ is $C_{1-6}$-alkyl, $C_{1-6}$-haloalkyl, —$OR^8$, —$SR^8$, heteroaryl, or heterocycloalkyl, wherein the heteroaryl and heterocycloalkyl are optionally substituted with $C_{1-6}$-alkyl.

In one embodiment, where $R^3$ is heteroarylaryl-($C_{1-8}$-alkyl)-, the heteroaryl is an optionally substituted 5-7-membered heteroaryl. In yet another embodiment, the $R^3$ heteroaryl is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, quinolinyl, indolyl, benzimidazolyl, or 2,3-dihydrobenzo[b][1,4]dioxinyl.

In one embodiment of formula (I), $R^4$ is hydrogen. In another embodiment of formula (I), $R^4$ is an unsubstituted branched or straight chain $C_{1-6}$ alkyl. In yet another embodiment of formula (I), $R^4$ is methyl, ethyl, propyl, isopropyl, n-butyl, sec-butyl, or t-butyl. Where $R^4$ is an unsubstituted branched or straight chain $C_{1-6}$ alkyl, then preferably $R^4$ is methyl.

In one embodiment of formula (I), $R^3$ and $R^4$ can be joined together to form a heterocycloalkyl ring, wherein the heterocycloalkyl ring is optionally substituted with one or more $R^5$. In another embodiment, $R^3$ and $R^4$ are joined together to form a 4-7 membered heterocycloalkyl, wherein the heterocycloalkyl is unsubstituted or substituted with one or two $R^7$. Preferably, the one or two substituents independently selected from the groups consisting of $C_{1-8}$-alkyl, halogen, —$OR^8$, —$NR^9R^{10}$, —$NHC(O)R^{11}$, —$NHSO_2R^{11}$, and —$SO_2NHNR^{11}$. More preferably, the heterocycloalkyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

In one embodiment where $R^3$ and $R^4$ are joined together to form a 4-7 membered heterocycloalkyl, the heterocycloalkyl is azetidinyl, pyrrolidinyl, imidazolidinyl, pyrazolidinyl, piperidinyl, piperazinyl, morpholinyl, 2-oxopyrrolidinyl, 2,5-dioxopyrrolidinyl, 2-oxopiperidinyl, 4-oxopiperidinyl, or 2,6-dioxopiperidinyl, and preferably pyrrolidinyl, tetrahydrofuryl, piperidinyl, or tetrahydropyranyl.

In one embodiment of formula (I), $NR^3R^4$ is selected from the group consisting of

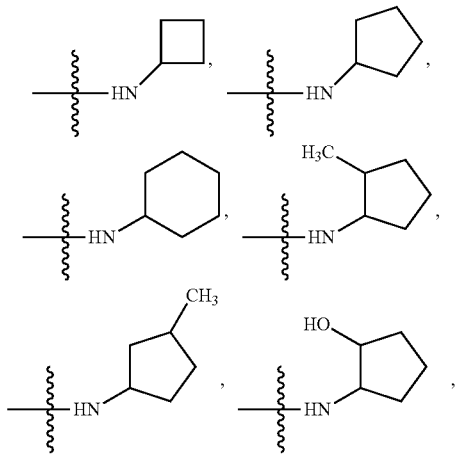

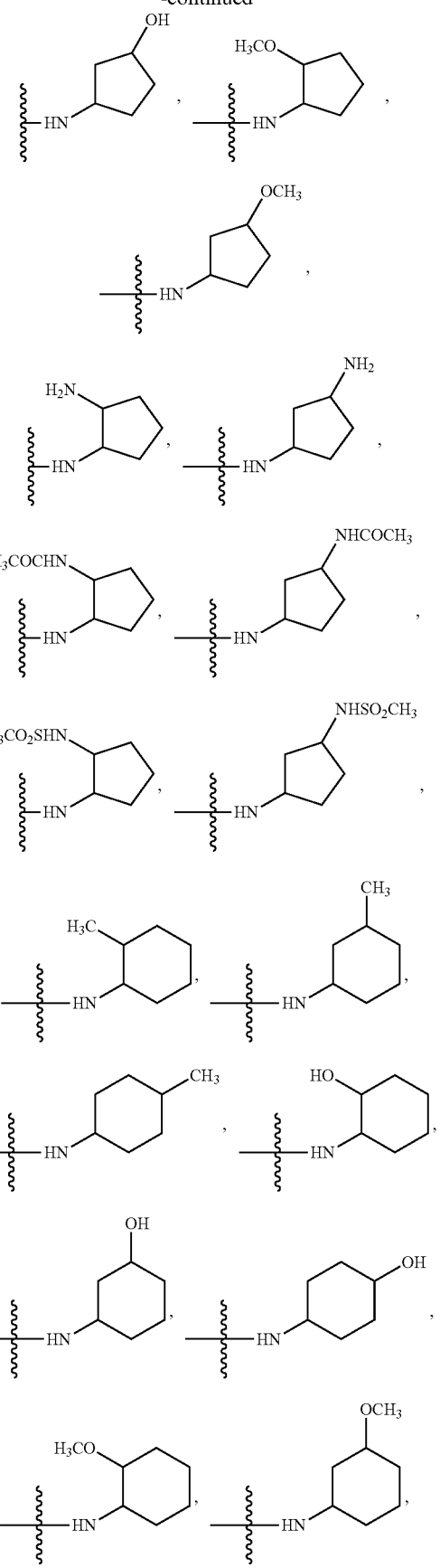

-continued
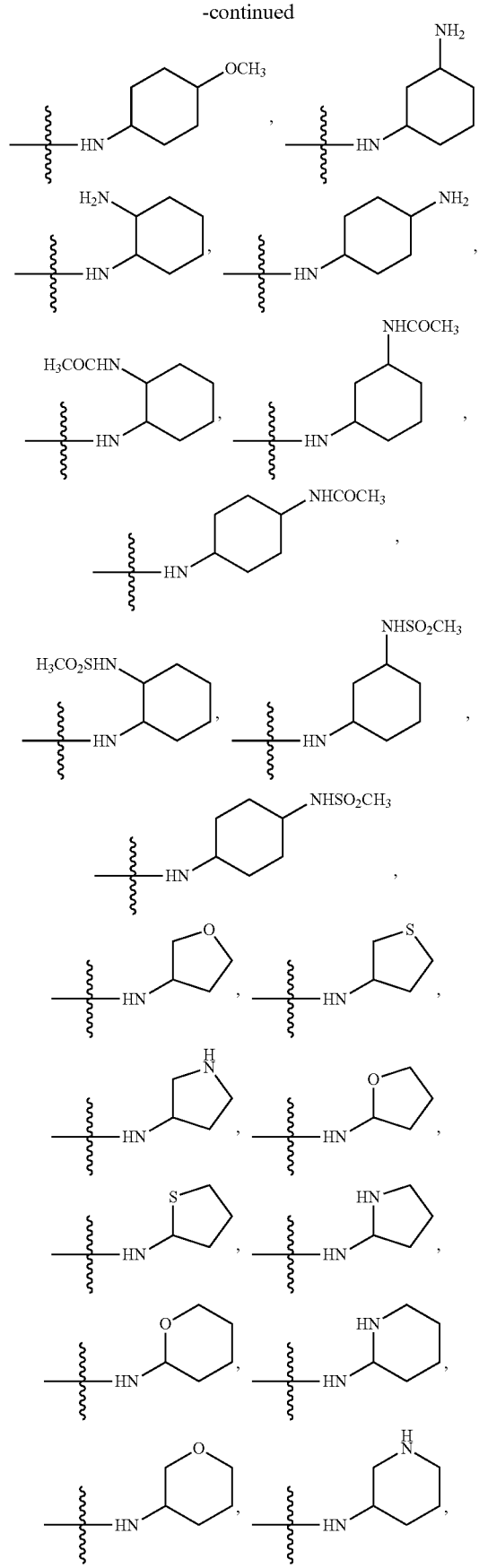
-continued
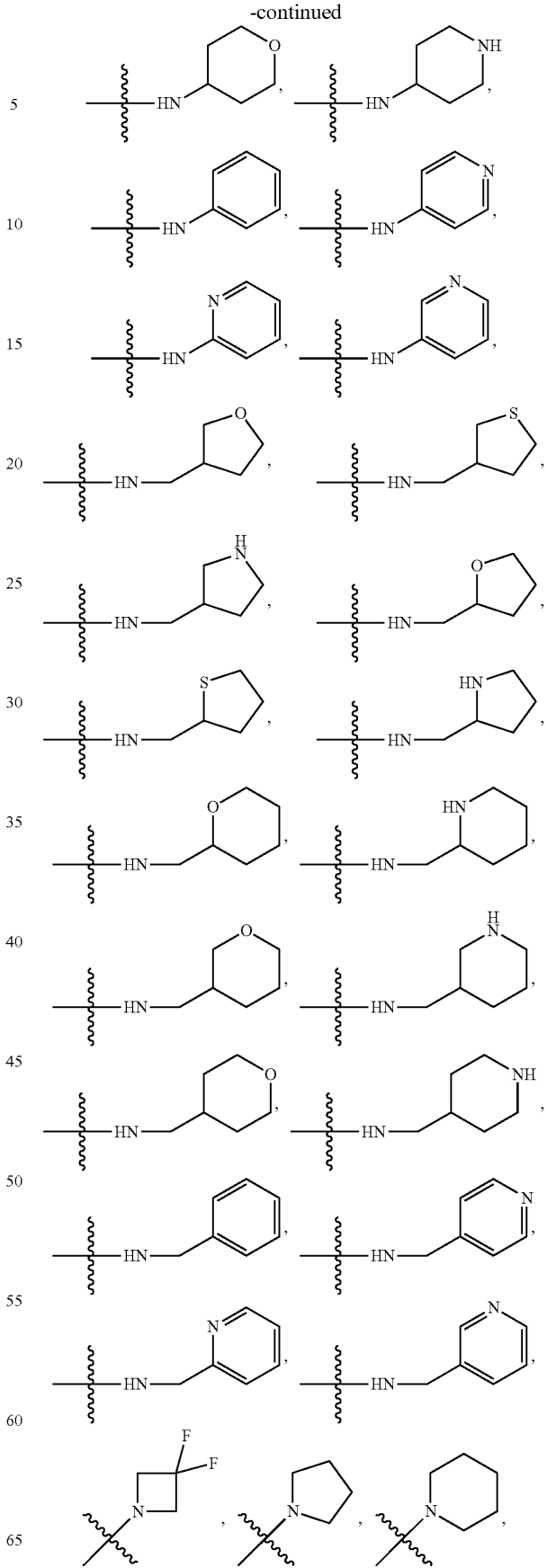

-continued
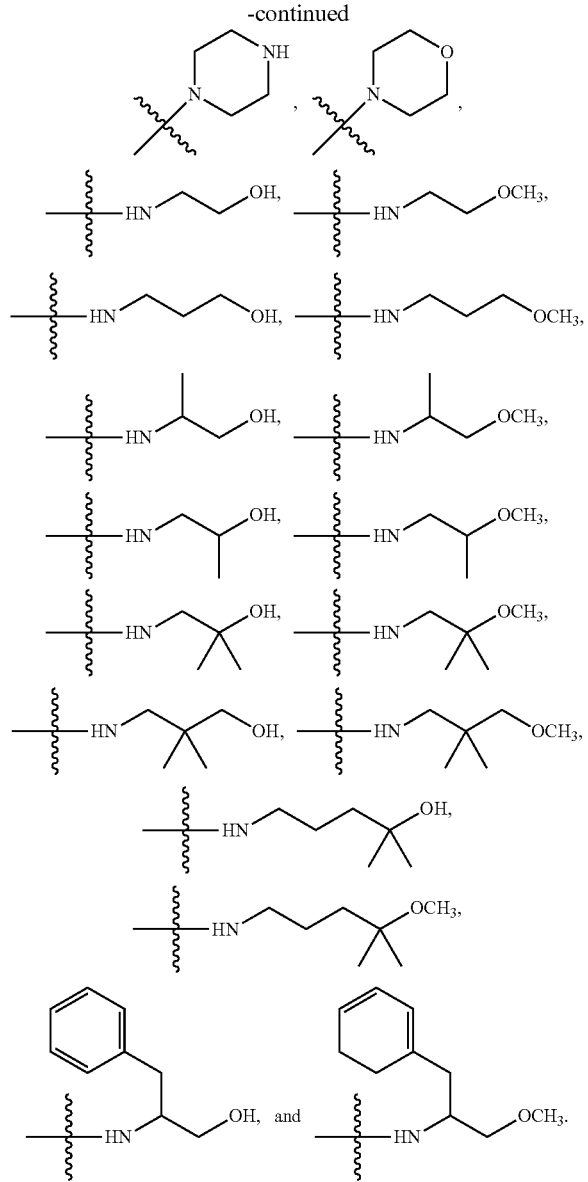
In another embodiment of formula (I), NR$^3$R$^4$ is
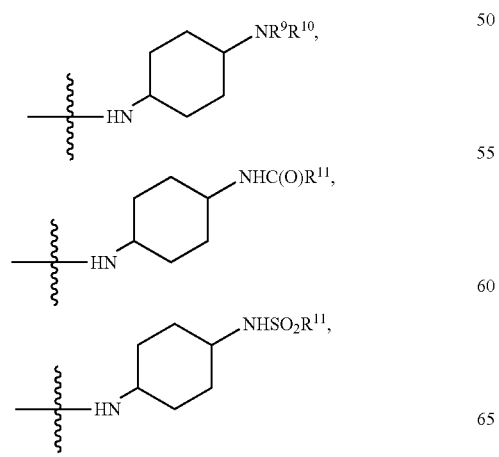
-continued
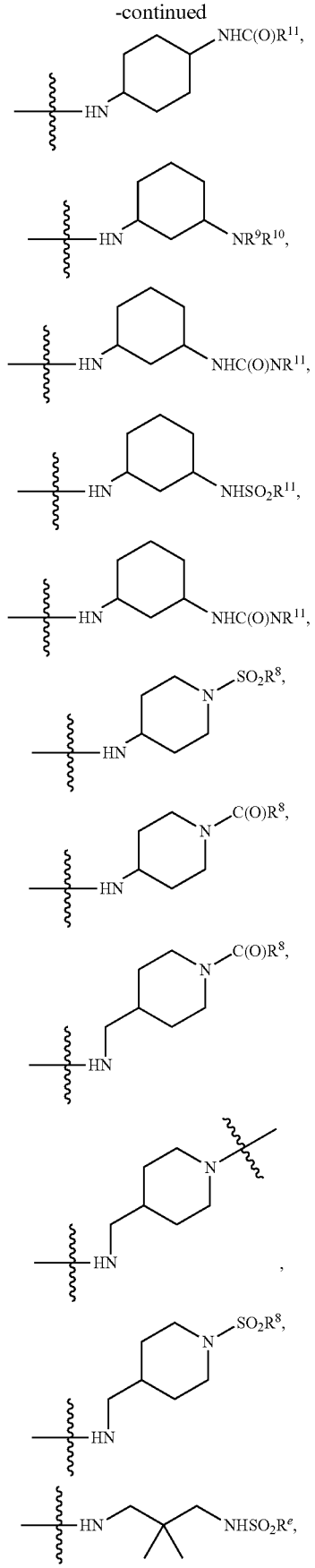
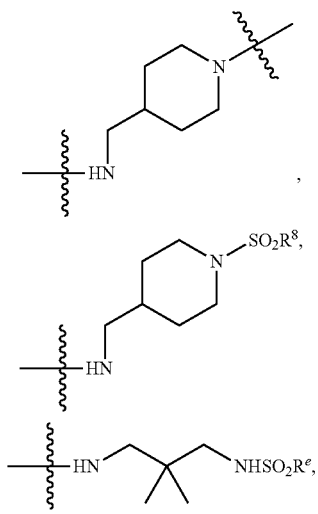

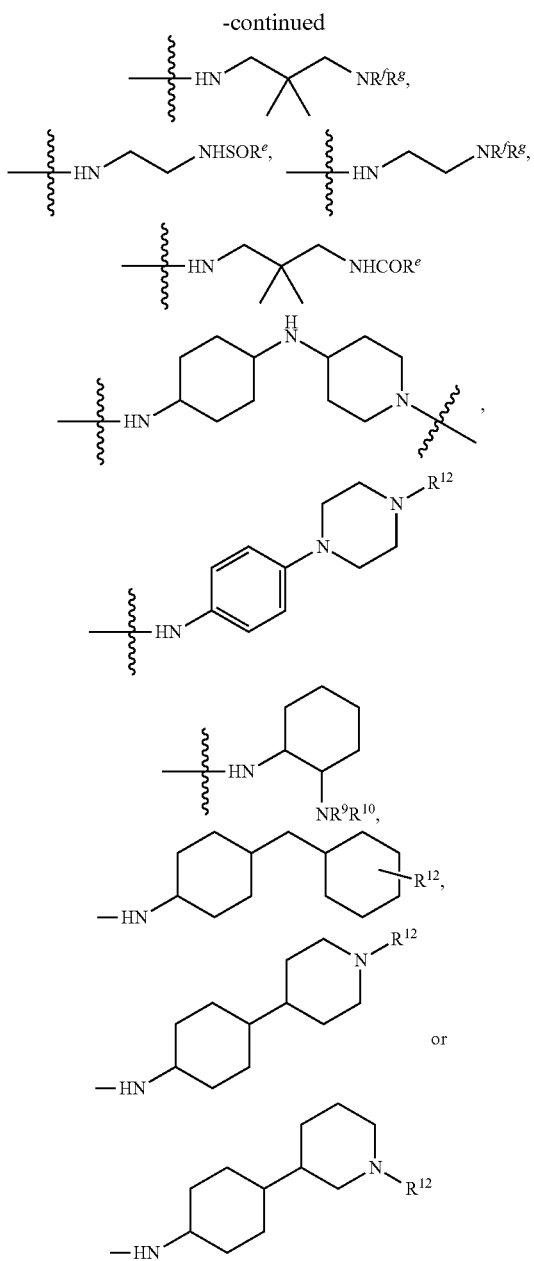

In an alternate embodiment of formula (I), Y is $NR^5C(O)R^6$ or $NR^5SO_2R^6$.

In one embodiment of formula (I), $R^5$ is hydrogen. In another embodiment of formula (I), $R^5$ is an unsubstituted branched or straight chain $C_{1-8}$-alkyl.

In one embodiment of formula (I), $R^6$ is optionally substituted $C_{1-8}$-alkyl. In one embodiment, the $R^6$ $C_{1-8}$-alkyl is unsubstituted. In another embodiment, the $R^6$ $C_{1-8}$-alkyl is substituted with one or two substituents as defined above. Preferably, the one or two substituents are independently selected from the groups consisting of halogen, hydroxy, $C_{1-6}$-alkoxy, $C_{1-6}$-haloalkoxy, —$NH_2$, —$NH(C_{1-6}$-alkyl), or —$N(C_{1-6}$-alkyl)$_2$.

In another embodiment of formula (I), $R^6$ is aryl or heteroaryl. In one embodiment of formula (I), $R^6$ is phenyl. In another embodiment of formula (I), $R^6$ is a 5-membered heteroaryl. In yet another embodiment, $R^6$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, and more preferably pyridinyl.

In one embodiment of formula (I), $R^6$ is an optionally substituted $C_{3-8}$-cycloalkyl or an optionally substituted heterocycloalkyl. In one embodiment, the $R^6$ $C_{3-8}$-cycloalkyl or heterocycloalkyl is unsubstituted.

Where $R^6$ is optionally substituted $C_{3-8}$-cycloalkyl, then preferably $R^6$ is cyclobutyl, cyclopentyl, or cyclohexyl. More preferably, $R^6$ is cyclohexyl.

Where $R^6$ is optionally substituted heterocycloalkyl, then preferably $R^6$ is an optionally substituted 5-7 membered heterocycloalkyl. In another embodiment, the $R^6$ heterocycloalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, and 2,6-dioxopiperidinyl. Preferably, $R^6$ is pyrrolidinyl, tetrahydrofuryl, piperidinyl, or tetrahydropyranyl.

In another embodiment of formula (I), $R^6$ is $C_{3-8}$-cycloalkyl-($C_{1-8}$-alkyl), heterocycloalkyl-($C_{1-8}$-alkyl), aryl-($C_{1-8}$-alkyl)-, or heteroaryl-($C_{1-8}$-alkyl)-.

In one embodiment, where $R^6$ is $C_{3-8}$-cycloalkyl-($C_{1-8}$-alkyl)-, heterocycloalkyl-($C_{1-8}$-alkyl)-, aryl-($C_{1-8}$-alkyl), or heteroaryl-($C_{1-8}$-alkyl), the $R^6$—($C_{1-8}$-alkyl)- is unsubstituted.

In one embodiment, where $R^6$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl), the $R^6$ cycloalkyl, heterocycloalkyl, aryl, or heteroaryl is unsubstituted. In another embodiment, the $R^6$ cycloalkyl, heterocycloalkyl, aryl, or heteroaryl is optionally substituted with one or two substituents independently selected from the groups consisting of $C_{1-6}$-alkyl, $C_{1-6}$-haloalkyl, halogen, cyano, hydroxy, $C_{1-6}$-alkoxy, $C_{1-6}$-haloalkoxy, —$NH_2$, —$NH(C_{1-6}$-alkyl), or —$N(C_{1-6}$-alkyl)$_2$.

Preferably, where $R^6$ is $C_{3-8}$-cycloalkyl-($C_{1-8}$-alkyl)-, heterocycloalkyl-($C_{1-8}$-alkyl)-, aryl-($C_{1-8}$-alkyl), or heteroaryl-($C_{1-8}$-alkyl), the —($C_{1-8}$-alkyl)- is —($C_1$-alkyl)-, —($C_2$-alkyl)-, or —($C_3$-alkyl)-, and more preferably —($C_1$-alkyl)-.

In one embodiment, where $R^6$ is $C_{3-8}$-cycloalkyl-($C_{1-8}$-alkyl)-, the $C_{3-8}$-cycloalkyl is optionally substituted cyclobutyl, cyclopentyl, or cyclohexyl.

In one embodiment, where $R^6$ is heterocycloalkyl-($C_{1-8}$-alkyl), the heterocycloalkyl is an optionally substituted 5-7 membered heterocycloalkyl. In another embodiment, the $R^7$ heterocycloalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, and preferably pyrrolidinyl, tetrahydrofuryl, piperidinyl, or tetrahydropyranyl.

In one embodiment, where $R^6$ is aryl-($C_{1-8}$-alkyl)-, the aryl is an optionally substituted phenyl.

In one embodiment, where $R^6$ is heteroarylaryl-($C_{1-8}$-alkyl)-, the heteroaryl is an optionally substituted 5-7-membered heteroaryl. In yet another embodiment, the $R^7$ heteroaryl is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, and more preferably pyridinyl.

In another embodiment, the present invention provides compounds of formula (I) wherein $R^{1a}$, $R^{1b}$, and $R^{1c}$ are hydrogen, X is $CR^2$, $R^2$ is hydrogen, Y is phenyl, wherein the phenyl is optionally substituted with one or more $C_{1-6}$-alkyl, halogen, cyano, hydroxy, $C_{1-6}$-alkoxy, $C_{1-6}$-haloalkoxy, $-NH_2$, $-NH(C_{1-6}$-alkyl), or $-N(C_{1-6}$-alkyl)$_2$.

In another embodiment, the present invention provides compounds of formula (I) wherein $R^{1a}$, $R^{1b}$, and $R^{1c}$ are hydrogen, X is N, Y is phenyl, wherein the phenyl is optionally substituted with one or more $C_{1-6}$-alkyl, halogen, cyano, hydroxy, $C_{1-6}$-alkoxy, $C_{1-6}$-haloalkoxy, $-NH_2$, $-NH(C_{1-6}$-alkyl), or $-N(C_{1-6}$-alkyl)$_2$.

In an alternative embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is $C_{1-8}$-alkyl, wherein the $C_{1-8}$-alkyl is optionally substituted one or two substituents independently selected from the group consisting of $-OR^e$, $-C(O)R^e$, $-C(O)OR^e$, $-NR^fR^g$, $-NR^fC(O)R^e$, $-NHC(O)NHR^f$, $-C(O)NR^fR^g$, $-NHSO_2R^e$, $-SO_2NR^fNR^g$, and benzyl; and wherein $R^4$ is hydrogen.

In another embodiment, the present invention provides compounds of formula (I) wherein $R^{1a}$, $R^{1b}$, and $R^{1c}$ are hydrogen, X is N, Y is $NR^3R^4$, wherein $R^3$ is $C_{1-8}$-alkyl, wherein the $C_{1-8}$-alkyl is optionally substituted one or two substituents independently selected from the group consisting of $-OR^e$, $-C(O)R^e$, $-C(O)OR^e$, $-NR^fR^g$, $-NR^fC(O)R^e$, $-NHC(O)NHR^f$, $-C(O)NR^fR^g$, $-NHSO_2R^e$, $-SO_2NR^fNR^g$, and benzyl; and wherein $R^4$ is hydrogen.

In an alternative embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is $C_{3-8}$-cycloalkyl, wherein the $C_{3-8}$-cycloalkyl is optionally substituted with one or two $R^7$, wherein $R^4$ is hydrogen, wherein $R^7$ is $C_{3-8}$-cycloalkyl-($C_{1-4}$-alkyl)-, heterocycloalkyl, heterocycloalkyl-($C_{1-4}$-alkyl)-, $-NR^9R^{10}$, $-NHC(O)R^{11}$, $-NHC(O)NHR^{11}$, $-NHC(O)OR^{11}$, or $-NHSO_2R^{11}$, wherein the $R^7$ cycloalkyl, heterocycloalkyl, aryl, and heteroaryl, alone or as part of another moiety, are optionally substituted with one or more $R^{12}$.

In another embodiment, the present invention provides compounds of formula (I) wherein $R^{1a}$, $R^{1b}$ and $R^{1c}$ are hydrogen, X is N, Y is $NR^3R^4$, wherein $R^3$ is $C_{3-8}$-cycloalkyl, wherein the $C_{3-8}$-cycloalkyl is optionally substituted with one or two $R^7$, wherein $R^4$ is hydrogen, wherein $R^7$ is $C_{3-8}$-cycloalkyl-($C_{1-4}$-alkyl)-, heterocycloalkyl, heterocycloalkyl-($C_{1-4}$-alkyl)-, $-NR^9R^{10}$, $-NHC(O)R^{11}$, $-NHC(O)NHR^{11}$, $-NHC(O)OR^{11}$, or $-NHSO_2R^{11}$, wherein the $R^7$ cycloalkyl, heterocycloalkyl, aryl, and heteroaryl, alone or as part of another moiety, are optionally substituted with one or more $R^{12}$.

In an alternative embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is heterocycloalkyl, wherein the heterocycloalkyl is optionally substituted with one or two $R^7$, wherein $R^4$ is hydrogen, wherein $R^7$ is $C_{1-6}$-alkyl, $C_{3-8}$-cycloalkyl, $C_{3-8}$-cycloalkyl-($C_{1-4}$-alkyl)-, heterocycloalkyl, heterocycloalkyl-($C_{1-4}$-alkyl)-, heteroaryl, $-C(O)R^8$, $-SO_2R^8$, $-NHC(O)R^{11}$, or $-C(O)NHR^{11}$, wherein the $R^7$ cycloalkyl, heterocycloalkyl, and heteroaryl, alone or as part of another moiety, are optionally substituted with one or more $R^{12}$.

In another embodiment, the present invention provides compounds of formula (I), wherein $R^{1a}$, $R^{1b}$, and $R^{1c}$ are hydrogen, X is N, Y is $NR^3R^4$, wherein $R^3$ is heterocycloalkyl, wherein the heterocycloalkyl is optionally substituted with one or two $R^7$, wherein $R^4$ is hydrogen, wherein $R^7$ is $C_{1-6}$-alkyl, $C_{3-8}$-cycloalkyl, $C_{3-8}$-cycloalkyl-($C_{1-4}$-alkyl)-, heterocycloalkyl, heterocycloalkyl-($C_{1-4}$-alkyl)-, heteroaryl, $-C(O)R^8$, $-SO_2R^8$, $-NHC(O)R^{11}$, or $-C(O)NHR^{11}$, wherein the $R^7$ cycloalkyl, heterocycloalkyl, and heteroaryl, alone or as part of another moiety, are optionally substituted with one or more $R^{12}$.

In an alternative embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is $C_{3-8}$-cycloalkyl-($C_{1-8}$-alkyl)-, wherein the $R^3$—($C_{1-8}$-alkyl)- is unsubstituted, wherein the $R^3$ $C_{3-8}$-cycloalkyl is optionally substituted with one or two $R^7$, and wherein $R^4$ is hydrogen.

In another embodiment, the present invention provides compounds of formula (I) wherein $R^{1a}$, $R^{1b}$, and $R^{1c}$ are hydrogen, X is N, Y is $NR^3R^4$, wherein $R^3$ is $C_{3-8}$-cycloalkyl-($C_{1-8}$-alkyl)-, wherein the $R^3$—($C_{1-8}$-alkyl)- is unsubstituted, wherein the $R^3$ $C_{3-8}$-cycloalkyl is optionally substituted with one or two $R^7$, and wherein $R^4$ is hydrogen.

In an alternative embodiment, the present invention provides compounds of formula (I) wherein $R^{1a}$, $R^{1b}$ and $R^{1c}$ are hydrogen, X is $CR^2$, $R^2$ is hydrogen, Y is $NR^3R^4$, wherein $R^3$ is heterocycloalkyl-($C_{1-8}$-alkyl), wherein the $R^3$—($C_{1-8}$-alkyl)- is unsubstituted, wherein the $R^3$ heterocycloalkyl is optionally substituted with one or two $R^7$, and wherein $R^4$ is hydrogen.

In another embodiment, the present invention provides compounds of formula (I) wherein $R^{1a}$, $R^{1b}$, and $R^{1c}$ are hydrogen, X is N, Y is $NR^3R^4$, wherein $R^3$ is heterocycloalkyl-($C_{1-8}$-alkyl)-, wherein the $R^3$—($C_{1-8}$-alkyl)- is unsubstituted, wherein the $R^3$ heterocycloalkyl is optionally substituted with one or two $R^7$, and wherein $R^4$ is hydrogen.

In an alternative embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is aryl-($C_{1-8}$-alkyl)-, wherein the $R^3$—($C_{1-8}$-alkyl)- is unsubstituted, wherein the $R^3$ aryl is optionally substituted with one or two $R^7$, and wherein $R^4$ is hydrogen.

In another embodiment, the present invention provides compounds of formula (I) wherein $R^{1a}$, $R^{1b}$, and $R^{1c}$ are hydrogen, X is N, Y is $NR^3R^4$, wherein $R^3$ is aryl-($C_{1-8}$-alkyl), wherein the $R^3$—($C_{1-8}$-alkyl)- is unsubstituted, wherein the $R^3$ aryl is optionally substituted with one or two $R^7$, and wherein $R^4$ is hydrogen.

In an alternative embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ is heteroaryl-($C_{1-8}$-alkyl)-, wherein the $R^3$—($C_{1-8}$-alkyl)- is unsubstituted, wherein the $R^3$ heteroaryl is optionally substituted with one or two $R^7$, and wherein $R^4$ is hydrogen.

In another embodiment, the present invention provides compounds of formula (I) wherein $R^{1a}$, $R^{1b}$ and $R^{1c}$ are hydrogen, X is N, Y is $NR^3R^4$, wherein $R^3$ is heteroaryl-($C_{1-8}$-alkyl)-, wherein the $R^3$—($C_{1-8}$-alkyl)- is unsubstituted, wherein the $R^3$ heteroaryl is optionally substituted with one or two $R^7$, and wherein $R^4$ is hydrogen.

In an alternative embodiment, the present invention provides compounds of formula (I) wherein $R^{1a}$, $R^{1b}$, and $R^{1c}$ are hydrogen, X is $CR^2$, $R^2$ is hydrogen, Y is $NR^3R^4$, wherein $R^3$ and $R^4$ are joined together to form a 4-7 membered heterocycloalkyl, wherein the heterocycloalkyl is optionally substituted with one or two $R^7$.

In another embodiment, the present invention provides compounds of formula (I) wherein $R^{1a}$, $R^{1b}$, and $R^{1c}$ are hydrogen, X is N, Y is $NR^3R^4$, wherein $R^3$ and $R^4$ are joined together to form a 4-7 membered heterocycloalkyl, wherein the heterocycloalkyl is optionally substituted with one or two with one or two $R^7$.

Another aspect of the invention provides compounds of formula (II), wherein $R^{1a}$, $R^{1b}$, $R^{1c}$, $R^3$ and $R^4$ are as defined generally and in subsets above.

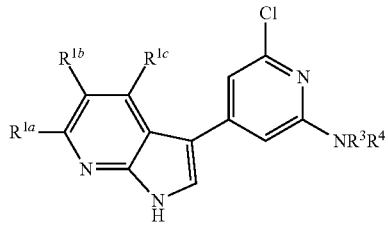

formula (II)

Specific embodiments contemplated as part of the invention include, but are not limited to, compounds of formula (I), for example:

6-chloro-N-cyclohexyl-4-(1H-pyrrolo[2,3-b]pyridin-3-yl)pyridin-2-amine;
N-benzyl-6-chloro-4-(1H-pyrrolo[2,3-b]pyridin-3-yl)pyridin-2-amine;
N-allyl-6-chloro-4-(1H-pyrrolo[2,3-b]pyridin-3-yl)pyridin-2-amine;
3-(2-chloro-6-piperidin-1-ylpyridin-4-yl)-1H-pyrrolo[2,3-b]pyridine;
N-benzyl-6-chloro-N-methyl-4-(1H-pyrrolo[2,3-b]pyridin-3-yl)pyridin-2-amine;
3-[2-chloro-6-(3,3-difluoroazetidin-1-yl)pyridin-4-yl]-1H-pyrrolo[2,3-b]pyridine;
3-[2-chloro-6-(2,3-dimethylphenyl)pyridin-4-yl]-1H-pyrrolo[2,3-b]pyridine;
6-chloro-4-(1H-pyrrolo[2,3-b]pyridin-3-yl)-N-tetrahydro-2H-pyran-4-ylpyridin-2-amine;
2-{[6-chloro-4-(1H-pyrrolo[2,3-b]pyridin-3-yl)pyridin-2-yl]amino}cyclohexanol;
6-chloro-N-(2-methoxyethyl)-4-(1H-pyrrolo[2,3-b]pyridin-3-yl)pyridin-2-amine;
2-{[6-chloro-4-(1H-pyrrolo[2,3-b]pyridin-3-yl)pyridin-2-yl]amino}ethanol;
6-chloro-N,N-bis(2-methoxyethyl)-4-(1H-pyrrolo[2,3-b]pyridin-3-yl)pyridin-2-amine;
6-chloro-4-(1H-pyrrolo[2,3-b]pyridin-3-yl)-N-(tetrahydrofuran-2-ylmethyl)pyridin-2-amine;
Trans 4-{[6-chloro-4-(1H-pyrrolo[2,3-b]pyridin-2-yl]amino}cyclohexanol;
N-[6-chloro-4-(1H-pyrrolo[2,3-b]pyridin-3-yl)pyridin-2-yl]cyclohexane-1,4-diamine;
6-chloro-N-(2-methoxycyclohexyl)-4-(1H-pyrrolo[2,3-b]pyridin-3-yl)pyridin-2-amine;
N-[6-chloro-4-(1H-pyrrolo[2,3-b]pyridin-3-yl)pyridin-2-yl]cyclohexane-1,2-diamine;
1-{[6-chloro-4-(1H-pyrrolo[2,3-b]pyridin-3-yl)pyridin-2-yl]amino}-2-methylpropan-2-ol;
4-{[6-chloro-4-(1H-pyrrolo[2,3-b]pyridin-3-yl)pyridin-2-yl]amino}butan-1-ol;
5-{[6-chloro-4-(1H-pyrrolo[2,3-b]pyridin-3-yl)pyridin-2-yl]amino}-2,2-dimethylpentan-1-ol;
N-(4-{[6-chloro-4-(1H-pyrrolo[2,3-b]pyridin-3-yl)pyridin-2-yl]amino}cyclohexyl)methanesulfonamide;
N-(4-{[6-chloro-4-(1H-pyrrolo[2,3-b]pyridin-3-yl)pyridin-2-yl]amino}cyclohexyl)acetamide;
N-[6-chloro-4-(1H-pyrrolo[2,3-b]pyridin-3-yl)pyridin-2-yl]cyclohexane-1,3-diamine;
N-(3-{[6-chloro-4-(1H-pyrrolo[2,3-b]pyridin-3-yl)pyridin-2-yl]amino}cyclohexyl)methanesulfonamide;
6-chloro-4-(1H-pyrrolo[2,3-b]pyridin-3-yl)-N-(tetrahydro-2H-pyran-4-ylmethyl)pyridin-2-amine;
3-{[6-chloro-4-(1H-pyrrolo[2,3-b]pyridin-3-yl)pyridin-2-yl]amino}cyclohexanol;
6-chloro-N-(pyridin-3-ylmethyl)-4-(1H-pyrrolo[2,3-b]pyridin-3-yl)pyridin-2-amine;
6-chloro-4-(1H-pyrrolo[2,3-b]pyridin-3-yl)-N-(tetrahydro-2H-pyran-3-ylmethyl)pyridin-2-amine;
6-chloro-N-(pyrrolidin-3-ylmethyl)-4-(1H-pyrrolo[2,3-b]pyridin-3-yl)pyridin-2-amine;
6-chloro-N-(2,3-dimethylbenzyl)-4-(1H-pyrrolo[2,3-b]pyridin-3-yl)pyridin-2-amine;
6-chloro-N-(pyridin-4-ylmethyl)-4-(1H-pyrrolo[2,3-b]pyridin-3-yl)pyridin-2-amine;
6-chloro-4-(1H-pyrrolo[2,3-b]pyridin-3-yl)-N-(tetrahydro-2H-pyran-2-ylmethyl)pyridin-2-amine;
6-chloro-N-piperidin-4-yl-4-(1H-pyrrolo[2,3-b]pyridin-3-yl)pyridin-2-amine;
6-chloro-N-(4-methoxycyclohexyl)-4-(1H-pyrrolo[2,3-b]pyridin-3-yl)pyridin-2-amine;
N-(3-{[6-chloro-4-(1H-pyrrolo[2,3-b]pyridin-3-yl)pyridin-2-yl]amino}cyclohexyl)acetamide;
6-chloro-N-(4-chloro-2-fluorobenzyl)-4-(1H-pyrrolo[2,3-b]pyridin-3-yl)pyridin-2-amine;
6-chloro-N-{[2-(pyridin-3-yloxy)pyridin-3-yl]methyl}-4-(1H-pyrrolo[2,3-b]pyridin-3-yl)pyridin-2-amine;
6-chloro-N-(piperidin-3-ylmethyl)-4-(1H-pyrrolo[2,3-b]pyridin-3-yl)pyridin-2-amine;
1-{[6-chloro-4-(1H-pyrrolo[2,3-b]pyridin-3-yl)pyridin-2-yl]amino}propan-2-ol;
2-(2-{[6-chloro-4-(1H-pyrrolo[2,3-b]pyridin-3-yl)pyridin-2-yl]amino}ethoxy)ethanol;
3-{[6-chloro-4-(1H-pyrrolo[2,3-b]pyridin-3-yl)pyridin-2-yl]amino}-2,2-dimethylpropan-1-ol;
Trans-N-[4-chloro-6-(1H-pyrrolo[2,3-b]pyridin-3-yl)pyrimidin-2-yl]cyclohexane-1,4-diamine;
N-[4-chloro-6-(1H-pyrrolo[2,3-b]pyridin-3-yl)pyrimidin-2-yl]cyclohexane-1,3-diamine;
Trans-4-{[4-chloro-6-(1H-pyrrolo[2,3-b]pyridin-3-yl)pyrimidin-2-yl]amino}cyclohexanol;
4-chloro-6-(1H-pyrrolo[2,3-b]pyridin-3-yl)-N-tetrahydro-2H-pyran-4-ylpyrimidin-2-amine;
N-benzyl-4-chloro-6-(1H-pyrrolo[2,3-b]pyridin-3-yl)pyrimidin-2-amine;
2-{[4-chloro-6-(1H-pyrrolo[2,3-b]pyridin-3-yl)pyrimidin-2-yl]amino}-3-phenylpropan-1-ol;
(S)-4-chloro-N-(1-methoxy-3-phenylpropan-2-yl)-6-(1H-pyrrolo[2,3-b]pyridine-3-yl)pyrimidin-2-amine;
4-chloro-N-cyclohexyl-6-(1H-pyrrolo[2,3-b]pyridin-3-yl)pyrimidin-2-amine;
6-chloro-N-[1-(methylsulfonyl)piperidin-4-yl]-4-(1H-pyrrolo[2,3-b]pyridin-3-yl)pyridin-2-amine;
N-(4-{[6-chloro-4-(1H-pyrrolo[2,3-b]pyridin-3-yl)pyridin-2-yl]amino}cyclohexyl)benzenesulfonamide;
N-(4-{[6-chloro-4-(1H-pyrrolo[2,3-b]pyridin-3-yl)pyridin-2-yl]amino}cyclohexyl)-1-phenylmethanesulfonamide;
N-(4-{[6-chloro-4-(1H-pyrrolo[2,3-b]pyridin-3-yl)pyridin-2-yl]amino}cyclohexyl)pyridine-3-sulfonamide;
N-(4-{[6-chloro-4-(1H-pyrrolo[2,3-b]pyridin-3-yl)pyridin-2-yl]amino}cyclohexyl)propane-1-sulfonamide;
6-chloro-N-[2-(morpholin-4-yl)ethyl]-4-(1H-pyrrolo[2,3-b]pyridin-3-yl)pyridin-2-amine;
3-(2-{[6-chloro-4-(1H-pyrrolo[2,3-b]pyridin-3-yl)pyridin-2-yl]amino}ethyl)phenol;
N-[6-chloro-4-(1H-pyrrolo[2,3-b]pyridin-3-yl)pyridin-2-yl]-N'-(2-methylpropyl)cyclohexane-1,3-diamine;

N'-[6-chloro-4-(1H-pyrrolo[2,3-b]pyridin-3-yl)pyridin-2-yl]-N,N-dimethylcyclohexane-1,3-diamine;
1-(4-{[6-chloro-4-(1H-pyrrolo[2,3-b]pyridin-3-yl)pyridin-2-yl]amino}cyclohexyl)-3-cyclopentylurea;
N-(trans-4-{[6-chloro-4-(1H-pyrrolo[2,3-b]pyridin-3-yl)pyridin-2-yl]amino}cyclohexyl)cyclopropanesulfonamide;
1-(4-{[6-chloro-4-(1H-pyrrolo[2,3-b]pyridin-3-yl)pyridin-2-yl]amino}cyclohexyl)-3-propylurea;
N-(trans-4-{[6-chloro-4-(1H-pyrrolo[2,3-b]pyridin-3-yl)pyridin-2-yl]amino}cyclohexyl)cyclopropanecarboxamide;
N-(4-{[6-chloro-4-(1H-pyrrolo[2,3-b]pyridin-3-yl)pyridin-2-yl]amino}cyclohexyl)-2-methylpropanamide;
N-(4-{[6-chloro-4-(1H-pyrrolo[2,3-b]pyridin-3-yl)pyridin-2-yl]amino}cyclohexyl)benzamide;
1-(4-{[6-chloro-4-(1H-pyrrolo[2,3-b]pyridin-3-yl)pyridin-2-yl]amino}cyclohexyl)-3-phenylurea;
N-[6-chloro-4-(1H-pyrrolo[2,3-b]pyridin-3-yl)pyridin-2-yl]-N'-(pyridin-3-ylmethyl)cyclohexane-1,3-diamine;
N-[6-chloro-4-(1H-pyrrolo[2,3-b]pyridin-3-yl)pyridin-2-yl]-N'-cyclobutylcyclohexane-1,3-diamine;
N-(3-{[6-chloro-4-(1H-pyrrolo[2,3-b]pyridin-3-yl)pyridin-2-yl]amino}cyclohexyl)cyclopropanecarboxamide;
N-(3-{[6-chloro-4-(1H-pyrrolo[2,3-b]pyridin-3-yl)pyridin-2-yl]amino}cyclohexyl)-1-propylpiperidine-4-carboxamide;
N-(3-{[6-chloro-4-(1H-pyrrolo[2,3-b]pyridin-3-yl)pyridin-2-yl]amino}cyclohexyl)-1H-pyrazole-3-carboxamide;
N-[6-chloro-4-(1H-pyrrolo[2,3-b]pyridin-3-yl)pyridin-2-yl]-N'-(piperidin-3-ylmethyl)cyclohexane-1,3-diamine;
N-{2-[(3-{[6-chloro-4-(1H-pyrrolo[2,3-b]pyridin-3-yl)pyridin-2-yl]amino}cyclohexyl)amino]-2-oxoethyl}benzamide;
N-[6-chloro-4-(1H-pyrrolo[2,3-b]pyridin-3-yl)pyridin-2-yl]-2,2-dimethylpropane-1,3-diamine;
N-(3-{[6-chloro-4-(1H-pyrrolo[2,3-b]pyridin-3-yl)pyridin-2-yl]amino}-2,2-dimethylpropyl)methanesulfonamide;
N-(3-{[6-chloro-4-(1H-pyrrolo[2,3-b]pyridin-3-yl)pyridin-2-yl]amino}cyclohexyl)cyclopropanesulfonamide;
N-(3-{[6-chloro-4-(1H-pyrrolo[2,3-b]pyridin-3-yl)pyridin-2-yl]amino}cyclohexyl)propane-1-sulfonamide;
N-(3-{[6-chloro-4-(1H-pyrrolo[2,3-b]pyridin-3-yl)pyridin-2-yl]amino}cyclohexyl)-4-methylbenzenesulfonamide;
1-(3-{[6-chloro-4-(1H-pyrrolo[2,3-b]pyridin-3-yl)pyridin-2-yl]amino}cyclohexyl)-3-ethylurea;
1-(3-{[6-chloro-4-(1H-pyrrolo[2,3-b]pyridin-3-yl)pyridin-2-yl]amino}cyclohexyl)-3-cyclopentylurea;
N-(3-{[6-chloro-4-(1H-pyrrolo[2,3-b]pyridin-3-yl)pyridin-2-yl]amino}-2,2-dimethylpropyl)pyridine-3-sulfonamide;
N-(3-{[6-chloro-4-(1H-pyrrolo[2,3-b]pyridin-3-yl)pyridin-2-yl]amino}-2,2-dimethylpropyl)cyclopropanesulfonamide;
N-(3-{[6-chloro-4-(1H-pyrrolo[2,3-b]pyridin-3-yl)pyridin-2-yl]amino}cyclohexyl)thiophene-2-sulfonamide;
N-[6-chloro-4-(1H-pyrrolo[2,3-b]pyridin-3-yl)pyridin-2-yl]pentanamide;
N-[6-chloro-4-(1H-pyrrolo[2,3-b]pyridin-3-yl)pyridin-2-yl]cyclohexanecarboxamide;
N-[6-chloro-4-(1H-pyrrolo[2,3-b]pyridin-3-yl)pyridin-2-yl]benzamide;
N-[6-chloro-4-(1H-pyrrolo[2,3-b]pyridin-3-yl)pyridin-2-yl]ethane-1,2-diamine;
N-(2-{[6-chloro-4-(1H-pyrrolo[2,3-b]pyridin-3-yl)pyridin-2-yl]amino}ethyl)methanesulfonamide;
N-(2-{[6-chloro-4-(1H-pyrrolo[2,3-b]pyridin-3-yl)pyridin-2-yl]amino}ethyl)cyclopropanesulfonamide;
N-(2-{[6-chloro-4-(1H-pyrrolo[2,3-b]pyridin-3-yl)pyridin-2-yl]amino}ethyl)pyridine-3-sulfonamide;
6-chloro-4-(1H-pyrrolo[2,3-b]pyridin-3-yl)pyridin-2-amine;
6-chloro-N-cyclobutyl-4-(1H-pyrrolo[2,3-b]pyridin-3-yl)pyridin-2-amine;
trans-N'-[6-chloro-4-(1H-pyrrolo[2,3-b]pyridin-3-yl)pyridin-2-yl]-N,N-dimethylcyclohexane-1,4-diamine;
6-chloro-N-[(1-ethylpiperidin-3-yl)methyl]-4-(1H-pyrrolo[2,3-b]pyridin-3-yl)pyridin-2-amine;
6-chloro-N-[(1-cyclobutylpiperidin-3-yl)methyl]-4-(1H-pyrrolo[2,3-b]pyridin-3-yl)pyridin-2-amine;
6-chloro-N-{[1-(pyridin-3-ylmethyl)piperidin-3-yl]methyl}-4-(1H-pyrrolo[2,3-b]pyridin-3-yl)pyridin-2-amine;
6-chloro-N-{[1-(methylsulfonyl)piperidin-3-yl]methyl}-4-(1H-pyrrolo[2,3-b]pyridin-3-yl)pyridin-2-amine;
3-({[6-chloro-4-(1H-pyrrolo[2,3-b]pyridin-3-yl)pyridin-2-yl]amino}methyl)-N-ethylpiperidine-1-carboxamide;
1-(trans-4-{[6-chloro-4-(1H-pyrrolo[2,3-b]pyridin-3-yl)pyridin-2-yl]amino}cyclohexyl)-3-methylurea;
1-[3-({[6-chloro-4-(1H-pyrrolo[2,3-b]pyridin-3-yl)pyridin-2-yl]amino}methyl)piperidin-1-yl]ethanone;
6-chloro-N-{[1-(cyclopropylsulfonyl)piperidin-3-yl]methyl}-4-(1H-pyrrolo[2,3-b]pyridin-3-yl)pyridin-2-amine;
(3-{[6-chloro-4-(1H-pyrrolo[2,3-b]pyridin-3-yl)pyridin-2-yl]amino}piperidin-1-yl)(cyclopropyl)methanone;
N-[6-chloro-4-(1H-pyrrolo[2,3-b]pyridin-3-yl)pyridin-2-yl]-N'-(cyclopropylmethyl)cyclohexane-1,3-diamine;
6-chloro-N-(1-cyclobutylpiperidin-3-yl)-4-(1H-pyrrolo[2,3-b]pyridin-3-yl)pyridin-2-amine;
trans-N-[6-chloro-4-(1H-pyrrolo[2,3-b]pyridin-3-yl)pyridin-2-yl]-N'-cyclobutylcyclohexane-1,4-diamine;
(2S)—N-(trans-4-{[6-chloro-4-(1H-pyrrolo[2,3-b]pyridin-3-yl)pyridin-2-yl]amino}cyclohexyl)azetidine-2-carboxamide;
N-[6-chloro-4-(1H-pyrrolo[2,3-b]pyridin-3-yl)pyridin-2-yl]pyridine-3-carboxamide;
N-[6-chloro-4-(1H-pyrrolo[2,3-b]pyridin-3-yl)pyridin-2-yl]butanamide;
trans-N-[6-chloro-4-(1H-pyrrolo[2,3-b]pyridin-3-yl)pyridin-2-yl]-N'-(cyclopropylmethyl)cyclohexane-1,4-diamine;
N-[(trans)-2-{[6-chloro-4-(1H-pyrrolo[2,3-b]pyridin-3-yl)pyridin-2-yl]amino}cyclohexyl]methanesulfonamide;
N-[6-chloro-4-(1H-pyrrolo[2,3-b]pyridin-3-yl)pyridin-2-yl]-2,6-difluorobenzamide;
N-[6-chloro-4-(1H-pyrrolo[2,3-b]pyridin-3-yl)pyridin-2-yl]piperidine-4-carboxamide;
N-(3-{[6-chloro-4-(1H-pyrrolo[2,3-b]pyridin-3-yl)pyridin-2-yl]amino}-2,2-dimethylpropyl)acetamide;
N-(trans-4-{[6-chloro-4-(1H-pyrrolo[2,3-b]pyridin-3-yl)pyridin-2-yl]amino}cyclohexyl)-$N^2,N^2$-dimethylglycinamide;
(2S)—N-(trans-4-{[6-chloro-4-(1H-pyrrolo[2,3-b]pyridin-3-yl)pyridin-2-yl]amino}cyclohexyl)-4-oxoazetidine-2-carboxamide;
N-(trans-4-{[6-chloro-4-(1H-pyrrolo[2,3-b]pyridin-3-yl)pyridin-2-yl]amino}cyclohexyl)-$N^2$-methyl-L-alaninamide;
azetidin-2-yl(4-{[6-chloro-4-(1H-pyrrolo[2,3-b]pyridin-3-yl)pyridin-2-yl]amino}piperidin-1-yl)methanone;
N-(3-{[6-chloro-4-(1H-pyrrolo[2,3-b]pyridin-3-yl)pyridin-2-yl]amino}cyclohexyl)-$N^2,N^2$-dimethylglycinamide;
N-(3-{[6-chloro-4-(1H-pyrrolo[2,3-b]pyridin-3-yl)pyridin-2-yl]amino}cyclohexyl)-1-methyl-L-prolinamide;
N-[(trans)-2-{[6-chloro-4-(1H-pyrrolo[2,3-b]pyridin-3-yl)pyridin-2-yl]amino}cyclohexyl]azetidine-2-carboxamide;

N'-[6-chloro-4-(1H-pyrrolo[2,3-b]pyridin-3-yl)pyridin-2-yl]-N,N,2,2-tetramethylpropane-1,3-diamine;
N-[6-chloro-4-(1H-pyrrolo[2,3-b]pyridin-3-yl)pyridin-2-yl]methanesulfonamide;
N-[6-chloro-4-(1H-pyrrolo[2,3-b]pyridin-3-yl)pyridin-2-yl]benzenesulfonamide;
N-(3-{[6-chloro-4-(1H-pyrrolo[2,3-b]pyridin-2-yl]amino}-2,2-dimethylpropyl)cyclopropanecarboxamide;
N-(trans-4-{[6-chloro-4-(1H-pyrrolo[2,3-b]pyridin-3-yl)pyridin-2-yl]amino}cyclohexyl)-1-methylpyrrolidine-3-carboxamide;
(4-{[6-chloro-4-(1H-pyrrolo[2,3-b]pyridin-3-yl)pyridin-2-yl]amino}piperidin-1-yl)(cyclopropyl)methanone;
N-(trans-4-{[6-chloro-4-(1H-pyrrolo[2,3-b]pyridin-3-yl)pyridin-2-yl]amino}cyclohexyl)-$N^2$,$N^2$-dimethyl-L-alaninamide;
6-chloro-N-(1-cyclobutylpiperidin-4-yl)-4-(1H-pyrrolo[2,3-b]pyridin-3-yl)pyridin-2-amine;
N-(3-{[6-chloro-4-(1H-pyrrolo[2,3-b]pyridin-3-yl)pyridin-2-yl]amino}cyclohexyl)piperidine-2-carboxamide;
N-(3-{[6-chloro-4-(1H-pyrrolo[2,3-b]pyridin-3-yl)pyridin-2-yl]amino}cyclohexyl)-2-(pyrrolidin-1-yl)acetamide;
(cis)-N-[6-chloro-4-(1H-pyrrolo[2,3-b]pyridin-3-yl)pyridin-2-yl]cyclohexane-1,2-diamine;
N-[(cis)-2-{[6-chloro-4-(1H-pyrrolo[2,3-b]pyridin-3-yl)pyridin-2-yl]amino}cyclohexyl]methanesulfonamide;
N-(trans-4-{[6-chloro-4-(1H-pyrrolo[2,3-b]pyridin-3-yl)pyridin-2-yl]amino}cyclohexyl)cyclobutanecarboxamide;
N-(trans-4-{[6-chloro-4-(1H-pyrrolo[2,3-b]pyridin-3-yl)pyridin-2-yl]amino}cyclohexyl)-1-ethylazetidine-2-carboxamide;
1-amino-N-(3-{[6-chloro-4-(1H-pyrrolo[2,3-b]pyridin-3-yl)pyridin-2-yl]amino}cyclohexyl)cyclobutanecarboxamide;
N-(trans-4-{[6-chloro-4-(1H-pyrrolo[2,3-b]pyridin-3-yl)pyridin-2-yl]amino}cyclohexyl)-1-cyclopentylazetidine-2-carboxamide;
N-(trans-4-{[6-chloro-4-(1H-pyrrolo[2,3-b]pyridin-3-yl)pyridin-2-yl]amino}cyclohexyl)-$N^2$-cyclopentylglycinamide;
6-chloro-N-[1-(methylsulfonyl)piperidin-3-yl]-4-(1H-pyrrolo[2,3-b]pyridin-3-yl)pyridin-2-amine;
N-(3-{[6-chloro-4-(1H-pyrrolo[2,3-b]pyridin-3-yl)pyridin-2-yl]amino}cyclohexyl)-5-oxoprolinamide;
(cis)-N'-[6-chloro-4-(1H-pyrrolo[2,3-b]pyridin-2-yl]-N,N-dimethylcyclohexane-1,2-diamine;
N-(trans-4-{[6-chloro-4-(1H-pyrrolo[2,3-b]pyridin-3-yl)pyridin-2-yl]amino}cyclohexyl)-2-(morpholin-4-yl)acetamide;
N-(trans-4-{[6-chloro-4-(1H-pyrrolo[2,3-b]pyridin-3-yl)pyridin-2-yl]amino}cyclohexyl)-2-[4-(pyridin-2-yl)piperazin-1-yl]acetamide;
N-{4-[(4-aminocyclohexyl)methyl]cyclohexyl}-6-chloro-4-(1H-pyrrolo[2,3-b]pyridin-3-yl)pyridin-2-amine;
N-(trans-4-{[6-chloro-4-(1H-pyrrolo[2,3-b]pyridin-3-yl)pyridin-2-yl]amino}cyclohexyl)-2,6-dioxopiperidine-4-carboxamide;
2-amino-N-(3-{[6-chloro-4-(1H-pyrrolo[2,3-b]pyridin-3-yl)pyridin-2-yl]amino}cyclohexyl)ethanesulfonamide;
6-chloro-N-[(1-methylpiperidin-3-yl)methyl]-4-(1H-pyrrolo[2,3-b]pyridin-3-yl)pyridin-2-amine;
1-(3-{[6-chloro-4-(1H-pyrrolo[2,3-b]pyridin-3-yl)pyridin-2-yl]amino}piperidin-1-yl)ethanone;
trans-N-[6-chloro-4-(1H-pyrrolo[2,3-b]pyridin-3-yl)pyridin-2-yl]-N'-(1-methylpiperidin-4-yl)cyclohexane-1,4-diamine;
trans-4-{[6-chloro-4-(5-methoxy-1H-pyrrolo[2,3-b]pyridin-3-yl)pyridin-2-yl]amino}cyclohexanol;
N-[6-chloro-4-(1H-pyrrolo[2,3-b]pyridin-3-yl)pyridin-2-yl]-2-(morpholin-4-yl)acetamide;
N-(trans-4-{[6-chloro-4-(1H-pyrrolo[2,3-b]pyridin-3-yl)pyridin-2-yl]amino}cyclohexyl)pyrrolidine-3-sulfonamide;
N-(trans-4-{[6-chloro-4-(1H-pyrrolo[2,3-b]pyridin-3-yl)pyridin-2-yl]amino}cyclohexyl)-$N^2$-(trans-4-hydroxycyclohexyl)glycinamide;
N-(trans-4-{[6-chloro-4-(1H-pyrrolo[2,3-b]pyridin-3-yl)pyridin-2-yl]amino}cyclohexyl)-$N^2$-[2-(morpholin-4-yl)ethyl]glycinamide;
N-(3-{[6-chloro-4-(1H-pyrrolo[2,3-b]pyridin-3-yl)pyridin-2-yl]amino}cyclohexyl)-2-(dimethylamino)ethanesulfonamide;
6-chloro-N-(4-{[4-(dimethylamino)cyclohexyl]methyl}cyclohexyl)-4-(1H-pyrrolo[2,3-b]pyridin-3-yl)pyridin-2-amine;
6-chloro-N-(4-{[4-(cyclohexylamino)cyclohexyl]methyl}cyclohexyl)-4-(1H-pyrrolo[2,3-b]pyridin-3-yl)pyridin-2-amine;
trans-N-[6-chloro-4-(1H-pyrrolo[2,3-b]pyridin-2-yl]-N'-(1-cyclohexylpiperidin-4-yl)cyclohexane-1,4-diamine;
trans-N-(4-aminocyclohexyl)-N'-[6-chloro-4-(1H-pyrrolo[2,3-b]pyridin-3-yl)pyridin-2-yl]cyclohexane-1,4-diamine;
6-chloro-N-[4-(piperidin-4-yl)cyclohexyl]-4-(1H-pyrrolo[2,3-b]pyridin-3-yl)pyridin-2-amine;
N-(trans-4-{[6-chloro-4-(1H-pyrrolo[2,3-b]pyridin-3-yl)pyridin-2-yl]amino}cyclohexyl)azetidine-3-carboxamide;
N-{4-[(trans-4-{[6-chloro-4-(1H-pyrrolo[2,3-b]pyridin-3-yl)pyridin-2-yl]amino}cyclohexyl)amino]cyclohexyl}acetamide;
N-{4-[(trans-4-{[6-chloro-4-(1H-pyrrolo[2,3-b]pyridin-3-yl)pyridin-2-yl]amino}cyclohexyl)amino]cyclohexyl}cyclopropanecarboxamide;
1-[4-(4-{[6-chloro-4-(1H-pyrrolo[2,3-b]pyridin-3-yl)pyridin-2-yl]amino}cyclohexyl)piperidin-1-yl]ethanone;
N-{2-[(3-{[6-chloro-4-(1H-pyrrolo[2,3-b]pyridin-3-yl)pyridin-2-yl]amino}cyclohexyl)sulfamoyl]ethyl}acetamide;
N-{2-[(3-{[6-chloro-4-(1H-pyrrolo[2,3-b]pyridin-3-yl)pyridin-2-yl]amino}cyclohexyl)sulfamoyl]ethyl}cyclopropanecarboxamide;
N-(trans-4-{[6-chloro-4-(1H-pyrrolo[2,3-b]pyridin-3-yl)pyridin-2-yl]amino}cyclohexyl)-1-(4-fluorobenzyl)azetidine-3-carboxamide;
N-(trans-4-{[6-chloro-4-(1H-pyrrolo[2,3-b]pyridin-3-yl)pyridin-2-yl]amino}cyclohexyl)-1-(methylsulfonyl)azetidine-3-carboxamide;
6-chloro-4-(4-chloro-1H-pyrrolo[2,3-b]pyridin-3-yl)-N-cyclohexylpyridin-2-amine;
N-{2-[(3-{[6-chloro-4-(1H-pyrrolo[2,3-b]pyridin-3-yl)pyridin-2-yl]amino}cyclohexyl)sulfamoyl]ethyl}benzamide;
N-(3-{[6-chloro-4-(1H-pyrrolo[2,3-b]pyridin-3-yl)pyridin-2-yl]amino}cyclohexyl)-2-(cyclobutylamino)ethanesulfonamide;
6-chloro-N-cyclohexyl-4-[5-(1H-pyrazol-4-yl)-1H-pyrrolo[2,3-b]pyridin-3-yl]pyridin-2-amine;
N-{2-[(3-{[6-chloro-4-(1H-pyrrolo[2,3-b]pyridin-3-yl)pyridin-2-yl]amino}cyclohexyl)sulfamoyl]ethyl}pyrazine-2-carboxamide;
4-(5-bromo-1H-pyrrolo[2,3-b]pyridin-3-yl)-6-chloro-N-cyclohexylpyridin-2-amine;
N-{4-[(4-{[6-chloro-4-(1H-pyrrolo[2,3-b]pyridin-3-yl)pyridin-2-yl]amino}cyclohexyl)methyl]cyclohexyl}acetamide;

{4-[(4-{[6-chloro-4-(1H-pyrrolo[2,3-b]pyridin-3-yl)pyridin-2-yl]amino}cyclohexyl)amino]piperidin-1-yl}(cyclopropyl)methanone;
6-chloro-N-cyclohexyl-4-[5-(1-methyl-1H-pyrazol-4-yl)-1H-pyrrolo[2,3-b]pyridin-3-yl]pyridin-2-amine;
{4-[(4-{[6-chloro-4-(1H-pyrrolo[2,3-b]pyridin-3-yl)pyridin-2-yl]amino}cyclohexyl)amino]piperidin-1-yl}(phenyl)methanone;
6-chloro-N-cyclohexyl-4-(5-methoxy-1H-pyrrolo[2,3-b]pyridin-3-yl)pyridin-2-amine;
2-amino-N-(trans-4-{[6-chloro-4-(1H-pyrrolo[2,3-b]pyridin-3-yl)pyridin-2-yl]amino}cyclohexyl)ethanesulfonamide;
3-[2-chloro-6-(cyclohexylamino)pyridin-4-yl]-1H-pyrrolo[2,3-b]pyridin-5-ol;
6-chloro-N-[4-(piperidin-3-yl)cyclohexyl]-4-(1H-pyrrolo[2,3-b]pyridin-3-yl)pyridin-2-amine;
6-chloro-N-[4-(1-cyclobutylpiperidin-4-yl)cyclohexyl]-4-(1H-pyrrolo[2,3-b]pyridin-3-yl)pyridin-2-amine;
6-chloro-N-{4-[1-(methylsulfonyl)piperidin-4-yl]cyclohexyl}-4-(1H-pyrrolo[2,3-b]pyridin-3-yl)pyridin-2-amine;
6-chloro-N-[4-(1-methylpiperidin-4-yl)cyclohexyl]-4-(1H-pyrrolo[2,3-b]pyridin-3-yl)pyridin-2-amine;
6-chloro-N-methyl-N-[4-(1-methylpiperidin-4-yl)cyclohexyl]-4-(1H-pyrrolo[2,3-b]pyridin-3-yl)pyridin-2-amine;
6-chloro-N-{4-[1-(methylsulfonyl)piperidin-3-yl]cyclohexyl}-4-(1H-pyrrolo[2,3-b]pyridin-3-yl)pyridin-2-amine;
6-chloro-N-cyclohexyl-4-(5-{1-[2-(morpholin-4-yl)ethyl]-1H-pyrazol-4-yl}-1H-pyrrolo[2,3-b]pyridin-3-yl)pyridin-2-amine;
[3-(4-{[6-chloro-4-(1H-pyrrolo[2,3-b]pyridin-3-yl)pyridin-2-yl]amino}cyclohexyl)piperidin-1-yl](cyclopropyl)methanone;
6-chloro-N-[4-(1-cyclobutylpiperidin-3-yl)cyclohexyl]-4-(1H-pyrrolo[2,3-b]pyridin-3-yl)pyridin-2-amine;
6-chloro-N-[4-(pyrrolidin-3-yl)cyclohexyl]-4-(1H-pyrrolo[2,3-b]pyridin-3-yl)pyridin-2-amine;
N-[6-chloro-4-(1H-pyrrolo[2,3-b]pyridin-3-yl)pyridin-2-yl]-1'-methyl-1,4'-bipiperidin-4-amine;
4-(4-{[6-chloro-4-(1H-pyrrolo[2,3-b]pyridin-3-yl)pyridin-2-yl]amino}cyclohexyl)piperazin-2-one;
N-{2-[(trans-4-{[6-chloro-4-(1H-pyrrolo[2,3-b]pyridin-3-yl)pyridin-2-yl]amino}cyclohexyl)sulfamoyl]ethyl}benzamide;
N-(trans-4-{[6-chloro-4-(1H-pyrrolo[2,3-b]pyridin-3-yl)pyridin-2-yl]amino}cyclohexyl)-2-[(methylsulfonyl)amino]ethanesulfonamide;
6-chloro-N-cyclohexyl-4-{5-[2-(morpholin-4-yl)ethoxy]-1H-pyrrolo[2,3-b]pyridin-3-yl}pyridin-2-amine;
6-chloro-N-cyclohexyl-4-{5-[(1-methyl-1H-imidazol-5-yl)methoxy]-1H-pyrrolo[2,3-b]pyridin-3-yl}pyridin-2-amine;
6-chloro-N-[4-(1-methylpyrrolidin-3-yl)cyclohexyl]-4-(1H-pyrrolo[2,3-b]pyridin-3-yl)pyridin-2-amine;
6-chloro-N-{4-[1-(4-fluorobenzyl)pyrrolidin-3-yl]cyclohexyl}-4-(1H-pyrrolo[2,3-b]pyridin-3-yl)pyridin-2-amine;
6-chloro-N-{4-[1-(methylsulfonyl)pyrrolidin-3-yl]cyclohexyl}-4-(1H-pyrrolo[2,3-b]pyridin-3-yl)pyridin-2-amine;
6-chloro-N-{1-[4-(cyclobutylamino)cyclohexyl]piperidin-4-yl}-4-(1H-pyrrolo[2,3-b]pyridin-3-yl)pyridin-2-amine;
3-[2-chloro-6-(cyclohexylamino)pyridin-4-yl]-1H-pyrrolo[2,3-b]pyridine-5-carbonitrile;
N-(trans-4-{[6-chloro-4-(1H-pyrrolo[2,3-b]pyridin-3-yl)pyridin-2-yl]amino}cyclohexyl)-2,4-difluorobenzamide;
N-(trans-4-{[6-chloro-4-(1H-pyrrolo[2,3-b]pyridin-3-yl)pyridin-2-yl]amino}cyclohexyl)-4-(trifluoromethoxy)benzamide;
6-chloro-N-cyclohexyl-4-(5-methyl-1H-pyrrolo[2,3-b]pyridin-3-yl)pyridin-2-amine;
6-chloro-N-phenyl-4-(1H-pyrrolo[2,3-b]pyridin-3-yl)pyridin-2-amine;
6-chloro-N-{2-methoxy-4-[4-(4-methylpiperazin-1-yl)piperidin-1-yl]phenyl}-4-(1H-pyrrolo[2,3-b]pyridin-3-yl)pyridin-2-amine;
1-(4-chlorobenzyl)-N-(trans-4-{[6-chloro-4-(1H-pyrrolo[2,3-b]pyridin-3-yl)pyridin-2-yl]amino}cyclohexyl)azetidine-3-carboxamide;
N-(trans-4-{[6-chloro-4-(1H-pyrrolo[2,3-b]pyridin-3-yl)pyridin-2-yl]amino}cyclohexyl)-2-[(prop-2-en-1-ylcarbamoyl)amino]ethanesulfonamide;
N-(trans-4-{[6-chloro-4-(1H-pyrrolo[2,3-b]pyridin-3-yl)pyridin-2-yl]amino}cyclohexyl)-1-(pyridin-3-ylmethyl)azetidine-3-carboxamide;
N-(trans-4-{[6-chloro-4-(1H-pyrrolo[2,3-b]pyridin-3-yl)pyridin-2-yl]amino}cyclohexyl)-1-(2,4-difluorobenzyl)azetidine-3-carboxamide;
N-(trans-4-{[6-chloro-4-(1H-pyrrolo[2,3-b]pyridin-3-yl)pyridin-2-yl]amino}cyclohexyl)-1-[(1-methyl-1H-pyrazol-3-yl)methyl]azetidine-3-carboxamide;
2-(4-{3-[2-chloro-6-(cyclohexylamino)pyridin-4-yl]-1H-pyrrolo[2,3-b]pyridin-5-yl}-1H-pyrazol-1-yl)ethanol;
trans-N-[6-chloro-4-(5-methoxy-1H-pyrrolo[2,3-b]pyridin-3-yl)pyridin-2-yl]cyclohexane-1,4-diamine;
6-chloro-N-cyclohexyl-4-[5-(pyridin-3-yl)-1H-pyrrolo[2,3-b]pyridin-3-yl]pyridin-2-amine;
6-chloro-N-cyclohexyl-4-[5-(thiophen-3-yl)-1H-pyrrolo[2,3-b]pyridin-3-yl]pyridin-2-amine;
N-(trans-4-{[6-chloro-4-(5-methoxy-1H-pyrrolo[2,3-b]pyridin-3-yl)pyridin-2-yl]amino}cyclohexyl)cyclopropanecarboxamide;
1-benzyl-N-(trans-4-{[6-chloro-4-(5-methoxy-1H-pyrrolo[2,3-b]pyridin-3-yl)pyridin-2-yl]amino}cyclohexyl)azetidine-3-carboxamide;
N-(trans-4-{[6-chloro-4-(5-methoxy-1H-pyrrolo[2,3-b]pyridin-3-yl)pyridin-2-yl]amino}cyclohexyl)cyclopropanesulfonamide;
N-(trans-4-{[6-chloro-4-(5-methoxy-1H-pyrrolo[2,3-b]pyridin-3-yl)pyridin-2-yl]amino}cyclohexyl)-1-ethylpyrrolidine-3-carboxamide;
N-(trans-4-{[6-chloro-4-(5-methoxy-1H-pyrrolo[2,3-b]pyridin-3-yl)pyridin-2-yl]amino}cyclohexyl)methanesulfonamide;
6-chloro-N-cyclohexyl-4-(5-{3-[(4-methylpiperazin-1-yl)methyl]phenyl}-1H-pyrrolo[2,3-b]pyridin-3-yl)pyridin-2-amine;
3-{3-[2-chloro-6-(cyclohexylamino)pyridin-4-yl]-1H-pyrrolo[2,3-b]pyridin-5-yl}benzenesulfonamide;
4-{3-[2-chloro-6-(cyclohexylamino)pyridin-4-yl]-1H-pyrrolo[2,3-b]pyridin-5-yl}benzenesulfonamide;
trans-N-[6-chloro-4-(5-ethoxy-1H-pyrrolo[2,3-b]pyridin-3-yl)pyridin-2-yl]cyclohexane-1,4-diamine;
3-[2-chloro-6-(cyclohexylamino)pyridin-4-yl]-1H-pyrrolo[2,3-b]pyridin-5-amine;
N-{3-[2-chloro-6-(cyclohexylamino)pyridin-4-yl]-1H-pyrrolo[2,3-b]pyridin-5-yl}acetamide;
N-(trans-4-{[6-chloro-4-(5-methoxy-1H-pyrrolo[2,3-b]pyridin-3-yl)pyridin-2-yl]amino}cyclohexyl)-$N^2$-methylglycinamide;

N-(trans-4-{[6-chloro-4-(5-methoxy-1H-pyrrolo[2,3-b]pyridin-3-yl)pyridin-2-yl]amino}cyclohexyl)-2-methylpropanamide;
N-(trans-4-{[6-chloro-4-(1H-pyrrolo[2,3-b]pyridin-3-yl)pyridin-2-yl]amino}cyclohexyl)-2-[4-(4-fluorophenyl)piperazin-1-yl]acetamide;
N-(trans-4-{[6-chloro-4-(1H-pyrrolo[2,3-b]pyridin-3-yl)pyridin-2-yl]amino}cyclohexyl)-2-[4-(pyridin-4-yl)piperazin-1-yl]acetamide;
N-(trans-4-{[6-chloro-4-(1H-pyrrolo[2,3-b]pyridin-3-yl)pyridin-2-yl]amino}cyclohexyl)-2-(4-cyclohexylpiperazin-1-yl)acetamide;
2-(4-butylpiperazin-1-yl)-N-(trans-4-{[6-chloro-4-(1H-pyrrolo[2,3-b]pyridin-3-yl)pyridin-2-yl]amino}cyclohexyl)acetamide;
N-(trans-4-{[6-chloro-4-(1H-pyrrolo[2,3-b]pyridin-3-yl)pyridin-2-yl]amino}cyclohexyl)-2-[4-(furan-2-ylcarbonyl)piperazin-1-yl]acetamide;
N-(trans-4-{[6-chloro-4-(1H-pyrrolo[2,3-b]pyridin-3-yl)pyridin-2-yl]amino}cyclohexyl)-2-[4-(2-cyanophenyl)piperazin-1-yl]acetamide;
3-[2-chloro-6-(cyclohexylamino)pyridin-4-yl]-1H-pyrrolo[2,3-b]pyridine-5-carboxylic acid;
6-chloro-4-(5-methoxy-1H-pyrrolo[2,3-b]pyridin-3-yl)-N-[4-(piperidin-4-yl)cyclohexyl]pyridin-2-amine;
N-{4-[(4-aminocyclohexyl)methyl]cyclohexyl}-6-chloro-4-(5-methoxy-1H-pyrrolo[2,3-b]pyridin-3-yl)pyridin-2-amine;
6-chloro-N-(4-{[4-(cyclohexylamino)cyclohexyl]methyl}cyclohexyl)-4-(5-methoxy-1H-pyrrolo[2,3-b]pyridin-3-yl)pyridin-2-amine;
3-[2-chloro-6-(cyclohexylamino)pyridin-4-yl]-N-phenyl-1H-pyrrolo[2,3-b]pyridin-5-amine;
N-{4-[(4-{[6-chloro-4-(5-methoxy-1H-pyrrolo[2,3-b]pyridin-3-yl)pyridin-2-yl]amino}cyclohexyl)methyl]cyclohexyl}cyclopropanecarboxamide;
trans-N-{6-chloro-4-[5-(prop-2-yn-1-yloxy)-1H-pyrrolo[2,3-b]pyridin-3-yl]pyridin-2-yl}cyclohexane-1,4-diamine;
3-[2-chloro-6-(cyclohexylamino)pyridin-4-yl]-N-(pyridin-2-ylmethyl)-1H-pyrrolo[2,3-b]pyridine-5-carboxamide;
6-chloro-N-cyclohexyl-4-[5-(pyrimidin-5-yl)-1H-pyrrolo[2,3-b]pyridin-3-yl]pyridin-2-amine;
N-(trans-4-{[6-chloro-4-(5-methoxy-1H-pyrrolo[2,3-b]pyridin-3-yl)pyridin-2-yl]amino}cyclohexyl)butane-1-sulfonamide;
4-[5-(6-aminopyridin-3-yl)-1H-pyrrolo[2,3-b]pyridin-3-yl]-6-chloro-N-cyclohexylpyridin-2-amine;
N-(trans-4-{[6-chloro-4-(5-methoxy-1H-pyrrolo[2,3-b]pyridin-3-yl)pyridin-2-yl]amino}cyclohexyl)glycinamide;
6-chloro-N-cyclohexyl-4-(4-methoxy-1H-pyrrolo[2,3-b]pyridin-3-yl)pyridin-2-amine;
1-{3-[2-chloro-6-(cyclohexylamino)pyridin-4-yl]-1H-pyrrolo[2,3-b]pyridin-5-yl}-3-ethylurea;
N-(trans-4-{[6-chloro-4-(1H-pyrrolo[2,3-b]pyridin-3-yl)pyridin-2-yl]amino}cyclohexyl)-1-(pyridin-4-ylmethyl)azetidine-3-carboxamide;
N-(trans-4-{[6-chloro-4-(1H-pyrrolo[2,3-b]pyridin-3-yl)pyridin-2-yl]amino}cyclohexyl)-1-(piperidin-4-yl)azetidine-3-carboxamide;
N-(trans-4-{[6-chloro-4-(5-methoxy-1H-pyrrolo[2,3-b]pyridin-3-yl)pyridin-2-yl]amino}cyclohexyl)-$N^2$-cyclohexylglycinamide;
6-chloro-N-[4-(1-cyclobutylpiperidin-4-yl)cyclohexyl]-4-(5-methoxy-1H-pyrrolo[2,3-b]pyridin-3-yl)pyridin-2-amine;
N-(trans-4-{[6-chloro-4-(5-methoxy-1H-pyrrolo[2,3-b]pyridin-3-yl)pyridin-2-yl]amino}cyclohexyl)cyclohexanesulfonamide;
N-(trans-4-{[6-chloro-4-(5-methoxy-1H-pyrrolo[2,3-b]pyridin-3-yl)pyridin-2-yl]amino}cyclohexyl)-2-(morpholin-4-yl)acetamide;
N-(3-{3-[2-chloro-6-(cyclohexylamino)pyridin-4-yl]-1H-pyrrolo[2,3-b]pyridin-5-yl}phenyl)acetamide;
N-{3-[2-chloro-6-(cyclohexylamino)pyridin-4-yl]-1H-pyrrolo[2,3-b]pyridin-5-yl}methanesulfonamide;
N-{4-[(4-{[6-chloro-4-(5-methoxy-1H-pyrrolo[2,3-b]pyridin-3-yl)pyridin-2-yl]amino}cyclohexyl)methyl]cyclohexyl}pyridine-3-carboxamide;
N-(trans-4-{[6-chloro-4-(5-methoxy-1H-pyrrolo[2,3-b]pyridin-3-yl)pyridin-2-yl]amino}cyclohexyl)-$N^2$-(2,2-dimethylpropyl)glycinamide;
6-chloro-N-(4-{[4-(dimethylamino)cyclohexyl]methyl}cyclohexyl)-4-(5-methoxy-1H-pyrrolo[2,3-b]pyridin-3-yl)pyridin-2-amine;
N-(3-{[6-chloro-4-(5-methoxy-1H-pyrrolo[2,3-b]pyridin-3-yl)pyridin-2-yl]amino}cyclohexyl)cyclopropanesulfonamide;
N-(3-{[6-chloro-4-(5-methoxy-1H-pyrrolo[2,3-b]pyridin-3-yl)pyridin-2-yl]amino}cyclohexyl)acetamide;
N-(3-{[6-chloro-4-(5-methoxy-1H-pyrrolo[2,3-b]pyridin-3-yl)pyridin-2-yl]amino}cyclohexyl)thiophene-2-sulfonamide;
N-(3-{[6-chloro-4-(5-methoxy-1H-pyrrolo[2,3-b]pyridin-3-yl)pyridin-2-yl]amino}cyclohexyl)-2-(pyrrolidin-1-yl)acetamide;
N-[4-chloro-6-(1H-pyrrolo[2,3-b]pyridin-3-yl)pyrimidin-2-yl]cyclohexane-1,2-diamine;
4-chloro-6-(1H-pyrrolo[2,3-b]pyridin-3-yl)-N-(tetrahydrofuran-2-ylmethyl)pyrimidin-2-amine;
4-chloro-N-(pyridin-4-ylmethyl)-6-(1H-pyrrolo[2,3-b]pyridin-3-yl)pyrimidin-2-amine;
4-chloro-N-(pyridin-3-ylmethyl)-6-(1H-pyrrolo[2,3-b]pyridin-3-yl)pyrimidin-2-amine;
4-chloro-N-(pyridin-2-ylmethyl)-6-(1H-pyrrolo[2,3-b]pyridin-3-yl)pyrimidin-2-amine;
4-chloro-N,N-dimethyl-6-(1H-pyrrolo[2,3-b]pyridin-3-yl)pyrimidin-2-amine;
N-(3-{[4-chloro-6-(1H-pyrrolo[2,3-b]pyridin-3-yl)pyrimidin-2-yl]amino}cyclohexyl)acetamide;
N-(trans-4-{[4-chloro-6-(1H-pyrrolo[2,3-b]pyridin-3-yl)pyrimidin-2-yl]amino}cyclohexyl)cyclopropanecarboxamide;
N-(3-{[4-chloro-6-(1H-pyrrolo[2,3-b]pyridin-3-yl)pyrimidin-2-yl]amino}cyclohexyl)cyclopropanecarboxamide;
N-(3-{[4-chloro-6-(1H-pyrrolo[2,3-b]pyridin-3-yl)pyrimidin-2-yl]amino}cyclohexyl)methanesulfonamide;
N-[4-chloro-6-(1H-pyrrolo[2,3-b]pyridin-3-yl)pyrimidin-2-yl]-N'-cyclobutylcyclohexane-1,3-diamine;
trans-N-[4-chloro-6-(1H-pyrrolo[2,3-b]pyridin-3-yl)pyrimidin-2-yl]-N'-cyclobutylcyclohexane-1,4-diamine;
N-(trans-4-{[4-chloro-6-(1H-pyrrolo[2,3-b]pyridin-3-yl)pyrimidin-2-yl]amino}cyclohexyl)methanesulfonamide;
N-(trans-4-{[4-chloro-6-(1H-pyrrolo[2,3-b]pyridin-3-yl)pyrimidin-2-yl]amino}cyclohexyl)-$N^2$-methylglycinamide;
N-[4-chloro-6-(1H-pyrrolo[2,3-b]pyridin-3-yl)pyrimidin-2-yl]-2,2-dimethylpropane-1,3-diamine;
4-chloro-N-(2-methoxyethyl)-6-(1H-pyrrolo[2,3-b]pyridin-3-yl)pyrimidin-2-amine;
1-(trans-4-{[4-chloro-6-(1H-pyrrolo[2,3-b]pyridin-3-yl)pyrimidin-2-yl]amino}cyclohexyl)-3-methylurea;
1-(trans-4-{[4-chloro-6-(1H-pyrrolo[2,3-b]pyridin-3-yl)pyrimidin-2-yl]amino}cyclohexyl)-3-phenylurea;

N-(trans-4-{[4-chloro-6-(1H-pyrrolo[2,3-b]pyridin-3-yl)pyrimidin-2-yl]amino}cyclohexyl)cyclopropanesulfonamide;
N-(4-{[6-chloro-4-(1H-pyrrolo[2,3-b]pyridin-3-yl)pyridin-2-yl]amino}cyclohexyl)-3,5-dimethyl-1,2-oxazole-4-sulfonamide;
6-chloro-N-[(2S)-1-methoxy-3-phenylpropan-2-yl]-4-(1H-pyrrolo[2,3-b]pyridin-3-yl)pyridin-2-amine;
N-[6-chloro-4-(1H-pyrrolo[2,3-b]pyridin-3-yl)pyridin-2-yl]-N'-cyclopentylcyclohexane-1,3-diamine;
ethyl N-[(4-{[6-chloro-4-(1H-pyrrolo[2,3-b]pyridin-3-yl)pyridin-2-yl]amino}cyclohexyl)carbamoyl]glycinate;
1-(4-{[6-chloro-4-(1H-pyrrolo[2,3-b]pyridin-3-yl)pyridin-2-yl]amino}cyclohexyl)-3-propan-2-ylurea;
1-tert-butyl-3-(4-{[6-chloro-4-(1H-pyrrolo[2,3-b]pyridin-3-yl)pyridin-2-yl]amino}cyclohexyl)urea;
N-(4-{[6-chloro-4-(1H-pyrrolo[2,3-b]pyridin-3-yl)pyridin-2-yl]amino}cyclohexyl)-2-methoxyacetamide;
N-[6-chloro-4-(1H-pyrrolo[2,3-b]pyridin-3-yl)pyridin-2-yl]-N'-(1,3-thiazol-2-ylmethyl)cyclohexane-1,3-diamine;
N-[6-chloro-4-(1H-pyrrolo[2,3-b]pyridin-3-yl)pyridin-2-yl]-N'-[3-(piperidin-1-ylmethyl)benzyl]cyclohexane-1,3-diamine;
N-(3-{[6-chloro-4-(1H-pyrrolo[2,3-b]pyridin-3-yl)pyridin-2-yl]amino}cyclohexyl)-2-ethoxyacetamide;
N-(3-{[6-chloro-4-(1H-pyrrolo[2,3-b]pyridin-3-yl)pyridin-2-yl]amino}cyclohexyl)-2-phenoxyacetamide;
N-(3-{[6-chloro-4-(1H-pyrrolo[2,3-b]pyridin-3-yl)pyridin-2-yl]amino}cyclohexyl)pyrazine-2-carboxamide;
N-(3-{[6-chloro-4-(1H-pyrrolo[2,3-b]pyridin-3-yl)pyridin-2-yl]amino}cyclohexyl)azetidine-2-carboxamide;
tert-butyl 2-[(3-{[6-chloro-4-(1H-pyrrolo[2,3-b]pyridin-3-yl)pyridin-2-yl]amino}cyclohexyl)carbamoyl]azetidine-1-carboxylate;
1-(4-{[6-chloro-4-(1H-pyrrolo[2,3-b]pyridin-3-yl)pyridin-2-yl]amino}cyclohexyl)-3-prop-2-en-1-ylurea;
N-(3-{[6-chloro-4-(1H-pyrrolo[2,3-b]pyridin-3-yl)pyridin-2-yl]amino}-2,2-dimethylpropyl)-1-methyl-1H-imidazole-4-sulfonamide;
N-(3-{[6-chloro-4-(1H-pyrrolo[2,3-b]pyridin-3-yl)pyridin-2-yl]amino}cyclohexyl)furan-2-sulfonamide;
N-(3-{[6-chloro-4-(1H-pyrrolo[2,3-b]pyridin-3-yl)pyridin-2-yl]amino}cyclohexyl)pyridine-3-sulfonamide;
1-(3-{[6-chloro-4-(1H-pyrrolo[2,3-b]pyridin-3-yl)pyridin-2-yl]amino}cyclohexyl)-3-propan-2-ylurea;
ethyl N-[(3-{[6-chloro-4-(1H-pyrrolo[2,3-b]pyridin-3-yl)pyridin-2-yl]amino}cyclohexyl)carbamoyl]glycinate;
1-(3-{[6-chloro-4-(1H-pyrrolo[2,3-b]pyridin-3-yl)pyridin-2-yl]amino}cyclohexyl)-3-(cyclohexylmethyl)urea;
4-acetyl-N-(3-{[6-chloro-4-(1H-pyrrolo[2,3-b]pyridin-3-yl)pyridin-2-yl]amino}-2,2-dimethylpropyl)benzenesulfonamide;
N-(3-{[6-chloro-4-(1H-pyrrolo[2,3-b]pyridin-3-yl)pyridin-2-yl]amino}-2,2-dimethylpropyl)-3,5-dimethyl-1,2-oxazole-4-sulfonamide;
N-(3-{[6-chloro-4-(1H-pyrrolo[2,3-b]pyridin-3-yl)pyridin-2-yl]amino}-2,2-dimethylpropyl)thiophene-2-sulfonamide;
N-(3-{[6-chloro-4-(1H-pyrrolo[2,3-b]pyridin-3-yl)pyridin-2-yl]amino}cyclohexyl)-3,5-dimethyl-1,2-oxazole-4-sulfonamide;
1-(3-{[6-chloro-4-(1H-pyrrolo[2,3-b]pyridin-3-yl)pyridin-2-yl]amino}cyclohexyl)-3-propylurea;
N-(3-{[6-chloro-4-(1H-pyrrolo[2,3-b]pyridin-3-yl)pyridin-2-yl]amino}-2,2-dimethylpropyl)propane-1-sulfonamide;
N-[6-chloro-4-(1H-pyrrolo[2,3-b]pyridin-3-yl)pyridin-2-yl]acetamide;
N-(trans-4-{[6-chloro-4-(1H-pyrrolo[2,3-b]pyridin-3-yl)pyridin-2-yl]amino}cyclohexyl)propane-2-sulfonamide;
N-(trans-4-{[6-chloro-4-(1H-pyrrolo[2,3-b]pyridin-3-yl)pyridin-2-yl]amino}cyclohexyl)ethanesulfonamide;
N-(2-{[6-chloro-4-(1H-pyrrolo[2,3-b]pyridin-3-yl)pyridin-2-yl]amino}ethyl)butane-1-sulfonamide;
N-(2-{[6-chloro-4-(1H-pyrrolo[2,3-b]pyridin-3-yl)pyridin-2-yl]amino}ethyl)thiophene-2-sulfonamide;
6-chloro-N-(1-methylpiperidin-3-yl)-4-(1H-pyrrolo[2,3-b]pyridin-3-yl)pyridin-2-amine;
[3-({[6-chloro-4-(1H-pyrrolo[2,3-b]pyridin-3-yl)pyridin-2-yl]amino}methyl)piperidin-1-yl] (cyclopropyl)methanone;
N-[6-chloro-4-(1H-pyrrolo[2,3-b]pyridin-3-yl)pyridin-2-yl]-N-{[1-(cyclopropylcarbonyl)piperidin-3-yl]methyl}cyclopropanecarboxamide;
6-chloro-N-{[1-(cyclopropylmethyl)piperidin-3-yl]methyl}-4-(1H-pyrrolo[2,3-b]pyridin-3-yl)pyridin-2-amine;
6-chloro-N-[1-(cyclopropylmethyl)piperidin-3-yl]-4-(1H-pyrrolo[2,3-b]pyridin-3-yl)pyridin-2-amine;
N-[6-chloro-4-(1H-pyrrolo[2,3-b]pyridin-3-yl)pyridin-2-yl]-2-(1H-indol-2-yl)acetamide;
trans-N-[6-chloro-4-(1H-pyrrolo[2,3-b]pyridin-3-yl)pyridin-2-yl]-N'-cyclopentylcyclohexane-1,4-diamine;
trans-N-[6-chloro-4-(1H-pyrrolo[2,3-b]pyridin-3-yl)pyridin-2-yl]-N'-(2-methylpropyl)cyclohexane-1,4-diamine;
6-chloro-N-[3-(pyrrolidin-1-yl)cyclohexyl]-4-(1H-pyrrolo[2,3-b]pyridin-3-yl)pyridin-2-amine;
6-chloro-N-[3-(piperidin-1-yl)cyclohexyl]-4-(1H-pyrrolo[2,3-b]pyridin-3-yl)pyridin-2-amine;
N-(trans-4-{[6-chloro-4-(1H-pyrrolo[2,3-b]pyridin-3-yl)pyridin-2-yl]amino}cyclohexyl)-$N^2$-methylglycinamide;
N-(trans-4-{[6-chloro-4-(1H-pyrrolo[2,3-b]pyridin-3-yl)pyridin-2-yl]amino}cyclohexyl)-1-ethylpyrrolidine-3-carboxamide;
N-(3-{[6-chloro-4-(1H-pyrrolo[2,3-b]pyridin-3-yl)pyridin-2-yl]amino}cyclohexyl)-$N^2$-methylalaninamide;
(2R)—N-[(1S,3S)-3-{[6-chloro-4-(1H-pyrrolo[2,3-b]pyridin-3-yl)pyridin-2-yl]amino}cyclohexyl]-2-(methylamino)-2-phenylethanamide;
(2R)—N-[(1R,3R)-3-{[6-chloro-4-(1H-pyrrolo[2,3-b]pyridin-3-yl)pyridin-2-yl]amino}cyclohexyl]-2-(methylamino)-2-phenylethanamide;
N-[(1R,2R)-2-{[6-chloro-4-(1H-pyrrolo[2,3-b]pyridin-3-yl)pyridin-2-yl]amino}cyclohexyl]cyclopropanesulfonamide;
N-[6-chloro-4-(1H-pyrrolo[2,3-b]pyridin-3-yl)pyridin-2-yl]-4-fluorobenzenesulfonamide;
N-[6-chloro-4-(1H-pyrrolo[2,3-b]pyridin-3-yl)pyridin-2-yl]cyclopropanesulfonamide;
N'-[6-chloro-4-(1H-pyrrolo[2,3-b]pyridin-3-yl)pyridin-2-yl]-N,N-diethyl-2,2-dimethylpropane-1,3-diamine;
trans-N'-[6-chloro-4-(1H-pyrrolo[2,3-b]pyridin-3-yl)pyridin-2-yl]-N,N-diethylcyclohexane-1,4-diamine;
N-(trans-4-{[6-chloro-4-(1H-pyrrolo[2,3-b]pyridin-3-yl)pyridin-2-yl]amino}cyclohexyl)-5-oxo-D-prolinamide;
N-(trans-4-{[6-chloro-4-(1H-pyrrolo[2,3-b]pyridin-3-yl)pyridin-2-yl]amino}cyclohexyl)-1-methylprolinamide;
N-(trans-4-{[6-chloro-4-(1H-pyrrolo[2,3-b]pyridin-3-yl)pyridin-2-yl]amino}cyclohexyl)-1-methylpiperidine-2-carboxamide;
N-(trans-4-{[6-chloro-4-(1H-pyrrolo[2,3-b]pyridin-3-yl)pyridin-2-yl]amino}cyclohexyl)-5-oxo-L-prolinamide;
N-(3-{[6-chloro-4-(1H-pyrrolo[2,3-b]pyridin-3-yl)pyridin-2-yl]amino}cyclohexyl)-1-methylpiperidine-2-carboxamide;

2-(azepan-1-yl)-N-(3-{[6-chloro-4-(1H-pyrrolo[2,3-b]pyridin-3-yl)pyridin-2-yl]amino}cyclohexyl)acetamide;

N-(trans-4-{[6-chloro-4-(1H-pyrrolo[2,3-b]pyridin-3-yl)pyridin-2-yl]amino}cyclohexyl)cyclopentanecarboxamide;

N-(trans-4-{[6-chloro-4-(1H-pyrrolo[2,3-b]pyridin-3-yl)pyridin-2-yl]amino}cyclohexyl)-1-methyl-5-oxoprolinamide;

N-(3-{[6-chloro-4-(1H-pyrrolo[2,3-b]pyridin-3-yl)pyridin-2-yl]amino}cyclohexyl)pyrrolidine-3-carboxamide;

N-(3-{[6-chloro-4-(1H-pyrrolo[2,3-b]pyridin-3-yl)pyridin-2-yl]amino}cyclohexyl)piperidine-4-carboxamide;

N-(3-{[6-chloro-4-(1H-pyrrolo[2,3-b]pyridin-3-yl)pyridin-2-yl]amino}cyclohexyl)piperidine-3-carboxamide;

N-(3-{[6-chloro-4-(1H-pyrrolo[2,3-b]pyridin-3-yl)pyridin-2-yl]amino}cyclohexyl)-1-methylpyrrolidine-3-carboxamide;

N-(3-{[6-chloro-4-(1H-pyrrolo[2,3-b]pyridin-3-yl)pyridin-2-yl]amino}cyclohexyl)-1-methylpiperidine-4-carboxamide;

N-(3-{[6-chloro-4-(1H-pyrrolo[2,3-b]pyridin-3-yl)pyridin-2-yl]amino}cyclohexyl)-1-methylpiperidine-3-carboxamide;

N-(3-{[6-chloro-4-(1H-pyrrolo[2,3-b]pyridin-3-yl)pyridin-2-yl]amino}cyclohexyl)-1-(dimethylamino)cyclobutanecarboxamide;

N-(3-{[6-chloro-4-(1H-pyrrolo[2,3-b]pyridin-3-yl)pyridin-2-yl]amino}cyclohexyl)-$N^2$,$N^2$-dimethyl-L-alaninamide;

$N^2$-1-azabicyclo[2.2.2]oct-3-yl-N-(trans-4-{[6-chloro-4-(1H-pyrrolo[2,3-b]pyridin-3-yl)pyridin-2-yl]amino}cyclohexyl)glycinamide;

N-(trans-4-{[6-chloro-4-(1H-pyrrolo[2,3-b]pyridin-3-yl)pyridin-2-yl]amino}cyclohexyl)-$N^2$-(2-hydroxyethyl)glycinamide;

N-(3-{[6-chloro-4-(1H-pyrrolo[2,3-b]pyridin-3-yl)pyridin-2-yl]amino}cyclohexyl)-2-(1,3-dioxo-1,3-dihydro-2H-isoindol-2-yl)ethanesulfonamide;

N-(trans-4-{[6-chloro-4-(1H-pyrrolo[2,3-b]pyridin-3-yl)pyridin-2-yl]amino}cyclohexyl)-$N^2$-(4-methylcyclohexyl)glycinamide;

N-(trans-4-{[6-chloro-4-(1H-pyrrolo[2,3-b]pyridin-3-yl)pyridin-2-yl]amino}cyclohexyl)-$N^2$-(2,2-dimethylpropyl)glycinamide;

N-(trans-4-{[6-chloro-4-(1H-pyrrolo[2,3-b]pyridin-3-yl)pyridin-2-yl]amino}cyclohexyl)-$N^2$-ethyl-$N^2$-(2-hydroxyethyl)glycinamide;

trans-N-[6-chloro-4-(1H-pyrrolo[2,3-b]pyridin-3-yl)pyridin-2-yl]-N'-(piperidin-4-yl)cyclohexane-1,4-diamine;

N-(trans-4-{[6-chloro-4-(1H-pyrrolo[2,3-b]pyridin-3-yl)pyridin-2-yl]amino}cyclohexyl)-2-(1,3-dioxo-1,3-dihydro-2H-isoindol-2-yl)ethanesulfonamide;

6-chloro-N-(4-{[4-(cyclobutylamino)cyclohexyl]methyl}cyclohexyl)-4-(1H-pyrrolo[2,3-b]pyridin-3-yl)pyridin-2-amine;

trans-N-[6-chloro-4-(1H-pyrrolo[2,3-b]pyridin-3-yl)pyridin-2-yl]-N'-(1-cyclobutylpiperidin-4-yl)cyclohexane-1,4-diamine;

tert-butyl 4-(4-{[6-chloro-4-(1H-pyrrolo[2,3-b]pyridin-3-yl)pyridin-2-yl]amino}cyclohexyl)piperidine-1-carboxylate;

benzyl {4-[(trans-4-{[6-chloro-4-(1H-pyrrolo[2,3-b]pyridin-3-yl)pyridin-2-yl]amino}cyclohexyl)amino]cyclohexyl}carbamate;

tert-butyl 3-[(trans-4-{[6-chloro-4-(1H-pyrrolo[2,3-b]pyridin-3-yl)pyridin-2-yl]amino}cyclohexyl)carbamoyl]azetidine-1-carboxylate;

N-[4-(acetylamino)cyclohexyl]-N-(trans-4-{[6-chloro-4-(1H-pyrrolo[2,3-b]pyridin-3-yl)pyridin-2-yl]amino}cyclohexyl)acetamide;

[4-(4-{[6-chloro-4-(1H-pyrrolo[2,3-b]pyridin-3-yl)pyridin-2-yl]amino}cyclohexyl)piperidin-1-yl](cyclopropyl)methanone;

N-(trans-4-{[6-chloro-4-(1H-pyrrolo[2,3-b]pyridin-3-yl)pyridin-2-yl]amino}cyclohexyl)-1-(2-hydroxyethyl)piperidine-4-carboxamide;

N-{4-[(4-{[6-chloro-4-(1H-pyrrolo[2,3-b]pyridin-3-yl)pyridin-2-yl]amino}cyclohexyl)methyl]cyclohexyl}cyclopropanecarboxamide;

1-{4-[(4-{[6-chloro-4-(1H-pyrrolo[2,3-b]pyridin-3-yl)pyridin-2-yl]amino]cyclohexyl)amino]piperidin-1-yl}ethanone;

N-[6-chloro-4-(1H-pyrrolo[2,3-b]pyridin-3-yl)pyridin-2-yl]-N-{4-[1-(methylsulfonyl)piperidin-4-yl]cyclohexyl}methanesulfonamide;

6-chloro-N-[4-(1-methylpiperidin-3-yl)cyclohexyl]-4-(1H-pyrrolo[2,3-b]pyridin-3-yl)pyridin-2-amine;

6-chloro-N-methyl-N-[4-(1-methylpiperidin-3-yl)cyclohexyl]-4-(1H-pyrrolo[2,3-b]pyridin-3-yl)pyridin-2-amine;

N-{2-[(trans-4-{[6-chloro-4-(1H-pyrrolo[2,3-b]pyridin-3-yl)pyridin-2-yl]amino}cyclohexyl)sulfamoyl]ethyl}cyclopropanecarboxamide;

3-{[6-chloro-4-(1H-pyrrolo[2,3-b]pyridin-3-yl)pyridin-2-yl]amino}propan-1-ol;

6-chloro-N-[3-(morpholin-4-yl)propyl]-4-(1H-pyrrolo[2,3-b]pyridin-3-yl)pyridin-2-amine;

6-chloro-N-[3-(1H-imidazol-1-yl)propyl]-4-(1H-pyrrolo[2,3-b]pyridin-3-yl)pyridin-2-amine;

5-{[6-chloro-4-(1H-pyrrolo[2,3-b]pyridin-3-yl)pyridin-2-yl]amino}pentan-1-ol;

6-chloro-N-[2-(pyridin-3-yl)ethyl]-4-(1H-pyrrolo[2,3-b]pyridin-3-yl)pyridin-2-amine;

N-[1-(4-aminocyclohexyl)piperidin-4-yl]-6-chloro-4-(1H-pyrrolo[2,3-b]pyridin-3-yl)pyridin-2-amine;

6-chloro-N-methyl-N-[4-(1-methylpyrrolidin-3-yl)cyclohexyl]-4-(1H-pyrrolo[2,3-b]pyridin-3-yl)pyridin-2-amine;

1-benzyl-N-(trans-4-{[6-chloro-4-(1H-pyrrolo[2,3-b]pyridin-3-yl)pyridin-2-yl]amino}cyclohexyl)azetidine-3-carboxamide;

4-chloro-N-(trans-4-{[6-chloro-4-(1H-pyrrolo[2,3-b]pyridin-3-yl)pyridin-2-yl]amino}cyclohexyl)-2-methoxybenzamide;

N-(trans-4-{[6-chloro-4-(1H-pyrrolo[2,3-b]pyridin-3-yl)pyridin-2-yl]amino}cyclohexyl)-3-(trifluoromethyl)benzamide;

3-chloro-N-(trans-4-{[6-chloro-4-(1H-pyrrolo[2,3-b]pyridin-3-yl)pyridin-2-yl]amino}cyclohexyl)benzamide;

6-chloro-N-[2-(3,4-dimethoxyphenyl)ethyl]-4-(1H-pyrrolo[2,3-b]pyridin-3-yl)pyridin-2-amine;

6-chloro-N-[2-(pyridin-2-yl)ethyl]-4-(1H-pyrrolo[2,3-b]pyridin-3-yl)pyridin-2-amine;

6-chloro-N-(2-phenylethyl)-4-(1H-pyrrolo[2,3-b]pyridin-3-yl)pyridin-2-amine;

6-chloro-N-[3-(4-methylpiperazin-1-yl)propyl]-4-(1H-pyrrolo[2,3-b]pyridin-3-yl)pyridin-2-amine;

6-chloro-N-(2-phenoxyethyl)-4-(1H-pyrrolo[2,3-b]pyridin-3-yl)pyridin-2-amine;

N'-[6-chloro-4-(1H-pyrrolo[2,3-b]pyridin-3-yl)pyridin-2-yl]-N,N-dimethylpropane-1,3-diamine;

N-(1-benzylpyrrolidin-3-yl)-6-chloro-4-(1H-pyrrolo[2,3-b]pyridin-3-yl)pyridin-2-amine;

N-{2-[(trans-4-{[6-chloro-4-(1H-pyrrolo[2,3-b]pyridin-3-yl)pyridin-2-yl]amino}cyclohexyl)sulfamoyl]ethyl}-2,4-difluorobenzamide;

N-(trans-4-{[6-chloro-4-(1H-pyrrolo[2,3-b]pyridin-3-yl)pyridin-2-yl]amino}cyclohexyl)-1-[3-(trifluoromethyl)benzyl]azetidine-3-carboxamide;

N-(trans-4-{[6-chloro-4-(1H-pyrrolo[2,3-b]pyridin-3-yl)pyridin-2-yl]amino}cyclohexyl)-1-(2,4-dichlorobenzyl)azetidine-3-carboxamide;

N-(trans-4-{[6-chloro-4-(1H-pyrrolo[2,3-b]pyridin-3-yl)pyridin-2-yl]amino}cyclohexyl)-1-(1-phenylethyl)azetidine-3-carboxamide;

6-chloro-N-(4-methoxybenzyl)-4-(1H-pyrrolo[2,3-b]pyridin-3-yl)pyridin-2-amine;

4-(2-{[6-chloro-4-(1H-pyrrolo[2,3-b]pyridin-3-yl)pyridin-2-yl]amino}ethyl)phenol;

N-[2-(1,3-benzodioxol-5-yl)ethyl]-6-chloro-4-(1H-pyrrolo[2,3-b]pyridin-3-yl)pyridin-2-amine;

N-(1,3-benzodioxol-5-ylmethyl)-6-chloro-4-(1H-pyrrolo[2,3-b]pyridin-3-yl)pyridin-2-amine;

6-chloro-N-[2-(4-methoxyphenyl)ethyl]-4-(1H-pyrrolo[2,3-b]pyridin-3-yl)pyridin-2-amine;

N-(1-benzylpiperidin-4-yl)-6-chloro-4-(1H-pyrrolo[2,3-b]pyridin-3-yl)pyridin-2-amine;

6-chloro-N-[2-(pyridin-4-yl)ethyl]-4-(1H-pyrrolo[2,3-b]pyridin-3-yl)pyridin-2-amine;

6-chloro-N-(2,3-dihydro-1H-inden-2-yl)-4-(1H-pyrrolo[2,3-b]pyridin-3-yl)pyridin-2-amine;

6-chloro-N-[2-(1H-indol-3-yl)ethyl]-4-(1H-pyrrolo[2,3-b]pyridin-3-yl)pyridin-2-amine;

N-(trans-4-{[6-chloro-4-(1H-pyrrolo[2,3-b]pyridin-3-yl)pyridin-2-yl]amino}cyclohexyl)-1-(2,3-dimethylbenzyl)azetidine-3-carboxamide;

N-(trans-4-{[6-chloro-4-(1H-pyrrolo[2,3-b]pyridin-3-yl)pyridin-2-yl]amino}cyclohexyl)-1-(1H-indol-6-ylmethyl)azetidine-3-carboxamide;

N-[4-(benzyloxy)phenyl]-6-chloro-4-(1H-pyrrolo[2,3-b]pyridin-3-yl)pyridin-2-amine;

N-(1H-benzimidazol-2-ylmethyl)-6-chloro-4-(1H-pyrrolo[2,3-b]pyridin-3-yl)pyridin-2-amine;

6-chloro-N-(1H-indol-5-ylmethyl)-4-(1H-pyrrolo[2,3-b]pyridin-3-yl)pyridin-2-amine;

6-chloro-N-(4-methoxyphenyl)-4-(1H-pyrrolo[2,3-b]pyridin-3-yl)pyridin-2-amine;

6-chloro-4-(1H-pyrrolo[2,3-b]pyridin-3-yl)-N-(3,4,5-trimethoxyphenyl)pyridin-2-amine;

6-chloro-N-[4-(1H-imidazol-1-yl)phenyl]-4-(1H-pyrrolo[2,3-b]pyridin-3-yl)pyridin-2-amine;

6-chloro-N-(3,4-dimethoxybenzyl)-4-(1H-pyrrolo[2,3-b]pyridin-3-yl)pyridin-2-amine;

2-{[6-chloro-4-(1H-pyrrolo[2,3-b]pyridin-3-yl)pyridin-2-yl]amino}-1-phenylethanol;

6-chloro-N-(3-phenylpropyl)-4-(1H-pyrrolo[2,3-b]pyridin-3-yl)pyridin-2-amine;

6-chloro-N-[4-(methylsulfonyl)benzyl]-4-(1H-pyrrolo[2,3-b]pyridin-3-yl)pyridin-2-amine;

6-chloro-N-[4-(methylsulfanyl)phenyl]-4-(1H-pyrrolo[2,3-b]pyridin-3-yl)pyridin-2-amine;

6-chloro-N-(4-phenoxyphenyl)-4-(1H-pyrrolo[2,3-b]pyridin-3-yl)pyridin-2-amine;

6-chloro-N-[4-(piperidin-1-yl)phenyl]-4-(1H-pyrrolo[2,3-b]pyridin-3-yl)pyridin-2-amine;

methyl 3-[2-chloro-6-(cyclohexylamino)pyridin-4-yl]-1H-pyrrolo[2,3-b]pyridine-5-carboxylate;

N-(trans-4-{[6-chloro-4-(1H-pyrrolo[2,3-b]pyridin-3-yl)pyridin-2-yl]amino}cyclohexyl)-2-[4-(2-hydroxyethyl)piperazin-1-yl]acetamide;

N-(trans-4-{[6-chloro-4-(1H-pyrrolo[2,3-b]pyridin-3-yl)pyridin-2-yl]amino}cyclohexyl)-2-[4-(2,6-dimethylphenyl)piperazin-1-yl]acetamide;

6-chloro-N-(4-{[4-(cyclobutylamino)cyclohexyl]methyl}cyclohexyl)-4-(5-methoxy-1H-pyrrolo[2,3-b]pyridin-3-yl)pyridin-2-amine;

6-chloro-4-(5-methoxy-1H-pyrrolo[2,3-b]pyridin-3-yl)-N-(4-{[4-(pentan-3-ylamino)cyclohexyl]methyl}cyclohexyl)pyridin-2-amine;

6-chloro-N-[4-({4-[(cyclopentylmethyl)amino]cyclohexyl}methyl)cyclohexyl]-4-(5-methoxy-1H-pyrrolo[2,3-b]pyridin-3-yl)pyridin-2-amine;

trans-N-(6-chloro-4-{5-[2-(pyridin-2-yl)ethoxy]-1H-pyrrolo[2,3-b]pyridin-3-yl}pyridin-2-yl)cyclohexane-1,4-diamine;

trans-N-{6-chloro-4-[5-(2-methylpropoxy)-1H-pyrrolo[2,3-b]pyridin-3-yl]pyridin-2-yl}cyclohexane-1,4-diamine;

N-(trans-4-{[6-chloro-4-(1H-pyrrolo[2,3-b]pyridin-3-yl)pyridin-2-yl]amino}cyclohexyl)-1-(pyridin-2-ylmethyl)azetidine-3-carboxamide;

N-(trans-4-{[6-chloro-4-(5-methoxy-1H-pyrrolo[2,3-b]pyridin-3-yl)pyridin-2-yl]amino}cyclohexyl)-2,2,2-trifluoroacetamide;

6-chloro-N-cyclohexyl-4-[5-(6-methoxypyridin-3-yl)-1H-pyrrolo[2,3-b]pyridin-3-yl]pyridin-2-amine;

N-(trans-4-{[6-chloro-4-(5-methoxy-1H-pyrrolo[2,3-b]pyridin-3-yl)pyridin-2-yl]amino}cyclohexyl)-$N^2$-ethyl-$N^2$-(2-hydroxyethyl)glycinamide;

N-(trans-4-{[6-chloro-4-(5-methoxy-1H-pyrrolo[2,3-b]pyridin-3-yl)pyridin-2-yl]amino}cyclohexyl)-$N^2$-(2-hydroxyethyl)glycinamide;

N'-[6-chloro-4-(1H-pyrrolo[2,3-b]pyridin-3-yl)pyridin-2-yl]-N,N-dimethylbenzene-1,4-diamine;

6-chloro-N-(2,3-dihydro-1H-inden-5-yl)-4-(1H-pyrrolo[2,3-b]pyridin-3-yl)pyridin-2-amine;

6-chloro-N-(2,3-dihydro-1,4-benzodioxin-6-yl)-4-(1H-pyrrolo[2,3-b]pyridin-3-yl)pyridin-2-amine;

6-chloro-N-{4-[1-(2,4-difluorobenzyl)piperidin-4-yl]cyclohexyl}-4-(5-methoxy-1H-pyrrolo[2,3-b]pyridin-3-yl)pyridin-2-amine;

6-chloro-N-[4-(morpholin-4-yl)phenyl]-4-(1H-pyrrolo[2,3-b]pyridin-3-yl)pyridin-2-amine;

6-chloro-4-(1H-pyrrolo[2,3-b]pyridin-3-yl)-N-(5,6,7,8-tetrahydronaphthalen-1-yl)pyridin-2-amine;

N-(4-tert-butylphenyl)-6-chloro-4-(1H-pyrrolo[2,3-b]pyridin-3-yl)pyridin-2-amine;

6-chloro-N-(2,3-dihydro-1H-inden-4-yl)-4-(1H-pyrrolo[2,3-b]pyridin-3-yl)pyridin-2-amine;

N-[6-chloro-4-(1H-pyrrolo[2,3-b]pyridin-3-yl)pyridin-2-yl]quinolin-6-amine;

6-chloro-N-[4-(4-methylpiperazin-1-yl)phenyl]-4-(1H-pyrrolo[2,3-b]pyridin-3-yl)pyridin-2-amine;

6-chloro-N-[4-(1,1-dioxidothiomorpholin-4-yl)phenyl]-4-(1H-pyrrolo[2,3-b]pyridin-3-yl)pyridin-2-amine;

N-(trans-4-{[6-chloro-4-(5-methoxy-1H-pyrrolo[2,3-b]pyridin-3-yl)pyridin-2-yl]amino}cyclohexyl)-$N^2$-(trans-4-hydroxycyclohexyl)glycinamide;

N-(trans-4-{[6-chloro-4-(5-methoxy-1H-pyrrolo[2,3-b]pyridin-3-yl)pyridin-2-yl]amino}cyclohexyl)-$N^2$-propan-2-ylglycinamide;

N-{4-[(4-{[6-chloro-4-(5-methoxy-1H-pyrrolo[2,3-b]pyridin-3-yl)pyridin-2-yl]amino}cyclohexyl)methyl]cyclohexyl}-3,5-dimethyl-1,2-oxazole-4-sulfonamide;

N-(3-{[6-chloro-4-(5-methoxy-1H-pyrrolo[2,3-b]pyridin-3-yl)pyridin-2-yl]amino}cyclohexyl)-$N^2,N^2$-dimethylglycinamide;

6-chloro-N-{4-[4-(pyridin-2-ylmethyl)piperazin-1-yl]phenyl}-4-(1H-pyrrolo[2,3-b]pyridin-3-yl)pyridin-2-amine;

6-chloro-N-{4-[4-(cyclohexylmethyl)piperazin-1-yl]phenyl}-4-(1H-pyrrolo[2,3-b]pyridin-3-yl)pyridin-2-amine;

6-chloro-N-{4-[4-(2-methylpropyl)piperazin-1-yl]phenyl}-4-(1H-pyrrolo[2,3-b]pyridin-3-yl)pyridin-2-amine;

N-[trans-4-({4-[5-(6-aminopyridin-3-yl)-1H-pyrrolo[2,3-b]pyridin-3-yl]-6-chloropyridin-2-yl}amino)cyclohexyl]cyclopropanesulfonamide;

N-[trans-4-({6-chloro-4-[5-(pyridin-3-yl)-1H-pyrrolo[2,3-b]pyridin-3-yl]pyridin-2-yl}amino)cyclohexyl]cyclopropanesulfonamide;

3-{3-[2-chloro-6-({trans-4-[(cyclopropylsulfonyl)amino]cyclohexyl}amino)pyridin-4-yl]-1H-pyrrolo[2,3-b]pyridin-5-yl}benzenesulfonamide;

N-[trans-4-({6-chloro-4-[5-(pyrimidin-5-yl)-1H-pyrrolo[2,3-b]pyridin-3-yl]pyridin-2-yl}amino)cyclohexyl]cyclopropanesulfonamide;

4-chloro-N-[(1R)-1-phenylethyl]-6-(1H-pyrrolo[2,3-b]pyridin-3-yl)pyrimidin-2-amine;

3-({[4-chloro-6-(1H-pyrrolo[2,3-b]pyridin-3-yl)pyrimidin-2-yl]amino}methyl)phenol;

4-({[4-chloro-6-(1H-pyrrolo[2,3-b]pyridin-3-yl)pyrimidin-2-yl]amino}methyl)phenol;

N'-[4-chloro-6-(1H-pyrrolo[2,3-b]pyridin-3-yl)pyrimidin-2-yl]-N,N-dimethylcyclohexane-1,4-diamine;

N'-[4-chloro-6-(1H-pyrrolo[2,3-b]pyridin-3-yl)pyrimidin-2-yl]-N,N-dimethylcyclohexane-1,3-diamine;

N-(trans-4-{[4-chloro-6-(1H-pyrrolo[2,3-b]pyridin-3-yl)pyrimidin-2-yl]amino}cyclohexyl)-$N^2,N^2$-dimethylglycinamide;

N-(trans-4-{[4-chloro-6-(1H-pyrrolo[2,3-b]pyridin-3-yl)pyrimidin-2-yl]amino}cyclohexyl)-1-ethylpyrrolidine-3-carboxamide;

N-(3-{[4-chloro-6-(1H-pyrrolo[2,3-b]pyridin-3-yl)pyrimidin-2-yl]amino}cyclohexyl)-$N^2,N^2$-dimethylglycinamide;

4-chloro-6-(1H-pyrrolo[2,3-b]pyridin-3-yl)pyrimidin-2-amine;

N-{4-[(4-aminocyclohexyl)methyl]cyclohexyl}-4-chloro-6-(1H-pyrrolo[2,3-b]pyridin-3-yl)pyrimidin-2-amine;

N-[4-chloro-6-(1H-pyrrolo[2,3-b]pyridin-3-yl)pyrimidin-2-yl]ethane-1,2-diamine;

2-{[4-chloro-6-(1H-pyrrolo[2,3-b]pyridin-3-yl)pyrimidin-2-yl]amino}ethanol;

N-{2-[2-(2-aminoethoxy)ethoxy]ethyl}-4-chloro-6-(1H-pyrrolo[2,3-b]pyridin-3-yl)pyrimidin-2-amine;

1-(trans-4-{[4-chloro-6-(1H-pyrrolo[2,3-b]pyridin-3-yl)pyrimidin-2-yl]amino}cyclohexyl)-3-ethylurea;

1-(trans-4-{[4-chloro-6-(1H-pyrrolo[2,3-b]pyridin-3-yl)pyrimidin-2-yl]amino}cyclohexyl)-3-cyclopentylurea;

1-(trans-4-{[4-chloro-6-(1H-pyrrolo[2,3-b]pyridin-3-yl)pyrimidin-2-yl]amino}cyclohexyl)-3-[4-(dimethylamino)phenyl]urea;

N-(trans-4-{[4-chloro-6-(1H-pyrrolo[2,3-b]pyridin-3-yl)pyrimidin-2-yl]amino}cyclohexyl)-2-(1,3-dioxo-1,3-dihydro-2H-isoindol-2-yl)acetamide;

N-(trans-4-{[4-chloro-6-(1H-pyrrolo[2,3-b]pyridin-3-yl)pyrimidin-2-yl]amino}cyclohexyl)-2-oxoimidazolidine-1-carboxamide;

2-(2-{[4-chloro-6-(1H-pyrrolo[2,3-b]pyridin-3-yl)pyrimidin-2-yl]amino}ethoxy)ethanol;

N-[2-(2-aminoethoxy)ethyl]-4-chloro-6-(1H-pyrrolo[2,3-b]pyridin-3-yl)pyrimidin-2-amine;

trans-N-[4-chloro-6-(1H-pyrrolo[2,3-b]pyridin-3-yl)pyrimidin-2-yl]-N'-(2-methylpropyl)cyclohexane-1,4-diamine;

trans-N-[4-chloro-6-(1H-pyrrolo[2,3-b]pyridin-3-yl)pyrimidin-2-yl]-N'-cyclopentylcyclohexane-1,4-diamine;

N-(trans-4-{[4-chloro-6-(1H-pyrrolo[2,3-b]pyridin-3-yl)pyrimidin-2-yl]amino}cyclohexyl)-$N^2$-cyclopentylglycinamide;

N-(trans-4-{[4-chloro-6-(1H-pyrrolo[2,3-b]pyridin-3-yl)pyrimidin-2-yl]amino}cyclohexyl)propane-1-sulfonamide;

N-(trans-4-{[4-chloro-6-(1H-pyrrolo[2,3-b]pyridin-3-yl)pyrimidin-2-yl]oxy}cyclohexyl)acetamide;

N-(trans-4-{[4-chloro-6-(1H-pyrrolo[2,3-b]pyridin-3-yl)pyrimidin-2-yl]amino}cyclohexyl)thiophene-3-sulfonamide;

N-(trans-4-{[4-chloro-6-(1H-pyrrolo[2,3-b]pyridin-3-yl)pyrimidin-2-yl]amino}cyclohexyl)thiophene-2-sulfonamide; and 3-{[4-chloro-6-(1H-pyrrolo[2,3-b]pyridin-3-yl)pyrimidin-2-yl]amino}-2,2-dimethylpropan-1-ol.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl(phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The present compounds may be prepared by a variety of processes well known for the preparation of compounds of this class. For example, the compounds of formula (I) wherein the groups X, Y, $R^1$, $R^2$, $R^3$, $R^4$, and n have the meanings as set forth in the summary unless otherwise noted, can be synthesized according to the general methods described in Schemes 1-4, using appropriate starting materials by methods generally available to one of ordinary skill in the art.

Abbreviations which have been used in the descriptions of the Schemes and the Examples that follow are: DMF for N,N-dimethylformamide, DMSO for dimethyl sulfoxide, DMSO-$d_6$ for deuteriated dimethyl sulfoxide, DME for dimethoxyethane, dppf for 1,1'-bis(diphenylphosphino)ferrocene, $Et_2O$ for diethyl ether, EtOAc for ethyl acetate, $Et_3N$ for triethylamine, Ts for toluene sulfonyl, and THF for tetrahydrofuran.

Scheme 1

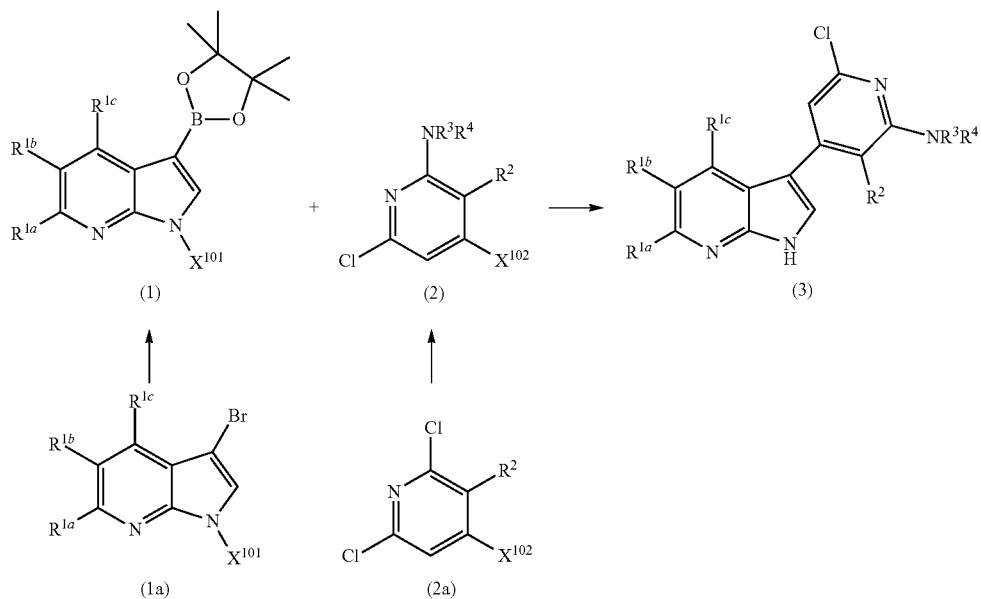

Azaindoles of formula (1) wherein $X^{101}$ is Ts or benzene sulfonyl can be treated with pyridines of formula (2) wherein $X^{102}$ is iodo or bromo to provide compounds of general formula (I) wherein X is $CR^2$ and Y is $NR^3R^4$ as shown in Scheme 1. This reaction may be performed in the presence of a palladium catalyst and a base at elevated temperature (e.g. at about 70° C. to about 150° C.) and in a suitable solvent such as DMF, dioxane, ethanol, water, DME, or mixtures thereof, and optionally under microwave irradiation. Non limiting examples of suitable palladium catalysts include dichlorobis (triphenylphosphine) palladium (II), $PdCl_2(dppf)_2$, and tetrakis(triphenylphosphine) palladium. Suitable bases include, but are not limited to, sodium carbonate, potassium acetate, cesium carbonate. In certain cases, the protecting group $X^{101}$ of the azaindole obtained may be spontaneously removed during the reaction. In other cases, it may be beneficial to treat the crude material with potassium hydroxide or sodium hydroxide in an alcoholic solvent such as methanol or a mixture of water and methanol, at about room temperature to about reflux temperature of the solvent employed.

Pyridines of formula (2) can be prepared by treating (2a) wherein $X^{102}$ is iodo, bromo, or chloro with amines of formula $N(H)R^3R^4$ or salt thereof. The reaction can be conducted in a suitable solvent (e.g. dioxane) or in excess of the amines employed, at a temperature from about 60° C. to about 150° C., optionally in the presence of a base (e.g. triethylamine, diisopropylethyl amine) and optionally under microwave irradiation.

The azaindoles of formula (1) can be prepared from the corresponding azaindoles by (a) brominating the corresponding azaindoles with a brominating agent such as, but not limited to, N-bromosuccinimide in a suitable solvent (e.g. THF); (2) protecting the product of step (a) with benzenesulfonyl chloride or tosyl chloride, in the presence of a base (e.g. sodium hydride, n-butyl lithium, sodium or potassium hydroxide) and in a suitable solvent (e.g. DMF, THF) to provide compounds of formula (1a); and (3) treating (1a) with bis(pincolato)diboron in the presence of a palladium catalyst (e.g. dichlorobis (triphenylphosphine) palladium (II), $PdCl_2$ (dppf)) and a base (e.g. potassium acetate), at a temperature from about 70° C. to about 150° C., in a suitable solvent such as THF, and optionally under microwave irradiation.

Alternatively, compounds of general formula (1) wherein X is $CR^2$ and Y is $NR^3R^4$ can be synthesized as shown in Scheme 2.

Scheme 2

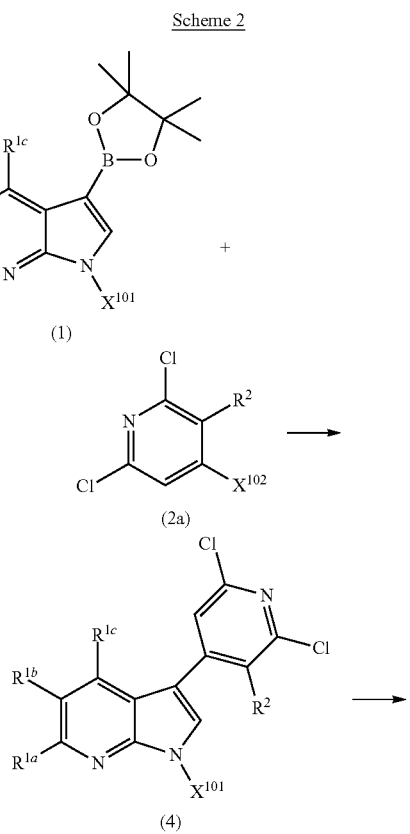

-continued

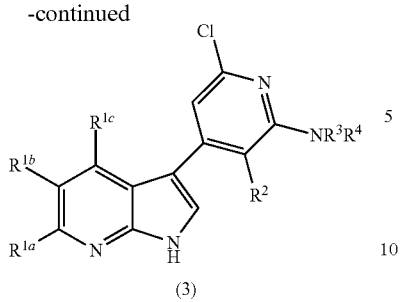

(3)

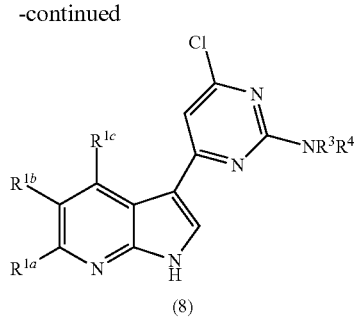

(8)

Compounds of formula (4) can be prepared by treating azaindoles of formula (1) with pyridines of formula (2a) wherein $X^{102}$ is bromo or iodo, using reaction conditions described for the transformation of (1) to (3) as described in Scheme 1.

Conversion of (4) to amines of formula (3) can be achieved either by utilizing again the reaction conditions as described for the transformation of (1) to (3), or by direct displacement of chloro with amines of formula $N(H)R^3R^4$ employing reaction conditions such as those described for the transformation of (2a) to (2).

Scheme (3) depicts general procedures for the synthesis of compounds of general formula (I) wherein X is N and Y is $NR^3R^4$.

Treatment of 4,6-dichloro-2-(methylthio)pyrimidine with compounds of formula (1) in the presence of a palladium catalyst (e.g. tetrakis(triphenylphosphine)palladium) and a base (e.g. $Cs_2CO_3$, $Na_2CO_3$), in a suitable solvent (e.g. DME, DMF, or mixtures thereof) and at temperature ranging from about 80° C. to about 150° C. provides compounds of formula (6).

Oxidation of the methylthio functionality with an oxidizing agent such as, but not limited to, OXONE® in a suitable solvent such as methanol/$H_2O$ or ethyl acetate/$H_2O$ provides compounds of formula (7).

Displacement of the methylsulfonyl group with amines of formula $N(H)R^3R^4$ can be accomplished by (a) utilizing reaction conditions as described for the transformation of (2a) to (2) in Scheme 1, and (b) treating the product of step (a) with sodium hydroxide or potassium hydroxide in an alcoholic solvent such as methanol.

Scheme (4) depicts an additional procedure for the synthesis of compounds of general formula (I) wherein X is N and Y is $NR^3R^4$.

Scheme 3

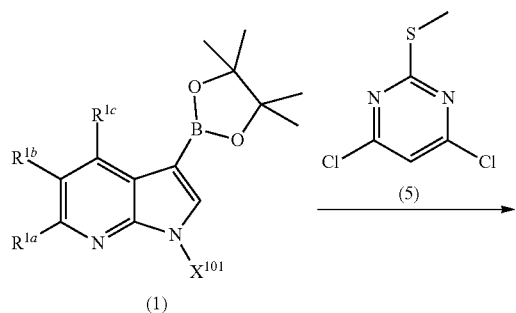

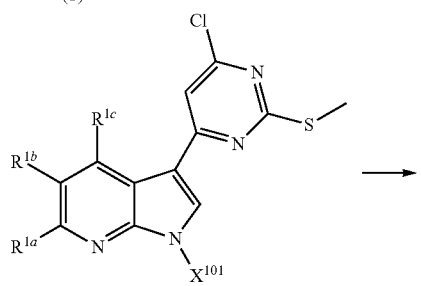

(6)

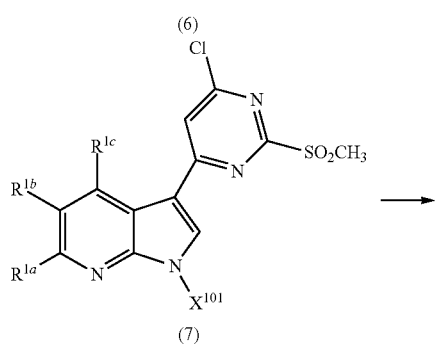

(7)

Scheme 4

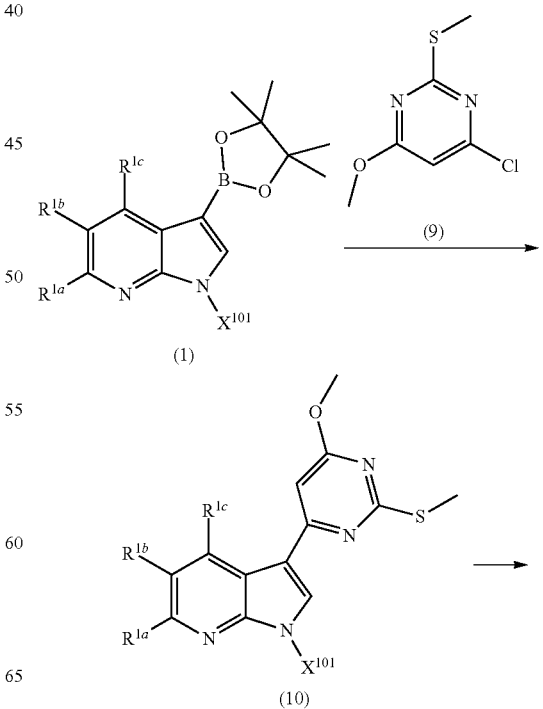

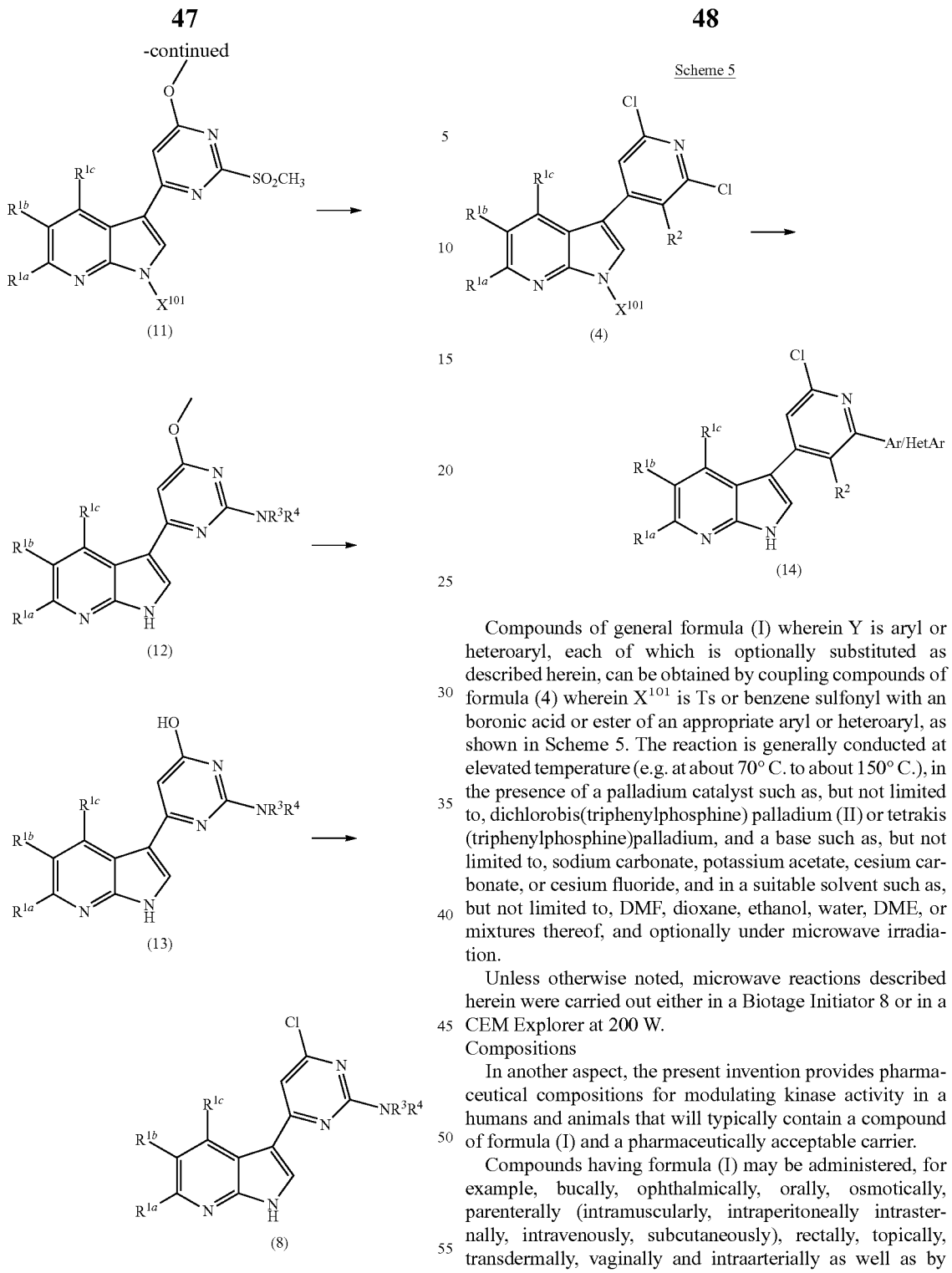

Compounds of formula (8) can be prepared by treating azaindoles of formula (1) with pyridines of formula (9) using reaction conditions described for the transformation of (1) to (3) as described in Scheme 3. Hydrolysis of the methoxy functionality with a base in a suitable solvent provides compounds of formula (13).

Compounds of formula (8) can be prepared from compounds of formula (13) by a substitution reaction with a halogenating agent such as, but not limited to, phosphoryl trichloride.

Compounds of general formula (I) wherein Y is aryl or heteroaryl, each of which is optionally substituted as described herein, can be obtained by coupling compounds of formula (4) wherein $X^{101}$ is Ts or benzene sulfonyl with an boronic acid or ester of an appropriate aryl or heteroaryl, as shown in Scheme 5. The reaction is generally conducted at elevated temperature (e.g. at about 70° C. to about 150° C.), in the presence of a palladium catalyst such as, but not limited to, dichlorobis(triphenylphosphine) palladium (II) or tetrakis (triphenylphosphine)palladium, and a base such as, but not limited to, sodium carbonate, potassium acetate, cesium carbonate, or cesium fluoride, and in a suitable solvent such as, but not limited to, DMF, dioxane, ethanol, water, DME, or mixtures thereof, and optionally under microwave irradiation.

Unless otherwise noted, microwave reactions described herein were carried out either in a Biotage Initiator 8 or in a CEM Explorer at 200 W.

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperitoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all CDC-7 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having formula (I) are expected to be useful when used with: alkylating agents, angiogenesis inhibitors, antibodies, antimetabolites, antimitotics, antiproliferatives, other apoptosis promoters (for example, Bcl-xL, Bcl-w and Bfl-1) inhibitors, Bcr-Abl kinase inhibitors, BiTE (Bi-Specific T cell Engager) antibodies, aurora kinase inhibitors, biologic response modifiers, cyclin-dependent kinase inhibitors, cell cycle inhibitors, cyclooxygenase-2 inhibitors, DVD's, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAP's) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNA's), topoisomerase inhibitors, combinations thereof and the like.

A BiTE antibody is a bi-specific antibody that directs T-cells to attach cancer cells by simultaneously binding the two cells. The T-cell then attacks the target cancer cell. Exemplary BiTE antibodies include adecatumumab (Micromet MT201), blinatumomab (Micromet MT103) and the like.

SiRNA's are molecules having endogenous RNA bases or chemically modified nucleotides. The modifications shall not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides or a combination thereof. The siRNA can have varying lengths (10-200 bps) and structures (hairpins, single/double strands, bulges, nicks/gaps, mismatches) and processed in the cell to provide active gene silencing. In certain embodiments, a double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. The multivalent binding protein is preferably engineered to have the three or more antigen binding sites and is generally not a naturally occurring antibody. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific, i.e., capable of binding one antigen or multispecific, i.e., capable of binding two or more antigens. DVD binding proteins comprising two heavy chain DVD polypeptides and two light chain DVD polypeptides are referred to as DVD Ig. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TRE-ANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (metrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Aurora kinase inhibitors include AZD-1152, MLN-8054, VX-680, ABT-348 and the like.

Bcl-2 proteins inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like. Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of apoptosis proteins include ApoMab (a fully human affinity-matured IgG1 monoclonal antibody), antibodies that target TRAIL or death receptors (e.g., pro-apoptotic receptor agonists DR4 and DR5), conatumumab, ETR2-ST01, GDC0145, (lexatumumab), HGS-1029, LBY-135, PRO-1762 and tratuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE®

(naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, TSP-1 and the like. VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like. Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds of this invention can also be used as radiosensitizeser that enhance the efficacy of radiotherapy. Examples of radiotherapy include external beam radiotherapy, teletherapy, brachtherapy and sealed, unsealed source radiotherapy and the like.

Additionally, compounds having formula (I) may be combined with other chemptherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®; P: prednisone), CYPAT™ (cyproterone acetate), combrestatin A4P, DAB (389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zoledronic acid), zorubicin and the like.

EXAMPLES

Example 1

6-Chloro-N-cyclohexyl-4-(1H-pyrrolo[2,3-b]pyridin-3-yl)pyridin-2-amine

Example 1a

3-Bromo-1H-pyrrolo[2,3-b]pyridine

To a solution of 1H-pyrrolo[2,3-b]pyridine (15.6 g, 132 mmol) in 400 mL tetrahydrofuran at −40° C. was added a suspension of N-bromosuccinimide in 120 mL tetrahydrofuran. Reaction mixture was warmed to room temperature and allowed to stir for 4 hours. Solid was filtered off. The reaction mixture was quenched with a sodium metabisulfite solution, and extracted with ethyl acetate. The combined organics were washed with brine, dried over MgSO$_4$, filtered, and concentrated. The residue was triturated with 1:1 hexane/ethyl acetate and filtered. The filtrate was concentrated and the trituration step was repeated three more times to afford a total of 25 g of the title compound, which was used without further purification. MS (DCI$^+$) m/z 196.9 (M+H)$^+$.

Example 1b

3-Bromo-1-(phenylsulfonyl)-1H-pyrrolo[2,3-b]pyridine

To a 0° C. solution of Example 1a (25 g, 127 mmol) in N,N-dimethylformamide (200 mL) was slowly added sodium hydride (3.37 g, 133 mmol) over several minutes. After stirring for 30 minutes in the cold water bath, benzenesulfonyl chloride (17.18 ml, 133 mmol) was added via a syringe. The solution was allowed to warm to room temperature overnight, quenched slowly with 500 mL water, stirred for 30 minutes, and then filtered. The solid obtained was washed with water, followed by 300 mL of hexanes, dried over high-vacuum for 16 hours to give 34 g of the title compound which was used without further purification. MS (ESI$^+$) m/z 338.7 (M+H)$^+$.

Example 1c 1-(Phenylsulfonyl)-3-(4,4,5,5-tetramethyl-1,3,2-dioxaborolan-2-yl)-1H-pyrrolo[2,3-b]pyridine A mixture of Example 1b (2.5 g, 7 mmol), dichlorobis(triphenylphosphine) palladium(II) (0.24 g, 0.29 mmol), bis(pinacolato)diboron (2.07 g, 8.15 mmol), and potassium acetate (2.18 g, 22 mmol) in degassed tetrahydrofuran (5 mL) was sealed and heated in a microwave (Biotage Initiator 8 or CEM Explorer at 200 W) at 140° C. for 20 minutes. The reaction mixture was cooled to room temperature, diluted with ethyl acetate, and washed with water. The aqueous layer was separated and extracted with dichloromethane. The combined organics were washed with brine, dried over MgSO$_4$, filtered, and concentrated. The residue was purified on silica gel using flash chromatography (20% ethyl acetate/hexane) to afford 1.9 g of the title compound as a solid. MS (ESI$^+$) m/z 385.0 (M+H)$^+$.

Example 1d

6-Chloro-N-cyclohexyl-4-iodopyridin-2-amine

To a solution of 2,6-dichloro-4-iodopyridine (0.1 g, 0.36 mmol) was added excess (1 mL) cyclohexylamine. The reaction mixture was heated at 150° C. in a microwave for 20 minutes. The reaction mixture was cooled to room temperature and diluted with ethyl acetate, at which time a white solid precipitated from the solution. The solid was filtered off and the organics were washed with sodium bicarbonate, water, brine, dried over MgSO$_4$, filtered, and concentrated. The residue was purified on silica gel by flash chromatography (gradient elution: 0% to 50% ethyl acetate/hexane) to afford the title compound as an oil. m/z 337.0 (DCI, M+H)$^+$.

Example 1e

6-Chloro-N-cyclohexyl-4-(1H-pyrrolo[2,3-b]pyridin-3-yl)pyridin-2-amine

A solution of Example 1c (0.103 g, 0.27 mmol), Example 1d (0.09 g, 0.27 mmol), catalytic dichlorobis(triphenylphosphine) palladium(II) and 1M sodium carbonate solution (267 L, 0.267 mmol) in 3 mL dimethoxyethane/ethanol/water (7:2:

3) was heated at 150° C. in a microwave for 15 minutes. The material was cooled to room temperature, diluted with ethyl acetate, washed with brine, dried over MgSO$_4$, filtered, and concentrated. The crude material was treated with potassium hydroxide (0.045 g, 0.8 mmol) in 3 mL methanol/water (5:1) at room temperature for 2 hours, diluted with ethyl acetate, washed with water, brine, dried over MgSO$_4$, filtered, and concentrated. The residue was purified on silica gel using flash chromatography (gradient elution: 10% to 100% ethyl acetate/hexane) to afford 39 mg of the title compound. $^1$H NMR (300 MHz, DMSO-d$_6$) ppm 1.11-1.45 (m, 5H) 1.49-1.63 (m, 1H) 1.63-1.81 (m, 2H) 1.81-2.04 (m, 2H) 3.51-3.83 (m, 1H) 6.75 (d, J=7.80 Hz, 1H) 6.81-6.92 (m, 2H) 7.21 (dd, J=8.14, 4.75 Hz, 1H) 8.11 (d, J=2.37 Hz, 1H) 8.26-8.35 (m, 2H) 12.13 (s, 1H). MS (DCI$^+$) m/z 327.1 (M+H)$^+$.

Example 2

N-Benzyl-6-chloro-4-(1H-pyrrolo[2,3-b]pyridin-3-yl)pyridin-2-amine

Example 2a

N-benzyl-6-chloro-4-iodopyridin-2-amine

Example 2a (1.8 g) was prepared as described in Example 1d, substituting cyclohexylamine with benzylamine MS (ESI$^+$) m/z 345.1 (M+H)$^+$.

Example 2b

N-Benzyl-6-chloro-4-(1H-pyrrolo[2,3-b]pyridin-3-yl)pyridin-2-amine

A solution of Example 1c (0.11 g, 0.284 mmol), Example 2a (0.093 g, 0.27 mmol), catalytic dichlorobis(triphenylphosphine) palladium(II) and 1M aqueous sodium carbonate (405 L, 0.405 mmol) in 2 mL dimethoxyethane/ethanol/water (7:2:3) was heated at 150° C. in a microwave for 15 minutes. The material was cooled to room temperature, diluted with ethyl acetate, washed with brine, dried over MgSO$_4$, filtered, and concentrated. The residue was purified on silica gel using flash chromatography (gradient elution: 10% to 65% ethyl acetate/hexane) to afford 30 mg of the title product. $^1$H NMR (300 MHz, DMSO-d$_6$) ppm 4.49 (d, J=6.10 Hz, 2H) 6.87 (s, 1H) 6.93 (d, J=1.36 Hz, 1H) 7.17 (dd, J=7.97, 4.58 Hz, 1H) 7.21-7.30 (m, 1H) 7.31-7.44 (m, 5H) 8.12 (s, 1H) 8.16 (d, J=7.12 Hz, 1H) 8.29 (dd, J=4.75, 1.36 Hz, 1H) 12.14 (s, 1H). MS (ESI$^+$) m/z 334.9 (M+H)$^+$.

Example 3

N-Allyl-6-chloro-4-(1H-pyrrolo[2,3-b]pyridin-3-yl)pyridin-2-amine

Example 3a

N-allyl-6-chloro-4-iodopyridin-2-amine

Example 3a (0.114 g) was prepared as described in Example 1d, substituting cyclohexylamine with allylamine MS (DCI$^+$) m/z 249.9 (M+H)$^+$.

Example 3b

N-allyl-6-chloro-4-(1H-pyrrolo[2,3-b]pyridin-3-yl)pyridin-2-amine

Example 3b (0.02 g) was prepared as described in Example 1e, substituting Example 1d with Example 3a. $^1$H NMR (300 MHz, DMSO-d$_6$) ppm 3.80-4.04 (m, 2H) 5.03-5.18 (m, 1H) 5.18-5.33 (m, 1H) 5.77-6.08 (m, 1H) 6.82-6.97 (m, 2H) 7.02 (t, J=5.76 Hz, 1H) 7.21 (dd, J=7.80, 5.09 Hz, 1H) 8.13 (s, 1H) 8.25-8.36 (m, 2H) 12.15 (s, 1H). MS (ESI$^+$) m/z 284.9 (M+H)$^+$.

Example 4

3-(2-chloro-6-piperidin-1-ylpyridin-4-yl)-1H-pyrrolo[2,3-b]pyridine

Example 4a 2-chloro-4-iodo-6-(piperidin-1-yl)pyridine

Example 4a (0.12 g) was prepared as described in Example 1d, substituting cyclohexylamine with piperidine. MS (DCI$^+$) m/z 323.0 (M+H)$^+$.

Example 4b 3-(2-chloro-6-piperidin-1-ylpyridin-4-yl)-1H-pyrrolo[2,3-b]pyridine

Example 4b (0.06 g) was prepared as described in Example 2b, substituting Example 2a with Example 4a. $^1$H NMR (300 MHz, DMSO-d$_6$) ppm 1.44-1.76 (m, 6H) 3.50-3.68 (m, 4H) 6.98 (d, J=2.71 Hz, 2H) 7.20 (dd, J=7.80, 4.75 Hz, 1H) 8.21 (s, 1H) 8.28-8.32 (m, 1H) 8.32-8.34 (m, 1H) 12.18 (s, 1H). MS (ESI$^+$) m/z 312.9 (M+H)$^+$.

Example 5

N-benzyl-6-chloro-N-methyl-4-(1H-pyrrolo[2,3-b]pyridin-3-yl)pyridin-2-amine

Example 5a

N-benzyl-6-chloro-4-iodo-N-methylpyridin-2-amine

Example 5a (0.12 g) was prepared as described in Example 1d, substituting cyclohexylamine with N-methyl-1-phenyl-methanamine MS (DCI$^+$) m/z 359.0 (M+H)$^+$.

Example 5b

N-benzyl-6-chloro-N-methyl-4-(1H-pyrrolo[2,3-b]pyridin-3-yl)pyridin-2-amine

Example 5b (0.013 g) was prepared as described in Example 2b, substituting Example 2a with Example 5a. $^1$H NMR (300 MHz, DMSO-d$_6$) ppm 3.15 (s, 3H) 4.82 (s, 2H) 6.78 (s, 1H) 6.98 (s, 1H) 7.14 (dd, J=8.14, 4.75 Hz, 1H) 7.22-7.32 (m, 3H) 7.31-7.43 (m, 2H) 8.07 (d, J=6.78 Hz, 1H) 8.16 (d, J=3.05 Hz, 1H) 8.28 (dd, J=4.58, 1.53 Hz, 1H) 12.18 (s, 1H). MS (ESI$^+$) m/z 348.9 (M+H)$^+$.

Example 6

3-[2-chloro-6-(3,3-difluoroazetidin-1-yl)pyridin-4-yl]-1-1H-pyrrolo[2,3-b]pyridine Example 6a 2-chloro-6-(3,3-difluoroazetidin-1-yl)-4-iodopyridine To a suspension of 2,6-dichloro-4-iodopyridine (1 g, 3.65 mmol) and 3,3-difluoroazetidine hydrochloric acid salt (0.497 g, 3.83 mmol) in 25 mL tetrahydrofuran was added diisopropylethylamine (0.797 ml, 4.56 mmol). The reaction mixture was heated at 90° C. for 16 hours. Further addition of another equivalent of amine and base was performed, and the suspension was heated at 100° C. for several hours, and then cooled, diluted with ethyl acetate, washed with water, brine, dried over MgSO$_4$, filtered, and concentrated. The residue was purified on silica gel using flash chromatography (5% to 20% ethyl acetate/hexane) to afford 0.6 g of the title compound. MS (DCI$^+$) m/z 331.0 (M+H)$^+$.

Example 6b

3-[2-chloro-6-(3,3-difluoroazetidin-1-yl)pyridin-4-yl]-1-1H-pyrrolo[2,3-b]pyridine Example 6b was prepared as described in Example 2b, substituting Example 2a with Example 6a, and triturating the crude material with dichloromethane to give 0.03 g of the title compound. $^1$H NMR (300 MHz, DMSO-d$_6$) ppm 4.49 (t, J=12.38 Hz, 4H) 6.81 (d, J=1.36 Hz, 1H) 7.11-7.31 (m, 2H) 8.24 (s, 1H) 8.31 (dd, J=4.58, 1.53 Hz, 1H) 8.40 (dd, J=7.97, 1.53 Hz, 1H) 12.25 (s, 1H). MS (ESI$^+$) m/z 320.9 (M+H)$^+$.

Example 7

3-[2-chloro-6-(2,3-dimethylphenyl)pyridin-4-yl]-1H-pyrrolo[2,3-b]pyridine

Example 7a 3-(2,6-dichloropyridin-4-yl)-1-(phenyl sulfonyl)-1H-pyrrolo[2,3-b]pyridine To a solution of 2,6-dichloro-4-iodopyridine (5 g, 18.26 mmol) and Example 1c (7.7 g, 20.1 mmol) in 50 mL dimethoxyethane/water (8:2) was added dichlorobis(triphenylphosphine) palladium(II) (0.64 g, 0.91 mmol) and 14.6 mL of 1M aqueous sodium carbonate. The resulting solution was heated at 80° C. for 16 hours, cooled, and diluted with ethyl acetate. The organics were washed with water, then both layers were filtered to give 6.1 g of the title compound. MS (ESI$^+$) m/z 403.9 (M+H)$^+$.

Example 7b

3-[2-chloro-6-(2,3-dimethylphenyl)pyridin-4-yl]-1H-pyrrolo[2,3-b]pyridine

To a solution of Example 7a (0.08 g, 0.2 mmol), in 2 mL dimethoxyethane/ethanol/water (7:2:3) was added 2,3-dimethylphenylboronic acid (0.036 g, 0.27 mmol), catalytic dichlorobis(triphenylphosphine) palladium(II) and 0.297 mL of 1M aqueous sodium carbonate. The contents were heated at 150 degrees for 30 minutes in a microwave. The reaction was diluted with ethyl acetate and washed with brine, dried over MgSO$_4$, filtered, and concentrated. The residue was purified on silica gel using flash chromatography (gradient elution, ethyl acetate/hexane 0-50%). The material obtained (35 mg) after concentration of the fractions was purified by preparative HPLC on a Phenomenex Luna C8(2) 5 µm 100 Å AXIA column (30 mm×75 mm), eluting with a gradient of acetonitrile (A) and 0.1% trifluoroacetic acid in water (B), at a flow rate of 50 mL/min (0-0.5 min 10% A, 0.5-7.0 min linear gradient 10-95% A, 7.0-10.0 min 95% A, 10.0-12.0 min linear gradient 95-10% A) to give 9 mg of the title compound. $^1$H NMR (300 MHz, DMSO-d$_6$) ppm 2.19-2.27 (m, 3H) 2.33 (s, 3H) 6.94-7.53 (m, 4H) 7.80 (d, J=9.52 Hz, 2H) 8.19-8.55 (m, 3H) 12.36 (s, 1H). MS (ESI$^+$) m/z 333.9 (M+H)$^+$.

Example 8

6-chloro-4-(1H-pyrrolo[2,3-b]pyridin-3-yl)-N-tetrahydro-2H-pyran-4-ylpyridin-2-amine Example 7a (0.1 g, 0.25 mmol) was heated at 150° C. for 30 minutes in a microwave in the presence of tetrahydro-2H-pyran-4-amine (0.075 g, 0.742 mmol). The resulting material was cooled, diluted with ethyl acetate, washed with saturated sodium bicarbonate, water, and brine, dried over MgSO$_4$, filtered, and concentrated. The residue was purified on silica gel using flash chromatography (gradient elution: 10-60% ethyl acetate/hexane) to afford 6.8 mg of the title compound. $^1$H NMR (300 MHz, DMSO-d$_6$) ppm 1.32-1.60 (m, 2H) 1.76-2.05 (m, 2H) 3.34-3.56 (m, 2H) 3.71-4.00 (m, 3H) 6.84-6.96 (m, 3H) 7.21 (dd, J=7.93, 4.76 Hz, 1H) 8.13 (d, J=2.78 Hz, 1H) 8.26-8.37 (m, 2H) 12.15 (s, 1H). MS (ESI$^+$) m/z 328.9 (M+H)$^+$.

Example 9

2-{[6-chloro-4-(1H-pyrrolo[2,3-b]pyridin-3-yl)pyridin-2-yl]amino}cyclohexanol

Example 9 was prepared as described in Example 8, substituting tetrahydro-2H-pyran-4-amine with 2-aminocyclohexanol, and triturating the crude material with dichloromethane to give 0.03 g of the title compound. $^1$H NMR (300 MHz, DMSO-d$_6$) ppm 1.20-1.43 (m, 3H) 1.45-1.70 (m, 5H) 1.72 (s, 1H) 3.85 (s, 1H) 4.61 (d, J=3.97 Hz, 1H) 6.57 (d, J=7.93 Hz, 1H) 6.87 (s, 1H) 7.05 (s, 1H) 7.20 (dd, J=8.13, 4.56 Hz, 1H) 8.13 (d, J=2.78 Hz, 1H) 8.30 (d, J=4.36 Hz, 1H) 8.41 (d, J=6.74 Hz, 1H) 12.13 (s, 1H). MS (ESI$^+$) m/z 343.0 (M+H)$^+$.

Example 10

6-chloro-N-(2-methoxyethyl)-4-(1H-pyrrolo[2,3-b]pyridin-3-yl)pyridin-2-amine

Example 10 (0.008 g) was prepared as described in Example 8, substituting tetrahydro-2H-pyran-4-amine with 2-methoxyethanamine $^1$H NMR (300 MHz, DMSO-d$_6$) ppm 3.30 (s, 3H) 3.37-3.59 (m, 4H) 6.83-7.02 (m, 3H) 7.21 (dd, J=7.93, 4.76 Hz, 1H) 8.14 (s, 1H) 8.22-8.41 (m, 2H) 12.15 (s, 1H). MS (ESI$^+$) m/z 302.9 (M+H)$^+$.

Example 11

2-{[6-chloro-4-(1H-pyrrolo[2,3-b]pyridin-3-yl)pyridin-2-yl]amino}ethanol

Example 11 (0.03 g) was prepared as described in Example 8, substituting tetrahydro-2H-pyran-4-amine with 2-aminoethanol. $^1$H NMR (300 MHz, DMSO-d$_6$) ppm 3.32-3.41 (m, 2H) 3.56 (q, J=5.76 Hz, 2H) 4.73 (t, J=5.43 Hz, 1H) 6.90 (t, J=10.17 Hz, 3H) 7.20 (dd, J=7.80, 4.75 Hz, 1H) 8.13 (s, 1H) 8.24-8.41 (m, 2H) 12.14 (s, 1H). MS (ESI$^+$) m/z 288.9 (M+H)$^+$.

Example 12

6-chloro-N,N-bis(2-methoxyethyl)-4-(1H-pyrrolo[2,3-b]pyridin-3-yl)pyridin-2-amine Example 12 was prepared as described in Example 8, substituting tetrahydro-2H-pyran-4-amine with bis-(2-methoxyethyl)amine, and treating the crude material with potassium hydroxide (10 eq) in ethanol/water (5 mL, 5:1) at 40° C. for 1 hour, prior to purification, to give 0.035 g of the title compound. $^1$H NMR (300 MHz, DMSO-d$_6$) ppm 3.29 (s, 6H) 3.55 (t, J=5.75 Hz, 4H) 3.72 (t, J=5.55 Hz, 4H) 6.93 (d, J=9.12 Hz, 2H) 7.20 (dd, J=7.54, 5.16 Hz, 1H) 8.17 (d, J=2.78 Hz, 1H) 8.25-8.37 (m, 2H) 12.18 (s, 1H). MS (ESI$^+$) m/z 288.9 (M+H)$^+$.

Example 13

6-chloro-4-(1H-pyrrolo[2,3-b]pyridin-3-yl)-N-(tetrahydrofuran-2-ylmethyl)pyridin-2-amine Example 13 was prepared as described in Example 8 substituting tetrahydro-2H-pyran-4-amine with (tetrahydrofuran-2-yl)methanamine, and treating the crude material with potassium hydroxide (10 eq) in ethanol/water (5 mL, 5:1) at 40° C. for 1 hour, prior to purification, to give 0.055 g of the title compound. $^1$H NMR (300 MHz, DMSO-d$_6$) ppm 1.47-1.68 (m, 1H) 1.74-1.99 (m, 3H) 3.33-3.49 (m, 2H) 3.56-3.75 (m, 1H) 3.75-3.91 (m, 1H) 3.91-4.12 (m, 1H) 6.88-6.96 (m, 2H) 7.00 (s, 1H) 7.21 (dd, J=7.93, 4.76 Hz, 1H) 8.14 (d, J=2.78 Hz, 1H) 8.22-8.46 (m, 2H) 12.14 (s, 1H). m/z 328.9 (ESI, M+H)$^+$.

Example 14

Trans 4-{[6-chloro-4-(1H-pyrrolo[2,3-b]pyridin-3-yl)pyridin-2-yl]amino}cyclohexanol Example 14 (0.03 g) was prepared as described in Example 8, substituting tetrahydro-2H-pyran-4-amine with trans-4-aminocyclohexanol. $^1$H NMR (300 MHz, DMSO-d$_6$) ppm 0.99-1.48 (m, 4H) 1.74-2.05 (m, 4H) 3.44 (dd, J=9.32, 4.92 Hz, 1H) 3.52-3.77 (m, 1H) 4.53 (d, J=4.07 Hz, 1H) 6.71 (d, J=7.80 Hz, 1H) 6.85 (d, J=3.39 Hz, 2H) 7.20 (dd, J=7.46, 5.09 Hz, 1H) 8.12 (d, J=2.03 Hz, 1H) 8.21-8.51 (m, 2H) 12.13 (s, 1H). MS (ESI$^+$) m/z 343.0 (M+H)$^+$.

Example 15

N-[6-chloro-4-(1H-pyrrolo[2,3-b]pyridin-3-yl)pyridin-2-yl]cyclohexane-1,4-diamine Example 15 (0.025 g) was prepared as described in Example 8, substituting tetrahydro-2H-pyran-4-amine with cyclohexane-1,4-diamine. $^1$H NMR (300 MHz, DMSO-d$_6$) ppm 1.01-1.33 (m, 4H) 1.70-1.87 (m, 2H) 1.88-2.02 (m 2H) 2.50-2.62 (m, 1H) 3.58 (d, 1H) 6.70 (d, J=7.80 Hz, 1H) 6.77-6.90 (m, 2H) 7.19 (dd, J=7.46, 5.09 Hz, 1H) 8.07-8.13 (m, 1H) 8.21-8.37 (m, 2H). MS (ESI$^+$) m/z 342.0 (M+H)$^+$.

Example 16

6-chloro-N-(2-methoxycyclohexyl)-4-(1H-pyrrolo[2,3-b]pyridin-3-yl)pyridin-2-amine Example 16 was prepared as described in Example 8, substituting tetrahydro-2H-pyran-4-amine with 2-methoxycyclohexanamine, and treating the crude material with potassium hydroxide (10 eq) in ethanol/water (5 mL, 5:1) at 40° C. for 1 hour, prior to purification, to give 0.033 g of the title compound. $^1$H NMR (300 MHz, DMSO-d$_6$) ppm 1.26-1.75 (m, 6H) 1.94 (d, J=6.44 Hz, 1H) 3.25-3.29 (m, 3H) 3.39-3.55 (m, 1H) 3.91-4.08 (m, 1H) 6.66 (d, J=8.48 Hz, 1H) 6.88 (d, J=1.36 Hz, 1H) 7.10 (s, 1H) 7.20 (dd, J=7.97, 4.58 Hz, 1H) 7.86-7.97 (m, 1H) 8.13 (d, J=2.71 Hz, 1H) 8.30 (dd, J=4.58, 1.53 Hz, 1H) 8.36-8.48 (m, 1H) 12.12 (s, 1H). MS (ESI$^+$) m/z 357.0 (M+H)$^+$.

Example 17

N-[6-chloro-4-(1H-pyrrolo[2,3-b]pyridin-3-yl)pyridin-2-yl]cyclohexane-1,2-diamine Example 17 (0.015 g) was prepared as described in Example 8, substituting tetrahydro-2H-pyran-4-amine with cyclohexane-1,2-diamine. $^1$H NMR (300 MHz, DMSO-d$_6$) ppm 1.20-1.42 (m, 3H) 1.41-1.72 (m, 4H) 1.73-1.96 (m, 2H) 2.66-2.85 (m, 1H) 3.02 (d, J=3.39 Hz, 1H) 3.79-3.96 (m, 1H) 6.56-6.81 (m, 1H) 6.83-7.06 (m, 2H) 7.21 (dd, J=7.80, 4.75 Hz, 1H) 8.07-8.17 (m, 1H) 8.24-8.44 (m, 2H) 11.53-12.57 (m, 1H). MS (ESI$^+$) m/z 342.0 (M+H)$^+$.

Example 18

1-{[6-chloro-4-(1H-pyrrolo[2,3-b]pyridin-3-yl)pyridin-2-yl]amino}-2-methylpropan-2-ol Example 18 was prepared as described in Example 8, substituting tetrahydro-2H-pyran-4-amine with 1-amino-2-methylpropan-2-ol, treating the crude material with potassium hydroxide (10 eq) in ethanol/water (5 mL, 5:1) at 40° C. for 1 hour, prior to purification, to give 0.025 g of the title compound. $^1$H NMR (300 MHz, DMSO-d$_6$) ppm 0.95-1.33 (m, 6H) 3.13-3.32 (m, 2H) 4.55 (s, 1H) 6.74 (t, J=5.55 Hz, 1H) 6.89 (s, 1H) 7.08 (s, 1H) 7.20 (dd, J=8.13, 4.56 Hz, 1H) 8.14 (s, 1H) 8.30 (d, J=4.76 Hz, 1H) 8.40 (d, J=6.74 Hz, 1H) 12.14 (s, 1H). MS (ESI$^+$) m/z 317.0 (M+H)$^+$.

Example 19

4-{[6-chloro-4-(1H-pyrrolo[2,3-b]pyridin-3-yl)pyridin-2-yl]amino}butan-1-ol

Example 19 (0.03 g) was prepared as described in Example 8, substituting tetrahydro-2H-pyran-4-amine with 4-aminobutan-1-ol. $^1$H NMR (300 MHz, DMSO-d$_6$) ppm 1.43-1.68 (m, 4H) 3.16-3.28 (m, 2H) 3.38-3.51 (m, 2H) 4.31-4.51 (m, 1H) 6.78-6.94 (m, 3H) 7.12-7.29 (m, 1H) 8.06-8.17 (m, 1H) 8.22-8.39 (m, 2H) 11.97-12.29 (m, 1H). MS (ESI$^+$) m/z 316.9 (M+H)$^+$.

Example 20

5-{[6-chloro-4-(1H-pyrrolo-2,3-b]pyridin-3-yl)pyridin-2-yl]amino}-2,2-dimethylpentan-1-ol Example 20 (0.04 g) was prepared as described in Example 8, substituting tetrahydro-2H-pyran-4-amine with 5-amino-2,2-dimethylpentan-1-ol. $^1$H NMR (300 MHz, DMSO-d$_6$) ppm 0.81 (s, 6H) 1.15-1.34 (m, 2H) 1.40-1.64 (m, 2H) 3.10 (t, J=5.59 Hz, 2H) 3.13-3.28 (m, 2H) 4.31-4.53 (m, 1H) 6.74-7.00 (m, 3H) 7.05-7.35 (m, 1H) 8.01-8.21 (m, 1H) 8.19-8.39 (m, 2H) 11.92-12.33 (m, 1H). MS (ESI$^+$) m/z 359.0 (M+H)$^+$.

Example 21

N-(4-{[6-chloro-4-(1H-pyrrolo[2,3-b]pyridin-3-yl)pyridin-2-yl]amino}cyclohexyl)methanesulfonamide To a solution of Example 15 (0.125 g, 0.366 mmol) in 2 mL of N,N-dimethyl acetamide was added diisopropylethylamine (0.095 g, 0.731 mmol) followed by methanesulfonyl chloride (0.052 g, 0.457 mmol). The reaction was heated at 50° C. for 2 hours, cooled, and diluted with ethyl acetate. The organics were washed with saturated NaHCO$_3$, brine, dried over MgSO$_4$, filtered, and concentrated. The residue was purified on silica gel using Flash chromatography (gradient elution, 0% to 10% methanol/dichloromethane) to afford 0.02 g of the title compound. $^1$H NMR (300 MHz, DMSO-d$_6$) ppm 1.07-1.54 (m, 4H) 1.73-2.12 (m, 4H) 2.81 (s, 3H) 3.47-3.68 (m, 1H) 6.77 (d, J=7.54 Hz, 1H) 6.86 (d, J=3.57 Hz, 2H) 7.01 (dd, J=15.07, 7.14 Hz, 2H) 7.21 (dd, J=7.73, 4.96 Hz, 1H) 8.12 (s, 1H) 8.24-8.37 (m, 2H) 12.14 (s, 1H). MS (ESI$^+$) m/z 420.0 (M+H)$^+$.

Example 22

N-(4-{[6-chloro-4-(1H-pyrrolo[2,3-b]pyridin-3-yl)pyridin-2-yl]-amino}cyclohexyl)acetamide Example 22 (0.014 g) was prepared as described in Example 21, substituting methanesulfonyl chloride with acetic anhydride. $^1$H NMR (300 MHz, DMSO-d$_6$) ppm 1.14-1.38 (m, 4H) 1.68-1.91 (m, 5H) 2.01 (s, 3H) 3.59 (d, J=36.88 Hz, 1H) 6.73-6.79 (m, 1H) 6.83-6.90 (m, 2H) 7.11-7.32 (m, 1H) 7.63-7.86 (m, 1H) 8.03-8.19 (m, 1H) 8.23-8.40 (m, 2H) 12.02-12.29 (m, 1H). MS (ESI$^+$) m/z 384.0 (M+H)$^+$.

Example 23

N-[6-chloro-4-(1H-pyrrolo[2,3-b]pyridin-3-yl)pyridin-2-yl]cyclohexane-1,3-diamine Example 23 (0.11 g) was prepared as described in Example 8, substituting tetrahydro-2H-pyran-4-amine with cyclohexane-1,3-diamine $^1$H NMR (300 MHz, DMSO-d$_6$) ppm 0.63-1.53 (m, 4H) 1.54-1.90 (m, 2H) 1.82-2.29 (m, 2H) 2.55-2.81 (m, 1H) 3.52-3.81 (m, 1H) 6.61-7.01 (m, 3H) 7.05-7.32 (m, 1H) 8.1 (s, 1H) 8.21-8.42 (m, 2H) 11.74-11.75 (brs, 1H). MS (ESI$^+$) m/z 342.0 (M+H)$^+$.

Example 24

N-(3-{[6-chloro-4-(1H-pyrrolo[2,3-b]pyridin-3-yl)pyridin-2-yl]-amino}cyclohexyl)methanesulfonamide Example 24 (0.03 g) was prepared as described in Example 21, substituting Example 15 with Example 23. $^1$H NMR (300 MHz, DMSO-d$_6$) ppm 0.86-1.50 (m, 4H) 1.61-2.01 (m, 4H) 2.13-2.35 (m, 1H) 2.93 (s, 3H) 3.73 (d, J=7.54 Hz, 1H) 6.69-7.00 (m, 3H) 7.09 (d, J=7.14 Hz, 1H) 7.21 (dd, J=7.54, 5.16 Hz, 1H) 8.13 (d, J=2.78 Hz, 1H) 8.21-8.42 (m, 2H) 12.14 (s, 1H). MS (ESI$^+$) m/z 419.9 (M+H)$^+$.

Example 25

6-chloro-4-(1H-pyrrolo[2,3-b]pyridin-3-yl)-N-(tetrahydro-2H-pyran-4-ylmethyl)pyridin-2-amine Example 25 (0.04 g) was prepared as described in Example 8, substituting tetrahydro-2H-pyran-4-amine with (tetrahydro-2H-pyran-4-yl)methanamine $^1$H NMR (300 MHz, DMSO-d$_6$) ppm 1.09-1.46 (m, 4H) 1.57-1.74 (m, 2H) 1.70-1.92 (m, 3H) 3.05-3.24 (m, 2H) 3.68-4.02 (m, 2H) 6.73-7.04 (m, 3H) 7.08-7.33 (m, 1H) 8.00-8.22 (m, 1H) 8.19-8.41 (m, 2H) 11.90-12.40 (m, 1H). MS (ESI$^+$) m/z 342.9 (M+H)$^+$.

Example 26

3-{[6-chloro-4-(1H-pyrrolo[2,3-b]pyridin-3-yl)pyridin-2-yl]amino}cyclohexanol

Example 26 (0.02 g) was prepared as described in Example 8, substituting tetrahydro-2H-pyran-4-amine with 3-aminocyclohexanol. $^1$H NMR (300 MHz, DMSO-d$_6$) ppm 0.96-1.59 (m, 4H) 1.60-1.97 (m, 4H) 2.04-2.28 (m, 1H) 3.40-3.76 (m, 1H) 4.54-4.73 (m, 1H) 6.68-6.97 (m, 3H) 7.12-7.31 (m, 1H) 8.05-8.20 (m, 1H) 8.22-8.39 (m, 2H) 11.90-12.42 (m, 1H). m/z 341.0 (ESI, M–H)$^-$.

Example 27

6-chloro-N-(pyridin-3-ylmethyl)-4-(1H-pyrrolo[2,3-b]pyridin-3-yl)pyridin-2-amine Example 27 (0.1 g) was prepared as described in Example 8, substituting tetrahydro-2H-pyran-4-amine with pyridin-3-ylmethanamine $^1$H NMR (300 MHz, DMSO-d$_6$) ppm 4.52 (d, J=5.95 Hz, 2H) 6.82-7.03 (m, 2H) 7.19 (dd, J=8.13, 4.56 Hz, 1H) 7.31-7.52 (m, 2H) 7.69-7.90 (m, 1H) 8.14 (s, 1H) 8.19-8.34 (m, 2H) 8.47 (dd, J=4.76, 1.59 Hz, 1H) 8.62 (d, J=1.98 Hz, 1H) 12.16 (s, 1H). MS (ESI$^+$) m/z 335.9 (M+H)$^+$.

Example 28

6-chloro-4-(1H-pyrrolo[2,3-b]pyridin-3-yl)-N-(tetrahydro-2H-pyran-3-ylmethyl)pyridin-2-amine Example 28 (0.05 g) was prepared as described in Example 8, substituting tetrahydro-2H-pyran-4-amine with (tetrahydro-2H-pyran-3-yl)methanamine $^1$H NMR (300 MHz, DMSO-d$_6$) ppm 1.15-1.39 (m, 1H) 1.41-1.69 (m, 2H) 1.72-1.98 (m, 2H) 3.06-3.20 (m, 4H) 3.63-3.92 (m, 2H) 6.78-7.01 (m, 3H) 7.06-7.30 (m, 1H) 8.01-8.21 (m, 1H) 8.21-8.40 (m, 2H) 11.95-12.33 (m, 1H). MS (ESI$^+$) m/z 343.0 (M+H)$^+$.

Example 29

6-chloro-N-(pyrrolidin-3-ylmethyl)-4-(1H-pyrrolo[2,3-b]pyridin-3-yl)pyridin-2-amine Example 29 was prepared as described in Example 8, substituting tetrahydro-2H-pyran-4-amine with tert-butyl 3-(aminomethyl)pyrrolidine-1-carboxylate. The intermediate obtained after chromatography was treated with trifluoroacetic acid (1 mL) at 25° C. for 1 hour, and concentrated to give 0.03 g of the title compound as a trifluoroacetic acid salt. $^1$H NMR (300 MHz, DMSO-d$_6$) ppm 1.42-1.72 (m, 2H) 1.98-2.21 (m, 2H) 2.92-3.20 (m, 2H) 3.19-3.45 (m, 2H) 3.85-4.15 (m, 1H) 6.83-7.02 (m, 2H) 6.95-7.14 (m, 1H) 7.14-7.39 (m, 1H) 8.04-8.23 (m, 1H) 8.21-8.43 (m, 2H) 8.39-8.62 (m, 1H) 12.02-12.34 (m, 1H). MS (ESI$^+$) m/z 327.9 (M+H)$^+$.

Example 30

6-chloro-N-(2,3-dimethylbenzyl)-4-(1H-pyrrolo[2,3-b]pyridin-3-yl)pyridin-2-amine Example 30 (0.08 g) was prepared as described in Example 8, substituting tetrahydro-2H-pyran-4-amine with (2,3-dimethylphenyl)methanamine $^1$H NMR (300 MHz, DMSO-d$_6$) ppm 2.20-2.31 (m, 6H) 4.45 (d, J=5.55 Hz, 2H) 6.93 (s, 2H)

6.98-7.12 (m, 2H) 7.12-7.23 (m, 3H) 8.13 (s, 1H) 8.22 (d, J=7.54 Hz, 1H) 8.29 (d, J=3.17 Hz, 1H) 12.14 (s, 1H). MS (ESI⁻) m/z 361.0 (M−H)⁻.

Example 31

6-chloro-N-(pyridin-4-ylmethyl)-4-(1H-pyrrolo[2,3-b]pyridin-3-yl)pyridin-2-amine Example 31 (0.02 g) was prepared as described in Example 8, substituting tetrahydro-2H-pyran-4-amine with pyridin-4-ylmethanamine $^1$H NMR (300 MHz, DMSO-d$_6$) ppm 4.45-4.62 (m, 2H) 6.91 (s, 1H) 6.96 (s, 1H) 7.19 (dd, J=8.14, 4.75 Hz, 1H) 7.37 (d, J=5.76 Hz, 2H) 7.51 (t, J=6.10 Hz, 1H) 8.14 (s, 1H) 8.21 (d, J=7.80 Hz, 1H) 8.30 (dd, J=4.75, 1.36 Hz, 1H) 8.47-8.56 (m, 2H) 12.16 (s, 1H). m/z 335.9 (ESI, M+H)⁺.

Example 32

6-chloro-4-(1H-pyrrolo[2,3-b]pyridin-3-yl)-N-(tetrahydro-2H-pyran-2-ylmethyl)pyridin-2-amine Example 32 (0.052 g) was prepared as described in Example 8, substituting tetrahydro-2H-pyran-4-amine with (tetrahydro-2H-pyran-2-yl)methanamine. $^1$H NMR (300 MHz, DMSO-d$_6$) ppm 1.10-1.40 (m, 4H) 1.59-1.74 (m, 2H) 1.69-1.86 (m, 1H) 3.09-3.23 (m, 2H) 3.76-3.98 (m, 2H) 6.78-7.01 (m, 3H) 7.11-7.31 (m, 1H) 8.06-8.21 (m, 1H) 8.22-8.40 (m, 2H) 12.04-12.25 (brs, 1H). MS (ESI⁺) m/z 342.0 (M+H)⁺.

Example 33

6-chloro-N-piperidin-4-yl-4-(1H-pyrrolo[2,3-b]pyridin-3-yl)pyridin-2-amine

Example 33 was prepared as described in Example 8, substituting tetrahydro-2H-pyran-4-amine with tert-butyl 4-aminopiperidine-1-carboxylate. The residue obtained after purification was treated with trifluoroacetic acid (1 mL) at 25° C. for 1 hour. The solvent was removed to give 0.05 g of the title compound as a trifluoroacetic acid salt. $^1$H NMR (300 MHz, DMSO-d$_6$) ppm 1.45-1.76 (m, 2H) 2.01-2.18 (m, 2H) 3.10 (s, 2H) 3.32 (d, J=12.29 Hz, 2H) 6.85-6.97 (m, 2H) 6.97-7.09 (m, 1H) 7.10-7.35 (m, 1H) 8.05-8.22 (m, 1H) 8.22-8.42 (m, 2H) 8.38-8.62 (m, 1H) 12.04-12.34 (m, 1H). MS (ESI⁺) m/z 327.9 (M+H)⁺.

Example 34

6-chloro-N-(4-methoxycyclohexyl)-4-(1H-pyrrolo[2,3-b]pyridin-3-yl)pyridin-2-amine Example 34 (0.03 g) was prepared as described in Example 8, substituting tetrahydro-2H-pyran-4-amine with 4-methoxycyclohexanamine $^1$H NMR (300 MHz, DMSO-d$_6$) ppm 1.45-1.86 (m, 8H) 1.89-2.09 (m, 1H) 3.20-3.28 (m, 3H) 3.79 (d, J=3.17 Hz, 1H) 6.70-6.97 (m, 2H) 7.14-7.32 (m, 1H) 7.89 (d, 1H) 8.23 (d, 2H) 8.47 (d, 1H) 12.28 (d, 1H). MS (ESI⁺) m/z 357.0 (M+H)⁺.

Example 35

N-(3-{[6-chloro-4-(1H-pyrrolo[2,3-b]pyridin-3-yl)pyridin-2-yl]amino}cyclohexyl)acetamide Example 35 (0.015 g) was prepared as described in Example 21, substituting Example 15 with Example 23 and substituting methanesulfonyl chloride with acetic anhydride. $^1$H NMR (300 MHz, DMSO-d$_6$) ppm 0.95-1.50 (m, 4H) 1.47-1.75 (m, 4H) 1.74-1.86 (m, 3H) 3.50-3.81 (m, 1H) 3.86-4.22 (m, 1H) 6.70-7.04 (m, 3H) 7.21 (dd, J=7.93, 4.76 Hz, 1H) 7.77 (dd, J=7.34, 2.97 Hz, 1H) 8.13 (d, J=2.78 Hz, 1H) 8.25-8.44 (m, 2H) 12.14 (s, 1H). MS (ESI⁺) m/z 384.0 (M+H)⁺.

Example 36

6-chloro-N-(4-chloro-2-fluorobenzyl)-4-(1H-pyrrolo[2,3-b]pyridin-3-yl)pyridin-2-amine Example 36 (0.07 g) was prepared as described in Example 8, substituting tetrahydro-2H-pyran-4-amine with (4-chloro-2-fluorophenyl)methanamine $^1$H NMR (300 MHz, DMSO-D6) ppm 4.51 (d, J=5.76 Hz, 2H) 6.95 (d, J=7.12 Hz, 2H) 7.20 (dd, J=8.14, 4.75 Hz, 1H) 7.28 (dd, J=8.31, 1.86 Hz, 1H) 7.33-7.52 (m, 3H) 8.14 (s, 1H) 8.20-8.35 (m, 2H) 12.16 (s, 1H), MS (ESI⁺) m/z 386.9 (M+H)⁺.

Example 37

6-chloro-N-{[2-(pyridin-3-yloxy)pyridin-3-yl]methyl}-4-(1H-pyrrolo[2,3-b]pyridin-3-yl)pyridin-2-amine Example 37 (0.04 g) was prepared as described in Example 8, substituting tetrahydro-2H-pyran-4-amine with (2-(pyridin-3-yloxy)pyridin-3-yl)methanamine. $^1$H NMR (300 MHz, DMSO-d$_6$) ppm 4.64 (d, J=5.55 Hz, 2H) 6.98 (d, J=9.91 Hz, 2H) 7.10-7.27 (m, 2H) 7.47 (dd, J=7.93, 4.76 Hz, 2H) 7.66 (dd, J=8.33, 1.59 Hz, 1H) 7.85 (d, J=5.95 Hz, 1H) 7.95-8.07 (m, 1H) 8.15 (s, 1H) 8.21-8.34 (m, 2H) 8.43 (d, J=4.36 Hz, 1H) 8.49 (d, J=2.78 Hz, 1H) 12.17 (s, 1H). m/z 429.9 (ESI, M+H)⁺.

Example 38

6-chloro-N-(piperidin-3-ylmethyl)-4-(1H-pyrrolo[2,3-b]pyridin-3-yl)pyridin-2-amine Example 38 was prepared as described in Example 8, substituting tetrahydro-2H-pyran-4-amine with tert-butyl 3-(aminomethyl)piperidine-1-carboxylate. The material obtained after purification was treated with trifluoroacetic acid (1 mL) at 25° C. for 1 hour. The reaction mixture was taken up in ethyl acetate, washed with a saturated NaHCO$_3$ solution, dried over MgSO$_4$, filtered, and concentrated to give 0.03 g of the title compound as a free base. $^1$H NMR (300 MHz, DMSO-d$_6$) ppm 1.01-1.28 (m, 2H) 1.42 (s, 1H) 1.55-1.89 (m, 3H) 2.18-2.41 (m, 2H) 2.90 (s, 1H) 3.04-3.20 (m, 3H) 6.79-7.02 (m, 3H) 7.05-7.32 (m, 1H) 8.04-8.22 (m, 1H) 8.22-8.39 (m, 2H) 11.97-12.30 (m, 1H). MS (ESI⁺) m/z 342.0 (M+H)⁺.

Example 39

1-{[6-chloro-4-(1H-pyrrolo[2,3-b]pyridin-3-yl)pyridin-2-yl]amino}propan-2-ol

Example 39 (0.011 g) was prepared as described in Example 8, substituting tetrahydro-2H-pyran-4-amine with 1-aminopropan-2-ol. $^1$H NMR (300 MHz, DMSO-d$_6$) ppm 1.06-1.19 (m, 3H) 3.12-3.27 (m, 2H) 3.72-3.86 (m, 1H) 4.74 (d, J=4.75 Hz, 1H) 6.77-6.87 (m, 1H) 6.86-6.92 (m, 1H)

6.95-6.99 (m, 1H) 7.08-7.32 (m, 1H) 8.02-8.21 (m, 1H) 8.22-8.44 (m, 2H) 12.01-12.27 (m, 1H). MS (ESI$^+$) m/z 302.9 (M+H)$^+$.

Example 40

3-{[6-chloro-4-(1H-pyrrolo[2,3-b]pyridin-3-yl)pyridin-2-yl]amino}-2,2-dimethylpropan-1-ol Example 40 (0.04 g) was prepared as described in Example 8, substituting tetrahydro-2H-pyran-4-amine with 3-amino-2,2-dimethylpropan-1-ol. $^1$H NMR (300 MHz, DMSO-d$_6$) ppm 0.79-0.97 (m, 6H) 3.16 (dd, J=5.76, 4.07 Hz, 4H) 4.57-4.75 (m, 1H) 6.76-6.84 (m, 1H) 6.86-6.92 (m, 1H) 6.97-7.05 (m, 1H) 7.16-7.27 (m, 1H) 8.07-8.20 (m, 1H) 8.25-8.40 (m, 2H) 12.08-12.20 (m, 1H). MS (ESI$^+$) m/z 330.9 (M+H)$^+$.

Example 41

2-(2-{[6-chloro-4-(1H-pyrrolo[2,3-b]pyridin-3-yl)pyridin-2-yl]amino}ethoxy)ethanol Example 41 (0.04 g) was prepared as described in Example 8, substituting tetrahydro-2H-pyran-4-amine with 2-(2-aminoethoxy)ethanol. $^1$H NMR (300 MHz, DMSO-d$_6$) ppm 3.37-3.68 (m, 8H) 4.59 (t, J=5.43 Hz, 1H) 6.78-7.01 (m, 3H) 7.15-7.28 (m, 1H) 8.07-8.19 (m, 1H) 8.24-8.40 (m, 2H) 11.78-12.39 (m, 1H). MS (ESI$^+$) m/z 332.9 (M+H)$^+$.

Example 42 trans-N-[4-chloro-6-(1H-pyrrolo[2,3-b]pyridin-3-yl)pyrimidin-2-yl]cyclohexane-1,4-diamine

Example 42a

3-[6-chloro-2-(methylthio)pyrimidin-4-yl]-1-(phenylsulfonyl)-1H-pyrrolo[2,3-b]pyridine A mixture of 4,6-dichloro-2-(methylthio)pyrimidine (0.558 g, 2.86 mmol), Example 1c (1 g, 2.60 mmol), 2M aqueous Cs$_2$CO$_3$ solution (1.30 mL, 2.60 mmol), 1,2-dimethoxyethane/dimethylfomamide (9/1, 12 mL), and tetrakis(triphenylphosphine)palladium (0.120 g, 0.104 mmol) was evacuated and purged with nitrogen. The mixture was heated at 80° C. under nitrogen for 30 minutes, then cooled to room temperature. Solids were collected by filtration, washed with hexanes, and dried under vacuum to give the title compound (606 mg, 56% yield).

Example 42b 3-(6-chloro-2-(methylsulfonyl)pyrimidin-4-yl)-1-(phenyl sulfonyl)-1H-pyrrolo[2,3-b]pyridine A mixture of Example 42a (3.0 g, 7.20 mmol) and OXONE® (45 g, 48.8 mmol) in ethyl acetate (400 ml) and H$_2$O (1 mL) was stirred at 80° C. for 16 hours. The reaction mixture was filtered and the solids were washed with ethyl acetate (about 600 mL). The filtrate was concentrated in vacuo to afford the title compound (2.8 g, 87% yield).

Example 42c trans-N-[4-chloro-6-(1H-pyrrolo[2,3-b]pyridin-3-yl)pyrimidin-2-yl]cyclohexane-1,4-diamine A mixture of Example 42b (160 mg, 0.356 mmol), trans-cyclohexane-1,4-diamine (81 mg, 0.713 mmol), triethylamine (0.10 mL, 0.713 mmol) and dioxane (4 ml) was heated at 60° C. for 2 hours. The reaction mixture was cooled and concentrated in vacuo. The residue was taken into methanol (3 mL), treated with dropwise addition of NaOH solution (1.0 mL, 1.0 mmol), stirred at room temperature for 1 hour, neutralized with dilute hydrochloric acid, and purified by reverse-phase HPLC (same condition as described in Example 7b) to afford the title product (28 mg, 23% yield). MS (ESI$^+$) m/z 343 (M+H)$^+$; $^1$H NMR (400 MHz, DMSO-d$_6$) ppm 1.33-1.63 (m, 4H) 1.98-2.20 (m, 4H) 2.99-3.15 (m, 1H) 3.73-3.87 (m, 1H) 7.11 (s, 1H) 7.17 (dd, J=7.93, 4.58 Hz, 1H) 7.73 (s, 2H) 8.30 (dd, J=4.58, 1.53 Hz, 1H) 8.36 (s, 1H) 8.78 (d, J=7.93 Hz, 1H) 12.05 (s, 1H).

Example 43

N-[4-chloro-6-(1H-pyrrolo[2,3-b]pyridin-3-yl)pyrimidin-2-yl]cyclohexane-1,3-diamine Example 43 was prepared as described in Example 42c, substituting trans-cyclohexane-1,4-diamine with cyclohexane-1,3-diamine MS (ESI$^+$) m/z 343 (M+H)$^+$; $^1$H NMR (400 MHz, DMSO-d$_6$) ppm 1.19-1.54 (m, 4H) 1.81-2.08 (m, 3H) 2.28-2.37 (m, 1H) 3.12-3.25 (m, 1H) 3.85-3.97 (m, 1H) 7.12 (s, 1H) 7.19 (dd, J=7.93, 4.58 Hz, 1H) 7.76 (s, 2H) 8.29 (dd, J=4.73, 1.68 Hz, 1H) 8.37 (s, 1H) 8.77 (d, J=7.93 Hz, 1H) 12.05 (s, 1H).

Example 44

Trans-4-{[4-chloro-6-(1H-pyrrolo[2,3-b]pyridin-3-yl)pyrimidin-2-yl]amino}cyclohexanol Example 44 was prepared as described in Example 42c, substituting trans-cyclohexane-1,4-diamine with trans-4-aminocyclohexanol. MS (ESI$^+$) m/z 344 (M+H)$^+$; $^1$H NMR (400 MHz, DMSO-d$_6$) ppm 1.24-1.47 (m, 4H) 1.84-2.08 (m, 4H) 3.42-3.54 (m, 1H) 3.73-3.84 (m, 1H) 7.08 (s, 1H) 7.15-7.21 (m, 1H) 8.29 (dd, J=4.58, 1.53 Hz, 1H) 8.35 (s, 1H) 8.80 (d, J=7.02 Hz, 1H) 12.04 (s, 1H).

Example 45

4-chloro-6-(1H-pyrrolo[2,3-b]pyridin-3-yl)-N-tetrahydro-2H-pyran-4-ylpyrimidin-2-amine Example 45 was prepared as described in Example 42c, substituting trans-cyclohexane-1,4-diamine with tetrahydro-2H-pyran-4-amine MS (ESI$^+$) m/z 330 (M+H)$^+$; $^1$H NMR (400 MHz, DMSO-d$_6$) ppm 1.51-1.70 (m, 2H) 1.85-2.01 (m, 2H) 3.40-3.54 (m, 2H) 3.86-3.97 (m, 2H) 3.98-4.14 (m, 1H) 7.10 (s, 1H) 7.13-7.25 (m, 2H) 8.28 (dd, J=4.73, 1.68 Hz, 1H) 8.35 (s, 1H) 8.77 (d, J=7.63 Hz, 1H) 12.02 (s, 1H).

Example 46

N-benzyl-4-chloro-6-(1H-pyrrolo[2,3-b]pyridin-3-yl)pyrimidin-2-amine

Example 46 was prepared as described in Example 42c, substituting trans-cyclohexane-1,4-diamine with phenylmethanamine MS (ESI$^+$) m/z 336 (M+H)$^+$; $^1$H NMR (400 MHz, DMSO-d$_6$) ppm 4.62 (d, J=6.41 Hz, 2H) 7.06-7.14 (m, 2H) 7.21 (t, J=7.32 Hz, 1H) 7.31 (t, J=7.63 Hz, 2H) 7.36-7.42 (m, 2H) 7.71 (s, 1H) 8.25 (dd, J=4.73, 1.68 Hz, 1H) 8.33 (s, 1H) 8.62 (s, 1H) 12.00 (s, 1H).

Example 47

2-{[4-chloro-6-(1H-pyrrolo[2,3-b]pyridin-3-yl)pyrimidin-2-yl]amino}-3-phenylpropan-1-ol Example 47 was prepared as described in Example 42c, substituting trans-cyclohexane-1,4-diamine with 2-amino-3-phenylpropan-1-ol. MS (ESI$^+$) m/z 380 (M+H)$^+$; $^1$H NMR (400 MHz, DMSO-d$_6$) ppm 2.83-2.91 (m, 1H) 3.49-3.61 (m, 2H) 4.25-4.34 (m, 1H) 4.50 (t, J=5.49 Hz, 1H) 6.87 (d, J=8.24 Hz, 1H) 7.06 (s, 1H) 7.09-7.19 (m, 2H) 7.22 (t, J=7.48 Hz, 2H) 7.27-7.32 (m, 2H) 8.28 (dd, J=4.73, 1.68 Hz, 1H) 8.32 (s, 1H) 8.75 (d, J=7.93 Hz, 1H) 11.97 (s, 1H).

Example 48

(S)-4-chloro-N-(1-methoxy-3-phenylpropan-2-yl)-6-(1H-pyrrolo[2,3-b]pyridine-3-yl)pyrimidin-2-amine Example 48 was prepared as described in Example 42c, substituting trans-cyclohexane-1,4-diamine with (2S)-1-methoxy-3-phenylpropan-2-amine MS (ESI$^+$) m/z 394 (M+H)$^+$; $^1$H NMR (400 MHz, DMSO-d$_6$) ppm 2.84-2.95 (m, 2H) 3.30 (s, 3H) 3.37-3.55 (m, 2H) 4.39-4.50 (m, 1H) 6.98-7.05 (m, 1H) 7.07 (s, 1H) 7.09-7.32 (m, 6H) 8.28 (dd, J=4.58, 1.53 Hz, 1H) 8.32 (s, 1H) 8.74 (d, J=7.93 Hz, 1H) 12.01 (s, 1H).

Example 49

4-chloro-N-cyclohexyl-6-(1H-pyrrolo[2,3-b]pyridin-3-yl)pyrimidin-2-amine

Example 49a 3-(6-methoxy-2-(methylthio)pyrimidin-4-yl)-1-(phenylsulfonyl)-1H-pyrrolo[2,3-b]pyridine A mixture of 4-chloro-6-methoxy-2-(methylthio)pyrimidine (10.2 g, 53.7 mmol), 1-(phenylsulfonyl)-3-(4,4,5,5-tetramethyl-1,3,2-dioxaborolan-2-yl)-1H-pyrrolo[2,3-b]pyridine (18.8 g, 48.8 mmol), 2M aqueous K$_2$CO$_3$ (48.8 mL, 98.0 mmol), 1,2-dimethoxyethane/dimethylfomamide (9/1, 200 mL) and tetrakis(triphenylphosphine)palladium (2.26 g, 1.95 mmol) was evacuated and purged with N$_2$, then heated at 85° C. for 20 min. The cooled reaction mixture was filtered to give the title compound (13.0 g, 31.5 mmol, 64.6% yield).

Example 49b 3-(6-methoxy-2-(methylsulfonyl)pyrimidin-4-yl)-1-(phenyl sulfonyl)-1H-pyrrolo[2,3-b]pyridine A mixture of Example 49a (6.2 g, 15.0 mmol) and OXONE® (92 g, 150 mmol) in ethyl acetate (350 ml) was stirred at 77° C. for 2 days. The reaction mixture was filtered and the solids were washed with dichloromethane. The organic phase was concentrated in vacuo to give the title compound (6.3 g, 14.2 mmol, 94% yield).

Example 49c

N-cyclohexyl-4-methoxy-6-(1-(phenylsulfonyl)-1H-pyrrolo[2,3-b]pyridin-3-yl)pyrimidin-2-amine A solution of Example 49b (6.7 g, 15.1 mmol) and cyclohexanamine (6.90 ml, 60.3 mmol) in dioxane (165 ml) was heated at 100° C. overnight. The reaction mixture was concentrated in vacuo to afford the desired product (crude, 6.99 g, ~15.1 mmol) which was used directly for the next step.

Example 49d 2-(cyclohexylamino)-6-(1H-pyrrolo[2,3-b]pyridin-3-yl)pyrimidin-4(3H)-one To Example 49d (crude, 6.99 g, ~15.1 mmol) were added dioxane (150 ml) and 1M aqueous NaOH (75 ml, 75 mmol). The reaction mixture was heated at 100° C. for 1.5 hours. After concentration, the residue was partitioned between water and dichloromethane. The organic layer was dried over Na$_2$SO$_4$, filtered through silica gel, eluted with ethyl acetate and concentrated. The residue was dissolved in HCl (12% in H2O, 55 mL) and heated at 80° C. for 2 days. The cooled reaction mixture was filtered and the title compound was collected as a white solid (3.8 g).

Example 49e 4-chloro-N-cyclohexyl-6-(1H-pyrrolo[2,3-b]pyridin-3-yl)pyrimidin-2-amine A mixture of Example 49d (100 mg, 0.323 mmol), phosphoryl trichloride (1 ml, 10.92 mmol) and pyridine (0.05 ml, 0.618 mmol) was stirred at room temperature for 4 hours. The reaction mixture was concentrated in vacuo and purified by HPLC on a Phenomenex Luna C8(2) 5 μm 100 Å AXIA column (30 mm×75 mm), eluting with a gradient of acetonitrile (A) and 0.1% trifluoroacetic acid in water (B), at a flow rate of 50 mL/min (0-0.5 min 10% A, 0.5-7.0 min linear gradient 10-95% A, 7.0-10.0 min 95% A, 10.0-12.0 min linear gradient 95-10% A) to give the title product (27 mg, 25.5% yield). MS (ESI) m/e 328 (M+H)$^+$; $^1$H NMR (400 MHz, DMSO-d$_6$) ppm 1.15-1.48 (m, 5H) 1.58-1.69 (m, 1H) 1.73-1.83 (m, J=9.31, 3.51 Hz, 2H) 1.94-2.03 (m, 2H) 3.76-3.90 (m, 1H) 6.93-7.04 (m, 1H) 7.07 (s, 1H) 7.17 (dd, J=7.93, 4.58 Hz, 1H) 8.28 (d, J=3.36 Hz, 1H) 8.34 (s, 1H) 8.79 (d, J=7.63 Hz, 1H) 12.01 (s, 1H).

Comparative Example 1

N-cyclohexyl-4-(1H-pyrrolo[2,3-b]pyridin-3-yl)pyridin-2-amine

Comparative Example 1a 4-bromo-N-cyclohexylpyridin-2-amine

A mixture of 4-bromo-2-chloropyridine (0.5 g, 2.6 mmol) and cyclohexylamine (0.26 g, 2.6 mmol) was heated in a CEM Microwave at 150 degrees for 15 minutes at 300 W. The resulting crude material was purified by flash chromatography (0% to 30% ethyl acetate/hexane) to give 85 mg of the title compound. MS m/z 256.8 (ESI: M+H)$^+$.

Comparative Example 1b

N-cyclohexyl-4-(1H-pyrrolo[2,3-b]pyridin-3-yl)pyridin-2-amine

To a solution of Comparative Example 1a (0.086 g, 0.337 mmol) in 2 mL 1,2-dimethoxyethane/ethanol/water (7:3:2) was added 1-(phenylsulfonyl)-3-(4,4,5,5-tetramethyl-1,3,2-dioxaborolan-2-yl)-1H-pyrrolo[2,3-b]pyridine (0.13 g, 0.337 mmol), dichlorobis(triphenylphosphine)palladium(II) (12 mg, 0.017 mmol) and 0.5 mL of a 1M sodium carbonate solution. The mixture was heated in a CEM Microwave at 135° C. for 15 min at 300 W. The reaction mixture was cooled to room temperature, diluted with ethyl acetate, washed with brine, dried over magnesium sulfate, filtered, and concentrated. The crude material was dissolved in 5 mL of a 5:1 ethanol/water solution, treated with 2 equivalents of KOH at room temperature for 1 hour. The solvent was evaporated and the crude material purified by flash chromatography (10% ethyl acetate/hexane to 100% ethyl acetate) to give 0.03 g of the title compound. $^1$H NMR (300 MHz, DMSO-$d_6$) δ ppm 1.06-1.46 (m, 5H), 1.49-1.66 (m, 1H), 1.66-1.80 (m, 2H), 1.83-2.05 (m, 2H), 3.75 (dd, J=7.34, 3.77 Hz, 1H), 6.27 (d, J=7.54 Hz, 1H), 6.80 (dd, J=5.55, 1.59 Hz, 1H), 6.88 (s, 1H), 7.18 (dd, J=7.93, 4.76 Hz, 1H), 7.84-8.05 (m, 2H), 8.20-8.41 (m, 2H), 12.02 (s, 1H). m/z 293.0 (ESI, M+H)$^+$ Comparative Example 2

N-cyclohexyl-6-methyl-4-(1H-pyrrolo[2,3-b]pyridin-3-yl)pyridin-2-amine

Comparative Example 2a 3-(2,6-dichloropyridin-4-yl)-1-(phenylsulfonyl)-1H-pyrrolo[2,3-b]pyridine A suspension of 1-(phenylsulfonyl)-3-(4,4,5,5-tetramethyl-1,3,2-dioxaborolan-2-yl)-1H-pyrrolo[2,3-b]pyridine (4.63 g, 12.1 mmol), 2,6-dichloro-4-iodopyridine (3.00 g, 11.0 mmol), dichlorobis(triphenylphosphine)palladium(II) (0.308 g, 0.438 mmol) and sodium carbonate (1M, 8.76 mL, 8.76 mmol) in 1,2-dimethoxyethane/ethanol/water (7:2:3) (30 mL) was degassed and heated at 80° C. overnight. After cooling, the suspension was diluted with ethyl acetate, filtered, washed with ethyl acetate and water, and oven-dried to give 3.98 g (90%) of the title compound.

Comparative Example 2b 6-chloro-N-cyclohexyl-4-(1-(phenylsulfonyl)-1H-pyrrolo[2,3-b]pyridin-3-yl)pyridin-2-amine A mixture of Comparative Example 2a (0.550 g, 1.36 mmol) and cyclohexanamine (2 mL, 17.5 mmol) in acetonitrile (3 mL) was heated at 170° C. for 60 minutes in a Biotage microwave reactor. The reaction mixture was cooled and concentrated. The residue was treated with water and extracted with ethyl acetate (2×). The combined organic layers were dried over MgSO$_4$, filtered, concentrated, and purified on a 40 g column using the ISCO Companion flash system eluted with (50% CH$_2$Cl$_2$ in hexane)/ethyl acetate=97:3 to 95:5 to give 0.301 g (47%) of the title product.

Comparative Example 2c

N-cyclohexyl-6-methyl-4-(1-(phenylsulfonyl)-1H-pyrrolo[2,3-b]pyridin-3-yl)pyridin-2-amine To a degassed suspension of Comparative Example 2b (90.0 mg, 0.193 mmol) and tetrakis(triphenylphosphine)palladium (22.27 mg, 0.019 mmol) in N,N-dimethylformamide (2.5 ml) was added trimethylaluminum in toluene (2M, 0.241 ml, 0.482 mmol). The mixture was heated at 80° C. in a capped vial for 2.5 hours. After cooling, 5% brine was slowly added to the reaction mixture and the resulting suspension was extracted with ethyl acetate (2×). The combined organic layers were washed with 5% brine (2×), dried, concentrated, and the residue purified on a 12 g column using the ISCO Companion flash system eluted with hexane/ethyl acetate=3:2 to 1:1 to give 43.2 mg (50%) of the title compound.

Comparative Example 2d

N-cyclohexyl-6-methyl-4-(1H-pyrrolo[2,3-b]pyridin-3-yl)pyridin-2-amine

A solution of Comparative Example 2c (42.0 mg, 0.094 mmol) and 20% sodium hydroxide (0.10 ml, 0.094 mmol) in dioxane (1 mL) was heated at 100° C. for 30 minutes. Some dark suspension was filtered through a syringe filter while the reaction mixture was still warm. The filtrate was concentrated and the resulting solid was treated with 3 mL of water, sonicated, stirred in water for 15 minutes, filtered, washed with water and ether, and oven-dried to give 14.2 mg (49%) of the title compound. $^1$H NMR (500 MHz, DMSO-$d_6$) ppm 1.13-1.26 (m, 3H), 1.27-1.42 (m, 2H), 1.52-1.64 (m, 1H), 1.67-1.79 (m, 2H), 1.86-1.99 (m, 2H), 2.29, (s, 3H), 3.65-3.81 (m, 1H), 6.13 (d, J=7.93 Hz, 1H), 6.68 (d, J=13.43 Hz, 2H), 7.18 (dd, J=8.09, 4.73 Hz, 1H), 7.94 (d, J=2.75 Hz, 1H), 8.19-8.40 (m, 2H), 11.98 (s, 1H). MS (DCI/NH$_3$) m/z 307.2 (M+H)$^+$.

Comparative Example 3

N-benzyl-6-methyl-4-(1H-pyrrolo[2,3-b]pyridin-3-yl)pyridin-2-amine

Comparative Example 3a

N-benzyl-6-chloro-4-(1-(phenylsulfonyl)-1H-pyrrolo[2,3-b]pyridin-3-yl)pyridin-2-amine The title compound was prepared using similar procedures as described in Comparative Example 2b, substituting cyclohexylamine with phenylmethanamine.

Comparative Example 3b

N-benzyl-6-methyl-4-(1H-pyrrolo[2,3-b]pyridin-3-yl)pyridin-2-amine

The title compound was prepared by following similar procedures as described in Comparative Examples 2c and 2d, substituting Comparative Example 2b with Example 3a. The final product was purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 min at a flow rate of 15 mL/minutes to provide the title compound as the trifluoroacetic acid salt. $^1$H NMR (500 MHz, DMSO-$d_6$) ppm 2.49 (s, 3H), 4.70 (d, J=5.19 Hz, 2H), 7.10 (s, 1H), 7.18-7.28 (m, 2H), 7.34 (t, J=7.02 Hz, 1H), 7.39-7.51 (m, 4H), 8.14 (d, J=7.63 Hz, 1H), 8.31-8.38 (m, 1H), 8.41 (d, J=3.05 Hz, 1H), 8.54 (s, 1H), 12.58 (s, 1H), 12.91-13.29 (m, brd, 1H). MS m/z 315.0 (ESI: M+H)$^+$.

Comparative Example 4

Trans-4-{[6-methyl-4-(1H-pyrrolo[2,3-b]pyridin-3-yl)pyridin-2-yl]amino}cyclohexanol

Comparative Example 4a trans-4-(6-chloro-4-(1-(phenylsulfonyl)-1H-pyrrolo[2,3-b]pyridin-3-yl)pyridin-2-ylamino)cyclohexanol The title compound was prepared by following similar procedures as described in Comparative Example 2b, substituting cyclohexylamine with trans-4-aminocyclohexanol.

Comparative Example 4b

Trans-4-{[6-methyl-4-(1H-pyrrolo[2,3-b]pyridin-3-yl)pyridin-2-yl]amino}cyclohexanol The title compound was prepared by following similar procedures as described in Comparative Examples 2c and 2d, substituting Comparative Example 2b with Comparative Example 4a. The final product was purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 min at a flow rate of 15 mL/minutes to provide the title compound as the trifluoroacetic acid salt. $^1$H NMR (500 MHz, DMSO-$d_6$) ppm 1.27-1.41 (m, 4H), 1.84-1.93 (m, 2H), 1.94-2.02 (m, 2H), 2.48 (s, 3H), 3.42-3.53 (m, 1H), 3.75-3.84 (m, 1H), 7.18 (s, 1H), 7.21 (s, 1H), 7.30 (dd, J=7.93, 4.58 Hz, 1H), 8.25 (d, J=5.80 Hz, 1H), 8.38 (d, J=4.88 Hz, 1H), 8.40-8.49 (m, 2H), 12.60 (s, 1H). MS m/z 323.0 (ESI: M+H)$^+$.

Comparative Example 5

6-(cyclohexylamino)-4-(1H-pyrrolo[2,3-b]pyridin-3-yl)pyridine-2-carbonitrile

Comparative Example 5a 6-(cyclohexylamino)-4-(1-(phenylsulfonyl)-1H-pyrrolo[2,3-b]pyridin-3-yl)picolinonitrile A suspension of Comparative Example 2b (80.0 mg, 0.171 mmol), 1,1'-bis(diphenylphosphino)ferrocene (7.60 mg, 0.014 mmol), tris(dibenzylideneacetone)dipalladium(0) (6.27 mg, 6.85 μmol), zinc (1.344 mg, 0.021 mmol) and zinc cyanide (20.1 mg, 0.171 mmol) in N,N-dimethylacetamide (3 mL) was degassed and heated at 120° C. for 1.5 hours. After cooling, the mixture was filtered through celite and washed with ethyl acetate. The filtrate was washed with 20% brine and water. The organic layer was dried over MgSO$_4$, filtered, and concentrated. The residue was purified on a 12 g column using the ISCO Companion flash system and eluted with CH$_2$Cl$_2$/ethyl acetate=97:3 to 95:5 to give 39.5 mg of the title compound.

Comparative Example 5b 6-(cyclohexylamino)-4-(1H-pyrrolo[2,3-b]pyridin-3-yl)pyridine-2-carbonitrile A solution of Comparative Example 5a (37.0 mg, 0.081 mmol) in dioxane (1 mL) was treated with 0.1 mL 20% NaOH. The reaction mixture was heated at 100° C. for 40 minutes. The solvent was evaporated. The residue was treated with 2 mL of water, sonicated, stirred for 15 minutes, filtered, and washed with water to give 16 mg of crude material. The crude material was purified by reversed-phase HPLC performed on a Zorbax RX-C18 column (250×21.2 mm, 7 nm particle size) using a gradient of 10% to 100% acetonitrile: 0.1% aqueous trifluoroacetic acid over 40 min at a flow rate of 15 mL/minutes to give 10.5 mg of the trifluoroacetic acid salt of the title compound. $^1$H NMR (500 MHz, DMSO-$d_6$) ppm 1.16-1.29 (m, 3H), 1.30-1.44 (m, 2H), 1.54-1.65 (m, 1H), 1.68-1.79 (m, 2H), 1.86-2.00 (m, 2H), 3.71-3.78 (m, 1H), 6.97 (s, 1H), 7.19-7.27 (m, 2H), 7.48 (s, 1H), 8.23 (d, J=2.75 Hz, 1H), 8.32 (d, J=4.58 Hz, 1H), 8.39 (d, J=7.32 Hz, 1H), 12.24 (s, 1H). MS (DCI/NH$_3$) m/z 318.2 (M+H)$^+$.

Comparative Example 6

6-(benzylamino)-4-(1H-pyrrolo[2,3-b]pyridin-3-yl)pyridine-2-carbonitrile

Comparative Example 6a 6-(benzylamino)-4-(1-(phenylsulfonyl)-1H-pyrrolo[2,3-b]pyridin-3-yl)picolinonitrile The title compound was prepared by following similar procedures as described in Comparative Example 5a, substituting Comparative Example 2b with Comparative Example 3a.

Comparative Example 6b 6-(benzylamino)-4-(1H-pyrrolo[2,3-b]pyridin-3-yl)pyridine-2-carbonitrile A solution of Comparative Example 6a (68.0 mg, 0.146 mmol) in dioxane (2 mL) was treated with 0.1 mL 20% NaOH. The reaction mixture was heated at 100° C. for 40 minutes. The solvent was evaporated. The crude was purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 min at a flow rate of 15 mL/minutes to give both Comparative Example 6b (1.1 mg) and Comparative Example 7 (21.2 mg) as trifluoroacetic acid salts. $^1$H NMR (500 MHz, DMSO-$d_6$) ppm 4.53 (d, J=4.58 Hz, 2H), 7.21 (dd, J=8.09, 4.73 Hz, 1H), 7.24-7.30 (m, 2H), 7.33-7.42 (m, 4H), 7.53-7.57 (m, 2H), 8.24 (d, J=3.05 Hz, 1H), 8.26-8.30 (m, 1H), 8.31 (dd, J=4.73, 1.37 Hz, 1H), 12.25 (s, 1H). MS (DCI/NH$_3$) m/z 326.1 (M+H)$^+$.

Comparative Example 7

6-(benzylamino)-4-(1H-pyrrolo[2,3-b]pyridin-3-yl)pyridine-2-carboxamide

See Comparative Example 6b for procedure. $^1$H NMR (500 MHz, DMSO-$d_6$) ppm 4.71 (s, 2H), 7.17-7.33 (m, 4H), 7.36-7.49 (m, 5H), 7.70-7.80 (m, 2H), 8.21 (d, J=7.63 Hz, 1H), 8.26 (s, 1H), 8.34 (d, J=4.58 Hz, 1H), 12.41 (s, 1H). MS (DCI/NH$_3$) m/z 344.2 (M+H)$^+$.

Comparative Example 8

6-piperidin-1-yl-4-(1H-pyrrolo[2,3-b]pyridin-3-yl)pyridine-2-carbonitrile

Comparative Example 8a

3-(2-chloro-6-(piperidin-1-yl)pyridin-4-yl)-1-(phenylsulfonyl)-1H-pyrrolo[2,3-b]pyridine

A mixture of Comparative Example 2a (0.250 g, 0.618 mmol) and piperidine (2 mL) was heated at 160° C. for 30 minutes in a Biotage microwave reactor. The reaction mixture was treated with 5% citric acid and extracted with ethyl acetate (2×). The combined organic layers were dried over $MgSO_4$, filtered, and concentrated. The residue was purified on a 12 g column using the ISCO Companion flash system eluted with $CH_2Cl_2$/ethyl acetate=97:3 to 80:20 to give the 0.168 g (60%) of the title compound.

Comparative Example 8b

4-(1-(phenylsulfonyl)-1H-pyrrolo[2,3-b]pyridin-3-yl)-6-(piperidin-1-yl)picolinonitrile

Comparative Example 8b was prepared by following similar procedures as described in Comparative Example 5a, substituting Comparative Example 2b with Comparative Example 8a.

Comparative Example 8c

6-piperidin-1-yl-4-(1H-pyrrolo[2,3-b]pyridin-3-yl)pyridine-2-carbonitrile

A solution of Comparative Example 8b (60.0 mg, 0.135 mmol) in dioxane (2 mL) was treated with 0.1 mL 20% NaOH. The reaction mixture was heated at 100° C. for 40 minutes. The solvent was evaporated. The crude was purified by reversed-phase HPLC performed on a Zorbax RX-C18 column (250×21.2 mm, 7 µm particle size) using a gradient of 10% to 100% acetonitrile: 0.1% aqueous trifluoroacetic acid over 40 min at a flow rate of 15 mL/minutes to give both Comparative Example 8c (16.2 mg) and Comparative Example 9 (16.8 mg) as trifluoroacetic acid salts. $^1$H NMR (500 MHz, DMSO-$d_6$) ppm 1.50-1.68 (m, 6H), 3.55-3.68 (m, 4H), 7.23 (dd, J=8.09, 4.73 Hz, 1H), 7.33 (s, 1H), 7.56 (s, 1H), 8.31 (d, J=2.44 Hz, 1H), 8.33 (dd, J=4.58, 1.22 Hz, 1H), 8.43 (d, J=7.93 Hz, 1H), 12.31 (s, 1H). MS (DCI/$NH_3$) m/z 304.1 $(M+H)^+$.

Comparative Example 9

6-piperidin-1-yl-4-(1H-pyrrolo[2,3-b]pyridin-3-yl)pyridine-2-carboxamide

See Comparative Example 8c for procedure. $^1$H NMR (500 MHz, DMSO-$d_6$) ppm 1.49-1.74 (m, 6H), 3.55-3.72 (m, 4H), 7.24 (s, 1H), 7.26 (dd, J=7.93, 4.58 Hz, 1H), 7.55 (s, 1H), 7.65 (s, 1H), 7.98 (s, 1H), 8.24 (d, J=2.75 Hz, 1H), 8.31-8.38 (m, 2H), 12.27 (s, 1H). MS (DCI/$NH_3$) m/z 322.1 $(M+H)^+$.

Comparative Example 10

6-[(trans-4-hydroxycyclohexyl)amino]-4-(1H-pyrrolo[2,3-b]pyridin-3-yl)pyridine-2-carbonitrile

Comparative Example 10a

6-(trans-4-hydroxycyclohexylamino)-4-(1-(phenylsulfonyl)-1H-pyrrolo[2,3-b]pyridin-3-yl)picolinonitrile

Comparative Example 10a was prepared by following similar procedures as described in Comparative Example 5a, substituting Comparative Example 2b with Comparative Example 4a.

Comparative Example 10b

6-[(trans-4-hydroxycyclohexyl)amino]-4-(1H-pyrrolo[2,3-b]pyridin-3-yl)pyridine-2-carbonitrile

A solution of Comparative Example 10a (78.0 mg, 0.165 mmol) in dioxane (2 mL) was treated with 0.1 mL 20% NaOH. The reaction mixture was heated at 90° C. for 40 minutes. The solvent was evaporated. The crude was purified by reversed-phase HPLC performed on a Zorbax RX-C18 column (250×21.2 mm, 7 µm particle size) using a gradient of 10% to 100% acetonitrile: 0.1% aqueous trifluoroacetic acid over 40 min at a flow rate of 15 mL/minutes to give both Comparative Example 10b (12.2 mg) and Comparative Example 11 (7.0 mg) as trifluoroacetic acid salts. $^1$H NMR (500 MHz, DMSO-$d_6$) ppm 1.15-1.35 (m, 4H), 1.80-1.90 (m, 2H), 1.94-2.03 (m, 2H), 3.37-3.50 (m, 1H), 3.62-3.73 (m, 1H), 6.94 (s, brd, 1H), 7.21 (s, 1H), 7.25 (dd, J=7.93, 4.58 Hz, 1H), 7.49 (d, J=1.22 Hz, 1H), 8.23 (d, J=2.75 Hz, 1H), 8.33 (d, J=5.80 Hz, 1H), 8.39 (d, J=7.93 Hz, 1H), 12.27 (s, 1H). MS (DCI/$NH_3$) m/z 334.1 $(M+H)^+$.

Comparative Example 11

6-[(trans-4-hydroxycyclohexyl)amino]-4-(1H-pyrrolo[2,3-b]pyridin-3-yl)pyridine-2-carboxamide

See Comparative Example 10. $^1$H NMR (500 MHz, DMSO-$d_6$) ppm 1.21-1.47 (m, 4H), 1.80-1.93 (m, 2H), 1.94-2.07 (m, 2H), 3.00-3.17 (m, 1H), 3.80-4.00 (m, 1H), 7.13-7.39 (m, 2H), 7.73 (s, brd, 1H), 8.24-8.51 (m, 3H), 12.55 (s, brd, 1H). MS (DCI/$NH_3$) m/z 352.2 $(M+H)^+$.

Comparative Example 12

N-cyclohexyl-4-(1H-pyrrolo[2,3-b]pyridin-3-yl)pyrimidin-2-amine

Comparative Example 12a

3-(2-chloropyrimidin-4-yl)-1-(phenylsulfonyl)-1H-pyrrolo[2,3-b]pyridine

2,4-dichloropyrimidine (0.192 g, 1.29 mmol), 1-(phenylsulfonyl)-3-(4,4,5,5-tetramethyl-1,3,2-dioxaborolan-2-yl)-1H-pyrrolo[2,3-b]pyridine (0.45 g, 1.17 mmol), $K_2CO_3$ (1.17 ml, 2.34 mmol), 1,2-dimethoxyethane (5 ml) and tetrakis (triphenylphosphine)palladium (0.054 g, 0.047 mmol) were placed in a 25 mL of flask. The flask was evacuated and purged with nitrogen. The mixture was heated at 85° C. for 20 min then cooled to room temperature. The reaction mixture was filtered to give the title compound (320 mg, 73.7% yield) as white solids.

Comparative Example 12b

N-cyclohexyl-4-(1H-pyrrolo[2,3-b]pyridin-3-yl)pyrimidin-2-amine

A mixture of Comparative Example 12a (40 mg, 0.108 mmol), cyclohexanamine (64.2 mg, 0.647 mmol) in 2-methoxyethanol (0.5 ml) was heated at 125° C. for 1 hour. The reaction mixture was concentrated in vacuo and purified by HPLC on a Phenomenex Luna C8(2) 5 μm 100 Å AXIA column (30 mm×75 mm), eluting with a gradient of acetonitrile (A) and 0.1% trifluoroacetic acid in water (B), at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title product (10 mg, 31.6% yield). $^1$H NMR (400 MHz, DMSO-$d_6$) ppm 1.10-1.56 (m, 5H), 1.60-1.73 (m, 1H), 1.73-1.87 (m, 2H), 1.90-2.13 (m, 2H), 3.92-4.13 (m, 1H), 7.24-7.46 (m, 2H), 8.20 (d, J=5.22 Hz, 1H), 8.38 (dd, J=4.60, 1.53 Hz, 1H), 8.45-8.63 (m, 1H), 8.81 (s, 1H), 12.82 (s, 1H). MS (ESI) m/e 294 (M+H)$^+$.

1Comparative Example 13

Trans-N-[4-(1H-pyrrolo[2,3-b]pyridin-3-yl)pyrimidin-2-yl]cyclohexane-1,4-diamine The title compound was prepared as described in Comparative Example 12, substituting cyclohexanamine with trans cyclohexane-1,4-diamine to give the title product. $^1$H NMR (400 MHz, DMSO-$d_6$) ppm 1.20-1.43 (m, 4H) 1.84-1.94 (m, 2H) 1.95-2.10 (m, 2H) 2.64-2.78 (m, 1H) 3.70-3.81 (m, 1H) 6.82 (d, J=7.67 Hz, 1H) 7.02 (d, J=5.22 Hz, 1H) 7.18 (dd, J=7.98, 4.60 Hz, 1H) 8.15 (d, J=5.22 Hz, 1H) 8.29 (dd, J=4.60, 1.53 Hz, 1H) 8.34 (s, 1H) 8.86 (s, 1H). MS (ESI) m/e 309 (M+H)$^+$.

Example 50

Enzyme Inhibition Data

This example describes the assays that may be used to identify compounds having kinase activity.

Cdc7 (BEV coexpressed huCDC7/DBF4) is prepared internally. Cdc7 assays are conducted as follows with final concentrations as listed. In 384-well v-bottom polypropylene plates, 6 μL compound (2% DMSO), is mixed with 6 μL of Cdc7 (2 ug/mL), and Jerini peptide substrate A-A11 (biotin-C6linker-TPSDSLIYDDGLS) (SEQ ID NO: 1) (2 μM), followed by immediate initiation with 6 μL λ-[33P]ATP (1 μM, 20 mCi/μmol) using a reaction buffer comprising 25 mM HEPES, pH 7.5, 1 mM DTT, 10 mM MgCl2, 100 μM Na3VO4, 0.075 mg/ml Triton X-100. Reactions are quenched after 1 hr by the addition of 90 μL stop buffer (50 mM EDTA, 2M NaCl). 85 μL of the stopped reactions are transferred to 384-well streptavidin-coated plates (FlashPlate Plus, Perkin Elmer), incubated 30 minutes at room temperature and washed 3 times with 0.05% Tween-20/PBS using an ELX-405 automated plate washer (BioTek), and counted on a Top-Count Scintillation Plate Reader (Packard). IC50 values are determined via non-linear regression fitting of enzyme inhibition data and corresponding Ki values are generated assuming ATP-competitive (equilibrium) inhibition and using the experimentally determined apparent ATP Km of 0.7 μM (as determined using the above assay condition, but varying ATP). ($K_i$) for exemplary compounds. In Table 1, "A" represents a $K_i$ of less than 10 nM and "B" represents a $K_i$ of between 10 nM and 100 nM.

TABLE 1

| Example | Cdc7 Inhibition |
|---------|-----------------|
| 1 | A |
| 2 | A |
| 3 | A |
| 4 | B |
| 5 | A |
| 6 | B |
| 7 | B |
| 8 | A |
| 9 | A |
| 10 | A |
| 11 | A |
| 12 | B |
| 13 | A |
| 14 | A |
| 15 | A |
| 16 | B |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | B |
| 29 | A |
| 30 | B |
| 31 | B |
| 32 | B |
| 33 | B |
| 34 | B |
| 35 | B |
| 36 | B |
| 37 | B |
| 38 | B |
| 39 | B |
| 40 | B |
| 41 | B |
| 42 | A |
| 43 | A |
| 44 | A |
| 45 | A |
| 46 | B |
| 47 | B |
| 48 | B |
| 49 | A |

Compounds of the present invention assessed by the above-described assays were found to have Cdc7 kinase-inhibiting activity.

Moreover, the compounds of the present invention unexpectedly demonstrated increased potency in inhibiting Cdc7 according to the above assay than compounds that lack the chloro substituent on either the pyridine or the pyrimidine ring in formula (I).

Table 2 presents comparative data depicting the increase in potency found in the compounds of the present invention. Column A shows the Example number and Columns B, C, and D show the substituents X, Y, Z corresponding to the Example. Column E shows the Comparative Example number and Columns F, G, and H show the substituents X, Y, Z corresponding to the Comparative Example. Column I shows the ratio of the $K_i$ ($K_i$ Comparative Example/$K_i$ Example).

TABLE 2 formula (III)

[Structure: 7-azaindole connected to pyrimidine bearing X, Y, Z substituents; NH position labeled E]

| Example (A) | X (B) | Y (C) | Z (D) | Comparative Example (E) | X (F) | Y (G) | Z (H) | $K_i$ ratio comparisons (I) |
|---|---|---|---|---|---|---|---|---|
| 49 | CH | HN-cyclohexyl | Cl | 1 | CH | HN-cyclohexyl | H | 10 |
| 49 | CH | HN-cyclohexyl | Cl | 2 | CH | HN-cyclohexyl | $CH_3$ | 14 |
| 2 | CH | $CH_2$—Ph | Cl | 3 | CH | $CH_2$—Ph | $CH_3$ | 75 |
| 14 | CH | trans-4-hydroxycyclohexylamino | Cl | 4 | CH | trans-4-hydroxycyclohexylamino | $CH_3$ | 54 |
| 49 | CH | HN-cyclohexyl | Cl | 5 | CH | HN-cyclohexyl | CN | 9 |
| 2 | CH | $CH_2$—Ph | Cl | 6 | CH | $CH_2$—Ph | CN | 5 |
| 4 | CH | piperidin-1-yl | Cl | 8 | CH | piperidin-1-yl | CN | 2 |
| 14 | CH | trans-4-hydroxycyclohexylamino | Cl | 10 | CH | trans-4-hydroxycyclohexylamino | CN | 10 |
| 2 | CH | $CH_2$—Ph | Cl | 7 | CH | $CH_2$—Ph | $C(O)NH_2$ | 45 |
| 4 | CH | piperidin-1-yl | Cl | 9 | CH | piperidin-1-yl | $C(O)NH_2$ | 84 |
| 14 | CH | trans-4-hydroxycyclohexylamino | Cl | 11 | CH | trans-4-hydroxycyclohexylamino | $C(O)NH_2$ | 134 |
| 49 | N | HN-cyclohexyl | Cl | 12 | N | HN-cyclohexyl | H | 3 |
| 44 | N | trans-4-aminocyclohexylamino | Cl | 13 | N | trans-4-aminocyclohexylamino | H | 12 |

The potency in inhibiting the Cdc7 enzyme of the chloro substituted pyridines or pyridines in the invention, as demonstrated by the ratio $K_i$, is surprisingly better than comparative examples lacking the chloro substituent, including, for example, comparative examples containing a hydrogen, cyano, methyl, or —C(O)NH$_2$ substituent.

Example 51

6-chloro-N-[1-(methylsulfonyl)piperidin-4-yl]-4-(1H-pyrrolo[2,3-b]pyridin 3-yl)pyridin-2-amine To a solution of Example 33 (0.04 g, 0.095 mmol) in 2 mL anhydrous THF was added diisopropylethylamine (0.07 mL, 0.38 mmol) followed by methanesulfonyl chloride (0.009 mL, 0.114 mmol). The resulting solution was stirred at room temperature for 2.5 hours. The reaction mixture was diluted with ethyl acetate and washed with water, brine, dried over magnesium sulfate, filtered, and concentrated to give the title compound as an off-white solid. $^1$H NMR (300 MHz, DMSO-d$_6$) ppm 1.16-1.35 (m, 1H) 1.38-1.61 (m, 3H) 1.93-2.10 (m, 3H) 2.90-3.04 (m, 2H) 3.52 (d, J=12.21 Hz, 2H) 3.84 (s, 1H) 6.82-7.00 (m, 3H) 7.21 (dd, J=7.80, 5.09 Hz, 1H) 8.14 (d, J=3.05 Hz, 1H) 8.24-8.37 (m, 2H) 12.16 (s, 1H). MS (ESI$^+$) m/z 406.0 (M+H)$^+$.

Example 52

N-(4-{[6-chloro-4-(1H-pyrrolo[2,3-b]pyridin-3-yl)pyridin-2-yl]amino}cyclohexyl)benzenesulfonamide Example 52 (0.04 g) was prepared as described in Example 21, substituting methanesulfonyl chloride with phenylsulfonyl chloride. $^1$H NMR (300 MHz, DMSO-d$_6$) ppm 0.99-1.46 (m, 4H) 1.67 (d, J=10.31 Hz, 2H) 1.89 (d, J=11.50 Hz, 2H) 2.84-3.11 (m, 1H) 3.38-3.65 (m, 1H) 6.69 (d, J=7.54 Hz, 1H) 6.83 (d, J=11.10 Hz, 2H) 7.19 (dd, J=7.34, 5.35 Hz, 1H) 7.51-7.68 (m, 3H) 7.73 (d, J=7.14 Hz, 1H) 7.78-7.91 (m, 2H) 8.10 (s, 1H) 8.20-8.39 (m, 2H) 12.13 (s, 1H). MS (ESI$^+$) m/z 482.0 (M+H)$^+$.

Example 53

N-(4-{[6-chloro-4-(1H-pyrrolo[2,3-b]pyridin-3-yl)pyridin-2-yl]amino}cyclohexyl)-1-phenylmethanesulfonamide Example 53 (0.025 g) was prepared as described in Example 21, substituting methanesulfonyl chloride with phenylmethanesulfonyl chloride. $^1$H NMR (300 MHz, DMSO-d$_6$) ppm 0.97-1.54 (m, 5H) 1.78-2.06 (m, 3H) 2.86-3.15 (m, 1H) 3.43-3.68 (m, 1H) 4.33 (s, 2H) 6.76 (d, J=7.93 Hz, 1H) 6.86 (d, J=5.95 Hz, 2H) 7.10 (d, J=7.54 Hz, 1H) 7.21 (dd, J=7.34, 5.35 Hz, 1H) 7.28-7.50 (m, 5H) 8.12 (d, J=2.78 Hz, 1H) 8.24-8.38 (m, 2H) 12.14 (s, 1H). MS (ESI$^+$) m/z 496.1 (M+H)$^+$.

Example 54

N-(4-{[6-chloro-4-(1H-pyrrolo[2,3-b]pyridin-3-yl)pyridin-2-yl]amino}cyclohexyl)pyridine-3-sulfonamide Example 54 (0.035 g) was prepared as described in Example 21, substituting methanesulfonyl chloride with pyridine-3-sulfonyl chloride. $^1$H NMR (300 MHz, DMSO-d$_6$) ppm 0.99-1.47 (m, 5H) 1.68 (d, J=9.91 Hz, 1H) 1.92 (s, 2H) 3.06 (d, J=11.10 Hz, 1H) 3.54 (dd, J=10.51, 3.37 Hz, 1H) 6.71 (d, J=7.54 Hz, 1H) 6.85 (t, J=8.53 Hz, 2H) 7.05-7.31 (m, 1H) 7.65 (dd, J=8.53, 4.56 Hz, 1H) 7.99 (s, 1H) 8.08-8.13 (m, 1H) 8.17-8.25 (m, 1H) 8.26-8.32 (m, 2H) 8.78-8.85 (m, 1H) 8.99 (d, J=1.59 Hz, 1H) 12.13 (s, 1H). MS (ESI$^+$) m/z 483.0 (M+H)$^+$.

Example 55

N-(4-{[6-chloro-4-(1H-pyrrolo[2,3-b]pyridin-3-yl)pyridin-2-yl]amino}cyclohexyl)propane-1-sulfonamide Example 55 (0.02 g) was prepared as described in Example 21, substituting methanesulfonyl chloride with propane-1-sulfonyl chloride. $^1$H NMR (300 MHz, DMSO-d$_6$) ppm 0.93-1.03 (m, 3H) 1.17-1.51 (m, 5H) 1.57-1.79 (m, 2H) 1.84-2.07 (m, 4H) 2.88-3.04 (m, 1H) 3.05-3.18 (m, 1H) 3.60 (s, 1H) 6.76 (d, J=7.46 Hz, 1H) 6.81-6.91 (m, 2H) 7.05 (d, J=7.46 Hz, 1H) 7.20 (dd, J=7.80, 4.75 Hz, 1H) 8.12 (d, J=2.71 Hz, 1H) 8.23-8.37 (m, 2H) 12.13 (s, 1H). MS (ESI$^+$) m/z 448.0 (M+H)$^+$.

Example 56

6-chloro-N-[2-(morpholin-4-yl)ethyl]-4-(1H-pyrrolo[2,3-b]pyridin-3-yl)pyridin-2-amine A mixture of Example 7a (75.0 mg, 0.186 mmol) and 2-morpholinoethanamine and (0.8 mL) was heated in a Biotage microwave reactor at 160° C. for 20 minutes. The reaction mixture was treated with 20% brine and extracted with EtOAc (2×). The combined organic layers were washed with 20% brine, dried over MgSO$_4$, filtered, concentrated, and purified by reverse-phase HPLC performed on a Zorbax RX-C18 column (250×21.2 mm, 7 μm particle size) using a gradient of 10% to 100% acetonitrile: 0.1% aqueous trifluoroacetic acid over 40 minutes at a flow rate of 15 mL/minutes to give the title compound (39.0 mg) as trifluoroacetic acid salts. $^1$H NMR (500 MHz, CD$_3$OD) ppm 3.14-3.29 (m, 2H), 3.37-3.47 (m, 2H), 3.71-3.82 (m, 4H), 3.86-3.99 (m, 2H), 4.02-4.17 (m, 2H), 6.91 (s, 1H) 7.04 (s, 1H), 7.38 (dd, J=8.09, 5.03 Hz, 1H), 7.99 (s, 1H), 8.37 (d, J=5.19 Hz, 1H), 8.53 (d, J=7.93 Hz, 1H). MS (DCI$^+$) m/z 358.0 (M+H)$^+$.

Example 57

3-(2-{[6-chloro-4-(1H-pyrrolo[2,3-b]pyridin-3-yl)pyridin-2-yl]amino}ethyl)phenol A mixture of Example 7a (75.0 mg, 0.186 mmol), 3-(2-aminoethyl)phenol.HCl (0.250 g, 1.44 mmol), and diisopropylethylamine (0.52 mL, 2.97 mmol) in acetonitrile (0.6 mL) was heated in a Biotage microwave reactor at 160° C. for 30 minutes. The reaction mixture was treated with 20% brine and extracted with EtOAc (2×). The combined organic layers were washed with 20% brine, dried over MgSO$_4$, filtered, and concentrated. The crude was dissolved in dioxane (1.3 mL) and treated with 20% NaOH (0.12 mL). The mixture was heated at 60° C. for 1 hour and concentrated. The residue was treated with water, sonicated, filtered, washed with water, and dried. The crude material was purified on a 4 g column using the ISCO Companion flash system eluting with CH$_2$Cl$_2$/MeOH (97:3 to 90:10) to give 5.5 mg of the title compound. $^1$H NMR (500 MHz, DMSO-d$_6$) ppm 2.77 (t, J=7.32 Hz, 2H), 3.46 (t, J=6.87 Hz, 2H), 6.61 (d, J=7.93 Hz, 1H), 6.65-6.74 (m, 2H), 6.87 (s, 1H), 6.89-6.98 (m, 2H), 7.09 (t, J=7.78 Hz, 1H), 7.21 (dd, J=7.93, 4.88 Hz, 1H), 8.14 (d, J=2.75 Hz, 1H), 8.25-8.35 (m, 2H), 9.27 (s, 1H), 12.16 (s, 1H). MS (DCI$^+$) m/z 365.0 (M+H)$^+$.

Example 58

N-[6-chloro-4-(1H-pyrrolo[2,3-b]pyridin-3-yl)pyridin-2-yl]-N'-(2-methylpropyl)cyclohexane-1,3-diamine To a mixture of Example 23 (50 mg, 0.15 mmol) in methanol (5 mL) was added isobutyraldehyde (22 mg, 0.29 mmol). The solution was stirred at room temperature for 10 minutes before NaBH$_3$CN (18 mg, 0.29 mmol) and ZnCl$_2$ (catalytic amount) were added. The reaction mixture was stirred at room temperature overnight. The solvent was removed and the residue was purified by reverse-phase HPLC performed on a Zorbax RX-C18 column (250×21.2 mm, 7 m particle size) using a gradient of 0% to 100% acetonitrile: 0.1% aqueous trifluoroacetic acid over 60 minutes at a flow rate of 15 mL/minutes to give the title compound as a trifluoroacetic acid salt. Yield: 30 mg (51%). MS (DCI/NH$_3$) m/z 398 (M+H)$^+$)$^+$, $^1$H NMR (300 MHz, CD$_3$OD): 1.05 (d, J=6.78 Hz, 6H), 1.15-1.69 (m, 4H), 1.87-2.28 (m, 4H), 2.61 (d, J=14.92 Hz, 1H), 2.91 (d, J=7.80 Hz, 2H), 3.11-3.39 (m, 1H), 3.80-4.04 (m, 1H), 6.77 (d, J=1.36 Hz, 1H), 6.89 (d, J=1.36 Hz, 1H), 7.36 (dd, J=8.14, 5.09 Hz, 1H), 7.92 (s, 1H), 8.35 (dd, J=5.09, 1.36 Hz, 1H), 8.50 (dd, J=8.14, 1.36 Hz, 1H).

Example 59

N'-[6-chloro-4-(1H-pyrrolo[2,3-b]pyridin-3-yl)pyridin-2-yl]-N,N-dimethylcyclohexane-1,3-diamine The trifluoroacetic acid salt of the title compound was prepared according to the procedure for Example 58, substituting formaldehyde for isobutyraldehyde. Yield: 30 mg (55%). MS (DCI/NH$_3$) m/z 370 (M+H)$^+$, $^1$H NMR (300 MHz, CD$_3$OD): 1.15-1.66 (m, 4H), 1.90-2.20 (m, 3H), 2.55 (d, J=11.50 Hz, 1H), 2.87 (s, 6H), 3.23-3.50 (m, 1H), 3.80-4.10 (m, 1H), 6.78 (s, 1H), 6.90 (s, 1H), 7.35 (dd, J=7.93, 5.16 Hz, 1H), 7.92 (s, 1H), 8.34 (d, J=5.16 Hz, 1H), 8.49 (d, J=7.93 Hz, 1H).

Example 60

1-(4-{[6-chloro-4-(1H-pyrrolo[2,3-b]pyridin-3-yl)pyridin-2-yl]amino}cyclohexyl)-3-cyclopentylurea Example 60 (0.015 g) was prepared as described in Example 21, substituting methanesulfonyl chloride with isocyanatocyclopentane. $^1$H NMR (300 MHz, DMSO-d$_6$) ppm 1.09-1.38 (m, 6H) 1.37-1.66 (m, 4H) 1.67-1.90 (m, 4H) 1.89-2.14 (m, 2H) 3.50-3.74 (m, 1H) 3.72-3.94 (m, 1H) 5.53 (t, J=7.34 Hz, 1H) 5.71 (d, J=7.14 Hz, 1H) 6.76 (d, J=7.93 Hz, 1H) 6.81-6.94 (m, 2H) 7.11-7.28 (m, 1H) 8.05-8.16 (m, 1H) 8.23-8.37 (m, 2H) 12.14 (s, 1H). MS (ESI$^+$) m/z 453.1 (M+H)$^+$.

Example 61

N-(trans-4-{[6-chloro-4-(1-pyrrolo[2,3-b]pyridin-3-yl)pyridin-2-yl]amino}cyclohexyl)cyclopropanesulfonamide

Example 61a 3-(2,6-dichloropyridin-4-yl)-1H-pyrrolo[2,3-b]pyridine

To a solution of Example 7a (5.72 g, 15 mmol) in 60 mL ethanol/water (5/1) was added powdered KOH (2 g, 35 mmol). The resulting solution was heated at 40° C. for 2 hours. Most of the solvent was removed in vacuo, and the residue was diluted with ethyl acetate. A solid was filtered from the material and discarded. The organics were washed with water, brine, dried over MgSO$_4$, filtered, and concentrated. The crude material was triturated with dichloromethane and filtered, giving 3.5 g of the title compound as a white solid. MS (ESI$^+$) m/z 263.6 (M+H)$^+$.

Example 61b trans-N-1-(6-chloro-4-(1H-pyrrolo[2,3-b]pyridin-3-yl)pyridin-2-yl)cyclohexane-1,4-diamine Example 61a (1.44 g, 5.45 mmol) and trans-cyclohexane-1,4-diamine (3 g, 27.3 mmol) were combined in a 20 mL Biotage microwave vessel and melted together using a sand bath at 150° C. for 5-6 hours, continuously scraping material from the vessel walls. The mixture eventually turned into a pasty solid. Cooled to room temperature, and then sonicated the suspension. The solid was filtered, washed with water, and dried over high-vac to give the title compound as a white solid. MS (ESI$^+$) m/z 342.4 (M+H)$^+$.

Example 61c

N-(trans-4-{[6-chloro-4-(1H-pyrrolo[2,3-b]pyridin-3-yl)pyridin-2-yl]amino}cyclohexyl)cyclopropanesulfonamide Example 61c (0.015 g) was prepared as described in Example 21, substituting methanesulfonyl chloride with cyclopropanesulfonyl chloride and Example 15 with Example 61b. $^1$H NMR (300 MHz, DMSO-d$_6$) ppm 0.79-1.03 (m, 4H) 1.08-1.57 (m, 4H) 1.76-2.14 (m, 4H) 2.53-2.65 (m, 1H) 3.09-3.26 (m, 1H) 3.60 (d, J=7.14 Hz, 1H) 6.69-6.82 (m, 1H) 6.81-6.94 (m, 2H) 6.96-7.13 (m, 1H) 7.20 (dd, J=7.73, 4.96 Hz, 1H) 8.12 (d, J=2.78 Hz, 1H) 8.25-8.37 (m, 2H) 12.14 (s, 1H). MS (ESI$^+$) m/z 446.0 (M+H)$^+$.

Example 62

1-(4-{[6-chloro-4-(1H-pyrrolo[2,3-b]pyridin-3-yl)pyridin-2-yl]amino}cyclohexyl)-3-propylurea Example 62 (0.08 g) was prepared as described in Example 21, substituting methanesulfonyl chloride with 1-isocyanatopropane. $^1$H NMR (300 MHz, DMSO-d$_6$) ppm 0.70-0.94 (m, 4H) 1.04-1.48 (m, 4H) 1.71-2.11 (m, 6H) 2.81-3.04 (m, 1H) 3.64 (s, 1H) 5.53-5.83 (m, 3H) 6.69-6.82 (m, 1H) 6.80-6.93 (m, 2H) 7.11-7.32 (m, 1H) 8.05-8.19 (m, 1H) 8.22-8.37 (m, 2H) 11.81-12.37 (m, 1H). MS (ESI$^+$) m/z 427.1 (M+H)$^+$.

Example 63

N-(trans-4-{[6-chloro-4-(1H-pyrrolo[2,3-b]pyridin-3-yl)pyridin-2-yl]amino}cyclohexyl)cyclopropanecarboxamide Example 63 (0.030 g) was prepared as described in Example 21, substituting methanesulfonyl chloride with cyclopropanecarbonyl chloride and substituting Example 15 with Example 61b. $^1$H NMR (300 MHz, DMSO-d$_6$) ppm 0.46-0.76 (m, 4H) 1.11-1.42 (m, 5H) 1.41-1.63 (m, 4H) 1.82 (t, J=9.52 Hz, 2H) 2.00 (d, J=9.12 Hz, 2H) 3.43-3.77 (m, 2H) 6.70-6.80 (m, 1H) 6.81-6.92 (m, 1H) 7.11-7.31 (m, 1H) 7.84-

8.00 (m, 1H) 8.04-8.20 (m, 1H) 8.20-8.41 (m, 2H) 11.95-12.35 (m, 1H). MS (ESI+) m/z 410.1 (M+H)+.

Example 64

N-(4-{[6-chloro-4-(1H-pyrrolo[2,3-b]pyridin-3-yl)pyridin-2-yl]amino}cyclohexyl)-2-methylpropanamide Example 64 (0.03 g) was prepared as described in Example 21, substituting methanesulfonyl chloride with isobutyryl chloride. $^1$H NMR (300 MHz, DMSO-d$_6$) ppm 0.87-1.05 (m, 6H) 1.09-1.40 (m, 4H) 1.66-1.88 (m, 2H) 1.91-2.08 (m, 2H) 2.22-2.40 (m, 1H) 3.52 (m, 2H) 6.71-6.81 (m, 1H) 6.80-6.91 (m, 2H) 7.14-7.27 (m, 1H) 7.55-7.64 (m, 1H) 8.08-8.16 (m, 1H) 8.25-8.36 (m, 2H) 11.94-12.30 (m, 1H). MS (ESI+) m/z 412.2 (M+H)+.

Example 65

N-(4-{[6-chloro-4-(1H-pyrrolo[2,3-b]pyridin-3-yl)pyridin-2-yl]amino}cyclohexyl)benzamide Example 65 (0.085 g) was prepared as described in Example 21, substituting methanesulfonyl chloride with benzoyl chloride. $^1$H NMR (300 MHz, DMSO-d$_6$) ppm 1.20-1.43 (m, 2H) 1.40-1.63 (m, 2H) 1.82-2.00 (m, 2H) 1.99 (s, 2H) 3.51-3.92 (m, 2H) 6.76-6.84 (m, 1H) 6.85-6.90 (m, 2H) 7.13-7.31 (m, 1H) 7.37-7.55 (m, 3H) 7.75-7.90 (m, 2H) 8.06-8.18 (m, 1H) 8.19-8.28 (m, 1H) 8.27-8.35 (m, 2H) 12.07-12.21 (m, 1H). MS (ESI+) m/z 446.7 (M+H)+.

Example 66

1-(4-{[6-chloro-4-(1H-pyrrolo[2,3-b]pyridin-3-yl)pyridin-2-yl]amino}cyclohexyl)-3-phenylurea Example 66 (0.015 g) was prepared as described in Example 21, substituting methanesulfonyl chloride with isocyanatobenzene. $^1$H NMR (300 MHz, DMSO-d$_6$) ppm 1.13-1.51 (m, 5H) 1.81-2.12 (m, 4H) 3.37-3.77 (m, 2H) 5.93-6.14 (m, 1H) 6.72-6.83 (m, 1H) 6.82-6.94 (m, 2H) 7.12-7.28 (m, 3H) 7.30-7.46 (m, 2H) 8.03-8.17 (m, 1H) 8.25-8.37 (m, 3H) 11.95-12.30 (m, 1H). MS (ESI+) m/z 460.3 (M+H)+.

Example 67

N-[6-chloro-4-(1H-pyrrolo[2,3-b]pyridin-3-yl)pyridin-2-yl]-N'-(pyridin-3-ylmethyl)cyclohexane-1,3-diamine The trifluoroacetic acid salt of the title compound was prepared according to the procedure for Example 58, substituting nicotinaldehyde for isobutyraldehyde. Yield: 50 mg (70%). MS (DCI/NH$_3$) m/z 433 (M+H)+, $^1$H NMR (300 MHz, CD$_3$OD): 1.25-1.69 (m, 3H), 1.77-1.96 (m, 1H), 1.98-2.15 (m, 2H), 2.27 (d, J=12.21 Hz, 1H), 2.73 (d, J=11.53 Hz, 1H), 3.33-3.49 (m, 1H), 3.89-4.03 (m, 1H), 4.41 (d, J=2.71 Hz, 2H), 6.78 (d, J=1.36 Hz, 1H), 6.90 (d, J=1.02 Hz, 1H), 7.39 (dd, J=7.97, 5.26 Hz, 1H), 7.65-7.72 (m, 1H), 7.94 (s, 1H), 8.15-8.22 (m, 1H), 8.36 (dd, J=5.09, 1.36 Hz, 1H), 8.54 (dd, J=8.14, 1.36 Hz, 1H), 8.71 (dd, J=5.09, 1.70 Hz, 1H), 8.78 (d, J=1.70 Hz, 1H).

Example 68

N-[6-chloro-4-(1H-pyrrolo[2,3-b]pyridin-3-yl)pyridin-2-yl]-1-N'-cyclobutylcyclohexane-1,3-diamine The trifluoroacetic acid salt of the title compound was prepared according to the procedure for Example 58 substituting cyclobutanone for isobutyraldehyde. Yield: 25 mg (40%). MS (DCI/NH$_3$) m/z 396 (M+H)+, $^1$H NMR (300 MHz, CD$_3$OD): 1.10-1.39 (m, 3H), 1.44-1.65 (m, 1H), 1.84-2.01 (m, 3H), 2.01-2.15 (m, 2H), 2.14-2.30 (m, 2H), 2.27-2.44 (m, 2H), 2.57 (d, J=13.09 Hz, 1H), 3.10-3.30 (m, 1H), 3.76-4.01 (m, 2H), 6.76 (d, J=1.19 Hz, 1H), 6.89 (d, J=0.79 Hz, 1H), 7.33 (dd, J=7.93, 5.16 Hz, 1H), 7.91 (s, 1H), 8.33 (d, J=5.16 Hz, 1H), 8.47 (dd, J=7.93, 1.19 Hz, 1H).

Example 69

N-(3-{[6-chloro-4-(1H-pyrrolo[2,3-b]pyridin-3-yl)pyridin-2-yl]amino}cyclohexyl)cyclopropanecarboxamide To a solution of Example 23 (50 mg, 0.15 mmol) in anhydrous DMF (2 mL) was added cyclopropanecarboxylic acid (16 mg, 0.19 mmol), EDC (36 mg, 0.19 mmol), 1-hydroxybenzotriazole monohydrate (29 mg, 0.19 mmol) and triethylamine (20 mg, 0.19 mmol). The mixture was heated till the mixture turned clear and 2 mL of DMF was added. The reaction was stirred at room temperature overnight. The reaction mixture was partitioned between dichloromethane and brine. The organic phase was concentrated and the residue was purified by HPLC as described in Example 58 to provide the trifluoroacetic acid salt of the title compound. Yield: 18 mg (30%). MS (DCI/NH$_3$) m/z 410 (M+H)+, $^1$H NMR (300 MHz, CD$_3$OD): 0.53-0.72 (m, 4H), 0.98-1.19 (m, 2H), 1.23-1.42 (m, 1H), 1.42-1.55 (m, 2H), 1.68-1.86 (m, 2H), 1.94 (d, J=11.53 Hz, 1H), 2.11 (d, J=11.87 Hz, 1H), 3.56-3.80 (m, 2H), 6.83 (d, J=1.02 Hz, 1H), 6.88 (d, J=1.02 Hz, 1H), 7.22 (dd, J=7.80, 4.75 Hz, 1H), 7.98 (s, 1H), 8.13 (d, J=2.71 Hz, 1H), 8.30 (s, 1H), 8.31 (s, 1H), 12.16 (s, 1H).

Example 70

N-(3-{[6-chloro-4-(1H-pyrrolo[2,3-b]pyridin-3-yl)pyridin-2-yl]amino}cyclohexyl)-1-propylpiperidine-4-carboxamide The trifluoroacetic acid salt of the title compound was prepared according to the procedure for Example 69, substituting 1-propylpiperidine-4-carboxylic acid for cyclopropanecarboxylic acid. Yield: 30 mg (41%). MS (DCI/NH$_3$) m/z 495 (M+H)+, $^1$H NMR (300 MHz, CD$_3$OD): 0.90 (t, J=7.46 Hz, 3H), 0.99-1.19 (m, 3H), 1.25-1.48 (m, 1H), 1.56-1.71 (m, 3H), 1.76 (d, J=11.87 Hz, 3H), 1.81-1.97 (m, 3H), 2.10 (d, J=11.53 Hz, 1H), 2.22-2.41 (m, 1H), 2.86 (q, J=10.74 Hz, 2H), 2.91-3.07 (m, 2H), 3.50 (d, J=11.53 Hz, 2H), 3.56-3.79 (m, 2H), 6.84 (s, 1H), 6.88 (s, 1H), 7.22 (dd, J=7.46, 5.09 Hz, 1H), 8.13 (d, J=3.05 Hz, 1H), 8.30 (s, 1H), 8.31-8.34 (m, 1H), 8.95 (s, 1H), 12.16 (s, 1H).

Example 71

N-(3-{[6-chloro-4-(1H-pyrrolo[2,3-b]pyridin-3-yl)pyridin-2-yl]amino}cyclohexyl)-1H-pyrazole-3-carboxamide The trifluoroacetic acid salt of the title compound was prepared according to the procedure for Example 69, substituting 1H-pyrazole-3-carboxylic acid for cyclopropanecarboxylic acid. Yield: 40 mg (70%). MS (DCI/NH$_3$) m/z 436 (M+H)$^+$, $^1$H NMR (300 MHz, CD$_3$OD): 1.03-1.20 (m, 1H), 1.20-1.55 (m, 3H), 1.79 (dd, J=12.72, 5.26 Hz, 2H), 1.96 (d, J=12.21 Hz, 1H), 2.14 (d, J=11.53 Hz, 1H), 3.49-3.84 (m, 1H), 3.84-3.99 (m, 1H), 6.67 (d, J=2.37 Hz, 1H), 6.87 (d, J=5.76 Hz, 2H), 7.23 (dd, J=8.14, 4.75 Hz, 1H), 7.73 (d, J=2.03 Hz, 1H), 7.98 (d, J=8.48 Hz, 1H), 8.14 (d, J=2.71 Hz, 1H), 8.27-8.36 (m, 2H), 12.17 (s, 1H).

Example 72

N-[6-chloro-4-(1H-pyrrolo[2,3-b]pyridin-3-yl)pyridin-2-yl]-N'-(piperidin-3-ylmethyl)cyclohexane-1,3-diamine A mixture of Example 23 (100 mg, 0.3 mmol) in methanol (10 mL) was added benzyl 3-formylpiperidine-1-carboxylate (111 mg, 0.45 mmol). The solution was stirred at room temperature for 10 minutes followed by the addition of NaBH$_3$CN (27 mg, 0.45 mmol) and ZnCl$_2$ (catalytic amount). The reaction mixture was stirred at room temperature overnight. The solvent was removed and the residue was partitioned between EtOAc (50 mL) and water (100 mL). The organic phase was concentrated and dissolved in CH$_2$Cl$_2$ (10 mL), followed by the addition of trifluoroacetic acid (1 mL). The reaction mixture was stirred at room temperature overnight and concentrated. The residue was purified by HPLC as described in Example 58 to provide the trifluoroacetic acid salt of the title compound. Yield: 30 mg (51%). MS (DCI/NH$_3$) m/z 439 (M+H)$^+$)$^+$, $^1$H NMR (300 MHz, CD$_3$OD): 1.19-1.43 (m, 3H), 1.40-1.63 (m, 1H), 1.68-1.90 (m, 1H), 1.90-2.11 (m, 4H), 2.12-2.31 (m, 2H), 2.62 (d, J=11.87 Hz, 1H), 2.80 (t, J=11.87 Hz, 2H), 2.85-3.01 (m, 2H), 3.00-3.13 (m, 2H), 3.21-3.38 (m, 1H), 3.48 (dd, J=12.88, 3.05 Hz, 1H), 3.84-4.02 (m, 1H), 6.77 (d, J=1.02 Hz, 1H), 6.89 (d, J=1.36 Hz, 1H), 7.34 (dd, J=8.14, 5.09 Hz, 1H), 7.91 (s, 1H), 8.33 (dd, J=4.92, 1.19 Hz, 1H), 8.47 (dd, J=8.14, 1.36 Hz, 1H).

Example 73

N-{2-[(3-{[6-chloro-4-(1H-pyrrolo[2,3-b]pyridin-3-yl)pyridin-2-yl]-amino}cyclohexyl)amino]-2-oxoethyl}benzamide The trifluoroacetic acid salt of the title compound was prepared according to the procedure for Example 69, substituting 2-benzamidoacetic acid for cyclopropanecarboxylic acid. Yield: 23 mg (39%). MS (DCI/NH$_3$) m/z 503 (M+H)$^+$, $^1$H NMR (300 MHz, DMSO-d$_6$) ppm 1.00-1.22 (m, 3H), 1.27-1.51 (m, 1H), 1.66-1.86 (m, 2H), 1.94 (d, J=11.19 Hz, 1H), 2.12 (d, J=10.85 Hz, 1H), 3.58-3.79 (m, 2H), 3.84 (d, J=6.10 Hz, 2H), 6.84 (s, 1H), 6.88 (s, 1H), 7.22 (dd, J=7.97, 4.92 Hz, 1H), 7.36-7.58 (m, 3H), 7.87 (dd, J=6.95, 1.53 Hz, 2H), 8.14 (d, J=2.71 Hz, 1H), 8.25-8.36 (m, 2H), 8.64 (t, J=5.93 Hz, 1H), 12.18 (s, 1H).

Example 74

N-[6-chloro-4-(1H-pyrrolo[2,3-b]pyridin-3-yl)pyridin-2-yl]-2,2-dimethylpropane-1,3-diamine A mixture of Example 61a (1.70 g, 6.44 mmol) and 2,2-dimethylpropane-1,3-diamine (10 mL) was heated in a Biotage microwave reactor at 160° C. for 25 minutes. The solution was diluted with 20% brine and washed with EtOAc (2×). The combined organic layers were washed with 20% brine, dried (MgSO$_4$), filtered, and concentrated. The residue was triturated with EtOAc and diethyl ether. The solids were filtered, washed with ether, and dried to give 1.19 g of the title compound. $^1$H NMR (300 MHz, DMSO-d$_6$) ppm 0.87 (s, 6H), 2.36 (s, 2H), 3.16 (d, J=6.10 Hz, 2H), 6.78-6.89 (m, 2H), 6.97 (d, J=1.02 Hz, 1H), 7.21 (dd, J=7.97, 4.58 Hz, 1H), 8.13 (s, 1H), 8.27-8.38 (m, 2H). MS (ESI$^+$) m/z 329.9 (M+H)$^+$.

Example 75

N-(3-{[6-chloro-4-(1H-pyrrolo[2,3-b]pyridin-3-yl)pyridin-2-yl]amino}-2,2-dimethylpropyl)methanesulfonamide To a solution of Example 74 (70.0 mg, 0.212 mmol) in DMF (1 mL) was added triethylamine (0.089 mL, 0.64 mmol) and methanesulfonyl chloride (0.018 mL, 0.23 mmol). After 5 hours, more methanesulfonyl chloride (0.010 mL) was added. The reaction mixture was stirred overnight and treated with water slowly. The precipitate was filtered, washed with water, and oven dried to give the title compound. $^1$H NMR (300 MHz, DMSO-d$_6$) ppm 0.92 (s, 6H), 2.81 (d, J=7.14 Hz, 2H), 2.87 (s, 3H), 3.15 (d, J=6.35 Hz, 2H), 6.79-7.02 (m, 4H), 7.22 (dd, J=7.93, 4.76 Hz, 1H), 8.15 (d, J=2.38 Hz, 1H), 8.28-8.37 (m, 2H), 12.16 (s, 1H). MS (ESI$^+$) m/z 408.0 (M+H)$^+$.

Example 76

N-(3-{[6-chloro-4-(1H-pyrrolo[2,3-b]pyridin-3-yl)pyridin-2-yl]amino}cyclohexyl)cyclopropanesulfonamide The solution of Example 23 (40 mg, 0.12 mmol) in THF (5 mL) was added cyclopropanesulfonyl chloride (20 mg, 0.14 mmol) and triethylamine (one drop). The mixture was stirred at room temperature overnight. The reaction mixture was concentrated and the residue was purified by HPLC as described in Example 58 to give the trifluoroacetic acid salt of the title compound. Yield: 44 mg (84%). MS (DCI/NH$_3$) m/z 446 (M+H)$^+$, $^1$H NMR (300 MHz, DMSO-d$_6$) ppm 0.80-0.97 (m, 3H), 0.99-1.26 (m, 3H), 1.39 (q, J=13.22 Hz, 1H), 1.59-1.82 (m, 2H), 1.91 (d, J=10.85 Hz, 2H), 2.30 (d, J=12.21 Hz, 1H), 2.49-2.61 (m, 1H), 3.14-3.34 (m, 1H), 3.63-3.79 (m, 1H), 6.85 (d, J=1.02 Hz, 1H), 6.89 (d, J=1.02 Hz, 1H), 7.14 (d, J=8.14 Hz, 1H), 7.22 (dd, J=8.14, 4.75 Hz, 1H), 8.14 (d, J=2.71 Hz, 1H), 8.27-8.38 (m, 2H), 12.19 (s, 1H).

Example 77

N-(3-{[6-chloro-4-(1H-pyrrolo[2,3-b]pyridin-3-yl)pyridin-2-yl]amino}cyclohexyl)propane-1-sulfonamide The trifluoroacetic acid salt of the title compound was prepared according to the procedure for Example 76, substituting propane-1-sulfonyl chloride for cyclopropanesulfonyl chloride. Yield: 15 mg (29%). MS (DCI/NH$_3$) m/z 448 (M+H)$^+$, $^1$H NMR (300 MHz, DMSO-d$_6$): 1.00-1.22 (m, 3H), 1.27-1.51 (m, 1H), 1.66-1.86 (m, 2H), 1.94 (d, J=11.19 Hz, 1H), 2.12 (d, J=10.85 Hz, 1H), 3.58-3.79 (m, 2H), 3.84 (d, J=6.10 Hz, 2H), 6.84 (s, 1H), 6.88 (s, 1H), 7.22 (dd, J=7.97, 4.92 Hz, 1H), 7.36-7.58 (m, 3H), 7.87 (dd, J=6.95, 1.53 Hz, 2H), 8.14 (d, J=2.71 Hz, 1H), 8.25-8.36 (m, 2H), 8.64 (t, J=5.93 Hz, 1H), 12.18 (s, 1H).

Example 78

N-(3-{[6-chloro-4-(1H-pyrrolo[2,3-b]pyridin-3-yl)pyridin-2-yl]amino}cyclohexyl)-4-methylbenzenesulfonamide The trifluoroacetic acid salt of the title compound was prepared according to the procedure for Example 76, substituting 4-methylbenzene-1-sulfonyl chloride for cyclopropanesulfonyl chloride. Yield: 45 mg (78%). MS (DCI/NH$_3$) m/z 448 (M+H)$^+$, $^1$H NMR (300 MHz, DMSO-d$_6$) ppm 0.89-1.15 (m, 3H), 1.16-1.35 (m, 1H), 1.64 (d, J=11.10 Hz, 2H), 1.88 (dd, J=25.78, 11.90 Hz, 2H), 2.31 (s, 3H), 2.97-3.17 (m, 1H), 3.47-3.64 (m, 1H), 6.77 (s, 1H), 6.88 (s, 1H), 7.11-7.26 (m, 1H), 7.31 (d, J=7.93 Hz, 2H), 7.63 (d, J=7.54 Hz, 1H), 7.70 (d, J=8.33 Hz, 2H), 8.14 (d, J=2.78 Hz, 1H), 8.30 (s, 1H), 8.32 (s, 1H), 12.19 (s, 1H).

Example 79

1-(3-{[6-chloro-4-(1H-pyrrolo[2,3-b]pyridin-3-yl)pyridin-2-yl]amino}cyclohexyl)-3-ethylurea The solution of Example 23 (40 mg, 0.12 mmol) in THF (5 mL) was added triethylamine (2 drops) and isocyanatoethane (8.5 mg, 0.12 mmol). The mixture was stirred at room temperature overnight. The reaction was partitioned between ethyl acetate (100 mL) and water (50 mL). The organic phase was concentrated and the residue was purified by HPLC as described in Example 58 to give the trifluoroacetic acid salt of the title compound. Yield: 32 mg (66%). MS (DCI/NH$_3$) m/z 413 (M+H)$^+$, $^1$H NMR (300 MHz, DMSO-d$_6$) ppm 0.97 (t, J=7.12 Hz, 3H), 1.00-1.09 (m, 2H), 1.21-1.45 (m, 1H), 1.57-1.87 (m, 3H), 1.93 (d, J=11.87 Hz, 1H), 2.13 (d, J=11.53 Hz, 1H), 2.99 (q, J=7.12 Hz, 2H), 3.36-3.54 (m, 1H), 3.60-3.77 (m, 1H), 6.83 (d, J=1.02 Hz, 1H), 6.87 (d, J=1.02 Hz, 1H), 7.22 (dd, J=8.14, 4.75 Hz, 1H), 8.13 (d, J=3.05 Hz, 1H), 8.26-8.36 (m, 2H), 12.16 (s, 1H).

Example 80

1-(3-{[6-chloro-4-(1H-pyrrolo[2,3-b]pyridin-3-yl)pyridin-2-yl]amino}cyclohexyl)-3-cyclopentylurea The trifluoroacetic acid salt of the title compound was prepared according to the procedure for Example 79, substituting isocyanatocyclopentane for isocyanatoethane. Yield: 15 mg (28%). MS (DCI/NH$_3$) m/z 453 (M+H)$^+$, $^1$H NMR (300 MHz, DMSO-d$_6$) ppm 0.77-1.14 (m, 1H), 1.08-1.39 (m, 5H), 1.35-1.67 (m, 5H), 1.67-1.85 (m, 2H), 3.70-3.89 (m, 2H), 4.03 (dd, J=14.41, 6.95 Hz, 3H), 5.56-5.88 (m, 1H), 6.70-7.01 (m, 2H), 7.22 (dd, J=7.97, 4.58 Hz, 1H), 8.12 (d, J=2.71 Hz, 1H), 8.20-8.43 (m, 2H), 12.15 (s, 1H).

Example 81

N-(3-{[6-chloro-4-(1H-pyrrolo[2,3-b]pyridin-3-yl)pyridin-2-yl]amino}-2,2-dimethylpropyl)pyridine-3-sulfonamide To a solution of Example 74 (55.0 mg, 0.167 mmol) in DMF (1 mL) was added triethylamine (0.070 mL, 0.50 mmol) and pyridine-3-sulfonyl chloride (35.5 mg, 0.200 mmol). After 4 hours, the reaction was quenched with 20% brine and extracted with EtOAc (2×). The organic layers were combined, concentrated, and purified by reverse-phase HPLC as described in Example 56 to give the title compound (28.5 mg) as trifluoroacetic acid salts. $^1$H NMR (500 MHz, DMSO-d$_6$) ppm 0.89 (s, 6H), 2.68 (d, J=7.02 Hz, 2H), 3.13 (s, 2H), 6.80 (s, brd, 1H), 6.89 (d, J=1.22 Hz, 1H), 6.94 (s, 1H), 7.22 (dd, J=8.09, 4.73 Hz, 1H), 7.60 (dd, J=7.63, 4.58 Hz, 1H), 7.77 (t, J=6.87 Hz, 1H), 8.12-8.18 (m, 2H), 8.28-8.35 (m, 2H), 8.77 (d, J=6.41 Hz, 1H), 8.94 (d, J=2.14 Hz, 1H), 12.19 (s, 1H). MS (APCI$^+$) m/z 471.2 (M+H)$^+$.

Example 82

N-(3-{[6-chloro-4-(1H-pyrrolo[2,3-b]pyridin-3-yl)pyridin-2-yl]amino}-2,2-dimethylpropyl)cyclopropanesulfonamide The trifluoroacetic acid salt of the title compound was prepared as described in Example 81, substituting pyridine-3-sulfonyl chloride with cyclopropanesulfonyl chloride. $^1$H NMR (500 MHz, DMSO-d$_6$) ppm 0.84-0.96 (m, 10H), 2.52 (m, 1H), 2.86 (d, J=6.71 Hz, 2H), 3.17 (s, 2H), 6.87 (s, brd, 1H), 6.92 (s, 1H), 6.95-7.04 (m, 2H), 7.25 (dd, J=8.09, 4.73 Hz, 1H), 8.17 (d, J=2.75 Hz, 1H), 8.33 (dd, J=4.58, 1.22 Hz, 1H), 8.38 (d, J=9.15 Hz, 1H), 12.24 (s, 1H).). MS (ESI$^+$) m/z 432.0 (M−H)$^+$.

Example 83

N-(3-{[6-chloro-4-(1H-pyrrolo[2,3-b]pyridin-3-yl)pyridin-2-yl]amino}cyclohexyl)thiophene-2-sulfonamide The trifluoroacetic acid salt of the title compound was prepared according to the procedure for Example 76, substituting thiophene-2-sulfonyl chloride for cyclopropanesulfonyl chloride. Yield: 25 mg (44%). MS (DCI/NH$_3$) m/z 489 (M+H)$^+$, $^1$H NMR (300 MHz, DMSO-d$_6$) ppm 0.94-1.19 (m, 3H), 1.19-1.42 (m, 2H), 1.52-1.75 (m, 2H), 1.86 (d, J=13.09 Hz, 1H), 1.99 (d, J=12.69 Hz, 1H), 3.12-3.29 (m, 1H), 6.79 (s, 1H), 6.88 (s, 1H), 7.11 (dd, J=4.96, 3.77 Hz, 1H), 7.16-7.25 (m, 1H), 7.60 (dd, J=3.77, 1.39 Hz, 1H), 7.83 (d, J=5.95 Hz, 1H), 7.93 (d, J=7.54 Hz, 1H), 8.13 (d, J=2.78 Hz, 1H), 8.30 (d, J=5.95 Hz, 2H), 12.16 (s, 1H).

Example 84

N-[6-chloro-4-(1H-pyrrolo[2,3-b]pyridin-3-yl)pyridin-2-yl]pentanamide

A mixture of Example 7a (82.5 mg, 0.204 mmol), pentanamide (28.9 mg, 0.286 mmol), cesium carbonate (100 mg, 0.306 mmol), palladium (II) acetate (2.29 mg, 10.2 μmol), and Xantphos (8.86 mg, 0.015 mmol) was degassed and heated at 85° C. in a sealed vial for 6 hours. The reaction mixture was cooled and concentrated. The residue was treated with 20% brine and extracted with EtOAc (2×). The organic layers were dried and concentrated. The crude intermediate was dissolved in dioxane (1.5 mL) and treated with 20% sodium hydroxide (0.15 mL, 0.20 mmol). The mixture was heated at 50° C. for 2 hours. The solvent was evaporated. The residue was treated with water, sonicated, filtered, and washed with water, and purified by reverse-phase HPLC as described in Example 56 to give the title compound (8.0 mg) as trifluoroacetic acid salts. $^1$H NMR (500 MHz, DMSO-d$_6$) ppm 0.90 (t, J=7.48 Hz, 3H), 1.27-1.38 (m, 2H), 1.54-1.64 (m, 2H), 2.43 (t, J=7.32 Hz, 2H), 7.29 (m, 1H), 7.57 (s, 1H), 8.28-8.37 (m, 3H), 8.60 (s, 1H), 10.74 (s, 1H), 12.36 (s, 1H). MS (ESI$^+$) m/z 328.9 (M+H)$^+$.

Example 85

N-[6-chloro-4-(1H-pyrrolo[2,3-b]pyridin-3-yl)pyridin-2-yl]cyclohexanecarboxamide The trifluoroacetic acid salt of the title compound was prepared as described in Example 84, substituting pentanamide with cyclohexanecarboxamide. $^1$H NMR (300 MHz, DMSO-$d_6$) ppm 0.98-1.52 (m, 5H), 1.57-1.91 (m, 5H), 2.47 (m, 1H), 7.28 (m, 1H), 7.56 (d, J=1.19 Hz, 1H), 8.22-8.41 (m, J=5.75, 5.75 Hz, 3H), 8.59 (s, 1H), 10.67 (s, 1H), 12.35 (s, 1H). MS (APCI$^+$) m/z 355.3 (M+H)$^+$.

Example 86

N-[6-chloro-4-(1H-pyrrolo[2,3-b]pyridin-3-yl)pyridin-2-yl]benzamide

The trifluoroacetic acid salt of the title compound was prepared as described in Example 84, substituting pentanamide with benzamide. $^1$H NMR (500 MHz, DMSO-$d_6$) ppm 7.31 (dd, J=7.93, 4.58 Hz, 1H), 7.53 (t, J=7.63 Hz, 2H), 7.59-7.67 (m, 2H), 8.08 (d, J=8.54 Hz, 2H), 8.34-8.38 (m, 2H), 8.43 (d, J=7.93 Hz, 1H), 8.70 (s, 1H), 11.08 (s, 1H), 12.40 (s, 1H). MS (APCI$^+$) m/z 349.0 (M+H)$^+$.

Example 87

N-[6-chloro-4-(1H-pyrrolo[2,3-b]pyridin-3-yl)pyridin-2-yl]ethane-1,2-diamine

The title compound was prepared as described in Example 74, substituting 2,2-dimethylpropane-1,3-diamine with ethane-1,2-diamine $^1$H NMR (300 MHz, DMSO-$d_6$) ppm 1.09 (t, J=6.95 Hz, 1H), 2.72 (t, J=6.27 Hz, 2H), 3.19-3.28 (m, 2H), 3.38 (q, J=6.89 Hz, 1H), 6.85-6.90 (m, 2H), 7.20 (dd, J=7.80, 4.75 Hz, 1H), 8.12 (s, 1H), 8.28-8.35 (m, 2H). MS (ESI$^+$) m/z 287.9 (M+H)$^+$.

Example 88

N-(2-{[6-chloro-4-(1H-pyrrolo[2,3-b]pyridin-3-yl)pyridin-2-yl]amino}ethyl)methanesulfonamide The title compound was prepared as described in Example 75, substituting Example 74 with Example 87. The reaction was completed in 4 hours. $^1$H NMR (300 MHz, DMSO-$d_6$) ppm 2.93 (s, 3H), 3.14 (q, J=6.35 Hz, 2H), 3.40 (q, J=6.35 Hz, 2H), 6.90 (s, 1H), 6.94 (s, 1H), 6.98 (t, J=5.95 Hz, 1H), 7.12 (t, J=5.35 Hz, 1H), 7.21 (dd, J=7.93, 4.76 Hz, 1H), 8.14 (s, 1H), 8.28-8.35 (m, 2H). MS (ESI$^+$) m/z 365.9 (M+H)$^+$.

Example 89

N-(2-{[6-chloro-4-(1H-pyrrolo[2,3-b]pyridin-3-yl)pyridin-2-yl]amino}ethyl)cyclopropanesulfonamide The title compound was prepared as described in Example 75, substituting Example 74 with Example 87 and substituting methanesulfonyl chloride with cyclopropanesulfonyl chloride. The reaction was completed in 3.5 hours. $^1$H NMR (300 MHz, DMSO-$d_6$) ppm 0.88-0.98 (m, J=10.17 Hz, 4H), 2.59 (m, 1H), 3.17 (q, J=6.44 Hz, 2H), 3.41 (q, J=6.22 Hz, 2H), 6.88 (s, 1H), 6.92-7.00 (m, 2H), 7.15-7.24 (m, 2H), 8.14 (d, J=2.71 Hz, 1H), 8.28-8.35 (m, 2H), 12.16 (s, 1H). MS (ESI$^+$) m/z 392.0 (M+H)$^+$.

Example 90

N-(2-{[6-chloro-4-(1H-pyrrolo[2,3-b]pyridin-3-yl)pyridin-2-yl]amino}ethyl)pyridine-3-sulfonamide The title compound was prepared as described in Example 75, substituting Example 74 with Example 87 and substituting methanesulfonyl chloride with pyridine-3-sulfonyl chloride. The reaction was completed in 3.5 hours. The final product was purified by reverse-phase HPLC as described in Example 56 to give the trifluoroacetic acid salt of the title compound. $^1$H NMR (300 MHz, DMSO-$d_6$) ppm 3.01 (q, J=6.35 Hz, 2H), 3.33 (t, J=6.35 Hz, 2H), 6.83 (s, 1H), 6.92 (s, 1H), 7.23 (dd, J=7.93, 4.76 Hz, 1H), 7.61 (dd, J=7.93, 4.76 Hz, 1H), 8.01 (t, J=5.75 Hz, 1H), 8.10-8.24 (m, 2H), 8.26-8.39 (m, 2H), 8.78 (dd, J=4.76, 1.59 Hz, 1H), 8.96 (d, J=2.38 Hz, 1H), 12.20 (s, 1H). MS (ESI$^+$) m/z 428.9 (M+H)$^+$.

Example 91

6-chloro-4-(1H-pyrrolo[2,3-b]pyridin-3-yl)pyridin-2-amine

Example 91a

N-(6-chloro-4-(1-(phenylsulfonyl)-1H-pyrrolo[2,3-b]pyridin-3-yl)pyridin-2-yl)acetamide A mixture of Example 7a (1.44 g, 3.57 mmol), acetamide (0.295 g, 4.99 mmol), cesium carbonate (1.743 g, 5.35 mmol), palladium (II) acetate (0.024 g, 0.107 mmol), and Xantphos (0.093 g, 0.161 mmol) was degassed and heated at 85° C. in a sealed vial for 6 hours. The reaction mixture was cooled and concentrated. The residue was treated with 20% brine and extracted with EtOAc (2×). The organic layers were dried, concentrated, and purified on a 40 g column using the ISCO Companion flash system eluting with $CH_2Cl_2$/EtOAc (90:10) to give 0.384 g of the title compound.

Example 91b 6-chloro-4-(1H-pyrrolo[2,3-b]pyridin-3-yl)pyridin-2-amine

A mixture of Example 91a (186.0 mg, 0.436 mmol) and HCl (0.20 mL, 6.6 mmol) in ethanol (6 mL) was heated at 95° C. for 3 hours and cooled. Half of the solvent was evaporated; the resulting suspension was filtered and washed with EtOH. The solids were stirred in saturated $NaHCO_3$ for 30 minutes, filtered, washed with water, and oven-dried to give 72.2 mg of the title compound. $^1$H NMR (300 MHz, DMSO-$d_6$) ppm 6.30 (s, 2H), 6.85 (s, 1H), 6.91 (s, 1H), 7.15 (m, 1H), 8.12 (s, 1H), 8.21-8.36 (m, 2H), 12.15 (s, brd, 1H). MS (ESI$^+$) m/z 244.8 (M+H)$^+$.

Example 92

6-chloro-N-cyclobutyl-4-(1H-pyrrolo[2,3-b]pyridin-3-yl)pyridin-2-amine

Example 92 (0.015 g) was prepared as described in Example 61b, substituting trans-cyclohexane-1,4-diamine with cyclobutanamine. $^1$H NMR (300 MHz, DMSO-$d_6$) ppm 1.54-1.80 (m, 2H) 1.79-2.03 (m, 2H) 2.17-2.41 (m, 2H) 4.09-4.42 (m, 1H) 6.72-6.80 (m, 1H) 6.82-6.98 (m, 1H) 7.04-7.37

(m, 2H) 7.97-8.25 (m, 1H) 8.20-8.39 (m, 2H) 11.94-12.30 (m, 1H). MS (ESI+) m/z 298.9 (M+H)+.

Example 93 trans-N'-[6-chloro-4-(1H-pyrrolo[2,3-b]pyridin-3-yl)pyridin-2-yl]-N,N-dimethylcyclohexane-1,4-diamine To a solution of Example 61b (0.15 g, 0.44 mmol) in 5 mL of methanol was added formaldehyde (0.16 mL, 2.2 mmol, 37% aqueous solution). The solution was stirred at room temperature for 10 minutes, when sodium cyanoborohydride (0.055 g, 0.88 mmol) and catalytic $ZnCl_2$ was added. The reaction mixture was stirred at room temperature for 16 hours. Solvent was removed and the crude material was purified by reverse-phase HPLC performed on a Phenomenex Luna C8 AXIA column (30×75 mm, 100 Å) using a gradient of 10% to 95% acetonitrile: 0.1% aqueous trifluoroacetic acid over 12 minutes at a flow rate of 50 mL/minutes to give 0.135 g of the title product as the trifluoroacetic acid salt. $^1$H NMR (300 MHz, DMSO-$d_6$) ppm 1.17-1.40 (m, 3H) 1.47-1.74 (m, 3H) 1.99 (s, 2H) 2.11 (s, 2H) 2.65-2.86 (m, 6H) 3.12-3.30 (m, 1H) 6.78-6.97 (m, 2H) 7.13-7.29 (m, 1H) 8.05-8.19 (m, 1H) 8.21-8.41 (m, 2H) 9.13-9.56 (m, 1H) 11.89-12.37 (m, 1H). MS (ESI+) m/z 370.0 (M+H)+.

Example 94

6-chloro-N-[(1-ethylpiperidin-3-yl)methyl]-4-(1H-pyrrolo[2,3-b]pyridin-3-yl)pyridin-2-amine

Example 94a benzyl 3-((6-chloro-4-iodopyridin-2-ylamino)methyl)piperidine-1-carboxylate To a mixture of 2,6-dichloro-4-iodopyridine (1.5 g, 5.5 mmol) and benzyl 3-(aminomethyl)piperidine-1-carboxylate (2.7 g, 11 mmol) in dioxane (10 mL) in a microwave tube was added ten drops of diisopropylethyl amine and sealed. The tube was heated at 150° C. for 72 hours. The reaction mixture was cooled to room temperature and concentrated, the residue was purified by flash chromatography eluting with EtOAc/hexane=1:3 to 1:2 to give the title compound. Yield: 1.0 g (38%). MS (DCI/NH$_3$) m/z 486 (M+H)+.

Example 94b

Benzyl 3-((6-chloro-4-(1-(phenylsulfonyl)-1H-pyrrolo[2,3-b]pyridin-3-yl)pyridin-2-ylamino)methyl)piperidine-1-carboxylate A suspension of Example 94a (1 g, 2.0 mmol), 1-(phenylsulfonyl)-3-(4,4,5,5-tetramethyl-1,3,2-dioxaborolan-2-yl)-1H-pyrrolo[2,3-b]pyridine (0.8 g, 2.2 mmol), dichlorobis(triphenylphosphine)palladium(II) (72 mg, 0.1 mmol) and sodium carbonate solution (2M, 1 mL, 2.0 mmol) in a mixture solvent of DME/EtOH/H$_2$O (7:2:3) (10 mL) was degassed and heated at 80° C. overnight. The reaction mixture was cooled to room temperature, quenched with water, and partitioned between water and ethyl acetate. The organic phase was dried and concentrated, the residue was purified flash chromatography eluting with EtOAc/hexane=1:3 to 1:2 to give the title compound. Yield: 1.0 g (79%). MS (DCI/NH$_3$) m/z 617 (M+H)+.

Example 94c 6-chloro-N-(piperidin-3-ylmethyl)-4-(1H-pyrrolo[2,3-b]pyridin-3-yl)pyridin-2-amine A solution of Example 94b (900 mg, 1.5 mmol) in trifluoroacetic acid (2 mL) was stirred at room temperature for 3 hours at 50° C. overnight. The reaction mixture was concentrated and the residue was dissolved in ethanol (5 mL). A solution of KOH (1N) in water (0.5 mL) was added into the mixture. The mixture was stirred at 50° C. for 3 hours. The residue was purified by HPLC as described in Example 58 to give the trifluoroacetic acid salt of the title compound. Yield: 380 mg (76%). MS (DCI/NH$_3$) m/z 342 (M+H)+.

Example 94d 6-chloro-N-[(1-ethylpiperidin-3-yl)methyl]-4-(1H-pyrrolo[2,3-b]pyridin-3-yl)pyridin-2-amine The title compound was also obtained in Example 94c. Yield: 80 mg (16%). MS (DCI/NH$_3$) m/z 370 (M+H)+, $^1$H NMR (300 MHz, CD$_3$OD): 1.35 (t, J=7.29 Hz, 3H), 1.66-1.85 (m, 1H), 1.94-2.10 (m, 2H), 2.13-2.33 (m, 1H), 2.70 (t, J=12.21 Hz, 1H), 2.76-2.93 (m, 1H), 3.18 (q, J=7.35 Hz, 2H), 3.30 (dd, 1H), 3.38 (dd, J=6.44, 2.71 Hz, 2H), 3.47-3.59 (m, 1H), 3.58-3.69 (m, 1H), 6.79 (d, J=1.02 Hz, 1H), 6.90 (d, J=1.36 Hz, 1H), 7.33 (dd, J=8.14, 5.09 Hz, 1H), 7.91 (s, 1H), 8.33 (d, J=4.75 Hz, 1H), 8.46 (dd, J=8.14, 1.36 Hz, 1H).

Example 95

6-chloro-N-[(1-cyclobutylpiperidin-3-yl)methyl]-4-(1H-pyrrolo[2,3-b]pyridin-3-yl)pyridin-2-amine The trifluoroacetic acid salt of the title compound was prepared according to the procedure for Example 58, substituting Example 94c for Example 23 and substituting cyclobutanone for isobutyraldehyde. Yield: 20 mg (34%). MS (DCI/NH$_3$) m/z 396 (M+H)+, $^1$H NMR (300 MHz, METHANOL-d$_4$) ppm 1.19-1.41 (m, 1H), 1.64-1.78 (m, 1H), 1.81-1.96 (m, 2H), 1.95-2.10 (m, 2H), 2.10-2.29 (m, 3H), 2.25-2.45 (m, 2H), 2.52 (t, J=12.10 Hz, 1H), 2.60-2.76 (m, 1H), 3.37 (t, J=5.75 Hz, 2H), 3.40-3.49 (m, 1H), 3.56 (d, J=13.48 Hz, 1H), 3.60-3.70 (m, 1H), 6.79 (d, J=1.19 Hz, 1H), 6.91 (d, J=0.79 Hz, 1H), 7.31 (dd, J=7.93, 5.16 Hz, 1H), 7.90 (s, 1H), 8.32 (dd, J=5.16, 1.19 Hz, 1H), 8.43 (dd, J=7.93, 1.19 Hz, 1H).

Example 96

6-chloro-N-{[1-(pyridin-3-ylmethyl)piperidin-3-yl]methyl}-4-(1H-pyrrolo[2,3-b]pyridin-3-yl)pyridin-2-amine The trifluoroacetic acid salt of the title compound was prepared according to the procedure for Example 58, substituting Example 94c for Example 23 and substituting nicotinaldehyde for isobutyraldehyde. Yield: 36 mg (71%). MS (DCI/NH$_3$) m/z 433 (M+H)+, $^1$H NMR (300 MHz, CD$_3$OD): 1.19-1.48 (m, 1H), 1.65-1.87 (m, 1H), 1.92-2.11 (m, 2H), 2.11-2.31 (m, 1H), 2.70-2.89 (m, 1H), 2.89-3.09 (m, 1H), 3.17-3.33 (m, 1H), 3.39 (d, J=6.44 Hz, 2H), 3.41-3.59 (m, 2H), 4.27-4.50 (m, 2H), 6.74 (s, 1H), 6.91 (s, 1H), 7.31 (dd, J=7.97, 4.92 Hz, 1H), 7.56 (dd, J=7.80, 5.09 Hz, 1H), 7.90 (s, 1H), 7.93-8.08 (m, 1H), 8.33 (dd, J=4.92, 1.19 Hz, 1H), 8.42 (dd, J=7.97, 1.53 Hz, 1H), 8.65 (dd, J=4.92, 1.53 Hz, 1H), 8.70 (d, J=1.70 Hz, 1H).

Example 97

6-chloro-N-((1-(methylsulfonyl)piperidin-3-yl)methyl)-4-(1H-pyrrolo[2,3-b]pyridin-3-yl)pyridin-2-amine The trifluoroacetic acid salt of the title compound was prepared according to the procedure for Example 76, substituting Example 94c for Example 23 and substituting methanesulfonyl chloride for cyclopropane-1-sulfonyl chloride. Yield: 10 mg (20%). MS (DCI/NH$_3$) m/z 420 (M+H)$^+$, $^1$H NMR (300 MHz, DMSO-d$_6$) ppm 0.98-1.29 (m, 2H), 1.35-1.62 (m, 1H), 1.67-1.95 (m, 3H), 2.65-2.78 (m, 1H), 2.84 (s, 3H), 3.13-3.28 (m, 2H), 3.46 (d, J=11.10 Hz, 1H), 3.61 (dd, J=11.50, 3.17 Hz, 1H), 6.90 (s, 1H), 6.91 (s, 1H), 7.23 (dd, J=7.93, 4.76 Hz, 1H), 8.15 (d, J=2.78 Hz, 1H), 8.28-8.36 (m, 2H), 12.18 (s, 1H).

Example 98

3-((6-chloro-4-(1H-pyrrolo[2,3-b]pyridin-3-yl)pyridin-2-ylamino)methyl)-N-ethylpiperidine-1-carboxamide The trifluoroacetic acid salt of the title compound was prepared according to the procedure for Example 79, substituting Example 94c for Example 23 and substituting isocyanatocyclopentane for isocyanatoethane. Yield: 20 mg (41%). MS (DCI/NH$_3$) m/z 413 (M+H)$^+$, $^1$H NMR (300 MHz, DMSO-d$_6$) ppm 0.99 (t, J=7.14 Hz, 3H), 1.09-1.25 (m, 1H), 1.19-1.42 (m, 1H), 1.54-1.74 (m, 2H), 1.82 (d, J=12.29 Hz, 1H), 2.45 (s, 1H), 2.70 (t, J=10.71 Hz, 1H), 3.03 (q, J=7.14 Hz, 2H), 3.10-3.19 (m, 2H), 3.77 (d, J=13.09 Hz, 1H), 3.96 (d, J=13.09 Hz, 1H), 6.88 (s, 1H), 6.89 (s, 1H), 7.23 (dd, J=8.33, 4.76 Hz, 1H), 8.14 (d, J=2.78 Hz, 1H), 8.20-8.45 (m, 2H), 12.19 (s, 1H).

Example 99

1-(trans-4-{[6-chloro-4-(1H-pyrrolo[2,3-b]pyridin-3-yl)pyridin-2-yl]amino}cyclohexyl)-3-methylurea Example 99 (0.11 g) was prepared as described in Example 21, substituting methanesulfonyl chloride with isocyanatomethane, and substituting Example 15 with Example 61b. $^1$H NMR (300 MHz, DMSO-d$_6$) ppm 1.13-1.36 (m, 5H) 1.85 (s, 2H) 1.99 (s, 2H) 3.28 (s, 3H) 3.63 (s, 1H) 5.51-5.64 (m, 1H) 5.67-5.79 (m, 1H) 6.70-6.80 (m, 1H) 6.83-6.90 (m, 2H) 7.14-7.28 (m, 1H) 8.07-8.16 (m, 1H) 8.24-8.36 (m, 2H) 11.92-12.42 (m, 1H). MS (ESI$^+$) m/z 398.9 (M+H)$^+$

Example 100

1-[3-({[6-chloro-4-(1H-pyrrolo[2,3-b]pyridin-3-yl)pyridin-2-yl]amino}methyl)piperidin-1-yl]ethanone The trifluoroacetic acid salt of the title compound was prepared according to the procedure for Example 69, substituting Example 94c for Example 23 and substituting acetic acid for cyclopropanecarboxylic acid. Yield: 28 mg (62%). MS (DCI/NH$_3$) m/z 384 (M+H)$^+$, $^1$H NMR (300 MHz, CD$_3$OD): 1.20-1.56 (m, 1H), 1.67-1.88 (m, 1H), 1.86-2.01 (m, 1H), 2.08 (s, 3H), 2.68 (dd, J=12.88, 10.17 Hz, 1H), 2.79-2.94 (m, 1H), 2.99-3.09 (m, 1H), 3.12-3.27 (m, 1H), 3.79 (d, J=13.56 Hz, 1H), 3.90 (dd, J=13.39, 3.56 Hz, 1H), 4.21 (d, J=12.88 Hz, 1H), 4.38 (dd, J=12.88, 3.73 Hz, 1H), 6.80 (s, 1H), 6.91 (s, 1H), 7.34-7.55 (m, 1H), 8.00 (d, J=6.78 Hz, 1H), 8.26-8.44 (m, 1H), 8.47-8.76 (m, 1H).

Example 101

6-chloro-N-{[1-(cyclopropylsulfonyl)piperidin-3-yl]methyl}-4-(1H-pyrrolo[2,3-b]pyridin-3-yl)pyridin-2-amine The trifluoroacetic acid salt of the title compound was prepared according to the procedure for Example 76, substituting Example 94c for Example 23. Yield: 28 mg (54%). MS (DCI/NH$_3$) m/z 446 (M+H)$^+$, $^1$H NMR (300 MHz, CD$_3$OD): 0.92-1.06 (m, 4H), 1.16-1.36 (m, 1H), 1.49-1.74 (m, 1H), 1.79 (s, 1H), 1.84-1.93 (m, 1H), 1.93-2.07 (m, 1H), 2.37-2.51 (m, 1H), 2.76 (dd, J=11.53, 9.83 Hz, 1H), 2.84-3.01 (m, 1H), 3.03-3.11 (m, 1H), 3.24 (d, J=4.75 Hz, 1H), 3.61 (d, J=11.87 Hz, 1H), 3.74 (dd, J=13.22, 2.37 Hz, 1H), 6.80 (d, J=1.02 Hz, 1H), 6.91 (d, J=1.02 Hz, 1H), 7.45 (dd, J=7.97, 5.26 Hz, 1H), 8.01 (s, 1H), 8.38 (d, J=4.07 Hz, 1H), 8.63 (dd, J=7.97, 1.19 Hz, 1H).

Example 102

(3-{[6-chloro-4-(1H-pyrrolo[2,3-b]pyridin-3-yl)pyridin-2-yl]amino}piperidin-1-yl)(cyclopropyl)methanone

Example 102a

Benzyl 3-(6-chloro-4-(1H-pyrrolo[2,3-b]pyridin-3-yl)pyridin-2-ylamino)piperidine-1-carboxylate The title compound was prepared according to the procedure for Example 8, substituting benzyl 3-aminopiperidine-1-carboxylate for tetrahydro-2H-pyran-4-amine. Yield: 430 mg (50%). MS (DCI/NH$_3$) m/z 462 (M+H)$^+$.

Example 102b 6-chloro-N-(piperidin-3-yl)-4-(1H-pyrrolo[2,3-b]pyridin-3-yl)pyridin-2-amine A solution of Example 102a (430 mg, 0.93 mmol) in trifluoroacetic acid (5 mL) was stirred at room temperature overnight. The mixture was concentrated and the residue was purified by HPLC as described in Example 58 to give the trifluoroacetic acid salt of the title compound. Yield: 180 mg (59%). MS (DCI/NH$_3$) m/z 328 (M+H)$^+$.

Example 102c (3-{[6-chloro-4-(1H-pyrrolo[2,3-b]pyridin-3-yl)pyridin-2-yl]amino}piperidin-1-yl)(cyclopropyl)methanone The trifluoroacetic acid salt of the title compound was prepared according to the procedure for Example 69, substituting Example 102b for Example 23. Yield: 26 mg (53%). MS (DCI/NH$_3$) m/z 396 (M+H)$^+$, $^1$H NMR (300 MHz, DMSO-d$_6$): 0.60-0.87 (m, 4H), 1.34-1.69 (m, 2H), 1.76 (dd, J=11.70, 5.93 Hz, 1H), 1.91-2.05 (m, 2H), 3.00-3.15 (m, 1H), 3.16-3.29 (m, 1H), 3.87-4.14 (m, 2H), 4.08-4.42 (m, 1H), 6.94 (s, 1H), 6.99 (s, 1H), 7.22 (dd, J=7.80, 4.75 Hz, 1H), 8.14 (d, J=2.71 Hz, 1H), 8.17-8.46 (m, 2H), 12.17 (s, 1H).

Example 103

N-[6-chloro-4-(1H-pyrrolo[2,3-b]pyridin-3-yl)pyridin-2-yl]-N'-(cyclopropylmethyl)cyclohexane-1,3-diamine The trifluoroacetic acid salt of the title compound was prepared according to the procedure for Example 58, substituting cyclopropanecarbaldehyde for isobutyraldehyde. Yield: 23 mg (50%). MS (DCI/NH$_3$) m/z 396 (M+H)$^+$, $^1$H NMR (300 MHz, CD$_3$OD): 0.41 (q, J=4.75 Hz, 2H), 0.67-0.78 (m, 2H), 0.99-1.16 (m, 1H), 1.17-1.43 (m, 3H), 1.43-1.66 (m, 1H), 1.72-1.90 (m, 1H), 1.91-2.23 (m, 3H), 2.61 (dd, J=9.83, 2.03 Hz, 1H), 2.96 (d, J=7.12 Hz, 2H), 3.78-4.01 (m, 1H), 6.77 (d, J=1.36 Hz, 1H), 6.89 (d, J=1.36 Hz, 1H), 7.33 (dd, J=7.97, 4.92 Hz, 1H), 7.90 (dd, 1H), 8.33 (dd, J=5.09, 1.36 Hz, 1H), 8.46 (dd, J=7.97, 1.53 Hz, 1H).

Example 104

6-chloro-N-(1-cyclobutylpiperidin-3-yl)-4-(1H-pyrrolo[2,3-b]pyridin-3-yl)pyridin-2-amine The trifluoroacetic acid salt of the title compound was prepared according to the procedure for Example 58, substituting Example 102b for Example 23 and substituting cyclobutanone for isobutyraldehyde. Yield: 44 mg (76%). MS (DCI/NH$_3$) m/z 382 (M+H)$^+$, $^1$H NMR (300 MHz, CD$_3$OD): 1.47-1.70 (m, 1H), 1.76-2.02 (m, 3H), 2.06-2.23 (m, 3H), 2.22-2.40 (m, 2H), 2.45 (t, J=11.30 Hz, 2H), 2.66-2.84 (m, 1H), 3.48 (d, J=13.88 Hz, 1H), 3.60-3.76 (m, 1H), 3.74-3.92 (m, 1H), 4.05-4.34 (m, 1H), 6.82 (s, 1H), 6.96 (s, 1H), 7.31 (dd, J=8.13, 4.96 Hz, 1H), 7.90 (s, 1H), 8.32 (d, J=5.16 Hz, 1H), 8.42 (d, J=7.93 Hz, 1H).

Example 105 trans-N-[6-chloro-4-(1H-pyrrolo[2,3-b]pyridin-3-yl)pyridin-2-yl]-N'-cyclobutylcyclohexane-1,4-diamine Example 105 (0.08 g) was prepared as described in Example 93, substituting formaldehyde with cyclobutanone. The solvent was removed in vacuo, and the crude material dissolved in dichloromethane. The organics were washed with saturated NaHCO$_3$, and the aqueous layer extracted with dichloromethane (3×). The organics was filtered, and the filtrate driedover MgSO$_4$, filtered, and concentrated. The residue was combined with the filtered solid to give the title compound as the free base. $^1$H NMR (300 MHz, DMSO-d$_6$) ppm 0.95-1.29 (m, 4H) 1.37 (s, 1H) 1.44-1.74 (m, 4H) 1.84 (s, 2H) 1.94 (s, 2H) 2.01-2.20 (m, 2H) 2.37 (s, 1H) 3.60 (s, 2H) 6.60-6.77 (m, 1H) 6.76-6.96 (m, 2H) 7.08-7.28 (m, 1H) 8.00-8.19 (m, 1H) 8.20-8.38 (m, 2H) 11.76-12.41 (m, 1H). MS (ESI$^+$) m/z 396.0 (M+H)$^+$.

Example 106

(2S)—N-(trans-4-{[6-chloro-4-(1H-pyrrolo[2,3-b]pyridin-3-yl)pyridin-2-yl]amino}cyclohexyl)azetidine-2-carboxamide

Example 106a (S)-tert-butyl 2-((1r,4S)-4-(6-chloro-4-(1H-pyrrolo[2,3-b]pyridin-3-yl)pyridin-2-ylamino)cyclohexylcarbamoyl)azetidine-1-carboxylate To a solution of Example 61b (0.125, 0.37 mmol) in 4 mL DMF was added EDC (0.14 g, 0.73 mmol), HOBT (0.11 g, 0.73 mmol), diisopropylethylamine (0.142 g, 1.09 mmol) and (S)-1-(tert-butoxycarbonyl)azetidine-2-carboxylic acid (0.088 g, 0.44 mmol). The reaction was allowed to stir at room temperature for 16 hours. The solution was diluted with ethyl acetate and washed with water (2×), brine, dried over magnesium sulfate, filtered, and concentrated. Flash chromatography performed with an Analogix280 using an SF 12-24 column (0% to 6% ethyl acetate/hexanes gradient over 30 minutes) to give 80 mg of the title compound as a solid. MS (ESI$^+$) m/z 525.1 (M+H)$^+$.

Example 106b (2S)—N-(trans-4-{[6-chloro-4-(1H-pyrrolo[2,3-b]pyridin-3-yl)pyridin-2-yl]amino}cyclohexyl)azetidine-2-carboxamide To a solution of Example 106a in 2 mL dichloromethane was added 1 mL trifluoroacetic acid. The reaction was stirred at room temperature for 2 hours and the solvent removed in vacuo. The crude material was azeotroped with dichloromethane (3×) and dried on high vacuum for 10 hours to give 0.08 g the title compound as the bis-trifluoroacetic acid salt. $^1$H NMR (300 MHz, DMSO-d$_6$) ppm 1.16-1.45 (m, 5H) 1.74-1.96 (m, 4H) 1.94-2.14 (m, 2H) 2.17-2.44 (m, 1H) 2.54-2.76 (m, 1H) 3.70 (m, 2H) 4.64-5.04 (m, 1H) 6.71-6.84 (m, 1H) 6.83-6.91 (m, 2H) 7.08-7.30 (m, 1H) 7.98-8.24 (m, 1H) 8.17-8.41 (m, 2H) 8.56-8.86 (m, 1H) 8.80-9.19 (m, 1H) 11.93-12.40 (m, 1H). MS (ESI$^+$) m/z 425.1 (M+H)$^+$.

Example 107

N-[6-chloro-4-(1H-pyrrolo[2,3-b]pyridin-3-yl)pyridin-2-yl]pyridine-3-carboxamide A mixture of Example 7a (0.250 g, 0.618 mmol), nicotinamide (0.098 g, 0.804 mmol), cesium carbonate (0.222 g, 0.680 mmol), palladium (II) acetate (6.9 mg, 0.031 mmol), and Xantphos (0.027 g, 0.046 mmol) in dioxane (6 mL) and DMF (0.6 mL) was heated at 150° C. for 30 minutes in a Biotage microwave reactor. After cooling the reaction mixture was filtered and the solid washed with CH$_2$Cl$_2$. The filtrate was concentrated. The residue was triturated with EtOAc/ether. The solid was filtered, washed with EtOAc/diethyl ether, and dried to give 0.240 g of the intermediate. The intermediate was suspended in dioxane (6 mL) and treated with 20% sodium hydroxide (0.60 mL, 0.62 mmol). The mixture was heated at 50° C. for 3 hours. After concentration, the residue was stirred in water for 15 minutes, filtered, and purified by reverse-phase HPLC as described in Example 56 to give the title compound (29.8 mg) as trifluoroacetic acid salts. $^1$H NMR (500 MHz, DMSO-d$_6$) ppm 7.31 (dd, J=8.09, 4.73 Hz, 1H), 7.62 (dd, J=7.93, 4.88 Hz, 1H), 7.69 (d, J=1.22 Hz, 1H), 8.33-8.40 (m, 2H), 8.40-8.50 (m, 2H), 8.70 (s, 1H), 8.80 (d, J=6.41 Hz, 1H), 9.21 (d, J=1.83 Hz, 1H), 11.40 (s, 1H), 12.41 (s, 1H). MS (ESI) m/z 349.9 (M+H)$^+$.

Example 108

N-[6-chloro-4-(1H-pyrrolo[2,3-b]pyridin-3-yl)pyridin-2-yl]butanamide

A mixture of Example 7a (0.600 g, 1.484 mmol), butyramide (0.194 g, 2.23 mmol), cesium carbonate (0.629 g, 1.93 mmol), palladium (II) acetate (0.017 g, 0.074 mmol), and Xantphos (0.064 g, 0.111 mmol) in dioxane (12 mL) was degassed and heated at 82° C. for 4.5 hours. The solvent was evaporated and the residue was treated with 20% brine and extracted with EtOAc. The organic layer was dried over MgSO$_4$, filtered, concentrated, and purified on a 40 g column using the ISCO Companion flash system eluting with hexanes/EtOAc (6:4 to 1:1) to give the intermediate (0.330 g). The intermediate (0.150 g) was suspended in dioxane (5 mL) and treated with 20% sodium hydroxide (0.50 mL, 1.5 mmol). The mixture was heated at 55° C. for 6 hours. After concentration, the residue was stirred in water for 15 minutes, filtered, and purified by reverse-phase HPLC as described in Example 56 to give the title compound (40.0 mg) as trifluoroacetic acid salts. $^1$H NMR (500 MHz, DMSO-d$_6$) ppm 0.92 (t, J=7.48 Hz, 3H), 1.58-1.69 (m, 2H), 2.36 (t, 2H), 7.30 (dd, J=7.63, 4.88 Hz, 1H), 7.57 (s, 1H), 8.21-8.45 (m, 3H), 8.60 (s, 1H), 10.74 (s, 1H), 12.39 (s, 1H). MS (ESI$^+$) m/z 314.9 (M+H)$^+$.

Example 109 trans-N-[6-chloro-4-(1H-pyrrolo[2,3-b]pyridin-3-yl)pyridin-2-yl]-N'-(cyclopropylmethyl)cyclohexane-1,4-diamine The trifluoroacetic acid salt of Example 109 (0.04 g) was prepared as described in Example 93, substituting formaldehyde with cyclopropanecarbaldehyde. $^1$H NMR (300 MHz, DMSO-d$_6$) ppm 0.27-0.46 (m, 2H) 0.53-0.69 (m, 2H) 0.94-1.12 (m, 1H) 1.14-1.35 (m, 3H) 1.35-1.64 (m, 2H) 1.97-2.21 (m, 4H) 2.79-2.95 (m, 2H) 2.97-3.20 (m, 1H) 3.52-3.75 (m, 1H) 6.74-6.95 (m, 3H) 7.13-7.27 (m, 1H) 8.07-8.18 (m, 1H) 8.24-8.36 (m, 2H) 8.34-8.49 (m, 2H) 11.80-12.47 (m, 1H). MS (ESI$^+$) m/z 396.0 (M+H)$^+$.

Example 110

N-[(trans)-2-{[6-chloro-4-(1H-pyrrolo[2,3-b]pyridin-3-yl)pyridin-2-yl]amino}cyclohexyl]methanesulfonamide Example 110a (trans)-N$^1$-(6-chloro-4-(1H-pyrrolo[2,3-b]pyridin-3-yl)pyridin-2-yl)cyclohexane-1,2-diamine A mixture of Example 61a (3.4 g) in acetonitrile (30 mL) and trans-cyclohexane-1,2-diamine was heated at 170° C. for 40 minutes in a Biotage microwave reactor. The reaction mixture was extracted with ethyl acetate (2×), washed with brine and sodium bicarbonate. The combined organic layers were treated with 1M HCl. The aqueous layer was treated with NaOH (1M) and the material crashed out of the solution to give 0.797 mg of the title compound.

Example 110b

N-[(trans)-2-{[6-chloro-4-(1H-pyrrolo[2,3-b]pyridin-3-yl)pyridin-2-yl]amino}cyclohexyl]methanesulfonamide To Example 110a in DMF (1.5 mL) was added triethylamine (0.098 mL, 0.704 mmol) and methanesulfonyl chloride (0.034 mL, 0.439 mmol) at room temperature overnight. Additionally, it was added one equivalent of methanesulfonyl chloride. The reaction was treated with water dropwise while being stirred. The crude was extracted with EtOAc (2×). The concentrated organic layers were combined and purified by reversed-phase HPLC performed on a Zorbax RX-C18 column (250×21.2 mm, 7 µm particle size) using a gradient of 10% to 100% acetonitrile: 0.1% aqueous trifluoroacetic acid over 40 minutes at a flow rate of 15 mL/minutes to give 21.0 mg (11%) of the title compound as trifluoroacetic acid salts. $^1$H NMR (500 MHz, DMSO-d$_6$) ppm 1.30-1.31 (m, 2H), 1.39-1.46 (m, 1H), 1.66-1.68 (m, 2H), 1.94-2.0 (m, 2H), 2.9 (s, 3H), 3.12-3.18 (m, 1H), 6.77-6.78 (m, 1H), 6.91-6.92 (m, 2H), 7.11 (d, 1H), 7.21-7.24 (m, 1H), 8.15-8.16 (m, 1H), 8.31-8.33 (m, 2H), 12.2 (s, 1H). MS (DCI$^+$) m/z 420.1 (M+H)$^+$.

Example 111

N-[6-chloro-4-(1H-pyrrolo[2,3-b]pyridin-3-yl)pyridin-2-yl]-2,6-difluorobenzamide A mixture of Example 7a (0.100 g, 0.247 mmol), 2,6-difluorobenzamide (0.066 g, 0.421 mmol), cesium carbonate (0.105 g, 0.322 mmol), palladium (II) acetate (2.78 mg, 0.012 mmol), and Xantphos (10.73 mg, 0.019 mmol) in dioxane (3 mL) and DMF (0.1 mL) was heated at 150° C. for 30 minutes in a Biotage microwave reactor. The mixture was concentrated. The solid was suspended in dioxane (3 mL), treated with NaOH (20%, 0.10 mL), and heated at 50° C. for 3 hours. The reaction mixture was concentrated. The residue was stirred in water for 15 minutes, filtered, and purified by reverse-phase HPLC as described in Example 56 to give the title compound (8.5 mg) as trifluoroacetic acid salts. $^1$H NMR (500 MHz, DMSO-d$_6$) ppm 7.24 (t, J=8.24 Hz, 2H), 7.30 (dd, J=8.09, 4.73 Hz, 1H), 7.52-7.65 (m, 2H), 7.70 (s, 1H), 8.34-8.41 (m, 3H), 8.65 (s, 1H), 11.66 (s, 1H), 12.41 (s, 1H). MS (ESI$^+$) m/z 384.9 (M+H)$^+$.

Example 112

N-[6-chloro-4-(1H-pyrrolo[2,3-b]pyridin-3-yl)pyridin-2-yl]piperidine-4-carboxamide A mixture of Example 7a (0.100 g, 0.247 mmol), tert-butyl 4-carbamoylpiperidine-1-carboxylate (0.0960 g, 0.421 mmol), cesium carbonate (0.105 g, 0.322 mmol), palladium (II) acetate (2.8 mg, 0.012 mmol), and Xantphos (10.7 mg, 0.019 mmol) in dioxane (3 mL) and DMF (0.1 mL) was degassed and heated at 150° C. for 30 minutes in a Biotage microwave reactor. The solvent was evaporated. The residue was treated with 20% brine and extracted with EtOAc. The organic layer was concentrated, dissolved in dioxane (2.5 mL), and treated with 20% sodium hydroxide (0.50 mL, 0.247 mmol). The mixture was heated at 50° C. for 2 hours. After concentration, the residue was triturated with water and filtered. The solid was purified by reverse-phase HPLC as described in Example 56 to give the title compound (12.7 mg) as trifluoroacetic acid salts. $^1$H NMR (500 MHz, METHANOL-d$_4$) ppm 1.81-2.07 (m, 2H), 2.10-2.23 (m, 2H), 2.84 (m, 1H), 3.01-3.15 (m, 2H), 3.45-3.57 (m, 2H), 7.30 (dd, J=7.93, 4.88 Hz, 1H), 7.48 (d, J=1.22 Hz, 1H), 8.04 (s, 1H), 8.32 (dd, J=4.73, 1.37 Hz, 1H), 8.48 (dd, J=8.09, 1.37 Hz, 1H), 8.54 (s, 1H). MS (ESI$^+$) m/z 356.0 (M+H)$^+$.

Example 113

N-(3-{[6-chloro-4-(1H-pyrrolo[2,3-b]pyridin-3-yl)pyridin-2-yl]amino}-2,2-dimethylpropyl)acetamide A mixture of Example 74 (100.0 mg, 0.303 mmol), triethylamine (0.055 mL, 0.394 mmol), and cetyl chloride (0.024 mL, 0.334 mmol) in DMF (2.2 mL) was stirred at 0° C. for 60 minutes. Water was added slowly to the reaction mixture and a white suspension formed. The suspension was filtered, washed with water and diethyl ether, and oven-dried to give 45.0 mg of the title compound. $^1$H NMR (300 MHz, DMSO-$d_6$) ppm 0.87 (s, 6H), 1.89 (s, 3H), 2.96 (d, J=6.44 Hz, 2H), 3.13 (d, J=6.10 Hz, 2H), 6.86 (t, J=6.27 Hz, 1H), 6.90 (d, J=1.36 Hz, 1H), 6.98 (s, 1H), 7.22 (dd, J=7.80, 4.75 Hz, 1H), 7.79 (t, J=6.27 Hz, 1H), 8.15 (d, J=2.37 Hz, 1H), 8.27-8.40 (m, 2H), 12.16 (s, 1H). MS (ESI$^+$) m/z 372.0 (M+H)$^+$.

Example 114

N-(trans-4-{[6-chloro-4-(1H-pyrrolo[2,3-b]pyridin-3-yl)pyridin-2-yl]amino}cyclohexyl)-N$^2$,N$^2$-dimethylglycinamide Example 114 (0.055 g) was prepared as described in Example 106a, substituting (S)-1-(tert-butoxycarbonyl)azetidine-2-carboxylic acid with 2-(dimethylamino)acetic acid. $^1$H NMR (300 MHz, DMSO-$d_6$) ppm 1.07-1.56 (m, 4H) 1.79 (t, J=4.96 Hz, 2H) 2.00 (d, J=10.71 Hz, 2H) 2.10-2.24 (m, 6H) 2.77-2.95 (m, 2H) 3.46-3.79 (m, 2H) 6.71-6.81 (m, 1H) 6.81-6.93 (m, 2H) 7.12-7.29 (m, 1H) 7.46-7.61 (m, 1H) 8.05-8.19 (m, 1H) 8.23-8.39 (m, 2H) 11.59-12.59 (m, 1H). MS (ESI$^+$) m/z 427.1 (M+H)$^+$

Example 115

(2S)—N-(trans-4-{[6-chloro-4-(1H-pyrrolo[2,3-b]pyridin-3-yl)pyridin-2-yl]-amino}cyclohexyl)-4-oxoazetidine-2-carboxamide Example 115 (0.055 g) was prepared as described in Example 106a, substituting (S)-1-(tert-butoxycarbonyl)azetidine-2-carboxylic acid with (S)-4-oxoazetidine-2-carboxylic acid $^1$H NMR (300 MHz, DMSO-$d_6$) ppm 1.15-1.44 (m, 4H) 1.74-1.92 (m, 2H) 1.94-2.07 (m, 2H) 2.62-2.76 (m, 1H) 3.01-3.15 (m, 1H) 3.62 (d, J=6.78 Hz, 2H) 3.93 (dd, J=5.42, 2.37 Hz, 1H) 6.75-6.83 (m, 1H) 6.83-6.91 (m, 2H) 7.12-7.26 (m, 1H) 8.01-8.10 (m, 1H) 8.09-8.15 (m, 2H) 8.25-8.36 (m, 2H) 11.78-12.49 (m, 1H). MS (ESI$^+$) m/z 439.0 (M+H)$^+$.

Example 116

N-(trans-4-{[6-chloro-4-(1H-pyrrolo[2,3-b]pyridin-3-yl)pyridin-2-yl]amino}cyclohexyl)-N$^2$-methyl-L-alaninamide Example 116 (0.055 g) was prepared as described in Example 106a, substituting (S)-1-(tert-butoxycarbonyl)azetidine-2-carboxylic acid with (S)-2-(tert-butoxycarbonyl(methyl)amino)propanoic acid. The intermediate was treated with trifluoroacetic acid in dichloromethane. Solvent was removed to give the title compound as the bis-trifluoroacetic acid salt. $^1$H NMR (300 MHz, DMSO-$d_6$) ppm 1.20-1.47 (m, 5H) 1.67-1.95 (m, 5H) 1.93-2.13 (m, 3H) 2.67-2.82 (m, 2H) 2.93-3.21 (m, 1H) 3.45-3.79 (m, 2H) 6.82-6.94 (m, 2H) 7.13-7.29 (m, 1H) 8.13 (d, J=2.71 Hz, 1H) 8.26-8.36 (m, 2H) 8.34-8.44 (m, 2H) 8.76 (s, 2H) 11.85-12.41 (m, 1H) MS (ESI$^+$) m/z 427.1 (M+H)$^+$.

Example 117

Azetidin-2-yl(4-{[6-chloro-4-(1H-pyrrolo[2,3-b]pyridin-3-yl)pyridin-2-yl]amino}piperidin-1-yl)methanone

Example 117a tert-butyl 2-(4-(6-chloro-4-(1H-pyrrolo[2,3-b]pyridin-3-yl)pyridin-2-ylamino)piperidine-1-carbonyl)azetidine-1-carboxylate Example 117a (0.045 g) was prepared as described in Example 106a, substituting Example 61b with Example 33 and (S)-1-(tert-butoxycarbonyl)azetidine-2-carboxylic acid with 1-(tert-butoxycarbonyl)azetidine-2-carboxylic acid. MS (ESI$^+$) m/z 511.2 (M+H)$^+$.

Example 117b

Azetidin-2-yl(4-{[6-chloro-4-(1H-pyrrolo[2,3-b]pyridin-3-yl)pyridin-2-yl]amino}piperidin-1-yl)methanone The trifluoroacetic acid salt of Example 117b (0.03 g) was prepared as described in Example 106b, substituting Example 106a with Example 117a. $^1$H NMR (300 MHz, DMSO-$d_6$) ppm 1.21-1.60 (m, 3H) 1.84-2.12 (m, 2H) 3.18 (d, J=10.17 Hz, 2H) 3.44 (s, 1H) 3.76 (s, 1H) 3.87-4.07 (m, 2H) 4.19 (s, 1H) 5.35 (s, 1H) 6.78-7.01 (m, 3H) 7.14-7.29 (m, 1H) 8.05-8.23 (m, 1H) 8.26-8.36 (m, 2H) 8.58-8.80 (m, 1H) 9.04-9.29 (m, 1H) 11.76-12.49 (m, 1H). MS (ESI$^+$) m/z 411.0 (M+H)$^+$.

Example 118

N-(3-{[6-chloro-4-(1H-pyrrolo[2,3-b]pyridin-3-yl)pyridin-2-yl]amino}cyclohexyl)-N$^2$,N$^2$-dimethylglycinamide The trifluoroacetic acid salt of the title compound was prepared according to the procedure for Example 69, substituting 2-(dimethylamino)acetic acid for cyclopropanecarboxylic acid. To a solution of the trifluoroacetic acid salt in dichloromethane (10 mL) was added HCl in ether (7N, 1 mL). The mixture was concentrated to give the title compound as an HCl salt (Yield: 80 mg, 90%). MS (DCI/NH$_3$) m/z 427 (M+H)$^+$, $^1$H NMR (300 MHz, DMSO-d6): 0.92-1.23 (m, 3H), 1.22-1.51 (m, 1H), 1.55-2.05 (m, 3H), 2.18 (d, J=14.24 Hz, 1H), 2.80 (s, 6H), 3.63-3.81 (m, 2H), 3.77-3.96 (m, 2H), 6.88 (d, J=9.49 Hz, 2H), 7.24 (dd, J=7.80, 4.75 Hz, 1H), 8.16 (s, 1H), 8.25-8.41 (m, 1H), 8.58 (d, J=7.46 Hz, 1H), 9.73 (s, 1H), 12.25 (s, 1H).

Example 119

N-(3-{[6-chloro-4-(1H-pyrrolo[2,3-b]pyridin-3-yl)pyridin-2-yl]amino}cyclohexyl)-1-methyl-L-prolinamide The trifluoroacetic acid salt of the title compound was prepared according to the procedure for Example 69, substituting (S)-1-methylpyrrolidine-2-carboxylic acid for cyclopropanecarboxylic acid. Yield: 50 mg (47%). MS (DCI/NH$_3$) m/z 453 (M+H)$^+$, $^1$H NMR (300 MHz, DMSO-d6): 0.95-1.26 (m, 3H), 1.43 (d, J=10.17 Hz, 1H), 1.58-2.01 (m, 4H), 2.00-2.12 (m, 1H), 2.10-2.30 (m, 1H), 2.71-2.75 (m, 1H), 2.80 (s, 3H), 3.15 (dd, J=10.17, 2.37 Hz, 1H), 3.55 (s, 1H), 3.77 (s, 2H), 3.84-4.02 (m, 2H), 6.72-7.01 (m, 2H), 7.22 (dd, J=7.12, 4.41 Hz, 1H), 8.13 (d, J=1.70 Hz, 1H), 8.20-8.39 (m, 2H), 8.55 (d, J=7.80 Hz, 1H), 9.59 (s, 1H), 12.17 (s, 1H).

Example 120

N-[(trans)-2-{[6-chloro-4-(1H-pyrrolo[2,3-b]pyridin-3-yl)pyridin-2-yl]amino}cyclohexyl]azetidine-2-carboxamide To Example 110a (0.12 g, 0.361 mmol) in anhydrous DMF (3.0 mL) was added 1-(tert-butoxycarbonyl)azetidine-2-carboxylic acid (0.092 g, 0.456 mmol), EDC (0.087 g, 0.456 mmol), HOBT (0.070 g, 0.456 mmol) and triethylamine (0.064 mL, 0.456 mmol) and the reaction mixture was stirred at room temperature overnight. Additionally, 0.7 equivalent of 1-(tert-butoxycarbonyl)azetidine-2-carboxylic acid, EDC, HOBT and triethylamine was added and the reaction mixture was stirred for another night. Water was added to precipitate 114.0 mg of fairly clean material. The material was dissolved in dichloromethane (2.0 mL) and trifluoroacetic acid (0.6 mL). The reaction mixture was stirred for 40 minutes at room temperature. The crude mixture was concentrated and purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 minutes at a flow rate of 15 mL/minutes to give 74.2 mg (44%) of the title compound as trifluoroacetic acid salts. $^1$H NMR (500 MHz, DMSO-$d_6$) ppm 1.31-1.33 (m, 4H), 1.70-1.72 (m, 2H), 1.8-2.09 (m, 2H), 2.29-2.39 (m, 1H), 3.53-3.56 (m, 1H), 3.66-3.73 (m, 2H), 4.70-4.78 (m, 1H), 6.70-6.75 (m, 1H), 6.87-6.91 (m, 2H), 7.20-7.23 (m, 1H), 8.13 (dd, J=9.76, 2.75 Hz, 1H), 8.24 (d, J=8.54 Hz, 1H), 8.30-8.31 (m, 2H), 8.38 (d, J=7.63 Hz, 1H), 8.59-8.88 (m, 3H). MS (DCI$^+$) m/z 425.2 (M+H)$^+$.

Example 121

N'-[6-chloro-4-(1H-pyrrolo[2,3-b]pyridin-2-yl)pyridin-2-yl]-N,N,2,2-tetramethylpropane-1,3-diamine A mixture of Example 74 (0.100 g, 0.303 mmol) and formaldehyde (37% in water, 0.042 mL, 1.516 mmol) was stirred at room temperature for 10 minutes followed by the addition of sodium cyanoborohydride (0.038 g, 0.606 mmol) and zinc chloride (0.413 mg, 3.03 μmol). After 5 hours, most of the solvent was evaporated. The remaining slurry was diluted with EtOAc and washed with a mixture of sat. NaHCO$_3$ and 50% brine. The organic layer was dried over MgSO$_4$, filtered, concentrated, and purified on a 12 g column using the ISCO Companion flash system eluting with MeOH/EtOAc (3:97 to 5:95). The material from the incomplete reaction was dissolved in MeOH and treated with NaCNBH$_3$ (10 mg) for 5 hours. The crude was purified by reverse-phase HPLC as described in Example 56 to give the title compound (53.8 mg) as trifluoroacetic acid salts. $^1$H NMR (500 MHz, DMSO-$d_6$) ppm 1.09 (s, 6H), 2.88 (d, J=4.88 Hz, 6H), 3.08 (d, J=4.27 Hz, 2H), 3.29 (d, J=5.19 Hz, 2H), 6.98 (s, 1H), 6.99-7.06 (m, 2H), 7.23 (dd, J=7.93, 4.88 Hz, 1H), 8.17 (d, J=2.75 Hz, 1H), 8.29-8.36 (m, 2H), 9.09 (s, brd, 1H), 12.22 (s, 1H). MS (ESI$^+$) m/z 358.0 (M+H)$^+$.

Example 122

N-[6-chloro-4-(1H-pyrrolo[2,3-b]pyridin-3-yl)pyridin-2-yl]methanesulfonamide

A mixture of Example 61a (0.130 g, 0.322 mmol), methanesulfonamide (0.046 g, 0.482 mmol), cesium carbonate (0.136 g, 0.418 mmol), palladium acetate (3.61 mg, 0.016 mmol), and Xantphos (0.014 g, 0.024 mmol) in dioxane (3 mL) and DMF (0.1 mL) was heated at 160° C. for 30 minutes in a Biotage microwave reactor. The mixture was concentrated. The residue was treated with EtOAc and washed with 20% brine. The emulsion of the organic layer was concentrated. The solid was suspended in dioxane (4 mL), treated with 20% sodium hydroxide (0.15 mL, 0.322 mmol), and heated at 50° C. for 3 hours. The reaction mixture was concentrated. The residue was treated with DMSO/MeOH and purified by reverse-phase HPLC as described in Example 56 to give the title compound (6.0 mg) as trifluoroacetic acid salts. $^1$H NMR (300 MHz, DMSO-$d_6$) ppm 3.36 (s, 3H), 7.26 (dd, J=7.93, 4.76 Hz, 1H), 7.41 (d, J=0.79 Hz, 1H), 7.55 (d, J=1.19 Hz, 1H), 8.27-8.40 (m, 3H), 10.76 (s, 1H), 12.36 (s, 1H). MS (ESI$^+$) m/z 322.8 (M+H)$^+$.

Example 123

N-[6-chloro-4-(1H-pyrrolo[2,3-b]pyridin-3-yl)pyridin-2-yl]benzenesulfonamide

The trifluoroacetic acid salt of the title compound was prepared as described in Example 122, substituting methanesulfonamide with benzenesulfonamide. $^1$H NMR (500 MHz, DMSO-$d_6$) ppm 7.26 (dd, J=7.93, 4.58 Hz, 1H), 7.39 (s, 1H) 7.47 (s, 1H), 7.57-7.68 (m, 3H), 7.98 (d, J=7.32 Hz, 2H), 8.17 (d, J=8.24 Hz, 1H), 8.26 (d, J=3.05 Hz, 1H), 8.32 (d, J=4.58 Hz, 1H), 11.35 (s, 1H), 12.34 (s, 1H). MS (ESI$^+$) m/z 384.9 (M+H)$^+$.

Example 124

N-(3-{[6-chloro-4-(1H-pyrrolo[2,3-b]pyridin-3-yl)pyridin-2-yl]amino}-2,2-dimethylpropyl)cyclopropanecarboxamide The title compound was prepared as described in Example 113, substituting acetyl chloride with cyclopropanecarbonyl chloride. The crude was purified by reverse-phase HPLC as described in Example 56 to give the title compound as trifluoroacetic acid salts.). $^1$H NMR (300 MHz, DMSO-$d_6$) ppm 0.54-0.74 (m, 4H), 0.88 (s, 6H), 1.64 (m, 1H), 3.00 (d, J=6.44 Hz, 2H), 3.14 (s, 2H), 6.85 (s, brd, 1H), 6.90 (d, J=1.02 Hz, 1H), 6.97 (s, 1H), 7.23 (dd, J=7.80, 4.75 Hz, 1H), 8.01 (t, J=6.44 Hz, 1H), 8.15 (d, J=2.71 Hz, 1H), 8.31 (dd, J=4.75, 1.36 Hz, 1H), 8.36 (dd, J=8.14, 1.36 Hz, 1H), 12.18 (s, 1H). MS (ESI$^+$) m/z 398.0 (M+H)$^+$.

Example 125

N-(trans-4-{[6-chloro-4-(1H-pyrrolo[2,3-b]pyridin-3-yl)pyridin-2-yl]amino}cyclohexyl)-1-methylpyrrolidine-3-carboxamide Example 125 (0.05 g) was prepared as described in Example 106a, substituting (S)-1-(tert-butoxycarbonyl)azetidine-2-carboxylic acid with 1-methylpyrrolidine-3-carboxylic acid. $^1$H NMR (300 MHz, DMSO-$d_6$) ppm 1.10-1.43 (m, 4H) 1.73-2.10 (m, 6H) 2.24-2.35 (m, 3H) 2.38-2.48 (m, 2H) 2.59-2.70 (m, 1H) 2.76-2.87 (m, 2H) 3.60 (s, 2H) 6.70-6.82 (m, 1H) 6.82-6.90 (m, 2H) 7.12-7.27 (m, 1H) 7.68-7.78 (m, 1H) 8.08-8.16 (m, 1H) 8.24-8.36 (m, 2H) 11.96-12.30 (m, 1H). MS (ESI$^+$) m/z 453.3 (M+H)$^+$

Example 126

(4-{[6-chloro-4-(1H-pyrrolo[2,3-b]pyridin-3-yl)pyridin-2-yl]amino}piperidin-1-yl)(cyclopropyl)methanone Example 126 (0.02 g) was prepared as described in Example 51, substituting methanesulfonyl chloride with cyclopropanecarbonyl chloride. $^1$H NMR (300 MHz, DMSO-d$_6$) ppm 0.60-0.84 (m, 5H) 1.22 (d, J=10.85 Hz, 3H) 1.81-2.14 (m, 2H) 2.90 (s, 1H) 4.03 (d, J=7.12 Hz, 1H) 4.17 (s, 2H) 6.83-6.95 (m, 3H) 7.15-7.27 (m, 1H) 8.10-8.17 (m, 1H) 8.26-8.36 (m, 2H) 12.09-12.20 (m, 1H). MS (ESI$^+$) m/z 396.0 (M+H)$^+$.

Example 127

N-(trans-4-{[6-chloro-4-(1H-pyrrolo[2,3-b]pyridin-3-yl)pyridin-2-yl]amino}cyclohexyl)-N$^2$,N$^2$-dimethyl-L-alaninamide Example 127 (0.05 g) was prepared as described in Example 106a, substituting (S)-1-(tert-butoxycarbonyl)azetidine-2-carboxylic acid with (S)-2-(dimethylamino)propanoic acid. $^1$H NMR (300 MHz, DMSO-d$_6$) ppm 0.98-1.15 (m, 3H) 1.13-1.55 (m, 5H) 1.77 (s, 2H) 1.99 (s, 1H) 2.10-2.26 (m, 6H) 2.79-2.98 (m, 1H) 3.44-3.75 (m, J=8.48 Hz, 2H) 6.76 (d, J=7.80 Hz, 1H) 6.81-6.93 (m, 2H) 7.20 (dd, J=7.80, 4.75 Hz, 1H) 7.55 (d, J=8.48 Hz, 1H) 8.12 (t, J=3.39 Hz, 1H) 8.24-8.38 (m, 2H) 12.13 (s, 1H). MS (ESI$^+$) m/z 441.1 (M+H)$^+$.

Example 128

6-chloro-N-(1-cyclobutylpiperidin-4-yl)-4-(1H-pyrrolo[2,3-b]pyridin-3-yl)pyridin-2-amine Example 128 (0.045 g) was prepared as described in Example 93, substituting Example 61b with Example 33 and substituting formaldehyde with cyclobutanone. The solvent was removed from the reaction and the residue diluted with ethyl acetate. The organics were washed with a saturated sodium bicarbonate solution, brine, dried over MgSO$_4$, filtered, and concentrated. The crude material was triturated with dichloromethane and the solid was filtered to give the title compound as the free base. $^1$H NMR (300 MHz, DMSO-d$_6$) ppm 1.40 (d, J=9.83 Hz, 3H) 1.53-1.69 (m, 1H) 1.67-2.04 (m, 6H) 2.04-2.41 (m, 2H) 2.61-2.83 (m, 3H) 3.55-3.79 (m, 1H) 6.79 (d, J=7.80 Hz, 1H) 6.83-6.95 (m, 2H) 7.21 (dd, J=7.97, 4.92 Hz, 1H) 8.05-8.19 (m, 1H) 8.25-8.37 (m, 2H) 12.14 (s, 1H). MS (ESI$^+$) m/z 382.0 (M+H)$^+$.

Example 129

N-(3-{[6-chloro-4-(1H-pyrrolo[2,3-b]pyridin-3-yl)pyridin-2-yl]amino}cyclohexyl)piperidine-2-carboxamide To a solution of Example 23 (50 mg, 0.15 mmol) in anhydrous DMF (2 mL) was added 1-(tert-butoxycarbonyl)piperidine-2-carboxylic acid (50 mg, 0.22 mmol), EDC (42 mg, 0.22 mmol), 1-hydroxybenzotriazole monohydrate (34 mg, 0.22 mmol), and triethylamine (22 mg, 0.22 mmol). The reaction was stirred at room temperature overnight. The reaction mixture was partitioned between methylenechloride (100 mL) and brine (20 mL). The organic phase was concentrated. The residue was dissolved in dichloromethane (10 mL). To the solution was added trifluoroacetic acid (1 mL). The mixture was stirred at room temperature for 1 hour. The reaction mixture was concentrated and the residue was purified by reverse-phase HPLC performed on a Zorbax RX-C18 column (250×21.2 mm, 7 m particle size) using a gradient of 0% to 100% acetonitrile: 0.1% aqueous trifluoroacetic acid over 60 minutes at a flow rate of 15 mL/minutes to give the trifluoroacetic acid salt of the title compound. Yield: 33 mg (50%). MS (DCI/NH$_3$) m/z 453 (M+H)$^+$, $^1$H NMR (300 MHz, DMSO-d6): 0.99-1.26 (m, 3H), 1.28-1.63 (m, 4H), 1.59-1.89 (m, 5H), 1.88-2.34 (m, 3H), 2.69-3.04 (m, 1H), 3.08-3.31 (m, 1H), 3.49-3.83 (m, 2H), 6.71-6.97 (m, 1H), 6.85 (s, 1H), 7.22 (dd, J=7.80, 5.09 Hz, 1H), 8.13 (d, J=2.71 Hz, 1H), 8.25-8.43 (m, 2H), 12.17 (s, 1H).

Example 130

N-(3-{[6-chloro-4-(1H-pyrrolo[2,3-b]pyridin-3-yl)pyridin-2-yl]amino}cyclohexyl)-2-(pyrrolidin-1-yl)acetamide The trifluoroacetic acid salt of the title compound was prepared according to the procedure for Example 69, substituting 2-(pyrrolidin-1-yl)acetic acid for cyclopropanecarboxylic acid. Yield: 45 mg (67%). MS (DCI/NH$_3$) m/z 453 (M+H)$^+$, $^1$H NMR (300 MHz, DMSO-d$_6$): ppm 0.79-1.23 (m, 3H), 1.27-1.53 (m, 1H), 1.53-2.06 (m, 7H), 2.09-2.21 (m, 1H), 3.02 (s, 2H), 3.55 (d, J=5.09 Hz, 2H), 3.64-3.83 (m, 2H), 3.87-4.01 (m, 2H), 6.85 (s, 1H), 6.89 (s, 1H), 7.22 (dd, J=7.63, 4.92 Hz, 1H), 8.13 (d, J=2.71 Hz, 1H), 8.23-8.35 (m, 2H), 8.43 (d, J=7.80 Hz, 1H), 9.88 (s, 1H), 12.17 (d, J=1.36 Hz, 1H).

Example 131

(cis)-N-[6-chloro-4-(1H-pyrrolo[2,3-b]pyridin-3-yl)pyridin-2-yl]cyclohexane-1,2-diamine Example 7a (1.5 g, 3.71 mmol) in ethanol (1.5 mL) was heated at 175° C. for 30 minutes in a Biotage microwave reactor in the presence of cis-1,2-diaminocyclohexane (3.5 mL). The reaction mixture was cooled to room temperature, diluted with ethyl acetate, washed with saturated sodium bicarbonate and water. Organic layer was treated with 1M HCl. The aqueous layer was treated with NaOH (1M) and the title compound precipitated out in the amount of 728 mg (57%) as a free base. $^1$H NMR (300 MHz, DMSO-d$_6$) ppm 1.31-1.33 (m, 2H), 1.52-1.6 (m, 4H), 3.03-3.05 (m, 1H), 3.9-3.93 (m, 1H), 6.61 (d, J=8.14 Hz, 1H), 6.88 (s, 1H), 7.02 (s, 1H), 7.19-7.23 (m, 1H), 8.13 (s, 1H), 8.30 (dd, J=4.58, 1.53 Hz, 1H), 8.38 (dd, 1H). MS (DCI$^+$) m/z 342.2 (M+H)$^+$.

Example 132

N-[(cis)-2-{[6-chloro-4-(1H-pyrrolo[2,3-b]pyridin-3-yl)pyridin-2-yl]amino}cyclohexyl]methanesulfonamide The trifluoroacetic acid salt of Example 132 was prepared as described in Example 110b, substituting Example 110a with Example 131. $^1$H NMR (400 MHz, DMSO-d$_6$) ppm 1.33-1.40 (m, 2H), 1.57-1.74 (m, 6H), 2.81 (s, 3H), 3.60-3.66 (m, 1H), 6.92 (s, 1H), 7.02 (s, 1H), 7.22 (dd, J=8.09, 4.73 Hz, 1H), 8.15-8.16 (m, 1H), 8.30 (dd, J=4.73, 1.37 Hz, 1H), 8.37 (dd, J=8.24, 1.53 Hz, 1H), 12.17 (s, 1H). MS (DCI$^+$) m/z 420.2 (M+H)$^+$.

Example 133

N-(trans-4-{[6-chloro-4-(1H-pyrrolo[2,3-b]pyridin-3-yl)pyridin-2-yl]amino}cyclohexyl)cyclobutanecarboxamide Example 133 (0.08 g) was prepared as described in Example 106a, substituting (S)-1-(tert-butoxycarbonyl)azetidine-2-carboxylic acid with cyclobutanecarboxylic acid. $^1$H NMR (300 MHz, DMSO-$d_6$) ppm 1.10-1.40 (m, 5H) 1.64-2.22 (m, 9H) 2.95 (q, J=8.70 Hz, 1H) 3.54 (s, 2H) 6.76 (d, J=7.46 Hz, 1H) 6.82-6.89 (m, 2H) 7.20 (dd, J=7.80, 4.75 Hz, 1H) 7.50 (d, J=7.80 Hz, 1H) 8.12 (d, J=2.71 Hz, 1H) 8.23-8.36 (m, 2H) 12.07-12.19 (m, 1H). MS (ESI$^+$) m/z 424.1 (M+H)$^+$.

Example 134

N-(trans-4-{[6-chloro-4-(1H-pyrrolo[2,3-b]pyridin-3-yl)pyridin-2-yl]amino}cyclohexyl)-1-ethylazetidine-2-carboxamide Example 134 (0.09 g) was prepared as described in Example 93, substituting Example 61b with Example 106b and formaldehyde with acetaldehyde. The solvent was removed from the reaction and the residue diluted with ethyl acetate. The organics were washed with a saturated sodium bicarbonate solution, brine, dried over MgSO$_4$, filtered, and concentrated, giving the title compound as the free base. $^1$H NMR (300 MHz, DMSO-$d_6$) ppm 0.89 (q, J=7.35 Hz, 3H) 1.11-1.36 (m, 4H) 1.36-1.60 (m, 2H) 1.65-2.09 (m, 4H) 2.11-2.33 (m, 2H) 2.37-2.47 (m, 2H) 2.69-2.89 (m, 1H) 3.47-3.75 (m, J=31.87 Hz, 2H) 6.77 (d, J=7.80 Hz, 1H) 6.82-6.91 (m, 2H) 7.21 (dd, J=7.80, 4.75 Hz, 1H) 7.45 (d, J=8.48 Hz, 1H) 8.12 (d, J=2.37 Hz, 1H) 8.25-8.35 (m, 2H) 12.13 (s, 1H). MS (ESI$^+$) m/z 453.1 (M+H)$^+$.

Example 135

1-amino-N-(3-{[6-chloro-4-(1H-pyrrolo[2,3-b]pyridin-3-yl)pyridin-2-yl]amino}cyclohexyl)cyclobutanecarboxamide The trifluoroacetic acid salt of the title compound was prepared according to the procedure for Example 129 substituting 1-(tert-butoxycarbonylamino)cyclobutanecarboxylic acid for 1-(tert-butoxycarbonyl)piperidine-2-carboxylic acid. Yield: 78 mg (76%). MS (DCI/NH$_3$) m/z 439 (M+H)$^+$, $^1$H NMR (300 MHz, DMSO-d6): 0.99-1.53 (m, 4H), 1.69-1.87 (m, 2H), 1.87-2.04 (m, 2H), 2.04-2.26 (m, 4H), 2.53-2.65 (m, 1H), 3.62-4.04 (m, 3H), 6.86 (s, 1H), 6.89 (s, 1H), 7.22 (dd, J=7.46, 5.09 Hz, 1H), 8.13 (d, J=2.71 Hz, 1H), 8.23 (d, J=8.14 Hz, 1H), 8.30 (s, 1H), 8.32 (d, J=3.05 Hz, 2H), 8.36 (s, 2H), 12.16 (d, J=2.03 Hz, 1H).

Example 136

N-(trans-4-{[6-chloro-4-(1H-pyrrolo[2,3-b]pyridin-3-yl)pyridin-2-yl]amino}cyclohexyl)-1-cyclopentylazetidine-2-carboxamide Example 136 (0.07 g) was prepared as described in Example 106a, substituting (S)-1-(tert-butoxycarbonyl)azetidine-2-carboxylic acid with 1-cyclopentylazetidine-2-carboxylic acid $^1$H NMR (300 MHz, DMSO-$d_6$) ppm 1.16-1.55 (m, 11H) 1.54-1.72 (m, 2H) 1.71-1.95 (m, 3H) 1.93-2.10 (m, 2H) 2.08-2.30 (m, 2H) 2.66-2.89 (m, 2H) 3.47-3.78 (m, 2H) 6.78 (d, J=7.80 Hz, 1H) 6.83-6.93 (m, 2H) 7.20 (dd, J=7.80, 4.75 Hz, 1H) 7.37 (d, J=8.82 Hz, 1H) 8.12 (t, J=3.05 Hz, 1H) 8.24-8.37 (m, 2H) 12.13 (s, 1H). MS (ESI$^+$) m/z 493.1 (M+H)$^+$.

Example 137

N-(trans-4-{[6-chloro-4-(1H-pyrrolo[2,3-b]pyridin-3-yl)pyridin-2-yl]amino}cyclohexyl)-N$^2$-cyclopentylglycinamide

Example 137a tert-butyl 2-((1r,4r)-4-(6-chloro-4-(1H-pyrrolo[2,3-b]pyridin-3-yl)pyridin-2-ylamino)cyclohexylamino)-2-oxoethyl(cyclopentyl)carbamate Example 137a (0.2 g) was prepared as described in Example 106a, substituting (S)-1-(tert-butoxycarbonyl)azetidine-2-carboxylic acid with 2-(tert-butoxycarbonyl(cyclopentyl)amino)acetic acid MS (ESI$^+$) m/z 567.1 (M+H)$^+$.

Example 137b

N-(trans-4-{[6-chloro-4-(1H-pyrrolo[2,3-b]pyridin-3-yl)pyridin-2-yl]amino}cyclohexyl)-N$^2$-cyclopentylglycinamide Example 137b (0.07 g) was prepared as described in Example 106b, substituting Example 106a with Example 137a. Solvent was removed and the residue dissolved in ethyl acetate. The organics were washed with saturated NaHCO$_3$, water, brine, dried over MgSO$_4$, filtered, and concentrated. The crude material was triturated with methylene chloride and the solid filtered to give the title compound as a free base. $^1$H NMR (300 MHz, DMSO-$d_6$) ppm 1.17-1.36 (m, 6H) 1.38-1.53 (m, 3H) 1.53-1.75 (m, 5H) 1.75-1.91 (m, 2H) 1.91-2.08 (m, 2H) 2.86-3.03 (m, 1H) 3.01-3.10 (m, 2H) 3.49-3.72 (m, 1H) 6.77 (d, J=7.46 Hz, 1H) 6.81-6.93 (m, 2H) 7.14-7.27 (m, 1H) 7.55-7.71 (m, 1H) 8.12 (d, J=2.37 Hz, 1H) 8.23-8.38 (m, 2H) 12.13 (s, 1H). MS (ESI$^+$) m/z 467.3 (M+H)$^+$.

Example 138

6-chloro-N-[1-(methylsulfonyl)piperidin-3-yl]-4-(1H-pyrrolo[2,3-b]pyridin-3-yl)pyridin-2-amine The title compound was prepared according to the procedure for Example 76, substituting Example 102b for 23 and methylsulfonyl chloride for cyclopropanesulfonyl chloride. The crude material was purified by flash chromatography eluting with EtOAc to provide the title compound-Yield: 25 mg (32%). MS (DCI/NH$_3$) m/z 406 (M+H)$^+$, $^1$H NMR (300 MHz, CD$_3$OD): 1.32-1.57 (m, 1H), 1.64 (d, J=9.52 Hz, 1H), 1.70-1.99 (m, 2H), 2.61-2.76 (m, 1H), 2.88 (s, 3H), 2.89-3.01 (m, 1H), 3.13-3.32 (m, 1H), 3.63 (dd, J=11.30, 3.37 Hz, 1H), 3.94 (d, J=7.93 Hz, 1H), 6.93-6.96 (m, 2H), 6.97 (s, 1H), 7.21 (dd, J=7.93, 4.76 Hz, 1H), 8.15 (s, 1H), 8.26-8.39 (m, 2H), 12.17 (s, 1H).

Example 139

N-(3-{[6-chloro-4-(1H-pyrrolo[2,3-b]pyridin-3-yl)pyridin-2-yl]amino}cyclohexyl)-5-oxoprolinamide The trifluoroacetic acid salt of the title compound was prepared according to the procedure for Example 69, substituting 5-oxopyrrolidine-2-carboxylic acid for cyclopropanecarboxylic acid. Yield: 32 mg (41%). MS (DCI/NH$_3$) m/z 453 (M+H)$^+$, $^1$H NMR (300 MHz, DMSO-d$_6$): 0.98-1.25 (m, 3H), 1.39 (d, J=13.88 Hz, 2H), 1.55-2.00 (m, 5H), 2.01-2.33 (m, 3H), 3.56-3.98 (m, 2H), 6.84 (s, 1H), 6.88 (s, 1H), 7.22 (dd, J=7.93, 4.76 Hz, 1H), 7.69-7.78 (m, 1H), 7.83-7.93 (m, 1H), 8.13 (d, J=2.78 Hz, 1H), 8.22-8.40 (m, 3H), 12.16 (s, 1H).

Example 140

(cis)-N'-[6-chloro-4-(1H-pyrrolo[2,3-b]pyridin-3-yl)pyridin-2-yl]-N,N-dimethylcyclohexane-1,2-diamine Example 131 (0.170 g, 0.497 mmol) was dissolved in methanol (3.5 mL). Formaldehyde (0.074 mL, 0.995 mmol) was added and the solution was stirred at room temperature for 15-30 minutes before sodium cyanoborohydride (0.063 g, 0.995 mmol) and catalytic amount of ZnCl$_2$ were added. The reaction mixture was stirred overnight. Two more equivalents of formaldehyde were added. The solvent was removed and the residue was dissolved in 1:1 DMSO and MeOH. The crude mixture was concentrated and the residue purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 minutes at a flow rate of 15 mL/minutes to give 15.3 mg of the title compound as trifluoroacetic salts. $^1$H NMR (400 MHz, DMSO-d$_6$) ppm 1.31-1.35 (m, 1H), 1.48-1.77 (m, 5H), 1.86-1.89 (m, 1H), 2.06-2.10 (m, 1H), 2.78-2.85 (m, 6H), 3.01 (s, 1H), 3.23-3.29 (m, 1H), 4.85 (s, 1H), 6.92 (d, J=10.38 Hz, 1H), 7.07 (s, 1H), 7.22-7.26 (m, 2H), 8.97 (s, 1H), 12.23 (s, 1H). MS (DCI$^+$) m/z 370.2 (M+H)$^+$.

Example 141

N-(trans-4-{[6-chloro-4-(1H-pyrrolo[2,3-b]pyridin-3-yl)pyridin-2-yl]amino}cyclohexyl)-2-(morpholin-4-yl)acetamide Example 141a (trans)-N$^1$-(6-chloro-4-(1H-pyrrolo[2,3-b]pyridin-3-yl)pyridin-2-yl)cyclohexane-1,4-diamine A mixture of Example 61b (1.6 g, 4.68 mmol), triethylamine (0.326 mL, 2.340 mmol) and 2-chloroacetyl chloride (0.633 mL, 7.96 mmol) in DMF (32 mL) was stirred at 0° C. for 18 hours. An additional 1.1 equivalents of 2-chloroacetyl chloride and 1.3 equivalents of triethylamine were added and the reaction mixture was stirred for 1 hour. Water was added; the precipitate was filtered and washed with ethyl ether to give 1.2 g (61%) of the title compound.

Example 141b

N-((trans)-4-(6-chloro-4-(1H-pyrrolo[2,3-b]pyridin-3-yl)pyridin-2-ylamino)cyclohexyl)-2-morpholinoacetamide A mixture of Example 141a (0.050 g, 0.12 mmol) and morpholine (0.031 mL, 0.359 mmol) in DMF (1.5 mL) was stirred at room temperature for 4 hours. The residue was treated with water, extracted with ethyl acetate (2×) and washed with brine. The organic layers were dried with MgSO$_4$, filtered, and concentrated. The residue was purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 minutes at a flow rate of 15 mL/minutes to give 24.0 mg (29%) of the product as trifluoroacetic salts. $^1$H NMR (500 MHz, DMSO-d$_6$) ppm 1.26-1.40 (m, 4H), 1.87-2.04 (m, 4H), 3.20-3.79 (m, 10H), 6.80 (br s, 1H), 6.87-6.89 (m, 2H), 7.21 (dd, J=7.93, 4.88 Hz, 1H), 7.13 (d, J=2.75 Hz, 1H), 8.30-8.31 (m, 2H), 8.52 (d, J=7.32 Hz, 1H), 10.0-10.3 (s, 1H), 12.17 (s, 1H). MS (DCI$^+$) m/z 469.3 (M+H)$^+$.

Example 142

N-(trans-4-{[6-chloro-4-(1H-pyrrolo[2,3-b]pyridin-3-yl)pyridin-2-yl]amino}cyclohexyl)-2-[4-(pyridin-2-yl)piperazin-1-yl]acetamide The trifluoroacetic acid salt of Example 142 (0.1 g, 0.239 mmol) was prepared as described in Example 141b, substituting morpholine with 1-(pyridin-2-yl)piperazine. $^1$H NMR (500 MHz, DMSO-d$_6$) ppm 1.27-1.41 (m, 4H), 1.89-2.05 (m, 4H), 3.24-4.32 (m, 10H), 6.77 (dd, J=7.02, 5.19 Hz, 1H), 6.88-6.89 (m, 2H), 6.96 (dd, J=dd, 8.85 Hz, 1H), 7.22 (dd, J=7.93, 4.88 Hz, 1H), 7.63-7.66 (m, 1H), 8.14 (d, J=2.75 Hz, 1H), 8.16-8.17 (m, 1H), 7.3-8.33 (m, 2H), 8.53 (d, J=7.63 Hz, 1H), 10.19 (s, 1H), 12.18 (s, 1H). MS (DCI$^+$) m/z 545.3 (M+H)$^+$.

Example 143

N-{4-[(4-aminocyclohexyl)methyl]cyclohexyl}-6-chloro-4-(1H-pyrrolo[2,3-b]pyridin-3-yl)pyridin-2-amine The trifluoroacetic acid salt of the title compound was prepared according to the procedure for Example 8 except purification by HPLC as described in Example 58, substituting 4,4'-methylenedicyclohexanamine for tetrahydro-2H-pyran-4-amine Yield: 80 mg (48%). MS (DCI/NH$_3$) m/z 439 (M+H)$^+$, $^1$H NMR (300 MHz, DMSO-d6): 0.78-1.48 (m, 10H), 1.40-1.82 (m, 6H), 1.67-2.13 (m, 4H), 3.43-3.85 (m, 2H), 6.78-6.91 (m, 2H), 7.16-7.24 (m, 1H), 7.42-7.85 (m, 3H), 8.12 (t, J=3.22 Hz, 1H), 8.20-8.38 (m, 2H), 12.14 (s, 1H).

Example 144

N-(trans-4-{[6-chloro-4-(1H-pyrrolo[2,3-b]pyridin-3-yl)pyridin-2-yl]amino}cyclohexyl)-2,6-dioxopiperidine-4-carboxamide Example 144 (0.05 g) was prepared as described in Example 106a, substituting (S)-1-(tert-butoxycarbonyl)azetidine-2-carboxylic acid with 2,6-dioxopiperidine-4-carboxylic acid $^1$H NMR (300 MHz, DMSO-d$_6$) ppm 1.10-1.44 (m, 5H) 1.80 (s, 2H) 1.91-2.09 (m, 2H) 2.51-2.63 (m, 2H) 2.84-2.98 (m, 1H) 3.41-3.70 (m, 2H) 6.77 (t, J=7.46 Hz, 1H) 6.87 (t, J=4.07 Hz, 2H) 7.14-7.28 (m, 1H) 7.94 (d, J=7.80 Hz, 1H) 8.12 (s, 1H) 8.26-8.36 (m, 2H) 10.63 (s, 1H) 12.13 (s, 1H). MS (ESI$^+$) m/z 482.0 (M+H)$^+$.

Example 145

2-amino-N-(3-{[6-chloro-4-(1H-pyrrolo[2,3-b]pyridin-3-yl)pyridin-2-yl]amino}cyclohexyl)ethanesulfonamide

Example 145a $N^1$-(6-chloro-4-iodopyridin-2-yl)cyclohexane-1,3-diamine

The title compound was prepared according to the procedure for Example 8, substituting 2,6-dichloro-4-iodopyridine for 3-(2,6-dichloropyridin-4-yl)-1H-pyrrolo[2,3-b]pyridine and cyclohexane-1,3-diamine for tetrahydro-2H-pyran-4-amine Yield: 800 mg (62%). MS (DCI/NH$_3$) m/z 352 (M+H)$^+$.

Example 145b

N-(3-(6-chloro-4-iodopyridin-2-ylamino)cyclohexyl)-2-(1,3-dioxoisoindolin-2-yl)ethanesulfonamide To a solution of Example 145a (280 mg, 0.8 mmol) in CH$_2$Cl$_2$ (10 mL) was added triethylamine (110 mg, 1 mmol) and followed by 2-(1,3-dioxoisoindolin-2-yl)ethanesulfonyl chloride (262 mg, 0.95 mmol). The mixture was stirred at room temperature overnight. The reaction mixture was concentrated and the residue was purified by flash chromophatography (EtOAc/hexanes=1:4) to give the title compound. Yield: 180 mg (32%). MS (DCI/NH$_3$) m/z 589 (M+H)$^+$.

Example 145c

N-(3-(6-chloro-4-(1-(phenylsulfonyl)-1H-indol-3-yl)pyridin-2-ylamino)cyclohexyl)-2-(1,3-dioxoisoindolin-2-yl)ethanesulfonamide The title compound was prepared according to the procedure for Example 94b, substituting Example 145b for Example 94a. Yield: 190 mg (57%). MS (DCI/NH$_3$) m/z 719 (M+H)$^+$.

Example 145d 2-amino-N-(3-(6-chloro-4-(1H-indol-3-yl)pyridin-2-ylamino)cyclohexyl)ethanesulfonamide A mixture of Example 145c (50 mg, 0.07 mmol) and hydrazine (0.1 mL) in ethanol (5 mL) was stirred at 80° C. overnight. LC/MS showed 100% conversion. The mixture was purified by HPLC as described in Example 129 to give the trifluoroacetic acid salt of the title compound. Yield: 30 mg (95%). MS (DCI/NH$_3$) m/z 449 (M+H)$^+$, $^1$H NMR (300 MHz, DMSO-d$_6$): 0.93-1.31 (m, 2H), 1.43 (s, 1H), 1.73 (d, J=3.39 Hz, 2H), 1.84-2.02 (m, 1H), 2.07-2.33 (m, 1H), 3.04-3.27 (m, 2H), 3.21-3.42 (m, 2H), 3.53-3.86 (m, 1H), 3.88-4.39 (m, 2H), 6.85 (s, 1H), 6.89 (s, 1H), 6.90-6.98 (m, 1H), 7.15-7.30 (m, 1H), 7.47-7.62 (m, 1H), 7.83 (d, 2H), 8.13 (d, J=2.71 Hz, 1H), 8.30 (s, 1H), 8.32 (s, 1H), 12.17 (d, J=1.70 Hz, 1H).

Example 146

6-chloro-N-[(1-methylpiperidin-3-yl)methyl]-4-(1H-pyrrolo[2,3-b]pyridin-3-yl)pyridin-2-amine The trifluoroacetic acid salt of the title compound was prepared according to the procedure for Example 58, substituting Example 94c for Example 23 and formaldehyde for isobutyraldehyde. Yield: 25 mg (28%). MS (DCI/NH$_3$) m/z 356 (M+H)$^+$, $^1$H NMR (300 MHz, DMSO-d$_6$): 1.00-1.31 (m, 1H), 1.45-1.74 (m, 1H), 1.73-1.96 (m, 1H), 1.96-2.18 (m, 1H), 2.61-2.73 (m, 2H), 2.78 (d, J=4.75 Hz, 3H), 3.13-3.31 (m, 3H), 3.40 (d, J=14.58 Hz, 2H), 6.89 (s, 1H), 6.94 (s, 1H), 7.04-7.34 (m, 1H), 8.14 (d, J=2.71 Hz, 1H), 8.18-8.48 (m, 2H), 9.22 (s, 1H), 12.18 (s, 1H).

Example 147

1-(3-{[6-chloro-4-(1H-pyrrolo[2,3-b]pyridin-3-yl)pyridin-2-yl]amino}piperidin-1-yl)ethanone The trifluoroacetic acid salt of the title compound was prepared according to the procedure for Example 69, substituting Example 102b for Example 23 and substituting acetic acid for cyclopropanecarboxylic acid. Yield: 26 mg (38%). MS (DCI/NH$_3$) m/z 370 (M+H)$^+$, $^1$H NMR (300 MHz, DMSO-d$_6$): 1.37-1.66 (m, 2H) 1.76 (d, J=2.71 Hz, 1H), 1.89-1.99 (m, 1H), 2.00 (s, 3H), 2.61-2.78 (m, 1H), 2.87-3.21 (m, 2H), 3.58-3.99 (m, 2H), 6.77-6.95 (m, 1H), 6.96 (s, 1H), 6.99 (s, 1H), 7.13-7.27 (m, 1H), 8.15 (s, 1H), 8.24-8.39 (m, 2H), 12.16 (s, 1H).

Example 148 trans-N-[6-chloro-4-(1H-pyrrolo[2,3-b]pyridin-3-yl)pyridin-2-yl]-N'-(1-methylpiperidin-4-yl)cyclohexane-1,4-diamine The trifluoroacetic acid salt of the title compound was prepared according to the procedure for Example 58, substituting Example 61b for example 23 and substituting 1-methylpiperidin-4-one for isobutyraldehyde. Yield: 80 mg (96%). MS (DCI/NH$_3$) m/z 440 (M+H)$^+$, $^1$H NMR (300 MHz, DMSO-d$_6$): 1.15-1.36 (m, 2H), 1.36-1.59 (m, 2H), 1.66-1.84 (m, 1H), 1.91-2.18 (m, 5H), 2.19-2.32 (m, 1H), 2.78 (d, J=1.98 Hz, 3H), 2.91-3.12 (m, 2H), 3.20 (d, J=17.45 Hz, 1H), 3.35-3.48 (m, 1H), 3.46-3.73 (m, 4H), 6.69-6.95 (m, 2H), 7.21 (dd, J=7.34, 5.35 Hz, 1H), 7.80 (d, J=3.97 Hz, 1H), 8.14 (d, J=2.38 Hz, 1H), 8.25-8.37 (m, 2H), 8.73 (s, 1H), 12.18 (s, 1H).

Example 149 trans-4-{[6-chloro-4-(5-methoxy-1H-pyrrolo[2,3-b]pyridin-3-yl)pyridin-2-yl]amino}cyclohexanol

Example 149a 3-bromo-5-methoxy-1H-pyrrolo[2,3-b]pyridine

To a solution of 5-methoxy-1H-pyrrolo[2,3-b]pyridine (0.439 g, 2.96 mmol) in tetrahydrofuran (10 mL) was added N-bromosuccinimide (0.527 g, 2.96 mmol) at 0° C. After 90 minutes at 0° C., the reaction was quenched with 30% Na$_2$S$_2$O$_3$ and extracted with EtOAc (2×). The combined organic layers were washed with water, dried and concentrated. The residue was triturated with EtOAc/diethyl ether (1:1) to give 0.375 g of the title compound.

Example 149b

To a solution of Example 149a (0.358 g, 1.577 mmol) in DMF (7 mL) was added sodium hydride (60%, 0.069 g, 1.73 mmol). After 20 minutes, benzenesulfonyl chloride (0.224 mL, 1.73 mmol) was added. The reaction was stirred for 2.5 hours and quenched with water slowly. The solid was filtered, washed with water, and oven-dried to give 0.505 g of the title compound.

Example 149c 5-methoxy-1-(phenylsulfonyl)-3-(4,4,5,5-tetramethyl-1,3,2-dioxaborolan-2-yl)-1H-pyrrolo[2,3-b]pyridine A mixture of Example 149b (350.0 mg, 0.953 mmol), bis(pinacolato)diboron (266 mg, 1.048 mmol), potassium acetate (281 mg, 2.86 mmol), and $PdCl_2$(dppf)-$CH_2Cl_2$ (31.1 mg, 0.038 mmol) in THF (8 mL) was degassed and heated at 78° C. in a capped vial overnight The reaction was treated with 20% brine and extracted with EtOAc (2×). The combined organic layers were dried over $MgSO_4$, filtered, concentrated, and purified on an 80 g column using the ISCO Companion flash system eluting with hexane/EtOAc (8:2 to 75:25) to give 0.150 g of the title compound.

Example 149d 3-(2,6-dichloropyridin-4-yl)-5-methoxy-1-(phenylsulfonyl)-1H-pyrrolo[2,3-b]pyridine A suspension of Example 149c (0.150 g, 0.362 mmol), 2,6-dichloro-4-iodopyridine (0.099 g, 0.362 mmol), dichlorobis(triphenylphosphine)palladium(II) (10.17 mg, 0.014 mmol) and 1M sodium carbonate (0.290 mL, 0.290 mmol) in dimethoxyethane/EtOH/water (7:2:3, 2.5 mL) was degassed and heated at 80° C. overnight. After cooling, the suspension was diluted with water and extracted with EtOAc (2×). The suspension in the aq. layer was filtered, washed with water, and dried to give 88.0 mg of the title compound

Example 149e 3-(2,6-dichloropyridin-4-yl)-5-methoxy-1H-pyrrolo[2,3-b]pyridine A suspension of Example 149d (88.0 mg, 0.203 mmol) in ethanol (2 mL) was treated with a solution of potassium hydroxide (45.5 mg, 0.811 mmol) in water (0.5 mL). The reaction mixture was heated at 50° C. for 1.5 hours. After concentration, water was added to the residue and the mixture was sonicated. The solid was filtered, washed with water, and oven-dried to give 51.3 mg of the title compound.

Example 149f trans-4-{[6-chloro-4-(5-methoxy-1H-pyrrolo[2,3-b]pyridin-3-yl)pyridin-2-yl]amino}cyclohexanol A mixture of Example 149e (43.9 mg, 0.146 mmol) and trans-4-aminocyclohexanol (0.337 g, 2.92 mmol) in acetonitrile (1.5 mL) and EtOH (1.5 mL) was heated at 190° C. for 3 hours in a Biotage microwave reactor. The solvent was evaporated. The residue was treated with 5% citric acid and brine, and extracted with EtOAc (2×). The combined organic layers were dried over $MgSO_4$, filtered, concentrated, and purified on a 12 g column using the ISCO Companion flash system eluting with $CH_2Cl_2$/EtOAc (5:95) to 100% EtOAc to give 22.0 mg of the title compound. $^1$H NMR (500 MHz, DMSO-$d_6$) ppm 1.15-1.33 (m, 3H), 1.84 (d, J=10.98 Hz, 2H), 1.96 (d, J=11.29 Hz, 2H), 2.07 (m, 1H), 3.40 (m, 1H), 3.59 (m, 1H), 3.89 (s, 3H), 6.76-6.90 (m, 2H), 7.78 (d, J=2.75 Hz, 1H), 8.07 (dd, J=6.71, 2.75 Hz, 2H), 12.03 (s, 1H). MS (APCI$^+$) m/z 373.4 (M+H)$^+$.

Example 150

N-[6-chloro-4-(1H-pyrrolo[2,3-b]pyridin-3-yl)pyridin-2-yl]-2-(morpholin-4-yl)acetamide

Example 150a 6-chloro-N-(4-methoxybenzyl)-4-(1-(phenylsulfonyl)-1H-pyrrolo[2,3-b]pyridin-3-yl)pyridin-2-amine A mixture of Example 7a (0.500 g, 1.24 mmol) and (4-methoxyphenyl)methanamine (1.018 g, 7.42 mmol) in acetonitrile (7 mL) was heated at 180° C. for 110 minutes The solvent was evaporated. The residue was treated with EtOAc and washed with 20% brine and 5% citric acid. The organic layer was concentrated and purified on a 100 g column using the ISCO Companion flash system eluting with $CH_2Cl_2$/EtOAc (98:2 to 95:5) to give 0.250 g of the title compound.

Example 150b 6-chloro-4-(1-(phenylsulfonyl)-1H-pyrrolo[2,3-b]pyridin-3-yl)pyridin-2-amine To a solution of Example 150a (0.500 g, 0.990 mmol) in $CH_2Cl_2$ (9 mL) was added trifluoroacetic acid (4 mL, 51.9 mmol). The mixture was heated at 35° C. for 6 hours and concentrated. The residue was treated with saturated $NaHCO_3$ and extracted with EtOAc. The organic layer was concentrated. The crude was triturated with EtOAc/diethyl ether to give 222 mg of the title compound. The filtrate was concentrated and purified on a 12 g column using the ISCO Companion flash system eluting with $CH_2Cl_2$/EtOAc (95:5 to 90:10) to give more title compound (84 mg).

Example 150c 2-chloro-N-(6-chloro-4-(1-(phenylsulfonyl)-1H-pyrrolo[2,3-b]pyridin-3-yl)pyridin-2-yl)acetamide To a solution of Example 150b (0.262 g, 0.681 mmol) in DMF (6 mL) was added pyridine (0.11 mL, 1.36 mmol) and 2-chloroacetyl chloride (0.060 mL, 0.749 mmol). After 2 hours, the suspension was filtered. The filtrate was treated with water slowly. The precipitate formed was filtered, washed with water, and oven-dried to give 0.289 g of the title compound.

Example 150d

N-[6-chloro-4-(1H-pyrrolo[2,3-b]pyridin-3-yl)pyridin-2-yl]-2-(morpholin-4-yl)acetamide To a solution of Example 150c (0.060 g, 0.13 mmol) in DMF (1.5 mL) were added morpholine (0.028 mL, 0.33 mmol) and triethylamine (0.091 mL, 0.65 mmol). The reaction mixture was heated at 60° C. for 2 hours. After cooling, water was slowing added to the reaction solution. The resulting precipitate was filtered, washed with water, and dried. This intermediate (55 mg) was suspended in dioxane (1.5 mL) and treated with 20% sodium hydroxide (0.1 mL, 0.13 mmol). The mixture was heated at 50° C. for 2 hours and concentrated. The residue was treated with DMSO/MeOH (1:1). The solid was filtered and the filtrate was purified by reverse-phase HPLC as described in Example 56 to give the title compound as trifluoroacetic acid salts. $^1$H NMR (300 MHz, METHANOL-$d_4$) ppm 3.38-3.58 (m, 4H), 3.89-4.08 (m, 4H), 4.18-4.30 (m, 2H), 7.27 (dd, J=8.14, 4.75 Hz, 1H), 7.54 (d, J=1.36 Hz, 1H), 8.05 (s, 1H), 8.33 (dd, J=4.75, 1.36 Hz, 1H), 8.45 (dd, J=8.14, 1.36 Hz, 1H), 8.55 (s, brd, 1H). MS (ESI$^+$) m/z 372.1 (M+H)$^+$.

Example 151

N-(trans-4-{[6-chloro-4-(1H-pyrrolo[2,3-b]pyridin-3-yl)pyridin-2-yl]amino}cyclohexyl)pyrrolidine-3-sulfonamide Example 151 (0.06 g) was prepared as described in Example 21, substituting methanesulfonyl chloride with tert-butyl 3-(chlorosulfonyl)pyrrolidine-1-carboxylate and Example 15 with Example 61b. The BOC intermediate was treated with 2N HCl in ether, and the solid filtered to give the title compound as an HCl salt. $^1$H NMR (300 MHz, DMSO-$d_6$) ppm 1.34 (m, 5H) 1.76-2.13 (m, 4H) 2.15-2.36 (m, 2H) 3.10-3.33 (m, 3H) 3.31-3.46 (m, 2H) 3.45-3.69 (m, 3H) 6.88 (d, J=3.05 Hz, 2H) 7.14-7.35 (m, 1H) 7.52-7.70 (m, 1H) 8.15 (t, J=3.22 Hz, 1H) 8.24-8.45 (m, 2H) 9.11-9.56 (m, 1H) 12.25 (s, 1H). MS (ESI$^+$) m/z 475.4 (M+H)$^+$.

Example 152

N-(trans-4-{[6-chloro-4-(1H-pyrrolo[2,3-b]pyridin-3-yl)pyridin-2-yl]amino}cyclohexyl)-N$^2$-(trans-4-hydroxycyclohexyl)glycinamide The trifluoroacetic acid salt of Example 152 (0.1 g, 0.239 mmol) was prepared as described in Example 141b, substituting morpholine with (trans)-4-aminocyclohexanol. $^1$H NMR (500 MHz, DMSO-$d_6$) ppm 1.11-1.19 (m, 2H), 1.26-1.4 (M, 4H), 1.87-2.04 (m, 6H), 3.31-3.37 (m, 2H), 3.66-3.69 (m, 2H), 6.87-6.88 (m, 2H), 7.20-7.23 (m, 1H), 8.13 (d, J=2.75 Hz, 1H), 8.30-8.33 (m, 2H), 8.39 (d, J=7.65 Hz, 1H), 8.75 (d, J=4.88 Hz, 2H), 12.18 (s, 1H). MS (DCI$^+$) m/z 497.3 (M+H)$^+$.

Example 153

N-(trans-4-{[6-chloro-4-(1H-pyrrolo[2,3-b]pyridin-3-yl)pyridin-2-yl]amino}cyclohexyl)-N$^2$-[2-(morpholin-4-yl)ethyl]glycinamide The trifluoroacetic acid salt of Example 153 (0.1 g, 0.239 mmol) was prepared as described in Example 141b, substituting morpholine with 2-morpholinoethanamine. $^1$H NMR (400 MHz, DMSO-$d_6$) ppm 1.26-1.41 (m, 4H), 1.87-1.90 (m, 2H), 2.02-2.05 (m, 2H), 3.15-3.9 (m, 14H), 6.88-6.89 (m, 2H), 7.22 (dd, J=7.93, 4.88 Hz, 1H), 8.13 (d, J=3.75 Hz, 1H), 8.30-8.33 (m, 2H), 8.46 (d, J=7.63 Hz, 1H). MS (DCI$^+$) m/z 512.3 (M+H)$^+$.

Example 154

N-(3-{[6-chloro-4-(1H-pyrrolo[2,3-b]pyridin-3-yl)pyridin-2-yl]amino}cyclohexyl)-2-(dimethylamino)ethanesulfonamide The trifluoroacetic acid salt of title compound was prepared according to the procedure for Example 58, substituting Example 145d for Example 23 and substituting formaldehyde for isobutyraldehyde. Yield: 21 mg (66%). MS (DCI/NH$_3$) m/z 448 (M+H)$^+$, $^1$H NMR (300 MHz, DMSO-$d_6$): 0.97-1.32 (m, 2H), 1.33-1.59 (m, 1H), 1.75 (t, J=6.35 Hz, 2H), 1.93 (d, J=11.10 Hz, 2H), 2.09-2.30 (m, 1H), 2.84 (s, 6H), 3.19-3.36 (m, 1H), 3.42 (d, J=6.74 Hz, 2H), 3.47-3.60 (m, 2H), 3.62-3.85 (m, 1H), 6.50-7.02 (m, 3H), 7.04-7.30 (m, 1H), 7.48-7.62 (m, 1H), 8.14 (d, J=2.78 Hz, 1H), 8.25-8.45 (m, 2H), 12.18 (s, 1H).

Example 155

6-chloro-N-(4-{[4-(dimethylamino)cyclohexyl]methyl}cyclohexyl)-4-(1H-pyrrolo[2,3-b]pyridin-3-yl)pyridin-2-amine The trifluoroacetic acid salt of title compound was prepared according to the procedure for Example 58, substituting Example 143 for Example 23 and substituting formaldehyde for isobutyraldehyde. Yield: 21 mg (66%). MS (DCI/NH$_3$) m/z 467 (M+H)$^+$, $^1$H NMR (300 MHz, DMSO-$d_6$): 0.85-1.08 (m, 4H), 1.04-1.24 (m, 3H), 1.19-1.45 (m, 4H), 1.46-1.65 (m, 3H), 1.65-1.89 (m, 4H), 1.89-2.06 (m, 2H), 2.73 (s, 6H), 2.98-3.18 (m, 1H), 3.50-3.68 (m, 1H), 6.55-6.92 (m, 3H), 7.09-7.33 (m, 1H), 8.12 (t, J=3.17 Hz, 1H), 8.26-8.44 (m, 2H), 12.15 (s, 1H).

Example 156

6-chloro-N-(4-{[4-(cyclohexylamino)cyclohexyl]methyl}cyclohexyl)-4-(1H-pyrrolo-2,3-b]pyridin-3-yl)pyridin-2-amine The trifluoroacetic acid salt of title compound was prepared according to the procedure for Example 58, substituting Example 143 for Example 23 and substituting cyclohexanone for isobutyraldehyde. Yield: 23 mg (58%). MS (DCI/NH$_3$) m/z 521 (M+H)$^+$, $^1$H NMR (300 MHz, DMSO-$d_6$): 0.82-1.19 (m, 5H), 1.20-1.45 (m, 5H), 1.42-1.67 (m, 6H), 1.64-1.85 (m, 7H), 1.89-2.17 (m, 4H), 2.39-2.46 (m, 1H), 2.52-2.66 (m, 2H), 2.92-3.25 (m, 2H), 3.49-3.74 (m, 1H), 3.87-4.05 (m, 1H), 6.63-6.93 (m, 2H), 7.17-7.42 (m, 1H), 8.13 (s, 1H), 8.24-8.56 (m, 4H), 12.22 (s, 1H).

Example 157 trans-N-[6-chloro-4-(1H-pyrrolo[2,3-b]pyridin-3-yl)pyridin-2-yl]-1-N'-(1-cyclohexylpiperidin-4-yl)cyclohexane-1,4-diamine

Example 157a tert-butyl 4-((1r,4r)-4-(6-chloro-4-(1H-pyrrolo[2,3-b]pyridin-3-yl)pyridin-2-ylamino)cyclohexylamino)piperidine-1-carboxylate The trifluoroacetic acid salt of the title compound was prepared according to the procedure for Example 58, substituting Example 61b for Example 23 and tert-butyl 4-oxopiperidine-1-carboxylate for isobutyraldehyde. Yield: 103 mg (83%). MS (DCI/NH$_3$) m/z 552 (M+H)$^+$.

Example 157b trans-N1-(6-chloro-4-(1H-pyrrolo[2,3-b]pyridin-3-yl)pyridin-2-yl)-N4-(piperidin-4-yl)cyclohexane-1,4-diamine The trifluoroacetic acid salt of the title compound was prepared according to the procedure for Example 102b substituting Example 157a for Example 102a. Yield: 140 mg (65%). MS (DCI/NH$_3$) m/z 425 (M+H)$^+$.

Example 157c trans-N-[6-chloro-4-(1H-pyrrolo[2,3-b]pyridin-3-yl)pyridin-2-yl]-N'-(1-cyclohexylpiperidin-4-yl)cyclohexane-1,4-diamine The trifluoroacetic acid salt of the title compound was prepared according to the procedure for Example 58, substituting Example 157b for Example 23 and substituting cyclohexanone for isobutyraldehyde. Yield: 30 mg (84%). MS (DCI/NH$_3$) m/z 508 (M+H)$^+$, $^1$H NMR (300 MHz, DMSO-d$_6$): 1.08-1.58 (m, 6H), 1.58-1.74 (m, 4H), 1.74-2.03 (m, 6H), 2.10 (d, J=9.91 Hz, 4H), 2.19-2.35 (m, 2H), 2.43-2.65 (m, 2H), 3.08 (d, J=11.90 Hz, 2H), 3.23 (d, J=4.36 Hz, 4H), 6.89 (d, J=7.14 Hz, 2H), 7.09-7.31 (m, 1H), 8.14 (d, J=2.78 Hz, 1H), 8.31 (d, J=5.95 Hz, 2H), 8.52-8.83 (m, 2H), 12.18 (d, J=1.98 Hz, 1H).

Example 158 trans-N-(4-aminocyclohexyl)-N'-[6-chloro-4-(1H-pyrrolo[2,3-b]pyridin-3-yl)pyridin-2-yl]cyclohexane-1,4-diamine

Example 158a

Benzyl 4-((1r,4r)-4-(6-chloro-4-(1H-pyrrolo[2,3-b]pyridin-3-yl)pyridin-2-ylamino)cyclohexylamino)cyclohexylcarbamate The trifluoroacetic acid salt of the title compound was prepared according to the procedure for Example 58, substituting Example 1b for Example 23 and benzyl 4-oxocyclohexylcarbamate for isobutyraldehyde. Yield: 110 mg (44%). MS (DCI/NH$_3$) m/z 574 (M+H)$^+$.

Example 158b trans-N-(4-aminocyclohexyl)-N'-[6-chloro-4-(1H-pyrrolo[2,3-b]pyridin-3-yl)pyridin-2-yl]cyclohexane-1,4-diamine The trifluoroacetic acid salt of the title compound was prepared according to the procedure for Example 102b, substituting Example 158a for Example 102a. Yield: 80 mg (95%). MS (DCI/NH$_3$) m/z 440 (M+H)$^+$, $^1$H NMR (300 MHz, DMSO-d$_6$): 1.11-1.61 (m, 6H), 1.67-1.92 (m, 3H), 1.93-2.22 (m, 4H), 2.94-3.08 (m, 1H), 3.09-3.28 (m, 1H), 3.49 (s, 4H), 6.89 (d, J=6.78 Hz, 2H), 7.06-7.26 (m, 1H), 7.86 (s, 2H), 8.13 (d, J=3.05 Hz, 2H), 8.31 (d, J=6.10 Hz, 3H), 8.34-8.45 (m, 1H), 12.16 (s, 1H).

Example 159

6-chloro-N-[4-(piperidin-4-yl)cyclohexyl]-4-(1H-pyrrolo[2,3-b]pyridin-3-yl)pyridin-2-amine

Example 159a tert-butyl 4-(4-(6-chloro-4-iodopyridin-2-ylamino)cyclohexyl)piperidine-1-carboxylate The title compound was prepared according to the procedure for Example 94a, substituting tert-butyl 4-(4-aminocyclohexyl)piperidine-1-carboxylate for benzyl 3-(aminomethyl)piperidine-1-carboxylate. Yield: 670 mg (57%). MS (DCI/NH$_3$) m/z 520 (M+H)$^+$.

Example 159b tert-butyl 4-(4-(6-chloro-4-(1-(phenylsulfonyl)-1H-pyrrolo[2,3-b]pyridin-3-yl)pyridin-2-ylamino)cyclohexyl)piperidine-1-carboxylate The title compound was prepared according to the procedure for Example 94b substituting Example 159a for Example 94a. Yield: 190 mg (97%). MS (DCI/NH$_3$) m/z 650 (M+H)$^+$.

Example 159c 6-chloro-N-(4-(piperidin-4-yl)cyclohexyl)-4-(1H-pyrrolo[2,3-b]pyridin-3-yl)pyridin-2-amine The trifluoroacetic acid salt of the title compound was prepared according to the procedure for Example 94c substituting Example 159b for Example 94b. Yield: 70 mg (79%). MS (DCI/NH$_3$) m/z 410 (M+H)$^+$, $^1$H NMR (300 MHz, DMSO-d$_6$): 1.04-1.28 (m, 2H), 1.25-1.43 (m, 3H), 1.42-1.65 (m, 2H), 1.67-1.93 (m, 3H), 1.94-2.13 (m, 1H), 2.34-2.49 (m, 1H), 2.74-2.95 (m, 2H), 3.30 (d, J=11.90 Hz, 2H), 3.42-3.69 (m, 1H), 3.91-4.04 (m, 2H), 6.74-6.92 (m, 2H), 6.98 (s, 1H), 7.11-7.38 (m, 1H), 8.10-8.14 (m, 2H), 8.22-8.58 (m, 2H), 12.16 (s, 1H).

Example 160

N-(trans-4-{[6-chloro-4-(1H-pyrrolo[2,3-b]pyridin-3-yl)pyridin-2-yl]amino}cyclohexyl)azetidine-3-carboxamide

Example 160a (S)-tert-butyl 2-((trans)-4-(6-chloro-4-(1H-pyrrolo[2,3-b]pyridin-3-yl)pyridin-2-ylamino)cyclohexylcarbamoyl)azetidine-1-carboxylate Example 160a (2.0 g) was prepared as described in Example 106a, substituting (S)-1-(tert-butoxycarbonyl)azetidine-2-carboxylic acid with 1-(tert-butoxycarbonyl)azetidine-3-carboxylic acid. MS (ESI$^+$) m/z 425.6 (M+H)$^+$

Example 160b (2S)—N-(trans-4-{[6-chloro-4-(1H-pyrrolo[2,3-b]pyridin-3-yl)pyridin-2-yl]amino}cyclohexyl)azetidine-2-carboxamide The TFA salt of Example 160b (1.7 g) was prepared as described in Example 106b, substituting Example 106a with Example 160a. A solution of the TFA salt in methanol was treated with 6 mL of 2N HCl/ether solution. The mixture was stirred for 20 minutes, diluted with 150 mL of ether and filtered to give the title compound as the HCl salt. $^1$H NMR (300 MHz, DMSO-d$_6$) ppm 1.13-1.50 (m, 5H) 1.70-1.94 (m, 3H) 1.91-2.16 (m, 2H) 3.44-3.76 (m, 4H) 3.88-4.08 (m, 4H) 6.76-7.00 (m, 1H) 7.16-7.36 (m, 1H) 7.97-8.23 (m, 2H) 8.23-8.47 (m, 2H) 8.70-8.94 (m, J=10.51 Hz, 1H) 9.18 (s, 1H) 12.33 (s, 1H). MS (ESI$^+$) m/z 425.2 (M+H)$^+$.

Example 161

N-{4-[(trans-4-{[6-chloro-4-(1H-pyrrolo[2,3-b]pyridin-3-yl)pyridin-2-yl]amino}cyclohexyl)amino]cyclohexyl}acetamide The trifluoroacetic acid salt of the title compound was prepared according to the procedure for Example 69, substituting Example 158b for Example 23 and substituting acetic acid for cyclopropanecarboxylic acid. Yield: 18 mg (54%). MS (DCI/NH$_3$) m/z 482 (M+H)$^+$, $^1$H NMR (300 MHz, DMSO-6$_6$): 1.16-1.67 (m, 6H), 1.78 (s, 3H), 1.80-1.95 (m, 4H), 2.08 (d, J=9.52 Hz, 4H), 3.05-3.30 (m, 3H), 3.39-3.56 (m, 1H), 3.56-3.78 (m, 2H), 6.76-6.96 (m, 2H), 7.21 (dd, J=7.93, 5.16 Hz, 1H), 7.80 (d, J=7.54 Hz, 1H), 8.14 (d, J=2.78 Hz, 1H), 8.18-8.44 (m, 4H), 12.18 (s, 1H).

Example 162

N-{4-[(trans-4-{[6-chloro-4-(1H-pyrrolo[2,3-b]pyridin-3-yl)pyridin-2-yl]amino}cyclohexyl)amino]cyclohexyl}cyclopropanecarboxamide The trifluoroacetic acid salt of the title compound was prepared according to the procedure for Example 69, substituting Example 158b for Example 23. Yield: 16 mg (46%). MS (DCI/NH$_3$) m/z 508 (M+H)$^+$, $^1$H NMR (300 MHz, DMSO-d$_6$): 0.57-0.74 (m, 4H), 1.08-1.56 (m, 7H), 1.54-1.72 (m, 2H), 1.76-1.97 (m, 3H), 2.09 (d, J=8.73 Hz, 4H), 3.04-3.32 (m, 2H), 3.50 (dd, J=7.34, 3.37 Hz, 1H), 3.58-3.77 (m, 2H), 6.77-6.97 (m, 3H), 7.21 (dd, J=7.73, 4.96 Hz, 1H), 8.01 (d, J=7.93 Hz, 1H), 8.14 (d, J=2.78 Hz, 1H), 8.21-8.49 (m, 4H).

Example 163

1-[4-(4-{[6-chloro-4-(1H-pyrrolo[2,3-b]pyridin-3-yl)pyridin-2-yl]amino}cyclohexyl)piperidin-1-yl]ethanone The trifluoroacetic acid salt of the title compound was prepared according to the procedure for Example 69, substituting Example 159c for Example 23 and acetic acid for cyclopropanecarboxylic acid. Yield: 15 mg (45%). MS (DCI/NH$_3$) m/z 452 (M+H)$^+$, $^1$H NMR (300 MHz, DMSO-d$_6$): 0.87-1.24 (m, 4H), 1.29-1.62 (m, 4H), 1.62-1.84 (m, 4H), 1.97 (s, 3H), 2.34-2.48 (m, 1H), 2.95 (t, J=12.89 Hz, 1H), 3.83 (d, J=11.90 Hz, 1H), 3.90-4.07 (m, 1H), 4.36-4.64 (m, 3H), 6.83-6.88 (m, 2H), 7.23 (dd, J=7.93, 4.76 Hz, 1H), 8.13 (t, J=2.97 Hz, 1H), 8.27-8.34 (m, 2H), 8.37 (d, J=7.93 Hz, 1H), 12.18 (s, 1H).

Example 164

N-{2-[(3-{[6-chloro-4-(1H-pyrrolo[2,3-b]pyridin-3-yl)pyridin-2-yl]amino}cyclohexyl)sulfamoyl]ethyl}acetamide The trifluoroacetic acid salt of the title compound was prepared according to the procedure for Example 69 substituting Example 145d for Example 23 and substituting acetic acid for cyclopropanecarboxylic acid. Yield: 20 mg (46%). MS (DCI/NH$_3$) m/z 492 (M+H)$^+$, $^1$H NMR (300 MHz, DMSO-d$_6$): 0.88-1.27 (m, 3H) 1.37 (d, J=13.88 Hz, 1H), 1.79 (s, 3H), 1.85-2.00 (m, 2H), 2.11-2.34 (m, 1H), 3.05-3.17 (m, 2H), 3.17-3.31 (m, 1H), 3.29-3.50 (m, 2H), 3.73 (d, J=4.36 Hz, 2H), 6.49-6.97 (m, 3H), 7.13-7.31 (m, 2H), 7.97 (t, J=5.75 Hz, 1H), 8.13 (d, J=2.78 Hz, 1H), 8.21-8.42 (m, 2H), 12.17 (d, J=1.98 Hz, 1H).

Example 165

N-{2-[(3-{[6-chloro-4-(1H-pyrrolo[2,3-b]pyridin-3-yl)pyridin-2-yl]amino}cyclohexyl)sulfamoyl]ethyl}cyclopropanecarboxamide The trifluoroacetic acid salt of the title compound was prepared according to the procedure for Example 69, substituting Example 145d for Example 23. Yield: 28 mg (61%). MS (DCI/NH$_3$) m/z 518 (M+H)$^+$, $^1$H NMR (300 MHz, DMSO-d$_6$): 0.54-0.71 (m, 4H), 0.94-1.09 (m, 1H), 1.07-1.29 (m, 2H), 1.29-1.56 (m, 3H), 1.66-1.81 (m, 1H), 1.83-2.02 (m, 1H), 2.11-2.34 (m, 1H), 3.09-3.22 (m, 2H), 3.18-3.31 (m, 1H), 3.33-3.51 (m, 2H), 3.56-3.98 (m, 1H), 6.72-6.96 (m, 3H), 7.13-7.34 (m, 2H), 8.13 (d, J=2.78 Hz, 1H), 8.19 (t, J=5.55 Hz, 1H), 8.23-8.41 (m, 2H), 12.16 (s, 1H).

Example 166

N-(trans-4-{[6-chloro-4-(1H-pyrrolo[2,3-b]pyridin-3-yl)pyridin-2-yl]amino}cyclohexyl)-1-(4-fluorobenzyl)azetidine-3-carboxamide Example 166 (0.1 g) was prepared as described in Example 106a, substituting (S)-1-(tert-butoxycarbonyl)azetidine-2-carboxylic acid with 1-(4-fluorobenzyl)azetidine-3-carboxylic acid. $^1$H NMR (300 MHz, DMSO-d$_6$) ppm 1.23 (d, 4H) 1.76 (d, 4H) 1.99 (d, 2H) 3.07 (d, 3H) 3.48 (d, 2H) 6.77 (d, J=7.80 Hz, 1H) 6.86 (t, J=4.41 Hz, 2H) 7.02-7.17 (m, 3H) 7.16-7.25 (m, 1H) 7.23-7.36 (m, 3H) 7.70 (dd, J=15.60, 7.80 Hz, 2H) 8.12 (t, J=3.39 Hz, 1H) 8.23-8.37 (m, 2H) 12.14 (s, 1H). MS (ESI$^+$) m/z 533.4 (M+H)$^+$.

Example 167

N-(trans-4-{[6-chloro-4-(1H-pyrrolo[2,3-b]pyridin-3-yl)pyridin-2-yl]amino}cyclohexyl)-1-(methylsulfonyl)azetidine-3-carboxamide Example 167 (0.04 g) was prepared as described in Example 21, substituting Example 15 with Example 160b. $^1$H NMR (300 MHz, DMSO-d$_6$) ppm 1.18-1.43 (m, 5H) 1.74-1.92 (m, 2H) 1.93-2.08 (m, 2H) 2.87-3.09 (m, 3H) 3.43-3.80 (m, 2H) 3.90 (d, 3H) 6.77 (d, J=7.80 Hz, 1H) 6.87 (t, J=3.39 Hz, 2H) 7.20 (dd, J=7.80, 5.09 Hz, 1H) 7.96 (d, J=7.80 Hz, 1H) 8.12 (t, J=3.22 Hz, 1H) 8.22-8.37 (m, 2H) 12.13 (s, 1H). MS (ESI$^+$) m/z 503.9 (M+H)$^+$.

Example 168

6-chloro-4-(4-chloro-1H-pyrrolo[2,3-b]pyridin-3-yl)-N-cyclohexylpyridin-2-amine

Example 168a 6-chloro-N-cyclohexyl-4-(4,4,5,5-tetramethyl-1,3,2-dioxaborolan-2-yl)pyridin-2-amine Cyclohexanamine (4.0 mL, 34.9 mmol) was added to 2,6-dichloro-4-iodo-pyridine (954 mg, 3.48 mmol) in a microwave tube and subjected to 300 watts at 150° C. for 30 minutes in a Biotage Microwave Reactor. The crude product was partitioned with water, dichloromethane and the organics combined and concentrated to dryness. The residue was partially purified using silica gel flash chromatography eluting with 2% ethyl acetate, 98% hexanes to give 916 mg 6-chloro-N-cyclohexyl-4-iodopyridin-2-amine as a purple gum. This material was dissolved in 15 mL DMF and 4,4,4',4',5,5,5',5'-octamethyl-2,2'-bi(1,3,2-dioxaborolane) (666 mg, 1.98 mmol) added followed by addition of potassium acetate (400 mg, 4.07 mmol). The mixture was degassed with nitrogen and 1,1'-bis(diphenylphosphino)-ferrocene)dichloropalladium (II) complex with dichloromethane (222 mg, 0.272 mmol) added and the reaction mixture heated at 75° C. for 4 hours and then cooled to room temperature and partitioned with water, ethyl acetate. The organics were combined, concentrated to dryness and purified by silica gel flash chromatography eluting with a gradient from 3% ethyl acetate, 97% hexanes to 6% ethyl acetate, 94% hexanes to provide the title compound as a clear gum in 73% yield. MS (DCI$^+$) m/z 337.2 (M+H)$^+$.

Example 168b 4-chloro-3-iodo-1-(phenylsulfonyl)-1H-pyrrolo[2,3-b]pyridine

To a mixture of 95% sodium hydride (28 mg, 1.1 mmol) and 4-chloro-3-iodo-1H-pyrrolo[2,3-b]pyridine (278 mg, 1.0 mmol) in 10 mL DMF was added benzenesulfonyl chloride (194 mg, 1.1 mmol) and the reaction mixture stirred for 2.5 hours then diluted with water and the resulting precipitate collected by filtration to give the title compound in 83% yield. MS (ESI$^+$) m/z 418.9 (M+H)$^+$ Example 168c 6-chloro-4-(4-chloro-1-(phenylsulfonyl)-1H-pyrrolo[2,3-b]pyridin-3-yl)-N-cyclohexylpyridin-2-amine To a mixture of Example 168a (126 mg, 0.373 mmol) in 3 mL DMF was added Example 168b (142 mg, 0.339 mmol). After degassing, a suspension of sodium bicarbonate (285 mg, 3.39 mmol) in 0.75 mL water was added followed by the addition of 1,1'-bis(diphenylphosphino)-ferrocene dichloropalladium(II) complex with dichloromethane (28 mg, 0.034 mmol). The reaction mixture was heated at 65° C. for 30 minutes and then partitioned with water and ethyl acetate. The organics were concentrated to dryness and purified by silica gel flash chromatography eluting with 8% ethyl acetate, 92% hexanes to give the title compound as a brown powder in 50% yield. MS (ESI$^+$) m/z 501.6 (M+H)$^+$.

Example 168d 6-chloro-4-(4-chloro-1H-pyrrolo[2,3-b]pyridin-3-yl)-N-cyclohexylpyridin-2-amine To a solution of Example 168c (82 mg, 0.164 mmol) in a mixture of 5 mL THF, 5 mL methanol was added a solution of 27 mg (0.654 mmol) lithium hydroxide in 0.5 mL water. After stirring for 16 hours the reaction mixture was concentrated to dryness and the residue suspended in water and a yellow solid was collected by filtration. Purified by silica gel flash chromatography (eluting with 10% ethyl acetate, 90% dichloromethane) provided the title compound as an off-white powder in 51% yield. MS (ESI$^+$) m/z 361.3 (M+H)$^+$; $^1$H NMR (300 MHz, DMSO-d$_6$) ppm 1.01-1.39 (m, 5H) 1.53-1.65 (m, 1H) 1.66-1.75 (m, 2H) 1.85-1.95 (m, 2H) 3.54-3.69 (m, 1H) 6.51 (s, 1H) 6.60 (s, 1H) 6.79 (d, 1H, J=7.54 Hz) 7.24 (d, 1H, J=5.16 Hz) 7.81 (s, 1H) 8.23 (d, 1H, J=4.76 Hz) 12.41 (bs, 1H).

Example 169

N-{2-[(3-{[6-chloro-4-(1H-pyrrolo[2,3-b]pyridin-3-yl)pyridin-2-yl]amino}cyclohexyl)sulfamoyl]ethyl}benzamide The trifluoroacetic acid salt of the title compound was prepared according to the procedure for Example 69, substituting Example 145d for Example 23 and substituting benzoic acid for cyclopropanecarboxylic acid. Yield: 28 mg (61%). MS (DCI/NH$_3$) m/z 518 (M+H)$^+$, $^1$H NMR (300 MHz, DMSO-6$_6$): 1.01 (m, 1H), 1.10-1.28 (m, 2H), 1.35 (s, 1H), 1.58-1.69 (m, 1H), 1.67-1.84 (m, 3H), 1.84-2.01 (m, 1H), 2.17-2.34 (m, 1H), 3.18-3.38 (m, 4H), 6.61-7.05 (m, 3H), 7.21 (dd, J=7.93, 4.76 Hz, 1H), 7.26 (d, J=17.85 Hz, 1H), 7.35-7.61 (m, 3H), 7.72-7.87 (m, 2H), 8.13 (d, J=2.78 Hz, 1H), 8.24-8.42 (m, 2H), 8.59 (t, J=5.55 Hz, 1H), 12.16 (s, 1H).

Example 170

N-(3-{[6-chloro-4-(1H-pyrrolo[2,3-b]pyridin-3-yl)pyridin-2-yl]amino}cyclohexyl)-2-(cyclobutylamino)ethanesulfonamide The trifluoroacetic acid salt of the title compound was prepared according to the procedure for Example 58, substituting Example 145d for Example 23 and substituting cyclobutanone for isobutyraldehyde. Yield: 28 mg (62%). MS (DCI/NH$_3$) m/z 504 (M+H)$^+$, $^1$H NMR (300 MHz, DMSO-d$_6$): 0.93-1.54 (m, 3H), 1.57-1.84 (m, 3H), 1.84-1.98 (m, 1H), 2.00-2.26 (m, 4H), 3.00-3.20 (m, 2H), 3.21-3.31 (m, 1H), 3.29-3.44 (m, 3H), 3.54-3.69 (m, 1H), 3.67-3.84 (m, 3H), 6.65-7.06 (m, 3H), 7.10-7.32 (m, 1H), 7.58 (d, J=7.93 Hz, 1H), 8.13 (d, J=2.78 Hz, 1H), 8.22-8.37 (m, 2H), 8.78 (s, 1H), 12.18 (s, 1H).

Example 171

6-chloro-N-cyclohexyl-4-[5-(1H-pyrazol-4-yl)-1H-pyrrolo[2,3-b]pyridin-3-yl]pyridin-2-amine Example 171a 4-(5-bromo-1-(phenylsulfonyl)-1H-pyrrolo[2,3-b]pyridin-3-yl)-6-chloro-N-cyclohexylpyridin-2-amine A solution of 5-bromo-3-iodo-1-(phenylsulfonyl)-1H-pyrrolo[2,3-b]pyridine (1.155 g, 2.49 mmol), Example 168a (0.924 g, 2.74 mmol), catalytic amount of [1,1'-bis(diphenylphosphino)ferrocene]-dichloropalladium(II), complex with dichloromethane (1:1) and saturated sodium bicarbonate solution (6 mL) in 24 mL dimethylformamide was heated at 65° C. for 30 minutes. The material was cooled to room temperature, diluted with ethyl acetate, washed with brine, dried over MgSO$_4$, filtered, and concentrated. The residue was purified on silica gel using flash chromatography (6% ethyl acetate/hexane) to afford 0.68 g of the title compound. m/z 547.4 (APCI, M+H)$^+$.

Example 171b 6-chloro-N-cyclohexyl-4-(1-(phenylsulfonyl)-5-(1-(phenylsulfonyl)-1H-pyrazol-4-yl)-1H-pyrrolo[2,3-b]pyridin-3-yl)pyridin-2-amine A solution of Example 171a (0.158 g, 0.29 mmol), 1-(phenylsulfonyl)-4-(4,4,5,5-tetramethyl-1,3,2-dioxaborolan-2-yl)-1H-pyrazole (0.100 g, 0.29 mmol), catalytic amount of [1,1'-bis(diphenylphosphino)ferrocene]-dichloropalladium (II), complex with dichloromethane (1:1) and saturated sodium bicarbonate solution (2 mL) in 8 mL dimethylformamide was heated at 65° C. for 2 hours. The material was cooled to room temperature, diluted with ethyl acetate, washed with brine, dried over MgSO$_4$, filtered, and concentrated. The residue was purified on silica gel using flash chromatography (20% ethyl acetate/hexane) to afford 0.11 g of the title compound. m/z 673.6 (ESI, M+H)$^+$.

Example 171c 4-(5-(1H-pyrazol-4-yl)-1H-pyrrolo[2,3-b]pyridin-3-yl)-6-chloro-N-cyclohexylpyridin-2-amine A solution of Example 171b (0.110 g, 0.16 mmol) in 18 mL tetrahydrofuran/methanol (2:1) was treated with 1N lithium hydroxide (0.048 g, 2.00 mmol) in 2 mL water at room temperature for 4 hours. The material was diluted with ethyl acetate, washed with brine, dried over MgSO$_4$, filtered, and concentrated. The residue was purified by trituration with diethyl ether/ethyl acetate and filtration to afford 15 mg of the title compound. $^1$H NMR (400 MHz, DMSO-d$_6$) ppm 1.17-1.44 (m, 5H) 1.56-1.66 (m, 1H) 1.69-1.80 (m, 2H) 1.92-2.01 (m, 2H) 3.66-3.78 (m, 1H) 6.39 (d, J=7.63 Hz, 1H) 6.83 (d, J=6.71 Hz, 2H) 7.95 (s, 1H) 7.95-8.16 (m, 2H) 8.33 (s, 1H) 8.52 (s, 1H) 11.79 (s, 1H) 12.73 (s, 1H). MS (ESI$^+$) m/z 393.7 (M+H)$^+$.

Example 172

N-{2-[(3-{[6-chloro-4-(1H-pyrrolo[2,3-b]pyridin-3-yl)pyridin-2-yl]amino}cyclohexyl)sulfamoyl]ethyl}pyrazine-2-carboxamide The trifluoroacetic acid salt of the title compound was prepared according to the procedure for Example 69, substituting Example 145d for Example 23 and substituting pyrazine-2-carboxylic acid for cyclopropanecarboxylic acid. Yield: 30 mg (61%). MS (DCI/NH$_3$) m/z 556 (M+H)$^+$, $^1$H NMR (300 MHz, DMSO-d$_6$): 0.95-1.13 (m, 1H), 1.08-1.29 (m, 2H), 1.34 (s, 1H), 1.55-1.73 (m, 1H), 1.66-1.83 (m, 1H), 1.86-2.01 (m, 1H), 2.17-2.31 (m, 1H), 2.41-2.65 (m, 2H), 3.23-3.40 (m, 2H), 3.64-3.80 (m, 2H), 6.67-6.99 (m, 3H), 7.21 (dd, J=7.93, 4.76 Hz, 1H), 7.36 (d, J=7.54 Hz, 1H), 8.12 (t, J=3.17 Hz, 1H), 8.23-8.43 (m, 2H), 8.70 (d, J=2.78 Hz, 1H), 8.85 (d, J=2.38 Hz, 1H), 9.06 (t, J=5.75 Hz, 1H), 9.17 (d, J=1.59 Hz, 1H), 12.16 (d, J=1.59 Hz, 1H).

Example 173

4-(5-bromo-1H-pyrrolo[2,3-b]pyridin-3-yl)-6-chloro-N-cyclohexylpyridin-2-amine

A solution of Example 171a (0.100 g, 0.16 mmol) in 9 mL tetrahydrofuran/methanol (2:1) was treated with 1N lithium hydroxide (0.024 g, 1.00 mmol) in 1 mL water at room temperature for 16 hours. The material was diluted with water and resulting precipitate collected by filtration. Trituration with dimethyl sulfoxide/methanol and filtration afforded 54 mg of the title compound. $^1$H NMR (300 MHz, DMSO-d$_6$) ppm 1.11-1.44 (m, 5H) 1.54-1.66 (m, 1H) 1.67-1.80 (m, 2H) 1.87-1.99 (m, 2H) 3.62-3.77 (m, 1H) 6.78 (d, J=7.93 Hz, 1H) 6.86 (d, J=4.36 Hz, 2H) 8.23 (s, 1H) 8.37 (s, 1H) 8.49 (s, 1H) 12.41 (s, 1H). MS (ESI$^-$) m/z 405.1 (M−H)$^-$.

Example 174

N-{4-[(4-{[6-chloro-4-(1H-pyrrolo[2,3-b]pyridin-3-yl)pyridin-2-yl]amino}cyclohexyl)methyl]cyclohexyl}acetamide The trifluoroacetic acid salt of the title compound was prepared according to the procedure for Example 69, substituting Example 143 for 23 and substituting acetic acid for cyclopropanecarboxylic acid. Yield: 7 mg (13%). MS (DCI/NH$_3$) m/z 481 (M+H)$^+$, $^1$H NMR (300 MHz, DMSO-d$_6$): 0.83-1.20 (m, 6H), 1.20-1.39 (m, 2H), 1.39-1.62 (m, 4H), 1.61-1.85 (m, 6H), 1.90-2.06 (m, 1H), 2.38-2.70 (m, 2H), 3.33-3.60 (m, 2H), 3.86-4.05 (m, 2H), 6.69-6.90 (m, 2H), 7.21 (dd, J=7.97, 4.58 Hz, 2H), 7.64 (s, 1H), 8.12 (t, J=3.05 Hz, 1H), 8.25-8.43 (m, 2H), 12.14 (s, 1H).

Example 175

{4-[(4-{[6-chloro-4-(1H-pyrrolo[2,3-b]pyridin-3-yl)pyridin-2-yl]amino}cyclohexyl)amino]piperidin-1-yl}(cyclopropyl)methanone The trifluoroacetic acid salt of the title compound was prepared according to the procedure for 69, substituting Example 157b for Example 23. Yield: 41 mg (59%). MS (DCI/NH$_3$) m/z 494 (M+H)$^+$, $^1$H NMR (300 MHz, DMSO-d$_6$): 0.72 (d, J=5.95 Hz, 4H), 1.15-1.61 (m, 6H), 1.88-2.24 (m, 6H), 2.54-2.79 (m, 1H), 2.99-3.37 (m, 1H), 3.41-3.59 (m, 1H), 3.59-3.75 (m, 1H), 3.96 (s, 2H), 4.39 (d, 2H), 6.89 (d, J=5.16 Hz, 2H), 7.21 (dd, J=7.54, 5.16 Hz, 1H), 8.14 (d, J=2.78 Hz, 1H), 8.25-8.36 (m, 2H), 8.40 (s, 2H). 12.18 (d, J=1.59 Hz, 1H).

Example 176

6-chloro-N-cyclohexyl-4-[5-(1-methyl-1H-pyrazol-4-yl)-1H-pyrrolo[2,3-b]pyridin-3-yl]pyridin-2-amine

Example 176a 6-chloro-N-cyclohexyl-4-(5-(1-methyl-1H-pyrazol-4-yl)-1-(phenylsulfonyl)-1H-pyrrolo[2,3-b]pyridin-3-yl)pyridin-2-amine Example 176a (0.085 g) was prepared as described in Example 171b, substituting 1-(phenylsulfonyl)-4-(4,4,5,5-tetramethyl-1,3,2-dioxaborolan-2-yl)-1H-pyrazole with 1-methyl-4-(4,4,5,5-tetramethyl-1,3,2-dioxaborolan-2-yl)-1H-pyrazole (0.053 g, 0.242 mmol). MS (ESI$^+$) m/z 547.5 (M+H)$^+$.

Example 176b 6-chloro-N-cyclohexyl-4-(5-(1-methyl-1H-pyrazol-4-yl)-1H-pyrrolo[2,3-b]pyridin-3-yl)pyridin-2-amine Example 176b (0.045 g) was prepared as described in Example 171c, substituting Example 171b with Example 176a. $^1$H NMR (300 MHz, DMSO-d$_6$) ppm 1.12-1.44 (m, 5H) 1.55-1.67 (m, 1H) 1.67-1.81 (m, 2H) 1.90-2.02 (m, 2H) 3.62-3.78 (m, 1H) 6.72 (d, J=7.93 Hz, 1H) 6.88 (s, 2H) 7.96 (s, 1H) 8.10 (s, 1H) 8.20 (s, 1H) 8.35 (s, 1H) 8.53 (s, 1H) 12.13 (s, 1H). MS (ESI$^+$) m/z 407.6 (M+H)$^+$.

Example 177

{4-[(4-{[6-chloro-4-(1H-pyrrolo[2,3-b]pyridin-2-yl]amino}cyclohexyl)amino]piperidin-1-yl}(phenyl)methanone The trifluoroacetic acid salt of the title compound was prepared according to the procedure for 69, substituting Example 157b for Example 23 and substituting benzoic acid for cyclopropanecarboxylic acid. Yield: 41 mg (59%). MS (DCI/NH$_3$) m/z 494 (M+H)$^+$, $^1$H NMR (300 MHz, DMSO-d$_6$): 1.17-1.37 (m, 3H), 1.45 (m, 3H), 1.90-2.19 (m, 5H), 2.66-3.08 (m, 1H), 3.17 (m, 2H), 3.42-3.65 (m, 1H), 3.60-3.81 (m, 2H), 3.90-4.28 (m, 2H), 6.89 (d, J=6.10 Hz, 3H), 7.09-7.25 (m, 1H), 7.30-7.39 (m, 2H), 7.42-7.62 (m, 3H), 8.13 (d, J=2.71 Hz, 1H), 8.23-8.39 (m, 2H), 8.43 (s, 1H), 12.16 (s, 1H).

Example 178

6-chloro-N-cyclohexyl-4-(5-methoxy-1H-pyrrolo[2,3-b]pyridin-3-yl)pyridin-2-amine Example 178a 6-chloro-N-cyclohexyl-4-(5-methoxy-1-(phenylsulfonyl)-1H-pyrrolo[2,3-b]pyridin-3-yl)pyridin-2-amine A suspension of Example 149b (1.940 g, 5.28 mmol), Example 168a (1.779 g, 5.28 mmol), dichlorobis(triphenylphosphine)palladium(II) (0.148 g, 0.211 mmol) and 1M sodium carbonate (4.23 mL, 4.23 mmol) in dimethoxyethane/EtOH/water (7:2:3, 70 mL) was degassed and heated at 80° C. for 6 hours. The reaction mixture was treated with water and brine and extracted with EtOAc (2×). The combined organic layers were dried over MgSO$_4$, filtered, concentrated, and purified on a 120 g column using the ISCO Companion flash system eluting with CH$_2$Cl$_2$/hexane (7:3 to 9:1) to give impure product. This material was triturated with diethyl ether/EtOAc (9:1) to give 1.227 g of the title compound.

Example 178b 6-chloro-N-cyclohexyl-4-(5-methoxy-1H-pyrrolo[2,3-b]pyridin-3-yl)pyridin-2-amine A solution of Example 178a (90.0 mg, 0.181 mmol) in dioxane (2.5 mL) was treated with 20% NaOH (0.12 mL). The reaction was heated at 50° C. for 4 hours. The solvent was evaporated and the residue was triturated with water. The solid was filtered and purified by reverse-phase HPLC as described in Example 56 to give the title compound (46.2 mg) as trifluoroacetic acid salts. $^1$H NMR (400 MHz, CD$_3$OD) ppm 1.23-1.39 (m, 3H), 1.40-1.55 (m, 2H), 1.69 (m, 1H), 1.76-1.88 (m, 2H), 2.00-2.12 (m, 2H), 3.75 (m, 1H), 3.96 (s, 3H), 6.90 (d, J=1.22 Hz, 1H), 7.00 (d, J=1.53 Hz, 1H), 7.91 (d, J=2.44 Hz, 1H), 7.99 (s, 1H), 8.09 (d, J=2.75 Hz, 1H). MS (ESI$^+$) m/z 357.5 (M+H)$^+$.

Example 179

2-amino-N-(trans-4-{[6-chloro-4-(1H-pyrrolo[2,3-b]pyridin-3-yl)pyridin-2-yl]amino}cyclohexyl)ethanesulfonamide Example 179a N-((trans)-4-(6-chloro-4-(1H-pyrrolo[2,3-b]pyridin-3-yl)pyridin-2-ylamino)cyclohexyl)-2-(1,3-dioxoisoindolin-2-yl)ethanesulfonamide Example 179a (1 g) was prepared as described in Example 21, substituting methanesulfonyl chloride with 2-(1,3-dioxoisoindolin-2-yl)ethanesulfonyl chloride and Example 15 with Example 61b. MS (ESI$^+$) m/z 579.8 (M+H)$^+$.

Example 179b 2-amino-N-(trans-4-{[6-chloro-4-(1H-pyrrolo[2,3-b]pyridin-3-yl)pyridin-2-yl]amino}cyclohexyl)ethanesulfonamide To a solution of Example 179a (0.73 g, 1.26 mmol) in 15 mL ethanol was added hydrazine (0.4 g, 12.6 mmol). The reaction was heated to 80° C. for 16 hours, then cooled to room temperature. Most of the solvent was removed in vacuo, and the residue was diluted with ethyl acetate, washed with saturated. NaHCO$_3$, water, and brine, and filtered. The solid collected was dried over high vacuum to give 0.5 g of the title compound as a white solid. $^1$H NMR (300 MHz, DMSO-d$_6$) ppm 1.09-1.52 (m, 5H) 1.76-2.17 (m, 4H) 2.78-2.98 (m, 2H) 2.99-3.17 (m, 3H) 3.46-3.70 (m, 1H) 6.73-6.84 (m, 1H) 6.83-6.92 (m, 2H) 7.13-7.27 (m, 1H) 8.07-8.18 (m, 1H) 8.26-8.35 (m, 2H) 12.16 (s, 1H). MS (ESI$^+$) m/z 450.0 (M+H)$^+$ Example 180

3-[2-chloro-6-(cyclohexylamino)pyridin-4-yl]-1H-pyrrolo[2,3-b]pyridin-5-ol

Example 180a 3-(2-chloro-6-(cyclohexylamino)pyridin-4-yl)-1-(phenylsulfonyl)-1H-pyrrolo[2,3-b]pyridin-5-ol To a solution of Example 178a (250.0 mg, 0.503 mmol) in CH$_2$Cl$_2$ (20 mL) was added 1M BBr$_3$ in dichloromethane (3.0 mL, 3.02 mmol) at −78° C. The reaction was slowly warmed to room temperature overnight. The clear solution was decanted. The solids remaining in the flask were stirred in saturated NaHCO$_3$ and EtOAc till all the solids were dissolved. The organic layer was dried over MgSO$_4$, filtered, concentrated, and purified on an 80 g column using the ISCO Companion flash system eluting with CH$_2$Cl$_2$/EtOAc (90:10 to 85:15) to give 0.166 g of the title compound.

Example 180b

3-[2-chloro-6-(cyclohexylamino)pyridin-4-yl]-1H-pyrrolo[2,3-b]pyridin-5-ol

A solution of Example 180a (80.0 mg, 0.166 mmol) in dioxane (2 mL) was treated with 20% NaOH (0.20 mL). The reaction was heated at 90° C. for 2 hours. The solvent was evaporated. The residue was dissolved in water, neutralized with trifluoroacetic acid, treated with DMSO/MeOH, and purified by reverse-phase HPLC as described in Example 56 to give the title compound (40.2 mg) as trifluoroacetic acid salts. $^1$H NMR (500 MHz, CD$_3$OD) ppm 1.30 (q, J=12.51 Hz, 3H), 1.39-1.56 (m, 2H), 1.69 (m, 1H), 1.75-1.86 (m, 2H), 2.04 (dd, J=12.51, 3.36 Hz, 2H), 3.72 (m, 1H), 6.76 (d, J=1.22 Hz, 1H), 6.90 (d, J=1.22 Hz, 1H), 7.84 (d, J=2.44 Hz, 1H), 7.91 (s, 1H), 7.97 (s, 1H). MS (DCI$^+$) m/z 343.2 (M+H)$^+$.

Example 181

6-chloro-N-[4-(piperidin-3-yl)cyclohexyl]-4-(1H-pyrrolo[2,3-b]pyridin-3-yl)pyridin-2-amine Example 181a tert-butyl 3-(4-(6-chloro-4-iodopyridin-2-ylamino)cyclohexyl)piperidine-1-carboxylate The title compound was prepared according to the procedure for Example 94a, substituting tert-butyl 3-(4-aminocyclohexyl)piperidine-1-carboxylate for benzyl 3-(aminomethyl)piperidine-1-carboxylate. Yield: 600 mg (33%). MS (DCI/NH$_3$) m/z 520 (M+H)$^+$.

Example 181b tert-butyl 3-(4-(6-chloro-4-(1-(phenylsulfonyl)-1H-indol-3-yl)pyridin-2-ylamino)cyclohexyl)piperidine-1-carboxylate The title compound was prepared according to the procedure for Example 94b, substituting Example 181a for Example 94a. Yield: 440 mg (86%). MS (DCI/NH$_3$) m/z 651 (M+H)$^+$.

Example 181c 6-chloro-N-(4-(piperidin-3-yl)cyclohexyl)-4-(1H-pyrrolo[2,3-b]pyridin-3-yl)pyridin-2-amine The trifluoroacetic acid salt of the title compound was prepared according to the procedure for Example 94c, substituting Example 181b for Example 94b. Yield: 260 mg (55%). MS (DCI/NH$_3$) m/z 410 (M+H)$^+$, $^1$H NMR (300 MHz, DMSO-d$_6$): 1.05-1.35 (m, 5H), 1.40-1.67 (m, 3H), 1.76 (d, J=13.88 Hz, 3H), 1.96-2.10 (m, 1H), 2.44 (d, J=1.98 Hz, 1H), 2.54-2.68 (m, 1H), 2.66-2.89 (m, 1H), 3.03-3.38 (m, 2H), 3.52-3.73 (m, 1H), 3.76-4.11 (m, 1H), 6.63-6.89 (m, 3H), 7.21 (dd, J=7.34, 5.35 Hz, 1H), 8.12 (d, J=2.78 Hz, 1H), 8.25-8.41 (m, 2H), 8.46-8.69 (m, 1H), 12.16 (d, J=1.59 Hz, 1H).

Example 182

6-chloro-N-[4-(1-cyclobutylpiperidin-4-yl)cyclohexyl]-4-(1H-pyrrolo[2,3-b]pyridin-3-yl)pyridin-2-amine The trifluoroacetic acid salt of the title compound was prepared according to the procedure for Example 58, substituting Example 159c for Example 23 and substituting cyclobutanone for isobutyraldehyde. Yield: 20 mg (32%). MS (DCI/NH$_3$) m/z 465 (M+H)$^+$, $^1$H NMR (300 MHz, DMSO-d$_6$): 1.02-1.62 (m, 4H), 1.59-2.02 (m, 5H), 1.95-2.31 (m, 6H), 2.33-2.51 (m, 1H), 2.58-2.83 (m, 2H), 3.23-3.47 (m, 2H), 3.60 (s, 1H), 3.83-4.14 (m, 2H), 4.26-4.92 (m, 2H), 6.75-6.93 (m, 2H), 6.98 (s, 1H), 7.08-7.30 (m, 1H), 8.12 (t, J=3.56 Hz, 1H), 8.20-8.51 (m, 2H), 9.11 (s, 1H), 12.16 (s, 1H).

Example 183

6-chloro-N-{4-[1-(methylsulfonyl)piperidin-4-yl]cyclohexyl}-4-(1H-pyrrolo[2,3-b]pyridin-3-yl)pyridin-2-amine The trifluoroacetic acid salt of the title compound was prepared according to the procedure for Example 76, substituting Example 159c for Example 23 and substituting methylsulfonyl chloride for cyclopropanesulfonyl chloride. Yield: 15 mg (31%). MS (DCI/NH$_3$) m/z 489 (M+H)$^+$, $^1$H NMR (300 MHz, METHANOL-d$_4$): 0.91-1.31 (m, 6H), 1.36-1.62 (m, J=39.67 Hz, 3H), 1.66-1.87 (m, 3H), 1.90-2.11 (m, 1H), 2.18-2.32 (m, 1H), 2.43 (d, J=1.70 Hz, 2H), 2.56-2.77 (m, 2H), 3.41-3.50 (m, 2H), 3.98 (d, J=10.17 Hz, 2H), 6.73-6.94 (m, 2H), 6.99 (s, 1H), 7.12-7.38 (m, 1H), 8.12 (t, J=3.05 Hz, 1H), 8.19-8.50 (m, 2H), 12.14 (s, 1H).

Example 184

6-chloro-N-[4-(1-methylpiperidin-4-yl)cyclohexyl]-4-(1H-pyrrolo[2,3-b]pyridin-3-yl)pyridin-2-amine The trifluoroacetic acid salt of the title compound was prepared according to the procedure for Example 58, substituting Example 159c for Example 23 and substituting formaldehyde for isobutyraldehyde. Yield: 12 mg (12%). MS (DCI/NH$_3$) m/z 424 (M+H)$^+$, $^1$H NMR (300 MHz, DMSO-d$_6$): 0.90-1.29 (m, 2H), 1.26-1.46 (m, 3H), 1.45-1.66 (m, 2H), 1.69-1.84 (m, 2H), 1.83-2.00 (m, 2H), 2.75 (d, J=4.41 Hz, 3H), 2.79-3.01 (m, 2H), 3.37-3.52 (m, 2H), 3.96 (s, 2H), 4.21-4.58 (m, 2H), 6.66-6.93 (m, 2H), 6.98 (s, 1H), 7.15-7.35 (m, 1H), 8.12 (t, J=3.39 Hz, 1H), 8.24-8.52 (m, 2H), 12.16 (s, 1H).

Example 185

6-chloro-N-methyl-N-[4-(1-methylpiperidin-4-yl)cyclohexyl]-4-(1H-pyrrolo[2,3-b]pyridin-3-yl)pyridin-2-amine The trifluoroacetic acid salt of the title compound was prepared according to the procedure for Example 58, substituting Example 159c for Example 23 and substituting formaldehyde for isobutyraldehyde. Yield: 9 mg (8%). MS (DCI/NH$_3$) m/z 439 (M+H)$^+$, $^1$H NMR (300 MHz, DMSO-d$_6$): 1.33 (d, J=56.29 Hz, 3H), 1.47-1.75 (m, J=3.05 Hz, 3H), 1.79 (d, J=24.41 Hz, 5H), 1.97-2.09 (m, 1H), 2.69-2.79 (m, 2H), 2.91 (s, 3H), 2.94 (s, 3H), 3.44 (s, 1H), 3.86-4.02 (m, 2H), 4.37 (s, 2H), 6.78 (d, J=3.05 Hz, 1H), 6.93 (s, 1H), 7.14-7.34 (m, 1H), 8.18 (t, J=2.54 Hz, 1H), 8.27-8.41 (m, 2H), 12.19 (s, 1H).

Example 186

6-chloro-N-{4-[1-(methylsulfonyl)piperidin-3-yl]cyclohexyl}-4-(1H-pyrrolo[2,3-b]pyridin-3-yl)pyridin-2-amine The trifluoroacetic acid salt of the title compound was prepared according to the procedure for Example 76, substituting Example 181c for Example 23 and substituting methylsulfonyl chloride for cyclopropanesulfonyl chloride. Yield: 18 mg (39%). MS (DCI/NH$_3$) m/z 489 (M+H)$^+$, $^1$H NMR (300 MHz, DMSO-d$_6$): 1.01-1.32 (m, 4H), 1.36-1.65 (m, 6H), 1.64-1.89 (m, 4H), 1.90-2.12 (m, 1H), 2.39-2.49 (m, 1H), 2.56-2.74 (m, 1H), 2.84 (s, 3H), 3.37-3.65 (m, 2H), 6.76-6.90 (m, 2H), 6.98 (s, 1H), 7.23 (dd, J=7.97, 4.58 Hz, 1H), 8.12 (t, J=2.71 Hz, 1H), 8.28-8.34 (m, 1H), 8.36 (d, J=8.14 Hz, 1H), 12.16 (s, 1H).

Example 187

6-chloro-N-cyclohexyl-4-(5-{1-[2-(morpholin-4-yl)ethyl]-1H-pyrazol-4-yl}-1H-pyrrolo[2,3-b]pyridin-3-yl)pyridin-2-amine Example 187a 6-chloro-N-cyclohexyl-4-(5-(1-(2-morpholinoethyl)-1H-pyrazol-4-yl)-1-(phenylsulfonyl)-1H-pyrrolo[2,3-b]pyridin-3-yl)pyridin-2-amine Example 187a (0.055 g) was prepared as described in Example 171b, substituting 1-(phenylsulfonyl)-4-(4,4,5,5-tetramethyl-1,3,2-dioxaborolan-2-yl)-1H-pyrazole with 4-(2-(4-(4,4,5,5-tetramethyl-1,3,2-dioxaborolan-2-yl)-1H-pyrazol-1-yl)ethyl)morpholine. MS (APCI$^+$) m/z 646.6 (M+H)$^+$.

Example 187b 6-chloro-N-cyclohexyl-4-(5-(1-(2-morpholinoethyl)-1H-pyrazol-4-yl)-1H-pyrrolo[2,3-b]pyridin-3-yl)pyridin-2-amine Example 187b (0.020 g) was prepared as described in Example 171c, substituting Example 171b with Example 187a. $^1$H NMR (300 MHz, DMSO-d$_6$) ppm 1.13-1.44 (m, 5H) 1.54-1.66 (m, 1H) 1.67-1.80 (m, 2H) 1.89-2.01 (m, 2H) 2.40-2.47 (m, 4H) 2.76 (t, J=6.74 Hz, 2H) 3.51-3.60 (m, 4H) 3.62-3.76 (m, 1H) 4.27 (t, J=6.74 Hz, 2H) 6.72 (d, J=7.93 Hz, 1H) 6.85-6.91 (m, 2H) 7.97 (s, 1H) 8.10 (s, 1H) 8.25 (s, 1H) 8.35 (s, 1H) 8.53 (s, 1H) 12.13 (s, 1H). MS (ESI$^+$) m/z 506.7 (M+H)$^+$.

Example 188

[3-(4-{[6-chloro-4-(1H-pyrrolo[2,3-b]pyridin-3-yl)pyridin-2-yl]amino}cyclohexyl)piperidin-1-yl](cyclopropyl)methanone The trifluoroacetic acid salt of the title compound was prepared according to the procedure for Example 69, substituting Example 181c for Example 23. Yield: 28 mg (60%). MS (DCI/NH$_3$) m/z 479 (M+H)$^+$, $^1$H NMR (300 MHz, DMSO-d$_6$): 0.55-0.80 (m, 4H), 1.00-1.39 (m, 6H), 1.38-1.67 (m, 6H), 1.66-2.11 (m, 3H), 2.19-2.47 (m, 1H), 2.52-2.75 (m, 1H), 2.81-3.10 (m, 2H), 4.10-4.50 (m, 1H), 6.81-6.89 (m, 2H), 6.98 (s, 1H), 7.14-7.27 (m, 1H), 8.13 (t, J=2.38 Hz, 1H), 8.28-8.33 (m, 1H), 8.37 (d, J=8.33 Hz, 1H), 12.18 (s, 1H).

Example 189

6-chloro-N-[4-(1-cyclobutylpiperidin-3-yl)cyclohexyl]-4-(1H-pyrrolo[2,3-b]pyridin-3-yl)pyridin-2-amine The trifluoroacetic acid salt of the title compound was prepared according to the procedure for Example 58, substituting Example 181c for Example 23 and substituting cyclobutanone for isobutyraldehyde. Yield: 32 mg (71%). MS (DCI/NH$_3$) m/z 465 (M+H)$^+$, $^1$H NMR (300 MHz, DMSO-d$_6$): 1.05-1.35 (m, 4H), 1.37-1.66 (m, 6H), 1.64-1.93 (m, 6H), 1.94-2.09 (m, 1H), 2.09-2.36 (m, 5H), 2.52-2.81 (m, 1H), 3.19-3.40 (m, 1H), 3.55-3.70 (m, 1H), 3.91-4.09 (m, 1H), 6.74-6.93 (m, 2H), 6.97 (s, 1H), 7.11-7.26 (m, 1H), 8.07-8.15 (m, 1H), 8.27-8.38 (m, 2H), 12.16 (s, 1H).

Example 190

6-chloro-N-[4-(pyrrolidin-3-yl)cyclohexyl]-4-(1H-pyrrolo[2,3-b]pyridin-3-yl)pyridin-2-amine Example 190a tert-butyl 3-(4-(6-chloro-4-iodopyridin-2-ylamino)cyclohexyl)pyrrolidine-1-carboxylate The title compound was prepared according to the procedure for Example 94a substituting tert-butyl 3-(4-aminocyclohexyl)pyrrolidine-1-carboxylate for benzyl 3-(aminomethyl)piperidine-1-carboxylate. Yield: 430 mg (31%). MS (DCI/NH$_3$) m/z 506 (M+H)$^+$.

Example 190b tert-butyl 3-(4-(6-chloro-4-(1-(phenylsulfonyl)-1H-pyrrolo[2,3-b]pyridin-3-yl)pyridin-2-ylamino)cyclohexyl)pyrrolidine-1-carboxylate The title compound was prepared according to the procedure for Example 94b, substituting Example 190a for Example 94a. Yield: 330 mg (58%). MS (DCI/NH$_3$) m/z 636 (M+H)$^+$.

Example 190c 6-chloro-N-(4-(pyrrolidin-3-yl)cyclohexyl)-4-(1H-pyrrolo[2,3-b]pyridin-3-yl)pyridin-2-amine The trifluoroacetic acid salt of the title compound was prepared according to the procedure for Example 94c, substituting Example 190b for Example 94b. Yield: 180 mg (77%). MS (DCI/NH$_3$) m/z 396 (M+H)$^+$. $^1$H NMR (300 MHz, DMSO-d$_6$): 1.07-1.68 (m, 6H), 1.66-1.87 (m, 1H), 1.90-2.18 (m, 2H), 2.60-2.84 (m, 1H), 3.00-3.19 (m, 1H), 3.17-3.46 (m, 2H), 3.84-4.11 (m, 4H), 6.71-6.91 (m, 2H), 6.97 (s, 1H), 7.22 (dd, J=7.97, 4.58 Hz, 1H), 8.13 (d, J=2.71 Hz, 1H), 8.22-8.42 (m, 2H), 8.61 (s, 1H), 12.16 (s, 1H).

Example 191

N-[6-chloro-4-(1H-pyrrolo[2,3-b]pyridin-3-yl)pyridin-2-yl]-1'-methyl-1,4'-bipiperidin-4-amine Example 191a tert-butyl 4-(6-chloro-4-iodopyridin-2-ylamino)piperidine-1-carboxylate The title compound was prepared according to the procedure for Example 94a, substituting tert-butyl-4-aminopiperidine-1-carboxylate for benzyl 3-(aminomethyl)piperidine-1-carboxylate. Yield: 230 mg (72%). MS (DCI/NH$_3$) m/z 438 (M+H)$^+$.

Example 191b tert-butyl 4-(6-chloro-4-(1-(phenylsulfonyl)-1H-pyrrolo[2,3-b]pyridin-3-yl)pyridin-2-ylamino)piperidine-1-carboxylate The title compound was prepared according to the procedure for Example 94b, substituting Example 190a for Example 94a. Yield: 280 mg (100%). MS (DCI/NH$_3$) m/z 569 (M+H)$^+$.

Example 191c 6-chloro-N-(piperidin-4-yl)-4-(1H-pyrrolo[2,3-b]pyridin-3-yl)pyridin-2-amine The trifluoroacetic acid salt of the title compound was prepared according to the procedure for Example 94c, substituting Example 191b for Example 94b. Yield: 200 mg (61%). MS (DCI/NH$_3$) m/z 328 (M+H)$^+$.

Example 191d

N-(6-chloro-4-(1H-pyrrolo[2,3-b]pyridin-3-yl)pyridin-2-yl)-1'-methyl-1,4'-bipiperidin-4-amine The trifluoroacetic acid salt of the title compound was prepared according to the procedure for Example 58, substituting Example 191c for Example 23 and substituting 1-methylpiperidin-4-one for isobutyraldehyde. Yield: 34 mg (75%). MS (DCI/NH$_3$) m/z 420 (M+H)$^+$, $^1$H NMR (300 MHz, DMSO-d$_6$): 1.49-1.78 (m, 2H), 1.79-1.99 (m, J=15.26 Hz, 2H), 1.99-2.15 (m, 1H), 2.15-2.41 (m, 3H), 2.79 (s, 3H), 3.01-3.12 (m, J=7.12 Hz, 2H), 3.04-3.37 (m, 2H), 3.29-3.47 (m, 2H), 3.35-3.70 (m, 3H), 3.83-4.22 (m, 1H), 6.93 (d, J=16.28 Hz, 2H), 7.05 (d, 1H), 7.17-7.34 (m, 1H), 8.15 (d, J=2.71 Hz, 1H), 8.32 (d, J=6.10 Hz, 2H), 12.20 (s, 1H).

Example 192

4-(4-{[6-chloro-4-(1H-pyrrolo[2,3-b]pyridin-3-yl)pyridin-2-yl]amino}cyclohexyl)piperazin-2-one

Example 192a 4-(6-chloro-4-iodopyridin-2-ylamino)-1,3'-bipiperidin-6'-one

The title compound was prepared according to the procedure for Example 94a, substituting 4-(4-aminocyclohexyl)piperazin-2-one for benzyl 3-(aminomethyl)piperidine-1-carboxylate. Yield: 100 mg (64%). MS (DCI/NH$_3$) m/z 435 (M+H)$^+$.

Example 192b 4-(6-chloro-4-(1-(phenylsulfonyl)-1H-indol-3-yl)pyridin-2-ylamino)-1,3'-bipiperidin-6'-one The title compound was prepared according to the procedure for Example 94b, substituting Example 192a for Example 94a. Yield: 80 mg (70%). MS (DCI/NH$_3$) m/z 569 (M+H)$^+$.

Example 192c 4-(6-chloro-4-(1H-indol-3-yl)pyridin-2-ylamino)-1,3'-bipiperidin-6'-one The trifluoroacetic acid salt of the title compound was prepared according to the procedure for Example 94b, substituting Example 192b for Example 94a. Yield: 50 mg (50%). MS (DCI/NH$_3$) m/z 435 (M+H)$^+$, $^1$H NMR (300 MHz, DMSO-d$_6$): 1.50-1.72 (m, 2H), 1.73-1.95 (m, 4H), 1.94-2.13 (m, 2H), 3.29-3.54 (m, 4H), 3.54-3.77 (m, 2H), 3.88-4.16 (m, 2H), 6.70-7.02 (m, 3H), 7.23 (dd, J=7.93, 4.76 Hz, 1H), 8.15 (d, J=2.78 Hz, 1H), 8.25-8.39 (m, 2H), 8.47 (s, 1H), 12.19 (s, 1H).

Example 193

N-{2-[(trans-4-{[6-chloro-4-(1H-pyrrolo[2,3-b]pyridin-3-yl)pyridin-2-yl]amino}cyclohexyl)sulfamoyl]ethyl}benzamide Example 193 (0.045 g) was prepared as described in Example 21, substituting Example 15 with Example 179b and methanesulfonyl chloride with benzoyl chloride. $^1$H NMR (300 MHz, DMSO-d$_6$) ppm 1.33 (d, 5H) 1.97 (d, 4H) 3.02-3.26 (m, 2H) 3.61 (d, 3H) 6.77 (d, J=7.54 Hz, 1H) 6.82-6.91 (m, 2H) 7.12-7.33 (m, 2H) 7.37-7.60 (m, 3H) 7.77-7.89 (m, 2H) 8.12 (d, J=1.98 Hz, 1H) 8.24-8.37 (m, 2H) 8.60 (t, J=5.75 Hz, 1H) 12.14 (s, 1H). MS (ESI$^+$) m/z 553.5 (M+H)$^+$

Example 194

N-(trans-4-{[6-chloro-4-(1H-pyrrolo[2,3-b]pyridin-3-yl)pyridin-2-yl]amino}cyclohexyl)-2-[(methylsulfonyl)amino]ethanesulfonamide Example 194 (0.025 g) was prepared as described in Example 21, substituting Example 15 with Example 179b. $^1$H NMR (300 MHz, DMSO-d$_6$) ppm 1.11-1.52 (m, 5H) 1.81-2.14 (m, 5H) 2.89-3.02 (m, 3H) 3.10-3.29 (m, 3H) 3.51-3.67 (m, 1H) 6.77 (d, J=7.80 Hz, 1H) 6.81-6.91 (m, 2H) 7.20 (dd, J=7.80, 4.75 Hz, 3H) 8.12 (s, 1H) 8.25-8.36 (m, 2H) 12.13 (s, 1H). MS (ESI$^+$) m/z 527.7 (M+H)$^+$.

Example 195

6-chloro-N-cyclohexyl-4-{5-[2-(morpholin-4-yl)ethoxy]-1H-pyrrolo[2,3-b]pyridin-3-yl}pyridin-2-amine A mixture of Example 180a (95.0 mg, 0.197 mmol), triphenylphosphine (PPh$_3$) on solid support (3 mmol/g, 98.3 mg, 0.375 mmol), di-tert-butyl azodicarboxylate (DBAD, 67.9 mg, 0.295 mmol), and 2-morpholinoethanol (0.036 mL, 0.295 mmol) in THF (2.5 mL) was stirred at room temperature overnight. Another 1.5 eq. each of DBAD, Ph$_3$P on solid support, and 2-morpholinoethanol were added. After 4 hours, the reaction mixture was filtered through celite. The filtrate was concentrated and purified on a 12 g column using the ISCO Companion flash system eluting with CH$_2$Cl$_2$/EtOAc (8:2 to 6:4) to give 75.1 mg of the intermediate. A solution of this intermediate in dioxane (2 mL) was treated with 20% NaOH (0.2 mL). The mixture was heated at 70° C. for 2 hours. The reaction mixture was concentrated, triturated with water, filtered, washed with water, and oven-dried to 38.9 mg of the title compound. $^1$H NMR (400 MHz, CD$_3$OD) ppm 1.17-1.35 (m, 3H), 1.38-1.56 (m, 2H), 1.68 (m, 1H), 1.75-1.87 (m, 2H), 1.98-2.11 (m, 2H), 2.63 (s, brd, 4H), 2.86 (t, J=5.34 Hz, 2H), 3.63-3.80 (m, 5H), 4.27 (t, J=5.49 Hz, 2H), 6.70 (s, 1H), 6.78 (s, 1H), 7.80 (s, 1H), 7.85 (d, J=2.44 Hz, 1H), 8.05 (d, J=2.14 Hz, 1H). MS (DCI$^+$) m/z 456.3 (M+H)$^+$.

Example 196

6-chloro-N-cyclohexyl-4-{5-[(1-methyl-1H-imidazol-5-yl)methoxy]-1H-pyrrolo[2,3-b]pyridin-3-yl}pyridin-2-amine The title compound was prepared as described in Example 195, substituting 2-morpholinoethanol with (1-methyl-1H-imidazol-5-yl)methanol. The title compound was purified by reverse-phase HPLC as described in Example 56 as trifluoroacetic acid salts. $^1$H NMR (400 MHz, DMSO-d$_6$) ppm 1.13-1.28 (m, 3H), 1.29-1.43 (m, 2H), 1.60 (m, 1H), 1.68-1.80 (m, 2H), 1.88-2.02 (m, 2H), 3.68 (m, 1H), 3.94 (s, 3H), 5.40 (s, 2H), 6.81 (s, 1H), 6.86 (s, 1H), 7.84 (s, 1H), 7.98 (d, J=2.75 Hz, 1H), 8.15 (dd, J=19.23, 2.75 Hz, 2H), 9.14 (s, 1H), 12.12 (s, 1H). MS (DCI$^+$) m/z 437.2 (M+H)$^+$.

Example 197

6-chloro-N-[4-(1-methylpyrrolidin-3-yl)cyclohexyl]-4-(1H-pyrrolo[2,3-b]pyridin-3-yl)pyridin-2-amine The trifluoroacetic acid salt of the title compound was prepared according to the procedure for Example 58, substituting 190c for 23 and formaldehyde for isobutyraldehyde. Yield: 10 mg (20%). MS (DCI/NH$_3$) m/z 410 (M+H)$^+$, $^1$H NMR (300 MHz, DMSO-d$_6$): 1.04-1.27 (m, 1H), 1.25-1.50 (m, 2H), 1.48-1.64 (m, 3H), 1.65-1.88 (m, 3H), 1.90-2.33 (m, 3H), 2.85 (s, 3H), 2.93-3.12 (m, 1H), 3.11-3.37 (m, 1H), 3.44-3.74 (m, 2H), 3.84-4.08 (m, 1H), 6.81-6.87 (m, 1H), 6.89 (s, 1H), 6.98 (s, 1H), 7.22 (dd, J=7.97, 4.58 Hz, 1H), 8.13 (t, J=3.39 Hz, 1H), 8.20-8.50 (m, 2H), 12.17 (s, 1H).

Example 198

6-chloro-N-{4-[1-(4-fluorobenzyl)pyrrolidin-3-yl]cyclohexyl}-4-(1H-pyrrolo[2,3-b]pyridin-3-yl)pyridin-2-amine The trifluoroacetic acid salt of the title compound was prepared according to the procedure for Example 58, substituting Example 190c for Example 23 and substituting 4-fluorobenzaldehyde for isobutyraldehyde. Yield: 20 mg (25%). MS (DCI/NH$_3$) m/z 505 (M+H)$^+$, $^1$H NMR (300 MHz, DMSO-d$_6$): 1.02-1.32 (m, 1H), 1.27-1.49 (m, 2H), 1.42-1.65 (m, 4H), 1.64-1.90 (m, 3H), 1.86-2.42 (m, 1H), 2.61-2.98 (m, 1H), 3.00-3.26 (m, 1H), 3.24-3.56 (m, 2H), 3.78-4.15 (m, 2H), 4.33-4.54 (m, 2H), 6.81-6.90 (m, 2H), 6.97 (d, J=2.37 Hz, 1H), 7.18-7.25 (m, 1H), 7.32 (t, J=8.82 Hz, 2H), 7.58 (dd, J=8.14, 6.10 Hz, 2H), 8.13 (s, 1H), 8.22-8.46 (m, 2H), 12.16 (s, 1H).

Example 199

6-chloro-N-{4-[1-(methylsulfonyl)pyrrolidin-3-yl]cyclohexyl}-4-(1H-pyrrolo[2,3-b]pyridin-3-yl)pyridin-2-amine The trifluoroacetic acid salt of the title compound was prepared according to the procedure for Example 76, substituting Example 190c for Example 23 and substituting methylsulfonyl chloride for cyclopropanesulfonyl chloride. Yield: 22 mg (39%). MS (DCI/NH$_3$) m/z 475 (M+H)$^+$, $^1$H NMR (300 MHz, DMSO-d$_6$): 1.05-1.35 (m, 1H), 1.27-1.51 (m, 2H), 1.50-1.65 (m, J=9.12 Hz, 3H), 1.65-1.84 (m, 2H), 1.94-2.14 (m, 2H), 2.17-2.37 (m, 1H), 2.37-2.47 (m, J=1.98 Hz, 1H), 2.88 (s, 3H), 3.05-3.29 (m, 1H), 3.28-3.50 (m, 4H), 6.77-6.89 (m, 2H), 6.99 (s, 1H), 7.22 (dd, J=8.13, 4.56 Hz, 1H), 8.13 (d, J=2.78 Hz, 1H), 8.25-8.35 (m, 1H), 8.36 (d, J=7.93 Hz, 1H), 12.15 (s, 1H).

Example 200

6-chloro-N-{1-[4-(cyclobutylamino)cyclohexyl]piperidin-4-yl}-4-(1H-pyrrolo[2,3-b]pyridin-3-yl)pyridin-2-amine Example 200a tert-butyl 4-(4-(6-chloro-4-(1H-pyrrolo[2,3-b]pyridin-3-yl)pyridin-2-ylamino)piperidin-1-yl)cyclohexylcarbamate The trifluoroacetic acid salt of the title compound was prepared according to the procedure for Example 58, substituting Example 191c for Example 23 and substituting tert-butyl 4-oxocyclohexylcarbamate for isobutyraldehyde. Yield: 370 mg (87%). MS (DCI/NH$_3$) m/z 525 (M+H)$^+$.

Example 200b

N-(1-(4-aminocyclohexyl)piperidin-4-yl)-6-chloro-4-(1H-pyrrolo[2,3-b]pyridin-3-yl)pyridin-2-amine The trifluoroacetic acid salt of the title compound was prepared according to the procedure for Example 102b, substituting Example 200a for Example 102a. Yield: 190 mg (87%). MS (DCI/NH$_3$) m/z 425 (M+H)$^+$.

Example 200c 6-chloro-N-(1-(4-(cyclobutylamino)cyclohexyl)piperidin-4-yl)-4-(1H-pyrrolo[2,3-b]pyridin-3-yl)pyridin-2-amine The trifluoroacetic acid salt of the title compound was prepared according to the procedure for Example 58, substituting Example 200b for Example 23 and substituting cyclobutanone for isobutyraldehyde. Yield: 20 mg (44%). MS (DCI/NH$_3$) m/z 479 (M+H)$^+$, $^1$H NMR (300 MHz, DMSO-d$_6$): 1.46-1.96 (m, 4H), 1.92-2.15 (m, 2H), 2.16-2.35 (m, 6H), 2.35-2.49 (m, 2H), 3.17 (s, 6H), 3.32-3.43 (m, 4H), 3.73-3.92 (m, 2H), 3.92-4.12 (m, 1H), 6.73-7.08 (m, 2H), 7.22 (dd, J=7.46, 5.43 Hz, 1H), 8.15 (d, J=2.71 Hz, 1H), 8.30 (d, J=2.37 Hz, 2H), 8.64 (s, 2H), 12.19 (s, 1H).

Example 201

3-[2-chloro-6-(cyclohexylamino)pyridin-4-yl]-1-1H-pyrrolo[2,3-b]pyridine-5-carbonitrile Example 201a 3-iodo-1-(phenylsulfonyl)-1H-pyrrolo[2,3-b]pyridine-5-carbonitrile Example 201a was prepared as described in Example 168b, substituting 4-chloro-3-iodo-1H-pyrrolo[2,3-b]pyridine with 3-iodo1H-pyrrolo[2,3-b]pyridine-5-carbonitrile to give the title compound as a yellow powder in 85% yield. MS (ESI$^+$) m/z 409.79 (M+H)$^+$.

Example 201b

3-(2-chloro-6-(cyclohexylamino)pyridin-4-yl)-1-(phenyl sulfonyl)-1H-pyrrolo[2,3-b]pyridine-5-carbonitrile Example 201b was prepared as described for Example 168c, substituting Example 168b with Example 201a to give the title compound as a brown powder in 43% yield. MS (ESI$^+$) m/z 492.5 (M+H)$^+$

Example 201c

3-[2-chloro-6-(cyclohexylamino)pyridin-4-yl]-1-1H-pyrrolo[2,3-b]pyridine-5-carbonitrile Example 201c was prepared as described for Example 168d substituting Example 168c with Example 201b to give the title compound as a yellow powder in 39% yield. MS (ESI$^+$) m/z 352.7 (M+H)$^+$; $^1$H NMR (300 MHz, DMSO-d$_6$) ppm 1.13-1.44 (m, 5H) 1.54-1.65 (m, 1H) 1.68-1.78 (m, 2H) 1.88-1.98 (m, 2H) 3.64-3.77 (m, 1H) 6.70 (d, 1H, J=7.80 Hz) 6.89 (s, 1H) 6.91 (s, 1H) 8.35 (s, 1H) 8.68 (s, 1H) 8.78 (s, 1H) 12.68 (bs, 1H).

Example 202

N-(trans-4-{[6-chloro-4-(1H-pyrrolo[2,3-b]pyridin-3-yl)pyridin-2-yl]amino}cyclohexyl)-2,4-difluorobenzamide Example 202 (0.045 g) was prepared as described in Example 21, substituting methanesulfonyl chloride with 2,4-difluorobenzoyl chloride and substituting Example 15 with Example 61b. $^1$H NMR (300 MHz, DMSO-d$_6$) ppm 1.16-1.70 (m, 4H) 1.83-2.15 (m, 4H) 3.49-3.89 (m, 2H) 6.80 (d, J=7.54 Hz, 1H) 6.88 (s, 2H) 7.07-7.26 (m, 2H) 7.26-7.41 (m, 1H) 7.56-7.71 (m, 1H) 8.13 (d, J=2.78 Hz, 1H) 8.23 (d, J=7.54 Hz, 1H) 8.27-8.37 (m, 2H) 12.14 (s, 1H). MS (ESI$^+$) m/z 482.8 (M+H)$^+$.

Example 203

N-(trans-4-{[6-chloro-4-(1H-pyrrolo[2,3-b]pyridin-3-yl)pyridin-2-yl]-amino}cyclohexyl)-4-(trifluoromethoxy)benzamide Example 203 (0.065 g) was prepared as described in Example 21, substituting methanesulfonyl chloride with 4-(trifluoromethoxy)benzoyl chloride and substituting Example 15 with Example 61b. $^1$H NMR (300 MHz, DMSO-d$_6$) ppm 1.16-1.65 (m, 4H) 1.82-2.01 (m, 2H) 2.00-2.14 (m, 2H) 3.55-3.90 (m, 2H) 6.81 (d, J=7.54 Hz, 1H) 6.88 (s, 2H) 7.21 (dd, J=7.93, 4.76 Hz, 1H) 7.46 (d, J=7.93 Hz, 2H) 7.97 (d, J=8.73 Hz, 2H) 8.13 (d, J=2.78 Hz, 1H) 8.26-8.44 (m, 3H) 12.03-12.26 (m, J=1.59 Hz, 1H). MS (ESI$^+$) m/z 531.0 (M+H)$^+$.

Example 204

6-chloro-N-cyclohexyl-4-(5-methyl-1H-pyrrolo[2,3-b]pyridin-3-yl)pyridin-2-amine

Example 204a

3-iodo-5-methyl-1-(phenylsulfonyl)-1H-pyrrolo[2,3-b]pyridine

Example 204a was prepared as described for Example 168b substituting 4-chloro-3-iodo-1H-pyrrolo-[2,3-b]pyridine with 3-iodo-5-methyl-1H-pyrrolo-[2,3-b]pyridine to give the title compound as an off-white powder in 93% yield. MS (ESI$^+$) m/z 399.4 (M+H)$^+$.

Example 204b

6-chloro-N-cyclohexyl-4-(5-methyl-1-(phenylsulfonyl)-1H-pyrrolo[2,3-b]pyridin-3-yl)-pyridin-2-amine Example 204b was prepared as described for Example 168c substituting Example 168b with Example 204a to give the title compound as a dark yellow powder in 35% yield. MS (ESI$^+$) m/z 481.4 (M+H)$^+$.

Example 204c

6-chloro-N-cyclohexyl-4-(5-methyl-1H-pyrrolo[2,3-b]pyridin-3-yl)pyridin-2-amine Example 204c was prepared as described for Example 168d substituting Example 168c with Example 204b to give the title compound as an off-white powder in 57% yield. MS (ESI+) m/z 341.5 (M+H)$^+$; $^1$H NMR (300 MHz, DMSO-d$_6$) ppm 1.13-1.40 (m, 5H) 1.55-1.65 (m, 1H) 1.68-1.78 (m, 2H) 1.88-1.98 (m, 2H) 2.44 (s, 3H) 3.63-3.74 (m, 1H) 6.74 (d, 1H, J=7.80 Hz) 6.84 (s, 2H) 8.06 (s, 1H) 8.11 (s, 1H) 8.14 (d, 1H, J=1.70 Hz) 11.98 (bs, 1H).

Example 205

6-chloro-N-phenyl-4-(1H-pyrrolo[2,3-b]pyridin-3-yl)pyridin-2-amine

A 50 mL round bottom flask was charged with aniline (28 mg, 0.297 mmol), Example 7a (100 mg, 0.247 mmol), Pd$_2$(dba)$_3$ (12 mg, 0.012 mmol) and 1,3-bis(2,6-diisopropylphenyl)imidazolium chloride (11 mg, 0.025 mmol), and was purged with nitrogen. Anhydrous dioxane (7 mL) and potassium tert-butoxide (1 M solution in THF, 0.618 mL, 0.618 mmol) were added. This solution was purged with nitrogen again, and heated at 95° C. overnight. After cooling, the reaction mixture was concentrated, and the residue was separated by HPLC (Zorbax, C-18, 250×2.54 column, Mobile phase A: 0.1% TFA in H$_2$O; B: 0.1% TFA in CH$_3$CN; 0-100% gradient) to provide the title compound as trifluoroacetic acid salt. Yield: 39 mg (49%). MS (ESI$^+$) m/z 321 (M+H)$^+$; $^1$H NMR (400 MHz, DMSO-d$_6$): 6.95 (t, J=7.32 Hz, 1H), 7.22 (s, 1H), 7.25-7.36 (m, 4H), 7.67 (d, J=7.63 Hz, 2H), 8.26 (d, J=2.75 Hz, 1H), 8.35 (dd, J=4.73, 1.37 Hz, 1H), 8.41 (d, J=8.24 Hz, 1H), 9.36 (s, 1H), 12.31 (s, 1H).

Example 206

6-chloro-N-{2-methoxy-4-[4-(4-methylpiperazin-1-yl)piperidin-1-yl]phenyl}-4-(1H-pyrrolo[2,3-b]pyridin-3-yl)pyridin-2-amine

Example 206a 1-(1-(3-methoxy-4-nitrophenyl)piperidin-4-yl)-4-methylpiperazine To a solution of 1-methyl-4-(piperidin-4-yl)piperazine (4.2 g, 22.91 mmol) in anhydrous DMF (40 mL) was added 4-fluoro-2-methoxy-1-nitrobenzene (3.92 g, 22.91 mmol) and potassium carbonate (3.80 g, 27.5 mmol). This suspension was heated at 70° C. overnight. After cooling, the reaction mixture was concentrated, and the residue partitioned between ethyl acetate and brine. The aqueous phase was extracted with ethyl acetate. The combined organic phases were concentrated. The residue was separated by flash chromatography (0-15% 2% ammonium hydroxide MeOH solution in dichloromethane) to give 6.88 g of the title compound. Yield: 90%. MS (DCI) m/z 335 (M+H)$^+$; $^1$H NMR (300 MHz, CDCl$_3$): δ 1.58-1.68 (m, 2H), 1.93-1.99 (m, J=11.53 Hz, 2H), 2.29 (s, 3H), 2.44-2.51 (m, 4H), 2.62 (s, 4H), 2.92-3.02 (m, 2H), 3.90-3.98 (m, 7H), 6.31 (d, J=2.37 Hz, 1H), 6.42 (dd, J=9.32, 2.54 Hz, 1H), 7.99 (d, J=9.49 Hz, 1H).

Example 206b 2-methoxy-4-(4-(4-methylpiperazin-1-yl)piperidin-1-yl)aniline

To a solution of Example 206a (6.88 g, 20.57 mmol) in a mixture of methanol (180 mL) and dichloromethane (20 mL) was added Raney nickel (50% in water, 3 g). This suspension was purged with hydrogen and stirred under hydrogen of 40 psi at 50° C. for 6 hours. Solid material was removed, and the filtrate was concentrated to provide the title product. Yield: 100%. MS (DCI) m/z 305 (M+H)$^+$; $^1$H NMR (300 MHz, DMSO-d$_6$): δ 1.47-1.59 (m, 2H), 1.84 (d, J=11.87 Hz, 2H), 2.33 (s, 3H), 2.44-2.71 (m, 12H), 3.28-3.48 (m, J=12.21 Hz, 4H), 3.73 (s, 2H), 6.29 (dd, J=8.31, 2.54 Hz, 1H), 6.46-6.54 (m, 2H).

Example 206c 6-chloro-N-{2-methoxy-4-[4-(4-methylpiperazin-1-yl)piperidin-1-yl]phenyl}-4-(1H-pyrrolo[2,3-b]pyridin-3-yl)pyridin-2-amine The title compound was prepared according to the protocol for Example 205, substituting Example 206b for aniline. Yield: 18%. MS (DCI) m/z 532 (M+H)$^+$; $^1$H NMR (400 MHz, DMSO-d$_6$): 1.76-1.85 (m, 2H), 2.09-2.16 (m, 2H), 2.86 (s, 3H), 2.94-3.04 (m, 2H), 3.20-3.26 (m, 2H), 3.47-3.56 (m, 4H), 3.78-3.86 (m, 4H), 3.88-4.02 (m, 4H), 6.78 (d, J=8.85 Hz, 1H), 6.91 (s, 1H), 7.16 (s, 1H), 7.25 (dd, J=8.09, 4.73 Hz, 1H), 7.38 (s, 1H), 8.02 (d, J=8.54 Hz, 1H), 8.22 (d, J=2.44 Hz, 1H), 8.33 (dd, J=4.73, 1.37 Hz, 1H), 8.48 (d, J=7.02 Hz, 1H), 8.52-8.56 (m, 1H), 12.26 (s, 1H).

Example 207

1-(4-chlorobenzyl)-N-(trans-4-{[6-chloro-4-(1H-pyrrolo[2,3-b]pyridin-3-yl)pyridin-2-yl]amino}cyclohexyl)azetidine-3-carboxamide Example 207 (0.12 g) was prepared as described in Example 106a, substituting (S)-1-(tert-butoxycarbonyl)azetidine-2-carboxylic acid with 1-(4-chlorobenzyl)azetidine-3-carboxylic acid $^1$H NMR (300 MHz, DMSO-d$_6$) ppm 1.15-1.46 (m, 5H) 1.70-1.90 (m, 2H) 1.91-2.09 (m, 2H) 3.01-3.26 (m, 3H) 3.43-3.69 (m, 5H) 6.71-6.81 (m, 1H) 6.81-6.92 (m, 2H) 7.14-7.26 (m, 1H) 7.24-7.44 (m, 4H) 7.74 (d, J=7.54 Hz, 1H) 8.13 (t, J=3.37 Hz, 1H) 8.25-8.36 (m, 2H) 12.14 (s, 1H). MS (ESI$^+$) m/z 549.6 (M+H)$^+$.

Example 208

N-(trans-4-{[6-chloro-4-(1H-pyrrolo[2,3-b]pyridin-3-yl)pyridin-2-yl]amino}cyclohexyl-2-[(prop-2-en-1-ylcarbamoyl)amino}ethanesulfonamide Example 208 (0.02 g) was prepared as described in Example 21, substituting methanesulfonyl chloride with allyl isocyanate and Example 15 with Example 179b. $^1$H NMR (300 MHz, DMSO-d$_6$) ppm 1.07-1.50 (m, 4H) 1.84-2.09 (m, 4H) 3.04-3.20 (m, 3H) 3.33-3.45 (m, 2H) 3.52-3.68 (m, 3H) 4.91-5.20 (m, 2H) 5.68-5.92 (m, 1H) 5.96-6.09 (m, 1H) 6.17-6.32 (m, 1H) 6.70-6.82 (m, 1H) 6.86 (d, J=3.73 Hz, 2H) 7.07-7.26 (m, 2H) 8.12 (d, J=2.71 Hz, 1H) 8.24-8.37 (m, 2H) 12.13 (s, 1H). MS (ESI$^+$) m/z 532.2 (M+H)$^+$.

Example 209

N-(trans-4-{[6-chloro-4-(1H-pyrrolo[2,3-b]pyridin-3-yl)pyridin-2-yl]amino}cyclohexyl)-1-(pyridin-3-ylmethyl)azetidine-3-carboxamide Example 209 (0.07 g) was prepared as described in Example 93, substituting Example 61b with Example 160b and formaldehyde with nicotinaldehyde. The solvent was removed from the reaction and the residue diluted with ethyl acetate. The organics were washed with a saturated sodium bicarbonate solution, brine, dried over MgSO$_4$, filtered, and concentrated. The crude material was triturated with ethyl acetate, and the solid was filtered to give the title compound as the free base. $^1$H NMR (300 MHz, DMSO-d$_6$) ppm 1.10-1.47 (m, 4H) 1.71-1.89 (m, 2H) 1.88-2.10 (m, 2H) 3.05-3.21 (m, 2H) 3.46-3.71 (m, 4H) 6.77 (t, J=7.93 Hz, 1H) 6.86 (t, J=4.36 Hz, 2H) 7.12-7.26 (m, 1H) 7.33 (dd, J=8.33, 4.76 Hz, 1H) 7.59-7.81 (m, 3H) 8.05-8.19 (m, 2H) 8.24-8.36 (m, 3H) 8.39-8.50 (m, 2H) 12.15 (s, 1H). MS (ESI$^+$) m/z 516.4 (M+H)$^+$.

Example 210

N-(trans-4-{[6-chloro-4-(1H-pyrrolo[2,3-b]pyridin-3-yl)pyridin-2-yl]amino}cyclohexyl)-1-(2,4-difluorobenzyl)azetidine-3-carboxamide Example 210 (0.055 g) was prepared as described in Example 93, substituting formaldehyde with 2,4-difluorobenzaldehyde and Example 61b with Example 160b. The solvent was removed from the reaction and the residue diluted with ethyl acetate. The organics were washed with a saturated sodium bicarbonate solution, brine, dried over MgSO4, filtered, and concentrated. The crude material was triturated with ethyl acetate, and the solid was filtered to give the title compound as the free base. $^1$H NMR (300 MHz, DMSO-$d_6$) ppm 1.26 (d, 4H) 1.78 (d, 3H) 2.00 (d, 2H) 3.12 (d, 4H) 3.42-3.66 (m, 4H) 6.76 (d, J=7.46 Hz, 1H) 6.82-6.90 (m, 2H) 6.95-7.09 (m, 1H) 7.10-7.25 (m, 2H) 7.32-7.48 (m, 1H) 7.71 (d, J=8.14 Hz, 1H) 8.11 (d, J=2.71 Hz, 1H) 8.24-8.35 (m, 2H) 12.13 (s, 1H). MS (ESI$^+$) m/z 551.2 (M+H)$^+$.

Example 211

N-(trans-4-{[6-chloro-4-(1H-pyrrolo[2,3-b]pyridin-3-yl)pyridin-2-yl]amino}cyclohexyl)-1-[(1-methyl-1H-pyrazol-3-yl)methyl]azetidine-3-carboxamide Example 211 (0.025 g) was prepared as described in Example 93, substituting formaldehyde with 1-methyl-1H-pyrazole-3-carbaldehyde and Example 61b with Example 160b. The solvent was removed from the reaction and the residue diluted with ethyl acetate. The organics were washed with a saturated sodium bicarbonate solution, brine, dried over MgSO$_4$, filtered, and concentrated. The crude material was triturated with ethyl acetate, and the solid was filtered to give the title compound as the free base. $^1$H NMR (300 MHz, DMSO-$d_6$) ppm 1.16-1.40 (m, 4H) 1.73-1.91 (m, 2H) 1.92-2.09 (m, 2H) 3.15-3.26 (m, 2H) 3.37-3.49 (m, 2H) 3.46-3.70 (m, 4H) 3.67-3.76 (m, 1H) 3.73-3.87 (m, 3H) 6.05-6.26 (m, 1H) 6.77 (d, J=7.54 Hz, 1H) 6.86 (d, J=3.97 Hz, 2H) 7.20 (dd, J=7.73, 4.96 Hz, 1H) 7.62 (d, J=1.98 Hz, 1H) 7.82 (d, J=7.54 Hz, 1H) 8.12 (d, J=2.78 Hz, 1H) 8.25-8.38 (m, 2H) 12.15 (s, 1H). MS (ESI$^+$) m/z 519.3 (M+H)$^+$.

Example 212

2-(4-{3-[2-chloro-6-(cyclohexylamino)pyridin-4-yl]-1H-pyrrolo[2,3-b]pyridin-5-yl}-1H-pyrazol-1-yl)ethanol Example 212a 2-(4-(4,4,5,5-tetramethyl-1,3,2-dioxaborolan-2-yl)-1H-pyrazol-1-yl)ethanol 4-(4,4,5,5-tetramethyl-1,3,2-dioxaborolan-2-yl)-1H-pyrazole (9.66 g, 49.8 mmol), 1,3-dioxolan-2-one (21 g, 238 mmol) and cesium carbonate (16 g, 49.1 mmol) were combined in a 100 mL round bottom flask. The reaction mixture was warmed from room temperature to 100° C. in an oil bath, by which time the carbonate had melted and served as the solvent for the reaction, which remained a slurry. After heating for 3.5 hours, the reaction mixture was cooled to room temperature and diluted with ethyl acetate, then filtered through Celite washing repeatedly with ethyl acetate. The filtrate was concentrated, then purified by chromatography on an Analogix(R) Intelliflash™ purification system using a SF60-200 g column at a flow rate of 80 mL/minutes, eluting as follows: 5 minutes at 20% ethyl acetate/hexanes, then ramped from 40% to 90% ethyl acetate/hexanes over 35 minutes, then 100% ethyl acetate for another 20 minutes, to provide the title compound. MS (ESI$^+$) m/z 239.0 (M+H)$^+$.

Example 212b 2-(4-(3-(2-chloro-6-(cyclohexylamino)pyridin-4-yl)-1-(phenylsulfonyl)-1H-pyrrolo[2,3-b]pyridin-5-yl)-1H-pyrazol-1-yl)ethanol Example 212b (0.16 g) was prepared as described in Example 171b, substituting 1-(phenylsulfonyl)-4-(4,4,5,5-tetramethyl-1,3,2-dioxaborolan-2-yl)-1H-pyrazole with Example 212a. MS (ESI$^+$) m/z 577.2 (M+H)$^+$.

Example 212c 2-(4-(3-(2-chloro-6-(cyclohexylamino)pyridin-4-yl)-1H-pyrrolo[2,3-b]pyridin-5-yl)-1H-pyrazol-1-yl)ethanol Example 212c (0.061 g) was prepared as described in Example 171c, substituting Example 171b with Example 212b. $^1$H NMR (300 MHz, DMSO-$d_6$) ppm 1.11-1.45 (m, 5H) 1.56-1.66 (m, 1H) 1.68-1.80 (m, 2H) 1.89-2.02 (m, 2H) 3.64-3.75 (m, 1H) 3.79 (dd, J=11.10, 5.55 Hz, 2H) 4.19 (t, J=5.55 Hz, 2H) 4.94 (t, J=5.55 Hz, 1H) 6.73 (d, J=7.93 Hz, 1H) 6.86-6.91 (m, 2H) 7.98 (s, 1H) 8.10 (s, 1H) 8.21 (s, 1H) 8.35 (s, 1H) 8.54 (s, 1H) 12.12 (s, 1H). MS (ESI$^+$) m/z 437.3 (M+H)$^+$.

Example 213 trans-N-[6-chloro-4-(5-methoxy-1H-pyrrolo[2,3-b]pyridin-3-yl)pyridin-2-yl]cyclohexane-1,4-diamine Example 213a (trans)-N$^1$-(6-chloro-4-iodopyridin-2-yl)cyclohexane-1,4-diamine A mixture of trans-cyclohexane-1,4-diamine (2.085 g, 18.26 mmol) and 2,6-dichloro-4-iodopyridine (1.000 g, 3.65 mmol) was heated in a capped vial at 120° C. After 5 hours, the reaction mixture was cooled. The solids were stirred in EtOAc for 30 minutes, and the suspension was filtered. The filtrate was diluted with EtOAc and washed with 20% brine and NaHCO$_3$. The organic layer was dried and concentrated to give 1.20 g of the title compound. The crude product was used in the next step without further purification.

Example 213b tert-butyl(trans)-4-(6-chloro-4-iodopyridin-2-ylamino)cyclohexylcarbamate To a mixture of Example 213a (7.00 g, 19.91 mmol) and triethylamine (3.61 mL, 25.9 mmol) in tetrahydrofuran (150 mL) was added BOC$_2$O (5.08 mL, 21.90 mmol) at 0° C. The ice bath was removed and the reaction mixture was stirred at room temperature for 90 minutes. The reaction mixture was diluted with EtOAc and washed with brine and saturated sodium bicarbonate. The organic layer was dried over MgSO$_4$, filtered, concentrated, and purified on a 150 g column using the ISCO Companion flash system eluting with hexane/EtOAc (8:2 to 6:4) to give 5.42 g of the title compound.

Example 213c tert-butyl(trans)-4-(6-chloro-4-(4,4,5,5-tetramethyl-1,3,2-dioxaborolan-2-yl)pyridin-2-ylamino)cyclohexylcarbamate A mixture of Example 213b (1.06 g, 2.347 mmol)), bis(pinacolato)diboron (0.894 g, 3.52 mmol), potassium acetate (0.345 g, 3.52 mmol), and PdCl$_2$(dppf)-CH$_2$Cl$_2$ adduct (0.077 g, 0.094 mmol) in DMF (25. mL) was degassed and heated at 80° C. for 4.5 hours. The reaction mixture was quenched with water, extracted with EtOAc, and washed with brine. The organic layer was concentrated. The residue was purified on 80 g column, using Analogix System, eluted with 20% EtOAc in hexane to give 0.59 g (56%) of the title compound.

Example 213d tert-butyl(trans)-4-(6-chloro-4-(5-methoxy-1-(phenylsulfonyl)-1H-pyrrolo[2,3-b]pyridin-3-yl)pyridin-2-ylamino)cyclohexylcarbamate A mixture of Example 213c (2.6 g, 5.75 mmol), Example 149b (2.219 g, 6.04 mmol), saturated sodium bicarbonate (19 mL, 466 mmol), and $PdCl_2(dppf)\text{-}CH_2Cl_2$ (0.329 g, 0.403 mmol) in DMF (76 mL)/water (19.00 mL) was degassed and heated at 65° C. for 3 hours. After cooling, the reaction was quenched with 20% brine and extracted with EtOAc (2×). The combined organic layers were washed with 20% brine, concentrated and purified on 220 g column using the Analogix System, eluted with hexane/EtOAc=65:35 to 50:50 to give 2.29 g (65%) of the title compound.

Example 213e tert-butyl(trans)-4-(6-chloro-4-(5-methoxy-1H-pyrrolo[2,3-b]pyridin-3-yl)pyridin-2-ylamino)cyclohexylcarbamate A solution of Example 213d (0.500 g, 0.817 mmol) in dioxane (3.0 mL) was treated with 20% NaOH. The reaction mixture was heated at 100° C. for an hour. The solvent was evaporated and the residue was treated with water, sonicated, filtered, washed with water again, and oven-dried to give 0.289 g (75%) of the title compound.

Example 213f trans-N-[6-chloro-4-(5-methoxy-1H-pyrrolo[2,3-b]pyridin-3-yl)pyridin-2-yl]cyclohexane-1,4-diamine Example 213e (0.280 g, 0.593 mmol) was dissolved in dichloromethane (4.0 mL) and trifluoroacetic acid (1.3 mL, 16.87 mmol) was added. The reaction mixture was left at the room temperature for 30 minutes. The reaction mixture was concentrated and the residue was dissolved in 1:1 DMSO and MeOH. The crude was purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 minutes at a flow rate of 15 mL/minutes to give 45.6 mg of the title compound as trifluoroacetic acid salts. $^1$H NMR (300 MHz, DMSO-$d_6$) ppm 1.21-1.50 (m, 4H), 1.96-2.09 (m, 4H), 3.90 (s, 3H), 6.82 (s, 1H), 6.88-6.89 (m, 1H), 7.76-7.79 (m, 4H), 8.08-8.10 (m, 2H), 12.05 (d, J=2.38 Hz, 1H). MS (DCI$^+$) m/z 372.2 (M+H)$^+$.

Example 214

6-chloro-N-cyclohexyl-4-[5-(pyridin-3-yl)-1H-pyrrolo[2,3-b]pyridin-3-yl]pyridin-2-amine

Example 214a 6-chloro-N-cyclohexyl-4-(1-(phenylsulfonyl)-5-(pyridin-3-yl)-1H-pyrrolo[2,3-b]pyridin-3-yl)pyridin-2-amine Example 214a (0.050 g) was prepared as described in Example 171b, substituting 1-(phenylsulfonyl)-4-(4,4,5,5-tetramethyl-1,3,2-dioxaborolan-2-yl)-1H-pyrazole with pyridin-3-ylboronic acid. MS (APCI$^+$) m/z 544.5 (M+H)$^+$.

Example 214b 6-chloro-N-cyclohexyl-4-(5-(pyridin-3-yl)-1H-pyrrolo[2,3-b]pyridin-3-yl)pyridin-2-amine Example 214b (0.023 g) was prepared as described in Example 171c, substituting Example 171b with Example 214a. $^1$H NMR (300 MHz, DMSO-$d_6$) ppm 1.10-1.43 (m, 5H) 1.55-1.66 (m, 1H) 1.67-1.79 (m, 2H) 1.88-2.01 (m, 2H) 3.63-3.77 (m, 1H) 6.75 (d, J=7.93 Hz, 1H) 6.93 (d, J=5.16 Hz, 2H) 7.51-7.58 (m, 1H) 8.16-8.23 (m, 2H) 8.52 (s, 1H) 8.59-8.65 (m, 2H) 9.01 (s, 1H) 12.31 (s, 1H). MS (ESI$^+$) m/z 404.2 (M+H)$^+$.

Example 215

6-chloro-N-cyclohexyl-4-[5-(thiophen-3-yl)-1H-pyrrolo[2,3-b]pyridin-3-yl]pyridin-2-amine

Example 215a 6-chloro-N-cyclohexyl-4-(1-(phenylsulfonyl)-5-(thiophen-3-yl)-1H-pyrrolo[2,3-b]pyridin-3-yl)pyridin-2-amine Example 215a (0.070 g) was prepared as described in Example 171b, substituting 1-(phenylsulfonyl)-4-(4,4,5,5-tetramethyl-1,3,2-dioxaborolan-2-yl)-1H-pyrazole with thiophen-3-ylboronic acid. MS (APCI$^+$) m/z 544.5 (M+H)$^+$.

Example 215b 6-chloro-N-cyclohexyl-4-[5-(thiophen-3-yl)-1H-pyrrolo[2,3-b]pyridin-3-yl]pyridin-2-amine Example 215b (0.049 g) was prepared as described in Example 171c, substituting Example 171b with Example 215a. $^1$H NMR (300 MHz, DMSO-$d_6$) ppm 1.12-1.44 (m, 5H) 1.55-1.66 (m, 1H) 1.67-1.80 (m, 2H) 1.90-2.01 (m, 2H) 3.63-3.78 (m, 1H) 6.75 (d, J=7.93 Hz, 1H) 6.91 (d, J=7.14 Hz, 2H) 7.66-7.69 (m, 1H) 7.70-7.75 (m, 1H) 7.94 (s, 1H) 8.15 (s, 1H) 8.49 (s, 1H) 8.67 (s, 1H) 12.21 (s, 1H). MS (ESI$^+$) m/z 409.2 (M+H)$^+$.

Example 216

N-(trans-4-{[6-chloro-4-(5-methoxy-1H-pyrrolo[2,3-b]pyridin-3-yl)pyridin-2-yl]amino}cyclohexyl)cyclopropanecarboxamide A mixture of Example 213f (0.90 g, 0.150 mmol), triethylamine (0.105 mL, 0.750 mmol), HOBT (0.046 g, 0.300 mmol), EDC (0.058 g, 0.300 mmol) and cyclopropanecarboxylic acid (0.014 mL, 0.180 mmol) was stirred at room temperature for 5 hours. The reaction mixture was concentrated and dissolved in 1:1 DMSO and MeOH. The crude material was purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 minutes at a flow rate of 15 mL/minutes to give 9.4 mg (11%) of the title compound as trifluoroacetic salts. $^1$H NMR (400 MHz, DMSO-$d_6$) ppm 0.61-0.66 (m, 4H), 1.27-1.30 (m, 4H), 1.83-1.86 (m, 2H), 2.0-2.3 (m, 2H), 3.90 (s, 3H), 6.81 (s, 1H), 6.86-6.87 (m, 1H), 7.79 (d, J=2.75 Hz, 1H0, 7.96-7.98 (m, 1H), 8.08 (dd, J=6.1, 2.75 Hz, 2H), 12.03 (d, J=2.14 Hz, 1H). MS (DCI$^+$) m/z 440.2 (M+H)$^+$.

Example 217

1-benzyl-N-(trans-4-{[6-chloro-4-(5-methoxy-1H-pyrrolo[2,3-b]pyridin-3-yl)pyridin-2-yl]amino}cyclohexyl)azetidine-3-carboxamide The trifluoroacetic acid salt of Example 217 (0.90 g, 0.150 mmol) was prepared as described in Example 216, substituting cyclopropanecarboxylic acid with 1-benzylazetidine-3-carboxylic acid. $^1$H NMR (400 MHz, DMSO-d$_6$) ppm 1.28-1.32 (m, 4H), 1.84-1.86 (m, 2H), 2.03-2.05 (m, 2H), 3.9 (s, 3H), 4.04-4.18 (m, 4H), 4.36-4.39 (m, 2H), 6.82 (s, 1 h), 6.87 (s, 1H), 7.46 (d, J=1.83 Hz, 4H), 7.79 (s, 1H), 8.08-8.12 (m, 2H), 10.25 (s, 1H), 12.04 (s, 1H). MS (DCI$^+$) m/z 545.4 (M+H)$^+$.

Example 218

N-(trans-4-{[6-chloro-4-(5-methoxy-1H-pyrrolo[2,3-b]pyridin-3-yl)pyridin-2-yl]amino}cyclohexyl)cyclopropanesulfonamide A mixture of Example 213f (0.2 g, 0.460 mmol), cyclopropanesulfonyl chloride (0.068 mL, 0.667 mmol) and triethylamine (0.279 mL, 2.000 mmol) in DMF (4.0 mL) was stirred at room temperature overnight. The reaction mixture was diluted with 20% brine and extracted with EtOAc (2×). The combined organic layers were washed with 20% brine, dried with MgSO$_4$, filtered, and concentrated. The residue was dissolved in 1:1 DMSO and MeOH. The crude mixture was purified by reversed-phase HPLC performed on a Zorbax RX-C18 column (250×21.2 mm, 7 µm particle size) using a gradient of 10% to 100% acetonitrile: 0.1% aqueous trifluoroacetic acid over 40 minutes at a flow rate of 15 mL/minutes to give 56.0 mg (29%) of the title compound as trifluoroacetic salts. $^1$H NMR (400 MHz, DMSO-d$_6$) ppm 0.91-0.95 (m, 4H), 1.26-1.42 (m, 4H), 1.96-2.02 (m, 4H), 6.81 (s, 1H), 6.86 (s, 1H), 7.08 (d, J=2.44 Hz, 1H), 7.79 (d, J=2.44, 1H), 8.08 (dd, J=6.41, 2.75 Hz, 2H). MS (DCI$^+$) m/z 476.3 (M+H)$^+$.

Example 219

N-(trans-4-{[6-chloro-4-(5-methoxy-1H-pyrrolo[2,3-b]pyridin-3-yl)pyridin-2-yl]amino}cyclohexyl)-1-ethylpyrrolidine-3-carboxamide The trifluoroacetic acid salt of Example 219 (0.90 g, 0.150 mmol) was prepared as described in Example 216, substituting cyclopropanecarboxylic acid with 1-ethylpyrrolidine-3-carboxylic acid. $^1$H NMR (400 MHz, DMSO-d$_6$) ppm 1.22 (t, J=7.32 Hz, 3H), 1.26-1.31 (m, 2H), 1.84-1.87 (m, 2H), 2.02-2.04 (m, 2H), 3.04-3.24 (m, 6 h0, 3.62-3.72 (m, 4H), 3.90 (s, 3H), 6.82 (s, 1H), 6.87 (s, 1H), 7.79 (d, J=2.75 Hz, 1H), 8.09 (dd, J=5.49, 2.75 Hz, 3H), 9.6-9.69 (m, 1H), 12.04 (s, 1H). MS (DCI$^+$) m/z 497.4 (M+H)$^+$.

Example 220

N-(trans-4-{[6-chloro-4-(5-methoxy-1H-pyrrolo[2,3-b]pyridin-3-yl)pyridin-2-yl]amino}cyclohexyl)methanesulfonamide The trifluoroacetic acid salt of Example 220 (0.90 g, 0.150 mmol) was prepared as described in Example 218, substituting cyclopropanesulfonyl chloride with methanesulfonyl chloride. $^1$H NMR (400 MHz, DMSO-d$_6$) ppm 1.23-1.42 (m, 4H), 1.94-2.01 (m, 4H), 2.93 (s, 3H), 3.07-3.16 (m, 2H), 3.90 (s, 3H), 6.81 (s, 1H), 3.86 (s, 1H), 7.05 (d, J=7.32 Hz, 1H), 7.79 (d, J=2.44 Hz, 1H), 8.08 (dd, J=6.71, 2.75 Hz, 2H), 12.04 (s, 1H). MS (DCI$^+$) m/z 450.2 (M+H)$^+$.

Example 221

6-chloro-N-cyclohexyl-4-(5-{3-[(4-methylpiperazin-1-yl)methyl]phenyl}-1H-pyrrolo[2,3-b]pyridin-3-yl)pyridin-2-amine Example 221a 4-(5-bromo-1-(phenylsulfonyl)-1H-pyrrolo[2,3-b]pyridine-3-yl)-6-chloro-N-cyclohexylpyridin-2-amine Example 221a was prepared as described for Example 168c substituting Example 168b with 5-bromo-3-iodo-1-(phenylsulfonyl)-1H-pyrrolo[2,3-b]pyridine to give the title compound as a brown powder in 68% yield. MS (ESI$^+$) m/z 547.4 (M+H)$^+$ Example 221b 6-chloro-N-cyclohexyl-4-(5-(3-((4-methylpiperazin-1-yl)methylphenyl-1-(phenylsulfonyl)-1H-pyrrolo[2,3-b]pyridin-3-yl)pyridine-2-amine To a solution of Example 221a (200 mg, 0.366 mmol) in 10 mL DMF was added 1-methyl-4-(3-(4,4,5,5-tetramethyl-1,3,2-dioxaborolan-2-yl)benzyl)piperazine (127 mg, 0.403 mmol). The solution was degassed and a suspension of sodium bicarbonate (208 mg, 3.66 mmol) in 2.5 mL water was added followed by the addition of 1,1'-bis(diphenylphosphino)-ferrocene)dichloropalladium(II) complex with dichloromethane (30 mg, 0.037 mmol). The reaction mixture was heated at 65° C. for 3 hours and then cooled to room temperature and partitioned with water, ethyl acetate. The organics were concentrated to dryness and then purified by silica gel flash chromatography eluting with 5% methanol, 95% dichloromethane to give the title compound as a gray powder in 68% yield. MS (ESI$^+$) m/z 655.3 (M+H)$^+$.

Example 221c 6-chloro-N-cyclohexyl-4-(5-{3-[(4-methylpiperazin-1-yl)methyl]phenyl}-1H-pyrrolo[2,3-b]pyridin-3-yl)pyridin-2-amine Example 221c was prepared as described for Example 168d, substituting Example 168c with Example 221b to give the title compound as a tan powder in 15% yield. MS (ESI$^+$) m/z 515.3 (M+H)$^+$; $^1$H NMR (300 MHz, DMSO-d$_6$) ppm 1.13-1.39 (m, 5H) 1.55-1.64 (m, 1H) 1.67-1.77 (m, 2H) 1.89-1.98 (m, 2H) 2.14 (s, 3H) 2.29-2.47 (m, 8H) 3.56 (s, 2H) 3.63-3.72 (m, 1H) 6.76 (d, 1H, J=7.46 Hz) 6.89 (s, 1H) 6.91 (s, 1H) 7.33 (d, 1H, J=8.14 Hz) 7.47 (t, 1H, J=8.14 Hz) 7.58-7.64 (m, 2H) 8.16 (s, 1H) 8.42 (d, 1H, J=2.03 Hz) 8.54 (d, 1H, J=2.03 Hz) 12.23 (bs, 1H).

Example 222

3-{3-[2-chloro-6-(cyclohexylamino)pyridin-4-yl]-1H-pyrrolo[2,3-b]pyridin-5-yl}benzenesulfonamide

Example 222a 3-(3-(2-chloro-6-(cyclohexylamino)pyridin-4-yl)-1-(phenylsulfonyl)-1H-pyrrolo[2,3-b]pyridin-5-yl)benzenesulfonamide Example 222a (0.10 g) was prepared as described in Example 171b, substituting 1-(phenylsulfonyl)-4-(4,4,5,5-tetramethyl-1,3,2-dioxaborolan-2-yl)-1H-pyrazole with 3-sulfamoylphenylboronic acid. MS (APCI$^+$) m/z 624.2 (M+H)$^+$.

Example 222b

3-{3-[2-chloro-6-(cyclohexylamino)pyridin-4-yl]-1H-pyrrolo[2,3-b]pyridin-5-yl}benzenesulfonamide Example 222b (0.055 g) was prepared as described in Example 171c, substituting Example 171b with Example 222a. $^1$H NMR (300 MHz, DMSO-$d_6$) ppm 1.09-1.43 (m, 5H) 1.54-1.65 (m, 1H) 1.66-1.79 (m, 2H) 1.88-1.99 (m, 2H) 3.61-3.77 (m, 1H) 6.75 (d, J=7.80 Hz, 1H) 6.89 (s, 2H) 7.42 (s, 2H) 7.72 (t, J=7.80 Hz, 1H) 7.84 (d, J=8.14 Hz, 1H) 7.99 (d, J=8.48 Hz, 1H) 8.18 (d, J=6.10 Hz, 2H) 8.48 (s, 1H) 8.59 (s, 1H) 12.31 (s, 1H). MS (ESI$^+$) m/z 482.2 (M+H)$^+$.

Example 223

4-{3-[2-chloro-6-(cyclohexylamino)pyridin-4-yl]-1H-pyrrolo[2,3-b]pyridin-5-yl}benzenesulfonamide

Example 223a 4-(3-(2-chloro-6-(cyclohexylamino)pyridin-4-yl)-1-(phenylsulfonyl)-1H-pyrrolo[2,3-b]pyridin-5-yl)benzenesulfonamide Example 223a (0.11 g) was prepared as described in Example 171b, substituting 1-(phenylsulfonyl)-4-(4,4,5,5-tetramethyl-1,3,2-dioxaborolan-2-yl)-1H-pyrazole with 4-(4,4,5,5-tetramethyl-1,3,2-dioxaborolan-2-yl)benzenesulfonamide. MS (APCI$^+$) m/z 622.9 (M+H)$^+$.

Example 223b

4-{3-[2-chloro-6-(cyclohexylamino)pyridin-4-yl]-1H-pyrrolo[2,3-b]pyridin-5-yl}benzenesulfonamide Example 223b (0.067 g) was prepared as described in Example 171c, substituting Example 171b with Example 223a. $^1$H NMR (300 MHz, DMSO-$d_6$) ppm 1.09-1.45 (m, 5H) 1.54-1.65 (m, 1H) 1.66-1.80 (m, 2H) 1.89-2.01 (m, 2H) 3.62-3.76 (m, 1H) 6.75 (d, J=7.54 Hz, 1H) 6.90-6.94 (m, 2H) 7.41 (s, 2H) 7.87-8.03 (m, 4H) 8.21 (s, 1H) 8.51 (s, 1H) 8.63 (s, 1H) 12.32 (s, 1H). MS (ESI$^+$) m/z 482.2 (M+H)$^+$.

Example 224 trans-N-[6-chloro-4-(5-ethoxy-1H-pyrrolo[2,3-b]pyridin-3-yl)pyridin-2-yl]cyclohexane-1,4-diamine

Example 224a tert-butyl(trans)-4-(6-chloro-4-(5-hydroxy-1-(phenylsulfonyl)-1H-pyrrolo[2,3-b]pyridin-3-yl)pyridin-2-ylamino)cyclohexylcarbamate To a solution of Example 213d (0.927 g, 1.514 mmol) in CH$_2$Cl$_2$ (50 mL) was added 1M BBr$_3$ in CH$_2$Cl$_2$ (10.6 mL, 10.6 mmol) at −78° C. The reaction was slowly warmed to room temperature and stirred overnight. The solvent was evaporated. To a suspension of the residue in THF (60.0 mL) was added triethylamine (1.48 mL, 10.6 mmol) and Boc$_2$O (0.380 g, 1.74 mmol). The reaction was stirred for 8 hours, diluted with 50% brine, and extracted with EtOAc. The organic layers was dried over MgSO$_4$, filtered, concentrated, and purified on a 40 g column using the ISCO Companion flash system eluting with CH$_2$Cl$_2$/EtOAc to give the title compound.

Example 224b tert-butyl(trans)-4-(6-chloro-4-(5-ethoxy-1-(phenylsulfonyl)-1H-pyrrolo[2,3-b]pyridin-3-yl)pyridin-2-ylamino)cyclohexylcarbamate A mixture of Example 224a (80.0 mg, 0.134 mmol), di-tert-butyl azodicarboxylate (77 mg, 0.334 mmol), triphenylphosphine on solid support (3 mmol/g, 112.0 mg, 0.427 mmol) and ethanol (0.039 mL, 0.669 mmol) in THF (3 mL) was stirred at room temperature overnight. The mixture was diluted with EtOac, filtered through celite, concentrated and purified on a 12 g column using the ISCO Companion flash system eluting with hexane/EtOAc (8:2 to 6:4) to give 76.1 mg of the title compound.

Example 224c trans-N-[6-chloro-4-(5-ethoxy-1H-pyrrolo[2,3-b]pyridin-3-yl)pyridin-2-yl]cyclohexane-1,4-diamine A solution of Example 224b (76.1 mg, 0.122 mmol) in dioxane (1.5 mL) was treated with 20% sodium hydroxide (0.10 mL, 0.122 mmol). The mixture was heated at 90° C. for 1 hour. The solvent was evaporated. The residue was treated with 20% brine and extracted with EtOAc (2×). The combined organic layers were dried. The crude intermediate was dissolved in CH$_2$Cl$_2$ (1.0 mL) and treated with TFA (0.19 mL, 2.4 mmol). After 1 hour, the reaction mixture was concentrated and purified by reverse-phase HPLC as described in Example 56 to give the title compound (6.5 mg) as trifluoroacetic acid salts. $^1$H NMR (400 MHz, CD$_3$OD) ppm 1.29-1.43 (m, 2H), 1.43-1.49 (m, 3H), 1.52-1.72 (m, 2H), 2.02-2.17 (m, 2H), 2.17-2.32 (m, 2H), 3.13 (m, 1H), 3.80 (m, 1H), 4.18 (q, J=7.02 Hz, 2H), 6.75 (d, J=1.22 Hz, 1H), 6.86 (d, J=1.22 Hz, 1H), 7.86 (s, 1H), 7.90 (d, J=2.44 Hz, 1H), 8.06 (d, J=2.44 Hz, 1H). MS (DCI$^+$) m/z 386.2 (M+H)$^+$.

Example 225

3-[2-chloro-6-(cyclohexylamino)pyridin-4-yl]-1H-pyrrolo[2,3-b]pyridin-5-amine

Example 225a tert.-butyl 3-iodo-1-(phenylsulfonyl)-1H-pyrrolo[2,3-b]pyridin-5-yl-carbamate Example 225a was prepared as described in Example 168b substituting 4-chloro-3-iodo-1H-pyrrolo[2,3-b]pyridine with tert.-butyl 3-iodo-1H-pyrrolo[2,3-b]pyridine-5-yl carbamate to give the title compound as a brown powder in 75% yield. MS (ESI$^+$) m/z 497.8 (M+H)$^+$

Example 225b tert.-butyl 3-(2-chloro-6-cyclohexylamino)pyridine-4-yl)-1-(phenylsulfonyl)-1H-pyrrolo[2,3-b]pyridine-5-yl carbamate Example 225b was prepared as described in Example 168c substituting Example 168b with tert.-butyl 3-iodo-1-(phenylsulfonyl)-1H-pyrrolo[2,3-b]pyridin-5-yl-carbamate to give the title compound as a dark brown powder in 63% yield. MS (ESI$^+$) m/z 582.2 (M+H)$^+$

Example 225c tert.-butyl 3-(2-chloro-6-(cyclohexylamino)pyridine-4-yl)-1H-pyrrolo[2,3-b]pyridine-5-yl carbamate Example 225c was prepared as described in Example 168d, substituting Example 168c with Example 225b to give the title compound as an off-white powder in 23% yield. MS (ESI$^+$) m/z 442.1 (M+H)$^+$.

Example 225d

3-[2-chloro-6-(cyclohexylamino)pyridin-4-yl]-1H-pyrrolo[2,3-b]pyridin-5-amine

To a solution of Example 225c (22 mg, 0.05 mmol) in 5 mL dichloromethane cooled in an ice bath was added trifluoroacetic acid (5 mL, 65 mmol) and the solution stirred 1.5 hours at room temperature then concentrated to dryness. The residue was suspended in 50% ether, 50% pentane and the suspension filtered. The collected solid was mixed with 50% methanol, 50% dichloromethane and the suspension filtered. The filtrate was concentrated to dryness to give the title compound as the bis trifluoroacetic acid salt in 48% yield. MS (ESI$^+$) m/z 342.1 (M+H)$^+$; $^1$H NMR (300 MHz, DMSO-d$_6$) ppm 1.13-1.43 (m, 5H) 1.54-1.65 (m, 1H) 1.67-1.79 (m, 2H) 1.86-1.97 (m, 2H) 3.30-3.76 (m, 4H) 6.70 (s, 1H) 6.78 (bs, 1H) 7.96 bs, 1H) 8.08 (d, 1H, J=2.38 Hz) 8.11 (d, 1H, J=1.59 Hz) 12.16 (bs, 1H).

Example 226

N-{3-[2-chloro-6-(cyclohexylamino)pyridin-4-yl]-1H-pyrrolo[2,3-b]pyridin-5-yl}acetamide

Example 226a 3-iodo-1-(phenylsulfonyl)-1H-pyrrolo[2,3-b]pyridine-5-amine trifluoroacetate Example 225a was dissolved in 4 mL dichloromethane and trifluoroacetic acid (1.174 mL, 15.24 mmol) added and the solution stirred at room temperature for 16 hours. The reaction solution was then concentrated to dryness and the residue purified by flash chromatography on silica gel eluting with 10% ethyl acetate, 90% dichloromethane to give the title compound as a tan powder in 46% yield. MS (ESI$^+$) m/z 400.0 (M+H)$^+$

Example 226b

N-3-iodo-1-(phenylsulfonyl)-1H-pyrrolo[2,3-b]pyridine-5-yl)acetamide

Example 226a (120 mg, 0.191 mmol) was dissolved in 4 mL dichloromethane and triethylamine (0.267 mL 1.913 mmol) added. The reaction was cooled in an ice bath and acetyl chloride (0.041 mL 0.574 mmol) added and the reaction mixture was stirred 16 hours at room temperature. The reaction solution was then concentrated to dryness and the residue partitioned with ethyl acetate and saturated sodium bicarbonate solution. The organics were dried (MgSO$_4$), filtered, and concentrated to give the title compound as a brown powder that was carried on without purification.

Example 226c

N-(3-(2-chloro-6-(cyclohexylamino)pyridine-4-yl)-1-(phenylsulfonyl)-1H-pyrrolo[2,3-b]pyridine-5-yl) acetamide Example 226c was prepared as described for Example 168c substituting Example 168b with Example 226b to give the title compound as a brown powder in 89% yield. MS (ESI$^+$) m/z 524.2 (M+H)$^+$.

Example 226d

N-{3-[2-chloro-6-(cyclohexylamino)pyridin-4-yl]-1H-pyrrolo[2,3-b]pyridin-5-yl}acetamide Example 226d was prepared as described for Example 168d, substituting Example 168c with Example 226c to give the title compound as a brown powder in 48% yield. MS (ESI$^+$) m/z 384.1 (M+H)$^+$; $^1$H NMR (300 MHz, DMSO-d$_6$) ppm 1.14-1.43 (m, 5H) 1.55-1.65 (m, 1H) 1.67-1.78 (m, 2H) 1.86-1.97 (m, 2H) 2.08 (s, 3H) 2.71-2.75 (m, 1H) 6.70 (s, 1H) 6.78 (s, 1H) 6.82 (d, 1H, J=7.93 Hz) 8.03 (s, 1H) 8.38 (d, 1H, J=1.98 Hz) 8.48 (d, 1H, J=1.98 Hz) 10.04 (s, 1H) 12.07 (bs, 1H).

Example 227

N-(trans-4-{[6-chloro-4-(5-methoxy-1H-pyrrolo[2,3-b]pyridin-3-yl)pyridin-2-yl]amino}cyclohexyl)-N$^2$-methylglycinamide The trifluoroacetic salt of Example 227 (0.90 g, 0.150 mmol) was prepared as described in Example 216, substituting cyclopropanecarboxylic acid with 2-(tert-utoxycarbonyl (methyl)amino)acetic acid. $^1$H NMR (500 MHz, DMSO-d$_6$) ppm 1.27-1.39 (m, 4H), 1.87-1.89 (m, 2H), 2.03-2.05 (m, 2H), 3.59-3.64 (m, 2H), 3.67 (t, J=5.95 Hz, 3H), 3.90 (s, 3H), 6.82 (s, 1H), 6.87 (s, 1H), 7.79 (d, J=2.44 Hz, 1H), 8.09 (dd, J=4.73, 2.9, 2H), 8.37 (d, J=7.63 Hz, 1H), 8.66 (d, J=5.49 Hz, 2H), 12.04 (s, 1H). MS (DCI$^+$) m/z 443.3 (M+H)$^+$.

Example 228

N-(trans-4-{[6-chloro-4-(5-methoxy-1H-pyrrolo[2,3-b]pyridin-3-yl)pyridin-2-yl]amino}cyclohexyl)-2-methylpropanamide The, trifluoroacetic acid salt of Example 228 (0.90 g, 0.150 mL) was prepared as described in Example 216, substituting cyclopropanecarboxylic acid with isobutyric acid. $^1$H NMR (500 MHz, DMSO-d$_6$) ppm 0.99 (d, J=7.02 Hz, 6H), 1.25-1.31 (m, 4H), 1.80-1.82 (m, 2H), 2.0-2.02 (m, 2H), 2.30-2.36 (m, 1H), 3.9 (s, 1H), 6.81 (s, 1H), 6.86 (d, J=0.92 Hz, 1H), 7.61 (d, J=7.93 Hz, 1H), 7.79 (d, J=2.44 Hz, 1H), 8.08 (dd, J=6.71, 2.75 Hz, 2H), 12.03 (s, 1H). MS (DCI$^+$) m/z 442.3 (M+H)$^+$.

Example 229

N-(trans-4-{[6-chloro-4-(1H-pyrrolo[2,3-b]pyridin-3-yl)pyridin-2-yl]amino}cyclohexyl)-2-[4-(4-fluorophenyl)piperazin-1-yl]acetamide The trifluoroacetic acid salt of Example 229 (0.085 g, 0.203 mmol) was prepared as described in Example 141b, substituting morpholine with 1-(4-fluorophenyl)piperazine. $^1$H NMR (500 MHz, DMSO-d$_6$) ppm 1.26-1.39 9 m, 4H), 1.88-1.91 (m, 2H), 2.02-2.05 (m, 2H), 3.07-3.78 (m, 8H), 3.99 (s, 2H), 6.80 (s, 1H), 6.87-6.89 (m, 2H), 7.0-7.03 (m, 2H), 7.09-7.13 (m, 2H), 7.21 (dd, J=7.78, 4.73 Hz, 1H), 8.13 (d, J=2.75 Hz, 1H), 8.30-8.33 (m, 2H), 8.53 (d, J=7.32 Hz, 1H), 10.07 (s, 1H), 12.17 (d, J=1.83 Hz, 1H). MS (DCI$^+$) m/z 562.4 (M+H)$^+$.

Example 230

N-(trans-4-{[6-chloro-4-(1H-pyrrolo[2,3-b]pyridin-3-yl)pyridin-2-yl]amino}cyclohexyl)-2-[4-(pyridin-4-yl)piperazin-1-yl]acetamide The trifluoroacetic acid salt of Example 230 (0.085 g, 0.203 mmol) was prepared as described in Example 141b, substituting morpholine with 1-(pyridin-4-yl)piperazine. $^1$H NMR (500 MHz, DMSO-d$_6$) ppm 1.26-1.43 (m, 4H), 1.88-1.91 (m, 2H), 2.02-2.05 (m, 2H), 3.29-3.43 (m, 4H), 3.64-3.68 (m, 2H), 3.89-3.97 (m, 4H), 6.88-6.89 (m, 2H), 7.22 (dd, J=7.93, 4.58 Hz, 1H), 7.27 (d, J=7.93 Hz, 2H), 8.14 (d, J=2.75 Hz, 1H), 8.32 (d, J=4.88 Hz, 2H), 8.39 (d, J=7.63 Hz, 2H), 8.58 (d, J=7.32 Hz, 1H), 12.20 (s, 1H), 13.9 (s, 1H). MS (APCI$^+$) m/z 545.7 (M+H)$^+$.

Example 231

N-(trans-4-{[6-chloro-4-(1H-pyrrolo[2,3-b]pyridin-3-yl)pyridin-2-yl]amino}cyclohexyl)-2-(4-cyclohexylpiperazin-1-yl)acetamide The trifluoroacetic acid salt of Example 231 (0.085 g, 0.203 mmol) was prepared as described in Example 141b, substituting morpholine with 1-cyclohexylpiperazine. $^1$H NMR (500 MHz, DMSO-d$_6$) ppm 1.07-1.14 (m, 1H), 1.23-1.43 (m, 8H), 1.61-1.63 (m, 1H), 1.83-1.85 (m, 1H), 2.02-2.04 (m, 4H), 3.15-3.23 (m, 4H), 3.41 (s, 2H), 3.75-3.87 (m, 2H), 6.87-6.88 (m, 2H), 7.22 (dd, J=8.09, 4.73 Hz, 1H), 8.00 (d, J=7.63 Hz, 1H), 8.13 (d, J=2.75 Hz, 1H), 8.30-8.33 (m, 2H), 12.19 (s, 1H). MS (DCI$^+$) m/z 550.4 (M+H)$^+$.

Example 232

2-(4-butylpiperazine-1-yl)-N-(trans-4-{[6-chloro-4-(1H-pyrrolo[2,3-b]pyridin-3-yl)pyridin-2-yl]amino}cyclohexyl)acetamide The trifluoroacetic acid salt of Example 232 (0.085 g, 0.203 mmol) was prepared as described in Example 141b, substituting morpholine with 1-butylpiperazine. $^1$H NMR (500 MHz, DMSO-d$_6$) ppm 0.92 (t, J=7.32 Hz, 3H), 1.24-1.42 (m, 6H), 1.57-1.63 (m, 2H), 1.83-1.85 (m, 2H), 2.01-2.03 (m, 2H), 3.03-3.07 (m, 4H), 3.29 (s, 2H), 3.59-3.66 (m, 4H), 6.86-6.88 (m, 2H), 7.21 (dd, J=7.93, 4.88 Hz, 1H), 7.9 (d, J=6.1 Hz, 8.13 (d, 3.05 Hz, 1H), 8.30-8.32 (m, 2H), 12.17 (s, 1H). MS (DCI$^+$) m/z 524.4 (M+H)$^+$.

Example 233

N-(trans-4-{[6-chloro-4-(1H-pyrrolo[2,3-b]pyridin-3-yl)pyridin-2-yl]amino}cyclohexyl)-2-[4-(furan-2-ylcarbonyl)piperazin-1-yl]acetamide The trifluoroacetic acid salt of Example 233 (0.085 g, 0.203 mmol) was prepared as described in Example 141b, substituting morpholine with furan-2-yl(piperazin-1-yl)methanone. $^1$H NMR (500 MHz, DMSO-d$_6$) ppm 1.23-1.41 (m, 4H), 1.88-1.90 (m, 2H), 2.02-2.05 (m, 2H), 3.26-3.42 (m, 3H), 4.26-4.59 (m, 3H), 3.95 (s, 2H), 6.67 (dd, J=3.66, 1.83 Hz, 1H), 6.87-6.88 (m, 2H), 7.11 (d, J=3.36 Hz, 1H), 7.22 (dd, J=7.93, 4.58 Hz, 1H), 7.89 (d, J=1.22 Hz, 1H), 8.13 (d, J=2.75 Hz, 1H), 8.31-8.33 (m, 2H), 8.55 (d, J=7.63 Hz, 1H), 12.18 (s, 1H). MS (APCI$^+$) m/z 562.6 (M+H)$^+$.

Example 234

N-(trans-4-{[6-chloro-4-(1H-pyrrolo[2,3-b]pyridin-3-yl)pyridin-2-yl]amino}cyclohexyl)-2-[4-(2-cyanophenyl)piperazin-1-yl]acetamide The trifluoroacetic acid salt of Example 234 (0.085 g, 0.203 mmol) was prepared as described in Example 141b substituting morpholine with 2-(piperazin-1-yl)benzonitrile. $^1$H NMR (500 MHz, DMSO-d$_6$) ppm 1.29-1.40 (m, 4H), 1.89-1.91 (m, 2H), 2.03-2.05 (m, 2H), 2.53-2.56 (m, 2H), 3.64-3.67 (m, 6H), 4.04 (s, 2H), 6.87-6.89 (m, 2H), 7.18-7.23 (m, 2H), 7.27 (d, J=8.24 Hz, 1H), 7.64-7.68 (m, 1H), 7.77 (dd, J=7.78, 1.68 Hz, 1H), 8.13 (d, J=2.75 Hz, 1H), 8.31-8.33 (m, 2H), 8.55 (d, J=7.63, 1H), 12.17 (s, 1H). MS (APCI$^+$) m/z 569.7 (M+H)$^+$.

Example 235

3-[2-chloro-6-(cyclohexylamino)pyridin-4-yl]-1H-pyrrolo[2,3-b]pyridine-5-carboxylic acid

Example 235a

Methyl-1H-pyrrolo[2,3-b]pyridine-5-carboxylate

A solution of 5-bromo-1H-pyrrolo[2,3-b]pyridine (1.3 g, 6.6 mmol) in 25 mL methanol was treated with 1,1'-bis (diphenylphosphino)-ferrocene dichloropalladium(II) complex with dichloromethane (97 mg, 0.132 mmol) and triethylamine (1.84 mL, 13.2 mmol) was added. The 50 mL pressure bottle was pressurized with carbon monoxide at 60 psi and heated at 90° C. for 16 hours. The pressure was released after cooling to room temperature and the reaction mixture was filtered. The filtrate was concentrated to dryness and the residue suspended in water, filtered and the collected solid dried to give the title compound as a brown powder in quantitative yield. MS (DCI$^+$) m/z 177.0 (M+H)$^+$ Example 235b Methyl-3-iodo-1H-pyrrolo[2,3-b]pyridine-5-carboxylate To a solution of Example 235a (1.04 g, 5.9 mmol) in 12 mL anhydrous DMF was added N-iodosuccinimide (1.46 g, 6.49 mmol) and the solution stirred at room temperature for 16 hours. The solvent was evaporated and the residue suspended in water and filtered. The collected solid was triturated with dichloromethane and the mixture filtered. The dichloromethane filtrate was concentrated to a brown powder that was carried on without purification.

Example 235c

Methyl-3-iodo-1-(phenylsulfonyl)-1H-pyrrolo[2,3-b]pyridine-5-carboxylate

Example 235c was prepared as described for Example 168b substituting 4-chloro-3-iodo-1H-pyrrolo[2,3-b]pyridine with Example 235b to give the title compound as a tan powder in 71% yield. MS (ESI$^+$) m/z 443.0 (M+H)$^+$.

Example 235d

Methyl-3-(2-chloro-6-(cyclohexylamino)pyridine-4-yl)-1-(phenylsulfonyl)-1H-pyrrolo[2,3-b]pyridine-5-carboxylate Example 235d was prepared as described for Example 168c substituting Example 168b with Example 235c to give the title compound as a reddish-brown powder that was carried on without purification Example 235e Methyl-3-(2-chloro-6-(cyclohexylamino)pyridine-4-yl)-1H-pyrrolo[2,3-b]pyridine-5-carboxylate Example 235e was prepared as described for Example 168d substituting Example 168c with Example 235d to give the title compound as a tan powder that was carried on without purification.

Example 235f

3-[2-chloro-6-(cyclohexylamino)pyridine-4-yl]-1-1H-pyrrolo[2,3-b]pyridine-5-carboxylic acid To a solution of Example 235e (53 mg, 0.138 mmol) in 1 mL THF, 0.5 mL methanol was added a solution of lithium hydroxide (23 mg, 0.551 mmol) in 0.6 mL water. The reaction solution was heated at reflux for 90 minutes and then cooled to room temperature and the solution concentrated to dryness. The residue was suspended in 1N HCl solution, filtered and the collected solid purified by silica gel flash chromatography eluting with 10% methanol, 90% dichloromethane to give the title compound as a tan powder in 47% yield. MS (ESI$^+$) m/z 371.1 (M+H)$^+$; $^1$H NMR (300 MHz, DMSO-d$_6$) ppm 1.11-1.44 (m, 5H) 1.54-1.66 (m, 1H) 1.68-1.79 (m, 2H) 1.88-1.99 (m, 2H) 3.62-3.75 (m, 1H) 6.85 (s, 1H) 6.86 (s, 1H) 7.01 (d, 1H, J=7.54 Hz) 8.25 (d, 1H, J=2.38 Hz) 8.80 (d, 1H, J=1.98 Hz) 8.86 (d, 1H, J=1.98 Hz) 12.52 (bs, 1H) 13.07 (bs, 1H).

Example 236

6-chloro-4-(5-methoxy-1H-pyrrolo[2,3-b]pyridin-3-yl)-N-[4-(piperidin-4-yl)cyclohexyl]pyridin-2-amine Example 236a tert-butyl 4-(4-(6-chloro-4-(5-methoxy-1H-pyrrolo[2,3-b]pyridin-3-yl)pyridin-2-ylamino)cyclohexyl)piperidine-1-carboxylate Example 236a (0.058 g) was prepared as described in Example 61b, substituting Example 61a with Example 149e and substituting trans-cyclohexane-1,4-diamine with tert-butyl 4-(4-aminocyclohexyl)piperidine-1-carboxylate. MS (ESI$^+$) m/z 540.6 (M+H)$^+$.

Example 236b 6-chloro-4-(5-methoxy-1H-pyrrolo[2,3-b]pyridin-3-yl)-N-[4-(piperidin-4-yl)cyclohexyl]pyridin-2-amine Example 236b (0.047 g) was prepared as described in Example 106b, substituting Example 106a with Example 236a. The crude material was treated with 2M HCl in diethyl ether for 30 min. The resulting suspension was diluted with more diethyl ether and the solid filtered to give the title compound as the HCl salt. $^1$H NMR (300 MHz, DMSO-d$_6$) ppm 1.04-1.29 (m, 4H) 1.27-1.64 (m, 8H) 1.67-1.91 (m, 4H) 2.65-2.95 (m, 2H) 3.19-3.32 (m, 2H) 3.85-3.96 (m, 3H) 3.95-4.05 (m, 1H) 6.81-6.92 (m, 2H) 6.95-7.04 (m, 1H) 7.77-7.94 (m, 1H) 8.04-8.16 (m, 2H) 8.49-8.73 (m, 1H) 8.78-8.92 (m, 1H) 12.09 (s, 1H). MS (ESI$^+$) m/z 440.2 (M+H)$^+$.

Example 237

N-{4-[(4-aminocyclohexyl)methyl]cyclohexyl}-6-chloro-4-(5-methoxy-1H-pyrrolo[2,3-b]pyridin-3-yl)pyridin-2-amine A mixture of Example 149e (0.634 g, 2.16 mmol) and 4,4'-methylenedicyclohexanamine (2.267 g, 10.78 mmol) was heated at 155° C. for 90 minutes and cooled. While still warm, the slurry was treated with water and extracted with EtOAc (2×). The combined organic layers were dried over MgSO$_4$, filtered, concentrated, and purified on a 28 g Biotage KP-NH column using the ISCO Companion flash system eluting with MeOH/EtOAc (3:97 to 5:95) to give 593 mg of the title compound. 55 mg of this material was further purified by reverse-phase HPLC as described in Example 56 to give 17 mg of the title compound as trifluoroacetic acid salts. $^1$H NMR (400 MHz, CD$_3$OD) ppm 1.02-1.45 (m, 9H), 1.57-1.92 (m, 9H), 1.99-2.18 (m, 2H), 3.02 (m, 1H), 3.70 (m, 1H), 3.95 (s, 3H), 6.72-6.92 (m, 2H), 7.80-7.91 (m, 2H), 8.06 (s, 1H). MS (DCI$^+$) m/z 468.3 (M+H)$^+$.

Example 238

6-chloro-N-(4-{[4-(cyclohexylamino)cyclohexyl]methyl}cyclohexyl)-4-(5-methoxy-1H-pyrrolo[2,3-b]pyridin-3-yl)pyridin-2-amine A suspension of Example 237 (80.0 mg, 0.171 mmol) in MeOH (3 mL) was treated with cyclohexanone (0.035 mL, 0.342 mmol). After 30 minutes, sodium cyanoborohydride (21.5 mg, 0.342 mmol) and zinc chloride (0.699 mg, 5.13 μmol) were added. The reaction was stirred at room temperature overnight. The mixture was concentrated. The residue was treated with sat. NaHCO$_3$ and extracted with EtOAc (2×). The combined organic layers were dried and purified by reverse-phase HPLC as described in Example 56 to give the title compound (32.4 mg) as trifluoroacetic acid salts. $^1$H NMR (400 MHz, CD$_3$OD) ppm 0.96-1.48 (m, 15H), 1.59-1.96 (m, 10H), 2.01-2.17 (m, 5H), 3.12-3.23 (m, 2H), 3.70 (m, 1H), 3.96 (s, 3H), 6.84-7.01 (m, 2H), 7.93 (m, 1H), 7.99 (s, 1H), 8.10 (s, 1H). MS (DCI$^+$) m/z 550.4 (M+H)$^+$.

Example 239

3-[2-chloro-6-(cyclohexylamino)pyridin-4-yl]-N-phenyl-1H-pyrrolo[2,3-b]pyridin-5-amine Example 239a 3-(2-chloro-6-(cyclohexylamino)pyridin-4-yl)-N-phenyl-1-(phenylsulfonyl)-1H-pyrrolo[2,3-b]pyridin-5-amine A solution of Example 171a (0.200 g, 0.366 mmol), aniline (0.044 g, 0.476 mmol), 2-dicyclohexylphosphino-2',4',6'-tri-1-propyl-1,1'-biphenyl (X-PHOS) (0.009 g, 0.018 mmol), catalytic tris(dibenzylideneacetone)dipalladium (0) and potassium carbonate (0.127 g, 0.916 mmol) in 4 mL tert-butanol was heated at 110° C. for 16 hours. The material was cooled to room temperature, diluted with ethyl acetate, washed with brine, dried over MgSO$_4$, filtered, and concentrated. The residue was purified on silica gel using flash chromatography (20% ethyl acetate/hexane) to afford 0.025 gm of the title compound. m/z 558.0 (APCI, M+H)$^+$.

Example 239b

3-[2-chloro-6-(cyclohexylamino)pyridin-4-yl]-N-phenyl-1H-pyrrolo[2,3-b]pyridin-5-amine Example 239b (0.007 g) was prepared as described in Example 171c, substituting Example 171b with Example 239a. $^1$H NMR (300 MHz, DMSO-d$_6$) ppm 1.07-1.38 (m, 5H) 1.49-1.61 (m, 1H) 1.61-1.76 (m, 2H) 1.82-1.96 (m, 2H) 3.54-3.71 (m, 1H) 6.67-6.83 (m, 4H) 6.85-6.97 (m, 2H) 7.17 (t, J=7.80 Hz, 2H) 7.96-8.10 (m, 3H) 8.14 (s, 1H) 12.03 (s, 1H). MS (ESI$^+$) m/z 418.2 (M+H)$^+$.

Example 240

N-[4-[(4-{[6-chloro-4-(5-methoxy-1H-pyrrolo[2,3-b]pyridin-3-yl)pyridin-2-yl]amino}cyclohexyl)methyl]cyclohexyl]cyclopropanecarboxamide A mixture of Example 237 (68.5 mg, 0.146 mmol), cyclopropanecarboxylic acid (0.013 mL, 0.161 mmol), HOBT (26.9 mg, 0.176 mmol), EDC (33.7 mg, 0.176 mmol), and triethylamine (0.027 mL, 0.190 mmol) in DMF (2.5 mL) was stirred at room temperature overnight. More EDC (0.6 eq), HOBT (0.6 eq), acid (0.6 eq) and triethylamine (0.7 eq) were added. After 6 hours, water was added to reaction mixture. The precipitate was filtered and purified by reverse-phase HPLC as described in Example 56 to give the title compound (29.0 mg) as trifluoroacetic acid salts. $^1$H NMR (400 MHz, CD$_3$OD) ppm 0.67-0.76 (m, 2H), 0.77-0.87 (m, 2H), 0.93-1.45 (m, 12H), 1.47-1.96 (m, 10H), 3.57 (m, 1H), 3.71 (m, 1H), 87 (m, 0.6H), 3.96 (s, 3H), 4.02 (m, 0.4H), 6.88-7.07 (m, 2H), 7.94 (m, 1H), 8.04 (s, 1H), 8.11 (s, 1H). MS (DCI$^+$) m/z 536.4 (M+H)$^+$.

Example 241 tert-butyl (1r,4r)-4-(6-chloro-4-(1-(phenylsulfonyl)-5-(prop-2-ynyloxy)-1H-pyrrolo[2,3-b]pyridin-3-yl)pyridin-2-ylamino)cyclohexylcarbamate Example 241a tert-butyl(trans)-4-(6-chloro-4-(1-(phenylsulfonyl)-5-(prop-2-ynyloxy)-1H-pyrrolo[2,3-b]pyridin-3-yl)pyridin-2-ylamino)cyclohexylcarbamate A mixture of Example 224a (0.075 g, 0.125 mmol), propargyl alcohol (0.018 mL, 0.313 mmol), di-tert-butyl azodicarboxylate (0.072 g, 0.313 mmol), and triphenylphosphine (3 mmol/1 g)-polymer supported (0.105 g, 0.4 mmol) in THF (3.0 mL) was stirred at room temperature overnight. The reaction mixture was diluted with EtOAc and dichloromethane, filtered through celite, concentrated and purified on 12 g column, using Analogix System, eluted with 0-30% EtOAc in hexanes to give 56.0 mg (70%) of the title compound.

Example 241b tert-butyl(trans)-4-(6-chloro-4-(5-(prop-2-ynyloxy)-1H-pyrrolo[2,3-b]pyridin-3-yl)pyridin-2-ylamino)cyclohexylcarbamate A solution of Example 241a (0.056 g, 0.088 mmol) in dioxane (1.5 mL) was treated with 20% sodium hydroxide (0.10 mL, 0.088 mmol). The mixture was heated at 90 C for an hour. The solvent was evaporated. The residue was treated with 20% brine and twice extracted with dichloromethane. The layers were combined, dried with MgSO$_4$ and concentrated to give 0.037 g of the title compound. The crude product was used in the next step without further purification.

Example 241c (trans)-N1-(6-chloro-4-(5-(prop-2-ynyloxy)-1H-pyrrolo[2,3-b]pyridin-3-yl)pyridin-2-yl)cyclohexane-1,4-diamine Example 241b (0.037 mg) was dissolved in dichloromethane (0.7 mL) and treated with trifluoroacetic acid (0.1 mL). After an hour, the reaction mixture was concentrated. The residue was dissolved in 1:1 DMSO and MeOH. The crude was purified by reversed-phase HPLC performed on a Zorbax RX-C18 column (250×21.2 mm, 7 μm particle size) using a gradient of 10% to 100% acetonitrile: 0.1% aqueous trifluoroacetic acid over 40 minutes at a flow rate of 15 mL/minutes to give 9.7 mg (18%) of the title compound as trifluoroacetic acid salts. $^1$H NMR (500 MHz, DMSO-d$_6$) ppm 1.22-1.32 (m, 2H), 1.39-1.49 (m, 2H), 1.95-2.07 (m, 4H), 4.93 (d, J=2.44 Hz, 2H), 6.75 (s, 1H0, 6.81 (s, 1H), 6.88 (s, 1H), 7.79-7.80 (m, 3H), 7.90 (d, J=2.75 Hz, 1H), 8.13 (t, J=3.05 Hz, 2H), 12.11 (s, 1H). MS (DCI$^+$) m/z 396.3 (M+H)$^+$.

Example 242

3-[2-chloro-6-(cyclohexylamino)pyridin-4-yl]-N-(pyridin-2-ylmethyl)-1H-pyrrolo[2,3-b]pyridine-5-carboxamide To a solution of Example 235f (33 mg, 0.074 mmol) in 3 mL anhydrous DMF was added 1H-benzo[d][1,2,3]triazol-1-ol (14.5 mg, 0.108 mmol) followed by the addition of 2-(aminomethyl)pyridine (0.015 mL, 0.149 mmol), N-ethyl-N-isopropylpropan-2-amine (0.065 mL, 0.372 mmol) and, finally, $N^1$-(ethylamino)methylene)-$N^3$,$N^3$-dimethylpropane-1,3-diamine hydrochloride (24 mg, 0.126 mmol). After stirring at room temperature for 16 hours, the DMF was removed and the residue partitioned with saturated aqueous sodium carbonate, ethyl acetate. The organics were dried (MgSO$_4$), filtered, and then concentrated and the residue purified by silica gel flash chromatography eluting with 5% methanol, 95% dichloromethane to give the title compound as a dark brown powder in 28% yield. MS (ESI$^+$) m/z 461.2 (M+H)$^+$; $^1$H NMR (300 MHz, DMSO-d$_6$) ppm 1.12-1.38 (m, 5H) 1.53-1.64 (m, 1H) 1.66-1.76 (m, 2H) 1.87-1.97 (m, 2H) 3.61-3.74 (m, 1H) 4.36 (dd, 1H, J=19.06, 5.76 Hz) 4.63 (d, 1H, J=5.76 Hz) 6.84 (d, 1H, J=10.51 Hz) 6.88 (s, 1H) 7.22-7.30 (m, 2H) 7.38 (d, 1H, J=8.14 Hz) 7.71-7.80 (m, 1H) 8.19 (s, 1H) 8.37-8.44 (m, 1H) 8.47-8.54 (m, 1H) 8.79 (d, 1H, J=2.03 Hz) 8.85 (d, 1H, J=1.7 Hz) 9.29 (t, 1H, J=5.76 Hz)

Example 243

6-chloro-N-cyclohexyl-4-[5-(pyrimidin-5-yl)-1H-pyrrolo[2,3-b]pyridin-3-yl]pyridin-2-amine

Example 243a 6-chloro-N-cyclohexyl-4-(1-(phenylsulfonyl)-5-(pyrimidin-5-yl)-1H-pyrrolo[2,3-b]pyridin-3-yl)pyridin-2-amine Example 243a (0.13 g) was prepared as described in Example 171b, substituting 1-(phenylsulfonyl)-4-(4,4,5,5-tetramethyl-1,3,2-dioxaborolan-2-yl)-1H-pyrazole with pyrimidin-5-ylboronic acid. MS (APCI$^+$) m/z 545.4 (M+H)$^+$.

Example 243b 6-chloro-N-cyclohexyl-4-[5-(pyrimidin-5-yl)-1H-pyrrolo[2,3-b]pyridin-3-yl]pyridin-2-amine Example 243b (0.046 g) was prepared as described in Example 171c, substituting Example 171b with Example 243a. $^1$H NMR (300 MHz, DMSO-d$_6$) ppm 1.14-1.44 (m, 5H) 1.55-1.66 (m, 1H) 1.67-1.78 (m, 2H) 1.90-2.01 (m, 2H) 3.63-3.77 (m, 1H) 6.69 (d, J=8.14 Hz, 1H) 6.93 (s, 2H) 8.23 (s, 1H) 8.60-8.62 (m, 1H) 8.70-8.72 (m, 1H) 9.22 (s, 1H) 9.27 (s, 2H) 12.38 (s, 1H). MS (ESI$^+$) m/z 405.2 (M+H)$^+$.

Example 244

N-(trans-4-{[6-chloro-4-(5-methoxy-1H-pyrrolo[2,3-b]pyridin-3-yl)pyridin-2-yl]amino}cyclohexyl)butane-1-sulfonamide The trifluoroacetic acid salt of Example 244 (0.90 g, 0.150 mmol) was prepared as described in Example 218, substituting cyclopropanesulfonyl chloride with butane-1-sulfonyl chloride. $^1$H NMR (400 MHz, DMSO-d$_6$) ppm 0.90 (t, J=7.32 Hz, 3H), 1.23-1.43 (m, 6H), 1.60-1.68 (m, 2H), 1.90-2.01 (m, 2H), 2.97-3.01 (m, 2H), 3.90 (s, 3H), 6.81 (s, 1H), 6.86 (s, 1H), 7.07 (d, J=7.63 Hz, 1H), 7.79 (d, J=2.75 Hz, 1H), 8.08 (dd, J=6.41, 2.75 Hz, 2H), 12.04 (s, 1H). MS (DCI$^+$) m/z 492.2 (M+H)$^+$.

Example 245

4-[5-(6-aminopyridin-3-yl)-1H-pyrrolo[2,3-b]pyridin-3-yl]-6-chloro-N-cyclohexylpyridin-2-amine

Example 245a 4-(5-(6-aminopyridin-3-yl)-1-(phenylsulfonyl)-1H-pyrrolo[2,3-b]pyridin-3-yl)-6-chloro-N-cyclohexylpyridin-2-amine Example 245a (0.14 g) was prepared as described in Example 171b, substituting 1-(phenylsulfonyl)-4-(4,4,5,5-tetramethyl-1,3,2-dioxaborolan-2-yl)-1H-pyrazole with 5-(4,4,5,5-tetramethyl-1,3,2-dioxaborolan-2-yl)pyridin-2-amine MS (APCI$^+$) m/z 559.4 (M+H)$^+$.

Example 245b

4-[5-(6-aminopyridin-3-yl)-1H-pyrrolo[2,3-b]pyridin-3-yl]-6-chloro-N-cyclohexylpyridin-2-amine Example 245b (0.053 g) was prepared as described in Example 171c, substituting Example 171b with Example 245a. $^1$H NMR (300 MHz, DMSO-d$_6$) ppm 1.11-1.43 (m, 5H) 1.55-1.66 (m, 1H) 1.67-1.79 (m, 2H) 1.90-2.00 (m, 2H) 3.62-3.76 (m, 1H) 6.03 (s, 2H) 6.58 (d, J=7.80 Hz, 1H) 6.76 (d, J=7.80 Hz, 1H) 6.90 (d, J=7.12 Hz, 2H) 7.74-7.80 (m, 1H) 8.14 (s, 1H) 8.29-8.37 (m, 2H) 8.47 (s, 1H) 12.14 (s, 1H). MS (ESI$^+$) m/z 419.2 (M+H)$^+$.

Example 246

N-(trans-4-{[6-chloro-4-(5-methoxy-1H-pyrrolo[2,3-b]pyridin-3-yl)pyridin-2-yl]amino}cyclohexyl)glycinamide

Example 246a tert-butyl 2-((trans)-4-(6-chloro-4-iodopyridin-2-ylamino)cyclohexylamino)-2-oxoethylcarbamate A mixture of Example 213a (3.950 g, 11.23 mmol), 2-(tert-butoxycarbonylamino)acetic acid (2.165 g, 12.36 mmol), HOBT (1.892 g, 12.36 mmol), EDC (2.369 g, 12.36 mmol), and triethylamine (2.04 mL, 14.6 mmol) in tetrahydrofuran (100 mL) was stirred at room temperature for 3 hours. The reaction was diluted with 50% brine and extracted with EtOAc (2×). The combined organic layers were dried over MgSO$_4$, filtered, and concentrated. The residue was triturated with EtOAc/hexane (8:2) to give 2.756 g of the title compound. The filtrate was purified on an 80 g column using the ISCO Companion flash system eluting with EtOAc/hexane (7:3 to 8:2) to give the 1.091 g more title compound.

Example 246b tert-butyl 2-((trans)-4-(6-chloro-4-(4,4,5,5-tetramethyl-1,3,2-dioxaborolan-2-yl)pyridin-2-ylamino)cyclohexylamino)-2-oxoethylcarbamate A mixture of Example 246a (1.400 g, 2.75 mmol), bis(pinacolato)diboron (1.048 g, 4.13 mmol), potassium acetate (0.405 g, 4.13 mmol), and PdCl$_2$(dppf)-CH$_2$Cl$_2$ (0.090 g, 0.110 mmol) in DMF (50 mL) was degassed and heated at 80° C. for 2 hours. After cooling, the reaction mixture was treated with water and brine and extracted by EtOAc (2×). The combined organic layers were washed with 20% brine, dried over MgSO$_4$, filtered, concentrated, and purified on an 80 g column using the ISCO Companion flash system eluting with hexane/EtOAc (1:9) to 100% EtOAc to give 0.831 g of the title compound.

Example 246c tert-butyl 2-((trans)-4-(6-chloro-4-(5-methoxy-1-(phenylsulfonyl)-1H-pyrrolo[2,3-b]pyridin-3-yl)pyridin-2-ylamino)cyclohexylamino)-2-oxoethylcarbamate A mixture of Example 246b (0.420 g, 0.825 mmol), Example 149b (0.318 g, 0.867 mmol), saturated NaHCO$_3$ (6 mL), and PdCl$_2$(dppf)-CH$_2$Cl$_2$ (0.034 g, 0.041 mmol) in DMF (24 mL) was degassed and heated at 65° C. for 2 hours. After cooling, the reaction was quenched with 20% brine and extracted with EtOAc (2×). The combined organic layers were washed with 20% brine, concentrated and purified on a 40 g column using the ISCO Companion flash system eluting with hexane/EtOAc (2:8 to 1:9) to give 0.277 g of the title compound.

Example 246d tert-butyl 2-((1r,4r)-4-(6-chloro-4-(5-methoxy-1H-pyrrolo[2,3-b]pyridin-3-yl)pyridin-2-ylamino)cyclohexylamino)-2-oxoethylcarbamate A solution example 246c (1.616 g, 2.415 mmol) in dioxane (12 mL) was treated with 20% NaOH (1.5 mL, 2.415 mmol). The mixture was heated at 80° C. for 1 hr. Most of the solvent was evaporated. Water was added to the resulting slurry slowly. The precipitate formed was filtered, washed with water, and oven-dried to give 0.953 g of the title compound.

Example 246e

N-(trans-4-{[6-chloro-4-(5-methoxy-1H-pyrrolo[2,3-b]pyridin-3-yl)pyridin-2-yl]amino}cyclohexyl)glycinamide A suspension of example 246d (0.953 g, 1.801 mmol) in CH$_2$Cl$_2$ (15 mL) was treated with trifluoroacetic acid (3.0 mL, 38.9 mmol). The mixture was stirred at room temperature for 60 minutes and concentrated. The residue was treated with MeOH and concentrated to give 1.487 g of the title compound as trifluoroacetic acid salts. $^1$H NMR (400 MHz, CD$_3$OD) ppm 1.31-1.56 (m, 4H), 2.02 (d, J=11.60 Hz, 2H), 2.16 (d, J=11.29 Hz, 2H), 3.64 (s, 2H), 3.69-3.84 (m, 2H), 3.96 (s, 3H), 6.80 (s, 1H), 6.90 (d, J=1.22 Hz, 1H), 7.89-7.94 (m, 2H), 8.08 (d, J=2.44 Hz, 1H). MS (DCI$^+$) m/z 429.3 (M+H)$^+$.

Example 247

6-chloro-N-cyclohexyl-4-(4-methoxy-1H-pyrrolo[2,3-b]pyridin-3-yl)pyridin-2-amine

Example 247a 3-iodo-4-methoxy-1-(phenylsulfonyl)-1H-pyrrolo[2,3-b]pyridine

A solution of 3-iodo-4-methoxy-1H-pyrrolo[2,3-b]pyridine (0.30 g, 1.08 mmol) in dimethylformamide (10 mL) at 0° C. was treated with sodium hydroxide (0.056 g, 1.41 mmol) for 15 minutes. To the material was added benzenesulfonyl chloride (0.25 g, 1.41 mmol) dropwise and stirred at room temperature for 3 hours. The material was diluted with water (40 mL), filtered, and dried in vacuo at 50° C. to afford 0.35 g of the title compound. MS (ESI) m/z 414.9 (M+H)$^+$.

Example 247b 6-chloro-N-cyclohexyl-4-(4-methoxy-1-(phenylsulfonyl)-1H-pyrrolo[2,3-b]pyridin-3-yl)pyridin-2-amine Example 247b (0.10 g) was prepared as described in Example 171a, substituting 5-bromo-3-iodo-1-(phenylsulfonyl)-1H-pyrrolo[2,3-b]pyridine with Example 247a. MS (APCI$^+$) m/z 497.4 (M+H)$^+$.

Example 247c 6-chloro-N-cyclohexyl-4-(4-methoxy-1H-pyrrolo[2,3-b]pyridin-3-yl)pyridin-2-amine Example 247c (0.042 g) was prepared as described in Example 171c, substituting Example 171b with Example 247b. $^1$H NMR (300 MHz, DMSO-d$_6$) ppm 1.08-1.43 (m, 5H) 1.54-1.66 (m, 1H) 1.67-1.79 (m, 2H) 1.86-1.98 (m, 2H) 3.49-3.66 (m, 1H) 3.93 (s, 3H) 6.66 (d, J=7.93 Hz, 1H) 6.69-6.78 (m, 3H) 7.67-7.71 (m, 1H) 8.16 (d, J=5.55 Hz, 1H) 12.00 (s, 1H). MS (ESI$^+$) m/z 357.2 (M+H)$^+$.

Example 248

1-{3-[2-chloro-6-(cyclohexylamino)pyridin-4-yl]-1H-pyrrolo[2,3-b]pyridin-5-yl}-3-ethylurea

Example 248a

1-Ethyl-3-(3-iodo-1-(phenylsulfonyl)-1H-pyrrolo[2,3-b]pyridine-5-yl)urea

To a suspension of Example 226a (120 mg, 0.234 mmol) in 5 mL dichloromethane was added triethylamine (0.326 mL, 2.34 mmol) followed by addition of ethyl isocyanate (0.074 mL, 0.935 mmol). The reaction mixture was stirred 16 hours at room temperature and then concentrated to dryness. The residue was partitioned with sodium bicarbonate solution and ethyl acetate. The organics were concentrated to dryness and the residue purified by silica gel flash chromatography eluting with 15% ethyl acetate, 85% dichloromethane to give the title compound as a pink-brown powder in quantitative yield. MS (ESI$^+$) m/z 471.0 (M+H)$^+$.

Example 248b 1-(3-(2-chloro-6-(cyclohexylamino)pyridine-4-yl)-1-(phenylsulfonyl)-1H-pyrrolo[2,3-b]pyridine-5-yl)-3-ethylurea Example 248b was prepared as described in Example 168c substituting Example 168b with Example 248a to give the title compound as a dark brown powder in 68% yield. MS (ESI$^+$) m/z 553.2 (M+H)$^+$.

Example 248c

1-{3-[2-chloro-6-(cyclohexylamino)pyridin-4-yl]-1H-pyrrolo[2,3-b]pyridin-5-yl}-3-ethylurea Example 248c was prepared as described in Example 168d substituting Example 168c with Example 248b to give the title compound as a brown powder in 73% yield. MS (ESI+) m/z 413.2 (M+H)+; $^1$H NMR (300 MHz, DMSO-$d_6$) ppm 1.06 (t, 3H, J=7.02 Hz) 1.15-1.26 (m, 3H) 1.31-1.42 (m, 2H) 1.56-1.63 (m, 1H) 1.69-1.76 (m, 2H) 1.86-1.96 (m, 2H) 3.13 (dt, 2H, J=12.82, 7.02 Hz) 3.60-3.69 (m, 1H) 6.19 (t, 1H, J=5.80 Hz) 6.71 (s, 1H) 6.78 (s, 1H) 6.82 (d, 1H, J=7.93 Hz) 7.99 (s, 1H) 8.20 (d, 1H, J=2.14 Hz) 8.37 (d, 1H, J=2.14 Hz) 8.47 (s, 1H) 11.95 (bs, 1H).

Example 249

N-(trans-4-{[6-chloro-4-(1H-pyrrolo[2,3-b]pyridin-3-yl)pyridin-2-yl]amino}cyclohexyl)-1-(pyridin-4-ylmethyl)azetidine-3-carboxamide Example 249 (0.01 g) was prepared as described in Example 93, substituting formaldehyde with isonicotinaldehyde and substituting Example 61b with Example 160b. $^1$H NMR (300 MHz, DMSO-$d_6$) ppm 1.14-1.38 (m, 4H) 1.75-1.89 (m, 2H) 1.93-2.10 (m, 2H) 3.10-3.27 (m, 3H) 3.36-3.53 (m, 2H) 3.50-3.78 (m, 4H) 6.76 (d, J=7.80 Hz, 1H) 6.86 (d, J=3.05 Hz, 2H) 7.11-7.29 (m, 2H) 7.33 (d, J=7.80 Hz, 1H) 7.66-7.86 (m, 2H) 8.12 (d, J=2.71 Hz, 1H) 8.24-8.37 (m, 2H) 8.41-8.54 (m, 1H) 12.02-12.27 (m, 1H). MS (ESI+) m/z 516.3 (M+H)+.

Example 250

N-(trans-4-{[6-chloro-4-(1H-pyrrolo[2,3-b]pyridin-3-yl)pyridin-2-yl]amino}cyclohexyl)-1-(piperidin-4-yl)azetidine-3-carboxamide Example 250 (0.05 g) was prepared as described in Example 93, substituting formaldehyde with tert-butyl 4-oxopiperidine-1-carboxylate and substituting Example 61b with Example 160b. The intermediate material was taken up in methanol and treated with 2N HCl in ether. The solid was filtered to give the title compound as an HCl salt. $^1$H NMR (300 MHz, DMSO-$d_6$) ppm 1.13-1.41 (m, 5H) 1.63-1.80 (m, 3H) 1.79-1.95 (m, 3H) 1.93-2.17 (m, 3H) 2.75-2.94 (m, 2H) 2.94-3.07 (m, 2H) 3.29-3.66 (m, 3H) 3.91-4.27 (m, 2H) 6.84-6.92 (m, 2H) 7.22-7.30 (m, 1H) 8.15 (d, J=2.71 Hz, 1H) 8.23 (d, J=7.46 Hz, 1H) 8.33 (dd, J=4.75, 1.36 Hz, 1H) 8.39 (d, J=8.14 Hz, 1H) 8.66-9.09 (m, H) 9.27 (s, 1H) 11.95 (s, 1H) 12.31 (s, 1H). MS (ESI+) m/z 508.3 (M+H)+.

Example 251

N-(trans-4-{[6-chloro-4-(5-methoxy-1H-pyrrolo[2,3-b]pyridin-3-yl)pyridin-2-yl]amino}cyclohexyl)-$N^2$-cyclohexylglycinamide

Example 251a 2-chloro-N-((trans)-4-(6-chloro-4-(5-methoxy-1H-pyrrolo[2,3-b]pyridin-3-yl)pyridin-2-ylamino)cyclohexyl)acetamide A mixture of Example 213f (650.0 mg, 1.748 mmol), 2-chloroacetic acid (248 mg, 2.62 mmol), HOBT (535 mg, 3.50 mmol), EDC (670 mg, 3.50 mmol), and triethylamine (0.487 mL, 3.50 mmol) in DMF (30 mL) was stirred at room temperature for 3 hours. Water was added the mixture. The solids formed were filtered, washed with water, and oven-dried to 0.760 g of the title compound.

Example 251b

N-(trans-4-{[6-chloro-4-(5-methoxy-1H-pyrrolo[2,3-b]pyridin-3-yl)pyridin-2-yl]amino}cyclohexyl)-$N^2$-cyclohexylglycinamide A mixture of Example 251a (50.0 mg, 0.112 mmol), cyclohexanamine (0.038 mL, 0.335 mmol) and triethylamine (0.054 mL, 0.39 mmol) in DMF (1.0 mL) was stirred at 60° C. for 2.5 hours. The reaction mixture was concentrated and purified by reverse-phase HPLC as described in Example 56 to give the title compound (44.6 mg) as trifluoroacetic acid salts. $^1$H NMR (400 MHz, $CD_3OD$) ppm 1.20-1.53 (m, 9H), 1.72 (m, 1H), 1.83-1.95 (m, 2H), 1.98-2.25 (m, 6H), 3.07 (m, 1H), 3.67-3.84 (m, 4H), 3.96 (s, 3H), 6.80 (d, J=1.53 Hz, 1H), 6.89 (d, J=1.22 Hz, 1H), 7.87-7.94 (m, 2H), 8.08 (d, J=2.44 Hz, 1H). MS (DCI+) m/z 511.3 (M+H)+.

Example 252

6-chloro-N-[4-(1-cyclobutylpiperidin-4-yl)cyclohexyl]-4-(5-methoxy-1H-pyrrolo[2,3-b]pyridin-3-yl)pyridin-2-amine Example 252 (0.021 g) was prepared as described in Example 93, substituting Example 61b with Example 236b and formaldehyde with cyclobutanone. The solvent was removed from the reaction and the residue diluted with ethyl acetate. The organics were washed with water, brine, dried over $MgSO_4$, filtered, and concentrated. The crude material was triturated with ethyl acetate, and the solid was filtered to give the title compound as the free base. $^1$H NMR (300 MHz, DMSO-$d_6$) ppm 0.87-1.30 (m, 7H) 1.35-1.86 (m, 16H) 1.87-2.14 (m, 3H) 2.74-2.97 (m, 2H) 3.92-4.04 (m, 1H) 6.67-6.77 (m, 1H) 6.81-6.94 (m, 2H) 7.82 (d, J=2.71 Hz, 1H) 8.08 (q, J=2.83 Hz, 2H) 12.02 (s, 1H). MS (ESI+) m/z 494.4 (M+H)+.

Example 253

N-(trans-4-{[6-chloro-4-(5-methoxy-1H-pyrrolo[2,3-b]pyridin-3-yl)pyridin-2-yl]amino}cyclohexyl)cyclohexanesulfonamide To a solution of Example 213f (80.0 mg, 0.215 mmol) in DMF (2 mL) was added triethylamine (0.090 mL, 0.645 mmol) and cyclohexanesulfonyl chloride (0.062 mL, 0.430 mmol). After consumption of the starting material, water was added to the reaction mixture. The solids formed were filtered, washed with water, and purified by reverse-phase HPLC as described in Example 56 to give the title compound (11.5 mg) as trifluoroacetic acid salts. $^1$H NMR (400 MHz, $CD_3OD$) ppm 1.14-1.77 (m, 10H), 1.82-1.96 (m, 2H), 2.00-2.22 (m, 6H), 2.88 (m, 1H), 3.22 (m, 1H), 3.74 (m, 1H), 3.96 (s, 3H), 6.84 (s, 1H), 6.95 (d, J=1.22 Hz, 1H), 7.92-7.98 (m, 2H), 8.09 (d, J=2.44 Hz, 1H). MS (APCI+) m/z 518.4 (M+H)+.

Example 254

N-(trans-4-{[6-chloro-4-(5-methoxy-1H-pyrrolo[2,3-b]pyridin-3-yl)pyridin-2-yl]amino}cyclohexyl)-2-(morpholin-4-yl)acetamide The trifluoroacetic acid salt of the title compound was prepared as described in Example 251b, substituting cyclohexanamine with morpholine. $^1$H NMR (400 MHz, CD3OD) ppm 1.28-1.56 (m, 4H), 2.03 (d, J=12.21 Hz, 2H), 2.16 (d, J=11.60 Hz, 2H), 3.77 (m, 1H), 3.94 (s, 2H), 3.96 (s, 3H), 6.81 (s, 1H), 6.91 (d, J=1.22 Hz, 1H), 7.86-7.96 (m, 2H), 8.09 (d, J=2.44 Hz, 1H). MS (DCI$^+$) m/z 499.3 (M+H)$^+$.

Example 255

N-(3-{3-[2-chloro-6-(cyclohexylamino)pyridin-4-yl]-1H-pyrrolo[2,3-b]pyridin-5-yl}phenyl)acetamide Example 255a N-(3-(3-(2-chloro-6-cyclohexylamino)pyridine-4-yl-1-(phenylsulfonyl)-1H-pyrrolo[2,3-b]pyridin-5-yl)phenyl)acetamide To a solution of Example 221a (140 mg, 0.256 mmol) in 8 mL anhydrous DMF was added 3-acetamidophenylboronic acid (50 mg, 0.28 mmol). The solution was degassed with nitrogen and sodium bicarbonate (215 mg, 2.56 mmol) was added as a suspension in 2 mL water followed by the addition of 1,1' bis(diphenylphosphino)-ferrocene)dichloropalladium (II) complex with dichloromethane (21 mg, 0.026 mmol). The reaction mixture was heated at 65° C. for 3 hours and then cooled to room temperature and partitioned with water, ethyl acetate. The organics were combined, concentrated to dryness and the residue purified by silica gel flash chromatography eluting with 2% methanol, 98% dichloromethane to give the title compound as a brown powder in 72% yield. MS (ESI$^+$) m/z 600.2 (M+H)$^+$.

Example 255b

N-(3-{3-[2-chloro-6-(cyclohexylamino)pyridin-4-yl]-1H-pyrrolo[2,3-b]pyridin-5-yl}phenyl)acetamide Example 255b was prepared as described for Example 168d substituting Example 168c with Example 255a to give the title compound as an off-white powder in 47% yield. MS (ESI$^+$) m/z 460.3 (M+H)$^+$; $^1$H NMR (300 MHz, DMSO-d$_6$) ppm 1.12-1.43 (m, 5H) 1.54-1.64 (m, 1H) 1.67-1.77 (m, 2H) 1.89-1.99 (m, 2H) 2.07 (s, 3H) 3.62-3.75 (m, 1H) 6.79 (d, 1H, J=7.8 Hz) 6.89 (s, 1H) 6.90 s, 1H) 7.39 (d, 1H, J=7.8 Hz) 7.44 (t, 1H, J=7.46 Hz) 7.68 (bd, 1H, J=7.46 Hz) 7.83 (s, 1H) 8.18 (s, 1H) 8.40 (d, 1H, J=2.03 Hz) 8.49 (d, 1H, J=2.03 Hz) 10.05 (bs, 1H) 12.25 (bs, 1H).

Example 256

N-{3-[2-chloro-6-(cyclohexylamino)pyridin-4-yl]-1H-pyrrolo[2,3-b]pyridin-5-yl}methanesulfonamide Example 256a N-(3-iodo-1-(phenylsulfonyl)-1H-pyrrolo[2,3-b]pyridin-5-yl)-N-(methylsulfonyl)methanesulfonamide compound with N-(3-iodo-1-(phenylsulfonyl)-1H-pyrrolo[2,3-b]pyridin-5-yl)methanesulfonamide To a suspension of Example 226a (118 mg, 0.23 mmol) in 4 mL dichloromethane was added triethylamine (0.64 mL, 4.6 mmol). The reaction flask was cooled in an ice bath and methanesulfonyl chloride (0.054 mL, 0.69 mmol) added. After stirring 10 minutes, the ice bath was removed and the reaction mixture stirred 2 days at room temperature. The solvent was evaporated to dryness to give a crude product that was a mixture of N-(3-iodo-1-(phenylsulfonyl)-1H-pyrrolo[2,3-b]pyridine-5-yl)methanesulfonamide and N-(3-iodo-1-(phenylsulfonyl)-1H-pyrrolo[2,3-b]pyridine-5-yl)-N-(methylsulfonyl)methansulfonamide that was carried on to the next step without purification.

Example 256b

N-(3-(2-chloro-6-(cyclohexylamino)pyridine-4-yl)-1-(phenylsulfonyl)-1H-pyrrolo[2,3-b]pyridine-5-yl)methanesulfonamide Example 256b was prepared as described for Example 168c substituting Example 168b with Example 256a to give the title compound as a brown powder in 74% yield. MS (ESI$^+$) m/z 560.2 (M+H)$^+$.

Example 256c

N-{3-[2-chloro-6-(cyclohexylamino)pyridin-4-yl]-1H-pyrrolo[2,3-b]pyridin-5-yl}methanesulfonamide Example 256c was prepared as described for Example 168d substituting Example 168c with Example 256b to give the title compound as a brown powder in 26% yield. MS (ESI$^+$) m/z 420.41 (M+H)$^+$; $^1$H NMR (300 MHz, DMSO-d$_6$) ppm 1.12-1.44 (m, 5H) 1.54-1.65 (m, 1H) 1.67-1.78 (m, 2H) 1.86-1.98 (m, 2H) 2.95 (s, 3H) 3.57-3.69 (m, 1H) 6.71 (s, 1H) 6.80 (s, 1H) 6.84 (d, 1H, J=7.8 Hz) 8.11 (s, 1H) 8.12 (s, 1H) 8.21 (d, 1H, J=2.37 Hz) 9.56 (bs, 1H) 12.23 (bs, 1H)

Example 257

N-{4-[(4-{[6-chloro-4-(5-methoxy-1H-pyrrolo[2,3-b]pyridin-3-yl)pyridin-2-yl]amino}cyclohexyl)methyl]cyclohexyl}pyridine-3-carboxamide A mixture of Example 237 (0.075 g, 0.160 mmol), nicotinic acid (0.049 g, 0.401 mmol), EDC (0.080 g, 0.417 mmol), HOBT (0.064 g, 0.417 mmol) and triethylamine (0.060 mL, 0.433 mmol) was stirred at room temperature overnight. The reaction mixture was treated with water and a precipitate was formed and filtered. The precipitate was purified by reversed-phase HPLC performed on a Zorbax RX-C18 column (250× 21.2 mm, 7 μm particle size) using a gradient of 10% to 100% acetonitrile: 0.1% aqueous trifluoroacetic acid over 40 minutes at a flow rate of 15 mL/minutes to give 16.7 mg (13%) of the title compound as trifluoroacetic acid salts.

$^1$H NMR (400 MHz, DMSO-d$_6$) ppm 1.06-1.88 (m, 12H), 2.01-2.14 (m, 4H), 3.96 (s, 3H), 6.80-6.81 (m, 1H), 6.88-6.92 (m, 2H), 7.71-7.76 (m, 1H), 7.87 (d, J=2.75 Hz, 1H), 7.90-7.91 (m, 2H), 8.06 (d, J=2.14 Hz, 1H), 8.46 (d, J=7.93, 1H), 8.76 (d, J=4.88 Hz, 1H), 9.04 (s, 1H). MS (DCI$^+$) m/z 573.4 (M+H)$^+$.

Example 258

N-(trans-4-{[6-chloro-4-(5-methoxy-1H-pyrrolo[2,3-b]pyridin-3-yl)pyridin-2-yl]amino}cyclohexyl)-N$^2$-(2,2-dimethylpropyl)glycinamide The trifluoroacetic acid salt of the title compound was prepared as described in Example 251b, substituting cyclohexanamine with 2,2-dimethylpropan-1-amine $^1$H NMR (400 MHz, CD$_3$OD) ppm 1.09 (s, 9H), 1.29-1.55 (m, 4H), 1.96-2.08 (m, 2H), 2.09-2.22 (m, 2H), 2.88 (s, 2H), 3.67-3.87

(m, 4H), 3.95 (s, 3H), 6.76 (s, 1H), 6.85 (d, J=1.22 Hz, 1H), 7.81-7.89 (m, 2H), 8.06 (d, J=2.75 Hz, 1H). MS (DCI$^+$) m/z 499.3 (M+H)$^+$.

Example 259

6-chloro-N-(4-{[4-(dimethylamino)cyclohexyl]methyl}cyclohexyl)-4-(5-methoxy-1H-pyrrolo[2,3-b]pyridin-3-yl)pyridin-2-amine A mixture of Example 237 (0.075 g, 0.160 mmol) and formaldehyde (8.83 µL, 0.320 mmol) in MeOH (2.5 mL) was stirred at room temperature for 30 minutes follow by addition of sodium cyanoborohydride (0.020 g, 0.320 mmol) and zinc chloride (0.655 mg, 4.81 µmol). The reaction mixture was left for 6 hours. Additionally, formaldehyde (7.2 µL) was added and reaction mixture was left overnight. The crude was concentrated. The residue was treated with saturated sodium bicarbonate and extracted with EtOAc (2×). The combined organic layers were dried with MgSO$_4$, filtered, concentrated and purified by reversed-phase HPLC performed on a Zorbax RX-C18 column (250×21.2 mm, 7 µm particle size) using a gradient of 10% to 100% acetonitrile: 0.1% aqueous trifluoroacetic acid over 40 minutes at a flow rate of 15 mL/minutes to give 10 mg (10%) of the title compound as trifluoroacetic acid salts. $^1$H NMR (400 MHz, DMSO-d$_6$) ppm 0.90-2.03 (m, 16H), 2.71-2.75 (m, 6H), 3.90-3.91 (m, 6H), 6.74 (s, 1H), 6.80 (s, 1H), 6.80 (s, 1H), 6.85-6.86 (m, 1H), 7.78-7.83 (m, 1H), 8.07-8.10 (m, 2H), 12.03 (s, 1H). MS (APCI$^+$) m/z 496.5 (M+H)$^+$.

Example 260

N-(3-{[6-chloro-4-(5-methoxy-1H-pyrrolo[2,3-b]pyridin-3-yl)pyridin-2-yl]amino}cyclohexyl)cyclopropanesulfonamide Example 260a N1-(6-chloro-4-iodopyridin-2-yl)cyclohexane-1,3-diamine A mixture of 2,6-dichloro-4-iodopyridine (2.500 g, 9.13 mmol) and cyclohexane-1,3-diamine (4.44 mL, 36.5 mmol) was heated at 120° C. in a capped vial for 2 hours. While warm, the reaction mixture was treated with EtOAc and washed with water (3×). The organic layer was dried and concentrated to give 2.62 g of the crude title compound. This material was carried into the next step without further purification.

Example 260b

N-(3-(6-chloro-4-iodopyridin-2-ylamino)cyclohexyl)cyclopropanesulfonamide

To a solution of Example 260a (0.320 g, 0.910 mmol) in DMF (6 mL) were added triethylamine (0.165 mL, 1.183 mmol) and cyclopropanesulfonyl chloride (0.102 mL, 1.001 mmol). The reaction mixture was stirred at room temperature overnight, quenched with brine and NaHCO$_3$ and extracted with EtOAc. The organic layer was dried over MgSO$_4$, filtered, concentrated, and purified on a 40 g column using the ISCO Companion flash system eluting with hexane/EtOAc (7:3 to 1:1) to give 0.092 g of the title compound.

Example 260c

N-(3-(6-chloro-4-(5-methoxy-1-(phenylsulfonyl)-1H-pyrrolo[2,3-b]pyridin-3-yl)pyridin-2-ylamino)cyclohexyl)cyclopropanesulfonamide A suspension of Example 149c (86.0 mg, 0.207 mmol), Example 260b (90.0 mg, 0.197 mmol), dichlorobis(triphenylphosphine)palladium(II) (5.54 mg, 7.90 µmol) and sodium carbonate (1M, 0.158 mL, 0.158 mmol) in dimethoxyethane/EtOH/water (7:2:3, 4.5 mL) was degassed and heated at 80° C. for 1.5 hours. The reaction mixture was cooled, treated with brine and NaHCO$_3$, and extracted with EtOAc (2×). The combined organic layers were dried over MgSO$_4$, filtered, concentrated, and purified on a 12 g column using the ISCO Companion flash system eluting with hexane/EtOAc (4:6 to 3:7) to give 86.0 mg of the title compound.

Example 260d

N-(3-{[6-chloro-4-(5-methoxy-1H-pyrrolo[2,3-b]pyridin-3-yl)pyridin-2-yl]amino}cyclohexyl)cyclopropanesulfonamide A solution of Example 260c (0.083 g, 0.135 mmol) in dioxane (2 mL) was treated with 20% NaOH (0.08 mL, 0.135 mmol). The mixture was heated at 70° C. for 90 minutes. The solvent was evaporated. The residue was treated with water and sonicated. The solid was filtered, washed with water, and purified by reverse-phase HPLC as described in Example 56 to give the title compound (43.2 mg) as trifluoroacetic acid salts. $^1$H NMR (400 MHz, DMSO-d$_6$) ppm 0.83-0.98 (m, 4H), 0.98-1.26 (m, 3H), 1.38 (m, 1H), 1.74 (m, 1H), 1.86-1.98 (m, 2H), 2.31 (d, J=13.43 Hz, 1H), 2.56 (m, 1H), 3.24 (m, 1H, 3.73 (m, 1H), 3.90 (s, 3H), 6.81 (s, 1H), 6.88 (d, J=1.22 Hz, 1H), 7.14 (d, J=8.24 Hz, 1H), 7.79 (d, J=2.75 Hz, 1H), 8.09 (dd, J=7.93, 2.75 Hz, 2H), 12.04 (s, 1H). MS (ESI$^+$) m/z 476.2 (M+H)$^+$.

Example 261

N-(3-{[6-chloro-4-(5-methoxy-1H-pyrrolo[2,3-b]pyridin-3-yl)pyridin-2-yl]amino}cyclohexyl)acetamide Example 261a tert-butyl 3-(6-chloro-4-iodopyridin-2-ylamino)cyclohexylcarbamate To a mixture of Example 260a (2.60 g, 7.39 mmol) and triethylamine (1.340 mL, 9.61 mmol) in tetrahydrofuran (50 mL) was added BOC$_2$O (1.78 g, 8.13 mmol) at 0° C. The ice bath was removed and the reaction was stirred at room temperature for 90 minutes. The reaction was diluted with EtOAc and washed with brine and sat. NaHCO$_3$. The organic layer was dried over MgSO$_4$, filtered, concentrated, and purified on an 80 g column using the ISCO Companion flash system eluting with hexane/EtOAc (8:2 to 6:4) to give 1.78 g of the title compound.

Example 261b tert-butyl 3-(6-chloro-4-(5-methoxy-1-(phenylsulfonyl)-1H-pyrrolo[2,3-b]pyridin-3-yl)pyridin-2-ylamino)cyclohexylcarbamate The title compound was prepared as described in Example 260c, substituting Example 260b with Example 261a.

Example 261c

N1-(6-chloro-4-(5-methoxy-1-(phenylsulfonyl)-1H-pyrrolo[2,3-b]pyridin-3-yl)pyridin-2-yl)cyclohexane-1,3-diamine A solution of Example 261b (1.76 g, 2.88 mmol) in CH$_2$Cl$_2$ (30 mL) was treated with trifluoroacetic acid (3.32 mL, 43.1 mmol). The mixture is stirred at room temperature for 3 hours and concentrated to give 2.34 of the title compound as trifluoroacetic acid salts.

Example 261d

N-(3-{[6-chloro-4-(5-methoxy-1H-pyrrolo[2,3-b]pyridin-3-yl)pyridin-2-yl]amino}cyclohexyl)acetamide A mixture of Example 261c (0.160 g, 0.216 mmol), acetic acid (0.019 mL, 0.324 mmol), HOBT (0.050 g, 0.324 mmol), EDC (0.062 g, 0.324 mmol), and triethylamine (0.151 mL, 1.081 mmol) in DMF (2.5 mL) was stirred at room temperature for 4 hours. Water was added the mixture. The solids formed were filtered, washed with water, and oven-dried to give the crude intermediate. This intermediate was dissolved in dioxane (2 mL) and treated with 20% NaOH (0.070 mL). The mixture was heated at 60° C. for 2.5 hours and concentrated. The residue was treated with water, filtered, washed with water, and purified by reverse-phase HPLC as described in Example 56 to give the title compound (28.4 mg) as trifluoroacetic acid salts. $^1$H NMR (500 MHz, DMSO-d$_6$) ppm 0.98-1.15 (m, 3H), 1.37 (m, 1H), 1.67-1.85 (m, 5H), 1.95 (d, J=11.29 Hz, 1H), 2.10 (d, J=11.60 Hz, 1H), 3.60-3.68 (m, 2H), 3.90 (s, 3H), 6.80 (s, 1H), 6.87 (s, 1H), 7.72-7.81 (m, 2H), 8.09 (dd, J=10.83, 2.90 Hz, 2H), 12.04 (s, 1H). MS (DCI$^+$) m/z 414.2 (M+H)$^+$.

Example 262

N-(3-{[6-chloro-4-(5-methoxy-1H-pyrrolo[2,3-b]pyridin-3-yl)pyridin-2-yl]amino}cyclohexyl)thiophene-2-sulfonamide A mixture of Example 261c (0.200 g, 0.270 mmol), thiophene-2-sulfonyl chloride (0.059 g, 0.324 mmol), and triethylamine (188 μL, 1.351 mmol) in DMF (2.5 mL) was stirred at room temperature for 3 hours. Water was added the mixture. The solids formed were filtered, washed with water, and oven-dried to give the desired intermediate. A mixture of the intermediate in dioxane (2 mL) and 20% NaOH (0.080 mL) was heated at 60° C. for 2.5 hours. The mixture was concentrated and the residue was treated with water, filtered, washed with water, and purified by reverse-phase HPLC as described in Example 56 to give the title compound (40.4 mg) as trifluoroacetic acid salts. $^1$H NMR (500 MHz, DMSO-d$_6$) ppm 0.94-1.18 (m, 3H), 1.30 (m, 1H), 1.68 (d, J=10.98 Hz, 2H), 1.89 (d, J=11.90 Hz, 1H), 2.00 (d, J=12.21 Hz, 1H), 3.18 (m, 1H), 3.64 (m, 1H), 3.90 (s, 3H), 6.76 (s, 1H), 6.87 (s, 1H), 7.11 (m, 1H), 7.60 (m, 1H), 7.78 (d, J=2.44 Hz, 1H), 7.85 (d, J=4.27 Hz, 1H), 7.95 (d, J=7.63 Hz, 1H), 8.09 (dd, J=7.02, 2.75 Hz, 2H), 12.06 (s, 1H). MS (ESI$^+$) m/z 518.1 (M+H)$^+$.

Example 263

N-(3-{[6-chloro-4-(5-methoxy-1H-pyrrolo[2,3-b]pyridin-3-yl)pyridin-2-yl]-amino}cyclohexyl)-2-(pyrrolidin-1-yl)acetamide The trifluoroacetic acid salt of the title compound was prepared as described in Example 261d, substituting acetic acid with 2-(pyrrolidin-1-yl)acetic acid. $^1$H NMR (500 MHz, DMSO-d$_6$) ppm 1.13 (q, J=11.70 Hz, 3H), 1.42 (q, J=13.43 Hz, 1H), 1.71-2.04 (m, 7H), 2.18 (d, J=11.60 Hz, 1H), 2.93-3.08 (m, 2H), 3.47-3.61 (m, 2H), 3.69-3.82 (m, 2H), 3.91 (s, 3H), 3.96 (d, J=4.88 Hz, 2H), 6.82 (s, 1H), 6.88 (s, 1H), 7.79 (d, J=2.75 Hz, 1H), 8.09 (dd, J=10.07, 2.75 Hz, 2H), 8.46 (d, J=7.93 Hz, 1H), 9.92 (s, 1H), 12.06 (s, 1H). MS (ESI$^+$) m/z 483.3 (M+H)$^+$.

Example 264

N-[4-chloro-6-(1H-pyrrolo[2,3-b]pyridin-3-yl)pyrimidin-2-yl]cyclohexane-1,2-diamine A mixture of Example 42b (160 mg, 0.356 mmol), cyclohexane-1,2-diamine (81 mg, 0.713 mmol), triethylamine (0.10 ml, 0.713 mmol) and dioxane (4 ml) was heated at 60° C. for 2 hours. The reaction mixture was concentrated in vacuo. To a mixture of the residue in methanol (10 mL) was added dropwise NaOH solution (1.43 ml, 1.43 mmol). The mixture was stirred at room temperature for 40 minutes. The reaction mixture was neutralized with dilute hydrochloric acid and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. MS (ESI) m/e 343 (M+H)$^+$; $^1$H NMR (400 MHz, DMSO-d$_6$) ppm 1.13-1.43 (m, 4H) 1.55-1.77 (m, 4H) 2.03-2.14 (m, 1H) 2.62-2.71 (m, 1H) 6.98-7.06 (m, 1H) 7.06-7.11 (m, 1H) 7.15-7.21 (m, 1H) 8.28 (dd, J=4.73, 1.68 Hz, 1H) 8.32-8.37 (m, 1H) 8.74-8.85 (m, 1H).

Example 265

4-chloro-6-(1H-pyrrolo[2,3-b]pyridin-3-yl)-N-(tetrahydrofuran-2-ylmethyl)pyrimidin-2-amine The trifluoroacetic acid salt of Example 265 was prepared as described in Example 42c substituting trans-cyclohexane-1,4-diamine with (tetrahydrofuran-2-yl)methanamine MS (ESI) m/e 330 (M+H)$^+$; $^1$H NMR (400 MHz, DMSO-d$_6$) ppm 1.61-2.01 (m, 4H) 3.39-3.55 (m, 2H) 3.60-3.70 (m, 1H) 3.76-3.85 (m, 1H) 4.03-4.12 (m, 1H) 7.11 (s, 1H) 7.18 (dd, J=7.93, 4.58 Hz, 1H) 8.28 (dd, J=4.58, 1.53 Hz, 1H) 8.35 (s, 1H) 8.80 (dd, J=7.93, 1.22 Hz, 1H) 12.02 (s, 1H).

Example 266

4-chloro-N-(pyridin-4-ylmethyl)-6-(1H-pyrrolo[2,3-b]pyridin-3-yl)pyrimidin-2-amine Example 266 was prepared as described in Example 264 substituting cyclohexane-1,2-diamine with pyridin-4-ylmethanamine. MS (ESI) m/e 337 (M+H)$^+$; $^1$H NMR (400

MHz, DMSO-d$_6$) ppm 4.63 (d, J=6.10 Hz, 2H) 7.09 (dd, J=7.78, 4.73 Hz, 1H) 7.16 (s, 1H) 7.37 (d, J=5.80 Hz, 2H) 7.82 (t, J=5.80 Hz, 1H) 8.25 (dd, J=4.58, 1.53 Hz, 1H) 8.33 (s, 1H) 8.46-8.50 (m, 2H) 8.53 (s, 1H) 12.01 (s, 1H).

Example 267

4-chloro-N-(pyridin-3-ylmethyl)-6-(1H-pyrrolo[2,3-b]pyridin-3-yl)pyrimidin-2-amine Example 267 was prepared as described in Example 264 substituting cyclohexane-1,2-diamine with pyridin-3-yl-methanamine MS (ESI) m/e 337 (M+H)$^+$; $^1$H NMR (400 MHz, DMSO-d$_6$) ppm 4.63 (d, J=6.10 Hz, 2H) 7.11 (dd, J=7.93, 4.88 Hz, 1H) 7.15 (s, 1H) 7.31 (dd, J=7.48, 4.43 Hz, 1H) 7.72-7.83 (m, 2H) 8.26 (dd, J=4.58, 1.53 Hz, 1H) 8.34 (s, 1H) 8.42 (dd, J=4.58, 1.53 Hz, 1H) 8.58-8.67 (m, J=1.53 Hz, 2H) 12.02 (s, 1H).

Example 268

4-chloro-N-(pyridin-2-ylmethyl)-6-(1H-pyrrolo[2,3-b]pyridin-3-yl)pyrimidin-2-amine Example 268 was prepared as described in Example 264 substituting cyclohexane-1,2-diamine with pyridin-2-yl-methanamine. MS (ESI) m/e 337 (M+H)$^+$; $^1$H NMR (400 MHz, DMSO-d$_6$) ppm 4.71 (d, J=6.10 Hz, 2H) 7.09 (dd, J=7.93, 4.58 Hz, 1H) 7.14 (s, 1H) 7.21 (dd, J=7.32, 4.88 Hz, 1H) 7.39 (d, J=7.63 Hz, 1H) 7.64-7.76 (m, 2H) 8.25 (dd, J=4.58, 1.53 Hz, 1H) 8.33 (s, 1H) 8.49-8.64 (m, 2H) 11.97 (s, 1H).

Example 269

4-chloro-N,N-dimethyl-6-(1H-pyrrolo[2,3-b]pyridin-3-yl)pyrimidin-2-amine

A mixture of 1-(phenylsulfonyl)-3-(4,4,5,5-tetramethyl-1,3,2-dioxaborolan-2-yl)-1H-pyrrolo[2,3-b]pyridine (120 mg, 0.31 mmol), 4,6-dichloro-N,N-dimethylpyrimidin-2-amine (66 mg, 0.34 mmol), tetrakis(triphenylphosphine)palladium (14 mg, 0.012 mmol), Cs$_2$CO$_3$ (0.16 mL, 0.31 mmol) and DME/DMF (9/1, 1 mL) in a pressure tube was evacuated under vacuo and refilled with nitrogen. The mixture was heated at 80° C. for 30 min, cooled to room temperature, filtered to collect the solids then washed with hexane. To a mixture of the solids (130 mg) in dioxone (1.5 mL) was added dropwise NaOH solution (20%, 0.3 mL) and stirred at 100° C. for 2 hours. The reaction mixture was neutralized with dilute hydrochloric acid and purified by reverse-phase HPLC performed on a Phenomenex Luna C8 AXIA column (30×75 mm, 100 Å) using a gradient of 10% to 95% acetonitrile: 0.1% aqueous trifluoroacetic acid over 12 minutes at a flow rate of 50 mL/minutes to give the title compound to afford the trifluoroacetic acid salt of the title compound (20 mg, 23% yield). MS (ESI) m/e 274 (M+H)$^+$; $^1$H NMR (400 MHz, DMSO-d$_6$) ppm 3.22 (s, 6H) 7.11 (s, 1H) 7.20 (dd, J=7.93, 4.58 Hz, 1H) 8.29 (dd, J=4.58, 1.53 Hz, 1H) 8.37 (s, 1H) 8.71 (dd, J=7.93, 1.53 Hz, 1H) 12.04 (s, 1H).

Example 270

N-(3-{[4-chloro-6-(1H-pyrrolo[2,3-b]pyridin-3-yl)pyrimidin-2-yl]amino}cyclohexyl)acetamide Example 270a N1-(4-chloro-6-(1-(phenylsulfonyl)-1H-pyrrolo[2,3-b]pyridin-3-yl)pyrimidin-2-yl)cyclohexane-1,3-diamine A mixture of Example 42b (1 g, 2.23 mmol), cyclohexane-1,3-diamine (0.509 g, 4.46 mmol) and triethylamine (0.62 mL, 4.46 mmol) in dioxane (25 mL) was heated at 60° C. for 2 hours. The reaction mixture was concentrated and used directly for the next step.

Example 270b

N-(3-{[4-chloro-6-(1H-pyrrolo[2,3-b]pyridin-3-yl)pyrimidin-2-yl]amino}cyclohexyl)acetamide To a mixture of Example 270a (875 mg, crude, ~1.035 mmol) and acetyl chloride (98 mg, 1.242 mmol) in THF (5 mL) was added dropwise Hunig's base (0.362 mL, 2.070 mmol), stirred at room temperature for 1 day then concentrated in vacuo. To the residue was added dioxane (10 mL) and NaOH (20%, 1 mL) and heated at 80° C. for 2 h. The reaction mixture was concentrated and purified by reverse-phase HPLC performed on a Phenomenex Luna C8 AXIA column (30×75 mm, 100 Å) using a gradient of 10% to 95% acetonitrile: 0.1% aqueous trifluoroacetic acid over 12 minutes at a flow rate of 50 mL/minutes to provide the trifluoroacetic acid of the title compound (18 mg, 0.047 mmol, 5% yield). MS (DCI) m/e 385 (M+H)$^+$; $^1$H NMR (400 MHz, DMSO-d$_6$) ppm 1.06-1.48 (m, 4H) 1.78 (s, 3H) 1.79-1.88 (m, 2H) 1.94-2.02 (m, 1H) 2.15-2.24 (m, J=11.60 Hz, 1H) 3.65-3.76 (m, 1H) 3.80-3.91 (m, 1H) 7.08 (s, 1H) 7.21 (dd, J=7.93, 4.58 Hz, 1H) 7.44 (d, J=7.32 Hz, 1H) 8.28 (dd, J=4.73, 1.68 Hz, 1H) 8.35 (s, 1H) 8.73-8.81 (m, 1H) 12.02 (s, 1H).

Example 271

N-(trans-4-{[4-chloro-6-(1H-pyrrolo[2,3-b]pyridin-3-yl)pyrimidin-2-yl]amino}cyclohexyl)cyclopropanecarboxamide A mixture of Example 42c (120 mg, 0.35 mmol), cyclopropanecarbonyl chloride (36.6 mg, 0.35 mmol), and Hunig's base (0.18 mL, 1.05 mmol) in THF (2.5 mL) was stirred at room temperature for 16 hours. The reaction mixture was concentrated and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to provide title compound (20 mg, 0.049 mmol, 14% yield). MS (ESI) m/e 411 (M+H)$^+$; $^1$H NMR (400 MHz, DMSO-d$_6$) ppm 0.56-0.64 (m, 2H) 0.65-0.72 (m, 2H) 1.30-1.47 (m, 4H) 1.49-1.59 (m, 1H) 1.84-1.95 (m, J=6.41 Hz, 2H) 2.00-2.10 (m, 2H) 3.51-3.66 (m, 1H) 3.73-3.86 (m, J=7.63 Hz, 1H) 7.03 (d, J=7.63 Hz, 1H) 7.08 (s, 1H) 7.18 (dd, J=7.93, 4.58 Hz, 1H) 7.54-7.64 (m, 1H) 8.27-8.31 (m, 1H) 8.34 (s, 1H) 8.79 (d, J=7.63 Hz, 1H) 12.00 (s, 1H).

Example 272

N-(3-{[4-chloro-6-(1H-pyrrolo[2,3-b]pyridin-3-yl)pyrimidin-2-yl]amino}cyclohexyl)cyclopropanecarboxamide To a mixture of Example 270a (350 mg, crude, ~0.414 mmol) and cyclopropanecarbonyl chloride (43.3 mg, 0.414 mmol), Hunig's base (0.217 mL, 1.242 mmol) in THF (4 ml) was stirred at room temperature for 2 hours and then concentrated in vacuo. To the residue was added dioxane (5 mL) and NaOH (20%, 0.8 mL) and heated at 90° C. for 3 hours. The reaction mixture was concentrated and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound (13 mg, 7.6% yield). MS (ESI) m/e 411 (M+H)$^+$; $^1$H NMR (400 MHz, DMSO-d$_6$) ppm 0.54-0.63 (m, 2H) 0.63-0.72 (m, 2H) 1.09-1.58 (m, 5H) 1.73-1.88 (m, 2H) 1.97 (s, 1H) 2.18 (s, 1H) 3.68-3.78 (m, 1H) 3.79-3.92 (m, J=7.93 Hz, 1H) 7.04-7.13 (m, 2H) 7.19 (dd, J=7.93, 4.58 Hz, 1H) 7.57-7.69 (m, 1H) 8.27 (dd, J=4.73, 1.37 Hz, 1H) 8.34 (s, 1H) 8.75 (d, J=7.93 Hz, 1H) 12.00 (s, 1H).

Example 273

N-(3-{[4-chloro-6-(1H-pyrrolo[2,3-b]pyridin-3-yl)pyrimidin-2-yl]amino}cyclohexyl)methanesulfonamide Example 273 was prepared as described in Example 272 substituting cyclopropanecarbonyl chloride with methanesulfonyl chloride to give the title compound. MS (ESI) m/e 421 (M+H)$^+$; $^1$H NMR (400 MHz, DMSO-d$_6$) ppm 1.13-2.02 (m, 8H) 2.26-2.34 (m, 1H) 2.87-2.91 (m, 3H) 3.24-3.37 (m, 1H) 7.04-7.15 (m, 2H) 7.16-7.24 (m, 1H) 8.25-8.30 (m, 1H) 8.34 (s, 1H) 8.73-8.84 (m, J=10.99 Hz, 1H) 12.01 (s, 1H) 12.01 (s, 1H).

Example 274

N-[4-chloro-6-(1H-pyrrolo[2,3-b]pyridin-3-yl)pyrimidin-2-yl]-N'-cyclobutylcyclohexane-1,3-diamine To a solution of Example 270a (350 mg, crude, ~0.414 mmol) in MeOH (5 mL) was added cyclobutanone (29.0 mg, 0.414 mmol) and the solution was stirred at room temperature for 10 minutes before NaCNBH$_3$ (52.0 mg, 0.828 mmol) and zinc chloride (0.6 mg, 0.004 mmol) were added. The reaction mixture was stirred at room temperature overnight and concentrated in vacuo. To the residue was added dioxone (5 mL) and NaOH (20%, 1 mL) and stirred at 90° C. for 1 hour. The reaction mixture was concentrated and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to provide the title compound (26 mg, 0.066 mmol, 16% yield). MS (ESI) m/e 397 (M+H)$^+$; $^1$H NMR (400 MHz, DMSO-d$_6$) ppm 0.95-2.21 (m, 16H) 2.55-2.65 (m, 1H) 3.26-3.36 (m, 1H) 3.79-3.92 (m, 1H) 7.07 (s, 1H) 7.11 (d, J=7.63 Hz, 1H) 7.17 (dd, J=7.93, 4.58 Hz, 1H) 8.29 (dd, J=4.73, 1.68 Hz, 1H) 8.34 (s, 1H) 8.77 (d, J=7.63 Hz, 1H).

Example 275 trans-N-[4-chloro-6-(1H-pyrrolo[2,3-b]pyridin-3-yl)pyrimidin-2-yl]-N'-cyclobutylcyclohexane-1,4-diamine

Example 275a trans-N1-(4-chloro-6-(1-(phenylsulfonyl)-1H-pyrrolo[2,3-b]pyridin-3-yl)pyrimidin-2-yl)cyclohexane-1,4-diamine A mixture of Example 42b (5 g, 11.14 mmol), trans-cyclohexane-1,4-diamine (2.54 g, 22.28 mmol), triethylamine (3.10 mL, 22.28 mmol) and dioxane (120 mL) in a 250 mL of flask was heated at 60° C. for 90 minutes. The reaction mixture was concentrated and used directly for the next step.

Example 275b trans-N-[4-chloro-6-(1H-pyrrolo[2,3-b]pyridin-3-yl)pyrimidin-2-yl]-N'-cyclobutylcyclohexane-1,4-diamine Example 275b was prepared as described in Example 274 substituting Example 270a with Example 275a. MS (ESI) m/e 397 (M+H)$^+$; $^1$H NMR (400 MHz, DMSO-d$_6$) ppm 1.10-1.24 (m, 2H) 1.28-1.42 (m, 2H) 1.50-1.73 (m, 4H) 1.83-1.92 (m, 2H) 1.97-2.06 (m, 2H) 2.08-2.18 (m, 2H) 2.39-2.45 (m, 1H) 3.25-3.39 (m, 1H) 3.68-3.83 (m, 1H) 6.97 (d, J=7.63 Hz, 1H) 7.06 (s, 1H) 7.17 (dd, J=7.93, 4.88 Hz, 1H) 8.28 (dd, J=4.73, 1.68 Hz, 1H) 8.33 (s, 1H) 8.77 (d, J=7.02 Hz, 1H).

Example 276

N-(trans-4-{[4-chloro-6-(1H-pyrrolo[2,3-b]pyridin-3-yl)pyrimidin-2-yl]amino}cyclohexyl)methanesulfonamide A mixture of Example 275a (350 mg, crude, ~0.414 mmol), methanesulfonyl chloride (95 mg, 0.828 mmol), and Hunig's base (0.217 mL, 1.242 mmol) in THF (4 mL) was stirred at room temperature for 1 day then concentrated in vacuo. To the residue was added dioxane (5 mL) and NaOH (20%, 1 mL) and heated at 90° C. for 3 hours. The reaction mixture was concentrated and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to provide the title compound (15 mg, 0.036 mmol, 9% yield). MS (ESI) m/e 421 (M+H)$^+$; $^1$H NMR (400 MHz, DMSO-d$_6$) ppm 1.35-1.51 (m, 4H) 1.98-2.09 (m, 4H) 2.91 (s, 3H) 3.14-3.23 (m, J=8.24 Hz, 1H) 3.71-3.83 (m, J=10.07 Hz, 1H) 6.66-6.76 (m, 1H) 7.04 (d, J=7.63 Hz, 1H) 7.08 (s, 1H) 7.18 (dd, J=7.93, 4.88 Hz, 1H) 8.29 (dd, J=4.58, 1.83 Hz, 1H) 8.34 (s, 1H) 8.78 (d, J=7.94 Hz, 1H).

Example 277

N-(trans-4-{[4-chloro-6-(1H-pyrrolo[2,3-b]pyridin-3-yl)pyrimidin-2-yl]amino}cyclohexyl)-N$^2$-methylglycinamide

Example 277a tert-butyl 2-(trans-4-(4-chloro-6-(1-(phenylsulfonyl)-1H-pyrrolo[2,3-b]pyridin-3-yl)pyrimidin-2-ylamino)cyclohexylamino)-2-oxoethyl(methyl)carbamate A mixture of 2-(tert-butoxycarbonyl(methyl)amino)acetic acid (188 mg, 0.994 mmol), 1-ethyl-3-(3-dimethylaminopropyl)carbodiimide (EDC) (191 mg, 0.994 mmol), 1-hydroxybenzotriazole (HOBT) (152 mg, 0.994 mmol), and Hunig's base (0.289 mL, 1.656 mmol) in DMF (4 mL) was stirred at room temperature for 10 minutes. Example 275a (700 mg, crude, ~0.828 mmol) was added. The mixture was stirred at room temperature overnight then concentrated in vacuo. To the residue was added dioxane (5 mL) and NaOH (20%, 0.6 mL) and stirred at room temperature for 1 day. The reaction mixture was concentrated and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to provide the title compound (23 mg, 0.045 mmol, 5.4% yield).

Example 277b

N-(trans-4-{[4-chloro-6-(1H-pyrrolo[2,3-b]pyridin-3-yl)pyrimidin-2-yl]amino}cyclohexyl)-N²-methylglycinamide To Example 277a was added HCl (0.3 mL, 4 N in dioxane) and the mixture was stirred at room temperature for 90 min. The reaction mixture was concentrated in vacuo to give the title compound as the HCl salt (23 mg, 0.045 mmol, 100% yield). MS (ESI) m/e 414 (M+H)$^+$; $^1$H NMR (400 MHz, DMSO-d$_6$) ppm 1.36-1.52 (m, 4H) 1.88-2.13 (m, 4H) 2.58 (s, 3H) 3.60-3.71 (m, 3H) 3.76-3.87 (m, 1H) 7.10 (s, 1H) 7.19 (dd, J=7.93, 4.88 Hz, 1H) 8.21-8.27 (m, 1H) 8.30 (dd, J=4.73, 1.68 Hz, 1H) 8.37 (s, 1H) 8.72-8.94 (m, J=7.02 Hz, 3H) 12.11 (s, 1H).

Example 278

N-[4-chloro-6-(1H-pyrrolo[2,3-b]pyridin-3-yl)pyrimidin-2-yl]-2,2-dimethylpropane-1,3-diamine Example 278 was prepared as described in Example 42c substituting trans-cyclohexane-1,4-diamine with 2,2-dimethylpropane-1,3-diamine with to give the trifluoroacetic acid salt of the title compound. MS (ESI) m/e 331 (M+H)$^+$; $^1$H NMR (400 MHz, DMSO-d$_6$) ppm 0.91 (s, 6H) 3.19 (s, 2H) 3.32-3.39 (m, J=5.19 Hz, 3H) 7.07 (s, 1H) 7.18 (dd, J=7.93, 4.58 Hz, 2H) 8.28 (dd, J=4.58, 1.83 Hz, 1H) 8.34 (s, 1H) 8.82 (dd, J=7.93, 1.53 Hz, 1H).

Example 279

4-chloro-N-(2-methoxyethyl)-6-(1H-pyrrolo[2,3-b]pyridin-3-yl)pyrimidin-2-amine

Example 279 was prepared as described in Example 42c substituting trans-cyclohexane-1,4-diamine with 2-methoxyethanamine to give the trifluoroacetic acid salt of the title compound. MS (ESI) m/e 304 (M+H)$^+$; $^1$H NMR (400 MHz, DMSO-d$_6$) ppm 3.31 (s, 3H) 3.56 (s, 4H) 7.11 (s, 1H) 7.18 (dd, J=7.93, 4.58 Hz, 1H) 8.28 (dd, J=4.73, 1.68 Hz, 1H) 8.35 (s, 1H) 8.78 (dd, J=7.93, 1.53 Hz, 1H) 12.02 (s, 1H).

Example 280

1-(trans-4-{[4-chloro-6-(1H-pyrrolo[2,3-b]pyridin-3-yl)pyrimidin-2-yl]amino}cyclohexyl)-3-methylurea A mixture of Example 275a (150 mg, 0.311 mmol), isocyanatomethane (21.26 mg, 0.373 mmol) and Hunig's base (0.108 mL, 0.621 mmol) in THF (4 mL) was stirred at room temperature for 16 hours. The resulting mixture was concentrated in vacuo. To the residue was added dioxane (5 mL) and NaOH (20%, 0.6 mL) and heated at 80° C. for 1 hour. The reaction mixture was concentrated and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to provide the title compound (10 mg, 0.025 mmol, 8% yield). MS (ESI) m/e 400 (M+H)$^+$; $^1$H NMR (400 MHz, DMSO-d$_6$) ppm 1.21-1.49 (m, 4H) 1.89-1.96 (m, 2H) 1.99-2.08 (m, J=10.68 Hz, 2H) 2.57 (d, J=4.58 Hz, 3H) 3.34-3.45 (m, 1H) 3.74-3.84 (m, 1H) 5.41-5.47 (m, J=4.27 Hz, 1H) 5.52 (d, J=7.63 Hz, 1H) 7.02 (d, J=7.63 Hz, 1H) 7.07 (s, 1H) 7.17 (dd, J=7.93, 4.58 Hz, 1H) 8.29 (dd, J=4.58, 1.53 Hz, 1H) 8.34 (s, 1H) 8.79 (d, J=7.32 Hz, 1H).

Example 281

1-(trans-4-{[4-chloro-6-(1H-pyrrolo[2,3-b]pyridin-3-yl)pyrimidin-2-yl]amino}cyclohexyl)-3-phenylurea Example 281 was prepared as described in Example 280 substituting isocyanatomethane with isocyanatobenzene to give the title compound. MS (ESI) m/e 462 (M+H)$^+$; $^1$H NMR (400 MHz, DMSO-d$_6$) ppm 1.27-1.54 (m, 4H) 1.96-2.12 (m, J=3.97 Hz, 4H) 3.44-3.57 (m, J=7.63, 3.97 Hz, 1H) 3.76-3.89 (m, J=4.27 Hz, 1H) 5.92 (d, J=7.63 Hz, 1H) 6.88 (t, J=7.32 Hz, 1H) 7.05 (d, J=7.32 Hz, 1H) 7.09 (s, 1H) 7.16-7.23 (m, 3H) 7.37 (d, J=8.24 Hz, 2H) 8.09 (s, 1H) 8.29 (dd, J=4.58, 1.53 Hz, 1H) 8.35 (s, 1H) 8.80 (d, J=7.63 Hz, 1H).

Example 282

N-(trans-4-{[4-chloro-6-(1H-pyrrolo[2,3-b]pyridin-3-yl)pyrimidin-2-yl]amino}cyclohexyl)cyclopropanesulfonamide A mixture of Example 275a (350 mg, crude, 0.414 mmol), cyclopropanesulfonyl chloride (116 mg, 0.828 mmol), and triethylamine (0.058 mL, 0.414 mmol) in THF (5 mL) was stirred at room temperature for 1 day and concentrated in vacuo. To the residue was added dioxane (5 mL) and NaOH (20%, 1 mL) and the mixture was heated at 85° C. for 1 hour. The reaction mixture was concentrated and purified by reverse-phase HPLC performed on a Phenomenex Luna C8 AXIA column (30×75 mm, 100 Å) using a gradient of 10% to 95% acetonitrile: 0.1% aqueous trifluoroacetic acid over 12 minutes at a flow rate of 50 mL/minutes to give the title compound (17 mg, 9.2% yield) as trifluoroacetic acid salts. MS (ESI) m/e 447 (M+H)$^+$; $^1$H NMR (400 MHz, DMSO-d$_6$) ppm 0.94 (d, J=6.41 Hz, 4H) 1.35-1.53 (m, 4H) 1.99-2.11 (m, 4H) 2.50-2.57 (m, 1H) 3.15-3.25 (m, 1H) 3.71-3.82 (m, 1H) 6.66-6.79 (m, 1H) 7.08 (s, 1H) 7.18 (dd, J=7.93, 4.58 Hz, 1H) 8.29 (dd, J=4.73, 1.68 Hz, 1H) 8.35 (s, 1H) 8.79 (d, J=7.02 Hz, 1H) 12.03 (s, 1H).

Examples 283-483 were made in a manner consistent with the teachings above.

| Example # | Name | ¹H NMR (ppm) |
|---|---|---|
| Example 283 | N-(4-{[6-chloro-4-(1H-pyrrolo[2,3-b]pyridin-3-yl)pyridin-2-yl]amino}cyclohexyl)-3,5-dimethyl-1,2-oxazole-4-sulfonamide | (300 MHz, DMSO-d₆) ppm 1.03-1.49 (m, 4 H) 1.62-1.88 (m, 2 H) 1.83-2.05 (m, 2 H) 2.32-2.39 (m, 3 H) 2.61 (d, 3 H) 2.97 (d, 1 H) 3.54 (d, 1 H) 6.72 (d, J = 7.80 Hz, 1 H) 6.79-6.91 (m, 2 H) 7.11-7.28 (m, 1 H) 8.00 (s, 1 H) 8.11 (s, 1 H) 8.29 (d, J = 5.76 Hz, 2 H) 12.13 (s, 1 H) |
| Example 284 | 6-chloro-N-[(2S)-1-methoxy-3-phenylpropan-2-yl]-4-(1H-pyrrolo[2,3-b]pyridin-3-yl)pyridin-2-amine | (500 MHz, METHANOL-d₄) ppm 2.82-2.98 (m, 2 H) 3.38 (s, 3 H) 3.43-3.47 (m, 2 H) 4.28-4.39 (m, 1 H) 6.75 (s, 1 H) 6.86 (s, 1 H) 7.16 (t, J = 7.17 Hz, 1 H) 7.22-7.35 (m, 5 H) 7.89 (s, 1 H) 8.32 (d, J = 4.27 Hz, 1 H) 8.43 (d, J = 7.93 Hz, 1 H) |
| Example 285 | N-[6-chloro-4-(1H-pyrrolo[2,3-b]pyridin-3-yl)pyridin-2-yl]-N'-cyclopentylcyclohexane-1,3-diamine | (300 MHz, METHANOL-d₄): 1.11-1.47 (m, 3 H), 1.47-1.76 (m, 5 H), 1.73-1.91 (m, 3 H), 1.93-2.30 (m, 5 H), 2.64 (d, J = 11.53 Hz, 1 H), 3.63-3.84 (m, 1 H), 3.82-4.01 (m, 1 H), 6.77 (d, J = 1.36 Hz, 1 H), 6.89 (d, J = 1.02 Hz, 1 H), 7.36 (dd, J = 7.97, 5.26 Hz, 1 H), 7.93 (s, 1 H), 8.35 (dd, J = 5.09, 1.36 Hz, 1 H), 8.50 (dd, J = 8.14, 1.36 Hz, 1 H). |
| Example 286 | ethyl N-[(4-{[6-chloro-4-(1H-pyrrolo[2,3-b]pyridin-3-yl)pyridin-2-yl]amino}cyclohexyl)carbamoyl]glycinate | (300 MHz, DMSO-d₆) ppm 1.01-1.37 (m, 6 H) 1.70-1.92 (m, 2 H) 1.99 (s, 2 H) 3.63 (t, 1 H) 3.74 (t, J = 5.95 Hz, 3 H) 3.98-4.14 (m, 2 H) 5.91-6.18 (m, 3 H) 6.69-6.93 (m, 3 H) 7.14-7.28 (m, 1 H) 8.08-8.16 (m, 1 H) 8.25-8.36 (m, 2 H) 12.14 (s, 1 H) |
| Example 287 | 1-(4-{[6-chloro-4-(1H-pyrrolo[2,3-b]pyridin-3-yl)pyridin-2-yl]amino}cyclohexyl)-3-propan-2-ylurea | (300 MHz, DMSO-d₆) ppm 0.93-1.07 (m, J = 5.93, 5.93 Hz, 7 H) 1.11-1.36 (m, 5 H) 1.69-2.08 (m, 4 H) 3.52-3.75 (m, 1 H) 5.43-5.64 (m, 2 H) 6.68-6.80 (m, 1 H) 6.81-6.91 (m, 2 H) 7.11-7.29 (m, 1 H) 8.01-8.19 (m, 1 H) 8.23-8.37 (m, 2 H) 12.07-12.17 (m, 1 H) |
| Example 288 | 1-tert-butyl-3-(4-{[6-chloro-4-(1H-pyrrolo[2,3-b]pyridin-3-yl)pyridin-2-yl]amino}cyclohexyl)urea | (300 MHz, DMSO-d₆) ppm 0.88-1.34 (m, 11 H) 1.66-2.06 (m, 6 H) 3.52-3.73 (m, 1 H) 5.38-5.62 (m, 3 H) 6.67-6.81 (m, 1 H) 6.81-6.92 (m, 2 H) 7.13-7.30 (m, 1 H) 8.06-8.17 (m, 1 H) 8.24-8.36 (m, 2 H) 12.14 (d, J = 1.98 Hz, 1 H) |
| Example 289 | N-(4-{[6-chloro-4-(1H-pyrrolo[2,3-b]pyridin-3-yl)pyridin-2-yl]amino}cyclohexyl)-2-methoxyacetamide | (300 MHz, DMSO-d₆) ppm 1.12-1.56 (m, 5 H) 1.78 (d, J = 10.31 Hz, 2 H) 1.91-2.07 (m, 2 H) 3.52-3.73 (m, 2 H) 3.72-3.83 (m, 3 H) 6.72-6.82 (m, 1 H) 6.81-6.91 (m, 2 H) 7.13-7.27 (m, 1 H) 7.52-7.63 (m, 1 H) 8.06-8.15 (m, 1 H) 8.24-8.35 (m, 2 H) 12.14 (s, 1 H) |
| Example 290 | N-[6-chloro-4-(1H-pyrrolo[2,3-b]pyridin-3-yl)pyridin-2-yl]-N'-(1,3-thiazol-2-ylmethyl)cyclohexane-1,3-diamine | (300 MHz, METHANOL-d₄) 1.16-1.66 (m, 4 H), 1.80-2.15 (m, 2 H), 2.25 (d, J = 11.90 Hz, 1 H), 2.66 (d, J = 11.50 Hz, 1 H), 3.37-3.57 (m, 1 H), 3.85-4.02 (m, 1 H), 4.69 (s, 2 H) 6.77 (d, J = 1.19 Hz, 1 H), 6.89 (d, J = 1.19 Hz, 1 H), 7.36 (dd, J = 8.33, 5.16 Hz, 1 H), 7.72 (d, J = 3.17 Hz, 1 H), 7.90 (d, |

| Example # | Name | ¹H NMR (ppm) |
|---|---|---|
| | | J = 3.17 Hz, 1 H), 7.93 (s, 1 H), 8.35 (d, J = 5.16 Hz, 1 H), 8.50 (dd, J = 7.93, 1.19 Hz, 1 H). |
| Example 291 | N-[6-chloro-4-(1H-pyrrolo[2,3-b]pyridin-3-yl)pyridin-2-yl]-N'-[3-(piperidin-1-ylmethyl)benzyl]cyclohexane-1,3-diamine | (300 MHz, METHANOL-d₄): 1.21-1.65 (m, 5 H), 1.62-2.00 (m, 7 H), 1.99-2.12 (m, 2 H), 2.24 (d, J = 11.10 Hz, 1 H), 2.75-3.07 (m, 4 H), 3.34-3.55 (m, 2 H), 3.78 (s, 1 H), 4.17-4.71 (m, 2 H), 6.82 (s, 1 H), 6.93 (s, 1 H), 7.34 (dd, J = 7.93, 5.16 Hz, 1 H), 7.58-7.67 (m, 3 H), 7.71 (s, 1 H), 7.92 (s, 1 H), 8.34 (d, J = 4.36 Hz, 1 H), 8.47 (dd, J = 7.93, 1.19 Hz, 1 H). |
| Example 292 | N-(3-{[6-chloro-4-(1H-pyrrolo[2,3-b]pyridin-3-yl)pyridin-2-yl]amino}cyclohexyl)-2-ethoxyacetamide | (300 MHz, DMSO-d₆): 1.13 (q, J = 6.78 Hz, 3 H), 1.18-1.48 (m, 3 H), 1.63-1.82 (m, 3 H), 1.94 (d, J = 11.53 Hz, 1 H), 2.06 (d, J = 11.53 Hz, 1 H), 3.47 (q, J = 6.89 Hz, 2 H), 3.66-3.79 (m, 2 H), 3.80 (s, 2 H), 6.79-6.89 (m, 2 H), 7.22 (dd, J = 8.14, 4.75 Hz, 1 H), 7.56 (d, J = 8.48 Hz, 1 H), 8.13 (d, J = 2.71 Hz, 1 H), 8.23-8.35 (m, 2 H), 12.17 (s, 1 H). |
| Example 293 | N-(3-{[6-chloro-4-(1H-pyrrolo[2,3-b]pyridin-3-yl)pyridin-2-yl]amino}cyclohexyl)-2-phenoxyacetamide | (300 MHz, DMSO-d₆): 0.96-1.47 (m, 3 H), 1.61-1.84 (m, 3 H), 1.94 (d, J = 11.10 Hz, 1 H), 2.09 (d, J = 11.50 Hz, 1 H), 3.61-3.86 (m, 2 H), 4.44 (s, 2 H), 6.85 (s, 1 H), 6.88 (s, 1 H), 6.91-6.99 (m, 4 H), 7.22 (dd, J = 7.93, 4.76 Hz, 1 H), 7.29 (t, J = 7.93 Hz, 2 H), 7.98 (d, J = 7.93 Hz, 1 H), 8.13 (d, J = 2.78 Hz, 1 H), 8.28-8.35 (m, 1 H), 12.17 (s, 1 H). |
| Example 294 | N-(3-{[6-chloro-4-(1H-pyrrolo[2,3-b]pyridin-3-yl)pyridin-2-yl]amino}cyclohexyl)pyrazine-2-carboxamide | (300 MHz, DMSO-d₆): 1.15 (s, 1 H), 1.43 (q, J = 11.75 Hz, 3 H), 1.68-1.91 (m, 2 H), 1.97 (d, J = 12.88 Hz, 1 H), 2.16 (d, J = 11.53 Hz, 1 H), 3.79 (t, J = 11.53 Hz, 2 H), 6.88 (d, J = 3.39 Hz, 2 H), 7.23 (dd, J = 8.14, 4.75 Hz, 1 H), 8.15 (d, J = 2.71 Hz, 1 H), 8.26-8.34 (m, 2 H), 8.35 (s, 1 H), 8.72 (dd, J = 2.54, 1.53 Hz, 1 H), 8.80 (d, J = 8.48 Hz, 1 H), 8.86 (d, J = 2.71 Hz, 1 H), 9.19 (d, J = 1.70 Hz, 1 H), 12.19 (d, J = 1.69 Hz, 1 H). |
| Example 295 | N-(3-{[6-chloro-4-(1H-pyrrolo[2,3-b]pyridin-3-yl)pyridin-2-yl]amino}cyclohexyl)azetidine-2-carboxamide | (300 MHz, METHANOL-d₄) 1.06-1.34 (m, 2 H), 1.42-1.65 (m, 1 H), 1.79-2.02 (m, 2 H), 2.07 (d, J = 11.53 Hz, 1 H), 2.27-2.43 (m, 1 H), 2.43-2.63 (m, 1 H), 2.68-2.94 (m, 1 H), 3.76-4.03 (m, 3 H), 4.01-4.26 (m, 1 H), 4.85-5.04 (m, 2 H), 6.77 (s, 1 H), 6.89 (s, 1 H), 7.42 (dd, J = 7.97, 5.26 Hz, 1 H), 7.99 (d, J = 1.36 Hz, 1 H), 8.37 (d, J = 4.41 Hz, 1 H), 8.52-8.61 (m, 1 H). |
| Example 296 | tert-butyl 2-[(3-{[6-chloro-4-(1H-pyrrolo[2,3-b]pyridin-3-yl)pyridin-2-yl]amino}cyclohexyl)carbamoyl]azetidine-1-carboxylate | (300 MHz, DMSO-d₆): 1.02-1.25 (m, 3 H), 1.34 (s, 9 H), 1.58-1.86 (m, 3 H), 1.84-2.04 (m, 2 H), 2.06 (m, 1 H), 2.23-2.42 (m, 1 H), 3.57-3.92 (m, 4 H), 4.35-4.52 (m, 1 H), 6.85 (s, 1 H), 6.88 (s, 1 H), 7.22 (dd, J = 7.93, 4.76 Hz, 1 |

-continued

| Example # | Name | ¹H NMR (ppm) |
|---|---|---|
| | | H), 7.86 (d, J = 7.54 Hz, 1 H), 8.14 (d, J = 2.78 Hz, 1 H), 8.28-8.36 (m, 2 H) 12.17 (s, 1 H). |
| Example 297 | 1-(4-{[6-chloro-4-(1H-pyrrolo[2,3-b]pyridin-3-yl)pyridin-2-yl]amino}cyclohexyl)-3-prop-2-en-1-ylurea | (300 MHz, DMSO-$d_6$) ppm 0.98-1.37 (m, 5 H) 1.61-2.08 (m, 4 H) 3.61 (q, J = 5.68 Hz, 2 H) 4.91-5.19 (m, 2 H) 5.67-5.91 (m, 3 H) 6.74 (d, 1 H) 6.81-6.92 (m, 2 H) 7.20 (d, 1 H) 8.11 (d, 1 H) 8.30 (d, 2 H) 12.14 (d, J = 3.57 Hz, 1 H) |
| Example 298 | N-(3-{[6-chloro-4-(1H-pyrrolo[2,3-b]pyridin-3-yl)pyridin-2-yl]amino}-2,2-dimethylpropyl)-1-methyl-1H-imidazole-4-sulfonamide | (500 MHz, METHANOL-$d_4$) ppm 0.97 (s, 6 H) 2.84 (s, 2 H) 3.26 (s, 2 H) 3.74 (s, 3 H) 6.82 (s, 1 H) 6.89 (s, 1 H) 7.37-7.47 (m, 1 H) 7.65 (s, 1 H) 7.76 (s, 1 H) 8.00 (s, 1 H) 8.38 (d, J = 4.88 Hz, 1 H) 8.61 (d, J = 7.93 Hz, 1 H) |
| Example 299 | N-(3-{[6-chloro-4-(1H-pyrrolo[2,3-b]pyridin-3-yl)pyridin-2-yl]amino}cyclohexyl)furan-2-sulfonamide | (300 MHz, DMSO-$d_6$): 0.83-1.22 (m, 2 H), 1.17-1.42 (m, 1 H), 1.45-1.73 (m, 2 H), 1.77-2.03 (m, 2 H), 3.02-3.35 (m, 1 H), 3.62 (t, J = 14.75 Hz, 2 H), 6.60 (dd, J = 3.56, 1.86 Hz, 1 H), 6.80 (d, J = 1.02 Hz, 1 H), 6.88 (s, 1 H), 7.06 (dd, J = 3.56, 0.85 Hz, 1 H), 7.15-7.25 (m, 1 H), 7.90 (dd, J = 1.70, 1.02 Hz, 2 H), 7.98-8.18 (m, 1 H), 8.22-8.36 (m, 2 H), 12.16 (s, 1 H), 12.16 (s, 1 H). |
| Example 300 | N-(3-{[6-chloro-4-(1H-pyrrolo[2,3-b]pyridin-3-yl)pyridin-2-yl]amino}cyclohexyl)pyridine-3-sulfonamide | (500 MHz, METHANOL-$d_4$) 0.99-1.28 (m, 2 H), 1.30-1.47 (m, 1 H), 1.59-1.82 (m, 2 H), 1.87-2.04 (m, 1 H), 2.10-2.23 (m, 1 H), 3.19-3.35 (m, 2 H), 3.67-3.79 (m, 1 H), 6.72 (d, J = 1.22 Hz, 1 H), 6.89 (d, J = 1.22 Hz, 1 H), 7.53 (dd, J = 7.93, 5.49 Hz, 1 H), 7.65 (dd, J = 7.93, 4.88 Hz, 1 H), 8.06 (s, 1 H), 8.32-8.36 (m, 1 H), 8.44 (d, J = 4.58 Hz, 1 H), 8.72 (dd, J = 8.24, 1.22 Hz, 1 H), 8.75 (d, J = 4.27 Hz, 1 H), 9.04 (s, 1 H). |
| Example 301 | 1-(3-{[6-chloro-4-(1H-pyrrolo[2,3-b]pyridin-3-yl)pyridin-2-yl]amino}cyclohexyl)-3-propan-2-ylurea | (500 MHz, DMSO-$d_6$): 0.99-1.02 (m, 1 H), 1.02 (s, 6 H), 1.05-1.19 (m, 1 H), 1.23-1.42 (m, 2 H), 1.57-1.69 (m, 2 H), 1.69-1.86 (m, 2 H), 2.14 (d, J = 11.60 Hz, 1 H), 3.55-3.74 (m, 2 H), 3.97-4.07 (m, 1 H), 6.84 (s, 1 H), 6.89 (d, J = 3.36 Hz, 1 H), 7.24 (dd, J = 7.93, 4.88 Hz, 1 H), 8.15 (t, J = 2.75 Hz, 1 H), 8.30-8.33 (m, 1 H), 8.37 (dd, J = 16.02, 7.48 Hz, 1 H), 12.22 (s, 1 H). |
| Example 302 | ethyl N-[(3-{[6-chloro-4-(1H-pyrrolo[2,3-b]pyridin-3-yl)pyridin-2-yl]amino}cyclohexyl)carbamoyl]glycinate | (500 MHz, DMSO-$d_6$): 0.97-1.12 (m, 3 H), 1.17 (t, J = 7.02 Hz, 3 H), 1.28-1.44 (m, 1 H), 1.69-1.77 (m, 2 H), 1.82 (d, J = 11.90 Hz, 1 H), 2.14 (d, J = 11.90 Hz, 1 H), 3.65-3.73 (m, 2 H), 3.75 (s, 2 H), 4.07 (q, J = 7.22 Hz, 2 H), 6.84 (s, 1 H), 6.88 (s, 1 H), 7.23 (dd, J = 7.93, 4.88 Hz, 1 H), 8.14 (d, J = 2.75 Hz, 1 H), 8.31 (d, J = 4.58 Hz, 1 H), 8.34 (d, J = 8.24 Hz, 1 H), 12.19 (s, 1 H). |
| Example 303 | 1-(3-{[6-chloro-4-(1H-pyrrolo[2,3-b]pyridin-3-yl)pyridin-2-yl]amino}cyclohexyl)-3-(cyclohexylmethyl)urea | (500 MHz, DMSO-$d_6$): 0.72-1.01 (m, 2 H), 1.04-1.23 (m, 5 H), 1.24-1.41 (m, 3 H), 1.46-1.56 (m, 1 H), 1.55-1.75 (m, 8 H), 1.78-1.85 (m, 1 H), |

| Example # | Name | ¹H NMR (ppm) |
|---|---|---|
| | | 2.13 (d, J = 11.90 Hz, 1 H), 2.59-2.70 (m, 1 H), 2.82 (t, J = 6.10 Hz, 2 H), 3.57-3.74 (m, 1 H), 3.96-4.05 (m, 1 H), 6.83 (s, 1 H), 6.88 (dd, J = 3.66, 0.92 Hz, 1 H), 7.16-7.24 (m, 1 H), 8.13 (t, J = 2.75 Hz, 1 H), 8.28-8.32 (m, 1 H), 8.31-8.40 (m, 1 H), 12.17 (s, 1 H). |
| Example 304 | 4-acetyl-N-(3-{[6-chloro-4-(1H-pyrrolo[2,3-b]pyridin-3-yl)pyridin-2-yl]amino}-2,2-dimethylpropyl)benzenesulfonamide | (500 MHz, DMSO-$d_6$) ppm 0.82 (s, 6 H) 2.49 (s, 3 H) 2.54-2.62 (m, 2 H) 3.05 (s, 1 H) 6.71 (s, 1 H) 6.82 (s, 1 H) 6.85 (s, 1 H) 7.14 (dd, J = 7.93, 4.88 Hz, 1 H) 7.61 (t, J = 6.87 Hz, 1 H) 7.83 (d, J = 8.24 Hz, 2 H) 8.00 (d, J = 8.54 Hz, 2 H) 8.07 (d, J = 2.75 Hz, 1 H) 8.20-8.27 (m, 2 H) 12.11 (s, 1 H) |
| Example 305 | N-(3-{[6-chloro-4-(1H-pyrrolo[2,3-b]pyridin-3-yl)pyridin-2-yl]amino}-2,2-dimethylpropyl)-3,5-dimethyl-1,2-oxazole-4-sulfonamide | (500 MHz, DMSO-$d_6$) ppm 0.88 (s, 6 H) 2.31 (s, 3 H) 2.54 (s, 3 H) 2.70 (d, J = 6.41 Hz, 2 H) 3.14 (s, 2 H) 6.82 (s, 1 H) 6.90 (s, 1 H) 6.96 (s, 1 H) 7.23 (dd, J = 7.93, 4.58 Hz, 1 H) 7.73 (t, J = 6.56 Hz, 1 H) 8.15 (d, J = 2.75 Hz, 1 H) 8.31 (d, J = 6.10 Hz, 1 H) 8.34 (d, J = 7.93 Hz, 1 H) 12.20 (s, 1 H) |
| Example 306 | N-(3-{[6-chloro-4-(1H-pyrrolo[2,3-b]pyridin-3-yl)pyridin-2-yl]amino}-2,2-dimethylpropyl)thiophene-2-sulfonamide | (500 MHz, DMSO-$d_6$) ppm 0.89 (s, 6 H) 2.68 (d, J = 7.02 Hz, 2 H) 3.14 (d, J = 5.19 Hz, 2 H) 6.83 (s, 1 H) 6.90 (s, 1 H) 6.95 (s, 1 H) 7.13 (dd, J = 4.88, 3.66 Hz, 1 H) 7.21 (dd, J = 7.93, 4.58 Hz, 1 H) 7.55 (dd, J = 3.66, 1.22 Hz, 1 H) 7.71 (t, J = 6.87 Hz, 1 H) 7.86 (dd, J = 4.88, 1.22 Hz, 1 H) 8.14 (d, J = 2.75 Hz, 1 H) 8.30 (dd, J = 4.58, 1.53 Hz, 1 H) 8.32 (d, J = 7.93 Hz, 1 H) 12.17 (s, 1 H) |
| Example 307 | N-(3-{[6-chloro-4-(1H-pyrrolo[2,3-b]pyridin-3-yl)pyridin-2-yl]amino}cyclohexyl)-3,5-dimethyl-1,2-oxazole-4-sulfonamide | (300 MHz, METHANOL-$d_4$) 0.99-1.32 (m, 3 H), 1.37-1.54 (m, 1 H), 1.83 (d, J = 11.50 Hz, 2 H), 1.91-2.07 (m, 1 H), 2.23 (d, J = 11.90 Hz, 1 H), 2.38 (s, 3 H), 2.64 (s, 3 H), 3.12-3.27 (m, 1 H), 3.65-3.88 (m, 1 H), 6.72 (s, 1 H), 6.88 (s, 1 H), 7.45 (dd, J = 8.13, 5.35 Hz, 1 H), 7.99 (s, 1 H), 8.39 (d, J = 4.36 Hz, 1 H), 8.62 (d, J = 6.74 Hz, 1 H). |
| Example 308 | 1-(3-{[6-chloro-4-(1H-pyrrolo[2,3-b]pyridin-3-yl)pyridin-2-yl]amino}cyclohexyl)-3-propylurea | (400 MHz, DMSO-$d_6$) 0.82 (t, J = 7.32 Hz, 3 H), 0.93-1.12 (m, 3 H), 1.28-1.42 (m, 3 H), 1.65-1.77 (m, 1 H), 1.81 (d, J = 11.29 Hz, 1 H), 1.94 (d, J = 11.29 Hz, 1 H), 2.13 (d, J = 12.21 Hz, 1 H), 2.93 (t, J = 7.02 Hz, 2 H), 3.47 (d, J = 11.60 Hz, 2 H), 6.83 (s, 1 H), 6.88 (s, 1 H), 7.23 (dd, J = 7.93, 4.88 Hz, 1 H), 8.14 (d, J = 2.75 Hz, 1 H), 8.31 (dd, J = 4.73, 1.37 Hz, 1 H), 8.34 (d, J = 7.93 Hz, 1 H), 12.20 (d, J = 1.83 Hz, 1 H). |
| Example 309 | N-(3-{[6-chloro-4-(1H-pyrrolo[2,3-b]pyridin-3-yl)pyridin-2-yl]amino}-2,2-dimethylpropyl)propane-1-sulfonamide | (500 MHz, DMSO-$d_6$) ppm 0.84-0.97 (m, 9 H) 1.56-1.71 (m, 2 H) 2.80 (d, J = 5.19 Hz, 2 H) 2.90-2.99 (m, 2 H) 3.16 (d, J = 6.10 Hz, 2 H) 6.84 (t, J = 5.95 Hz, 1 H) 6.90-6.96 (m, 2 H) 6.99 (s, 1 H) 7.22 (dd, J = 7.93, 4.58 Hz, 1 H) 8.16 (s, 1 H) 8.31 (dd, J = 4.58, 1.53 Hz, |

| Example # | Name | ¹H NMR (ppm) |
|---|---|---|
| | | 1 H) 8.35 (dd, J = 8.09, 1.37 Hz, 1 H) 12.17 (s, 1 H) |
| Example 310 | N-[6-chloro-4-(1H-pyrrolo[2,3-b]pyridin-3-yl)pyridin-2-yl]acetamide | (500 MHz, DMSO-d₆) ppm 2.13 (s, 3 H) 7.27 (dd, J = 7.93, 4.88 Hz, 1 H) 7.57 (s, 1 H) 8.25-8.37 (m, 3 H) 8.57 (s, 1 H) 10.79 (s, 1 H) 12.35 (s, 1 H) |
| Example 311 | N-(trans-4-{[6-chloro-4-(1H-pyrrolo[2,3-b]pyridin-3-yl)pyridin-2-yl]amino}cyclohexyl)propane-2-sulfonamide | (400 MHz, DMSO-d₆) ppm 1.22 (s, 3 H), 1.24 (s, 3 H), 1.25-1.31 (m, 1 H), 1.88-2.03 (m, 4 H), 3.06-3.19 (m, 2 H), 6.86 (d, J = 6.71 Hz, 2 H), 7.02 (d, J = 8.24 Hz, 1 H), 7.21 (dd, J = 7.93, 4.88 Hz, 1 H), 8.13 (d, J = 2.75 Hz, 1 H), 8.29-8.34 (m, 2 H), 12.14-12.20 (m, 1 H). |
| Example 312 | N-(trans-4-{[6-chloro-4-(1H-pyrrolo[2,3-b]pyridin-3-yl)pyridin-2-yl]amino}cyclohexyl)ethanesulfonamide | (300 MHz, DMSO-d₆) ppm 1.20 (t, J = 7.29 Hz, 3 H), 1.26-1.46 (m, 4 H), 1.87-2.03 (m, 4 H), 3.00 (q, J = 7.12 Hz, 1 H), 3.07-3.17 (m, 1 H), 3.53-3.65 (m, 1 H), 6.71-6.80 (m, 1 H), 6.83-6.88 (m, 2 H), 7.05 (d, J = 7.80 Hz, 1 H), 7.20 (dd, J = 7.80, 5.09 Hz, 1 H), 8.12 (d, J = 2.71 Hz, 1 H), 8.28-8.34 (m, 2 H), 12.14 (s, 1 H). |
| Example 313 | N-(2-{[6-chloro-4-(1H-pyrrolo[2,3-b]pyridin-3-yl)pyridin-2-yl]amino}ethyl)butane-1-sulfonamide | (300 MHz, DMSO-d₆) ppm 0.85 (t, J = 7.34 Hz, 3 H) 1.27-1.45 (m, 2 H) 1.54-1.71 (m, 2 H) 2.95-3.06 (m, 2 H) 3.12 (q, J = 6.21 Hz, 2 H) 3.38 (q, J = 6.08 Hz, 2 H) 6.89 (s, 1 H) 6.92-7.00 (m, 2 H) 7.14 (t, J = 5.55 Hz, 1 H) 7.21 (dd, J = 7.93, 4.76 Hz, 1 H) 8.14 (s, 1 H) 8.28-8.36 (m, 2 H) 12.16 (s, 1 H) |
| Example 314 | N-(2-{[6-chloro-4-(1H-pyrrolo[2,3-b]pyridin-3-yl)pyridin-2-yl]amino}ethyl)thiophene-2-sulfonamide | (300 MHz, DMSO-d₆) ppm 3.02 (q, J = 6.56 Hz, 2 H) 3.36 (t, J = 6.61 Hz, 2 H) 6.86 (s, 1 H) 6.93 (s, 1 H) 7.17 (dd, J = 4.92, 3.56 Hz, 1 H) 7.22 (dd, J = 7.97, 4.92 Hz, 1 H) 7.61 (dd, J = 3.73, 1.36 Hz, 1 H) 7.86-7.98 (m, 2 H) 8.14 (d, J = 2.71 Hz, 1 H) 8.29-8.37 (m, 2 H) 12.19 (s, 1 H) |
| Example 315 | 6-chloro-N-(1-methylpiperidin-3-yl)-4-(1H-pyrrolo[2,3-b]pyridin-3-yl)pyridin-2-amine | (300 MHz, METHANOL-d₄) 1.45-1.70 (m, 1 H), 1.84-2.03 (m, 2 H), 2.06-2.22 (m, 2 H), 2.69 (t, J = 11.53 Hz, 1 H), 2.92 (s, 3 H), 3.40-3.62 (m, 1 H), 3.70-3.87 (m, 1 H), 4.15-4.36 (m, 1 H), 6.82 (s, 1 H), 6.96 (s, 1 H), 7.36 (dd, J = 8.14, 5.09 Hz, 1 H), 8.35 (d, J = 5.09 Hz, 1 H), 8.49 (dd, J = 7.97, 1.53 Hz, 1 H). |
| Example 316 | [3-({[6-chloro-4-(1H-pyrrolo[2,3-b]pyridin-3-yl)pyridin-2-yl]amino}methyl)piperidin-1-yl](cyclopropyl)methanone | (300 MHz, METHANOL-d₄): 0.62-0.99 (m, 4 H), 1.28-1.67 (m, 2 H), 1.69-2.15 (m, 4 H), 2.73 (dd, J = 12.49, 10.11 Hz, 1 H), 2.86-3.07 (m, 1 H), 3.06-3.27 (m, 1 H), 4.16 (d, J = 13.09 Hz, 2 H), 4.36 (d, J = 12.69 Hz, 1 H), 6.78 (s, 1 H), 6.89 (s, 1 H) 7.24-7.48 (m, 1 H), 7.95 (s, 1 H), 8.35 (d, J = 4.76 Hz, 1 H), 8.52 (t, J = 8.13 Hz, 1 H). |
| Example 317 | N-[6-chloro-4-(1H-pyrrolo[2,3-b]pyridin-3-yl)pyridin-2-yl]-N-{[1-(cyclopropylcarbonyl)piperidin-3-yl]methyl}cyclopropanecarboxamide | (300 MHz, METHANOL-d₄): 0.65-1.02 (m, 4 H), 1.14-1.35 (m, 4 H), 1.35-1.67 (m, 3 H), 1.68-1.89 (m, 1 H), 1.88-2.09 (m, 3 H), 2.58-3.02 (m, 1 |

| Example # | Name | ¹H NMR (ppm) |
|---|---|---|
| | | H), 3.03-3.27 (m, 2 H), 4.03-4.44 (m, 3 H), 6.74 (d, J = 3.39 Hz, 1 H), 6.84 (d, J = 9.49 Hz, 1 H), 7.39 (dd, J = 7.80, 4.75 Hz, 1 H), 8.30 (dd, J = 8.14, 1.36 Hz, 1 H), 8.33 (s, 1 H), 8.45 (dd, J = 4.75, 1.36 Hz, 1 H). |
| Example 318 | 6-chloro-N-{[1-(cyclopropylmethyl)piperidin-3-yl]methyl}-4-(1H-pyrrolo[2,3-b]pyridin-3-yl)pyridin-2-amine | (300 MHz, METHANOL-d₄): 0.39-0.42 (m, 2 H), 0.60-0.86 (m, 2 H), 0.98-1.21 (m, 1 H), 1.23-1.46 (m, 1 H), 1.66-1.92 (m, 1 H), 1.95-2.10 (m, 2 H), 2.16-2.35 (m, 1 H), 2.74 (t, J = 12.49 Hz, 1 H), 2.82-2.95 (m, 1 H), 2.96-3.11 (m, 1 H), 3.22-3.29 (m, 1 H), 3.33 (d, J = 1.59 Hz, 1 H), 3.39 (d, J = 2.38 Hz, 1 H), 3.41 (d, J = 1.59 Hz, 1 H), 3.53-3.67 (m, 1 H), 3.74 (d, J = 12.29 Hz, 1 H), 6.79 (s, 1 H), 6.91 (s, 1 H), 7.34 (dd, J = 8.33, 5.16 Hz, 1 H), 7.92 (s, 1 H), 8.34 (d, J = 5.16 Hz, 1 H), 8.47 (dd, J = 7.93, 1.19 Hz, 1 H). |
| Example 319 | 6-chloro-N-[1-(cyclopropylmethyl)piperidin-3-yl]-4-(1H-pyrrolo[2,3-b]pyridin-3-yl)pyridin-2-amine | (300 MHz, METHANOL-d₄): 0.39-0.56 (m, 2 H), 0.71-0.89 (m, 2 H), 1.06-1.23 (m, 1 H), 1.49-1.68 (m, 1 H), 1.85-2.07 (m, 1 H), 2.08-2.25 (m, 2 H), 2.66 (t, J = 11.50 Hz, 1 H), 2.84-3.02 (m, 1 H), 3.08 (d, J = 7.54 Hz, 2 H), 3.67 (d, J = 11.50 Hz, 1 H), 3.88-4.15 (m, 1 H), 4.21-4.39 (m, 1 H), 6.82 (s, 1 H), 6.96 (s, 1 H), 7.32 (dd, J = 8.13, 4.96 Hz, 1 H), 7.91 (s, 1 H), 8.33 (d, J = 4.76 Hz, 1 H), 8.45 (dd, J = 7.93, 1.59 Hz, 1 H). |
| Example 320 | N-[6-chloro-4-(1H-pyrrolo[2,3-b]pyridin-3-yl)pyridin-2-yl]-2-(1H-indol-2-yl)acetamide | (300 MHz, DMSO-d₆) ppm 3.86 (s, 2 H) 6.99 (t, J = 7.97 Hz, 1 H) 7.04-7.12 (m, 1 H) 7.24 (dd, J = 8.14, 4.75 Hz, 1 H) 7.31 (d, J = 2.71 Hz, 1 H) 7.36 (d, J = 7.80 Hz, 1 H) 7.56 (d, J = 1.36 Hz, 1 H) 7.62 (d, J = 7.80 Hz, 1 H) 8.25-8.33 (m, 3 H) 8.56 (d, J = 1.36 Hz, 1 H) 10.83-10.99 (m, 2 H) 12.32 (s, 1 H) |
| Example 321 | trans-N-[6-chloro-4-(1H-pyrrolo[2,3-b]pyridin-3-yl)pyridin-2-yl]-N'-cyclopentylcyclohexane-1,4-diamine | (300 MHz, DMSO-d₆) ppm 0.99-1.34 (m, 8 H) 1.35-1.85 (m, 6 H) 1.94 (s, 4 H) 3.50-3.71 (m, 1 H) 6.65-6.76 (m, 1 H) 6.80-6.90 (m, 2 H) 7.12-7.24 (m, 1 H) 8.06-8.15 (m, 1 H) 8.25-8.34 (m, 2 H) |
| Example 322 | trans-N-[6-chloro-4-(1H-pyrrolo[2,3-b]pyridin-3-yl)pyridin-2-yl]-N'-(2-methylpropyl)cyclohexane-1,4-diamine | (300 MHz, DMSO-d₆) ppm 0.73-1.08 (m, 7 H) 1.05-1.38 (m, 2 H) 1.46-1.77 (m, 2 H) 1.78-2.09 (m, 3 H) 2.26-2.45 (m, 4 H) 3.48-3.73 (m, 2 H) 6.69-6.80 (m, 1 H) 6.80-6.91 (m, 2 H) 7.11-7.29 (m, 1 H) 8.06-8.17 (m, 1 H) 8.23-8.37 (m, 2 H) 12.01-12.25 (m, 1 H) |
| Example 323 | 6-chloro-N-[3-(pyrrolidin-1-yl)cyclohexyl]-4-(1H-pyrrolo[2,3-b]pyridin-3-yl)pyridin-2-amine | (300 MHz, METHANOL-d₄): 1.23-1.41 (m, 2 H), 1.43-1.62 (m, 3 H), 1.70-1.90 (m, 3 H), 1.92-2.17 (m, 4 H), 2.58 (d, J = 10.51 Hz, 1 H), 2.95-3.18 (m, 2 H), 3.42-3.61 (m, 2 H), 3.85-4.09 (m, 1 H), 6.77 (d, J = 1.36 Hz, 1 H), 6.89 (s, 1 H), 7.31 (dd, J = 7.97, 4.92 Hz, 1 H), 7.89 (s, 1 H), 8.32 (dd, |

-continued

| Example # | Name | ¹H NMR (ppm) |
|---|---|---|
| Example 324 | 6-chloro-N-[3-(piperidin-1-yl)cyclohexyl]-4-(1H-pyrrolo[2,3-b]pyridin-3-yl)pyridin-2-amine | J = 4.75, 1.36 Hz, 1 H), 8.44 (dd, J = 7.97, 1.53 Hz, 1 H). (300 MHz, METHANOL-d₄): 1.15-1.64 (m, 4 H), 1.91-2.08 (m, 4 H), 2.09-2.31 (m, 4 H), 2.64 (d, J = 13.22 Hz, 1 H), 3.08-3.27 (m, 4 H), 3.54-3.75 (m, 2 H), 3.83-4.05 (m, 1 H), 6.77 (d, J = 1.36 Hz, 1 H), 6.89 (d, J = 1.36 Hz, 1 H), 7.32 (dd, J = 7.97, 4.92 Hz, 1 H), 7.90 (s, 1 H), 8.33 (dd, J = 4.75, 1.36 Hz, 1 H), 8.45 (dd, J = 7.97, 1.53 Hz, 1 H). |
| Example 325 | N-(trans-4-{[6-chloro-4-(1H-pyrrolo[2,3-b]pyridin-3-yl)pyridin-2-yl]amino}cyclohexyl)-N~2~-methylglycinamide | (300 MHz, DMSO-d₆) ppm 1.16-1.46 (m, 7 H) 1.72-1.93 (m, 3 H) 1.99 (s, 2 H) 2.52-2.63 (m, 3 H) 2.67-2.84 (m, 1 H) 2.92-3.12 (m, 2 H) 6.81-6.93 (m, 2 H) 7.14-7.30 (m, 1 H) 8.08-8.19 (m, 1 H) 8.25-8.40 (m, 2 H) 8.54-8.74 (m, 2 H) 12.12-12.20 (m, 1 H) |
| Example 326 | N-(trans-4-{[6-chloro-4-(1H-pyrrolo[2,3-b]pyridin-3-yl)pyridin-2-yl]amino}cyclohexyl)-1-ethylpyrrolidine-3-carboxamide | (300 MHz, DMSO-d₆) ppm 0.93-1.13 (m, 3 H) 1.15-1.44 (m, 5 H) 1.66-2.09 (m, 4 H) 2.27-2.47 (m, 5 H) 2.54-2.70 (m, 1 H) 2.69-2.86 (m, 2 H) 3.40-3.76 (m, 2 H) 6.71-6.81 (m, 1 H) 6.80-6.92 (m, 2 H) 7.12-7.28 (m, 1 H) 7.62-7.76 (m, 1 H) 8.07-8.17 (m, 1 H) 8.24-8.36 (m, 2 H) 12.09-12.19 (m, 1 H) |
| Example 327 | N-(3-{[6-chloro-4-(1H-pyrrolo[2,3-b]pyridin-3-yl)pyridin-2-yl]amino}cyclohexyl)-N~2~-methylalaninamide | (500 MHz, DMSO-d₆) 1.06-1.22 (m, 3 H), 1.36 (t, J = 6.56 Hz, 3 H), 1.38-1.53 (m, 1 H), 1.73-1.87 (m, 3 H), 1.95 (d, J = 11.29 Hz, 1 H), 2.17 (dd, J = 22.28, 11.90 Hz, 1 H), 3.61-3.83 (m, 3 H), 6.86 (s, 1 H), 6.90 (s, 1 H), 7.23 (dd, J = 7.78, 4.73 Hz, 1 H), 8.14 (s, 1 H), 8.29-8.35 (m, 2 H), 8.46 (d, J = 7.63 Hz, 1 H), 8.67-8.94 (m, 2 H), 12.21 (s, 1 H). |
| Example 328 | (2R)—N-[(1S,3S)-3-{[6-chloro-4-(1H-pyrrolo[2,3-b]pyridin-3-yl)pyridin-2-yl]amino}cyclohexyl]-2-(methylamino)-2-phenylethanamide | (500 MHz, DMSO-d₆): 0.94 (q, J = 11.90 Hz, 1 H), 1.00-1.12 (m, 1 H), 1.13-1.26 (m, 1 H), 1.35-1.51 (m, 1 H), 1.71-1.86 (m, 2 H), 1.87-1.97 (m, 2 H), 2.46 (t, J = 4.73 Hz, 3 H), 3.59-3.86 (m, 2 H), 4.79 (t, J = 5.95 Hz, 1 H), 6.80 (s, 1 H), 6.87 (s, 1 H), 7.21 (dd, J = 7.93, 4.88 Hz, 1 H), 7.41-7.49 (m, 3 H), 7.48-7.54 (m, 2 H), 8.12 (d, J = 2.75 Hz, 1 H), 8.25-8.34 (m, 2 H), 8.60 (d, J = 7.63 Hz, 1 H), 9.08-9.35 (m, 1 H), 9.34-9.53 (m, 1 H), 12.19 (s, 1 H). |
| Example 329 | (2R)—N-[(1R,3R)-3-{[6-chloro-4-(1H-pyrrolo[2,3-b]pyridin-3-yl)pyridin-2-yl]amino}cyclohexyl]-2-(methylamino)-2-phenylethanamide | (500 MHz, DMSO-D₆): 0.94 (m, 1 H), 1.04-1.21 (m, 1 H), 1.28-1.44 (m, 1 H), 1.59 (d, J = 11.29 Hz, 1 H), 1.65-1.74 (m, 1 H), 1.75-1.84 (m, 1 H), 1.91 (d, J = 11.29 Hz, 1 H), 2.21 (d, J = 11.60 Hz, 1 H), 2.44 (t, J = 4.88 Hz, 3 H), 3.66-3.84 (m, 2 H), 4.78 (t, J = 6.10 Hz, 1 H), 6.87 (s, 1 H), 6.90 (s, 1 H), 7.24 (dd, J = 7.93, 4.58 Hz, 1 H), 7.38-7.63 (m, 5 H), 8.15 (d, J = 2.44 Hz, 1 H), 8.25-8.37 (m, 2 H), 8.62 (d, J = 7.63 Hz, |

| Example # | Name | ¹H NMR (ppm) |
|---|---|---|
| | | 1 H), 9.26 (d, J = 4.88 Hz, 1 H), 9.42 (d, J = 4.88 Hz, 1 H), 12.23 (s, 1 H). |
| Example 330 | N-[(1R,2R)-2-{[6-chloro-4-(1H-pyrrolo[2,3-b]pyridin-3-yl)pyridin-2-yl]amino}cyclohexyl]cyclopropanesulfonamide | (500 MHz, DMSO-d$_6$) ppm 0.68-0.77 (m, 2 H) 0.84-0.93 (m, 2 H) 1.41-1.50 (m, 1 H) 1.63-1.70 (m, 2 H) 1.97-2.05 (m, 2 H) 2.60-2.68 (m, 1 H) 3.15-3.24 (m, 1 H) 6.73 (s, 1 H) 6.91-6.94 (m, 2 H) 7.11 (d, J = 7.63 Hz, 1 H) 7.22 (dd, J = 7.93, 4.58 Hz, 1 H) 8.16 (d, J = 2.75 Hz, 1 H) 8.30-8.34 (m, 2 H) 12.19 (s, 1 H) |
| Example 331 | N-[6-chloro-4-(1H-pyrrolo[2,3-b]pyridin-3-yl)pyridin-2-yl]-4-fluorobenzenesulfonamide | (500 MHz, DMSO-d$_6$) ppm 7.26 (dd, J = 7.93, 4.58 Hz, 1 H) 7.38 (s, 1 H) 7.42-7.50 (m, 3 H) 8.05 (dd, J = 8.85, 4.88 Hz, 2 H) 8.21 (d, J = 7.63 Hz, 1 H) 8.27 (d, J = 2.75 Hz, 1 H) 8.32 (d, J = 4.58 Hz, 1 H) 11.37 (s, 1 H) 12.35 (s, 1 H) |
| Example 332 | N-[6-chloro-4-(1H-pyrrolo[2,3-b]pyridin-3-yl)pyridin-2-yl]cyclopropanesulfonamide | (501 MHz, DMSO-d$_6$) ppm 0.95-1.23 (m, 4 H) 2.92-3.15 (m, 1 H) 7.21-7.33 (m, 1 H) 7.47 (s, 1 H) 7.56 (s, 1 H) 8.27-8.38 (m, 3 H) 10.78 (s, 1 H) 12.40 (s, 1 H) |
| Example 333 | N'-[6-chloro-4-(1H-pyrrolo[2,3-b]pyridin-3-yl)pyridin-2-yl]-N,N-diethyl-2,2-dimethylpropane-1,3-diamine | (300 MHz, DMSO-d$_6$) ppm 1.13 (s, 6 H) 1.23 (t, J = 7.12 Hz, 6 H) 3.08 (d, J = 3.39 Hz, 2 H) 3.12-3.24 (m, 4 H) 3.30 (d, J = 4.75 Hz, 2 H) 6.92 (t, J = 5.59 Hz, 1 H) 6.98 (d, J = 1.02 Hz, 1 H) 7.04 (s, 1 H) 7.23 (dd, J = 8.14, 4.75 Hz, 1 H) 8.16 (d, J = 2.71 Hz, 1 H) 8.28-8.35 (m, 2 H) 12.21 (s, 1 H) |
| Example 334 | trans-N'-[6-chloro-4-(1H-pyrrolo[2,3-b]pyridin-3-yl)pyridin-2-yl]-N,N-diethylcyclohexane-1,4-diamine | (300 MHz, DMSO-d$_6$) ppm 1.25 (t, J = 7.29 Hz, 7 H) 1.69 (s, 2 H) 2.00 (s, 2 H) 2.10 (s, 2 H) 3.10 (s, 2 H) 3.25 (s, 2 H) 6.86 (s, 3 H) 7.22 (s, 1 H) 8.11 (s, 1 H) 8.31 (s, 2 H) 8.66 (s, 1 H) 12.17 (s, 1 H) |
| Example 335 | N-(trans-4-{[6-chloro-4-(1H-pyrrolo[2,3-b]pyridin-3-yl)pyridin-2-yl]amino}cyclohexyl)-5-oxo-D-prolinamide | (300 MHz, DMSO-d$_6$) ppm 1.14-1.50 (m, 5 H) 1.73-1.94 (m, 3 H) 1.95-2.35 (m, 5 H) 3.65 (d, J = 12.54 Hz, 2 H) 6.74-6.84 (m, 1 H) 6.82-6.92 (m, 2 H) 7.12-7.28 (m, 1 H) 7.74-7.79 (m, 1 H) 7.81-7.90 (m, 1 H) 8.09-8.15 (m, 1 H) 8.24-8.37 (m, 2 H) 12.07-12.23 (m, 1 H) |
| Example 336 | N-(trans-4-{[6-chloro-4-(1H-pyrrolo[2,3-b]pyridin-3-yl)pyridin-2-yl]amino}cyclohexyl)-1-methylprolinamide | (300 MHz, DMSO-d$_6$) ppm 1.16-1.52 (m, 5 H) 1.53-1.86 (m, 5 H) 1.89-2.14 (m, 4 H) 2.13-2.35 (m, 3 H) 2.93-3.12 (m, 1 H) 3.62 (t, J = 14.24 Hz, 2 H) 6.70-6.80 (m, 1 H) 6.81-6.92 (m, 2 H) 7.12-7.30 (m, 1 H) 7.42-7.56 (m, 1 H) 8.05-8.16 (m, 1 H) 8.25-8.36 (m, 2 H) 12.10-12.17 (m, 1 H) |
| Example 337 | N-(trans-4-{[6-chloro-4-(1H-pyrrolo[2,3-b]pyridin-3-yl)pyridin-2-yl]amino}cyclohexyl)-1-methylpiperidine-2-carboxamide | (300 MHz, DMSO-d$_6$) ppm 1.13-1.85 (m, 10 H) 1.86-2.06 (m, 4 H) 2.03-2.15 (m, 3 H) 2.20-2.40 (m, 2 H) 2.79-2.89 (m, 1 H) 3.48-3.72 (m, 2 H) 6.71-6.82 (m, 1 H) 6.82-6.91 (m, 2 H) 7.13-7.27 (m, 1 H) 7.39-7.55 (m, 1 H) 8.05-8.19 (m, 1 H) 8.22-8.37 (m, 2 H) 12.08-12.21 (m, 1 H) |
| Example 338 | N-(trans-4-{[6-chloro-4-(1H-pyrrolo[2,3-b]pyridin-3-yl)pyridin-2-yl]amino}cyclohexyl)-5-oxo-L-prolinamide | (300 MHz, DMSO-d$_6$) ppm 1.17-1.46 (m, 4 H) 1.75-1.95 (m, 3 H) 1.93-2.08 (m, 3 H) |

| Example # | Name | $^1$H NMR (ppm) |
|---|---|---|
| | | 2.04-2.33 (m, 3 H) 3.63 (s, 1 H) 3.89-4.01 (m, 1 H) 6.73-6.83 (m, 1 H) 6.82-6.90 (m, 2 H) 7.15-7.27 (m, 1 H) 7.74-7.80 (m, 1 H) 7.82-7.88 (m, 1 H) 8.08-8.16 (m, 1 H) 8.24-8.35 (m, 2 H) 12.10-12.19 (m, 1 H) |
| Example 339 | N-(3-{[6-chloro-4-(1H-pyrrolo[2,3-b]pyridin-3-yl)pyridin-2-yl]amino}cyclohexyl)-1-methylpiperidine-2-carboxamide | (500 MHz, DMSO-d$_6$): 1.01-1.26 (m, 3 H), 1.28-1.50 (m, 2 H), 1.54-1.88 (m, J = 2.37 Hz, 6 H), 2.08-2.24 (m, 1 H), 2.69 (d, J = 6.10 Hz, 3 H), 3.03 (d, J = 12.21 Hz, 1 H), 3.27-3.43 (m, 1 H), 3.47-3.67 (m, 2 H), 3.67-3.88 (m, 2 H), 6.85 (s, 2 H), 6.89 (s, 1 H), 7.16-7.24 (m, 1 H), 8.14 (d, J = 2.71 Hz, 1 H), 8.30 (s, 1 H), 8.32 (s, 1 H), 8.58 (d, J = 7.46 Hz, 1 H), 9.62 (s, 1 H), 12.17 (s, 1 H). |
| Example 340 | 2-(azepan-1-yl)-N-(3-{[6-chloro-4-(1H-pyrrolo[2,3-b]pyridin-3-yl)pyridin-2-yl]amino}cyclohexyl)acetamide | (500 MHz, DMSO-d$_6$): 1.11 (q, J = 11.75 Hz, 3 H), 1.30-1.50 (m, 1 H), 1.52-1.70 (m, 4 H), 1.71-1.89 (m, 6 H), 1.94 (d, J = 12.21 Hz, 1 H), 2.10-2.27 (m, 1 H), 3.06-3.22 (m, 2 H), 3.24-3.41 (m, 2 H), 3.66-3.83 (m, 2 H), 3.88 (d, J = 4.75 Hz, 2 H), 6.85 (s, 1 H), 6.89 (s, 1 H), 7.22 (dd, J = 7.80, 5.09 Hz, 1 H), 8.14 (d, J = 2.71 Hz, 1 H), 8.24-8.37 (m, 2 H), 8.48 (d, J = 7.46 Hz, 1 H), 9.53 (s, 1 H), 12.18 (d, J = 2.03 Hz, 1 H). |
| Example 341 | N-(trans-4-{[6-chloro-4-(1H-pyrrolo[2,3-b]pyridin-3-yl)pyridin-2-yl]amino}cyclohexyl)cyclopentanecarboxamide | (300 MHz, DMSO-d$_6$) ppm 1.14-1.40 (m, 5 H) 1.39-1.77 (m, 9 H) 1.75-1.88 (m, 3 H) 1.90-2.09 (m, 3 H) 3.38-3.73 (m, 2 H) 7.15-7.27 (m, 1 H) 7.55-7.67 (m, 1 H) 8.05-8.18 (m, 1 H) 8.25-8.35 (m, 2 H) 12.05-12.20 (m, 1 H) |
| Example 342 | N-(trans-4-{[6-chloro-4-(1H-pyrrolo[2,3-b]pyridin-3-yl)pyridin-2-yl]amino}cyclohexyl)-1-methyl-5-oxoprolinamide | (300 MHz, DMSO-d$_6$) ppm 1.28 (q, J = 9.16 Hz, 5 H) 1.76-1.93 (m, 2 H) 2.01 (d, J = 7.80 Hz, 2 H) 2.38 (dd, J = 8.48, 2.37 Hz, 2 H) 2.64-2.75 (m, 3 H) 2.97-3.15 (m, 1 H) 3.52-3.70 (m, 2 H) 6.76 (d, J = 7.80 Hz, 1 H) 6.82-6.91 (m, 2 H) 7.20 (dd, J = 7.80, 5.09 Hz, 1 H) 7.94 (d, J = 7.80 Hz, 1 H) 8.12 (d, J = 3.05 Hz, 1 H) 8.24-8.36 (m, 2 H) 12.13 (s, 1 H) |
| Example 343 | N-(3-{[6-chloro-4-(1H-pyrrolo[2,3-b]pyridin-3-yl)pyridin-2-yl]amino}cyclohexyl)pyrrolidine-3-carboxamide | (500 MHz, DMSO-d$_6$): 0.95-1.26 (m, 2 H), 1.27-1.52 (m, 1 H), 1.60-1.84 (m, 3 H), 1.85-1.99 (m, 2 H), 2.04-2.20 (m, 2 H), 2.86-3.07 (m, 1 H), 3.06-3.41 (m, 4 H), 3.71 (d, J = 12.54 Hz, 2 H), 6.84 (s, 1 H) 6.88 (s, 1 H), 7.22 (dd, J = 7.63, 5.26 Hz, 1 H), 8.11 (d, J = 7.80 Hz, 1 H), 8.14 (d, J = 2.71 Hz, 1 H), 8.30 (s, 1 H), 8.32 (d, J = 2.71 Hz, 1 H), 8.74 (s, 1 H), 12.17 (d, J = 2.03 Hz, 1 H). |
| Example 344 | N-(3-{[6-chloro-4-(1H-pyrrolo[2,3-b]pyridin-3-yl)pyridin-2-yl]amino}cyclohexyl)piperidine-4-carboxamide | (500 MHz, DMSO-d$_6$): 0.94-1.23 (m, 3 H), 1.23-1.50 (m, 2 H), 1.59-1.88 (m, 4 H), 1.93 (d, J = 11.87 Hz, 1 H), 2.09 (d, J = 12.21 Hz, 1 H), 2.20-2.44 (m, 1 H), 2.80-2.94 (m, 1 H), 2.98-3.09 (m, 1 H), 3.15-3.40 (m, 3 H), 3.48-3.92 (m, 2 H), 6.84 (s, 1 H), 6.88 (s, 1 H), 7.22 (dd, J = 7.80, 5.09 Hz, 1 |

-continued

| Example # | Name | ¹H NMR (ppm) |
|---|---|---|
| | | H), 8.14 (d, J = 2.71 Hz, 1 H), 8.30 (s, 1 H), 8.31-8.34 (m, 1 H), 12.06-12.31 (m, 1 H). |
| Example 345 | N-(3-{[6-chloro-4-(1H-pyrrolo[2,3-b]pyridin-3-yl)pyridin-2-yl]amino}cyclohexyl)piperidine-3-carboxamide | (500 MHz, DMSO-$d_6$): 0.93-1.22 (m, 3 H), 1.26-1.47 (m, 1 H), 1.47-2.00 (m, 8 H), 2.03-2.18 (m, 1 H), 2.79-2.93 (m, 1 H), 2.93-3.06 (m, 1 H), 3.04-3.29 (m, 2 H), 3.52-3.83 (m, 2 H), 6.84 (s, 1 H), 6.88 (s, 1 H), 7.22 (dd, J = 7.63, 4.92 Hz, 1 H), 8.03 (d, J = 7.80 Hz, 1 H), 8.13 (d, J = 2.71 Hz, 1 H), 8.30 (s, 1 H), 8.32 (t, J = 1.70 Hz, 1 H), 8.41 (s, 1 H), 12.16 (d, J = 2.03 Hz, 1 H). |
| Example 346 | N-(3-{[6-chloro-4-(1H-pyrrolo[2,3-b]pyridin-3-yl)pyridin-2-yl]amino}cyclohexyl)-1-methylpyrrolidine-3-carboxamide | (500 MHz, DMSO-$d_6$): 0.97-1.24 (m, 3 H), 1.40 (d, J = 12.55 Hz, 1 H), 1.63-1.84 (m, 2 H), 1.92 (d, J = 8.82 Hz, 2 H), 2.02-2.22 (m, 2 H), 2.73-2.83 (m, 2 H), 2.87 (dd, J = 4.92, 1.86 Hz, 2 H), 2.99-3.39 (m, 3 H), 3.54 (s, 3 H), 6.84 (s, 1 H), 6.88 (s, 1 H), 7.22 (dd, J = 7.63, 5.26 Hz, 1 H), 8.09 (s, 1 H), 8.13 (d, J = 3.05 Hz, 1 H), 8.30 (s, 1 H), 8.32 (t, J = 2.03 Hz, 1 H), 12.17 (d, J = 2.03 Hz, 1 H). |
| Example 347 | N-(3-{[6-chloro-4-(1H-pyrrolo[2,3-b]pyridin-3-yl)pyridin-2-yl]amino}cyclohexyl)-1-methylpiperidine-4-carboxamide | (500 MHz, DMSO-$d_6$): 0.95-1.22 (m, 4 H), 1.20-1.53 (m, 2 H), 1.54-2.06 (m, 8 H), 2.01-2.32 (m, 1 H), 2.68-2.81 (m, 4 H), 2.82-3.10 (m, 1 H), 3.17-3.32 (m, 1 H), 3.29-3.51 (m, 1 H), 6.84 (s, 1 H), 6.88 (s, 1 H), 7.22 (dd, J = 7.80, 5.09 Hz, 1 H), 8.13 (d, J = 2.71 Hz, 1 H), 8.30 (s, 1 H), 8.32 (s, 1 H), 12.17 (s, 1 H). |
| Example 348 | N-(3-{[6-chloro-4-(1H-pyrrolo[2,3-b]pyridin-3-yl)pyridin-2-yl]amino}cyclohexyl)-1-methylpiperidine-3-carboxamide | (500 MHz, DMSO-$d_6$): 1.32-1.53 (m, 4 H), 1.52-1.70 (m, 3 H), 1.70-1.99 (m, 5 H), 2.65-2.82 (m, 4 H), 2.92 (s, 3 H), 3.27-3.51 (m, 1 H), 3.59-3.86 (m, 1 H), 6.82 (s, 1 H), 6.96 (s, 1 H), 7.21 (dd, J = 8.14, 4.75 Hz, 1 H), 8.08 (d, J = 7.80 Hz, 1 H), 8.20 (d, J = 2.71 Hz, 1 H), 8.28-8.39 (m, 2 H), 12.20 (s, 1 H). |
| Example 349 | N-(3-{[6-chloro-4-(1H-pyrrolo[2,3-b]pyridin-3-yl)pyridin-2-yl]amino}cyclohexyl)-1-(dimethylamino)cyclobutanecarboxamide | (500 MHz, DMSO-$d_6$): 0.99-1.55 (m, 6 H), 1.59-1.89 (m, 6 H), 1.95 (d, J = 11.87 Hz, 1 H), 2.14 (d, J = 11.19 Hz, 1 H), 2.70 (s, 6 H), 3.64-4.01 (m, 2 H), 6.85 (s, 1 H), 6.89 (s, 1 H), 7.22 (dd, J = 7.46, 5.09 Hz, 1 H), 8.13 (d, J = 3.05 Hz, 1 H), 8.30 (s, 1 H), 8.31-8.34 (m, 1 H), 8.36 (d, J = 8.14 Hz, 1 H), 12.17 (d, J = 1.70 Hz, 1 H). |
| Example 350 | N-(3-{[6-chloro-4-(1H-pyrrolo[2,3-b]pyridin-3-yl)pyridin-2-yl]amino}cyclohexyl)-N~2~-,N~2~-dimethyl-L-alaninamide | (500 MHz, DMSO-$d_6$): 1.04-1.25 (m, 3 H), 1.41 (dd, J = 6.94, 3.77 Hz, 3 H), 1.64-1.89 (m, 3 H), 1.94 (d, J = 10.31 Hz, 1 H), 2.13-2.30 (m, 1 H), 2.75 (s, 3 H), 2.77 (s, 3 H), 3.51-3.88 (m, 3 H), 6.85 (s, 1 H), 6.89 (d, J = 1.19 Hz, 1 H), 7.22 (dd, J = 7.34, 5.35 Hz, 1 H), 8.30 (s, 1 H), 8.32 (d, J = 1.98 Hz, 1 H), 8.52 (d, J = 7.54 Hz, 1 H), 12.17 (s, 1 H). |

| Example # | Name | ¹H NMR (ppm) |
|---|---|---|
| Example 351 | N~2~-1-azabicyclo[2.2.2]oct-3-yl-N-(trans-4-{[6-chloro-4-(1H-pyrrolo[2,3-b]pyridin-3-yl)pyridin-2-yl]amino}cyclohexyl)glycinamide | (400 MHz, DMSO-$d_6$) ppm 1.23-1.42 (m, 4 H), 1.85-2.08 (m, 6 H), 2.10-2.21 (m, 1 H), 2.28-2.34 (m, 1 H), 3.97-4.01 (m, 2 H), 6.86-6.90 (m, 2 H), 7.21 (dd, J = 7.32, 5.19 Hz, 1 H), 8.13 (d, J = 2.75 Hz, 1 H), 8.30-8.33 (m, 2 H), 8.34-8.39 (m, 2H), 8.64 (d, J = 7.63 Hz, 1 H) 12.14-12.22 (m, 1 H). |
| Example 352 | N-(trans-4-{[6-chloro-4-(1H-pyrrolo[2,3-b]pyridin-3-yl)pyridin-2-yl]amino}cyclohexyl)-N~2~-(2-hydroxyethyl)glycinamide | (400 MHz, DMSO-$d_6$) ppm 1.27-1.37 (m, 4 H), 1.85-1.91 (m, 2 H), 1.98-2.06 (m, 2 H), 6.69-6.84 (m, 1 H), 6.84-6.89 (m, 2 H), 7.21 (dd, J = 7.93, 4.58 Hz, 1 H), 8.13 (d, J = 2.75 Hz, 1 H), 8.28-8.38 (m, 2 H), 8.65-8.76 (m, 2 H), 12.12-12.22 (m, 1 H). |
| Example 353 | N-(3-{[6-chloro-4-(1H-pyrrolo[2,3-b]pyridin-3-yl)pyridin-2-yl]amino}cyclohexyl)-2-(1,3-dioxo-1,3-dihydro-2H-isoindol-2-yl)ethanesulfonamide | (500 MHz, DMSO-$d_6$): 0.82-1.28 (m, 3 H), 1.44 (s, 2 H), 1.55-1.83 (m, 3 H), 1.93 (d, J = 9.49 Hz, 2 H), 2.11-2.30 (m, 2 H), 3.20-3.45 (m, 2 H), 6.84 (s, 1 H), 6.88 (d, J = 3.05 Hz, 1 H), 7.56-7.61 (m, 2 H), 7.61-7.69 (m, 2 H), 7.74-7.80 (m, 1 H), 8.12 (d, J = 1.36 Hz, 1 H), 8.30 (d, J = 7.12 Hz, 2 H), 12.15 (s, 1 H). |
| Example 354 | N-(trans-4-{[6-chloro-4-(1H-pyrrolo[2,3-b]pyridin-3-yl)pyridin-2-yl]amino}cyclohexyl)-N~2~-(4-methylcyclohexyl)glycinamide | (500 MHz, DMSO-$d_6$) ppm 0.83-0.93 (m, 3 H), 1.25-1.39 (m, 5 H), 1.42-1.52 (m, 2 H), 1.61-1.78 (m, 4 H), 1.85-1.93 (m, 2 H), 2.00-2.06 (m, 2 H), 3.65-3.72 (m, 2 H), 6.75-6.84 (m, 1 H), 6.84-6.92 (m, 2 H), 7.21 (dd, J = 7.93, 4.88 Hz, 1 H), 8.13 (d, J = 3.05 Hz, 1 H), 8.29-8.35 (m, 2 H), 8.38 (dd, J = 7.48, 3.20 Hz, 1 H), 8.70 (dd, J = 28.38, 5.19 Hz, 2 H), 12.14-12.20 (m, 1 H). |
| Example 355 | N-(trans-4-{[6-chloro-4-(1H-pyrrolo[2,3-b]pyridin-3-yl)pyridin-2-yl]amino}cyclohexyl)-N~2~-(2,2-dimethylpropyl)glycinamide | (400 MHz, DMSO-$d_6$) ppm 0.99 (s, 9 H), 1.22-1.43 (m, 4 H), 1.84-1.94 (m, 2 H), 1.98-2.09 (m, 2 H), 2.74-2.82 (m, 2 H), 3.62-3.70 (m, 2 H), 6.84-6.92 (m, 2 H), 7.22 (dd, J = 7.93, 4.58 Hz, 1 H), 8.13 (d, J = 2.75 Hz, 1 H), 8.28-8.35 (m, 2 H), 8.41 (d, J = 7.32 Hz, 1 H), 8.49 (s, 2 H), 12.12-12.23 (m, 1 H). |
| Example 356 | N-(trans-4-{[6-chloro-4-(1H-pyrrolo[2,3-b]pyridin-3-yl)pyridin-2-yl]amino}cyclohexyl)-N~2~-ethyl-N~2~-(2-hydroxyethyl)glycinamide | (400 MHz, DMSO-$d_6$) ppm 1.21 (t, J = 7.17 Hz, 3 H), 1.25-1.44 (m, 4 H), 1.84-1.94 (m, 2 H), 1.98-2.07 (m, 2 H), 3.19-3.30 (m, 4 H), 3.86-4.05 (m, 4 H), 6.85-6.91 (m, 2 H), 7.21 (dd, J = 7.93, 4.58 Hz, 1 H), 8.29-8.35 (m, 2 H), 8.51 (d, J = 7.63 Hz, 1 H), 9.34 (s, 1 H), 12.14-12.20 (m, 1H) |
| Example 357 | trans-N-[6-chloro-4-(1H-pyrrolo[2,3-b]pyridin-3-yl)pyridin-2-yl]-N'-(piperidin-4-yl)cyclohexane-1,4-diamine | (500 MHz, DMSO-$d_6$): 1.13-1.37 (m, 2 H), 1.36-1.55 (m, 2 H), 1.56-1.80 (m, 2 H), 1.96-2.25 (m, 6 H), 2.84-3.08 (m, 2 H), 3.07-3.31 (m, 2 H), 3.31-3.56 (m, 2 H), 3.57-3.81 (m, 2 H), 6.88 (s, 1 H), 6.90 (s, 1 H), 7.16-7.25 (m, 1 H), 8.14 (d, J = 2.78 Hz, 1 H), 8.30 (s, 1 H), 8.32 (s, 1 H), 12.18 (d, J = 1.98 Hz, 1 H). |
| Example 358 | N-(trans-4-{[6-chloro-4-(1H-pyrrolo[2,3-b]pyridin-3-yl)pyridin-2- | (500 MHz, DMSO-$d_6$): 1.07-1.59 (m, 5 H), 1.98 (t, J = 8.99 Hz, |

| Example # | Name | ¹H NMR (ppm) |
|---|---|---|
| | yl]amino}cyclohexyl)-2-(1,3-dioxo-1,3-dihydro-2H-isoindol-2-yl)ethanesulfonamide | 4 H), 3.04-3.26 (m, 1 H), 3.28-3.45 (m, 2 H), 3.89-4.04 (m, 2 H), 6.86 (s, 1 H), 6.87 (s, 1 H), 7.05-7.30 (m, 2 H), 7.35 (d, J = 7.80 Hz, 1 H), 7.73-8.03 (m, 2 H), 8.12 (d, J = 2.71 Hz, 1 H), 8.20-8.39 (m, 2 H), 8.47 (d, J = 3.05 Hz, 1 H), 12.15 (d, J = 2.03 Hz, 1 H). |
| Example 359 | 6-chloro-N-(4-{[4-(cyclobutylamino)cyclohexyl]methyl}cyclohexyl)-4-(1H-pyrrolo[2,3-b]pyridin-3-yl)pyridin-2-amine | (500 MHz, DMSO-$d_6$): 0.73-1.44 (m, 10 H), 1.41-1.89 (m, 10 H), 1.97 (t, J = 11.53 Hz, 2 H), 2.04-2.39 (m, 4 H), 2.75-3.12 (m, 1 H), 3.60 (t, J = 10.34 Hz, 1 H), 3.66-3.95 (m, 1 H), 6.79-6.90 (m, 2 H), 7.15-7.28 (m, 1 H), 8.12 (t, J = 3.22 Hz, 1 H), 8.26-8.33 (m, 2 H), 12.15 (d, J = 1.36 Hz, 1 H). |
| Example 360 | N-[6-chloro-4-(1H-pyrrolo[2,3-b]pyridin-3-yl)pyridin-2-yl]-2-(piperidin-1-yl)acetamide | (400 MHz, METHANOL-$d_4$) ppm 1.78-2.10 (m, 6 H) 3.13 (t, J = 10.53 Hz, 2 H) 3.68 (d, J = 10.68 Hz, 2 H) 4.19 (s, 2 H) 7.39 (dd, J = 8.09, 5.04 Hz, 1 H) 7.55 (d, J = 1.22 Hz, 1 H) 8.10 (s, 1 H) 8.38 (dd, J = 5.04, 1.07 Hz, 1 H) 8.54 (s, 1 H) 8.59 (dd, J = 8.09, 1.37 Hz, 1 H) |
| Example 361 | trans-N-[6-chloro-4-(1H-pyrrolo[2,3-b]pyridin-3-yl)pyridin-2-yl]-N'-(1-cyclobutylpiperidin-4-yl)cyclohexane-1,4-diamine | (500 MHz, DMSO-$d_6$): 1.14-1.60 (m, 5 H), 1.72 (d, J = 16.28 Hz, 4 H), 1.93-2.33 (m, 10 H), 2.65-2.93 (m, 2 H), 3.11-3.37 (m, 1 H), 3.37-3.70 (m, 4 H), 6.88 (s, 1 H), 6.90 (d, J = 1.36 Hz, 1 H), 7.09-7.25 (m, 1 H), 8.13 (d, J = 2.71 Hz, 1 H), 8.30 (s, 1 H), 8.32 (s, 1 H), 12.17 (d, J = 2.37 Hz, 1 H). |
| Example 362 | tert-butyl 4-(4-{[6-chloro-4-(1H-pyrrolo[2,3-b]pyridin-3-yl)pyridin-2-yl]amino}cyclohexyl)piperidine-1-carboxylate | (500 MHz, DMSO-$d_6$): 0.90-1.25 (m, 6 H), 1.38 (s, 9 H), 1.43-1.59 (m, 3 H), 1.61-1.84 (m, 4 H), 2.55-2.75 (m, 2 H), 3.23-3.30 (m, 1 H), 3.84-4.10 (m, 3 H), 6.98 (s, 1 H), 7.38-7.47 (m, 1 H), 7.64 (s, 1 H), 7.66 (s, 1 H), 8.17 (d, J = 1.59 Hz, 1 H), 8.45 (s, 1 H) 8.46 (s, 1 H). |
| Example 363 | benzyl {4-[(trans-4-{[6-chloro-4-(1H-pyrrolo[2,3-b]pyridin-3-yl)pyridin-2-yl]amino}cyclohexyl)amino]cyclohexyl}carbamate | (500 MHz, DMSO-$d_6$): 1.24-1.65 (m, 6 H), 1.68-1.86 (m, 6 H), 2.08 (d, J = 6.44 Hz, 4 H), 3.09-3.40 (m, 4 H), 4.99 (s, 2 H), 6.88-6.90 (m, 2 H), 7.27-7.41 (m, 7 H), 8.13 (d, J = 2.71 Hz, 1 H), 8.30 (s, 1 H). |
| Example 364 | tert-butyl 3-[(trans-4-{[6-chloro-4-(1H-pyrrolo[2,3-b]pyridin-3-yl)pyridin-2-yl]amino}cyclohexyl)carbamoyl]azetidine-1-carboxylate | (300 MHz, DMSO-$d_6$) ppm 1.12-1.31 (m, 4 H) 1.32-1.43 (m, 9 H) 1.67-1.93 (m, 2 H) 1.93-2.11 (m, 2 H) 3.12-3.30 (m, 2 H) 3.74-3.96 (m, 4 H) 6.74-6.81 (m, 1 H) 6.82-6.90 (m, 2 H) 7.14-7.26 (m, 1 H) 7.82-7.93 (m, 2 H) 8.08-8.16 (m, 1 H) 8.25-8.35 (m, 2 H) 12.11-12.18 (m, 1 H) |
| Example 365 | N-[4-(acetylamino)cyclohexyl]-N-(trans-4-{[6-chloro-4-(1H-pyrrolo[2,3-b]pyridin-3-yl)pyridin-2-yl]amino}cyclohexyl)acetamide | (500 MHz, DMSO-$d_6$): 1.14-1.66 (m, 9 H), 1.78 (s, 3 H), 1.84 (s, 3 H), 1.86-1.93 (m, 1 H), 1.99-2.16 (m, 5 H), 3.07-3.29 (m, 2 H), 3.39-3.52 (m, 1 H), 3.55-3.77 (m, 2 H), 6.88 (s, 1 H), 6.90 (s, 1 H), 7.21 (dd, J = 7.46, 5.09 Hz, 1 H), 7.79 (d, J = 7.80 Hz, 1 H), 8.13 (d, J = 2.71 Hz, 1 H), 8.30 (s, 1 H), 8.32 (d, J = 3.05 Hz, 1 H), 12.17 (s, 1 H). |

-continued

| Example # | Name | ¹H NMR (ppm) |
|---|---|---|
| Example 366 | [4-(4-{[6-chloro-4-(1H-pyrrolo[2,3-b]pyridin-3-yl)pyridin-2-yl]amino}cyclohexyl)piperidin-1-yl](cyclopropyl)methanone | (500 MHz, DMSO-$d_6$): 0.49-0.79 (m, 4 H), 0.88-1.30 (m, 5 H), 1.28-1.62 (m, 6 H), 1.62-1.85 (m, 5 H), 1.85-2.13 (m, 2 H), 2.85-3.16 (m, 1 H), 3.98 (d, J = 9.49 Hz, 1 H), 6.76-6.92 (m, 2 H), 6.99 (s, 1 H), 7.23 (dd, J = 7.97, 4.58 Hz, 1 H), 8.13 (t, J = 2.88 Hz, 1 H), 8.23-8.56 (m, 2 H), 12.17 (s, 1 H). |
| Example 367 | N-(trans-4-{[6-chloro-4-(1H-pyrrolo[2,3-b]pyridin-3-yl)pyridin-2-yl]amino}cyclohexyl)-1-(2-hydroxyethyl)piperidine-4-carboxamide | (300 MHz, DMSO-$d_6$) ppm 1.18-1.41 (m, 5 H) 1.45-1.68 (m, 5 H) 1.71-2.09 (m, 6 H) 2.17-2.31 (m, 1 H) 2.35 (t, J = 6.15 Hz, 1 H) 2.72-2.97 (m, 2 H) 3.10-3.25 (m, 1 H) 3.41-3.53 (m, 2 H) 3.56-3.68 (m, 1 H) 6.69-6.83 (m, 1 H) 6.82-6.92 (m, 2 H) 7.12-7.29 (m, 1 H) 7.57-7.66 (m, 1 H) 8.07-8.18 (m, 1 H) 8.25-8.36 (m, 2 H) 12.09-12.19 (m, 1 H) |
| Example 368 | N-{4-[(4-{[6-chloro-4-(1H-pyrrolo[2,3-b]pyridin-3-yl)pyridin-2-yl]amino}cyclohexyl)methyl]cyclohexyl}cyclopropanecarboxamide | (500 MHz, DMSO-$d_6$): 0.42-0.73 (m, 4 H), 0.81-1.39 (m, 6 H), 1.39-1.59 (m, 6 H), 1.59-1.84 (m, 6 H), 1.99 (d, J = 12.69 Hz, 2 H), 3.27-3.53 (m, 2 H), 6.80-6.92 (m, 2 H), 7.15-7.30 (m, 1 H), 7.87 (t, J = 6.35 Hz, 1 H), 8.12 (t, J = 3.17 Hz, 1 H), 8.24-8.42 (m, 2 H), 12.15 (s, 1 H). |
| Example 369 | 1-{4-[(4-{[6-chloro-4-(1H-pyrrolo[2,3-b]pyridin-3-yl)pyridin-2-yl]amino}cyclohexyl)amino]piperidin-1-yl}ethanone | (500 MHz, DMSO-$d_6$): 1.11-1.57 (m, 6 H), 2.02 (s, 3 H), 2.10 (d, J = 10.85 Hz, 5 H), 2.93-3.30 (m, 6 H), 3.79-4.05 (m, 1 H), 4.45 (d, J = 13.90 Hz, 1 H), 6.89 (d, J = 5.76 Hz, 2 H), 7.21 (dd, J = 7.46, 5.43 Hz, 1 H), 8.13 (d, J = 2.71 Hz, 1 H), 8.25-8.36 (m, 2 H), 12.16 (s, 1 H). |
| Example 370 | N-[6-chloro-4-(1H-pyrrolo[2,3-b]pyridin-3-yl)pyridin-2-yl]-N-{4-[1-(methylsulfonyl)piperidin-4-yl]cyclohexyl}methanesulfonamide | (500 MHz, DMSO-$d_6$): 0.95-1.30 (m, 5 H), 1.35-1.66 (m, 6 H), 1.67-1.95 (m, 5 H), 2.64-2.97 (m, 1 H), 3.10-3.33 (m, 1 H), 3.81 (s, 6 H), 4.34 (d, J = 15.26 Hz, 1 H), 6.80-6.86 (m, 1 H), 6.87 (s, 1 H), 6.98 (s, 1 H), 7.23 (dd, J = 8.14, 4.75 Hz, 1 H), 8.31 (dd, J = 4.75, 1.36 Hz, 1 H), 8.36 (d, J = 8.14 Hz, 1 H), 12.15 (s, 1 H). |
| Example 371 | 6-chloro-N-[4-(1-methylpiperidin-3-yl)cyclohexyl]-4-(1H-pyrrolo[2,3-b]pyridin-3-yl)pyridin-2-amine | (500 MHz, DMSO-$d_6$): 1.02-1.30 (m, 3 H), 1.33-1.69 (m, 6 H), 1.68-1.97 (m, 4 H), 1.97-2.12 (m, 1 H), 2.71-2.76 (m, 1 H), 2.77 (s, 3 H), 2.81 (d, J = 4.75 Hz, 1 H), 3.28-3.52 (m, 2 H), 3.94-4.12 (m, 1 H), 6.89 (s, 1 H), 6.97 (s, 1 H), 7.22 (dd, J = 7.97, 4.58 Hz, 1 H), 8.13 (d, J = 2.71 Hz, 1 H), 8.28-8.33 (m, 1 H), 8.35 (d, J = 8.14 Hz, 1 H), 12.16 (s, 1 H). |
| Example 372 | 6-chloro-N-methyl-N-[4-(1-methylpiperidin-3-yl)cyclohexyl]-4-(1H-pyrrolo[2,3-b]pyridin-3-yl)pyridin-2-amine | (500 MHz, DMSO-$d_6$): 1.08-1.41 (m, 3 H), 1.33-2.06 (m, 10 H), 2.68-2.85 (m, 4 H), 2.91 (s, 3 H), 2.94 (s, 3 H), 3.22-3.68 (m, 2 H), 6.82-7.06 (m, 2 H), 7.13-7.32 (m, 1 H), 8.14-8.19 (m, 1 H), 8.23-8.36 (m, 2 H), 12.20 (s, 1 H). |
| Example 373 | N-{2-[(trans-4-{[6-chloro-4-(1H-pyrrolo[2,3-b]pyridin-3-yl)pyridin-2- | (300 MHz, DMSO-$d_6$) ppm 0.59-0.78 (m, 4 H) |

| Example # | Name | ¹H NMR (ppm) |
|---|---|---|
| | yl]amino}cyclohexyl)sulfamoyl]ethyl}cyclopropanecarboxamide | 1.18-1.46 (m, 5 H) 1.44-1.60 (m, 1 H) 1.85-2.07 (m, 5 H) 3.06-3.21 (m, 2 H) 3.35-3.50 (m, 2 H) 3.60 (d, J = 16.28 Hz, 1 H) 6.72-6.81 (m, 1 H) 6.82-6.90 (m, 2 H) 7.11-7.29 (m, 1 H) 8.08-8.16 (m, 1 H) 8.14-8.25 (m, 1 H) 8.26-8.35 (m, 2 H) 12.14 (s, 1 H) |
| Example 374 | 3-{[6-chloro-4-(1H-pyrrolo[2,3-b]pyridin-3-yl)pyridin-2-yl]amino}propan-1-ol | (400 MHz, d₆-DMSO) δ 1.71-1.77 (m, 2 H), 3.35 (t, J = 5.1 Hz, 2 H), 3.58 (t, J = 4.5 Hz, 2 H), 6.65 (d, J = 1.2 Hz, 1 H), 6.75 (d, J = 0.6 Hz, 1 H), 7.12 (dd, J = 6.0 Hz, 1 H), 7.75 (s, 1 H), 8.17 (dd, J = 3.6 Hz, 1 H), 8.24 (dd, J = 6.0 Hz, 1 H). |
| Example 375 | 6-chloro-N-[3-(morpholin-4-yl)propyl]-4-(1H-pyrrolo[2,3-b]pyridin-3-yl)pyridin-2-amine | (400 MHz, d₆-DMSO) δ 1.78-1.71 (m, 2 H), 2.41 (s, 3 H), 2.38 (s, 3 H), 3.30 (t, J = 5.1 Hz, 2 H), 3.60 (t, J = 3.6 Hz, 2 H), 6.67 (d, J = 0.6 Hz, 1 H), 6.69 (d, J = 0.6 Hz, 1 H), 7.13 (dd, J = 6.0 Hz, 1 H), 7.75 (s, 1 H), 8.17 (dd, J = 3.6 Hz, 1 H), 8.23 (dd, J = 6.0 Hz, 1 H). |
| Example 376 | 6-chloro-N-[3-(1H-imidazol-1-yl)propyl]-4-(1H-pyrrolo[2,3-b]pyridin-3-yl)pyridin-2-amine | (400 MHz, d₆-DMSO) δ 2.07-2.00 (m, 2 H), 3.27 (t, J = 5.4 Hz, 2 H), 4.08 (t, J = 5.1 Hz, 2 H), 6.64 (d, J = 0.6 Hz, 1 H), 6.79 (d, J = 0.6 Hz, 1 H), 6.92 (s, 1 H), 7.12 (s, 1 H), 7.13 (dd, J = 6.0 Hz, 1 H), 7.66 (s, 1 H), 7.76 (s, 1 H), 8.18 (dd, J = 3.6 Hz, 1 H), 8.24 (dd, J = 5.7 Hz, 1 H). |
| Example 377 | 5-{[6-chloro-4-(1H-pyrrolo[2,3-b]pyridin-3-yl)pyridin-2-yl]amino}pentan-1-ol | (400 MHz, d₆-DMSO) δ 1.58-1.35 (m, 6 H), 3.24 (t, J = 5.4 Hz, 2 H), 3.48 (t, J = 5.1 Hz, 2 H), 6.67 (d, J = 0.9 Hz, 1 H), 6.69 (d, J = 0.9 Hz, 1 H), 7.13 (dd, J = 6.0 Hz, 1 H), 7.75 (s, 1 H), 8.17 (dd, J = 3.3 Hz, 1 H), 8.23 (d, J = 6.0 Hz, 1 H). |
| Example 378 | 6-chloro-N-[2-(pyridin-3-yl)ethyl]-4-(1H-pyrrolo[2,3-b]pyridin-3-yl)pyridin-2-amine | (400 MHz, d₆-DMSO) δ 2.88 (t, J = 5.1 Hz, 2 H), 3.54 (t, J = 5.4 Hz, 2 H), 6.61 (s, 1 H), 6.76 (s, 1 H), 7.12 (dd, J = 6.0 Hz, 1 H), 7.70-7.68 (m, 1 H), 7.29-7.25 (m, 1 H), 7.74 (s, 1 H), 8.17 (d, J = 3.6 Hz, 1 H), 8.21 (d, J = 6.0 Hz, 1 H), 8.26 (d, J = 3.3 Hz, 1 H), 8.36 (d, J = 0.9 Hz, 1 H). |
| Example 379 | N-[1-(4-aminocyclohexyl)piperidin-4-yl]-6-chloro-4-(1H-pyrrolo[2,3-b]pyridin-3-yl)pyridin-2-amine | (500 MHz, DMSO-d₆): 1.25-1.48 (m, 1 H) 1.47-1.98 (m, 7 H), 2.08 (t, J = 11.30 Hz, 2 H), 2.15-2.32 (m, 2 H), 2.36-2.48 (m, 1 H), 3.12-3.57 (m, 6 H), 6.91 (d, J = 2.78 Hz, 1 H), 6.96 (s, 1 H), 7.18-7.27 (m, 1 H), 7.90 (dd, J = 11.10, 4.36 Hz, 2 H), 8.15 (d, J = 2.78 Hz, 1 H), 8.31 (s, 1 H), 8.33 (s, 1 H), 12.21 (d, J = 1.98 Hz, 1 H). |
| Example 380 | 6-chloro-N-methyl-N-[4-(1-methylpyrrolidin-3-yl)cyclohexyl]-4-(1H-pyrrolo[2,3-b]pyridin-3-yl)pyridin-2-amine | (500 MHz, DMSO-d₆): 1.36-2.31 (m, 10 H), 2.80-2.85 (m, 2 H), 2.86 (s, 3 H), 2.96 (s, 3 H), 3.01-3.35 (m, 2 H), 3.48-3.84 (m, 3 H), 6.79 (s, 1 H), 6.94 (s, 1 H), 7.21 (dd, J = 7.93, 4.76 Hz, 1 H), 8.19 (d, J = 2.78 Hz, 1 H), 8.26-8.35 (m, 2 H), 12.21 (s, 1 H). |
| Example 381 | 1-benzyl-N-(trans-4-{[6-chloro-4-(1H-pyrrolo[2,3-b]pyridin-3-yl)pyridin-2-yl]amino}cyclohexyl)azetidine-3-carboxamide | (300 MHz, DMSO-d₆) ppm 1.09-1.43 (m, 5 H) 1.64-1.91 (m, 3 H) 1.90-2.11 (m, 2 H) 3.01-3.19 (m, 4 H) |

| Example # | Name | ¹H NMR (ppm) |
|---|---|---|
| | | 3.41-3.66 (m, 4 H) 6.72-6.82 (m, 1 H) 6.82-6.92 (m, 2 H) 7.14-7.38 (m, 5 H) 7.61-7.77 (m, 1 H) 8.08-8.16 (m, 1 H) 8.24-8.35 (m, 2 H) 12.10-12.19 (m, 1 H) |
| Example 382 | 4-chloro-N-(trans-4-{[6-chloro-4-(1H-pyrrolo[2,3-b]pyridin-3-yl)pyridin-2-yl]amino}cyclohexyl)-2-methoxybenzamide | (300 MHz, DMSO-d₆) ppm 1.19-1.65 (m, 4 H) 1.82-2.15 (m, 4 H) 3.59-3.88 (m, 2 H) 3.91 (s, 3 H) 6.76-6.84 (m, 1 H) 6.84-6.92 (m, 2 H) 7.04-7.14 (m, 1 H) 7.15-7.26 (m, 2 H) 7.60-7.72 (m, 1 H) 7.91-8.00 (m, 1 H) 8.07-8.18 (m, 1 H) 8.26-8.37 (m, 2 H) 12.10-12.18 (m, 1 H) |
| Example 383 | N-(trans-4-{[6-chloro-4-(1H-pyrrolo[2,3-b]pyridin-3-yl)pyridin-2-yl]amino}cyclohexyl)-3-(trifluoromethyl)benzamide | (300 MHz, DMSO-d₆) ppm 1.23-1.64 (m, 4 H) 1.80-2.19 (m, 4 H) 3.51-3.91 (m, 2 H) 6.77-6.85 (m, 1 H) 6.84-6.92 (m, 2 H) 7.13-7.29 (m, 1 H) 7.65-7.78 (m, 1 H) 7.86-7.96 (m, 1 H) 8.08-8.22 (m, 3 H) 8.25-8.38 (m, 2 H) 8.44-8.61 (m, 1 H) 12.01-12.26 (m, 1 H) |
| Example 384 | 6-chloro-4-(5-chloro-1H-pyrrolo[2,3-b]pyridin-3-yl)-N-cyclohexylpyridin-2-amine | (300 MHz, DMSO-d₆) ppm 1.12-1.44 (m, 5H) 1.54-1.65 (m, 1H) 1.67-1.79 (m, 2H) 1.88-1.99 (m, 2H) 3.63-3.76 (m, 1H) 6.76 (d, 1H, J = 7.93 Hz) 6.86 (s, 1H) 6.87 (s, 1H) 8.25 (s, 1H) 8.30 (d, 1H, J = 1.98 Hz) 8.37 (d, 1H, J = 1.98 Hz) 12.35 (bs, 1H) |
| Example 385 | 3-chloro-N-(trans-4-{[6-chloro-4-(1H-pyrrolo[2,3-b]pyridin-3-yl)pyridin-2-yl]amino}cyclohexyl)benzamide | (300 MHz, DMSO-d₆) ppm 1.19-1.66 (m, 4 H) 1.80-2.16 (m, 4 H) 3.56-3.95 (m, 2 H) 6.75-6.85 (m, 1 H) 6.84-6.91 (m, 2 H) 7.13-7.30 (m, 1 H) 7.43-7.57 (m, 1 H) 7.56-7.64 (m, 1 H) 7.77-7.85 (m, 1 H) 7.87-7.93 (m, 1 H) 8.08-8.16 (m, 1 H) 8.26-8.36 (m, 2 H) 8.35-8.42 (m, 1 H) 12.11-12.17 (m, 1 H) |
| Example 386 | 6-chloro-N-[2-(3,4-dimethoxyphenyl)ethyl]-4-(1H-pyrrolo[2,3-b]pyridin-3-yl)pyridin-2-amine | (400 MHz, d₆-DMSO) δ 3.73 (s, 3 H), 3.75 (s, 3 H), 4.40 (d, J = 4.2 Hz, 2 H), 6.86 (s, 1 H), 6.94-6.92 (m, 3 H), 7.05 (s, 1 H), 7.17 (dd, J = 6.0 Hz, 1 H), 7.34 (t, J = 4.5 Hz, 1 H), 8.13 (d, J = 1.8 Hz, 1 H), 8.17 (d, J = 5.7 Hz, 1 H), 8.29 (dd, J = 3.3 Hz, 1 H). |
| Example 387 | 6-chloro-N-[2-(pyridin-2-yl)ethyl]-4-(1H-pyrrolo[2,3-b]pyridin-3-yl)pyridin-2-amine | (400 MHz, d₆-DMSO) δ 3.01 (t, J = 5.4 Hz, 2 H), 3.63 (t, J = 5.4 Hz, 2 H), 6.62 (d, J = 0.9 Hz, 1 H), 6.75 (d, J = 0.9 Hz, 1 H), 7.17-7.11 (m, 2 H), 7.28 (d, J = 6.0 Hz, 1 H), 7.68-7.62 (m, 1 H), 7.75 (s, 1 H), 8.17 (dd, J = 3.6 Hz, 1 H), 8.24 (d, J = 6.0 Hz, 1 H), 8.37-8.35 (m, 1 H). |
| Example 388 | 6-chloro-N-(2-phenylethyl)-4-(1H-pyrrolo[2,3-b]pyridin-3-yl)pyridin-2-amine | (400 MHz, d₆-DMSO) δ 2.84 (t, J = 5.4 Hz, 2 H), 3.55-3.50 (m, 2 H), 6.07 (s, 1 H), 6.78 (dd, J = 6.6 Hz, 2 H), 7.10-7.04 (m, 2 H), 7.19-7.17 (m, 4 H),, 7.92 (s, 1H), 8.20-8.18 (m, 2 H). |
| Example 389 | 6-chloro-N-[3-(4-methylpiperazin-1-yl)propyl]-4-(1H-pyrrolo[2,3-b]pyridin-3-yl)pyridin-2-amine | (400 MHz, d₆-DMSO) δ 1.71-1.67 (m, 2 H), 2.13 (s, 3 H), 2.38-2.33 (m, 8 H), 3.27-3.25 (m, 2 H), 6.85 (s, 1 H), |

-continued

| Example # | Name | ¹H NMR (ppm) |
|---|---|---|
| | | 6.92-6.89 (m, 2 H), 7.23-7.19 (m, 1 H),, 8.13 (s, 1 H), 8.32-8.30 (m, 2 H). |
| Example 390 | 6-chloro-N-(2-phenoxyethyl)-4-(1H-pyrrolo[2,3-b]pyridin-3-yl)pyridin-2-amine | (400 MHz, d$_6$-DMSO) δ 4.24-4.20 (m, 2 H), 4.67-4.64 (m, 2 H), 7.41-7.37 (m, 3 H), 7.51-7.49 (m, 3 H), 7.67-7.64 (m, 1 H), 7.78-7.74 (m, 2 H),, 8.53 (s, 1 H), 8.78 (dd, J = 3.3 Hz, 1 H), 8.83 (dd, J = 6.3 Hz, 1 H). |
| Example 391 | N'-[6-chloro-4-(1H-pyrrolo[2,3-b]pyridin-3-yl)pyridin-2-yl]-N,N-dimethylpropane-1,3-diamine | (400 MHz, d$_6$-DMSO) δ 1.86-1.72 (m, 2 H), 2.19 (s, 6 H), 2.38 (t, J = 5.7 Hz, 2 H), 3.30 (t, J = 5.4 Hz, 2 H), 6.67 (d, J = 0.9 Hz, 1 H), 6.78 (d, J = 0.9 Hz, 1 H), 7.16 (dd, J = 6.0 Hz, 1 H),, 7.78 (s, 1 H), 8.20 (dd, J = 3.3 Hz, 1 H), 8.27 (dd, J = 6.0 Hz, 1 H). |
| Example 392 | N-(1-benzylpyrrolidin-3-yl)-6-chloro-4-(1H-pyrrolo[2,3-b]pyridin-3-yl)pyridin-2-amine | (400 MHz, d$_6$-DMSO) δ 1.68-1.60 (m, 1 H), 2.28-2.19 (m, 1 H), 2.46-2.39 (m, 2 H), 2.69-2.63 (m, 1 H), 2.82-2.78 (m, 1 H), 3.65-3.51 (m, 2 H), 6.91-6.89 (m, 1 H), 7.65 (d, J = 5.4 Hz, 1 H), 7.33-7.20 (m, 8 H), 8.14 (s, 1 H), 8.33-8.30 (m, 2 H). |
| Example 393 | N-{2-[(trans-4-{[6-chloro-4-(1H-pyrrolo[2,3-b]pyridin-3-yl)pyridin-2-yl]amino}cyclohexyl)sulfamoyl]ethyl}-2,4-difluorobenzamide | (300 MHz, DMSO-d$_6$) ppm 1.09-1.62 (m, 5 H) 1.85-2.09 (m, 5 H) 3.04-3.24 (m, 1 H) 3.53-3.69 (m, 3 H) 6.73-6.82 (m, 1 H) 6.83-6.91 (m, 2 H) 7.12-7.31 (m, 3 H) 7.31-7.44 (m, 1 H) 7.69-7.85 (m, 1 H) 8.08-8.16 (m, 1 H) 8.25-8.35 (m, 2 H) 8.35-8.46 (m, 1 H) 12.14 (s, 1 H) |
| Example 394 | N-(trans-4-{[6-chloro-4-(1H-pyrrolo[2,3-b]pyridin-3-yl)pyridin-2-yl]amino}cyclohexyl)-1-[3-(trifluoromethyl)benzyl]azetidine-3-carboxamide | (300 MHz, DMSO-d$_6$) ppm 1.18-1.38 (m, 4 H) 1.72-1.91 (m, 2 H) 2.01 (s, 3 H) 3.06-3.24 (m, 4 H) 3.46-3.70 (m, 4 H) 6.68-6.82 (m, 1 H) 6.80-6.94 (m, 2 H) 7.09-7.30 (m, 1 H) 7.49-7.65 (m, 4 H) 7.65-7.77 (m, 1 H) 8.02-8.18 (m, 1 H) 8.21-8.39 (m, 2 H) 12.14 (s, 1 H) |
| Example 395 | N-(trans-4-{[6-chloro-4-(1H-pyrrolo[2,3-b]pyridin-3-yl)pyridin-2-yl]amino}cyclohexyl)-1-(2,4-dichlorobenzyl)azetidine-3-carboxamide | (300 MHz, DMSO-d$_6$) ppm 1.12-1.41 (m, 5 H) 1.71-2.08 (m, 4 H) 3.12-3.26 (m, 3 H) 3.34-3.47 (m, 2 H) 3.49-3.67 (m, 3 H) 6.69-6.80 (m, 1 H) 6.80-6.90 (m, 2 H) 7.14-7.26 (m, 1 H) 7.35-7.47 (m, 2 H) 7.51-7.61 (m, 1 H) 7.67-7.80 (m, 1 H) 8.05-8.18 (m, 1 H) 8.24-8.37 (m, 2 H) 12.13 (s, 1 H) |
| Example 396 | N-(trans-4-{[6-chloro-4-(1H-pyrrolo[2,3-b]pyridin-3-yl)pyridin-2-yl]amino}cyclohexyl)-1-(1-phenylethyl)azetidine-3-carboxamide | (300 MHz, DMSO-d$_6$) ppm 1.01-1.18 (m, 4 H) 1.19-1.36 (m, 4 H) 1.79 (s, 3 H) 1.90-2.08 (m, 3 H) 3.06 (d, J = 10.51 Hz, 2 H) 3.37-3.65 (m, 3 H) 6.71-6.79 (m, 1 H) 6.81-6.91 (m, 2 H) 7.16-7.25 (m, 1 H) 7.24-7.33 (m, 5 H) 7.59-7.75 (m, 1 H) 8.06-8.15 (m, 1 H) 8.25-8.36 (m, 2 H) 12.13 (s, 1 H) |
| Example 397 | 6-chloro-N-(4-methoxybenzyl)-4-(1H-pyrrolo[2,3-b]pyridin-3-yl)pyridin-2-amine | (400 MHz, d$_6$-DMSO) δ 3.73 (s, 3 H), 4.40 (d, J = 4.5 Hz, 2 H), 6.86 (s, 1 H), 6.93-6.90 (m, 3 H), 7.17 (dd, J = 6.0 Hz, 1 H), 7.34-7.30 (m, 3 H), |

| Example # | Name | ¹H NMR (ppm) |
|---|---|---|
| | | 8.13 (d, J = 2.1 Hz, 1 H), 8.16 (d, J = 5.4 Hz, 1 H), 8.29 (dd, J = 3.6 Hz, 1 H). |
| Example 398 | 4-(2-{[6-chloro-4-(1H-pyrrolo[2,3-b]pyridin-3-yl)pyridin-2-yl]amino}ethyl)phenol | (400 MHz, d₆-DMSO) δ 2.74 (t, J = 5.7 Hz, 2 H), 3.45-3.40 (m, 2 H), 6.71-6.87 (m, 2 H), 6.87 (s, 1 H), 6.90 (d, J = 0.3 Hz, 2 H), 7.08-7.06 (m, 2 H), 7.22-7.19 (m, 1 H), 8.14 (s, 1 H), 8.29 (s, 1 H), 8.31 (d, J = 1.2 Hz, 1 H), 9.17 (s, 1 H). |
| Example 399 | N-[2-(1,3-benzodioxol-5-yl)ethyl]-6-chloro-4-(1H-pyrrolo[2,3-b]pyridin-3-yl)pyridin-2-amine | (400 MHz, d₆-DMSO) δ 2.78 (t, J = 5.4 Hz, 2 H), 3.48-3.43 (m, 2 H), 5.96 (s, 2 H), 6.74 (dd, J = 6.3 Hz, 1 H), 6.93-6.83 (m, 5 H), 7.21 (dd, J = 5.4 Hz, 1 H), 8.14 (s, 1 H), 8.32-8.30 (m, 2 H). |
| Example 400 | N-(1,3-benzodioxol-5-ylmethyl)-6-chloro-4-(1H-pyrrolo[2,3-b]pyridin-3-yl)pyridin-2-amine | (400 MHz, d₆-DMSO) δ 4.98 (d, J = 4.2 Hz, 2 H), 5.98 (s, 2 H), 6.87-6.86 (m, 3 H), 6.95-6.93 (m, 2 H), 7.18 (dd, J = 6.0 Hz, 1 H), 7.33 (t, J = 4.2 Hz, 1 H), 8.13 (d, J = 1.2 Hz, 1 H), 8.19 (d, J = 6.6 Hz, 1 H), 8.30 (dd, J = 3.6 Hz, 1 H). |
| Example 401 | 6-chloro-N-[2-(4-methoxyphenyl)ethyl]-4-(1H-pyrrolo[2,3-b]pyridin-3-yl)pyridin-2-amine | (400 MHz, d₆-DMSO) δ 2.80 (t, J = 5.1 Hz, 2 H), 3.47-3.42 (m, 2 H), 3.72 (s, 3 H), 6.93-6.86 (m, 6 H), 7.21-7.19 (m, 2 H), 8.14 (d, J = 1.8 Hz, 1 H), 8.31-8.29 (m, 2 H). |
| Example 402 | N-(1-benzylpiperidin-4-yl)-6-chloro-4-(1H-pyrrolo[2,3-b]pyridin-3-yl)pyridin-2-amine | (400 MHz, d₆-DMSO) δ 1.49-1.41 (m, 4 H), 1.92-1.89 (m, 2 H), 2.11 (t, J = 8.1 Hz, 2 H), 2.80-2.77 (m, 2 H), 3.49 (s, 2 H), 6.83 (d, J = 5.7 Hz, 1 H), 6.88 (s, 2 H), 7.27-7.20 (m, 2 H), 7.35-7.30 (m, 4 H), 8.14 (s, 1 H), 8.32-8.30 (m, 2 H). |
| Example 403 | 6-chloro-N-[2-(pyridin-4-yl)ethyl]-4-(1H-pyrrolo[2,3-b]pyridin-3-yl)pyridin-2-amine | (400 MHz, d₆-DMSO) δ 2.91-2.88 (m, 2 H), 3.57-3.53 (m, 2 H), 6.88 (s, 1 H), 6.93 (d, J = 0.6 Hz, 1 H), 7.00 (t, J = 3.9 Hz, 1 H), 7.23-7.20 (m, 1 H), 7.31 (dd, J = 4.5 Hz, 2 H), 8.15 (s, 1 H), 8.30 (d, J = 0.9 Hz, 1 H), 8.31 (s, 1 H), 8.48 (dd, J = 3.3 Hz, 2 H). |
| Example 404 | 6-chloro-N-(2,3-dihydro-1H-inden-2-yl)-4-(1H-pyrrolo[2,3-b]pyridin-3-yl)pyridin-2-amine | (400 MHz, d₆-DMSO) δ 2.85 (dd, J = 12.0 Hz, 2 H), 4.62-4.58 (m, 1 H), 6.91 (s, 1 H), 6.94 (d, J = 0.9 Hz, 1 H), 7.28-7.16 (m, 7 H), 8.16 (d, J = 2.1 Hz, 1 H), 8.32-8.29 (m, 2 H). |
| Example 405 | 6-chloro-N-[2-(1H-indol-3-yl)ethyl]-4-(1H-pyrrolo[2,3-b]pyridin-3-yl)pyridin-2-amine | (400 MHz, d₆-DMSO) δ 2.98 (t, J = 5.7 Hz, 2 H), 3.58-3.53 (m, 2 H), 6.88 (s, 1 H), 6.91 (s, 1 H), 7.00-6.96 (m, 2 H), 7.08 (t, J = 5.1 Hz, 1 H), 7.21-7.18 (m, 2 H), 7.34 (d, J = 6.0 Hz, 1 H), 7.66 (d, J = 6.3 Hz, 1 H), 8.13 (s, 1 H), 8.31-8.30 (m, 2 H), 10.83 (s, 1 H). |
| Example 406 | N-(trans-4-{[6-chloro-4-(1H-pyrrolo[2,3-b]pyridin-3-yl)pyridin-2-yl]amino}cyclohexyl)-1-(2,3-dimethylbenzyl)azetidine-3-carboxamide | (300 MHz, DMSO-d₆) ppm 1.15-1.40 (m, 5 H) 1.71-1.88 (m, 2 H) 1.91-2.08 (m, 3 H) 2.11-2.20 (m, 3 H) 2.19-2.25 (m, 3 H) 3.02-3.21 (m, 3 H) 3.41-3.70 (m, 4 H) 6.69-6.81 (m, 1 H) 6.82-6.91 (m, 2 H) 6.94-7.10 (m, 3 H) 7.16-7.27 (m, 1 H) 7.59-7.79 (m, 1 H) 8.07-8.16 (m, 1 H) 8.26-8.34 (m, 2 H) 12.10-12.19 (m, 1 H) |
| Example 407 | N-(trans-4-{[6-chloro-4-(1H-pyrrolo[2,3-b]pyridin-3-yl)pyridin-2- | (300 MHz, DMSO-d₆) ppm 1.21-1.37 (m, 4 H) |

| Example # | Name | ¹H NMR (ppm) |
|---|---|---|
| | yl]amino}cyclohexyl)-1-(1H-indol-6-ylmethyl)azetidine-3-carboxamide | 1.67-1.89 (m, 3 H) 1.90-2.08 (m, 2 H) 3.04-3.21 (m, 3 H) 3.44-3.72 (m, 4 H) 6.26-6.42 (m, 1 H) 6.71-6.81 (m, 1 H) 6.81-6.94 (m, 3 H) 7.15-7.32 (m, 4 H) 7.38-7.49 (m, 1 H) 7.62-7.77 (m, 1 H) 8.07-8.15 (m, 1 H) 8.25-8.36 (m, 2 H) 10.97 (s, 1 H) 12.14 (s, 1 H) |
| Example 408 | N-[4-(benzyloxy)phenyl]-6-chloro-4-(1H-pyrrolo[2,3-b]pyridin-3-yl)pyridin-2-amine | (400 MHz, $d_6$-DMSO) δ 5.08 (s, 2 H), 7.00 (dd, J = 5.4 Hz, 2 H), 7.15 (dd, J = 7.2 Hz, 2 H), 7.25 (dd, J = 6.0 Hz, 1 H), 7.35-7.33 (m, 1 H), 7.41-7.38 (m, 2 H), 7.47-7.45 (m, 2 H), 7.56-7.53 (m, 2 H), 8.21 (s, 1 H), 8.35-8.31 (m, 2 H). |
| Example 409 | N-(1H-benzimidazol-2-ylmethyl)-6-chloro-4-(1H-pyrrolo[2,3-b]pyridin-3-yl)pyridin-2-amine | (400 MHz, $d_6$-DMSO) δ 4.71 (d, J = 4.5 Hz, 2 H), 7.01 (d, J = 0.9 Hz, 1 H), 7.05 (s, 1 H), 7.19-7.13 (m, 3 H), 7.52-7.49 (m, 1 H), 8.17 (d, J = 2.1 Hz, 1H), 8.30 (d, J = 3.9 Hz, 2 H), 12.19 (s, 1 H). |
| Example 410 | 6-chloro-N-(1H-indol-5-ylmethyl)-4-(1H-pyrrolo[2,3-b]pyridin-3-yl)pyridin-2-amine | (400 MHz, $d_6$-DMSO) δ 4.53 (s, 2 H), 6.40 (t, J = 1.5 Hz, 1 H), 6.87 (s, 1 H), 6.90 (s, 1 H), 7.11-7.08 (m, 1 H), 7.13 (dd, J = 6.6 Hz, 1 H), 7.38-7.31 (m, 3 H), 7.56 (s, 1 H), 8.26 (dd, J = 2.1 Hz, 1 H), 11.05 (s, 1 H), 12.15 (s, 1 H). |
| Example 411 | 6-chloro-N-(4-methoxyphenyl)-4-(1H-pyrrolo[2,3-b]pyridin-3-yl)pyridin-2-amine | (400 MHz, $d_6$-DMSO) δ 3.74 (s, 3 H), 6.94-6.90 (m, 2 H), 7.13 (d, J = 0.9 Hz, 1 H), 7.17 (d, J = 0.9 Hz, 1 H), 7.25 (dd, J = 6.0 Hz, 1 H), 7.57-7.53 (m, 2 H), 8.21 (d, J = 2.4 Hz, 1 H), 8.33 (dd, J = 3.6 Hz, 1 H), 8.36 (dd, J = 6.0 Hz, 1 H), 9.20 (s, 1 H). |
| Example 412 | 6-chloro-4-(1H-pyrrolo[2,3-b]pyridin-3-yl)-N-(3,4,5-trimethoxyphenyl)pyridin-2-amine | (400 MHz, $d_6$-DMSO) δ 3.63 (s, 3 H), 3.79 (s, 6 H), 7.10 (s, 2 H), 7.21 (d, J = 0.9 Hz, 1 H), 7.29 (d, J = 0.6 Hz, 1 H), 7.32 (dd, J = 6.0 Hz, 1 H), 8.28 (d, J = 1.8 Hz, 1 H), 8.38 (dd, J = 3.9 Hz, 1 H), 8.50 (dd, J = 6.0 Hz, 1 H), 9.46 (s, 1 H). |
| Example 413 | 6-chloro-N-[4-(1H-imidazol-1-yl)phenyl]-4-(1H-pyrrolo[2,3-b]pyridin-3-yl)pyridin-2-amine | (400 MHz, $d_6$-DMSO) δ 7.09 (s, 1 H), 7.29-7.25 (m, 3 H), 7.60-7.58 (m, 2 H), 7.68 (s, 1 H), 7.81-7.79 (m, 2 H), 8.17 (s, 1 H), 8.27 (d, J = 2.1 Hz, 1 H), 8.35-8.33 (m, 1 H), 8.41-8.39 (m, 2 H), 9.58 (s, 1 H). |
| Example 414 | 6-chloro-N-(3,4-dimethoxybenzyl)-4-(1H-pyrrolo[2,3-b]pyridin-3-yl)pyridin-2-amine | (400 MHz, $d_6$-DMSO) δ 3.73 (s, 3 H), 3.75 (s, 3 H), 4.40 (d, J = 4.2 Hz, 2 H), 6.86 (s, 1 H), 6.94-6.92 (m, 3 H), 7.05 (s, 1 H), 7.17 (dd, J = 6.0 Hz, 1 H), 7.34 (t, J = 4.5 Hz, 1 H), 8.13 (d, J = 1.8 Hz, 1 H), 8.17 (d, J = 5.7 Hz, 1 H), 8.29 (dd, J = 3.3 Hz, 1 H). |
| Example 415 | 2-{[6-chloro-4-(1H-pyrrolo[2,3-b]pyridin-3-yl)pyridin-2-yl]amino}-1-phenylethanol | (400 MHz, $d_6$-DMSO) δ 3.67 (t, J = 4.5 Hz, 2 H), 4.91 (s, 1 H), 4.98 (t, J = 4.2 Hz, 1 H), 6.90 (d, J = 0.6 Hz, 1 H), 7.16 (dd, J = 6.0 Hz, 1 H), 7.27-7.23 (m, 1 H), 7.37-7.30 (m, 3 H), 7.44-7.42 (m, 2 H), 8.11 (s, 1 H), 8.29 (dd, J = 3.6 Hz, 1 H). |
| Example 416 | 6-chloro-N-(3-phenylpropyl)-4-(1H-pyrrolo[2,3-b]pyridin-3-yl)pyridin-2-amine | (400 MHz, $d_6$-DMSO) δ 1.90-1.83 (m, 2 H), 2.70 (t, J = 5.7 Hz, 2 H), 3.28-3.24 (m, 2 H), 6.86 (s, 1 H), 6.89 (d, J = 0.6 Hz, |

-continued

| Example # | Name | ¹H NMR (ppm) |
|---|---|---|
| | | 1 H), 6.99 (t, J = 4.2 Hz, 1 H), 7.31-7.17 (m, 6 H), 8.14 (s, 1 H), 8.32-8.30 (m, 2 H). |
| Example 417 | 6-chloro-N-[4-(methylsulfonyl)benzyl]-4-(1H-pyrrolo[2,3-b]pyridin-3-yl)pyridin-2-amine | (400 MHz, d₆-DMSO) δ 3.19 (s, 3 H), 4.61 (d, J = 4.5 Hz, 2 H), 6.90 (s, 1 H), 6.96 (d, J = 0.6 Hz, 1 H), 7.19 (dd, J = 5.7 Hz, 1 H), 7.57 (t, J = 4.5 Hz, 1 H), 7.63 (d, J = 6.3 Hz, 2 H), 7.91 (dd, J = 5.1 Hz, 2 H), 8.15 (s, 1 H), 8.30 (dd, J = 3.3 Hz, 1 H). |
| Example 418 | 6-chloro-N-[4-(methylsulfanyl)phenyl]-4-(1H-pyrrolo[2,3-b]pyridin-3-yl)pyridin-2-amine | (400 MHz, d₆-DMSO) δ 2.45 (s, 3 H), 7.28-7.21 (m, 5 H), 7.65-7.62 (m, 2 H), 8.24 (s, 1 H), 8.33 (dd, J = 3.3 Hz, 1 H), 8.37 (dd, J = 6.0 Hz, 1 H), 9.38 (s, 1 H). |
| Example 419 | 6-chloro-N-(4-phenoxyphenyl)-4-(1H-pyrrolo[2,3-b]pyridin-3-yl)pyridin-2-amine | (400 MHz, d₆-DMSO) δ 6.97 (d, J = 6.0 Hz, 2 H), 7.04-7.02 (m, 2 H), 7.08 (t, J = 5.4 Hz, 1 H), 7.19 (s, 1 H), 7.22 (s, 1 H), 7.26-7.24 (m, 1 H), 7.38-7.34 (m, 2 H), 7.69-7.67 (m, 2 H), 8.24 (s, 1 H), 8.37-8.32 (m, 2 H), 9.37 (s, 1 H). |
| Example 420 | 6-chloro-N-[4-(piperidin-1-yl)phenyl]-4-(1H-pyrrolo[2,3-b]pyridin-3-yl)pyridin-2-amine | (400 MHz, d₆-DMSO) δ 1.54-1.48 (m, 2 H), 1.66-1.60 (m, 4 H), 3.05, (t, J = 3.9 Hz, 4 H), 6.93-6.91 (m, 2 H), 7.10 (d, J = 0.9 Hz, 1 H), 7.13 (d, J = 0.9 Hz, 1 H), 7.24 (dd, J = 6.0 Hz, 1 H), 7.47-7.44 (m, 2 H), 8.20 (d, J = 1.5 Hz, 1 H), 8.34-8.31 (m, 2 H), 9.05 (s, 1 H). |
| Example 421 | methyl 3-[2-chloro-6-(cyclohexylamino)pyridin-4-yl]-1H-pyrrolo[2,3-b]pyridine-5-carboxylate | (300 MHz, DMSO-d₆) ppm 1.14-1.44 (m, 5H) 1.56-1.65 (m, 1H) 1.67-1.79 (m, 2H) 1.89-2.00 (m, 2H) 3.60-3.75 (m, 1H) 3.92 (s, 3H) 6.84 (s, 1H) 6.86 (s, 1H) 6.97 (d, 1H, J = 7.93 Hz) 8.26 (s, 1H) 8.79 (d, 1H, J = 1.98 Hz) 8.88 (d, 1H, J = 1.98 Hz) 12.59 (bs, 1H) |
| Example 422 | N-(trans-4-{[6-chloro-4-(1H-pyrrolo[2,3-b]pyridin-3-yl)pyridin-2-yl]amino}cyclohexyl)-2-[4-(2-hydroxyethyl)piperazin-1-yl]acetamide | (400 MHz, DMSO-d₆) ppm 1.22-1.43 (m, 4 H), 1.77-1.89 (m, 2 H), 1.95-2.07 (m, 2 H), 2.52-2.54 (m, 2 H), 2.93-3.08 (m, 3 H), 3.14-3.20 (m, 2 H), 3.33-3.37 (m, 4 H), 3.69-3.77 (m, 5 H), 6.81-6.89 (m, 2 H), 7.20 (dd, J = 7.93, 4.88 Hz, 1 H), 7.95 (d, J = 7.63 Hz, 1 H), 8.11 (d, J = 2.75 Hz, 1 H), 8.26-8.35 (m, 2 H), 12.11-12.20 (m, 1H) |
| Example 423 | N-(trans-4-{[6-chloro-4-(1H-pyrrolo[2,3-b]pyridin-3-yl)pyridin-2-yl]amino}cyclohexyl)-2-[4-(2,6-dimethylphenyl)piperazin-1-yl]acetamide | (400 MHz, DMSO-d₆) ppm 1.25-1.44 (m, 4 H), 1.87-1.94 (m, 2 H), 1.99-2.08 (m, 2 H), 2.30 (s, 6 H), 2.96-3.04 (m, 2 H), 3.23-3.31 (m, 4 H), 3.63-3.72 (m, 2 H), 4.02 (s, 2 H), 6.85-6.90 (m, 2 H), 6.95-7.01 (m, 2 H), 7.04 (s, 1 H), 7.22 (dd, J = 7.78, 4.43 Hz, 1 H), 8.13 (d, J = 2.75 Hz, 1 H), 8.32 (d, J = 7.93 Hz, 2 H), 8.54 (d, J = 7.93 Hz, 1 H), 9.93 (s, 1 H), 12.18 (s, 1 H). |
| Example 424 | 6-chloro-N-(4-{[4-(cyclobutylamino)cyclohexyl]methyl}cyclohexyl)-4-(5-methoxy-1H-pyrrolo[2,3-b]pyridin-3-yl)pyridin-2-amine | (400 MHz, METHANOL-d₄) ppm 0.94-1.52 (m, 10 H) 1.52-1.99 (m, 9 H) 2.02-2.27 (m, 4 H) 2.28-2.41 (m, 2 H) 2.68-2.81 (m, 1 H) 2.91-3.05 (m, 0.6 H) 3.10-3.19 (m, 0.4 H) 3.66-3.72 (m, 1 H) 3.84-3.93 (m, 1 H) 3.95 (s, 3 H) 6.81 (d, J = 1.22 Hz, 0.6 H) |

| Example # | Name | ¹H NMR (ppm) |
|---|---|---|
| Example 425 | 6-chloro-4-(5-methoxy-1H-pyrrolo[2,3-b]pyridin-3-yl)-N-(4-{[4-(pentan-3-ylamino)cyclohexyl]methyl}cyclohexyl)pyridin-2-amine | 6.88 (d, J = 1.22 Hz, 0.4 H) 6.90-6.94 (m, 1 H) 7.87-7.91 (m, 1 H) 7.92 (d, J = 1.53 Hz, 1 H) 8.07 (d, J = 2.14 Hz, 1 H) (400 MHz, METHANOL-$d_4$) ppm 1.00 (t, J = 7.48 Hz, 6 H) 1.04-1.48 (m, 11 H) 1.59-1.97 (m, 12 H) 2.12 (d, J = 11.60 Hz, 2 H) 3.04-3.24 (m, 2 H) 3.59-3.76 (m, 1 H) 3.95 (s, 3 H) 6.84 (d, J = 1.22 Hz, 0.6 H) 6.91 (d, J = 1.22 Hz, 0.4 H) 6.93-6.97 (m, 1 H) 7.88-7.94 (m, 1 H) 7.95 (s, 1 H) 8.08 (d, J = 2.44 Hz, 1 H) |
| Example 426 | 6-chloro-N-[4-({4-[(cyclopentylmethyl)amino]cyclohexyl}methyl)cyclohexyl]-4-(5-methoxy-1H-pyrrolo[2,3-b]pyridin-3-yl)pyridin-2-amine | (400 MHz, METHANOL-$d_4$) ppm 0.93-1.49 (m, 12 H) 1.57-1.99 (m, 14 H) 2.07-2.20 (m, 3 H) 2.95-3.01 (m, 2 H) 3.01-3.17 (m, 1 H) 3.62-3.75 (m, 1 H) 3.95 (s, 3 H) 6.77-6.94 (m, 2 H) 7.85-7.93 (m, 2 H) 8.07 (d, J = 2.14 Hz, 1 H) |
| Example 427 | trans-N-(6-chloro-4-{5-[2-(pyridin-2-yl)ethoxy]-1H-pyrrolo[2,3-b]pyridin-3-yl}pyridin-2-yl)cyclohexane-1,4-diamine | (400 MHz, DMSO-$d_6$) ppm 1.20-1.32 (m, 2 H), 1.37-1.51 (m, 2 H), 1.93-2.01 (m, 2 H), 2.01-2.10 (m, 2 H), 4.52 (t, J = 6.41 Hz, 2 H), 6.80 (s, 2 H), 6.87 (s, 1 H), 7.41-7.46 (m, 1 H), 7.58 (d, J = 8.54 Hz, 1 H), 7.79 (d, J = 2.44 Hz, 3 H), 7.91-7.98 (m, 1 H), 8.04 (d, J = 2.44 Hz, 1 H), 8.09 (d, J = 2.75 Hz, 1 H), 8.62 (d, J = 4.58 Hz, 1 H), 12.03-12.07 (m, 1 H) |
| Example 428 | trans-N-{6-chloro-4-[5-(2-methylpropoxy)-1H-pyrrolo[2,3-b]pyridin-3-yl]pyridin-2-yl}cyclohexane-1,4-diamine | (300 MHz, DMSO-$d_6$) ppm 1.03 (d, J = 6.78 Hz, 6 H), 1.22-1.48 (m, 4 H), 1.94-2.07 (m, 4 H), 3.88 (d, J = 6.44 Hz, 2 H), 6.79-6.82 (m, 1 H), 6.87 (d, J = 1.02 Hz, 1 H), 7.76 (d, J = 2.71 Hz, 3 H), 8.09 (t, J = 2.88 Hz, 2 H), 12.00-12.05 (m, 1 H) |
| Example 429 | N-(trans-4-{[6-chloro-4-(1H-pyrrolo[2,3-b]pyridin-3-yl)pyridin-2-yl]amino}cyclohexyl)-1-(pyridin-2-ylmethyl)azetidine-3-carboxamide | (300 MHz, DMSO-$d_6$) ppm 1.16-1.42 (m, 5 H) 1.72-2.09 (m, 5 H) 3.09-3.24 (m, 2 H) 3.35-3.44 (m, 2 H) 3.49-3.70 (m, 3 H) 6.72-6.81 (m, 1 H) 6.81-6.93 (m, 2 H) 7.14-7.37 (m, 3 H) 7.68-7.81 (m, 1 H) 8.08-8.16 (m, 1 H) 8.26-8.36 (m, 2 H) 8.44-8.53 (m, 2 H) 12.07-12.21 (m, 1 H) |
| Example 430 | N-(trans-4-{[6-chloro-4-(5-methoxy-1H-pyrrolo[2,3-b]pyridin-3-yl)pyridin-2-yl]amino}cyclohexyl)-2,2,2-trifluoroacetamide | (500 MHz, DMSO-$d_6$) ppm 0.88-0.96 (m, 4 H), 1.23-1.33 (m, 2 H), 1.35-1.46 (m, 2 H), 1.93-2.05 (m, 14.19 Hz, 4 H), 3.90 (s, 3 H), 6.81 (s, 1 H), 6.86 (s, 1 H),, 7.08 (d, J = 7.93 Hz, 1 H), 7.79 (d, J = 2.44 Hz, 1 H), 8.08 (dd, J = 8.39, 2.59 Hz, 2 H), 11.95-12.10 (m, 1 H) |
| Example 431 | 6-chloro-N-cyclohexyl-4-[5-(6-methoxypyridin-3-yl)-1H-pyrrolo[2,3-b]pyridin-3-yl]pyridin-2-amine | (300 MHz, DMSO-d6) ppm 1.11-1.43 (m, 5 H) 1.54-1.66 (m, 1 H) 1.67-1.78 (m, 2 H) 1.90-2.00 (m, 2 H) 3.63-3.76 (m, 1 H) 3.92 (s, 3 H) 6.74 (d, J = 7.80 Hz, 1 H) 6.89-7.00 (m, 3 H) 8.12 (dd, J = 8.82, 2.37 Hz, 1 H) 8.18 (s, 1 H) 8.45 (s, 1 H) 8.55-8.59 (m, 2 H) 12.24 (s, 1 H). |

| Example # | Name | ¹H NMR (ppm) |
|---|---|---|
| Example 432 | N-(trans-4-{[6-chloro-4-(5-methoxy-1H-pyrrolo[2,3-b]pyridin-3-yl)pyridin-2-yl]amino}cyclohexyl)-N~2~-ethyl-N~2~-(2-hydroxyethyl)glycinamide | (400 MHz, METHANOL-d₄) ppm 1.29-1.55 (m, 7 H) 2.03 (d, J = 11.90 Hz, 2 H) 2.16 (d, J = 11.90 Hz, 2 H) 3.34-3.43 (m, 4 H) 3.68-3.84 (m, 2 H) 3.86-3.93 (m, 2 H) 3.93-4.12 (m, 5 H) 6.79 (d, J = 1.22 Hz, 1 H) 6.88 (d, J = 1.22 Hz, 1 H) 7.88-7.93 (m, 2 H) 8.07 (d, J = 2.44 Hz, 1 H) |
| Example 433 | N-(trans-4-{[6-chloro-4-(5-methoxy-1H-pyrrolo[2,3-b]pyridin-3-yl)pyridin-2-yl]amino}cyclohexyl)-N~2~-(2-hydroxyethyl)glycinamide | (400 MHz, METHANOL-d₄) ppm 1.22-1.58 (m, 4 H) 2.02 (d, J = 14.65 Hz, 2 H) 2.15 (d, J = 12.21 Hz, 2 H) 3.11-3.21 (m, 2 H) 3.67-3.85 (m, 6 H) 3.94 (s, 3 H) 6.75 (d, J = 1.22 Hz, 1 H) 6.84 (d, J = 0.92 Hz, 1 H) 7.84 (s, 1 H) 7.86 (d, J = 2.75 Hz, 1 H) 8.05 (d, J = 2.44 Hz, 1 H) |
| Example 434 | N'-[6-chloro-4-(1H-pyrrolo[2,3-b]pyridin-3-yl)pyridin-2-yl]-N,N-dimethylbenzene-1,4-diamine | (400 MHz, d₆-DMSO) δ 2.86 (s, 6 H), 6.76 (d, J = 8.8 Hz, 2 H), 7.10 (d, J = 11.2 Hz, 2 H), 7.25-7.22 (m, 1 H), 7.43 (d, J = 8.8 Hz, 2 H), 8.18 (d, J = 2.8 Hz, 1 H), 8.32 (d, J = 5.6 Hz, 2 H), 8.95 (s, 1 H), 12.23 (s, 1 H). |
| Example 435 | 6-chloro-N-(2,3-dihydro-1H-inden-5-yl)-4-(1H-pyrrolo[2,3-b]pyridin-3-yl)pyridin-2-amine | (400 MHz, d₆-DMSO) δ 2.09-1.99 (m, 2 H), 2.88-2.80 (m, 4 H), 7.17-7.15 (s, 2 H), 7.22 (s, 1 H), 7.26 (dd, J = 13.2, 3.2 Hz, 1 H), 7.35 (dd, J = 9.6, 6.4 Hz, 1 H), 7.55 (s, 1 H), 8.23 (d, J = 2.8 Hz, 1 H), 8.37-8.33 (m, 2H), 9.21 (s, 1 H), 12.24 (s, 1 H). |
| Example 436 | 6-chloro-N-(2,3-dihydro-1,4-benzodioxin-6-yl)-4-(1H-pyrrolo[2,3-b]pyridin-3-yl)pyridin-2-amine | (400 MHz, d₆-DMSO) δ 4.25-4.21 (m, 4 H), 6.81 (d, J = 7.2 Hz, 1 H), 6.97 (dd, J = 9.2, 5.2 Hz, 1 H), 7.16 (d, J = 5.6 Hz, 2 H), 7.25 (dd, J = 10.0, 3.2 Hz, 1 H), 7.37 (d, J = 2.0 Hz, 1 H), 8.23 (s, 1 H), 8.33 (dd, J = 5.2, 2.8 Hz, 1 H), 8.35 (dd, J = 7.2, 5.2 Hz, 1 H), 9.18 (s, 1 H), 12.21 (s, 1 H). |
| Example 437 | 6-chloro-N-{4-[1-(2,4-difluorobenzyl)piperidin-4-yl]cyclohexyl}-4-(5-methoxy-1H-pyrrolo[2,3-b]pyridin-3-yl)pyridin-2-amine | (300 MHz, DMSO-d₆) ppm 0.81-2.10 (m, 11 H) 2.73-2.94 (m, 3 H) 3.45 (s, 2 H) 3.87-4.06 (m, 5 H) 4.50 (d, J = 5.43 Hz, 2 H) 5.26 (t, J = 5.76 Hz, 1 H) 6.80-6.94 (m, 1 H) 6.97-7.12 (m, 1 H) 7.11-7.22 (m, 1 H) 7.37-7.54 (m, 3 H) 7.76-7.85 (m, 1 H) 8.02-8.14 (m, 2 H) 12.01 (s, 1 H) |
| Example 438 | 6-chloro-N-[4-(morpholin-4-yl)phenyl]-4-(1H-pyrrolo[2,3-b]pyridin-3-yl)pyridin-2-amine | (400 MHz, d₆-DMSO) δ 3.76-3.73 (m, 4 H), 3.06-3.04 (m, 4 H), 6.94 (d, J = 8.8 Hz, 2 H), 7.11 (d, J = 0.8 Hz, 1 H), 7.15 (d, J = 1.2 Hz, 1 H), 7.25 (dd, J = 12.8, 3.6 Hz, 1 H), 7.50 (d, J = 9.2 Hz, 2 H), 8.20 (s, 1 H), 8.36-8.32 (m, 2 H), 9.11 (s, 1 H), 12.23 (s, 1 H). |
| Example 439 | 6-chloro-4-(1H-pyrrolo[2,3-b]pyridin-3-yl)-N-(5,6,7,8-tetrahydronaphthalen-1-yl)pyridin-2-amine | (400 MHz, d₆-DMSO) δ 1.76-1.71 (m, 4 H), 2.68-2.65 (m, 2 H), 2.78-2.75 (m, 2 H), 6.86 (d, J = 7.6 Hz, 1 H), 7.13-7.09 (m, 3 H), 7.21 (dd, J = 12.4, 3.6 Hz, 1 H), 7.42 (d, J = 8.4 Hz, 1 H), 8.18 (d, J = 2.8 Hz, 1 H), 8.27 (dd, J = 9.2, 6.8 Hz, 1 H), 8.30 (dd, J = 6.0, 3.2 Hz, 1 H), 8.38 (s, 1 H), 12.22 (s, 1 H). |

-continued

| Example # | Name | ¹H NMR (ppm) |
|---|---|---|
| Example 440 | N-(4-tert-butylphenyl)-6-chloro-4-(1H-pyrrolo[2,3-b]pyridin-3-yl)pyridin-2-amine | (400 MHz, d₆-DMSO) δ 1.28 (s, 9 H), 7.17 (d, J = 0.8 Hz, 1 H), 7.27-7.23 (m, 2 H), 7.34 (d, J = 8.8 Hz, 2 H), 7.56 (d, J = 8.8 Hz, 2 H), 8.23 (s, 1 H), 8.33 (dd, J = 6.0, 3.2 Hz, 1 H), 8.38 (dd, J = 9.6, 6.4 Hz, 1 H), 9.27 (s, 1 H). |
| Example 441 | 6-chloro-N-(2,3-dihydro-1H-inden-4-yl)-4-(1H-pyrrolo[2,3-b]pyridin-3-yl)pyridin-2-amine | (400 MHz, d₆-DMSO) δ 2.05-2.03 (m, 2 H), 2.91-2.86 (m, 4 H), 6.94 (d, J = 7.2 Hz, 1 H), 7.14-7.10 (m, 1 H), 7.16 (d, J = 0.8 Hz, 1 H), 7.23 (dd, J = 12.8, 3.2 Hz, 1 H), 7.27 (d, J = 1.2 Hz, 1 H), 7.66 (d, J = 8.0 Hz, 1 H), 8.22 (s, 1 H), 8.32 (dd, J = 6.0, 3.2 Hz, 1 H), 8.36 (dd, J = 9.6, 6.4 Hz, 1 H), 8.58 (s, 1 H). |
| Example 442 | N-[6-chloro-4-(1H-pyrrolo[2,3-b]pyridin-3-yl)pyridin-2-yl]quinolin-6-amine | (400 MHz, d₆-DMSO) δ 7.28 (dd, J = 12.4, 3.6 Hz, 1 H), 7.32 (d, J = 0.8 Hz, 1 H), 7.40 (s, 1 H), 7.46 (dd, J = 12.8, 4.0 Hz, 1 H), 7.89-7.87 (m, 1 H), 7.98 (d, J = 8.8 Hz, 1 H), 8.22 (d, J = 7.6 Hz, 1 H), 8.29 (d, J = 2.8 Hz, 1 H), 8.34 (dd, J = 6.0, 3.2 Hz, 1 H), 8.40 (d, J = 2.4 Hz, 1H), 8.43 (dd, J = 8.8, 7.2 Hz, 1 H), 8.72 (dd, J = 6.0, 2.4 Hz, 1 H), 9.81 (s, 1 H), 12.31 (s, 1 H). |
| Example 443 | 6-chloro-N-[4-(4-methylpiperazin-1-yl)phenyl]-4-(1H-pyrrolo[2,3-b]pyridin-3-yl)pyridin-2-amine | (400 MHz, d₆-DMSO) δ 2.22 (s, 3 H), 2.46 (t, J = 4.8 Hz, 5 H), 3.34 (s, 4 H), 6.92 (d, J = 9.2 Hz, 1 H), 7.11 (br s, 1 H), 7.15 (br s, 1 H), 7.25 (dd, J = 12.4, 3.2 Hz, 1 H), 7.48 (d, J = 9.2 Hz, 2 H), 8.21 (d, J = 1.6 Hz, 1 H), 8.35-8.32 (m, 2 H), 9.09 (s, 1 H), 12.24 (s, 1 H). |
| Example 444 | 6-chloro-N-[4-(1,1-dioxidothiomorpholin-4-yl)phenyl]-4-(1H-pyrrolo[2,3-b]pyridin-3-yl)pyridin-2-amine | (400 MHz, d₆-DMSO) δ 2.08 (s, 1 H), 3.16-3.14 (m, 4 H), 3.72-3.69 (m, 4 H), 7.03 (d, J = 9.2 Hz, 2 H), 7.13 (br s, 1H), 7.17 (br s, 1 H), 7.25 (dd, J = 12.4, 3.2 Hz, 1 H), 7.55 (d, J = 8.8 Hz, 2 H), 8.21 (d, J = 2.8 Hz, 1 H), 8.36-8.32 (m, 2 H), 9.16 (s, 1 H), 12.24 (s, 1 H). |
| Example 445 | N-(trans-4-{[6-chloro-4-(5-methoxy-1H-pyrrolo[2,3-b]pyridin-3-yl)pyridin-2-yl]amino}cyclohexyl)-N~2~-(trans-4-hydroxycyclohexyl)glycinamide | (400 MHz, METHANOL-d₄) ppm 1.23-1.57 (m, 8 H) 1.91-2.28 (m, 8 H) 3.00-3.15 (m, 1 H) 3.48-3.62 (m, 1 H) 3.68-3.84 (m, 4 H) 3.95 (s, 3 H) 6.79 (s, 1 H) 6.89 (s, 1 H) 7.88-7.94 (m, 2 H) 8.08 (d, J = 2.44 Hz, 1 H) |
| Example 446 | N-(trans-4-{[6-chloro-4-(5-methoxy-1H-pyrrolo[2,3-b]pyridin-3-yl)pyridin-2-yl]amino}cyclohexyl)-N~2~-propan-2-ylglycinamide | (400 MHz, METHANOL-d₄) ppm 1.34 (d, J = 6.41 Hz, 6 H) 1.36-1.55 (m, 4 H) 2.02 (d, J = 11.60 Hz, 2 H) 2.16 (d, J = 11.90 Hz, 2 H) 3.36-3.46 (m, 1 H) 3.65-3.85 (m, 4 H) 3.95 (s, 3 H) 6.78 (d, J = 1.22 Hz, 1 H) 6.88 (d, J = 1.22 Hz, 1 H) 7.85-7.93 (m, 2 H) 8.07 (d, J = 2.75 Hz, 1 H) |
| Example 447 | N-{4-[(4-{[6-chloro-4-(5-methoxy-1H-pyrrolo[2,3-b]pyridin-3-yl)pyridin-2-yl]amino}cyclohexyl)methyl]cyclohexyl}-3,5-dimethyl-1,2-oxazole-4-sulfonamide | (400 MHz, METHANOL-d₄) ppm 0.85-0.98 (m, 1 H), 1.02-1.13 (m, 2 H), 1.14-1.41 (m, 6 H), 1.44-1.66 (m, 4 H), 1.66-1.84 (m, 6 H), 2.06-2.14 (m, 1 H), 2.34-2.43 (m, 3 H), 2.61 (s, 3 H), 2.92-3.02 (m, 1 H), 3.62-3.71 (m, 1 H), |

| Example # | Name | ¹H NMR (ppm) |
|---|---|---|
| | | 3.93 (s, 3 H), 6.74 (s, 1 H), 6.83 (t, J = 6.26 Hz, 1 H), 7.80-7.90 (m, 2 H), 8.04 (s, 1 H). |
| Example 448 | N-(3-{[6-chloro-4-(5-methoxy-1H-pyrrolo[2,3-b]pyridin-3-yl)pyridin-2-yl]amino}cyclohexyl)-N~2~,N~2~-dimethylglycinamide | (500 MHz, DMSO-d₆) ppm 1.13 (q, J = 12.00 Hz, 3 H) 1.43 (q, J = 13.32 Hz, 1 H) 1.72-1.88 (m, 2 H) 1.96 (d, J = 11.29 Hz, 1 H) 2.18 (d, J = 11.60 Hz, 1 H) 2.80 (s, 6 H) 3.68-3.84 (m, 2 H) 3.86 (s, 2 H) 3.91 (s, 3 H) 6.82 (s, 1 H) 6.88 (s, 1 H) 7.79 (d, J = 2.75 Hz, 1 H) 7.93-8.20 (m, 2 H) 8.52 (d, J = 7.63 Hz, 1 H) 9.67 (s, 1 H) 12.07 (s, 1 H) |
| Example 449 | 6-chloro-N-{4-[4-(pyridin-2-ylmethyl)piperazin-1-yl]phenyl}-4-(1H-pyrrolo[2,3-b]pyridin-3-yl)pyridin-2-amine | (400 MHz, DMSO-d₆) δ 2.59 (t, J = 4.8 Hz, 4 H), 3.10 (t, J = 4.8 Hz, 4 H), 3.66 (s, 2 H), 7.15 (s, 1 H), 6.93 (d, J = 9.2 Hz, 2 H), 7.11 (s, 1 H), 7.29~7.23 (m, 2 H), 7.49~7.47 (m, 3 H), 7.81~7.76 (m, 1 H), 8.20 (d, J = 2.4 Hz, 1 H), 8.35~8.32 (m, 2 H), 8.51 (dd, J = 4.8, 0.8 Hz, 1 H), 9.10 (s, 1 H). |
| Example 450 | 6-chloro-N-{4-[4-(cyclohexylmethyl)piperazin-1-yl]phenyl}-4-(1H-pyrrolo[2,3-b]pyridin-3-yl)pyridin-2-amine | (400 MHz, DMSO-d₆) δ 2.46 (t, J = 4.8 Hz, 4 H), 2.12 (d, J = 7.6 Hz, 2 H), 3.06 (t, J = 4.4 Hz, 4 H), 6.92 (d, J = 9.2 Hz, 2 H), 7.10 (s, 1 H), 7.14 (s, 1 H), 7.26~7.23 (m, 1 H), 7.47 (d, J = 8.8 Hz, 2 H), 8.20 (s, 1 H), 8.35~8.31 (m, 2 H), 9.08 (s, 1 H). |
| Example 451 | 6-chloro-N-{4-[4-(2-methylpropyl)piperazin-1-yl]phenyl}-4-(1H-pyrrolo[2,3-b]pyridin-3-yl)pyridin-2-amine | (400 MHz, DMSO-d₆) δ 0.89~0.87 (m, 7 H), 2.09 (d, J = 7.6 Hz, 2 H), 3.07 (t, J = 4.4 Hz, 4 H), 6.93 (d, J = 9.2 Hz, 2 H), 7.10 (s, 1 H), 7.14 (s, 1 H), 7.26~7.23 (m, 1 H), 7.47 (d, J = 8.8 Hz, 1 H), 8.20 (s, 1 H), 8.34~8.312 (m, 2 H), 9.07 (s, 1 H). |
| Example 452 | N-[trans-4-({4-[5-(6-aminopyridin-3-yl)-1H-pyrrolo[2,3-b]pyridin-3-yl]-6-chloropyridin-2-yl}amino)cyclohexyl]cyclopropanesulfonamide | (400 MHz, DMSO-d₆) ppm 0.89-0.96 (m, 1 H), 1.20-1.47 (m, 1 H), 1.93-2.05 (m, 4 H), 6.41-6.64 (m, 1 H), 6.70 (d, J = 7.63 Hz, 1 H), 6.88 (s, 1 H), 6.93 (d, J = 1.22 Hz, 1 H), 7.09 (t, J = 8.54 Hz, 2 H), 7.88-8.02 (m, 1 H), 8.19 (d, J = 2.75 Hz, 1 H), 8.35-8.40 (m, 3 H), 8.44 (d, J = 2.14 Hz, 1 H), 8.56 (d, J = 2.14 Hz, 1 H), 12.32 (d, J = 2.44 Hz, 1 H). |
| Example 453 | N-[trans-4-({6-chloro-4-[5-(pyridin-3-yl)-1H-pyrrolo[2,3-b]pyridin-3-yl]pyridin-2-yl}amino)cyclohexyl]cyclopropanesulfonamide | (400 MHz, DMSO-d₆) ppm 0.91-0.94 (m, 1 H), 1.20-1.48 (m, 4 H), 1.91-2.06 (m, 4 H), 2.53-2.62 (m, 1 H), 3.17 (d, J = 5.49 Hz, 2 H), 3.58-3.68 (m, 1 H), 4.09 (q, J = 5.19 Hz, 1 H), 6.77 (d, J = 7.32 Hz, 2 H), 6.94 (s, 2 H), 7.08 (d, J = 7.93 Hz, 1 H), 7.55 (dd, J = 7.93, 4.58 Hz, 1 H), 8.16-8.26 (m, 2 H), 8.52 (d, J = 2.14 Hz, 1 H), 8.58-8.68 (m, 2 H), 9.01 (d, J = 2.14 Hz, 1 H), 12.32 (s, 1 H). |
| Example 454 | 3-{3-[2-chloro-6-({trans-4-[(cyclopropylsulfonyl)amino]cyclohexyl}amino)pyridin-4-yl]-1H-pyrrolo[2,3-b]pyridin-5-yl}benzenesulfonamide | (400 MHz, DMSO-d₆) ppm 0.88-0.96 (m, 4 H), 1.21-1.46 (m, 4 H), 1.91-2.05 (m, 4 H), 3.11-3.22 (m, 1 H), 3.55-3.66 (m, 1 H), 6.77 (s, 1 H), 6.91 (d, J = 8.85 Hz, 2 H), 7.06 (d, J = 7.63 Hz, 1 H), 7.43 (s, 2 H), 7.72 (t, J = 7.78 Hz, 1 H), 7.84 (d, J = 8.24 Hz, 1 H), |

-continued

| Example # | Name | ¹H NMR (ppm) |
|---|---|---|
| | | 7.99 (s, 1 H), 8.17 (s, 1 H), 8.20 (d, J = 3.05 Hz, 1 H), 8.48 (d, J = 2.14 Hz, 1 H), 8.59 (d, J = 2.14 Hz, 1 H), 12.34 (d, J = 3.05 Hz, 1 H). |
| Example 455 | N-[trans-4-({6-chloro-4-[5-(pyrimidin-5-yl)-1H-pyrrolo[2,3-b]pyridin-3-yl]pyridin-2-yl}amino)cyclohexyl] cyclopropanesulfonamide | (400 MHz, DMSO-d$_6$) ppm 0.88-0.96 (m, 4 H), 1.21-1.46 (m, 4 H), 1.91-2.05 (m, 4 H), 3.11-3.22 (m, 1 H), 3.55-3.66 (m, 1 H), 6.77 (s, 1 H), 6.91 (d, J = 8.85 Hz, 2 H), 7.06 (d, J = 7.63 Hz, 1 H), 7.43 (s, 2 H), 7.72 (t, J = 7.78 Hz, 1 H), 7.84 (d, J = 8.24 Hz, 1 H), 7.99 (s, 1 H), 8.17 (s, 1 H), 8.20 (d, J = 3.05 Hz, 1 H), 8.48 (d, J = 2.14 Hz, 1 H), 8.59 (d, J = 2.14 Hz, 1 H), 12.34 (d, J = 3.05 Hz, 1 H) |
| Example 456 | 4-chloro-N-[(1R)-1-phenylethyl]-6-(1H-pyrrolo[2,3-b]pyridin-3-yl)pyrimidin-2-amine | (400 MHz, DMSO-d$_6$) ppm 1.52 (d, J = 7.02 Hz, 3 H) 5.16-5.26 (m, 1 H) 7.08 (s, 1 H) 7.13 (dd, J = 7.93, 4.58 Hz, 1 H) 7.18 (t, J = 7.32 Hz, 1 H) 7.27-7.33 (m, 2 H) 7.45 (d, J = 7.32 Hz, 2 H) 7.62 (d, J = 7.63 Hz, 1 H) 8.26 (dd, J = 4.73, 1.68 Hz, 1 H) 8.30 (s, 1 H) 8.57-8.65 (m, 1 H) 11.97 (s, 1 H) |
| Example 457 | 3-({[4-chloro-6-(1H-pyrrolo[2,3-b]pyridin-3-yl)pyrimidin-2-yl]amino}methyl)phenol | (400 MHz, DMSO-d$_6$) ppm 4.54 (d, J = 6.10 Hz, 2 H) 6.61 (dd, J = 7.48, 1.98 Hz, 1 H) 6.77-6.84 (m, 2 H) 7.06-7.14 (m, 3 H) 7.64 (t, J = 6.26 Hz, 1 H) 8.25 (dd, J = 4.73, 1.68 Hz, 1 H) 8.33 (s, 1 H) 8.58-8.69 (m, 1 H) 8.92 (s, 1 H) 11.62 (s, 1 H) |
| Example 458 | 4-({[4-chloro-6-(1H-pyrrolo[2,3-b]pyridin-3-yl)pyrimidin-2-yl]amino}methyl)phenol | (400 MHz, DMSO-d$_6$) ppm 4.50 (s, 2 H) 6.69-6.73 (m, 2 H) 7.09-7.11 (m, 1 H) 7.11-7.14 (m, 1 H) 7.16-7.20 (m, 2 H) 7.53 (s, 1 H) 8.26 (dd, J = 4.73, 1.68 Hz, 1 H) 8.33 (s, 1 H) 8.69 (d, J = 7.63 Hz, 1 H) 12.01 (s, 1 H) |
| Example 459 | N'-[4-chloro-6-(1H-pyrrolo[2,3-b]pyridin-3-yl)pyrimidin-2-yl]-N,N-dimethylcyclohexane-1,4-diamine | (400 MHz, DMSO-d$_6$) ppm 1.36-2.24 (m, 8 H) 2.76-2.81 (m, 6 H) 3.01-3.11 (m, 1 H) 3.75-3.92 (m, 1 H) 7.07-7.26 (m, 3 H) 8.30 (dd, J = 4.58, 1.53 Hz, 1 H) 8.33-8.41 (m, 1 H) 8.69-8.85 (m, 1 H) 11.96-12.16 (m, 1 H) |
| Example 460 | N'-[4-chloro-6-(1H-pyrrolo[2,3-b]pyridin-3-yl)pyrimidin-2-yl]-N,N-dimethylcyclohexane-1,3-diamine | (400 MHz, DMSO-D6) ppm 1.07-2.02 (m, 9 H) 2.21 (s, 6 H) 3.77-3.96 (m, 2 H) 7.05-7.10 (m, 2 H) 7.18 (dd, J = 7.93, 4.88 Hz, 1 H) 8.26-8.31 (m, 1 H) 8.35 (s, 1 H) 8.78 (d, J = 7.93 Hz, 1 H) |
| Example 461 | N-(trans-4-{[4-chloro-6-(1H-pyrrolo[2,3-b]pyridin-3-yl)pyrimidin-2-yl]amino}cyclohexyl)-N~2~,N~2~-dimethylglycinamide | (400 MHz, DMSO-d$_6$) ppm 1.35-1.51 (m, 4 H) 1.84-1.92 (m, 2 H) 2.00-2.09 (m, J = 6.71 Hz, 2 H) 2.23 (s, 6 H) 2.84 (s, 2 H) 3.57-3.68 (m, 1 H) 3.80 (s, 1 H) 7.03 (d, J = 7.63 Hz, 1 H) 7.08 (s, 1 H) 7.19 (dd, J = 7.93, 4.58 Hz, 1 H) 7.26 (d, J = 7.93 Hz, 1 H) 8.29 (dd, J = 4.73, 1.68 Hz, 1 H) 8.34 (s, 1 H) 8.79 (d, J = 7.94 Hz, 1 H) |
| Example 462 | N-(trans-4-{[4-chloro-6-(1H-pyrrolo[2,3-b]pyridin-3-yl)pyrimidin-2-yl]amino}cyclohexyl)-1-ethylpyrrolidine-3-carboxamide | (400 MHz, DMSO-d$_6$) ppm 1.02 (t, J = 7.17 Hz, 3 H) 1.29-1.47 (m, 4 H) 1.83-1.91 (m, 6 H) 2.01-2.08 (m, 2 H) 2.38-2.46 (m, 4 H) 2.54-2.61 (m, 1 H) 2.71-2.81 (m, 1 H) |

| Example # | Name | ¹H NMR (ppm) |
|---|---|---|
| | | 3.50-3.62 (m, 1 H) 3.74-3.84 (m, 1 H) 7.03 (d, J = 7.63 Hz, 1 H) 7.08 (s, 1 H) 7.17 (dd, J = 7.93, 4.58 Hz, 1 H) 7.33 (d, J = 7.63 Hz, 1 H) 8.29 (dd, J = 4.73, 1.68 Hz, 1 H) 8.34 (s, 1 H) 8.78 (d, J = 7.63 Hz, 1 H) |
| Example 463 | N-(3-{[4-chloro-6-(1H-pyrrolo[2,3-b]pyridin-3-yl)pyrimidin-2-yl]amino}cyclohexyl)-N~2~,N~2~-dimethylglycinamide | (400 MHz, DMSO-d₆) ppm 1.09-1.48 (m, 5 H) 1.75-1.85 (m, 2 H) 1.94-2.02 (m, 1 H) 2.20 (s, 6 H) 2.82 (s, 2 H) 3.73-3.93 (m, 2 H) 7.08 (s, 1 H) 7.21 (dd, J = 7.93, 4.58 Hz, 1 H) 7.27-7.33 (m, 1 H) 8.27 (dd, J = 4.73, 1.68 Hz, 1 H) 8.34 (s, 1 H) 8.77 (d, J = 7.93 Hz, 1 H) |
| Example 464 | 4-chloro-6-(1H-pyrrolo[2,3-b]pyridin-3-yl)pyrimidin-2-amine | (400 MHz, DMSO-d₆) ppm 7.11 (s, 1 H) 7.17 (dd, J = 7.93, 4.58 Hz, 1 H) 8.28 (dd, J = 4.58, 1.53 Hz, 1 H) 8.33 (s, 1 H) 8.85 (dd, J = 7.93, 1.53 Hz, 1 H) 11.94-12.10 (m, 1 H) |
| Example 465 | N-{4-[(4-aminocyclohexyl)methyl]cyclohexyl}-4-chloro-6-(1H-pyrrolo[2,3-b]pyridin-3-yl)pyrimidin-2-amine | (400 MHz, DMSO-d₆) ppm 0.88-2.10 (m, 20 H) 2.87-2.99 (m, 1 H) 3.70-3.82 (m, 1 H) 7.01-7.11 (m, 1 H) 7.12-7.20 (m, 1 H) 7.51-7.72 (m, 3 H) 8.28 (dd, J = 4.58, 1.53 Hz, 1 H) 8.32-8.36 (m, 1 H) 8.78 (d, J = 7.93 Hz, 1 H) 12.02 (s, 1 H) |
| Example 466 | N-[4-chloro-6-(1H-pyrrolo[2,3-b]pyridin-3-yl)pyrimidin-2-yl]ethane-1,2-diamine | (400 MHz, DMSO-d₆) ppm 3.06-3.17 (m, 2 H) 3.60-3.73 (m, 2 H) 7.13-7.30 (m, 2 H) 7.63-7.90 (m, 3 H) 8.30 (dd, J = 4.58, 1.53 Hz, 1 H) 8.36-8.44 (m, 1 H) 8.75 (dd, J = 7.93, 1.53 Hz, 1 H) 12.10 (s, 1 H) |
| Example 467 | 2-{[4-chloro-6-(1H-pyrrolo[2,3-b]pyridin-3-yl)pyrimidin-2-yl]amino}ethanol | (400 MHz, DMSO-d₆) ppm 3.49 (t, J = 6.10 Hz, 2 H) 3.63 (t, J = 5.95 Hz, 2 H) 7.10 (s, 1 H) 7.18 (dd, J = 7.93, 4.58 Hz, 1 H) 8.28 (dd, J = 4.58, 1.53 Hz, 1 H) 8.35 (s, 1 H) 8.79 (dd, J = 7.93, 1.53 Hz, 1 H) 12.02 (s, 1 H) |
| Example 468 | N-{2-[2-(2-aminoethoxy)ethoxy]ethyl}-4-chloro-6-(1H-pyrrolo[2,3-b]pyridin-3-yl)pyrimidin-2-amine | (400 MHz, DMSO-d₆) ppm 2.97 (t, J = 5.34 Hz, 2 H) 3.54-3.72 (m, 11 H) 7.13 (s, 1 H) 7.18 (dd, J = 7.93, 4.58 Hz, 1 H) 7.70 (d, J = 12.21 Hz, 3 H) 8.29 (dd, J = 4.73, 1.68 Hz, 1 H) 8.36 (s, 1 H) 8.78 (dd, J = 7.78, 1.68 Hz, 1 H) 11.95-12.19 (m, 1 H) |
| Example 469 | 1-(trans-4-{[4-chloro-6-(1H-pyrrolo[2,3-b]pyridin-3-yl)pyrimidin-2-yl]amino}cyclohexyl)-3-ethylurea | (400 MHz, DMSO-d₆) ppm 1.04-1.11 (m, 3 H) 1.27-1.55 (m, 6 H) 1.96-2.14 (m, 4 H) 3.41-3.53 (m, 1 H) 3.80-3.91 (m, 1 H) 5.51-5.61 (m, 2 H) 7.08 (d, J = 7.63 Hz, 1 H) 7.14 (s, 1 H) 7.24 (dd, J = 7.93, 4.58 Hz, 1 H) 8.36 (dd, J = 4.73, 1.68 Hz, 1 H) 8.41 (s, 1 H) 8.86 (d, J = 7.02 Hz, 1 H) 12.07 (s, 1 H) |
| Example 470 | 1-(trans-4-{[4-chloro-6-(1H-pyrrolo[2,3-b]pyridin-3-yl)pyrimidin-2-yl]amino}cyclohexyl)-3-cyclopentylurea | (400 MHz, DMSO-d₆) ppm 1.14-2.14 (m, 19 H) 3.35-3.45 (m, 1 H) 3.72-3.91 (m, 2 H) 7.07 (s, 1 H) 7.17 (dd, J = 7.93, 4.58 Hz, 1 H) 8.29 (dd, J = 4.58, 1.53 Hz, 1 H) 8.34 (s, 1 H) 8.79 (d, J = 7.63 Hz, 1 H) 12.00 (s, 1 H) |
| Example 471 | 1-(trans-4-{[4-chloro-6-(1H-pyrrolo[2,3-b]pyridin-3-yl)pyrimidin-2-yl]amino}cyclohexyl)-3-[4-(dimethylamino)phenyl]urea | (400 MHz, DMSO-d₆) ppm 1.26-1.54 (m, 4 H) 1.94-2.11 (m, 4 H) 2.81 (s, 6 H) 3.42-3.57 (m, 1 H) 3.75-3.91 (m, 1 H) 5.72 (d, J = 7.32 Hz, 1 H) |

-continued

| Example # | Name | ¹H NMR (ppm) |
|---|---|---|
| | | 6.65 (d, J = 8.85 Hz, 2 H) 7.04 (d, J = 7.63 Hz, 1 H) 7.08 (s, 1 H) 7.15-7.22 (m, 3 H) 7.71 (s, 1 H) 8.29 (dd, J = 4.58, 1.53 Hz, 1 H) 8.35 (s, 1 H) 8.80 (d, J = 7.63 Hz, 1 H) 12.01 (s, 1 H) |
| Example 472 | N-(trans-4-{[4-chloro-6-(1H-pyrrolo[2,3-b]pyridin-3-yl)pyrimidin-2-yl]amino}cyclohexyl)-2-(1,3-dioxo-1,3-dihydro-2H-isoindol-2-yl)acetamide | (400 MHz, DMSO-d₆) ppm 1.33-1.63 (m, 6 H) 1.83-1.93 (m, 2 H) 2.02-2.10 (m, 2 H) 3.57-3.68 (m, 1 H) 3.73-3.86 (m, 3 H) 7.01 (d, J = 7.93 Hz, 1 H) 7.07 (s, 1 H) 7.24 (dd, J = 7.93, 4.58 Hz, 1 H) 7.35-7.44 (m, 2 H) 7.74 (dd, J = 6.41, 2.44 Hz, 1 H) 8.02 (s, 1 H) 8.25-8.30 (m, 1 H) 8.32-8.35 (m, 1 H) 8.75-8.82 (m, 1 H) |
| Example 473 | N-(trans-4-{[4-chloro-6-(1H-pyrrolo[2,3-b]pyridin-3-yl)pyrimidin-2-yl]amino}cyclohexyl)-2-oxoimidazolidine-1-carboxamide | (400 MHz, DMSO-d₆) ppm 1.31-1.54 (m, 4 H) 1.95-2.10 (m, 4 H) 3.29-3.35 (m, 2 H) 3.52-3.62 (m, 1 H) 3.72-3.78 (m, 2 H) 3.79-3.90 (m, 1 H) 7.08 (s, 1 H) 7.20 (dd, J = 7.93, 4.58 Hz, 1 H) 8.00-8.07 (m, 1 H) 8.29 (dd, J = 4.58, 1.83 Hz, 1 H) 8.35 (s, 1 H) 8.79 (d, J = 7.32 Hz, 1 H) 11.95-12.09 (m, 1 H) |
| Example 474 | 2-(2-{[4-chloro-6-(1H-pyrrolo[2,3-b]pyridin-3-yl)pyrimidin-2-yl]amino}ethoxy)ethanol | (400 MHz, DMSO-d₆) ppm 3.47-3.69 (m, 10 H) 7.11 (s, 1 H) 7.19 (dd, J = 7.93, 4.88 Hz, 1 H) 8.29 (dd, J = 4.73, 1.68 Hz, 1 H) 8.36 (s, 1 H) 8.79 (dd, J = 7.93, 1.83 Hz, 1 H) 11.95-12.11 (m, 1 H) |
| Example 475 | N-[2-(2-aminoethoxy)ethyl]-4-chloro-6-(1H-pyrrolo[2,3-b]pyridin-3-yl)pyrimidin-2-amine | (400 MHz, DMSO-d₆) ppm 3.00-3.05 (m, 2 H) 3.59-3.73 (m, 6 H) 7.14 (s, 1 H) 7.17-7.21 (m, 1 H) 7.58-7.87 (m, 2 H) 8.29-8.31 (m, 1 H) 8.37 (s, 1 H) 8.74-8.78 (m, 1 H) 11.95-12.15 (m, 1 H) |
| Example 476 | trans-N-[4-chloro-6-(1H-pyrrolo[2,3-b]pyridin-3-yl)pyrimidin-2-yl]-N'-(2-methylpropyl)cyclohexane-1,4-diamine | (400 MHz, DMSO-d₆) ppm 0.92-2.25 (m, 15 H) 2.77-2.86 (m, 2 H) 3.08 (s, 1 H) 3.76-3.89 (m, 1 H) 7.11 (s, 1 H) 7.17 (dd, J = 7.93, 4.58 Hz, 1 H) 8.10-8.21 (m, 2 H) 8.30 (dd, J = 4.73, 1.68 Hz, 1 H) 8.36 (s, 1 H) 8.77 (d, J = 7.32 Hz, 1 H) 12.05 (s, 1 H) |
| Example 477 | trans-N-[4-chloro-6-(1H-pyrrolo[2,3-b]pyridin-3-yl)pyrimidin-2-yl]-N'-cyclopentylcyclohexane-1,4-diamine | (400 MHz, DMSO-d₆) ppm 1.33-1.82 (m, 10 H) 1.94-2.23 (m, 6 H) 3.03-3.14 (m, 1 H) 3.58-3.75 (m, 2 H) 7.11 (s, 1 H) 7.17 (dd, J = 7.93, 4.58 Hz, 1 H) 8.24-8.35 (m, 2 H) 8.36 (s, 1 H) 8.77 (d, J = 6.71 Hz, 1 H) 12.06 (s, 1 H) |
| Example 478 | N-(trans-4-{[4-chloro-6-(1H-pyrrolo[2,3-b]pyridin-3-yl)pyrimidin-2-yl]amino}cyclohexyl)-N~2~-cyclopentylglycinamide | (400 MHz, DMSO-d₆) ppm 1.08-2.14 (m, 16 H) 2.94-3.10 (m, 5 H) 3.55-3.68 (m, 1 H) 3.73-3.89 (m, 1 H) 7.04 (d, J = 7.32 Hz, 1 H) 7.09 (s, 1 H) 7.18 (dd, J = 7.78, 4.73 Hz, 1 H) 7.35-7.46 (m, 1 H) 8.29 (d, J = 3.05 Hz, 1 H) 8.35 (s, 1 H) 8.75-8.86 (m, 1 H) |
| Example 479 | N-(trans-4-{[4-chloro-6-(1H-pyrrolo[2,3-b]pyridin-3-yl)pyrimidin-2-yl]amino}cyclohexyl)propane-1-sulfonamide | (400 MHz, DMSO-d₆) ppm 1.00 (t, J = 7.48 Hz, 3 H) 1.35-1.52 (m, 4 H) 1.66-1.78 (m, 2 H) 1.94-2.08 (m, 4 H) 2.94-2.99 (m, 2 H) 3.10-3.20 (m, 1 H) 3.71-3.83 (m, 1 H) 6.63-6.73 (m, 1 H) 7.08 (s, 1 H) 7.18 (dd, J = 7.93, 4.58 Hz, 1 H) |

| Example # | Name | ¹H NMR (ppm) |
|---|---|---|
| | | 8.29 (dd, J = 4.73, 1.68 Hz, 1 H) 8.34 (s, 1 H) 8.78 (d, J = 7.02 Hz, 1 H) 12.02 (s, 1 H) |
| Example 480 | N-(trans-4-{[4-chloro-6-(1H-pyrrolo[2,3-b]pyridin-3-yl)pyrimidin-2-yl]oxy}cyclohexyl)acetamide | (400 MHz, DMSO-d₆) ppm 1.34-1.49 (m, 2 H) 1.52-1.68 (m, 2 H) 1.81 (s, 3 H) 1.87-1.99 (m, 2 H) 2.13-2.25 (m, 2 H) 4.96-5.09 (m, 1 H) 7.23 (dd, J = 8.09, 4.73 Hz, 1 H) 7.44 (d, J = 6.10 Hz, 1 H) 7.63 (s, 1 H) 8.32 (dd, J = 4.58, 1.83 Hz, 1 H) 8.52 (s, 1 H) 8.69 (dd, J = 7.93, 1.53 Hz, 1 H) 12.23 (s, 1 H) |
| Example 481 | N-(trans-4-{[4-chloro-6-(1H-pyrrolo[2,3-b]pyridin-3-yl)pyrimidin-2-yl]amino}cyclohexyl)thiophene-3-sulfonamide | (400 MHz, DMSO-d₆) ppm 1.22-1.46 (m, 4 H) 1.74-1.84 (m, 2 H) 1.93-2.02 (m, 2 H) 3.65-3.79 (m, 2 H) 6.97 (d, J = 7.63 Hz, 1 H) 7.06 (s, 1 H) 7.15 (dd, J = 7.93, 4.88 Hz, 1 H) 7.35 (dd, J = 5.19, 1.22 Hz, 1 H) 7.68 (dd, J = 5.19, 3.05 Hz, 1 H) 8.09 (dd, J = 3.05, 1.53 Hz, 1 H) 8.28 (dd, J = 4.73, 1.68 Hz, 1 H) 8.33 (s, 1 H) 8.74 (d, J = 7.02 Hz, 1 H) |
| Example 482 | N-(trans-4-{[4-chloro-6-(1H-pyrrolo[2,3-b]pyridin-3-yl)pyrimidin-2-yl]amino}cyclohexyl)thiophene-2-sulfonamide | (400 MHz, DMSO-d₆) ppm 1.27-1.48 (m, 4 H) 1.78-1.87 (m, 2 H) 1.95-2.03 (m, 2 H) 3.08-3.16 (m, 1 H) 3.67-3.79 (m, 1 H) 6.98 (d, J = 7.63 Hz, 1 H) 7.06 (s, 1 H) 7.12-7.17 (m, 2 H) 7.59 (dd, J = 3.81, 1.37 Hz, 1 H) 7.84 (dd, J = 5.04, 1.37 Hz, 1 H) 8.28 (dd, J = 4.73, 1.68 Hz, 1 H) 8.33 (s, 1 H) 8.74 (d, J = 7.02 Hz, 1 H) |
| Example 483 | 3-{[4-chloro-6-(1H-pyrrolo[2,3-b]pyridin-3-yl)pyrimidin-2-yl]amino}-2,2-dimethylpropan-1-ol | (400 MHz, DMSO-d₆) ppm 0.90 (s, 6 H) 3.25 (s, 2 H) 3.36 (s, 2 H) 6.91-7.02 (m, 1 H) 7.08 (s, 1 H) 7.18 (dd, J = 7.93, 4.58 Hz, 1 H) 8.28 (dd, J = 4.58, 1.83 Hz, 1 H) 8.34 (s, 1 H) 8.82 (dd, J = 7.93, 1.53 Hz, 1 H) 12.01 (s, 1 H) |

Table 3 depicts enzyme inhibition data ($K_i$) for exemplary compounds. In Table 3, "A" represents a $K_i$ of less than 10 nM and "B" represents a $K_i$ of between 10 nM and 100 nM.

| Example | Cdc7 Inhibition |
|---|---|
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | B |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |

| Example | Cdc7 Inhibition |
|---|---|
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | A |
| 200 | A |
| 201 | B |
| 202 | A |
| 203 | B |
| 204 | A |
| 205 | A |
| 206 | A |
| 207 | A |
| 208 | A |
| 209 | A |
| 210 | A |
| 211 | A |
| 212 | A |
| 213 | A |
| 214 | A |
| 215 | B |
| 216 | A |
| 217 | A |
| 218 | A |
| 219 | A |
| 220 | A |
| 221 | A |
| 222 | A |
| 223 | A |
| 224 | A |
| 225 | A |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | B |
| 240 | A |
| 241 | B |
| 242 | A |
| 243 | A |
| 244 | A |
| 245 | A |
| 246 | A |
| 247 | A |
| 248 | A |

| Example | Cdc7 Inhibition |
|---|---|
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |
| 283 | A |
| 284 | A |
| 285 | B |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | B |
| 304 | B |
| 305 | B |
| 306 | B |
| 307 | A |
| 308 | A |
| 309 | A |
| 310 | A |
| 311 | A |
| 312 | A |
| 313 | A |
| 314 | A |
| 315 | A |
| 316 | A |
| 317 | B |
| 318 | B |
| 319 | A |
| 320 | B |
| 321 | A |
| 322 | A |
| 323 | A |
| 324 | A |
| 325 | A |
| 326 | A |
| 327 | A |
| 328 | A |
| 329 | A |
| 330 | B |
| 331 | A |
| 332 | A |
| 333 | A |
| 334 | A |
| 335 | A |
| 336 | A |
| 337 | A |
| 338 | A |
| 339 | A |
| 340 | A |
| 341 | A |
| 342 | A |
| 343 | A |
| 344 | A |
| 345 | A |
| 346 | A |
| 347 | A |
| 348 | B |
| 349 | B |
| 350 | A |
| 351 | A |
| 352 | A |
| 353 | A |
| 354 | A |
| 355 | A |
| 356 | A |
| 357 | A |
| 358 | A |
| 359 | A |
| 360 | A |
| 361 | A |
| 362 | B |
| 363 | A |
| 364 | A |
| 365 | A |
| 366 | A |
| 367 | A |
| 368 | A |
| 369 | A |
| 370 | B |
| 371 | A |
| 372 | A |
| 373 | A |
| 374 | A |
| 375 | B |
| 376 | A |
| 377 | A |
| 378 | A |
| 379 | A |
| 380 | A |
| 381 | A |
| 382 | A |
| 383 | A |
| 384 | B |
| 385 | A |
| 386 | B |
| 387 | A |
| 388 | A |
| 389 | B |
| 390 | A |
| 391 | A |
| 392 | A |
| 393 | A |
| 394 | A |
| 395 | A |
| 396 | A |
| 397 | A |
| 398 | A |
| 399 | A |
| 400 | A |
| 401 | A |
| 402 | A |

| Example | Cdc7 Inhibition |
|---|---|
| 403 | A |
| 404 | A |
| 405 | A |
| 406 | A |
| 407 | A |
| 408 | A |
| 409 | A |
| 410 | A |
| 411 | A |
| 412 | A |
| 413 | A |
| 414 | A |
| 415 | A |
| 416 | A |
| 417 | A |
| 418 | A |
| 419 | A |
| 420 | A |
| 421 | A |
| 422 | A |
| 423 | A |
| 424 | A |
| 425 | A |
| 426 | A |
| 427 | A |
| 428 | A |
| 429 | A |
| 430 | A |
| 431 | A |
| 432 | A |
| 433 | A |
| 434 | A |
| 435 | A |
| 436 | A |
| 437 | A |
| 438 | A |
| 439 | A |
| 440 | A |
| 441 | A |
| 442 | A |
| 443 | A |
| 444 | A |
| 445 | A |
| 446 | A |
| 447 | A |
| 448 | A |
| 449 | A |
| 450 | A |
| 451 | A |
| 452 | A |
| 453 | A |
| 454 | A |
| 455 | A |
| 456 | A |
| 457 | A |
| 458 | A |
| 459 | A |
| 460 | A |
| 461 | A |
| 462 | A |
| 463 | A |
| 464 | A |
| 465 | A |
| 466 | A |
| 467 | A |
| 468 | A |
| 469 | A |
| 470 | A |
| 471 | A |
| 472 | A |
| 473 | A |
| 474 | A |
| 475 | A |
| 476 | A |
| 477 | A |
| 478 | A |
| 479 | A |
| 480 | B |
| 481 | A |
| 482 | A |

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:
1. A compound having formula (I)

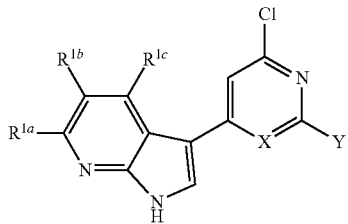

formula (I)

wherein
R$^{1a}$ and R$^{1c}$ are independently hydrogen, nitro, halogen, cyano, hydroxy, C$_{1-6}$-alkyl, C$_{1-6}$-haloalkyl, C$_{1-6}$-alkoxy, C$_{1-6}$-haloalkoxy, —NH$_2$, —NH(C$_{1-6}$-alkyl), or —N(C$_{1-6}$-alkyl)$_2$;
R$^{1b}$ is hydrogen, nitro, halogen, cyano, C$_{1-6}$-alkyl, C$_{1-6}$-haloalkyl, —OR$^a$, —NR$^b$R$^c$; —C(O)OR$^a$, —C(O)NR$^b$R$^c$, —NR$^b$C(O)R$^c$, —NHC(O)NHR$^b$, —NHSO$_2$R$^a$, —SO$_2$NR$^b$R$^c$, phenyl, or heteroaryl, wherein the phenyl and heteroaryl are optionally substituted with R$^d$;
X is CR$^2$;
R$^2$ is hydrogen;
Y is NR$^3$R$^4$, NR$^5$C(O)R$^6$, NR$^5$SO$_2$R$^6$, or phenyl, wherein the phenyl is optionally substituted with one or more C$_{1-6}$-alkyl, C$_{1-6}$-haloalkyl, halogen, cyano, hydroxy, C$_{1-6}$-alkoxy, C$_{1-6}$-haloalkoxy, —NH$_2$, —NH(C$_{1-6}$-alkyl), or —N(C$_{1-6}$-alkyl)$_2$;
R$^3$ is hydrogen, C$_{1-8}$-alkyl, C$_{2-8}$-alkenyl, C$_{1-8}$-alkyl-O—C$_{1-8}$-alkyl-, C$_{3-8}$-cycloalkyl, C$_{3-8}$-cycloalkyl-(C$_{1-8}$-alkyl)-, heterocycloalkyl, heterocycloalkyl-(C$_{1-8}$-alkyl)-, aryl, aryl-(C$_{1-8}$-alkyl)-, heteroaryl, or heteroaryl-(C$_{1-8}$-alkyl)-, wherein (a) the R$^3$ C$_{1-8}$-alkyl and C$_{2-8}$-alkenyl substituents, alone or as part of another moiety, are optionally substituted with one or more substituents selected from the group consisting of halogen, cyano, nitro, —OR$^e$, —C(O)R$^e$, —C(O)OR$^e$, —OC(O)R$^e$, —NR$^f$R$^g$, —NR$^f$C(O)R$^e$, —NHC(O)NHR$^f$, —C(O)NR$^f$R$^g$, —NHSO$_2$R$^e$, —SO$_2$NR$^f$NR$^g$, and benzyl; and (b) the R$^3$ C$_{3-8}$-cycloalkyl, heterocycloalkyl, aryl, and heteroaryl, alone or as part of another moiety, are optionally substituted with one or more R$^7$;
R$^4$ is hydrogen, C$_{1-6}$-alkyl, —C(O)C$_{1-6}$-alkyl, —C(O)C$_{3-8}$-cycloalkyl, —S(O)$_2$C$_{1-6}$-alkyl, or —S(O)$_2$C$_{3-8}$-cycloalkyl, wherein the R$^4$ C$_{1-6}$-alkyl is optionally substituted with one or more substituents selected from the group consisting of halogen, hydroxy, C$_{1-6}$-alkoxy, —NH$_2$, —NH(C$_{1-6}$-alkyl), and —N(C$_{1-6}$-alkyl)$_2$;
or R$^3$ and R$^4$ can be joined together to form a 4-7 membered heterocycloalkyl ring; wherein the heterocycloalkyl ring is optionally substituted with one or more R$^7$;
R$^5$ is hydrogen or C$_{1-8}$-alkyl;
R$^6$ is C$_{1-8}$-alkyl, C$_{2-8}$-alkenyl, C$_{3-8}$-cycloalkyl, C$_{3-8}$-cycloalkyl-(C$_{1-8}$-alkyl)-, heterocycloalkyl, heterocycloalkyl-(C$_{1-8}$-alkyl)-, aryl, aryl-(C$_{1-8}$-alkyl)-, heteroaryl, or heteroaryl-(C$_{1-8}$-alkyl)-, wherein (a) the R$^6$ C$_{1-8}$-alkyl and C$_{2-8}$-alkenyl substituents, alone or as part of another moiety, are optionally substituted with one or more substituents selected from the group consisting of halogen, hydroxy, C$_{1-6}$-alkoxy, C$_{1-6}$-haloalkoxy, —NH$_2$, —NH(C$_{1-6}$-alkyl), and —N(C$_{1-6}$-alkyl)$_2$, and (b) the R$^6$ C$_{3-8}$-cycloalkyl, heterocycloalkyl, aryl, and heteroaryl, alone or as part of another moiety, are optionally substituted with one or more substituents selected from the group consisting of C$_{1-6}$-alkyl, C$_{1-6}$-haloalkyl, halogen, cyano, hydroxy, C$_{1-6}$-alkoxy, C$_{1-6}$-haloalkoxy, —NH$_2$, —NH(C$_{1-6}$-alkyl), and —N(C$_{1-6}$-alkyl)$_2$;
R$^7$ is C$_{1-6}$-alkyl, C$_{1-6}$-haloalkyl, C$_{2-6}$-alkenyl, C$_{3-8}$-cycloalkyl, C$_{3-8}$-cycloalkyl-(C$_{1-4}$-alkyl)-, heterocycloalkyl, heterocycloalkyl-(C$_{1-4}$-alkyl)-, aryl, aryl-(C$_{1-4}$-alkyl)-, heteroaryl, heteroaryl-(C$_{1-4}$-alkyl)-, halogen, oxo, cyano, nitro, —OR$^8$, —C(O)R$^8$, —C(O)OR$^8$, —OC(O)R$^8$, —SR$^8$, —S(O)R$^8$, —SO$_2$R$^8$, —NR$^9$R$^{10}$, —NHC(O)R$^{11}$, —NHC(O)NHR$^{11}$, —NHC(O)OR$^{11}$, —NHSO$_2$R$^{11}$, —C(O)NHR$^{11}$, or —SO$_2$NHNR$^{11}$, wherein the R$^7$ cycloalkyl, heterocycloalkyl, aryl, and heteroaryl, alone or as part of another moiety, are optionally substituted with one or more R$^{12}$;
R$^8$ is hydrogen, C$_{1-6}$-alkyl, C$_{1-6}$-haloalkyl, C$_{2-6}$-alkenyl, C$_{3-8}$-cycloalkyl, aryl, heteroaryl, or heterocycloalkyl;
R$^9$ is hydrogen, C$_{1-6}$-alkyl, C$_{1-6}$-haloalkyl, C$_{2-6}$-alkenyl, C$_{3-8}$-cycloalkyl, C$_{3-8}$-cycloalkyl-(C$_{1-4}$-alkyl)-, heterocycloalkyl, heterocycloalkyl-(C$_{1-4}$-alkyl)-, aryl, aryl-(C$_{1-4}$-alkyl)-, heteroaryl, heteroaryl-(C$_{1-4}$-alkyl)-, wherein the R$^9$ cycloalkyl, heterocycloalkyl, aryl, and heteroaryl, alone or as part of another moiety, are optionally substituted with one or more substituents selected from the group consisting of C$_{1-6}$-alkyl, C$_{3-8}$-cycloalkyl, heterocycloalkyl, heterocycloalkyl-(C$_{1-4}$-alkyl)-, —C(O)R$^h$, —C(O)OR$^h$, —NR$^i$R$^j$, and —NHC(O)R$^j$;
R$^{10}$ is hydrogen or C$_{1-6}$-alkyl;
R$^{11}$ is C$_{1-6}$-alkyl, C$_{1-6}$-haloalkyl, C$_{2-6}$-alkenyl, C$_{3-8}$-cycloalkyl, C$_{3-8}$-cycloalkyl-(C$_{1-4}$-alkyl)-, heterocycloalkyl, heterocycloalkyl-(C$_{1-4}$-alkyl)-, aryl, aryl-(C$_{1-4}$-alkyl)-, heteroaryl, heteroaryl-(C$_{1-4}$-alkyl)-, —(C$_{1-4}$-alkyl)-NR$^k$R$^l$, —(C$_{1-4}$-alkyl)-NHC(O)R$^m$, —(C$_{1-4}$-alkyl)-NHSO$_2$R$^m$, —(C$_{1-4}$-alkyl)-NHC(O)NHR$^k$, —(C$_{1-4}$-alkyl)-OR$^m$, or —(C$_{1-4}$-alkyl)-C(O)OR$^m$, wherein the R$^{11}$ C$_{3-8}$-cycloalkyl, heterocycloalkyl, aryl, and heteroaryl, alone or as part of another moiety, are optionally substituted with one or more substituents selected from the group consisting of C$_{1-6}$-alkyl, C$_{1-6}$-haloalkyl, C$_{1-6}$-hydroxyalkyl, halogen, cyano, hydroxy, oxo, C$_{1-6}$-alkoxy, C$_{1-6}$-haloalkoxy, —NH$_2$, —NH(C$_{1-6}$-alkyl), —NH(C$_{3-8}$-cycloalkyl), N(C$_{1-6}$-alkyl)$_2$, —N(C$_{1-6}$-alkyl)(C$_{1-6}$-hydroxylalkyl), —C(O)OC$_{1-6}$-alkyl, —S(O)$_2$C$_{1-6}$-alkyl, heteroaryl, phenyl, benzyl, cycloalkyl, and heterocycloalkyl, wherein the heteroaryl, phenyl, benzyl, cycloalkyl, and heterocycloalkyl are optionally substituted with one or more C$_{1-6}$-alkyl or halogen;
R$^{12}$ is selected from the group consisting of C$_{1-6}$-alkyl, C$_{3-8}$-cycloalkyl, —C(O)R$^n$, —C(O)OR$^n$, —NR$^o$R$^p$, —NHC(O)R$^n$, —SO$_2$R$^n$, oxo, phenyl, benzyl, and heterocycloalkyl, wherein the phenyl, benzyl, and heterocycloalkyl are optionally substituted with one or more halogen or C$_{1-6}$ alkyl;
R$^a$, at each occurrence, is selected from the group consisting of hydrogen, C$_{1-6}$-alkyl, C$_{1-6}$-haloalkyl, C$_{2-6}$-alkenyl, C$_{2-6}$-alkynyl, aryl, heterocycloalkyl, heteroaryl, and C$_{3-8}$-cycloalkyl, wherein the C$_{1-6}$-alkyl, C$_{2-6}$-alkenyl, aryl, heterocycloalkyl, heteroaryl, and C$_{3-8}$-cycloalkyl are optionally substituted with one or more substituents independently selected from the group consisting of C$_{1-6}$-alkyl, aryl, heterocycloalkyl, heteroaryl, C$_{3-8}$-cycloalkyl, halogen, cyano, oxo, hydroxy, C$_{1-6}$-alkoxy, —NH$_2$, —NH(C$_{1-6}$-alkyl), and —N(C$_{1-6}$-alkyl)$_2$, wherein the heteroaryl is optionally substituted with C$_{1-6}$-alkyl;

$R^b$ and $R^c$, at each occurrence, are independently selected from the group consisting of hydrogen, $C_{1-6}$-alkyl, $C_{2-6}$-alkenyl, $C_{2-6}$-alkynyl, aryl, heterocycloalkyl, heteroaryl, and $C_{3-8}$-cycloalkyl, wherein the $C_{1-6}$-alkyl, $C_{2-6}$-alkenyl, $C_{2-6}$-alkynyl, aryl, heterocyclyl, $C_{3-8}$-cycloalkyl are optionally substituted with one or more substituents independently selected from the group consisting of $C_{1-6}$-alkyl, aryl, heterocyclyl, $C_{3-8}$-cycloalkyl, halogen, cyano, oxo, hydroxy, $C_{1-6}$-alkoxy, —$NH_2$, —$NH(C_{1-6}$-alkyl), and —$N(C_{1-6}$-alkyl)$_2$;

$R^d$ at each occurrence, is selected from the group consisting of $C_{1-6}$-alkyl, —$NH_2$, —$NH(C_{1-6}$-alkyl), —$N(C_{1-6}$-alkyl)$_2$; $SO_2NH_2$, heterocycloalkyl-$(C_{1-4})$—, and —$C_{1-4}$-hydroxyalkyl, wherein the heterocycloalkyl is optionally substituted with $C_{1-6}$-alkyl;

$R^e$, at each occurrence, is selected from the group consisting of hydrogen, $C_{1-6}$-alkyl, $C_{2-6}$-alkenyl, aryl, heteroaryl, heterocycloalkyl, and $C_{3-8}$-cycloalkyl, wherein the $C_{1-6}$-alkyl, $C_{2-6}$-alkenyl, aryl, heteroaryl, heterocycloalkyl, and $C_{3-8}$-cycloalkyl are optionally substituted with one or more substituents independently selected from the group consisting of $C_{1-6}$-alkyl, aryl, heterocyclyl, $C_{3-8}$-cycloalkyl, halogen, cyano, oxo, hydroxy, $C_{1-6}$-alkoxy, —$NH_2$, —$NH(C_{1-6}$-alkyl), and —$N(C_{1-6}$-alkyl)$_2$;

$R^f$ and $R^g$, at each occurrence, are independently selected from the group consisting of hydrogen, $C_{1-6}$-alkyl, $C_{2-6}$-alkenyl, aryl, heteroaryl, heterocycloalkyl, and $C_{3-8}$-cycloalkyl, wherein the $C_{1-6}$-alkyl, $C_{2-6}$-alkenyl, aryl, heteroaryl, heterocycloalkyl, $C_{3-8}$-cycloalkyl are optionally substituted with one or more substituents independently selected from the group consisting of $C_{1-6}$-alkyl, aryl, heterocyclyl, $C_{3-8}$-cycloalkyl, halogen, cyano, oxo, hydroxy, $C_{1-6}$-alkoxy, —$NH_2$, —$NH(C_{1-6}$-alkyl), and —$N(C_{1-6}$-alkyl)$_2$;

$R^h$, at each occurrence, is independently selected from the group consisting of $C_{1-6}$-alkyl, phenyl, benzyl, heterocycloalkyl, and $C_{3-8}$-cycloalkyl;

$R^i$ and $R^j$, at each occurrence, are independently selected from the group consisting of hydrogen, $C_{1-6}$-alkyl, phenyl, benzyl, and $C_{3-8}$-cycloalkyl;

$R^k$, at each occurrence, is selected from the group consisting of hydrogen, $C_{1-6}$-alkyl, $C_{2-6}$-alkenyl, aryl, heterocycloalkyl, heteroaryl, and $C_{3-8}$-cycloalkyl, wherein the aryl and heteroaryl are optionally substituted with one or more substituents independently selected from the group consisting of $C_{1-6}$-alkyl and —$C(O)C_{1-6}$-alkyl;

$R^l$, at each occurrence, is selected from the group consisting of hydrogen and $C_{1-6}$-alkyl;

$R^m$, at each occurrence, is selected from the group consisting of hydrogen, $C_{1-6}$-alkyl, $C_{2-6}$-alkenyl, aryl, heterocycloalkyl, heteroaryl, and $C_{3-8}$-cycloalkyl, wherein the aryl and heteroaryl are optionally substituted with one or more substituents independently selected from the group consisting of $C_{1-6}$-alkyl and —$C(O)C_{1-6}$-alkyl;

$R^n$, at each occurrence, is selected from the group consisting of hydrogen, $C_{1-6}$-alkyl, $C_{2-6}$-alkenyl, aryl, heterocyloalkyl, heteroaryl, and $C_{3-8}$-cycloalkyl, wherein the aryl and heteroaryl are optionally substituted with one or more substituents independently selected from the group consisting of $C_{1-6}$-alkyl and —$C(O)C_{1-6}$-alkyl;

$R^o$, at each occurrence, is selected from the group consisting of hydrogen, $C_{1-6}$-alkyl, aryl, heteroaryl, heterocycloalkyl, and $C_{3-8}$-cycloalkyl, wherein the aryl and heteroaryl are optionally substituted with one or more substituents independently selected from the group consisting of $C_{1-6}$-alkyl and —$C(O)C_{1-6}$-alkyl;

$R^p$, at each occurrence, is selected from the group consisting of hydrogen and $C_{1-6}$-alkyl;

or a pharmaceutically acceptable salt thereof.

2. The compound of claim 1, wherein $R^{1a}$, $R^{1b}$, and $R^{1c}$ are each hydrogen.

3. The compound of claim 1, wherein $R^{1a}$ and $R^{1c}$ are hydrogen and $R^{1b}$ is halogen, cyano, $C_{1-6}$-alkyl, $C_{1-6}$-haloalkyl, —$OR^a$, phenyl, or heteroaryl.

4. The compound of claim 1, wherein Y is $NR^3R^4$.

5. The compound of claim 4, wherein $R^3$ is $C_{1-8}$-alkyl or $C_{2-8}$-alkenyl, wherein the $C_{1-8}$-alkyl or $C_{2-8}$-alkenyl are optionally substituted with one or two substituents selected from the group consisting of —$OR^e$, —$NR^fR^g$, —$NR^fC(O)R^e$, —$NHSO_2R^e$, —$SO_2NR^fNR^g$, and benzyl, wherein $R^e$, $R^f$, and $R^g$ are independently selected from the group consisting of H, $C_{1-6}$-alkyl, $C_{3-8}$-cycloalkyl, heteroaryl, and phenyl.

6. The compound of claim 4, wherein $R^3$ is aryl or heteroaryl, wherein the aryl and heteroaryl are optionally substituted with one or more $R^7$, wherein $R^7$ is $C_{1-6}$-alkyl, $C_{1-6}$-haloalkyl, —$OR^8$, —$SR^8$, heteroaryl, or heterocycloalkyl, wherein the heteroaryl and heterocycloalkyl are optionally substituted with $C_{1-6}$-alkyl.

7. The compound of claim 4, wherein $R^3$ is $C_{3-8}$-cycloalkyl optionally substituted with one or two $R^7$, wherein $R^7$ is heterocycloalkyl, $C_{3-8}$-cycloalkyl-$(C_{1-4}$-alkyl)-, $OR^8$, —$NR^9R^{10}$, —$NHC(O)R^{11}$, —$NHC(O)NHR^{11}$, or —$NHSO_2R^{11}$.

8. The compound of claim 4, wherein $R^3$ is heterocycloalkyl optionally substituted with one or two $R^7$, wherein $R^7$ is —$S(O)_2R^8$, —$C(O)R^8$, $C_{3-8}$-cycloalkyl, $C_{1-6}$-alkyl, heterocycloalkyl, or aryl-$(C_{1-4}$-alkyl)-.

9. The compound of claim 4, wherein $R^3$ is $C_{3-8}$-cycloalkyl-$(C_{1-8}$-alkyl)-, wherein the $R^3$ $C_{3-8}$-cycloalkyl is optionally substituted with one or two $R^7$, wherein $R^7$ is heterocycloalkyl, $C_{3-8}$-cycloalkyl-$(C_{1-4}$-alkyl)-, $OR^8$, —$NR^9R^{10}$, —$NHC(O)R^{11}$, —$NHC(O)NHR^{11}$, or —$NHSO_2R^{11}$.

10. The compound of claim 4, wherein $R^3$ is heterocycloalkyl-$(C_{1-8}$-alkyl)-, wherein the $R^3$ heterocycloalkyl is optionally substituted with one or two $R^7$, wherein $R^7$ is —$S(O)_2R^8$, —$C(O)R^8$, $C_{3-8}$-cycloalkyl, $C_{1-6}$-alkyl, heterocycloalkyl, or aryl-$(C_{1-4}$-alkyl)-.

11. The compound of claim 4, wherein $R^3$ is aryl-$(C_{1-8}$-alkyl)- or heteroaryl-$(C_{1-8}$-alkyl)-, wherein the $R^3$ aryl and heteroaryl are optionally substituted with one or two $R^7$, wherein $R^7$ is $C_{1-6}$-alkyl, $C_{1-6}$-haloalkyl, —$OR^8$, —$SR^8$, heteroaryl, or heterocycloalkyl, wherein the heteroaryl and heterocycloalkyl are optionally substituted with $C_{1-6}$-alkyl.

12. The compound of claim 4, wherein $R^4$ is hydrogen.

13. The compound of claim 1, wherein Y is $NR^5C(O)R^6$ or $NR^5SO_2R^6$, $R^5$ is hydrogen, and $R^6$ is $C_{1-8}$-alkyl, $C_{3-8}$-cycloalkyl, heterocycloalkyl, aryl, or heteroaryl.

14. A compound selected from the group consisting of
6-chloro-N-cyclohexyl-4-(1H-pyrrolo[2,3-b]pyridin-3-yl)pyridin-2-amine;
N-benzyl-6-chloro-4-(1H-pyrrolo[2,3-b]pyridin-3-yl)pyridin-2-amine;
N-allyl-6-chloro-4-(1H-pyrrolo[2,3-b]pyridin-3-yl)pyridin-2-amine;
3-(2-chloro-6-piperidin-1-ylpyridin-4-yl)-1H-pyrrolo[2,3-b]pyridine;
N-benzyl-6-chloro-N-methyl-4-(1H-pyrrolo[2,3-b]pyridin-3-yl)pyridin-2-amine;
3-[2-chloro-6-(3,3-difluoroazetidin-1-yl)pyridin-4-yl]-1H-pyrrolo[2,3-b]pyridine;
3-[2-chloro-6-(2,3-dimethylphenyl)pyridin-4-yl]-1H-pyrrolo[2,3-b]pyridine;

6-chloro-4-(1H-pyrrolo[2,3-b]pyridin-3-yl)-N-tetrahydro-2H-pyran-4-ylpyridin-2-amine;
2-{[6-chloro-4-(1H-pyrrolo[2,3-b]pyridin-3-yl)pyridin-2-yl]amino}cyclohexanol;
6-chloro-N-(2-methoxyethyl)-4-(1H-pyrrolo[2,3-b]pyridin-3-yl)pyridin-2-amine;
2-{[6-chloro-4-(1H-pyrrolo[2,3-b]pyridin-3-yl)pyridin-2-yl]amino}ethanol;
6-chloro-N,N-bis(2-methoxyethyl)-4-(1H-pyrrolo[2,3-b]pyridin-3-yl)pyridin-2-amine;
6-chloro-4-(1H-pyrrolo[2,3-b]pyridin-3-yl)-N-(tetrahydrofuran-2-ylmethyl)pyridin-2-amine;
Trans 4-{[6-chloro-4-(1H-pyrrolo[2,3-b]pyridin-2-yl]amino}cyclohexanol;
N-[6-chloro-4-(1H-pyrrolo[2,3-b]pyridin-3-yl)pyridin-2-yl]cyclohexane-1,4-diamine;
6-chloro-N-(2-methoxycyclohexyl)-4-(1H-pyrrolo[2,3-b]pyridin-3-yl)pyridin-2-amine;
N-[6-chloro-4-(1H-pyrrolo[2,3-b]pyridin-3-yl)pyridin-2-yl]cyclohexane-1,2-diamine;
1-{[6-chloro-4-(1H-pyrrolo[2,3-b]pyridin-3-yl)pyridin-2-yl]amino}-2-methylpropan-2-ol;
4-{[6-chloro-4-(1H-pyrrolo[2,3-b]pyridin-3-yl)pyridin-2-yl]amino}butan-1-ol;
5-{[6-chloro-4-(1H-pyrrolo[2,3-b]pyridin-3-yl)pyridin-2-yl]amino}-2,2-dimethylpentan-1-ol;
N-(4-{[6-chloro-4-(1H-pyrrolo[2,3-b]pyridin-3-yl)pyridin-2-yl]amino}cyclohexyl)methanesulfonamide;
N-(4-{[6-chloro-4-(1H-pyrrolo[2,3-b]pyridin-3-yl)pyridin-2-yl]amino}cyclohexyl)acetamide;
N-[6-chloro-4-(1H-pyrrolo[2,3-b]pyridin-3-yl)pyridin-2-yl]cyclohexane-1,3-diamine;
N-(3-{[6-chloro-4-(1H-pyrrolo[2,3-b]pyridin-3-yl)pyridin-2-yl]amino}cyclohexyl)methanesulfonamide;
6-chloro-4-(1H-pyrrolo[2,3-b]pyridin-3-yl)-N-(tetrahydro-2H-pyran-4-ylmethyl)pyridin-2-amine;
3-{[6-chloro-4-(1H-pyrrolo[2,3-b]pyridin-3-yl)pyridin-2-yl]amino}cyclohexanol;
6-chloro-N-(pyridin-3-ylmethyl)-4-(1H-pyrrolo[2,3-b]pyridin-3-yl)pyridin-2-amine;
6-chloro-4-(1H-pyrrolo[2,3-b]pyridin-3-yl)-N-(tetrahydro-2H-pyran-3-ylmethyl)pyridin-2-amine;
6-chloro-N-(pyrrolidin-3-ylmethyl)-4-(1H-pyrrolo[2,3-b]pyridin-3-yl)pyridin-2-amine;
6-chloro-N-(2,3-dimethylbenzyl)-4-(1H-pyrrolo[2,3-b]pyridin-3-yl)pyridin-2-amine;
6-chloro-N-(pyridin-4-ylmethyl)-4-(1H-pyrrolo[2,3-b]pyridin-3-yl)pyridin-2-amine;
6-chloro-4-(1H-pyrrolo[2,3-b]pyridin-3-yl)-N-(tetrahydro-2H-pyran-2-ylmethyl)pyridin-2-amine;
6-chloro-N-piperidin-4-yl-4-(1H-pyrrolo[2,3-b]pyridin-3-yl)pyridin-2-amine;
6-chloro-N-(4-methoxycyclohexyl)-4-(1H-pyrrolo[2,3-b]pyridin-3-yl)pyridin-2-amine;
N-(3-{[6-chloro-4-(1H-pyrrolo[2,3-b]pyridin-3-yl)pyridin-2-yl]amino}cyclohexyl)acetamide;
6-chloro-N-(4-chloro-2-fluorobenzyl)-4-(1H-pyrrolo[2,3-b]pyridin-3-yl)pyridin-2-amine;
6-chloro-N-{[2-(pyridin-3-yloxy)pyridin-3-yl]methyl}-4-(1H-pyrrolo[2,3-b]pyridin-3-yl)pyridin-2-amine;
6-chloro-N-(piperidin-3-ylmethyl)-4-(1H-pyrrolo[2,3-b]pyridin-3-yl)pyridin-2-amine;
1-{[6-chloro-4-(1H-pyrrolo[2,3-b]pyridin-3-yl)pyridin-2-yl]amino}propan-2-ol;
2-(2-{[6-chloro-4-(1H-pyrrolo[2,3-b]pyridin-3-yl)pyridin-2-yl]amino}ethoxy)ethanol;
3-{[6-chloro-4-(1H-pyrrolo[2,3-b]pyridin-3-yl)pyridin-2-yl]amino}-2,2-dimethylpropan-1-ol;
6-chloro-N-[1-(methylsulfonyl)piperidin-4-yl]-4-(1H-pyrrolo[2,3-b]pyridin-3-yl)pyridin-2-amine;
N-(4-{[6-chloro-4-(1H-pyrrolo[2,3-b]pyridin-3-yl)pyridin-2-yl]amino}cyclohexyl)benzenesulfonamide;
N-(4-{[6-chloro-4-(1H-pyrrolo[2,3-b]pyridin-3-yl)pyridin-2-yl]amino}cyclohexyl)-1-phenylmethanesulfonamide;
N-(4-{[6-chloro-4-(1H-pyrrolo[2,3-b]pyridin-3-yl)pyridin-2-yl]amino}cyclohexyl)pyridine-3-sulfonamide;
N-(4-{[6-chloro-4-(1H-pyrrolo[2,3-b]pyridin-3-yl)pyridin-2-yl]amino}cyclohexyl)propane-1-sulfonamide;
6-chloro-N-[2-(morpholin-4-yl)ethyl]-4-(1H-pyrrolo[2,3-b]pyridin-3-yl)pyridin-2-amine;
3-(2-{[6-chloro-4-(1H-pyrrolo[2,3-b]pyridin-3-yl)pyridin-2-yl]amino}ethyl)phenol;
N-[6-chloro-4-(1H-pyrrolo[2,3-b]pyridin-3-yl)pyridin-2-yl]-N'-(2-methylpropyl)cyclohexane-1,3-diamine;
N'-[6-chloro-4-(1H-pyrrolo[2,3-b]pyridin-3-yl)pyridin-2-yl]-N,N-dimethylcyclohexane-1,3-diamine;
1-(4-{[6-chloro-4-(1H-pyrrolo[2,3-b]pyridin-3-yl)pyridin-2-yl]amino}cyclohexyl)-3-cyclopentylurea;
N-(trans-4-{[6-chloro-4-(1H-pyrrolo[2,3-b]pyridin-3-yl)pyridin-2-yl]amino}cyclohexyl)cyclopropanesulfonamide;
1-(4-{[6-chloro-4-(1H-pyrrolo[2,3-b]pyridin-3-yl)pyridin-2-yl]amino}cyclohexyl)-3-propylurea;
N-(trans-4-{[6-chloro-4-(1H-pyrrolo[2,3-b]pyridin-3-yl)pyridin-2-yl]amino}cyclohexyl)cyclopropanecarboxamide;
N-(4-{[6-chloro-4-(1H-pyrrolo[2,3-b]pyridin-3-yl)pyridin-2-yl]amino}cyclohexyl)-2-methylpropanamide;
N-(4-{[6-chloro-4-(1H-pyrrolo[2,3-b]pyridin-3-yl)pyridin-2-yl]amino}cyclohexyl)benzamide;
1-(4-{[6-chloro-4-(1H-pyrrolo[2,3-b]pyridin-3-yl)pyridin-2-yl]amino}cyclohexyl)-3-phenylurea;
N-[6-chloro-4-(1H-pyrrolo[2,3-b]pyridin-3-yl)pyridin-2-yl]-N'-(pyridin-3-ylmethyl)cyclohexane-1,3-diamine;
N-[6-chloro-4-(1H-pyrrolo[2,3-b]pyridin-3-yl)pyridin-2-yl]-N'-cyclobutylcyclohexane-1,3-diamine;
N-(3-{[6-chloro-4-(1H-pyrrolo[2,3-b]pyridin-3-yl)pyridin-2-yl]amino}cyclohexyl)cyclopropanecarboxamide;
N-(3-{[6-chloro-4-(1H-pyrrolo[2,3-b]pyridin-3-yl)pyridin-2-yl]amino}cyclohexyl)-1-propylpiperidine-4-carboxamide;
N-(3-{[6-chloro-4-(1H-pyrrolo[2,3-b]pyridin-3-yl)pyridin-2-yl]amino}cyclohexyl)-1H-pyrazole-3-carboxamide;
N-[6-chloro-4-(1H-pyrrolo[2,3-b]pyridin-3-yl)pyridin-2-yl]-N'-(piperidin-3-ylmethyl)cyclohexane-1,3-diamine;
N-{2-[(3-{[6-chloro-4-(1H-pyrrolo[2,3-b]pyridin-3-yl)pyridin-2-yl]amino}cyclohexyl)amino]-2-oxoethyl}benzamide;
N-[6-chloro-4-(1H-pyrrolo[2,3-b]pyridin-3-yl)pyridin-2-yl]-2,2-dimethylpropane-1,3-diamine;
N-(3-{[6-chloro-4-(1H-pyrrolo[2,3-b]pyridin-3-yl)pyridin-2-yl]amino}-2,2-dimethylpropyl)methanesulfonamide;
N-(3-{[6-chloro-4-(1H-pyrrolo[2,3-b]pyridin-3-yl)pyridin-2-yl]amino}cyclohexyl)cyclopropanesulfonamide;
N-(3-{[6-chloro-4-(1H-pyrrolo[2,3-b]pyridin-3-yl)pyridin-2-yl]amino}cyclohexyl)propane-1-sulfonamide;

N-(3-{[6-chloro-4-(1H-pyrrolo[2,3-b]pyridin-3-yl)pyridin-2-yl]amino}cyclohexyl)-4-methylbenzenesulfonamide;
1-(3-{[6-chloro-4-(1H-pyrrolo[2,3-b]pyridin-3-yl)pyridin-2-yl]amino}cyclohexyl)-3-ethylurea;
1-(3-{[6-chloro-4-(1H-pyrrolo[2,3-b]pyridin-3-yl)pyridin-2-yl]amino}cyclohexyl)-3-cyclopentylurea;
N-(3-{[6-chloro-4-(1H-pyrrolo[2,3-b]pyridin-3-yl)pyridin-2-yl]amino}-2,2-dimethylpropyl)pyridine-3-sulfonamide;
N-(3-{[6-chloro-4-(1H-pyrrolo[2,3-b]pyridin-3-yl)pyridin-2-yl]amino}-2,2-dimethylpropyl)cyclopropanesulfonamide;
N-(3-{[6-chloro-4-(1H-pyrrolo[2,3-b]pyridin-3-yl)pyridin-2-yl]amino}cyclohexyl)thiophene-2-sulfonamide;
N-[6-chloro-4-(1H-pyrrolo[2,3-b]pyridin-3-yl)pyridin-2-yl]pentanamide;
N-[6-chloro-4-(1H-pyrrolo[2,3-b]pyridin-3-yl)pyridin-2-yl]cyclohexanecarboxamide;
N-[6-chloro-4-(1H-pyrrolo[2,3-b]pyridin-3-yl)pyridin-2-yl]benzamide;
N-[6-chloro-4-(1H-pyrrolo[2,3-b]pyridin-3-yl)pyridin-2-yl]ethane-1,2-diamine;
N-(2-{[6-chloro-4-(1H-pyrrolo[2,3-b]pyridin-3-yl)pyridin-2-yl]amino}ethyl)methanesulfonamide;
N-(2-{[6-chloro-4-(1H-pyrrolo[2,3-b]pyridin-3-yl)pyridin-2-yl]amino}ethyl)cyclopropanesulfonamide;
N-(2-{[6-chloro-4-(1H-pyrrolo[2,3-b]pyridin-3-yl)pyridin-2-yl]amino}ethyl)pyridine-3-sulfonamide;
6-chloro-4-(1H-pyrrolo[2,3-b]pyridin-3-yl)pyridin-2-amine;
6-chloro-N-cyclobutyl-4-(1H-pyrrolo[2,3-b]pyridin-3-yl)pyridin-2-amine;
trans-N'-[6-chloro-4-(1H-pyrrolo[2,3-b]pyridin-3-yl)pyridin-2-yl]-N,N-dimethylcyclohexane-1,4-diamine;
6-chloro-N-[(1-ethylpiperidin-3-yl)methyl]-4-(1H-pyrrolo[2,3-b]pyridin-3-yl)pyridin-2-amine;
6-chloro-N-[(1-cyclobutylpiperidin-3-yl)methyl]-4-(1H-pyrrolo[2,3-b]pyridin-3-yl)pyridin-2-amine;
6-chloro-N-{[1-(pyridin-3-ylmethyl)piperidin-3-yl]methyl}-4-(1H-pyrrolo[2,3-b]pyridin-3-yl)pyridin-2-amine;
6-chloro-N-{[1-(methylsulfonyl)piperidin-3-yl]methyl}-4-(1H-pyrrolo[2,3-b]pyridin-3-yl)pyridin-2-amine;
3-({[6-chloro-4-(1H-pyrrolo[2,3-b]pyridin-3-yl)pyridin-2-yl]amino}methyl)-N-ethylpiperidine-1-carboxamide;
1-(trans-4-{[6-chloro-4-(1H-pyrrolo[2,3-b]pyridin-3-yl)pyridin-2-yl]amino}cyclohexyl)-3-methylurea;
1-[3-({[6-chloro-4-(1H-pyrrolo[2,3-b]pyridin-3-yl)pyridin-2-yl]amino}methyl)piperidin-1-yl]ethanone;
6-chloro-N-{[1-(cyclopropylsulfonyl)piperidin-3-yl]methyl}-4-(1H-pyrrolo[2,3-b]pyridin-3-yl)pyridin-2-amine;
(3-{[6-chloro-4-(1H-pyrrolo[2,3-b]pyridin-2-yl]amino}piperidin-1-yl)(cyclopropyl)methanone;
N-[6-chloro-4-(1H-pyrrolo[2,3-b]pyridin-3-yl)pyridin-2-yl]-N'-(cyclopropylmethyl)cyclohexane-1,3-diamine;
6-chloro-N-(1-cyclobutylpiperidin-3-yl)-4-(1H-pyrrolo[2,3-b]pyridin-3-yl)pyridin-2-amine;
trans-N-[6-chloro-4-(1H-pyrrolo[2,3-b]pyridin-3-yl)pyridin-2-yl]-N'-cyclobutylcyclohexane-1,4-diamine;
(2S)—N-(trans-4-{[6-chloro-4-(1H-pyrrolo[2,3-b]pyridin-3-yl)pyridin-2-yl]amino}cyclohexyl)azetidine-2-carboxamide;
N-[6-chloro-4-(1H-pyrrolo[2,3-b]pyridin-3-yl)pyridin-2-yl]pyridine-3-carboxamide;
N-[6-chloro-4-(1H-pyrrolo[2,3-b]pyridin-3-yl)pyridin-2-yl]butanamide;
trans-N-[6-chloro-4-(1H-pyrrolo[2,3-b]pyridin-3-yl)pyridin-2-yl]-N'-(cyclopropylmethyl)cyclohexane-1,4-diamine;
N-[(trans)-2-{[6-chloro-4-(1H-pyrrolo[2,3-b]pyridin-3-yl)pyridin-2-yl]amino}cyclohexyl]methanesulfonamide;
N-[6-chloro-4-(1H-pyrrolo[2,3-b]pyridin-3-yl)pyridin-2-yl]-2,6-difluorobenzamide;
N-[6-chloro-4-(1H-pyrrolo[2,3-b]pyridin-3-yl)pyridin-2-yl]piperidine-4-carboxamide;
N-(3-{[6-chloro-4-(1H-pyrrolo[2,3-b]pyridin-3-yl)pyridin-2-yl]amino}-2,2-dimethylpropyl)acetamide;
N-(trans-4-{[6-chloro-4-(1H-pyrrolo[2,3-b]pyridin-3-yl)pyridin-2-yl]amino}cyclohexyl)-$N^2,N^2$-dimethylglycinamide;
(2S)—N-(trans-4-{[6-chloro-4-(1H-pyrrolo[2,3-b]pyridin-3-yl)pyridin-2-yl]amino}cyclohexyl)-4-oxoazetidine-2-carboxamide;
N-(trans-4-{[6-chloro-4-(1H-pyrrolo[2,3-b]pyridin-3-yl)pyridin-2-yl]amino}cyclohexyl)-$N^2$-methyl-L-alaninamide;
azetidin-2-yl(4-{[6-chloro-4-(1H-pyrrolo[2,3-b]pyridin-3-yl)pyridin-2-yl]amino}piperidin-1-yl)methanone;
N-(3-{[6-chloro-4-(1H-pyrrolo[2,3-b]pyridin-3-yl)pyridin-2-yl]amino}cyclohexyl)-$N^2,N^2$-dimethylglycinamide;
N-(3-{[6-chloro-4-(1H-pyrrolo[2,3-b]pyridin-3-yl)pyridin-2-yl]amino}cyclohexyl)-1-methyl-L-prolinamide;
N-[(trans)-2-{[6-chloro-4-(1H-pyrrolo[2,3-b]pyridin-3-yl)pyridin-2-yl]amino}cyclohexyl]azetidine-2-carboxamide;
N'-[6-chloro-4-(1H-pyrrolo[2,3-b]pyridin-3-yl)pyridin-2-yl]-N,N,2,2-tetramethylpropane-1,3-diamine;
N-[6-chloro-4-(1H-pyrrolo[2,3-b]pyridin-3-yl)pyridin-2-yl]methanesulfonamide;
N-[6-chloro-4-(1H-pyrrolo[2,3-b]pyridin-3-yl)pyridin-2-yl]benzenesulfonamide;
N-(3-{[6-chloro-4-(1H-pyrrolo[2,3-b]pyridin-3-yl)pyridin-2-yl]amino}-2,2-dimethylpropyl)cyclopropanecarboxamide;
N-(trans-4-{[6-chloro-4-(1H-pyrrolo[2,3-b]pyridin-3-yl)pyridin-2-yl]amino}cyclohexyl)-1-methylpyrrolidine-3-carboxamide;
(4-{[6-chloro-4-(1H-pyrrolo[2,3-b]pyridin-3-yl)pyridin-2-yl]amino}piperidin-1-yl)(cyclopropyl)methanone;
N-(trans-4-{[6-chloro-4-(1H-pyrrolo[2,3-b]pyridin-3-yl)pyridin-2-yl]amino}cyclohexyl)-$N^2,N^2$-dimethyl-L-alaninamide;
6-chloro-N-(1-cyclobutylpiperidin-4-yl)-4-(1H-pyrrolo[2,3-b]pyridin-3-yl)pyridin-2-amine;
N-(3-{[6-chloro-4-(1H-pyrrolo[2,3-b]pyridin-3-yl)pyridin-2-yl]amino}cyclohexyl)piperidine-2-carboxamide;
N-(3-{[6-chloro-4-(1H-pyrrolo[2,3-b]pyridin-3-yl)pyridin-2-yl]amino}cyclohexyl)-2-(pyrrolidin-1-yl)acetamide;
(cis)-N-[6-chloro-4-(1H-pyrrolo[2,3-b]pyridin-3-yl)pyridin-2-yl]cyclohexane-1,2-diamine;
N-[(cis)-2-{[6-chloro-4-(1H-pyrrolo[2,3-b]pyridin-3-yl)pyridin-2-yl]amino}cyclohexyl]methane sulfonamide;
N-(trans-4-{[6-chloro-4-(1H-pyrrolo[2,3-b]pyridin-3-yl)pyridin-2-yl]amino}cyclohexyl)cyclobutanecarboxamide;
N-(trans-4-{[6-chloro-4-(1H-pyrrolo[2,3-b]pyridin-3-yl)pyridin-2-yl]amino}cyclohexyl)-1-ethylazetidine-2-carboxamide;

1-amino-N-(3-{[6-chloro-4-(1H-pyrrolo[2,3-b]pyridin-3-yl)pyridin-2-yl]amino}cyclohexyl)cyclobutanecarboxamide;

N-(trans-4-{[6-chloro-4-(1H-pyrrolo[2,3-b]pyridin-3-yl)pyridin-2-yl]amino}cyclohexyl)-1-cyclopentylazetidine-2-carboxamide;

N-(trans-4-{[6-chloro-4-(1H-pyrrolo[2,3-b]pyridin-3-yl)pyridin-2-yl]amino}cyclohexyl)-N$^2$-cyclopentylglycinamide;

6-chloro-N-[1-(methylsulfonyl)piperidin-3-yl]-4-(1H-pyrrolo[2,3-b]pyridin-3-yl)pyridin-2-amine;

N-(3-{[6-chloro-4-(1H-pyrrolo[2,3-b]pyridin-3-yl)pyridin-2-yl]amino}cyclohexyl)-5-oxoprolinamide;

(cis)-N'-[6-chloro-4-(1H-pyrrolo[2,3-b]pyridin-3-yl)pyridin-2-yl]-N,N-dimethylcyclohexane-1,2-diamine;

N-(trans-4-{[6-chloro-4-(1H-pyrrolo[2,3-b]pyridin-3-yl)pyridin-2-yl]amino}cyclohexyl)-2-(morpholin-4-yl)acetamide;

N-(trans-4-{[6-chloro-4-(1H-pyrrolo[2,3-b]pyridin-3-yl)pyridin-2-yl]amino}cyclohexyl)-2-[4-(pyridin-2-yl)piperazin-1-yl]acetamide;

N-{4-[(4-aminocyclohexyl)methyl]cyclohexyl}-6-chloro-4-(1H-pyrrolo[2,3-b]pyridin-3-yl)pyridin-2-amine;

N-(trans-4-{[6-chloro-4-(1H-pyrrolo[2,3-b]pyridin-3-yl)pyridin-2-yl]amino}cyclohexyl)-2,6-dioxopiperidine-4-carboxamide;

2-amino-N-(3-{[6-chloro-4-(1H-pyrrolo[2,3-b]pyridin-3-yl)pyridin-2-yl]amino}cyclohexyl)ethanesulfonamide;

6-chloro-N-[(1-methylpiperidin-3-yl)methyl]-4-(1H-pyrrolo[2,3-b]pyridin-3-yl)pyridin-2-amine;

1-(3-{[6-chloro-4-(1H-pyrrolo[2,3-b]pyridin-3-yl)pyridin-2-yl]amino}piperidin-1-yl)ethanone;

trans-N-[6-chloro-4-(1H-pyrrolo[2,3-b]pyridin-3-yl)pyridin-2-yl]-N'-(1-methylpiperidin-4-yl)cyclohexane-1,4-diamine;

trans-4-{[6-chloro-4-(5-methoxy-1H-pyrrolo[2,3-b]pyridin-3-yl)pyridin-2-yl]amino}cyclohexanol;

N-[6-chloro-4-(1H-pyrrolo[2,3-b]pyridin-3-yl)pyridin-2-yl]-2-(morpholin-4-yl)acetamide;

N-(trans-4-{[6-chloro-4-(1H-pyrrolo[2,3-b]pyridin-3-yl)pyridin-2-yl]amino}cyclohexyl)pyrrolidine-3-sulfonamide;

N-(trans-4-{[6-chloro-4-(1H-pyrrolo[2,3-b]pyridin-3-yl)pyridin-2-yl]amino}cyclohexyl)-N$^2$-(trans-4-hydroxycyclohexyl)glycinamide;

N-(trans-4-{[6-chloro-4-(1H-pyrrolo[2,3-b]pyridin-3-yl)pyridin-2-yl]amino}cyclohexyl)-N$^2$-[2-(morpholin-4-yl)ethyl]glycinamide;

N-(3-{[6-chloro-4-(1H-pyrrolo[2,3-b]pyridin-3-yl)pyridin-2-yl]amino}cyclohexyl)-2-(dimethylamino)ethanesulfonamide;

6-chloro-N-(4-{[4-(dimethylamino)cyclohexyl]methyl}cyclohexyl)-4-(1H-pyrrolo[2,3-b]pyridin-3-yl)pyridin-2-amine;

6-chloro-N-(4-{[4-(cyclohexylamino)cyclohexyl]methyl}cyclohexyl)-4-(1H-pyrrolo[2,3-b]pyridin-3-yl)pyridin-2-amine;

trans-N-[6-chloro-4-(1H-pyrrolo[2,3-b]$^{pyridin}$-3-yl)pyridin-2-yl]-N'-(1-cyclohexylpiperidin-4-yl)cyclohexane-1,4-diamine;

trans-N-(4-aminocyclohexyl)-N'-[6-chloro-4-(1H-pyrrolo[2,3-b]pyridin-3-yl)pyridin-2-yl]cyclohexane-1,4-diamine;

6-chloro-N-[4-(piperidin-4-yl)cyclohexyl]-4-(1H-pyrrolo[2,3-b]pyridin-3-yl)pyridin-2-amine;

N-(trans-4-{[6-chloro-4-(1H-pyrrolo[2,3-b]pyridin-3-yl)pyridin-2-yl]amino}cyclohexyl)azetidine-3-carboxamide;

N-{4-[(trans-4-{[6-chloro-4-(1H-pyrrolo[2,3-b]pyridin-3-yl)pyridin-2-yl]amino}cyclohexyl)amino]cyclohexyl}acetamide;

N-{4-[(trans-4-{[6-chloro-4-(1H-pyrrolo[2,3-b]pyridin-3-yl)pyridin-2-yl]amino}cyclohexyl)amino]cyclohexyl}cyclopropanecarboxamide;

1-[4-(4-{[6-chloro-4-(1H-pyrrolo[2,3-b]pyridin-3-yl)pyridin-2-yl]amino}cyclohexyl)piperidin-1-yl]ethanone;

N-{2-[(3-{[6-chloro-4-(1H-pyrrolo[2,3-b]pyridin-3-yl)pyridin-2-yl]amino}cyclohexyl)sulfamoyl]ethyl}acetamide;

N-{2-[(3-{[6-chloro-4-(1H-pyrrolo[2,3-b]pyridin-3-yl)pyridin-2-yl]amino}cyclohexyl)sulfamoyl]ethyl}cyclopropanecarboxamide;

N-(trans-4-{[6-chloro-4-(1H-pyrrolo[2,3-b]pyridin-3-yl)pyridin-2-yl]amino}cyclohexyl)-1-(4-fluorobenzyl)azetidine-3-carboxamide;

N-(trans-4-{[6-chloro-4-(1H-pyrrolo[2,3-b]pyridin-3-yl)pyridin-2-yl]amino}cyclohexyl)-1-(methylsulfonyl)azetidine-3-carboxamide;

6-chloro-4-(4-chloro-1H-pyrrolo[2,3-b]pyridin-3-yl)-N-cyclohexylpyridin-2-amine;

N-{2-[(3-{[6-chloro-4-(1H-pyrrolo[2,3-b]pyridin-3-yl)pyridin-2-yl]amino}cyclohexyl)sulfamoyl]ethyl}benzamide;

N-(3-{[6-chloro-4-(1H-pyrrolo[2,3-b]pyridin-3-yl)pyridin-2-yl]amino}cyclohexyl)-2-(cyclobutylamino)ethanesulfonamide;

6-chloro-N-cyclohexyl-4-[5-(1H-pyrazol-4-yl)-1H-pyrrolo[2,3-b]pyridin-3-yl]pyridin-2-amine;

N-{2-[(3-{[6-chloro-4-(1H-pyrrolo[2,3-b]pyridin-3-yl)pyridin-2-yl]amino}cyclohexyl)sulfamoyl]ethyl}pyrazine-2-carboxamide;

4-(5-bromo-1H-pyrrolo[2,3-b]pyridin-3-yl)-6-chloro-N-cyclohexylpyridin-2-amine;

N-{4-[(4-{[6-chloro-4-(1H-pyrrolo[2,3-b]pyridin-3-yl)pyridin-2-yl]amino}cyclohexyl)methyl]cyclohexyl}acetamide;

{4-[(4-{[6-chloro-4-(1H-pyrrolo[2,3-b]pyridin-3-yl)pyridin-2-yl]amino}cyclohexyl)amino]piperidin-1-yl}(cyclopropyl)methanone;

6-chloro-N-cyclohexyl-4-[5-(1-methyl-1H-pyrazol-4-yl)-1H-pyrrolo[2,3-b]pyridin-3-yl]pyridin-2-amine;

{4-[(4-{[6-chloro-4-(1H-pyrrolo[2,3-b]pyridin-3-yl)pyridin-2-yl]amino}cyclohexyl)amino]piperidin-1-yl}(phenyl)methanone;

6-chloro-N-cyclohexyl-4-(5-methoxy-1H-pyrrolo[2,3-b]pyridin-3-yl)pyridin-2-amine;

2-amino-N-(trans-4-{[6-chloro-4-(1H-pyrrolo[2,3-b]pyridin-3-yl)pyridin-2-yl]amino}cyclohexyl)ethanesulfonamide;

3-[2-chloro-6-(cyclohexylamino)pyridin-4-yl]-1H-pyrrolo[2,3-b]pyridin-5-ol;

6-chloro-N-[4-(piperidin-3-yl)cyclohexyl]-4-(1H-pyrrolo[2,3-b]pyridin-3-yl)pyridin-2-amine;

6-chloro-N-[4-(1-cyclobutylpiperidin-4-yl)cyclohexyl]-4-(1H-pyrrolo[2,3-b]pyridin-3-yl)pyridin-2-amine;

6-chloro-N-{4-[1-(methylsulfonyl)piperidin-4-yl]cyclohexyl}-4-(1H-pyrrolo[2,3-b]pyridin-3-yl)pyridin-2-amine;

6-chloro-N-[4-(1-methylpiperidin-4-yl)cyclohexyl]-4-(1H-pyrrolo[2,3-b]pyridin-3-yl)pyridin-2-amine;

6-chloro-N-methyl-N-[4-(1-methylpiperidin-4-yl)cyclohexyl]-4-(1H-pyrrolo[2,3-b]pyridin-3-yl)pyridin-2-amine;

6-chloro-N-{4-[1-(methylsulfonyl)piperidin-3-yl]cyclohexyl}-4-(1H-pyrrolo[2,3-b]pyridin-3-yl)pyridin-2-amine;

6-chloro-N-cyclohexyl-4-(5-{1-[2-(morpholin-4-yl)ethyl]-1H-pyrazol-4-yl}-1H-pyrrolo[2,3-b]pyridin-3-yl)pyridin-2-amine;

[3-(4-{[6-chloro-4-(1H-pyrrolo[2,3-b]pyridin-3-yl)pyridin-2-yl]amino}cyclohexyl)piperidin-1-yl](cyclopropyl)methanone;

6-chloro-N-[4-(1-cyclobutylpiperidin-3-yl)cyclohexyl]-4-(1H-pyrrolo[2,3-b]pyridin-3-yl)pyridin-2-amine;

6-chloro-N-[4-(pyrrolidin-3-yl)cyclohexyl]-4-(1H-pyrrolo[2,3-b]pyridin-3-yl)pyridin-2-amine;

N-[6-chloro-4-(1H-pyrrolo[2,3-b]pyridin-3-yl)pyridin-2-yl]-1'-methyl-1,4'-bipiperidin-4-amine;

4-(4-{[6-chloro-4-(1H-pyrrolo[2,3-b]pyridin-3-yl)pyridin-2-yl]amino}cyclohexyl)piperazin-2-one;

N-{2-[(trans-4-{[6-chloro-4-(1H-pyrrolo[2,3-b]pyridin-3-yl)pyridin-2-yl]amino}cyclohexyl)sulfamoyl]ethyl}benzamide;

N-(trans-4-{[6-chloro-4-(1H-pyrrolo[2,3-b]pyridin-3-yl)pyridin-2-yl]amino}cyclohexyl)-2-[(methylsulfonyl)amino]ethanesulfonamide;

6-chloro-N-cyclohexyl-4-{5-[2-(morpholin-4-yl)ethoxy]-1H-pyrrolo[2,3-b]pyridin-3-yl}pyridin-2-amine;

6-chloro-N-cyclohexyl-4-{5-[(1-methyl-1H-imidazol-5-yl)methoxy]-1H-pyrrolo[2,3-b]pyridin-3-yl}pyridin-2-amine;

6-chloro-N-[4-(1-methylpyrrolidin-3-yl)cyclohexyl]-4-(1H-pyrrolo[2,3-b]pyridin-3-yl)pyridin-2-amine;

6-chloro-N-{4-[1-(4-fluorobenzyl)pyrrolidin-3-yl]cyclohexyl}-4-(1H-pyrrolo[2,3-b]pyridin-3-yl)pyridin-2-amine;

6-chloro-N-{4-[1-(methylsulfonyl)pyrrolidin-3-yl]cyclohexyl}-4-(1H-pyrrolo[2,3-b]pyridin-3-yl)pyridin-2-amine;

6-chloro-N-{1-[4-(cyclobutylamino)cyclohexyl]piperidin-4-yl}-4-(1H-pyrrolo[2,3-b]pyridin-3-yl)pyridin-2-amine;

3-[2-chloro-6-(cyclohexylamino)pyridin-4-yl]-1H-pyrrolo[2,3-b]pyridine-5-carbonitrile;

N-(trans-4-{[6-chloro-4-(1H-pyrrolo[2,3-b]pyridin-3-yl)pyridin-2-yl]amino}cyclohexyl)-2,4-difluorobenzamide;

N-(trans-4-{[6-chloro-4-(1H-pyrrolo[2,3-b]pyridin-3-yl)pyridin-2-yl]amino}cyclohexyl)-4-(trifluoromethoxy)benzamide;

6-chloro-N-cyclohexyl-4-(5-methyl-1H-pyrrolo[2,3-b]pyridin-3-yl)pyridin-2-amine;

6-chloro-N-phenyl-4-(1H-pyrrolo[2,3-b]pyridin-3-yl)pyridin-2-amine;

6-chloro-N-{2-methoxy-4-[4-(4-methylpiperazin-1-yl)piperidin-1-yl]phenyl}-4-(1H-pyrrolo[2,3-b]pyridin-3-yl)pyridin-2-amine;

1-(4-chlorobenzyl)-N-(trans-4-{[6-chloro-4-(1H-pyrrolo[2,3-b]pyridin-3-yl)pyridin-2-yl]amino}cyclohexyl)azetidine-3-carboxamide;

N-(trans-4-{[6-chloro-4-(1H-pyrrolo[2,3-b]pyridin-3-yl)pyridin-2-yl]amino}cyclohexyl)-2-[(prop-2-en-1-ylcarbamoyl)amino]ethanesulfonamide;

N-(trans-4-{[6-chloro-4-(1H-pyrrolo[2,3-b]pyridin-3-yl)pyridin-2-yl]amino}cyclohexyl)-1-(pyridin-3-ylmethyl)azetidine-3-carboxamide;

N-(trans-4-{[6-chloro-4-(1H-pyrrolo[2,3-b]pyridin-3-yl)pyridin-2-yl]amino}cyclohexyl)-1-(2,4-difluorobenzyl)azetidine-3-carboxamide;

N-(trans-4-{[6-chloro-4-(1H-pyrrolo[2,3-b]pyridin-3-yl)pyridin-2-yl]amino}cyclohexyl)-1-[(1-methyl-1H-pyrazol-3-yl)methyl]azetidine-3-carboxamide;

2-(4-{3-[2-chloro-6-(cyclohexylamino)pyridin-4-yl]-1H-pyrrolo[2,3-b]pyridin-5-yl}-1H-pyrazol-1-yl)ethanol;

trans-N-[6-chloro-4-(5-methoxy-1H-pyrrolo[2,3-b]pyridin-3-yl)pyridin-2-yl]cyclohexane-1,4-diamine;

6-chloro-N-cyclohexyl-4-[5-(pyridin-3-yl)-1H-pyrrolo[2,3-b]pyridin-3-yl]pyridin-2-amine;

6-chloro-N-cyclohexyl-4-[5-(thiophen-3-yl)-1H-pyrrolo[2,3-b]pyridin-3-yl]pyridin-2-amine;

N-(trans-4-{[6-chloro-4-(5-methoxy-1H-pyrrolo[2,3-b]pyridin-3-yl)pyridin-2-yl]amino}cyclohexyl)cyclopropanecarboxamide;

1-benzyl-N-(trans-4-{[6-chloro-4-(5-methoxy-1H-pyrrolo[2,3-b]pyridin-3-yl)pyridin-2-yl]amino}cyclohexyl)azetidine-3-carboxamide;

N-(trans-4-{[6-chloro-4-(5-methoxy-1H-pyrrolo[2,3-b]pyridin-3-yl)pyridin-2-yl]amino}cyclohexyl)cyclopropanesulfonamide;

N-(trans-4-{[6-chloro-4-(5-methoxy-1H-pyrrolo[2,3-b]pyridin-3-yl)pyridin-2-yl]amino}cyclohexyl)-1-ethylpyrrolidine-3-carboxamide;

N-(trans-4-{[6-chloro-4-(5-methoxy-1H-pyrrolo[2,3-b]pyridin-3-yl)pyridin-2-yl]amino}cyclohexyl)methanesulfonamide;

6-chloro-N-cyclohexyl-4-(5-{3-[(4-methylpiperazin-1-yl)methyl]phenyl}-1H-pyrrolo[2,3-b]pyridin-3-yl)pyridin-2-amine;

3-{3-[2-chloro-6-(cyclohexylamino)pyridin-4-yl]-1H-pyrrolo[2,3-b]pyridin-5-yl}benzenesulfonamide;

4-{3-[2-chloro-6-(cyclohexylamino)pyridin-4-yl]-1H-pyrrolo[2,3-b]pyridin-5-yl}benzenesulfonamide;

trans-N-[6-chloro-4-(5-ethoxy-1H-pyrrolo[2,3-b]pyridin-3-yl)pyridin-2-yl]cyclohexane-1,4-diamine;

3-[2-chloro-6-(cyclohexylamino)pyridin-4-yl]-1H-pyrrolo[2,3-b]pyridin-5-amine;

N-{3-[2-chloro-6-(cyclohexylamino)pyridin-4-yl]-1H-pyrrolo[2,3-b]pyridin-5-yl}acetamide;

N-(trans-4-{[6-chloro-4-(5-methoxy-1H-pyrrolo[2,3-b]pyridin-3-yl)pyridin-2-yl]amino}cyclohexyl)-$N^2$-methylglycinamide;

N-(trans-4-{[6-chloro-4-(5-methoxy-1H-pyrrolo[2,3-b]pyridin-3-yl)pyridin-2-yl]amino}cyclohexyl)-2-methylpropanamide;

N-(trans-4-{[6-chloro-4-(1H-pyrrolo[2,3-b]pyridin-3-yl)pyridin-2-yl]amino}cyclohexyl)-2-[4-(4-fluorophenyl)piperazin-1-yl]acetamide;

N-(trans-4-{[6-chloro-4-(1H-pyrrolo[2,3-b]pyridin-3-yl)pyridin-2-yl]amino}cyclohexyl)-2-[4-(pyridin-4-yl)piperazin-1-yl]acetamide;

N-(trans-4-{[6-chloro-4-(1H-pyrrolo[2,3-b]pyridin-3-yl)pyridin-2-yl]amino}cyclohexyl)-2-(4-cyclohexylpiperazin-1-yl)acetamide;

2-(4-butylpiperazin-1-yl)-N-(trans-4-{[6-chloro-4-(1H-pyrrolo[2,3-b]pyridin-3-yl)pyridin-2-yl]amino}cyclohexyl)acetamide;

N-(trans-4-{[6-chloro-4-(1H-pyrrolo[2,3-b]pyridin-3-yl)pyridin-2-yl]amino}cyclohexyl)-2-[4-(furan-2-ylcarbonyl)piperazin-1-yl]acetamide;

N-(trans-4-{[6-chloro-4-(1H-pyrrolo[2,3-b]pyridin-3-yl)pyridin-2-yl]amino}cyclohexyl)-2-[4-(2-cyanophenyl)piperazin-1-yl]acetamide;

3-[2-chloro-6-(cyclohexylamino)pyridin-4-yl]-1H-pyrrolo[2,3-b]pyridine-5-carboxylic acid;

6-chloro-4-(5-methoxy-1H-pyrrolo[2,3-b]pyridin-3-yl)-N-[4-(piperidin-4-yl)cyclohexyl]pyridin-2-amine;

N-{4-[(4-aminocyclohexyl)methyl]cyclohexyl}-6-chloro-4-(5-methoxy-1H-pyrrolo[2,3-b]pyridin-3-yl)pyridin-2-amine;

6-chloro-N-(4-{[4-(cyclohexylamino)cyclohexyl]methyl}cyclohexyl)-4-(5-methoxy-1H-pyrrolo[2,3-b]pyridin-3-yl)pyridin-2-amine;

3-[2-chloro-6-(cyclohexylamino)pyridin-4-yl]-N-phenyl-1H-pyrrolo[2,3-b]pyridin-5-amine;

N-{4-[(4-{[6-chloro-4-(5-methoxy-1H-pyrrolo[2,3-b]pyridin-3-yl)pyridin-2-yl]amino}cyclohexyl)methyl]cyclohexyl}cyclopropanecarboxamide;

trans-N-{6-chloro-4-[5-(prop-2-yn-1-yloxy)-1H-pyrrolo[2,3-b]pyridin-3-yl]pyridin-2-yl}cyclohexane-1,4-diamine;

3-[2-chloro-6-(cyclohexylamino)pyridin-4-yl]-N-(pyridin-2-ylmethyl)-1H-pyrrolo[2,3-b]pyridine-5-carboxamide;

6-chloro-N-cyclohexyl-4-[5-(pyrimidin-5-yl)-1H-pyrrolo[2,3-b]pyridin-3-yl]pyridin-2-amine;

N-(trans-4-{[6-chloro-4-(5-methoxy-1H-pyrrolo[2,3-b]pyridin-3-yl)pyridin-2-yl]amino}cyclohexyl)butane-1-sulfonamide;

4-[5-(6-aminopyridin-3-yl)-1H-pyrrolo[2,3-b]pyridin-3-yl]-6-chloro-N-cyclohexylpyridin-2-amine;

N-(trans-4-{[6-chloro-4-(5-methoxy-1H-pyrrolo[2,3-b]pyridin-3-yl)pyridin-2-yl]amino}cyclohexyl)glycinamide;

6-chloro-N-cyclohexyl-4-(4-methoxy-1H-pyrrolo[2,3-b]pyridin-3-yl)pyridin-2-amine;

1-{3-[2-chloro-6-(cyclohexylamino)pyridin-4-yl]-1H-pyrrolo[2,3-b]pyridin-5-yl}-3-ethylurea;

N-(trans-4-{[6-chloro-4-(1H-pyrrolo[2,3-b]pyridin-3-yl)pyridin-2-yl]amino}cyclohexyl)-1-(pyridin-4-ylmethyl)azetidine-3-carboxamide;

N-(trans-4-{[6-chloro-4-(1H-pyrrolo[2,3-b]pyridin-3-yl)pyridin-2-yl]amino}cyclohexyl)-1-(piperidin-4-yl)azetidine-3-carboxamide;

N-(trans-4-{[6-chloro-4-(5-methoxy-1H-pyrrolo[2,3-b]pyridin-3-yl)pyridin-2-yl]amino}cyclohexyl)-$N^2$-cyclohexylglycinamide;

6-chloro-N-[4-(1-cyclobutylpiperidin-4-yl)cyclohexyl]-4-(5-methoxy-1H-pyrrolo[2,3-b]pyridin-3-yl)pyridin-2-amine;

N-(trans-4-{[6-chloro-4-(5-methoxy-1H-pyrrolo[2,3-b]pyridin-3-yl)pyridin-2-yl]amino}cyclohexyl)cyclohexanesulfonamide;

N-(trans-4-{[6-chloro-4-(5-methoxy-1H-pyrrolo[2,3-b]pyridin-3-yl)pyridin-2-yl]amino}cyclohexyl)-2-(morpholin-4-yl)acetamide;

N-(3-{3-[2-chloro-6-(cyclohexylamino)pyridin-4-yl]-1H-pyrrolo[2,3-b]pyridin-5-yl}phenyl)acetamide;

N-{3-[2-chloro-6-(cyclohexylamino)pyridin-4-yl]-1H-pyrrolo[2,3-b]pyridin-5-yl}methanesulfonamide;

N-{4-[(4-{[6-chloro-4-(5-methoxy-1H-pyrrolo[2,3-b]pyridin-3-yl)pyridin-2-yl]amino}cyclohexyl)methyl]cyclohexyl}pyridine-3-carboxamide;

N-(trans-4-{[6-chloro-4-(5-methoxy-1H-pyrrolo[2,3-b]pyridin-3-yl)pyridin-2-yl]amino}cyclohexyl)-$N^2$-(2,2-dimethylpropyl)glycinamide;

6-chloro-N-(4-{[4-(dimethylamino)cyclohexyl]methyl}cyclohexyl)-4-(5-methoxy-1H-pyrrolo[2,3-b]pyridin-3-yl)pyridin-2-amine;

N-(3-{[6-chloro-4-(5-methoxy-1H-pyrrolo[2,3-b]pyridin-3-yl)pyridin-2-yl]amino}cyclohexyl)cyclopropanesulfonamide;

N-(3-{[6-chloro-4-(5-methoxy-1H-pyrrolo[2,3-b]pyridin-3-yl)pyridin-2-yl]amino}cyclohexyl)acetamide;

N-(3-{[6-chloro-4-(5-methoxy-1H-pyrrolo[2,3-b]pyridin-3-yl)pyridin-2-yl]amino}cyclohexyl)thiophene-2-sulfonamide;

N-(3-{[6-chloro-4-(5-methoxy-1H-pyrrolo[2,3-b]pyridin-3-yl)pyridin-2-yl]amino}cyclohexyl)-2-(pyrrolidin-1-yl)acetamide;

N-(4-{[6-chloro-4-(1H-pyrrolo[2,3-b]pyridin-3-yl)pyridin-2-yl]amino}cyclohexyl)-3,5-dimethyl-1,2-oxazole-4-sulfonamide;

6-chloro-N-[(2S)-1-methoxy-3-phenylpropan-2-yl]-4-(1H-pyrrolo[2,3-b]pyridin-3-yl)pyridin-2-amine;

N-[6-chloro-4-(1H-pyrrolo[2,3-b]pyridin-3-yl)pyridin-2-yl]-N'-cyclopentylcyclohexane-1,3-diamine;

ethyl N-[(4-{[6-chloro-4-(1H-pyrrolo[2,3-b]pyridin-3-yl)pyridin-2-yl]amino}cyclohexyl)carbamoyl]glycinate;

1-(4-{[6-chloro-4-(1H-pyrrolo[2,3-b]pyridin-3-yl)pyridin-2-yl]amino}cyclohexyl)-3-propan-2-ylurea;

1-tert-butyl-3-(4-{[6-chloro-4-(1H-pyrrolo[2,3-b]pyridin-3-yl)pyridin-2-yl]amino}cyclohexyl)urea;

N-(4-{[6-chloro-4-(1H-pyrrolo[2,3-b]pyridin-3-yl)pyridin-2-yl]amino}cyclohexyl)-2-methoxyacetamide;

N-[6-chloro-4-(1H-pyrrolo[2,3-b]pyridin-3-yl)pyridin-2-yl]-N'-(1,3-thiazol-2-ylmethyl)cyclohexane-1,3-diamine;

N-[6-chloro-4-(1H-pyrrolo[2,3-b]pyridin-3-yl)pyridin-2-yl]-N'-[3-(piperidin-1-ylmethyl)benzyl]cyclohexane-1,3-diamine;

N-(3-{[6-chloro-4-(1H-pyrrolo[2,3-b]pyridin-3-yl)pyridin-2-yl]amino}cyclohexyl)-2-ethoxyacetamide;

N-(3-{[6-chloro-4-(1H-pyrrolo[2,3-b]pyridin-3-yl)pyridin-2-yl]amino}cyclohexyl)-2-phenoxyacetamide;

N-(3-{[6-chloro-4-(1H-pyrrolo[2,3-b]pyridin-3-yl)pyridin-2-yl]amino}cyclohexyl)pyrazine-2-carboxamide;

N-(3-{[6-chloro-4-(1H-pyrrolo[2,3-b]pyridin-3-yl)pyridin-2-yl]amino}cyclohexyl)azetidine-2-carboxamide;

tert-butyl 2-[(3-{[6-chloro-4-(1H-pyrrolo[2,3-b]pyridin-3-yl)pyridin-2-yl]amino}cyclohexyl)carbamoyl]azetidine-1-carboxylate;

1-(4-{[6-chloro-4-(1H-pyrrolo[2,3-b]pyridin-3-yl)pyridin-2-yl]amino}cyclohexyl)-3-prop-2-en-1-ylurea;

N-(3-{[6-chloro-4-(1H-pyrrolo[2,3-b]pyridin-3-yl)pyridin-2-yl]amino}-2,2-dimethylpropyl)-1-methyl-1H-imidazole-4-sulfonamide;

N-(3-{[6-chloro-4-(1H-pyrrolo[2,3-b]pyridin-3-yl)pyridin-2-yl]amino}cyclohexyl)furan-2-sulfonamide;

N-(3-{[6-chloro-4-(1H-pyrrolo[2,3-b]pyridin-3-yl)pyridin-2-yl]amino}cyclohexyl)pyridine-3-sulfonamide;

1-(3-{[6-chloro-4-(1H-pyrrolo[2,3-b]pyridin-3-yl)pyridin-2-yl]amino}cyclohexyl)-3-propan-2-ylurea;

ethyl N-[(3-{[6-chloro-4-(1H-pyrrolo[2,3-b]pyridin-3-yl)pyridin-2-yl]amino}cyclohexyl)carbamoyl]glycinate;

1-(3-{[6-chloro-4-(1H-pyrrolo[2,3-b]pyridin-3-yl)pyridin-2-yl]amino}cyclohexyl)-3-(cyclohexylmethyl)urea;

4-acetyl-N-(3-{[6-chloro-4-(1H-pyrrolo[2,3-b]pyridin-3-yl)pyridin-2-yl]amino}-2,2-dimethylpropyl)benzenesulfonamide;

N-(3-{[6-chloro-4-(1H-pyrrolo[2,3-b]pyridin-3-yl)pyridin-2-yl]amino}-2,2-dimethylpropyl)-3,5-dimethyl-1,2-oxazole-4-sulfonamide;

N-(3-{[6-chloro-4-(1H-pyrrolo[2,3-b]pyridin-3-yl)pyridin-2-yl]amino}-2,2-dimethylpropyl)thiophene-2-sulfonamide;
N-(3-{[6-chloro-4-(1H-pyrrolo[2,3-b]pyridin-3-yl)pyridin-2-yl]amino}cyclohexyl)-3,5-dimethyl-1,2-oxazole-4-sulfonamide;
1-(3-{[6-chloro-4-(1H-pyrrolo[2,3-b]pyridin-3-yl)pyridin-2-yl]amino}cyclohexyl)-3-propylurea;
N-(3-{[6-chloro-4-(1H-pyrrolo[2,3-b]pyridin-3-yl)pyridin-2-yl]amino}-2,2-dimethylpropyl)propane-1-sulfonamide;
N-[6-chloro-4-(1H-pyrrolo[2,3-b]pyridin-3-yl)pyridin-2-yl]acetamide;
N-(trans-4-{[6-chloro-4-(1H-pyrrolo[2,3-b]pyridin-3-yl)pyridin-2-yl]amino}cyclohexyl)propane-2-sulfonamide;
N-(trans-4-{[6-chloro-4-(1H-pyrrolo[2,3-b]pyridin-3-yl)pyridin-2-yl]amino}cyclohexyl)ethanesulfonamide;
N-(2-{[6-chloro-4-(1H-pyrrolo[2,3-b]pyridin-3-yl)pyridin-2-yl]amino}ethyl)butane-1-sulfonamide;
N-(2-{[6-chloro-4-(1H-pyrrolo[2,3-b]pyridin-3-yl)pyridin-2-yl]amino}ethyl)thiophene-2-sulfonamide;
6-chloro-N-(1-methylpiperidin-3-yl)-4-(1H-pyrrolo[2,3-b]pyridin-3-yl)pyridin-2-amine;
[3-({[6-chloro-4-(1H-pyrrolo[2,3-b]pyridin-3-yl)pyridin-2-yl]amino}methyl)piperidin-1-yl](cyclopropyl)methanone;
N-[6-chloro-4-(1H-pyrrolo[2,3-b]pyridin-3-yl)pyridin-2-yl]-N-{[1-(cyclopropylcarbonyl)piperidin-3-yl]methyl}cyclopropanecarboxamide;
6-chloro-N-{[1-(cyclopropylmethyl)piperidin-3-yl]methyl}-4-(1H-pyrrolo[2,3-b]pyridin-3-yl)pyridin-2-amine;
6-chloro-N-[1-(cyclopropylmethyl)piperidin-3-yl]-4-(1H-pyrrolo[2,3-b]pyridin-3-yl)pyridin-2-amine;
N-[6-chloro-4-(1H-pyrrolo[2,3-b]pyridin-3-yl)pyridin-2-yl]-2-(1H-indol-2-yl)acetamide;
trans-N-[6-chloro-4-(1H-pyrrolo[2,3-b]pyridin-3-yl)pyridin-2-yl]-N'-cyclopentylcyclohexane-1,4-diamine;
trans-N-[6-chloro-4-(1H-pyrrolo[2,3-b]pyridin-3-yl)pyridin-2-yl]-N'-(2-methylpropyl)cyclohexane-1,4-diamine;
6-chloro-N-[3-(pyrrolidin-1-yl)cyclohexyl]-4-(1H-pyrrolo[2,3-b]pyridin-3-yl)pyridin-2-amine;
6-chloro-N-[3-(piperidin-1-yl)cyclohexyl]-4-(1H-pyrrolo[2,3-b]pyridin-3-yl)pyridin-2-amine;
N-(trans-4-{[6-chloro-4-(1H-pyrrolo[2,3-b]pyridin-3-yl)pyridin-2-yl]amino}cyclohexyl)-$N^2$-methylglycinamide;
N-(trans-4-{[6-chloro-4-(1H-pyrrolo[2,3-b]pyridin-3-yl)pyridin-2-yl]amino}cyclohexyl)-1-ethylpyrrolidine-3-carboxamide;
N-(3-{[6-chloro-4-(1H-pyrrolo[2,3-b]pyridin-3-yl)pyridin-2-yl]amino}cyclohexyl)-$N^2$-methylalaninamide;
(2R)—N-[(1S,3S)-3-{[6-chloro-4-(1H-pyrrolo[2,3-b]pyridin-3-yl)pyridin-2-yl]amino}cyclohexyl]-2-(methylamino)-2-phenylethanamine;
(2R)—N-[(1R,3R)-3-{[6-chloro-4-(1H-pyrrolo[2,3-b]pyridin-3-yl)pyridin-2-yl]amino}cyclohexyl]-2-(methylamino)-2-phenylethanamine;
N-[(1R,2R)-2-{[6-chloro-4-(1H-pyrrolo[2,3-b]pyridin-3-yl)pyridin-2-yl]amino}cyclohexyl]cyclopropanesulfonamide;
N-[6-chloro-4-(1H-pyrrolo[2,3-b]pyridin-3-yl)pyridin-2-yl]-4-fluorobenzenesulfonamide;
N-[6-chloro-4-(1H-pyrrolo[2,3-b]pyridin-3-yl)pyridin-2-yl]cyclopropanesulfonamide;
N'-[6-chloro-4-(1H-pyrrolo[2,3-b]pyridin-3-yl)pyridin-2-yl]-N,N-diethyl-2,2-dimethylpropane-1,3-diamine;
trans-N'-[6-chloro-4-(1H-pyrrolo[2,3-b]pyridin-3-yl)pyridin-2-yl]-N,N-diethylcyclohexane-1,4-diamine;
N-(trans-4-{[6-chloro-4-(1H-pyrrolo[2,3-b]pyridin-3-yl)pyridin-2-yl]amino}cyclohexyl)-5-oxo-D-prolinamide;
N-(trans-4-{[6-chloro-4-(1H-pyrrolo[2,3-b]pyridin-3-yl)pyridin-2-yl]amino}cyclohexyl)-1-methylprolinamide;
N-(trans-4-{[6-chloro-4-(1H-pyrrolo[2,3-b]pyridin-3-yl)pyridin-2-yl]amino}cyclohexyl)-1-methylpiperidine-2-carboxamide;
N-(trans-4-{[6-chloro-4-(1H-pyrrolo[2,3-b]pyridin-3-yl)pyridin-2-yl]amino}cyclohexyl)-5-oxo-L-prolinamide;
N-(3-{[6-chloro-4-(1H-pyrrolo[2,3-b]pyridin-3-yl)pyridin-2-yl]amino}cyclohexyl)-1-methylpiperidine-2-carboxamide;
2-(azepan-1-yl)-N-(3-{[6-chloro-4-(1H-pyrrolo[2,3-b]pyridin-3-yl)pyridin-2-yl]amino}cyclohexyl)acetamide;
N-(trans-4-{[6-chloro-4-(1H-pyrrolo[2,3-b]pyridin-3-yl)pyridin-2-yl]amino}cyclohexyl)cyclopentanecarboxamide;
N-(trans-4-{[6-chloro-4-(1H-pyrrolo[2,3-b]pyridin-3-yl)pyridin-2-yl]amino}cyclohexyl)-1-methyl-5-oxoprolinamide;
N-(3-{[6-chloro-4-(1H-pyrrolo[2,3-b]pyridin-3-yl)pyridin-2-yl]amino}cyclohexyl)pyrrolidine-3-carboxamide;
N-(3-{[6-chloro-4-(1H-pyrrolo[2,3-b]pyridin-3-yl)pyridin-2-yl]amino}cyclohexyl)piperidine-4-carboxamide;
N-(3-{[6-chloro-4-(1H-pyrrolo[2,3-b]pyridin-3-yl)pyridin-2-yl]amino}cyclohexyl)piperidine-3-carboxamide;
N-(3-{[6-chloro-4-(1H-pyrrolo[2,3-b]pyridin-3-yl)pyridin-2-yl]amino}cyclohexyl)-1-methylpyrrolidine-3-carboxamide;
N-(3-{[6-chloro-4-(1H-pyrrolo[2,3-b]pyridin-3-yl)pyridin-2-yl]amino}cyclohexyl)-1-methylpiperidine-4-carboxamide;
N-(3-{[6-chloro-4-(1H-pyrrolo[2,3-b]pyridin-3-yl)pyridin-2-yl]amino}cyclohexyl)-1-methylpiperidine-3-carboxamide;
N-(3-{[6-chloro-4-(1H-pyrrolo[2,3-b]pyridin-3-yl)pyridin-2-yl]amino}cyclohexyl)-1-(dimethylamino)cyclobutanecarboxamide;
N-(3-{[6-chloro-4-(1H-pyrrolo[2,3-b]pyridin-3-yl)pyridin-2-yl]amino}cyclohexyl)-$N^2$,$N^2$-dimethyl-L-alaninamide;
$N^2$-1-azabicyclo[2.2.2]oct-3-yl-N-(trans-4-{[6-chloro-4-(1H-pyrrolo[2,3-b]pyridin-3-yl)pyridin-2-yl]amino}cyclohexyl)glycinamide;
N-(trans-4-{[6-chloro-4-(1H-pyrrolo[2,3-b]pyridin-3-yl)pyridin-2-yl]amino}cyclohexyl)-$N^2$-(2-hydroxyethyl)glycinamide;
N-(3-{[6-chloro-4-(1H-pyrrolo[2,3-b]pyridin-3-yl)pyridin-2-yl]amino}cyclohexyl)-2-(1,3-dioxo-1,3-dihydro-2H-isoindol-2-yl)ethanesulfonamide;
N-(trans-4-{[6-chloro-4-(1H-pyrrolo[2,3-b]pyridin-3-yl)pyridin-2-yl]amino}cyclohexyl)-$N^2$-(4-methylcyclohexyl)glycinamide;
N-(trans-4-{[6-chloro-4-(1H-pyrrolo[2,3-b]pyridin-3-yl)pyridin-2-yl]amino}cyclohexyl)-$N^2$-(2,2-dimethylpropyl)glycinamide;
N-(trans-4-{[6-chloro-4-(1H-pyrrolo[2,3-b]pyridin-3-yl)pyridin-2-yl]amino}cyclohexyl)-$N^2$-ethyl-$N^2$-(2-hydroxyethyl)glycinamide;
trans-N-[6-chloro-4-(1H-pyrrolo[2,3-b]pyridin-3-yl)pyridin-2-yl]-N'-(piperidin-4-yl)cyclohexane-1,4-diamine;

N-(trans-4-{[6-chloro-4-(1H-pyrrolo[2,3-b]pyridin-3-yl)pyridin-2-yl]amino}cyclohexyl)-2-(1,3-dioxo-1,3-dihydro-2H-isoindol-2-yl)ethanesulfonamide;
6-chloro-N-(4-{[4-(cyclobutylamino)cyclohexyl]methyl}cyclohexyl)-4-(1H-pyrrolo[2,3-b]pyridin-3-yl)pyridin-2-amine;
trans-N-[6-chloro-4-(1H-pyrrolo[2,3-b]pyridin-2-yl]-N'-(1-cyclobutylpiperidin-4-yl)cyclohexane-1,4-diamine;
tert-butyl 4-(4-{[6-chloro-4-(1H-pyrrolo[2,3-b]pyridin-3-yl)pyridin-2-yl]amino}cyclohexyl)piperidine-1-carboxylate;
benzyl {4-[(trans-4-{[6-chloro-4-(1H-pyrrolo[2,3-b]pyridin-3-yl)pyridin-2-yl]amino}cyclohexyl)amino]cyclohexyl}carbamate;
tert-butyl 3-[(trans-4-{[6-chloro-4-(1H-pyrrolo[2,3-b]pyridin-3-yl)pyridin-2-yl]amino}cyclohexyl)carbamoyl]azetidine-1-carboxylate;
N-[4-(acetylamino)cyclohexyl]-N-(trans-4-{[6-chloro-4-(1H-pyrrolo[2,3-b]pyridin-3-yl)pyridin-2-yl]amino}cyclohexyl)acetamide;
[4-(4-{[6-chloro-4-(1H-pyrrolo[2,3-b]pyridin-3-yl)pyridin-2-yl]amino}cyclohexyl)piperidin-1-yl] (cyclopropyl)methanone;
N-(trans-4-{[6-chloro-4-(1H-pyrrolo[2,3-b]pyridin-3-yl)pyridin-2-yl]amino}cyclohexyl)-1-(2-hydroxyethyl)piperidine-4-carboxamide;
N-{4-[(4-{[6-chloro-4-(1H-pyrrolo[2,3-b]pyridin-3-yl)pyridin-2-yl]amino}cyclohexyl)methyl]cyclohexyl}cyclopropanecarboxamide;
1-{4-[(4-{[6-chloro-4-(1H-pyrrolo[2,3-b]pyridin-3-yl)pyridin-2-yl]amino}cyclohexyl)amino]piperidin-1-yl}ethanone;
N-[6-chloro-4-(1H-pyrrolo[2,3-b]pyridin-3-yl)pyridin-2-yl]-N-{4-[1-(methylsulfonyl)piperidin-4-yl]cyclohexyl}methanesulfonamide;
6-chloro-N-[4-(1-methylpiperidin-3-yl)cyclohexyl]-4-(1H-pyrrolo[2,3-b]pyridin-3-yl)pyridin-2-amine;
6-chloro-N-methyl-N-[4-(1-methylpiperidin-3-yl)cyclohexyl]-4-(1H-pyrrolo[2,3-b]pyridin-3-yl)pyridin-2-amine;
N-{2-[(trans-4-{[6-chloro-4-(1H-pyrrolo[2,3-b]pyridin-3-yl)pyridin-2-yl]amino}cyclohexyl)sulfamoyl]ethyl}cyclopropanecarboxamide;
3-{[6-chloro-4-(1H-pyrrolo[2,3-b]pyridin-3-yl)pyridin-2-yl]amino}propan-1-ol;
6-chloro-N-[3-(morpholin-4-yl)propyl]-4-(1H-pyrrolo[2,3-b]pyridin-3-yl)pyridin-2-amine;
6-chloro-N-[3-(1H-imidazol-1-yl)propyl]-4-(1H-pyrrolo[2,3-b]pyridin-3-yl)pyridin-2-amine;
5-{[6-chloro-4-(1H-pyrrolo[2,3-b]pyridin-3-yl)pyridin-2-yl]amino}pentan-1-ol;
6-chloro-N-[2-(pyridin-3-yl)ethyl]-4-(1H-pyrrolo[2,3-b]pyridin-3-yl)pyridin-2-amine;
N-[1-(4-aminocyclohexyl)piperidin-4-yl]-6-chloro-4-(1H-pyrrolo[2,3-b]pyridin-3-yl)pyridin-2-amine;
6-chloro-N-methyl-N-[4-(1-methylpyrrolidin-3-yl)cyclohexyl]-4-(1H-pyrrolo[2,3-b]pyridin-3-yl)pyridin-2-amine;
1-benzyl-N-(trans-4-{[6-chloro-4-(1H-pyrrolo[2,3-b]pyridin-3-yl)pyridin-2-yl]amino}cyclohexyl)azetidine-3-carboxamide;
4-chloro-N-(trans-4-{[6-chloro-4-(1H-pyrrolo[2,3-b]pyridin-3-yl)pyridin-2-yl]amino}cyclohexyl)-2-methoxybenzamide;
N-(trans-4-{[6-chloro-4-(1H-pyrrolo[2,3-b]pyridin-3-yl)pyridin-2-yl]amino}cyclohexyl)-3-(trifluoromethyl)benzamide;
3-chloro-N-(trans-4-{[6-chloro-4-(1H-pyrrolo[2,3-b]pyridin-3-yl)pyridin-2-yl]amino}cyclohexyl)benzamide;
6-chloro-N-[2-(3,4-dimethoxyphenyl)ethyl]-4-(1H-pyrrolo[2,3-b]pyridin-3-yl)pyridin-2-amine;
6-chloro-N-[2-(pyridin-2-yl)ethyl]-4-(1H-pyrrolo[2,3-b]pyridin-3-yl)pyridin-2-amine;
6-chloro-N-(2-phenylethyl)-4-(1H-pyrrolo[2,3-b]pyridin-3-yl)pyridin-2-amine;
6-chloro-N-[3-(4-methylpiperazin-1-yl)propyl]-4-(1H-pyrrolo[2,3-b]pyridin-3-yl)pyridin-2-amine;
6-chloro-N-(2-phenoxyethyl)-4-(1H-pyrrolo[2,3-b]pyridin-3-yl)pyridin-2-amine;
N'-[6-chloro-4-(1H-pyrrolo[2,3-b]pyridin-3-yl)pyridin-2-yl]-N,N-dimethylpropane-1,3-diamine;
N-(1-benzylpyrrolidin-3-yl)-6-chloro-4-(1H-pyrrolo[2,3-b]pyridin-3-yl)pyridin-2-amine;
N-{2-[(trans-4-{[6-chloro-4-(1H-pyrrolo[2,3-b]pyridin-3-yl)pyridin-2-yl]amino}cyclohexyl)sulfamoyl]ethyl}-2,4-difluorobenzamide;
N-(trans-4-{[6-chloro-4-(1H-pyrrolo[2,3-b]pyridin-3-yl)pyridin-2-yl]amino}cyclohexyl)-1-[3-(trifluoromethyl)benzyl]azetidine-3-carboxamide;
N-(trans-4-{[6-chloro-4-(1H-pyrrolo[2,3-b]pyridin-3-yl)pyridin-2-yl]amino}cyclohexyl)-1-(2,4-dichlorobenzyl)azetidine-3-carboxamide;
N-(trans-4-{[6-chloro-4-(1H-pyrrolo[2,3-b]pyridin-3-yl)pyridin-2-yl]amino}cyclohexyl)-1-(1-phenylethyl)azetidine-3-carboxamide;
6-chloro-N-(4-methoxybenzyl)-4-(1H-pyrrolo[2,3-b]pyridin-3-yl)pyridin-2-amine;
4-(2-{[6-chloro-4-(1H-pyrrolo[2,3-b]pyridin-3-yl)pyridin-2-yl]amino}ethyl)phenol;
N-[2-(1,3-benzodioxol-5-yl)ethyl]-6-chloro-4-(1H-pyrrolo[2,3-b]pyridin-3-yl)pyridin-2-amine;
N-(1,3-benzodioxol-5-ylmethyl)-6-chloro-4-(1H-pyrrolo[2,3-b]pyridin-3-yl)pyridin-2-amine;
6-chloro-N-[2-(4-methoxyphenyl)ethyl]-4-(1H-pyrrolo[2,3-b]pyridin-3-yl)pyridin-2-amine;
N-(1-benzylpiperidin-4-yl)-6-chloro-4-(1H-pyrrolo[2,3-b]pyridin-3-yl)pyridin-2-amine;
6-chloro-N-[2-(pyridin-4-yl)ethyl]-4-(1H-pyrrolo[2,3-b]pyridin-3-yl)pyridin-2-amine;
6-chloro-N-(2,3-dihydro-1H-inden-2-yl)-4-(1H-pyrrolo[2,3-b]pyridin-3-yl)pyridin-2-amine;
6-chloro-N-[2-(1H-indol-3-yl)ethyl]-4-(1H-pyrrolo[2,3-b]pyridin-3-yl)pyridin-2-amine;
N-(trans-4-{[6-chloro-4-(1H-pyrrolo[2,3-b]pyridin-3-yl)pyridin-2-yl]amino}cyclohexyl)-1-(2,3-dimethylbenzyl)azetidine-3-carboxamide;
N-(trans-4-{[6-chloro-4-(1H-pyrrolo[2,3-b]pyridin-3-yl)pyridin-2-yl]amino}cyclohexyl)-1-(1H-indol-6-ylmethyl)azetidine-3-carboxamide;
N-[4-(benzyloxy)phenyl]-6-chloro-4-(1H-pyrrolo[2,3-b]pyridin-3-yl)pyridin-2-amine;
N-(1H-benzimidazol-2-ylmethyl)-6-chloro-4-(1H-pyrrolo[2,3-b]pyridin-3-yl)pyridin-2-amine;
6-chloro-N-(1H-indol-5-ylmethyl)-4-(1H-pyrrolo[2,3-b]pyridin-3-yl)pyridin-2-amine;
6-chloro-N-(4-methoxyphenyl)-4-(1H-pyrrolo[2,3-b]pyridin-3-yl)pyridin-2-amine;
6-chloro-4-(1H-pyrrolo[2,3-b]pyridin-3-yl)-N-(3,4,5-trimethoxyphenyl)pyridin-2-amine;
6-chloro-N-[4-(1H-imidazol-1-yl)phenyl]-4-(1H-pyrrolo[2,3-b]pyridin-3-yl)pyridin-2-amine;

6-chloro-N-(3,4-dimethoxybenzyl)-4-(1H-pyrrolo[2,3-b]pyridin-3-yl)pyridin-2-amine;
2-{[6-chloro-4-(1H-pyrrolo[2,3-b]pyridin-3-yl)pyridin-2-yl]amino}-1-phenylethanol;
6-chloro-N-(3-phenylpropyl)-4-(1H-pyrrolo[2,3-b]pyridin-3-yl)pyridin-2-amine;
6-chloro-N-[4-(methylsulfonyl)benzyl]-4-(1H-pyrrolo[2,3-b]pyridin-3-yl)pyridin-2-amine;
6-chloro-N-[4-(methylsulfanyl)phenyl]-4-(1H-pyrrolo[2,3-b]pyridin-3-yl)pyridin-2-amine;
6-chloro-N-(4-phenoxyphenyl)-4-(1H-pyrrolo[2,3-b]pyridin-3-yl)pyridin-2-amine;
6-chloro-N-[4-(piperidin-1-yl)phenyl]-4-(1H-pyrrolo[2,3-b]pyridin-3-yl)pyridin-2-amine;
methyl 3-[2-chloro-6-(cyclohexylamino)pyridin-4-yl]-1H-pyrrolo[2,3-b]pyridine-5-carboxylate;
N-(trans-4-{[6-chloro-4-(1H-pyrrolo[2,3-b]pyridin-3-yl)pyridin-2-yl]amino}cyclohexyl)-2-[4-(2-hydroxyethyl)piperazin-1-yl]acetamide;
N-(trans-4-{[6-chloro-4-(1H-pyrrolo[2,3-b]pyridin-3-yl)pyridin-2-yl]amino}cyclohexyl)-2-[4-(2,6-dimethylphenyl)piperazin-1-yl]acetamide;
6-chloro-N-(4-{[4-(cyclobutylamino)cyclohexyl]methyl}cyclohexyl)-4-(5-methoxy-1H-pyrrolo[2,3-b]pyridin-3-yl)pyridin-2-amine;
6-chloro-4-(5-methoxy-1H-pyrrolo[2,3-b]pyridin-3-yl)-N-(4-{[4-(pentan-3-ylamino)cyclohexyl]methyl}cyclohexyl)pyridin-2-amine;
6-chloro-N-[4-({4-[(cyclopentylmethyl)amino]cyclohexyl}methyl)cyclohexyl]-4-(5-methoxy-1H-pyrrolo[2,3-b]pyridin-3-yl)pyridin-2-amine;
trans-N-(6-chloro-4-{5-[2-(pyridin-2-yl)ethoxy]-1H-pyrrolo[2,3-b]pyridin-3-yl}pyridin-2-yl)cyclohexane-1,4-diamine;
trans-N-{6-chloro-4-[5-(2-methylpropoxy)-1H-pyrrolo[2,3-b]pyridin-3-yl]pyridin-2-yl}cyclohexane-1,4-diamine;
N-(trans-4-{[6-chloro-4-(1H-pyrrolo[2,3-b]pyridin-3-yl)pyridin-2-yl]amino}cyclohexyl)-1-(pyridin-2-ylmethyl)azetidine-3-carboxamide;
N-(trans-4-{[6-chloro-4-(5-methoxy-1H-pyrrolo[2,3-b]pyridin-3-yl)pyridin-2-yl]amino}cyclohexyl)-2,2,2-trifluoroacetamide;
6-chloro-N-cyclohexyl-4-[5-(6-methoxypyridin-3-yl)-1H-pyrrolo[2,3-b]pyridin-3-yl]pyridin-2-amine;
N-(trans-4-{[6-chloro-4-(5-methoxy-1H-pyrrolo[2,3-b]pyridin-3-yl)pyridin-2-yl]amino}cyclohexyl)-$N^2$-ethyl-$N^2$-(2-hydroxyethyl)glycinamide;
N-(trans-4-{[6-chloro-4-(5-methoxy-1H-pyrrolo[2,3-b]pyridin-3-yl)pyridin-2-yl]amino}cyclohexyl)-$N^2$-(2-hydroxyethyl)glycinamide;
N'-[6-chloro-4-(1H-pyrrolo[2,3-b]pyridin-3-yl)pyridin-2-yl]-N,N-dimethylbenzene-1,4-diamine;
6-chloro-N-(2,3-dihydro-1H-inden-5-yl)-4-(1H-pyrrolo[2,3-b]pyridin-3-yl)pyridin-2-amine;
6-chloro-N-(2,3-dihydro-1,4-benzodioxin-6-yl)-4-(1H-pyrrolo[2,3-b]pyridin-3-yl)pyridin-2-amine;
6-chloro-N-{4-[1-(2,4-difluorobenzyl)piperidin-4-yl]cyclohexyl}-4-(5-methoxy-1H-pyrrolo[2,3-b]pyridin-3-yl)pyridin-2-amine;
6-chloro-N-[4-(morpholin-4-yl)phenyl]-4-(1H-pyrrolo[2,3-b]pyridin-3-yl)pyridin-2-amine;
6-chloro-4-(1H-pyrrolo[2,3-b]pyridin-3-yl)-N-(5,6,7,8-tetrahydronaphthalen-1-yl)pyridin-2-amine;
N-(4-tert-butylphenyl)-6-chloro-4-(1H-pyrrolo[2,3-b]pyridin-3-yl)pyridin-2-amine;
6-chloro-N-(2,3-dihydro-1H-inden-4-yl)-4-(1H-pyrrolo[2,3-b]pyridin-3-yl)pyridin-2-amine;
N-[6-chloro-4-(1H-pyrrolo[2,3-b]pyridin-3-yl)pyridin-2-yl]quinolin-6-amine;
6-chloro-N-[4-(4-methylpiperazin-1-yl)phenyl]-4-(1H-pyrrolo[2,3-b]pyridin-3-yl)pyridin-2-amine;
6-chloro-N-[4-(1,1-dioxidothiomorpholin-4-yl)phenyl]-4-(1H-pyrrolo[2,3-b]pyridin-3-yl)pyridin-2-amine;
N-(trans-4-{[6-chloro-4-(5-methoxy-1H-pyrrolo[2,3-b]pyridin-3-yl)pyridin-2-yl]amino}cyclohexyl)-$N^2$-(trans-4-hydroxycyclohexyl)glycinamide;
N-(trans-4-{[6-chloro-4-(5-methoxy-1H-pyrrolo[2,3-b]pyridin-3-yl)pyridin-2-yl]amino}cyclohexyl)-$N^2$-propan-2-ylglycinamide;
N-{4-[(4-{[6-chloro-4-(5-methoxy-1H-pyrrolo[2,3-b]pyridin-3-yl)pyridin-2-yl]amino}cyclohexyl)methyl]cyclohexyl}-3,5-dimethyl-1,2-oxazole-4-sulfonamide;
N-(3-{[6-chloro-4-(5-methoxy-1H-pyrrolo[2,3-b]pyridin-3-yl)pyridin-2-yl]amino}cyclohexyl)-$N^2,N^2$-dimethylglycinamide;
6-chloro-N-{4-[4-(pyridin-2-ylmethyl)piperazin-1-yl]phenyl}-4-(1H-pyrrolo[2,3-b]pyridin-3-yl)pyridin-2-amine;
6-chloro-N-{4-[4-(cyclohexylmethyl)piperazin-1-yl]phenyl}-4-(1H-pyrrolo[2,3-b]pyridin-3-yl)pyridin-2-amine;
6-chloro-N-{4-[4-(2-methylpropyl)piperazin-1-yl]phenyl}-4-(1H-pyrrolo[2,3-b]pyridin-3-yl)pyridin-2-amine;
N-[trans-4-({4-[5-(6-aminopyridin-3-yl)-1H-pyrrolo[2,3-b]pyridin-3-yl]-6-chloropyridin-2-yl}amino)cyclohexyl]cyclopropanesulfonamide;
N-[trans-4-({6-chloro-4-[5-(pyridin-3-yl)-1H-pyrrolo[2,3-b]pyridin-3-yl]pyridin-2-yl}amino)cyclohexyl]cyclopropanesulfonamide;
3-{3-[2-chloro-6-({trans-4-[(cyclopropylsulfonyl)amino]cyclohexyl}amino)pyridin-4-yl]-1H-pyrrolo[2,3-b]pyridin-5-yl}benzenesulfonamide; and
N-[trans-4-({6-chloro-4-[5-(pyrimidin-5-yl)-1H-pyrrolo[2,3-b]pyridin-3-yl]pyridin-2-yl}amino)cyclohexyl]cyclopropanesulfonamide.

15. A pharmaceutical composition comprising a compound or pharmaceutically acceptable salt of claim 1 and pharmaceutically acceptable excipient.

* * * * *

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin-C6-linker

<400> SEQUENCE: 1

Thr Pro Ser Asp Ser Leu Ile Tyr Asp Asp Gly Leu Ser
1               5                   10
```